US009222087B2

(12) United States Patent
Feinstein et al.

(10) Patent No.: US 9,222,087 B2
(45) Date of Patent: Dec. 29, 2015

(54) THERAPEUTIC USES OF INHIBITORS OF RTP801L

(71) Applicants: Elena Feinstein, Rehovot (IL); Igor Mett, Rehovot (IL)

(72) Inventors: Elena Feinstein, Rehovot (IL); Igor Mett, Rehovot (IL)

(73) Assignee: QUARK PHARMACEUTICALS, INC., Fremont, CA (US)

( * ) Notice: Subject to any disclaimer, the term of this patent is extended or adjusted under 35 U.S.C. 154(b) by 56 days.

(21) Appl. No.: 13/869,635

(22) Filed: Apr. 24, 2013

(65) Prior Publication Data

US 2013/0303590 A1 Nov. 14, 2013

Related U.S. Application Data

(63) Continuation of application No. 13/218,053, filed on Aug. 25, 2011, now abandoned, which is a continuation of application No. 12/589,972, filed on Oct. 29, 2009, now Pat. No. 8,017,764, which is a continuation of application No. 11/811,112, filed on Jun. 8, 2007, now Pat. No. 7,626,015.

(60) Provisional application No. 60/812,229, filed on Jun. 9, 2006.

(51) Int. Cl.
*A61K 48/00* (2006.01)
*C07H 21/02* (2006.01)
*C07H 21/04* (2006.01)
*C12N 15/113* (2010.01)

(52) U.S. Cl.
CPC .......... *C12N 15/113* (2013.01); *C12N 2310/14* (2013.01); *C12N 2310/321* (2013.01); *C12N 2320/31* (2013.01)

(58) Field of Classification Search
CPC .............................. A61K 48/00; C12N 15/113
See application file for complete search history.

(56) References Cited

PUBLICATIONS

Scherer et al., Approaches for the sequence-specific knockdown of mRNA, 2003, Nat. Biotechnol., 21(12), pp. 1457-1465.*
Zhang et al., Targeted Gene Silencing by Small Interfering RNA-Based Knock-Down Technology, 2004, Current Pharmaceutical Biotechnology, vol. 5, p. 1-7.*

* cited by examiner

*Primary Examiner* — Amy Bowman
(74) *Attorney, Agent, or Firm* — John P. White; Cooper & Dunham LLP

(57) ABSTRACT

The present invention provides novel molecules, compositions, methods and uses for treating microvascular disorders, eye diseases respiratory conditions and hearing disorders based upon inhibition of the RTP801L gene and/or protein.

7 Claims, 6 Drawing Sheets

Figure 1

Coding sequence of RTP801Like (Ddit4L) (GI:34222182), orf = nucleotides 204-785

```
   1 agccggcgca gggtggccgg ggaggggtga gcagggtgcc gctggctgct ggggtctgca
  61 ggtcaccgag tccccaggag agggggactcc taagaagcca cctgcctgtg tttacccggc
 121 agcgagcgcg caggccccccg cgaactcctg gcagcgctca ggaaaggccg ttgcgcctcg
 181 cgaaggaaac agagccgttg accatggttg caactgcag tttgagcagc aagaacccgg
 241 ccagcatttc agaattgctg gactgtggct atcacccaga gagcctgcta agtgattttg
 301 actactggga ttatgttgtt cctgaaccca acctcaacga ggtaatattt gaggaatcaa
 361 cttgccagaa tttggttaaa atgctggaga actgtctgtc caaatcaaag caaactaaac
 421 ttggttgctc aaaggtcctt gtccctgaga aactgaccca gagaattgct caagatgtcc
 481 tgcggctttc ctcaacggag ccctgcggct tgcgaggttg tgttatgcac gtgaacttgg
 541 aaattgaaaa tgtatgtaaa aagctggata ggattgtgtg tgattctagc gtcgtaccta
 601 cttttgagct tacacttgtg tttaagcagg agaactgctc atggactagc ttcagggact
 661 ttttctttag tagaggtcgc ttctcctctg gtttcaggag aactctgatc ctcagctcag
 721 gatttcgact tgttaagaaa aaactttact cactgattgg aacaacagtg attgaagggt
 781 cctaaaaagg gaaaatatat aaagattatt tcatgattgg gtagtaaaac tattcagcta
 841 gtcagctaaa gtcatttgta gtttgcccca cctgccctaa ataagaaacc ccaaatgtag
 901 tctcttttct ttctgtgttt cacattcata gcaactgcag ctaacaggct gattttctgg
 961 cctttggaga agtgattcaa aatagtgtag attttctgca tagatcccat ttttgtacag
1021 aattgaatgg gatggaatag gtaagcaaaa gtagaagccc atttgagttt tacatttgat
1081 tccacaattt ggtttcaggt aggcttggta atagactata taaaccagat ttgcctattt
1141 tgattttcat atggcttttt tttctctaag ttttcagagg attttttaaa tcacagaatc
1201 atactaaatg atatttagcc tatcaaaact tccaaaagcc cacaccacca gttcctgact
1261 caaatttgaa gggtttttag acaggaaggt aggattaagt aggtgagttt aattaaagct
1321 taaccctagg taagagtaaa tgagaaatat tacggcaata atggaactgc ttcactgttt
1381 cttggtgact tcctcactct aatgtttaa agaggcaaca aaagcttgtg gtgccattttc
1441 agtaaccacg gtgttgtttt agatgccttt ataagctcag tttcccctgt tcttaagtgt
1501 tgaatactgt cttaaacta gaaaaatgca aaatattgaa ctgatattttt tgtgtgtagt
1561 tgattactct tccattgagt gaatgatgaa tacctgtgag gataggaaat tagttctgag
1621 atctagtccc tctctgattc acttagtaat ctatcctctt ttcagtatta catgtgctta
1681 atctcagatg aaccatttca ccatggcagt gttatctcat ctctgggctt ttctgggaat
1741 tgaagtatct ctccttaacc ccaattgtca agggtagtag ctgtatacta ccactttgaa
1801 ttattgaaac gggtcaattt acgaagtctg cattggctat ggagatatgg tttatagtac
1861 agcctagaga atgaaactca ccgtccagat aaccatgcat gcacccagat tttttccacc
1921 ttggatacct gtcactaggg aataataaag gccttatttt ttgtcttatt ccaactaagt
1981 agatcattat ctctttcctt ttttatgtta atgagagaat ttagcctcca ctcaacaatg
2041 ttcaattcag caaggctttc atatccttgc tgtgggtcgt ggataaggag cttattcagg
2101 tttcctgccc tagctattag ctccacttca catgctggag accggcgtag ggacagatgt
2161 attcatcctg gtgttactga aaaacaggtg tgatcctgtt actgatacta taagtgacct
2221 aaaatgtcac tgttcaaatt agccagtgtt ctaacaaact aaactcttca aatgcttgga
2281 aagatactac aaagccaatc tttatagaat tgggccaaga taaatcaatg ttgtttttgca
2341 tgtctattgt taagctccaa aggttcactg tgtttctgcc gctgtcctgg agttgtcacc
2401 actgactggg caaggcttct tgggcatcga tgtagaactg ttgtccttttt tccactaaca
2461 gttatctttg actctctttgc ctgttatgct tacaaaatgg tgatggctta tggaaggctg
2521 ttaaattaat attcctgtta aaggaaatta aagtttgtct atttttgaca ataaaacatt
2581 atatatttttt aaaaaaaaaa aaaaaaa
```

Figure 2

Amino acid sequence of RTP801Like (gi:21687001)

```
  1 mvatgslssk npasiselld cgyhpeslls dfdywdyvvp epnlnevife estcqnlvkm
 61 lenclskskq tklgcskvlv pekltqriaq dvlrlsstep cglrgcvmhv nleienvckk
121 ldrivcdssv vptfeltlvf kqencswtsf rdfffsrgrf ssgfrrtlil ssgfrlvkkk
181 lysligttvi egs
```

Activity of REDD2 siRNAs on the endogenous REDD2 gene in wt MEF cells following H2O2 treatment Results are presented as residual REDD2 expression.

Dose dependent activity of REDD2 siRNA oligos as measured in 801 wt MEF cells. Results are presented as residual REDD2 expression.

Activity of REDD2 siRNAs on the endogenous REDD2 gene in wt 293T Results are presented as residual REDD2 expression.

Dose dependent activity of RTP801L siRNA as measured in 293T cells. Results are presented as residual RTP801L expression.

SEQUENCE LISTING

<160> NUMBER OF SEQ ID NOS: 1852

<210> SEQ ID NO 1
<211> LENGTH: 2607
<212> TYPE: DNA
<213> ORGANISM: Homo sapiens
<220> FEATURE:
<221> NAME/KEY: CDS
<222> LOCATION: (204)..(785)

<400> SEQUENCE: 1

```
agccggcgca gggtggccgg ggaggggtga gcagggtgcc gctggctgct ggggtctgca      60
ggtcaccgag tccccaggag aggggactcc taagaagcca cctgcctgtg tttacccggc     120
agcgagcgcg caggccccccg cgaactcctg cagcgctca ggaaaggccg ttgcgcctcg     180
cgaaggaaac agagccgttg acc atg gtt gca act ggc agt ttg agc agc aag    233
                          Met Val Ala Thr Gly Ser Leu Ser Ser Lys
                           1               5                   10 aac ccg gcc agc att tca gaa ttg ctg gac tgt ggc tat cac cca gag      281
Asn Pro Ala Ser Ile Ser Glu Leu Leu Asp Cys Gly Tyr His Pro Glu
                15                  20                  25 agc ctg cta agt gat ttt gac tac tgg gat tat gtt gtt cct gaa ccc      329
Ser Leu Leu Ser Asp Phe Asp Tyr Trp Asp Tyr Val Val Pro Glu Pro
            30                  35                  40 aac ctc aac gag gta ata ttt gag gaa tca act tgc cag aat ttg gtt      377
Asn Leu Asn Glu Val Ile Phe Glu Glu Ser Thr Cys Gln Asn Leu Val
        45                  50                  55 aaa atg ctg gag aac tgt ctg tcc aaa tca aag caa act aaa ctt ggt      425
Lys Met Leu Glu Asn Cys Leu Ser Lys Ser Lys Gln Thr Lys Leu Gly
    60                  65                  70 tgc tca aag gtc ctt gtc cct gag aaa ctg acc cag aga att gct caa      473
Cys Ser Lys Val Leu Val Pro Glu Lys Leu Thr Gln Arg Ile Ala Gln
75                  80                  85                  90 gat gtc ctg cgg ctt tcc tca acg gag ccc tgc ggc ttg cga ggt tgt      521
Asp Val Leu Arg Leu Ser Ser Thr Glu Pro Cys Gly Leu Arg Gly Cys
                95                  100                 105 gtt atg cac gtg aac ttg gaa att gaa aat gta tgt aaa aag ctg gat      569
Val Met His Val Asn Leu Glu Ile Glu Asn Val Cys Lys Lys Leu Asp
            110                 115                 120 agg att gtg tgt gat tct agc gtc gta cct act ttt gag ctt aca ctt      617
Arg Ile Val Cys Asp Ser Ser Val Val Pro Thr Phe Glu Leu Thr Leu
        125                 130                 135 gtg ttt aag cag gag aac tgc tca tgg act agc ttc agg gac ttt ttc      665
Val Phe Lys Gln Glu Asn Cys Ser Trp Thr Ser Phe Arg Asp Phe Phe
    140                 145                 150 ttt agt aga ggt cgc ttc tcc tct ggt ttc agg aga act ctg atc ctc      713
Phe Ser Arg Gly Arg Phe Ser Ser Gly Phe Arg Arg Thr Leu Ile Leu
155                 160                 165                 170 agc tca gga ttt cga ctt gtt aag aaa aaa ctt tac tca ctg att gga      761
Ser Ser Gly Phe Arg Leu Val Lys Lys Lys Leu Tyr Ser Leu Ile Gly
                175                 180                 185 aca aca gtg att gaa ggg tcc taa aaagggaaaa tatataaga ttatttcatg      815
Thr Thr Val Ile Glu Gly Ser
            190 attgggtagt aaaactattc agctagtcag ctaaagtcat tgtagtttg ccccacctgc     875 cctaaataag aaacccccaaa tgtagtctct tttctttctg tgtttcacat tcatagcaac    935 tgcagctaac aggctgattt tctggccttt ggagaagtga ttcaaaatag tgtagatttt    995 ctgcatagat cccattttg tacagaattg aatgggatgg aataggtaag caaaagtaga    1055
```

```
agcccatttg agttttacat ttgattccac aatttggttt caggtaggct tggtaataga   1115
ctatataaac cagatttgcc tatttttgatt ttcatatggc ttttttttct ctaagttttc   1175
agaggatttt ttaaatcaca gaatcatact aaatgatatt tagcctatca aaacttccaa   1235
aagcccacac caccagttcc tgactcaaat ttgaagggtt tttagacagg aaggtaggat   1295
taagtaggtg agtttaatta aagcttaacc ctaggtaaga gtaaatgaga aatattacgg   1355
caataatgga actgcttcac tgtttcttgg tgacttcctc actctaatgt tttaaagagg   1415
caacaaaagc ttgtggtgcc atttcagtaa ccacggtgtt gttttagatg cctttataag   1475
ctcagtttcc cctgttctta agtgttaat actgtcttta aactagaaaa atgcaaaata   1535
ttgaactgat atttttgtgt gtagttgatt actcttccat tgagtgaatg atgaatacct   1595
gtgaggatag gaaattagtt ctgagatcta gtccctctct gattcactta gtaatctatc   1655
ctcttttcag tattacatgt gcttaatctc agatgaacca tttcaccatg gcagtgttat   1715
ctcatctctg ggcttttctg ggaattgaag tatctctcct taaccccaat tgtcaagggt   1775
agtagctgta tactaccact ttgaattatt gaaacgggtc aatttacgaa gtctgcattg   1835
gctatggaga tatggtttat agtacagcct agagaatgaa actcaccgtc cagataacca   1895
tgcatgcacc cagatttttt ccaccttgga tacctgtcac tagggaataa taaaggcctt   1955
atttttttgtc ttattccaac taagtagatc attatctctt tccttttta tgttaatgag   2015
agaatttagc ctccactcaa caatgttcaa ttcagcaagg cttcatatc cttgctgtgg   2075
gtcgtggata aggagcttat tcaggtttcc tgccctagct attagctcca cttcacatgc   2135
tggagaccgg cgtagggaca gatgtattca tcctggtgtt actgaaaaac aggtgtgatc   2195
ctgttactga tactataagt gacctaaaat gtcactgttc aaattagcca gtgttctaac   2255
aaactaaact cttcaaatgc ttggaaagat actacaaagc caatctttat agaattgggc   2315
caagataaat caatgttgtt ttgcatgtct attgttaagc tccaaaggtt cactgtgttt   2375
ctgccgctgt cctggagttg tcaccactga ctgggcaagg cttcttgggc atcgatgtag   2435
aactgttgtc cttttttccac taacagttat ctttgactct cttgcctgtt atgcttacaa   2495
aatggtgatg gctatggaa ggctgttaaa ttaatattcc tgttaaagga aattaaagtt   2555
tgtctatttt tgacaataaa acattatata tttttaaaaa aaaaaaaaa aa           2607
```

```
<210> SEQ ID NO 2
<211> LENGTH: 193
<212> TYPE: PRT
<213> ORGANISM: Homo sapiens

<400> SEQUENCE: 2

Met Val Ala Thr Gly Ser Leu Ser Ser Lys Asn Pro Ala Ser Ile Ser
1               5                   10                  15

Glu Leu Leu Asp Cys Gly Tyr His Pro Glu Ser Leu Leu Ser Asp Phe
            20                  25                  30

Asp Tyr Trp Asp Tyr Val Val Pro Glu Pro Asn Leu Asn Glu Val Ile
        35                  40                  45

Phe Glu Glu Ser Thr Cys Gln Asn Leu Val Lys Met Leu Glu Asn Cys
    50                  55                  60

Leu Ser Lys Ser Lys Gln Thr Lys Leu Gly Cys Ser Lys Val Leu Val
65                  70                  75                  80

Pro Glu Lys Leu Thr Gln Arg Ile Ala Gln Asp Val Leu Arg Leu Ser
                85                  90                  95

Ser Thr Glu Pro Cys Gly Leu Arg Gly Cys Val Met His Val Asn Leu
```

|     |     |     |     | 100 |     |     |     |     | 105 |     |     |     |     | 110 |     |     |     |     |
|-----|-----|-----|-----|-----|-----|-----|-----|-----|-----|-----|-----|-----|-----|-----|-----|-----|-----|-----|

Glu Ile Glu Asn Val Cys Lys Lys Leu Asp Arg Ile Val Cys Asp Ser
    115             120             125

Ser Val Val Pro Thr Phe Glu Leu Thr Leu Val Phe Lys Gln Glu Asn
    130             135             140

Cys Ser Trp Thr Ser Phe Arg Asp Phe Phe Ser Arg Gly Arg Phe
145             150            155            160

Ser Ser Gly Phe Arg Arg Thr Leu Ile Leu Ser Ser Gly Phe Arg Leu
    165             170             175

Val Lys Lys Lys Leu Tyr Ser Leu Ile Gly Thr Thr Val Ile Glu Gly
    180             185             190

Ser

```
<210> SEQ ID NO 3
<211> LENGTH: 19
<212> TYPE: RNA
<213> ORGANISM: Artificial sequence
<220> FEATURE:
<223> OTHER INFORMATION: Chemically synthesized

<400> SEQUENCE: 3
gccaguguuc uaacaaacu                                                 19

<210> SEQ ID NO 4
<211> LENGTH: 19
<212> TYPE: RNA
<213> ORGANISM: Artificial sequence
<220> FEATURE:
<223> OTHER INFORMATION: Chemically synthesized

<400> SEQUENCE: 4
uagccagugu ucuaacaaa                                                 19

<210> SEQ ID NO 5
<211> LENGTH: 19
<212> TYPE: RNA
<213> ORGANISM: Artificial sequence
<220> FEATURE:
<223> OTHER INFORMATION: Chemically synthesized

<400> SEQUENCE: 5
gugacuuccu cacucuaau                                                 19

<210> SEQ ID NO 6
<211> LENGTH: 19
<212> TYPE: RNA
<213> ORGANISM: Artificial sequence
<220> FEATURE:
<223> OTHER INFORMATION: Chemically synthesized

<400> SEQUENCE: 6
agccaguguu cuaacaaac                                                 19

<210> SEQ ID NO 7
<211> LENGTH: 19
<212> TYPE: RNA
<213> ORGANISM: Artificial sequence
<220> FEATURE:
<223> OTHER INFORMATION: Chemically synthesized

<400> SEQUENCE: 7
gagugaauga ugaauaccu                                                 19
```

<210> SEQ ID NO 8
<211> LENGTH: 19
<212> TYPE: RNA
<213> ORGANISM: Artificial sequence
<220> FEATURE:
<223> OTHER INFORMATION: Chemically synthesized

<400> SEQUENCE: 8 gacuccuca cucuaaugu                                                    19

<210> SEQ ID NO 9
<211> LENGTH: 19
<212> TYPE: RNA
<213> ORGANISM: Artificial sequence
<220> FEATURE:
<223> OTHER INFORMATION: Chemically synthesized

<400> SEQUENCE: 9
guucuaacaa acuaaacuc                                                   19

<210> SEQ ID NO 10
<211> LENGTH: 19
<212> TYPE: RNA
<213> ORGANISM: Artificial sequence
<220> FEATURE:
<223> OTHER INFORMATION: Chemically synthesized

<400> SEQUENCE: 10
gaaugaugaa uaccuguga                                                   19

<210> SEQ ID NO 11
<211> LENGTH: 19
<212> TYPE: RNA
<213> ORGANISM: Artificial sequence
<220> FEATURE:
<223> OTHER INFORMATION: Chemically synthesized

<400> SEQUENCE: 11
uccucacucu aauguuuua                                                   19

<210> SEQ ID NO 12
<211> LENGTH: 19
<212> TYPE: RNA
<213> ORGANISM: Artificial sequence
<220> FEATURE:
<223> OTHER INFORMATION: Chemically synthesized

<400> SEQUENCE: 12
gccagaauuu gguuaaaau                                                   19

<210> SEQ ID NO 13
<211> LENGTH: 19
<212> TYPE: RNA
<213> ORGANISM: Artificial sequence
<220> FEATURE:
<223> OTHER INFORMATION: Chemically synthesized

<400> SEQUENCE: 13
acgggucaau uuacgaagu                                                   19

<210> SEQ ID NO 14
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 14
uccauugagu gaaugauga                                          19

<210> SEQ ID NO 15
<211> LENGTH: 19
<212> TYPE: RNA
<213> ORGANISM: Artificial sequence
<220> FEATURE:
<223> OTHER INFORMATION: Chemically synthesized

<400> SEQUENCE: 15
uuccucacuc uaauguuuu                                          19

<210> SEQ ID NO 16
<211> LENGTH: 19
<212> TYPE: RNA
<213> ORGANISM: Artificial sequence
<220> FEATURE:
<223> OTHER INFORMATION: Chemically synthesized

<400> SEQUENCE: 16
gcacccagau uuuuccac                                           19

<210> SEQ ID NO 17
<211> LENGTH: 19
<212> TYPE: RNA
<213> ORGANISM: Artificial sequence
<220> FEATURE:
<223> OTHER INFORMATION: Chemically synthesized

<400> SEQUENCE: 17
guggugccau uucaguaac                                          19

<210> SEQ ID NO 18
<211> LENGTH: 19
<212> TYPE: RNA
<213> ORGANISM: Artificial sequence
<220> FEATURE:
<223> OTHER INFORMATION: Chemically synthesized

<400> SEQUENCE: 18
ccucacucua auguuuaa                                           19

<210> SEQ ID NO 19
<211> LENGTH: 19
<212> TYPE: RNA
<213> ORGANISM: Artificial sequence
<220> FEATURE:
<223> OTHER INFORMATION: Chemically synthesized

<400> SEQUENCE: 19
cuuccucacu cuaauguuu                                          19

<210> SEQ ID NO 20
<211> LENGTH: 19
<212> TYPE: RNA
<213> ORGANISM: Artificial sequence
<220> FEATURE:
<223> OTHER INFORMATION: Chemically synthesized

<400> SEQUENCE: 20
ggcuuuuuuu ucucuaagu                                          19

<210> SEQ ID NO 21
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 21
ucccauuuuu guacagaau                                                     19

<210> SEQ ID NO 22
<211> LENGTH: 19
<212> TYPE: RNA
<213> ORGANISM: Artificial sequence
<220> FEATURE:
<223> OTHER INFORMATION: Chemically synthesized

<400> SEQUENCE: 22
gagaagugau ucaaaauag                                                     19

<210> SEQ ID NO 23
<211> LENGTH: 19
<212> TYPE: RNA
<213> ORGANISM: Artificial sequence
<220> FEATURE:
<223> OTHER INFORMATION: Chemically synthesized

<400> SEQUENCE: 23
ggagaaguga uucaaaaua                                                     19

<210> SEQ ID NO 24
<211> LENGTH: 19
<212> TYPE: RNA
<213> ORGANISM: Artificial sequence
<220> FEATURE:
<223> OTHER INFORMATION: Chemically synthesized

<400> SEQUENCE: 24
gucagcuaaa gucauuugu                                                     19

<210> SEQ ID NO 25
<211> LENGTH: 19
<212> TYPE: RNA
<213> ORGANISM: Artificial sequence
<220> FEATURE:
<223> OTHER INFORMATION: Chemically synthesized

<400> SEQUENCE: 25
ccggccagca uuucagaau                                                     19

<210> SEQ ID NO 26
<211> LENGTH: 19
<212> TYPE: RNA
<213> ORGANISM: Artificial sequence
<220> FEATURE:
<223> OTHER INFORMATION: Chemically synthesized

<400> SEQUENCE: 26
augcuggaga acugucugu                                                     19

<210> SEQ ID NO 27
<211> LENGTH: 19
<212> TYPE: RNA
<213> ORGANISM: Artificial sequence
<220> FEATURE:
<223> OTHER INFORMATION: Chemically synthesized

<400> SEQUENCE: 27
```
aaaugcugga gaacugucu                                                    19

<210> SEQ ID NO 28
<211> LENGTH: 19
<212> TYPE: RNA
<213> ORGANISM: Artificial sequence
<220> FEATURE:
<223> OTHER INFORMATION: Chemically synthesized

<400> SEQUENCE: 28
ugguuaaaau gcuggagaa                                                    19

<210> SEQ ID NO 29
<211> LENGTH: 19
<212> TYPE: RNA
<213> ORGANISM: Artificial sequence
<220> FEATURE:
<223> OTHER INFORMATION: Chemically synthesized

<400> SEQUENCE: 29
uugguuaaaa ugcuggaga                                                    19

<210> SEQ ID NO 30
<211> LENGTH: 19
<212> TYPE: RNA
<213> ORGANISM: Artificial sequence
<220> FEATURE:
<223> OTHER INFORMATION: Chemically synthesized

<400> SEQUENCE: 30
uagcuccacu ucacaugcu                                                    19

<210> SEQ ID NO 31
<211> LENGTH: 19
<212> TYPE: RNA
<213> ORGANISM: Artificial sequence
<220> FEATURE:
<223> OTHER INFORMATION: Chemically synthesized

<400> SEQUENCE: 31
agccuccacu caacaaugu                                                    19

<210> SEQ ID NO 32
<211> LENGTH: 19
<212> TYPE: RNA
<213> ORGANISM: Artificial sequence
<220> FEATURE:
<223> OTHER INFORMATION: Chemically synthesized

<400> SEQUENCE: 32
acccagauuu uuuccaccu                                                    19

<210> SEQ ID NO 33
<211> LENGTH: 19
<212> TYPE: RNA
<213> ORGANISM: Artificial sequence
<220> FEATURE:
<223> OTHER INFORMATION: Chemically synthesized

<400> SEQUENCE: 33
ugcacccaga uuuuuucca                                                    19

<210> SEQ ID NO 34
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 34
aaacggguca auuuacgaa                                                        19

<210> SEQ ID NO 35
<211> LENGTH: 19
<212> TYPE: RNA
<213> ORGANISM: Artificial sequence
<220> FEATURE:
<223> OTHER INFORMATION: Chemically synthesized

<400> SEQUENCE: 35
augaugaaua ccugugagg                                                        19

<210> SEQ ID NO 36
<211> LENGTH: 19
<212> TYPE: RNA
<213> ORGANISM: Artificial sequence
<220> FEATURE:
<223> OTHER INFORMATION: Chemically synthesized

<400> SEQUENCE: 36
uugagugaau gaugaauac                                                        19

<210> SEQ ID NO 37
<211> LENGTH: 19
<212> TYPE: RNA
<213> ORGANISM: Artificial sequence
<220> FEATURE:
<223> OTHER INFORMATION: Chemically synthesized

<400> SEQUENCE: 37
cggcaauaau ggaacugcu                                                        19

<210> SEQ ID NO 38
<211> LENGTH: 19
<212> TYPE: RNA
<213> ORGANISM: Artificial sequence
<220> FEATURE:
<223> OTHER INFORMATION: Chemically synthesized

<400> SEQUENCE: 38
gccuaucaaa acuuccaaa                                                        19

<210> SEQ ID NO 39
<211> LENGTH: 19
<212> TYPE: RNA
<213> ORGANISM: Artificial sequence
<220> FEATURE:
<223> OTHER INFORMATION: Chemically synthesized

<400> SEQUENCE: 39
uggcuuuuuu uucucuaag                                                        19

<210> SEQ ID NO 40
<211> LENGTH: 19
<212> TYPE: RNA
<213> ORGANISM: Artificial sequence
<220> FEATURE:
<223> OTHER INFORMATION: Chemically synthesized

<400> SEQUENCE: 40
gcccauuuga guuuuacau                                                        19
```

```
<210> SEQ ID NO 41
<211> LENGTH: 19
<212> TYPE: RNA
<213> ORGANISM: Artificial sequence
<220> FEATURE:
<223> OTHER INFORMATION: Chemically synthesized

<400> SEQUENCE: 41
ggccagcauu ucagaauug                                              19

<210> SEQ ID NO 42
<211> LENGTH: 19
<212> TYPE: RNA
<213> ORGANISM: Artificial sequence
<220> FEATURE:
<223> OTHER INFORMATION: Chemically synthesized

<400> SEQUENCE: 42
cggccagcau uucagaauu                                              19

<210> SEQ ID NO 43
<211> LENGTH: 19
<212> TYPE: RNA
<213> ORGANISM: Artificial sequence
<220> FEATURE:
<223> OTHER INFORMATION: Chemically synthesized

<400> SEQUENCE: 43
gcgucguacc uacuuuuga                                              19

<210> SEQ ID NO 44
<211> LENGTH: 19
<212> TYPE: RNA
<213> ORGANISM: Artificial sequence
<220> FEATURE:
<223> OTHER INFORMATION: Chemically synthesized

<400> SEQUENCE: 44
uagcgucgua ccuacuuuu                                              19

<210> SEQ ID NO 45
<211> LENGTH: 19
<212> TYPE: RNA
<213> ORGANISM: Artificial sequence
<220> FEATURE:
<223> OTHER INFORMATION: Chemically synthesized

<400> SEQUENCE: 45
augcacguga acuuggaaa                                              19

<210> SEQ ID NO 46
<211> LENGTH: 19
<212> TYPE: RNA
<213> ORGANISM: Artificial sequence
<220> FEATURE:
<223> OTHER INFORMATION: Chemically synthesized

<400> SEQUENCE: 46
uuguccuuuu uccacuaac                                              19

<210> SEQ ID NO 47
<211> LENGTH: 19
<212> TYPE: RNA
<213> ORGANISM: Artificial sequence
<220> FEATURE:
```

```
<223> OTHER INFORMATION: Chemically synthesized

<400> SEQUENCE: 47
guugnccuuu uuccacuaa                                                19

<210> SEQ ID NO 48
<211> LENGTH: 19
<212> TYPE: RNA
<213> ORGANISM: Artificial sequence
<220> FEATURE:
<223> OTHER INFORMATION: Chemically synthesized

<400> SEQUENCE: 48 cguugnccu uuuccacu                                                  19

<210> SEQ ID NO 49
<211> LENGTH: 19
<212> TYPE: RNA
<213> ORGANISM: Artificial sequence
<220> FEATURE:
<223> OTHER INFORMATION: Chemically synthesized

<400> SEQUENCE: 49
cuggagaacu gucugucca                                                19

<210> SEQ ID NO 50
<211> LENGTH: 19
<212> TYPE: RNA
<213> ORGANISM: Artificial sequence
<220> FEATURE:
<223> OTHER INFORMATION: Chemically synthesized

<400> SEQUENCE: 50
gccaaucuuu auagaauug                                                19

<210> SEQ ID NO 51
<211> LENGTH: 19
<212> TYPE: RNA
<213> ORGANISM: Artificial sequence
<220> FEATURE:
<223> OTHER INFORMATION: Chemically synthesized

<400> SEQUENCE: 51
guucaaauua gccaguguu                                                19

<210> SEQ ID NO 52
<211> LENGTH: 19
<212> TYPE: RNA
<213> ORGANISM: Artificial sequence
<220> FEATURE:
<223> OTHER INFORMATION: Chemically synthesized

<400> SEQUENCE: 52
ugccagaauu ugguuaaaa                                                19

<210> SEQ ID NO 53
<211> LENGTH: 19
<212> TYPE: RNA
<213> ORGANISM: Artificial sequence
<220> FEATURE:
<223> OTHER INFORMATION: Chemically synthesized

<400> SEQUENCE: 53
cccagauuuu uuccaccuu                                                19
```

```
<210> SEQ ID NO 54
<211> LENGTH: 19
<212> TYPE: RNA
<213> ORGANISM: Artificial sequence
<220> FEATURE:
<223> OTHER INFORMATION: Chemically synthesized

<400> SEQUENCE: 54
cacccagauu uuuccacc                                                       19

<210> SEQ ID NO 55
<211> LENGTH: 19
<212> TYPE: RNA
<213> ORGANISM: Artificial sequence
<220> FEATURE:
<223> OTHER INFORMATION: Chemically synthesized

<400> SEQUENCE: 55
caauuuacga agucugcau                                                      19

<210> SEQ ID NO 56
<211> LENGTH: 19
<212> TYPE: RNA
<213> ORGANISM: Artificial sequence
<220> FEATURE:
<223> OTHER INFORMATION: Chemically synthesized

<400> SEQUENCE: 56
gggucaauuu acgaagucu                                                      19

<210> SEQ ID NO 57
<211> LENGTH: 19
<212> TYPE: RNA
<213> ORGANISM: Artificial sequence
<220> FEATURE:
<223> OTHER INFORMATION: Chemically synthesized

<400> SEQUENCE: 57 aacggucaa uuuacgaag                                                       19

<210> SEQ ID NO 58
<211> LENGTH: 19
<212> TYPE: RNA
<213> ORGANISM: Artificial sequence
<220> FEATURE:
<223> OTHER INFORMATION: Chemically synthesized

<400> SEQUENCE: 58
ugaaacgggu caauuuacg                                                      19

<210> SEQ ID NO 59
<211> LENGTH: 19
<212> TYPE: RNA
<213> ORGANISM: Artificial sequence
<220> FEATURE:
<223> OTHER INFORMATION: Chemically synthesized

<400> SEQUENCE: 59
uggugccauu ucaguaacc                                                      19

<210> SEQ ID NO 60
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 60
uggaacugcu ucacuguuu                                                    19

<210> SEQ ID NO 61
<211> LENGTH: 19
<212> TYPE: RNA
<213> ORGANISM: Artificial sequence
<220> FEATURE:
<223> OTHER INFORMATION: Chemically synthesized

<400> SEQUENCE: 61
aagguaggau uaaguaggu                                                    19

<210> SEQ ID NO 62
<211> LENGTH: 19
<212> TYPE: RNA
<213> ORGANISM: Artificial sequence
<220> FEATURE:
<223> OTHER INFORMATION: Chemically synthesized

<400> SEQUENCE: 62
caggaaggua ggauuaagu                                                    19

<210> SEQ ID NO 63
<211> LENGTH: 19
<212> TYPE: RNA
<213> ORGANISM: Artificial sequence
<220> FEATURE:
<223> OTHER INFORMATION: Chemically synthesized

<400> SEQUENCE: 63
agccuaucaa aacuuccaa                                                    19

<210> SEQ ID NO 64
<211> LENGTH: 19
<212> TYPE: RNA
<213> ORGANISM: Artificial sequence
<220> FEATURE:
<223> OTHER INFORMATION: Chemically synthesized

<400> SEQUENCE: 64
aaccagauuu gccuauuuu                                                    19

<210> SEQ ID NO 65
<211> LENGTH: 19
<212> TYPE: RNA
<213> ORGANISM: Artificial sequence
<220> FEATURE:
<223> OTHER INFORMATION: Chemically synthesized

<400> SEQUENCE: 65
guacagaauu gaaugggau                                                    19

<210> SEQ ID NO 66
<211> LENGTH: 19
<212> TYPE: RNA
<213> ORGANISM: Artificial sequence
<220> FEATURE:
<223> OTHER INFORMATION: Chemically synthesized

<400> SEQUENCE: 66
aucccauuuu uguacagaa                                                    19

<210> SEQ ID NO 67
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 67
cagcuaaagu cauuuguag                                                    19

<210> SEQ ID NO 68
<211> LENGTH: 19
<212> TYPE: RNA
<213> ORGANISM: Artificial sequence
<220> FEATURE:
<223> OTHER INFORMATION: Chemically synthesized

<400> SEQUENCE: 68
augauugggu aguaaaacu                                                    19

<210> SEQ ID NO 69
<211> LENGTH: 19
<212> TYPE: RNA
<213> ORGANISM: Artificial sequence
<220> FEATURE:
<223> OTHER INFORMATION: Chemically synthesized

<400> SEQUENCE: 69
aggguccuaa aaagggaaa                                                    19

<210> SEQ ID NO 70
<211> LENGTH: 19
<212> TYPE: RNA
<213> ORGANISM: Artificial sequence
<220> FEATURE:
<223> OTHER INFORMATION: Chemically synthesized

<400> SEQUENCE: 70
acgugaacuu ggaaauuga                                                    19

<210> SEQ ID NO 71
<211> LENGTH: 19
<212> TYPE: RNA
<213> ORGANISM: Artificial sequence
<220> FEATURE:
<223> OTHER INFORMATION: Chemically synthesized

<400> SEQUENCE: 71
gaauugcuca agauguccu                                                    19

<210> SEQ ID NO 72
<211> LENGTH: 19
<212> TYPE: RNA
<213> ORGANISM: Artificial sequence
<220> FEATURE:
<223> OTHER INFORMATION: Chemically synthesized

<400> SEQUENCE: 72
gagaauugcu caagauguc                                                    19

<210> SEQ ID NO 73
<211> LENGTH: 19
<212> TYPE: RNA
<213> ORGANISM: Artificial sequence
<220> FEATURE:
<223> OTHER INFORMATION: Chemically synthesized

<400> SEQUENCE: 73
```
agagaauugc ucaagaugu            19

<210> SEQ ID NO 74
<211> LENGTH: 19
<212> TYPE: RNA
<213> ORGANISM: Artificial sequence
<220> FEATURE:
<223> OTHER INFORMATION: Chemically synthesized

<400> SEQUENCE: 74
ccagagaauu gcucaagau            19

<210> SEQ ID NO 75
<211> LENGTH: 19
<212> TYPE: RNA
<213> ORGANISM: Artificial sequence
<220> FEATURE:
<223> OTHER INFORMATION: Chemically synthesized

<400> SEQUENCE: 75
cccagagaau ugcucaaga            19

<210> SEQ ID NO 76
<211> LENGTH: 19
<212> TYPE: RNA
<213> ORGANISM: Artificial sequence
<220> FEATURE:
<223> OTHER INFORMATION: Chemically synthesized

<400> SEQUENCE: 76
aacugucugu ccaaaucaa            19

<210> SEQ ID NO 77
<211> LENGTH: 19
<212> TYPE: RNA
<213> ORGANISM: Artificial sequence
<220> FEATURE:
<223> OTHER INFORMATION: Chemically synthesized

<400> SEQUENCE: 77
uguccuuuuu ccacuaaca            19

<210> SEQ ID NO 78
<211> LENGTH: 19
<212> TYPE: RNA
<213> ORGANISM: Artificial sequence
<220> FEATURE:
<223> OTHER INFORMATION: Chemically synthesized

<400> SEQUENCE: 78
gaacuguugu ccuuuuucc            19

<210> SEQ ID NO 79
<211> LENGTH: 19
<212> TYPE: RNA
<213> ORGANISM: Artificial sequence
<220> FEATURE:
<223> OTHER INFORMATION: Chemically synthesized

<400> SEQUENCE: 79
ggagaacugu cuguccaaa            19

<210> SEQ ID NO 80
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 80
caguguucua acaaacuaa                                                      19

<210> SEQ ID NO 81
<211> LENGTH: 19
<212> TYPE: RNA
<213> ORGANISM: Artificial sequence
<220> FEATURE:
<223> OTHER INFORMATION: Chemically synthesized

<400> SEQUENCE: 81
aaauuagcca guguucuaa                                                      19

<210> SEQ ID NO 82
<211> LENGTH: 19
<212> TYPE: RNA
<213> ORGANISM: Artificial sequence
<220> FEATURE:
<223> OTHER INFORMATION: Chemically synthesized

<400> SEQUENCE: 82
gaccuaaaau gucacuguu                                                      19

<210> SEQ ID NO 83
<211> LENGTH: 19
<212> TYPE: RNA
<213> ORGANISM: Artificial sequence
<220> FEATURE:
<223> OTHER INFORMATION: Chemically synthesized

<400> SEQUENCE: 83
uugccagaau uugguuaaa                                                      19

<210> SEQ ID NO 84
<211> LENGTH: 19
<212> TYPE: RNA
<213> ORGANISM: Artificial sequence
<220> FEATURE:
<223> OTHER INFORMATION: Chemically synthesized

<400> SEQUENCE: 84
uggauaagga gcuuauuca                                                      19

<210> SEQ ID NO 85
<211> LENGTH: 19
<212> TYPE: RNA
<213> ORGANISM: Artificial sequence
<220> FEATURE:
<223> OTHER INFORMATION: Chemically synthesized

<400> SEQUENCE: 85
agcaaggcuu ucauauccu                                                      19

<210> SEQ ID NO 86
<211> LENGTH: 19
<212> TYPE: RNA
<213> ORGANISM: Artificial sequence
<220> FEATURE:
<223> OTHER INFORMATION: Chemically synthesized

<400> SEQUENCE: 86
cuccacucaa caauguuca                                                      19
```

<210> SEQ ID NO 87
<211> LENGTH: 19
<212> TYPE: RNA
<213> ORGANISM: Artificial sequence
<220> FEATURE:
<223> OTHER INFORMATION: Chemically synthesized

<400> SEQUENCE: 87
uuagccucca cucaacaau                                                19

<210> SEQ ID NO 88
<211> LENGTH: 19
<212> TYPE: RNA
<213> ORGANISM: Artificial sequence
<220> FEATURE:
<223> OTHER INFORMATION: Chemically synthesized

<400> SEQUENCE: 88
agagaauuua gccuccacu                                                19

<210> SEQ ID NO 89
<211> LENGTH: 19
<212> TYPE: RNA
<213> ORGANISM: Artificial sequence
<220> FEATURE:
<223> OTHER INFORMATION: Chemically synthesized

<400> SEQUENCE: 89
agaucauuau cucuuuccu                                                19

<210> SEQ ID NO 90
<211> LENGTH: 19
<212> TYPE: RNA
<213> ORGANISM: Artificial sequence
<220> FEATURE:
<223> OTHER INFORMATION: Chemically synthesized

<400> SEQUENCE: 90
ggccuuauuu uuugucuua                                                19

<210> SEQ ID NO 91
<211> LENGTH: 19
<212> TYPE: RNA
<213> ORGANISM: Artificial sequence
<220> FEATURE:
<223> OTHER INFORMATION: Chemically synthesized

<400> SEQUENCE: 91
cagauuuuuu ccaccuugg                                                19

<210> SEQ ID NO 92
<211> LENGTH: 19
<212> TYPE: RNA
<213> ORGANISM: Artificial sequence
<220> FEATURE:
<223> OTHER INFORMATION: Chemically synthesized

<400> SEQUENCE: 92
ccagauuuuu uccaccuug                                                19

<210> SEQ ID NO 93
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 93
gccuagagaa ugaaacuca                                                    19

<210> SEQ ID NO 94
<211> LENGTH: 19
<212> TYPE: RNA
<213> ORGANISM: Artificial sequence
<220> FEATURE:
<223> OTHER INFORMATION: Chemically synthesized

<400> SEQUENCE: 94
uacgaagucu gcauuggcu                                                    19

<210> SEQ ID NO 95
<211> LENGTH: 19
<212> TYPE: RNA
<213> ORGANISM: Artificial sequence
<220> FEATURE:
<223> OTHER INFORMATION: Chemically synthesized

<400> SEQUENCE: 95
cgggucaauu uacgaaguc                                                    19

<210> SEQ ID NO 96
<211> LENGTH: 19
<212> TYPE: RNA
<213> ORGANISM: Artificial sequence
<220> FEATURE:
<223> OTHER INFORMATION: Chemically synthesized

<400> SEQUENCE: 96
gaaacggguc aauuuacga                                                    19

<210> SEQ ID NO 97
<211> LENGTH: 19
<212> TYPE: RNA
<213> ORGANISM: Artificial sequence
<220> FEATURE:
<223> OTHER INFORMATION: Chemically synthesized

<400> SEQUENCE: 97
gucccucucu gauucacuu                                                    19

<210> SEQ ID NO 98
<211> LENGTH: 19
<212> TYPE: RNA
<213> ORGANISM: Artificial sequence
<220> FEATURE:
<223> OTHER INFORMATION: Chemically synthesized

<400> SEQUENCE: 98 gagagggac uccuaagaa                                                     19

<210> SEQ ID NO 99
<211> LENGTH: 19
<212> TYPE: RNA
<213> ORGANISM: Artificial sequence
<220> FEATURE:
<223> OTHER INFORMATION: Chemically synthesized

<400> SEQUENCE: 99
gaagguagga uuaaguagg                                                    19

<210> SEQ ID NO 100
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 100
uagccuauca aaacuucca                                                    19

<210> SEQ ID NO 101
<211> LENGTH: 19
<212> TYPE: RNA
<213> ORGANISM: Artificial sequence
<220> FEATURE:
<223> OTHER INFORMATION: Chemically synthesized

<400> SEQUENCE: 101
ccauuuuugu acagaauug                                                    19

<210> SEQ ID NO 102
<211> LENGTH: 19
<212> TYPE: RNA
<213> ORGANISM: Artificial sequence
<220> FEATURE:
<223> OTHER INFORMATION: Chemically synthesized

<400> SEQUENCE: 102
uagaucccau uuuuguaca                                                    19

<210> SEQ ID NO 103
<211> LENGTH: 19
<212> TYPE: RNA
<213> ORGANISM: Artificial sequence
<220> FEATURE:
<223> OTHER INFORMATION: Chemically synthesized

<400> SEQUENCE: 103
gcagcuaaca ggcugauuu                                                    19

<210> SEQ ID NO 104
<211> LENGTH: 19
<212> TYPE: RNA
<213> ORGANISM: Artificial sequence
<220> FEATURE:
<223> OTHER INFORMATION: Chemically synthesized

<400> SEQUENCE: 104
guguuucaca uucauagca                                                    19

<210> SEQ ID NO 105
<211> LENGTH: 19
<212> TYPE: RNA
<213> ORGANISM: Artificial sequence
<220> FEATURE:
<223> OTHER INFORMATION: Chemically synthesized

<400> SEQUENCE: 105
guccuaaaaa gggaaaaua                                                    19

<210> SEQ ID NO 106
<211> LENGTH: 19
<212> TYPE: RNA
<213> ORGANISM: Artificial sequence
<220> FEATURE:
<223> OTHER INFORMATION: Chemically synthesized

<400> SEQUENCE: 106
```

| gggguccuaaa aagggaaaa | 19 |

<210> SEQ ID NO 107
<211> LENGTH: 19
<212> TYPE: RNA
<213> ORGANISM: Artificial sequence
<220> FEATURE:
<223> OTHER INFORMATION: Chemically synthesized

<400> SEQUENCE: 107

| aaggguccua aaaagggaa | 19 |

<210> SEQ ID NO 108
<211> LENGTH: 19
<212> TYPE: RNA
<213> ORGANISM: Artificial sequence
<220> FEATURE:
<223> OTHER INFORMATION: Chemically synthesized

<400> SEQUENCE: 108

| cagggacuuu uucuuuagu | 19 |

<210> SEQ ID NO 109
<211> LENGTH: 19
<212> TYPE: RNA
<213> ORGANISM: Artificial sequence
<220> FEATURE:
<223> OTHER INFORMATION: Chemically synthesized

<400> SEQUENCE: 109

| ugcacgugaa cuuggaaau | 19 |

<210> SEQ ID NO 110
<211> LENGTH: 19
<212> TYPE: RNA
<213> ORGANISM: Artificial sequence
<220> FEATURE:
<223> OTHER INFORMATION: Chemically synthesized

<400> SEQUENCE: 110

| guguuaugca cgugaacuu | 19 |

<210> SEQ ID NO 111
<211> LENGTH: 19
<212> TYPE: RNA
<213> ORGANISM: Artificial sequence
<220> FEATURE:
<223> OTHER INFORMATION: Chemically synthesized

<400> SEQUENCE: 111

| guuguguuau gcacgugaa | 19 |

<210> SEQ ID NO 112
<211> LENGTH: 19
<212> TYPE: RNA
<213> ORGANISM: Artificial sequence
<220> FEATURE:
<223> OTHER INFORMATION: Chemically synthesized

<400> SEQUENCE: 112

| gagguugugu uaugcacgu | 19 |

<210> SEQ ID NO 113
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 113
gacccagaga auugcucaa                                                    19

<210> SEQ ID NO 114
<211> LENGTH: 19
<212> TYPE: RNA
<213> ORGANISM: Artificial sequence
<220> FEATURE:
<223> OTHER INFORMATION: Chemically synthesized

<400> SEQUENCE: 114
aagcaaacua aacugguu                                                     19

<210> SEQ ID NO 115
<211> LENGTH: 19
<212> TYPE: RNA
<213> ORGANISM: Artificial sequence
<220> FEATURE:
<223> OTHER INFORMATION: Chemically synthesized

<400> SEQUENCE: 115
ccaaaucaaa gcaaacuaa                                                    19

<210> SEQ ID NO 116
<211> LENGTH: 19
<212> TYPE: RNA
<213> ORGANISM: Artificial sequence
<220> FEATURE:
<223> OTHER INFORMATION: Chemically synthesized

<400> SEQUENCE: 116
ggaaggcugu uaaauuaau                                                    19

<210> SEQ ID NO 117
<211> LENGTH: 19
<212> TYPE: RNA
<213> ORGANISM: Artificial sequence
<220> FEATURE:
<223> OTHER INFORMATION: Chemically synthesized

<400> SEQUENCE: 117
ugccuguuau gcuuacaaa                                                    19

<210> SEQ ID NO 118
<211> LENGTH: 19
<212> TYPE: RNA
<213> ORGANISM: Artificial sequence
<220> FEATURE:
<223> OTHER INFORMATION: Chemically synthesized

<400> SEQUENCE: 118
uugccuguua ugcuuacaa                                                    19

<210> SEQ ID NO 119
<211> LENGTH: 19
<212> TYPE: RNA
<213> ORGANISM: Artificial sequence
<220> FEATURE:
<223> OTHER INFORMATION: Chemically synthesized

<400> SEQUENCE: 119
ugacucucuu gccuguuau                                                    19
```

<210> SEQ ID NO 120
<211> LENGTH: 19
<212> TYPE: RNA
<213> ORGANISM: Artificial sequence
<220> FEATURE:
<223> OTHER INFORMATION: Chemically synthesized

<400> SEQUENCE: 120 guccuuuuc cacuaacag                                                19

<210> SEQ ID NO 121
<211> LENGTH: 19
<212> TYPE: RNA
<213> ORGANISM: Artificial sequence
<220> FEATURE:
<223> OTHER INFORMATION: Chemically synthesized

<400> SEQUENCE: 121
uagaacuguu guccuuuuu                                               19

<210> SEQ ID NO 122
<211> LENGTH: 19
<212> TYPE: RNA
<213> ORGANISM: Artificial sequence
<220> FEATURE:
<223> OTHER INFORMATION: Chemically synthesized

<400> SEQUENCE: 122
guagaacugu uguccuuuu                                               19

<210> SEQ ID NO 123
<211> LENGTH: 19
<212> TYPE: RNA
<213> ORGANISM: Artificial sequence
<220> FEATURE:
<223> OTHER INFORMATION: Chemically synthesized

<400> SEQUENCE: 123
gagaacuguc uguccaaau                                               19

<210> SEQ ID NO 124
<211> LENGTH: 19
<212> TYPE: RNA
<213> ORGANISM: Artificial sequence
<220> FEATURE:
<223> OTHER INFORMATION: Chemically synthesized

<400> SEQUENCE: 124
gccaagauaa aucaauguu                                               19

<210> SEQ ID NO 125
<211> LENGTH: 19
<212> TYPE: RNA
<213> ORGANISM: Artificial sequence
<220> FEATURE:
<223> OTHER INFORMATION: Chemically synthesized

<400> SEQUENCE: 125
acaaagccaa ucuuuauag                                               19

<210> SEQ ID NO 126
<211> LENGTH: 19
<212> TYPE: RNA
<213> ORGANISM: Artificial sequence
<220> FEATURE:

<223> OTHER INFORMATION: Chemically synthesized

<400> SEQUENCE: 126
augucacugu ucaaauuag                                              19

<210> SEQ ID NO 127
<211> LENGTH: 19
<212> TYPE: RNA
<213> ORGANISM: Artificial sequence
<220> FEATURE:
<223> OTHER INFORMATION: Chemically synthesized

<400> SEQUENCE: 127
gugauccugu uacugauac                                              19

<210> SEQ ID NO 128
<211> LENGTH: 19
<212> TYPE: RNA
<213> ORGANISM: Artificial sequence
<220> FEATURE:
<223> OTHER INFORMATION: Chemically synthesized

<400> SEQUENCE: 128
gaauuugguu aaaaugcug                                              19

<210> SEQ ID NO 129
<211> LENGTH: 19
<212> TYPE: RNA
<213> ORGANISM: Artificial sequence
<220> FEATURE:
<223> OTHER INFORMATION: Chemically synthesized

<400> SEQUENCE: 129
aggcuuucau auccuugcu                                              19

<210> SEQ ID NO 130
<211> LENGTH: 19
<212> TYPE: RNA
<213> ORGANISM: Artificial sequence
<220> FEATURE:
<223> OTHER INFORMATION: Chemically synthesized

<400> SEQUENCE: 130
cagcaaggcu uucauaucc                                              19

<210> SEQ ID NO 131
<211> LENGTH: 19
<212> TYPE: RNA
<213> ORGANISM: Artificial sequence
<220> FEATURE:
<223> OTHER INFORMATION: Chemically synthesized

<400> SEQUENCE: 131
gccuccacuc aacaauguu                                              19

<210> SEQ ID NO 132
<211> LENGTH: 19
<212> TYPE: RNA
<213> ORGANISM: Artificial sequence
<220> FEATURE:
<223> OTHER INFORMATION: Chemically synthesized

<400> SEQUENCE: 132
gaauuuagcc uccacucaa                                              19

```
<210> SEQ ID NO 133
<211> LENGTH: 19
<212> TYPE: RNA
<213> ORGANISM: Artificial sequence
<220> FEATURE:
<223> OTHER INFORMATION: Chemically synthesized

<400> SEQUENCE: 133
gagagaauuu agccuccac                                                    19

<210> SEQ ID NO 134
<211> LENGTH: 19
<212> TYPE: RNA
<213> ORGANISM: Artificial sequence
<220> FEATURE:
<223> OTHER INFORMATION: Chemically synthesized

<400> SEQUENCE: 134
uagaucauua ucucuuucc                                                    19

<210> SEQ ID NO 135
<211> LENGTH: 19
<212> TYPE: RNA
<213> ORGANISM: Artificial sequence
<220> FEATURE:
<223> OTHER INFORMATION: Chemically synthesized

<400> SEQUENCE: 135
aggccuuauu uuuugucuu                                                    19

<210> SEQ ID NO 136
<211> LENGTH: 19
<212> TYPE: RNA
<213> ORGANISM: Artificial sequence
<220> FEATURE:
<223> OTHER INFORMATION: Chemically synthesized

<400> SEQUENCE: 136
aaggccuuau uuuugucu                                                     19

<210> SEQ ID NO 137
<211> LENGTH: 19
<212> TYPE: RNA
<213> ORGANISM: Artificial sequence
<220> FEATURE:
<223> OTHER INFORMATION: Chemically synthesized

<400> SEQUENCE: 137
gcaugcaccc agauuuuuu                                                    19

<210> SEQ ID NO 138
<211> LENGTH: 19
<212> TYPE: RNA
<213> ORGANISM: Artificial sequence
<220> FEATURE:
<223> OTHER INFORMATION: Chemically synthesized

<400> SEQUENCE: 138
ggucaauuua cgaagucug                                                    19

<210> SEQ ID NO 139
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 139
gggcuuuucu gggaauuga                                              19

<210> SEQ ID NO 140
<211> LENGTH: 19
<212> TYPE: RNA
<213> ORGANISM: Artificial sequence
<220> FEATURE:
<223> OTHER INFORMATION: Chemically synthesized

<400> SEQUENCE: 140
auaccuguga ggauaggaa                                              19

<210> SEQ ID NO 141
<211> LENGTH: 19
<212> TYPE: RNA
<213> ORGANISM: Artificial sequence
<220> FEATURE:
<223> OTHER INFORMATION: Chemically synthesized

<400> SEQUENCE: 141
acucuuccau ugagugaau                                              19

<210> SEQ ID NO 142
<211> LENGTH: 19
<212> TYPE: RNA
<213> ORGANISM: Artificial sequence
<220> FEATURE:
<223> OTHER INFORMATION: Chemically synthesized

<400> SEQUENCE: 142
gggauuaugu uguuccuga                                              19

<210> SEQ ID NO 143
<211> LENGTH: 19
<212> TYPE: RNA
<213> ORGANISM: Artificial sequence
<220> FEATURE:
<223> OTHER INFORMATION: Chemically synthesized

<400> SEQUENCE: 143
ugccauuuca guaaccacg                                              19

<210> SEQ ID NO 144
<211> LENGTH: 19
<212> TYPE: RNA
<213> ORGANISM: Artificial sequence
<220> FEATURE:
<223> OTHER INFORMATION: Chemically synthesized

<400> SEQUENCE: 144 ugggugcca uuucaguaa                                               19

<210> SEQ ID NO 145
<211> LENGTH: 19
<212> TYPE: RNA
<213> ORGANISM: Artificial sequence
<220> FEATURE:
<223> OTHER INFORMATION: Chemically synthesized

<400> SEQUENCE: 145
agcuuguggu gccauuuca                                              19

<210> SEQ ID NO 146
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 146
cucuaauguu uuaaagagg                                              19

<210> SEQ ID NO 147
<211> LENGTH: 19
<212> TYPE: RNA
<213> ORGANISM: Artificial sequence
<220> FEATURE:
<223> OTHER INFORMATION: Chemically synthesized

<400> SEQUENCE: 147
gaacugcuuc acuguuucu                                              19

<210> SEQ ID NO 148
<211> LENGTH: 19
<212> TYPE: RNA
<213> ORGANISM: Artificial sequence
<220> FEATURE:
<223> OTHER INFORMATION: Chemically synthesized

<400> SEQUENCE: 148
ggaacugcuu cacuguuuc                                              19

<210> SEQ ID NO 149
<211> LENGTH: 19
<212> TYPE: RNA
<213> ORGANISM: Artificial sequence
<220> FEATURE:
<223> OTHER INFORMATION: Chemically synthesized

<400> SEQUENCE: 149
acggcaauaa uggaacugc                                              19

<210> SEQ ID NO 150
<211> LENGTH: 19
<212> TYPE: RNA
<213> ORGANISM: Artificial sequence
<220> FEATURE:
<223> OTHER INFORMATION: Chemically synthesized

<400> SEQUENCE: 150
acccuaggua agaguaaau                                              19

<210> SEQ ID NO 151
<211> LENGTH: 19
<212> TYPE: RNA
<213> ORGANISM: Artificial sequence
<220> FEATURE:
<223> OTHER INFORMATION: Chemically synthesized

<400> SEQUENCE: 151
cucuaaguuu ucagaggau                                              19

<210> SEQ ID NO 152
<211> LENGTH: 19
<212> TYPE: RNA
<213> ORGANISM: Artificial sequence
<220> FEATURE:
<223> OTHER INFORMATION: Chemically synthesized

<400> SEQUENCE: 152
```

```
gcuugguaau agacuauau                                              19

<210> SEQ ID NO 153
<211> LENGTH: 19
<212> TYPE: RNA
<213> ORGANISM: Artificial sequence
<220> FEATURE:
<223> OTHER INFORMATION: Chemically synthesized

<400> SEQUENCE: 153
aggcuuggua auagacuau                                              19

<210> SEQ ID NO 154
<211> LENGTH: 19
<212> TYPE: RNA
<213> ORGANISM: Artificial sequence
<220> FEATURE:
<223> OTHER INFORMATION: Chemically synthesized

<400> SEQUENCE: 154
gaguuuuaca uuugauucc                                              19

<210> SEQ ID NO 155
<211> LENGTH: 19
<212> TYPE: RNA
<213> ORGANISM: Artificial sequence
<220> FEATURE:
<223> OTHER INFORMATION: Chemically synthesized

<400> SEQUENCE: 155
gaagcccauu ugaguuuua                                              19

<210> SEQ ID NO 156
<211> LENGTH: 19
<212> TYPE: RNA
<213> ORGANISM: Artificial sequence
<220> FEATURE:
<223> OTHER INFORMATION: Chemically synthesized

<400> SEQUENCE: 156
gagccugcua agugauuuu                                              19

<210> SEQ ID NO 157
<211> LENGTH: 19
<212> TYPE: RNA
<213> ORGANISM: Artificial sequence
<220> FEATURE:
<223> OTHER INFORMATION: Chemically synthesized

<400> SEQUENCE: 157
uguacagaau ugaauggga                                              19

<210> SEQ ID NO 158
<211> LENGTH: 19
<212> TYPE: RNA
<213> ORGANISM: Artificial sequence
<220> FEATURE:
<223> OTHER INFORMATION: Chemically synthesized

<400> SEQUENCE: 158
uuguacagaa uugaauggg                                              19

<210> SEQ ID NO 159
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 159
gugauucaaa auaguguag                                                    19

<210> SEQ ID NO 160
<211> LENGTH: 19
<212> TYPE: RNA
<213> ORGANISM: Artificial sequence
<220> FEATURE:
<223> OTHER INFORMATION: Chemically synthesized

<400> SEQUENCE: 160
uuggagaagu gauucaaaa                                                    19

<210> SEQ ID NO 161
<211> LENGTH: 19
<212> TYPE: RNA
<213> ORGANISM: Artificial sequence
<220> FEATURE:
<223> OTHER INFORMATION: Chemically synthesized

<400> SEQUENCE: 161
caggcugauu uucuggccu                                                    19

<210> SEQ ID NO 162
<211> LENGTH: 19
<212> TYPE: RNA
<213> ORGANISM: Artificial sequence
<220> FEATURE:
<223> OTHER INFORMATION: Chemically synthesized

<400> SEQUENCE: 162
gcuaacaggc ugauuuucu                                                    19

<210> SEQ ID NO 163
<211> LENGTH: 19
<212> TYPE: RNA
<213> ORGANISM: Artificial sequence
<220> FEATURE:
<223> OTHER INFORMATION: Chemically synthesized

<400> SEQUENCE: 163
gcuaaaguca uuuguaguu                                                    19

<210> SEQ ID NO 164
<211> LENGTH: 19
<212> TYPE: RNA
<213> ORGANISM: Artificial sequence
<220> FEATURE:
<223> OTHER INFORMATION: Chemically synthesized

<400> SEQUENCE: 164
uagucagcua aagucauuu                                                    19

<210> SEQ ID NO 165
<211> LENGTH: 19
<212> TYPE: RNA
<213> ORGANISM: Artificial sequence
<220> FEATURE:
<223> OTHER INFORMATION: Chemically synthesized

<400> SEQUENCE: 165
cuagucagcu aaagucauu                                                    19
```

<210> SEQ ID NO 166
<211> LENGTH: 19
<212> TYPE: RNA
<213> ORGANISM: Artificial sequence
<220> FEATURE:
<223> OTHER INFORMATION: Chemically synthesized

<400> SEQUENCE: 166
ugauugggua guaaaacua                                                    19

<210> SEQ ID NO 167
<211> LENGTH: 19
<212> TYPE: RNA
<213> ORGANISM: Artificial sequence
<220> FEATURE:
<223> OTHER INFORMATION: Chemically synthesized

<400> SEQUENCE: 167
gcauuucaga auugcugga                                                    19

<210> SEQ ID NO 168
<211> LENGTH: 19
<212> TYPE: RNA
<213> ORGANISM: Artificial sequence
<220> FEATURE:
<223> OTHER INFORMATION: Chemically synthesized

<400> SEQUENCE: 168
gaaggguccu aaaaaggga                                                    19

<210> SEQ ID NO 169
<211> LENGTH: 19
<212> TYPE: RNA
<213> ORGANISM: Artificial sequence
<220> FEATURE:
<223> OTHER INFORMATION: Chemically synthesized

<400> SEQUENCE: 169
gguuucagga gaacucuga                                                    19

<210> SEQ ID NO 170
<211> LENGTH: 19
<212> TYPE: RNA
<213> ORGANISM: Artificial sequence
<220> FEATURE:
<223> OTHER INFORMATION: Chemically synthesized

<400> SEQUENCE: 170
uccucugguu ucaggagaa                                                    19

<210> SEQ ID NO 171
<211> LENGTH: 19
<212> TYPE: RNA
<213> ORGANISM: Artificial sequence
<220> FEATURE:
<223> OTHER INFORMATION: Chemically synthesized

<400> SEQUENCE: 171
agggacuuuu ucuuuagua                                                    19

<210> SEQ ID NO 172
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 172
cuacuuuuga gcuuacacu                                                   19

<210> SEQ ID NO 173
<211> LENGTH: 19
<212> TYPE: RNA
<213> ORGANISM: Artificial sequence
<220> FEATURE:
<223> OTHER INFORMATION: Chemically synthesized

<400> SEQUENCE: 173
cuagcgucgu accuacuuu                                                   19

<210> SEQ ID NO 174
<211> LENGTH: 19
<212> TYPE: RNA
<213> ORGANISM: Artificial sequence
<220> FEATURE:
<223> OTHER INFORMATION: Chemically synthesized

<400> SEQUENCE: 174
guaaaaagcu ggauaggau                                                   19

<210> SEQ ID NO 175
<211> LENGTH: 19
<212> TYPE: RNA
<213> ORGANISM: Artificial sequence
<220> FEATURE:
<223> OTHER INFORMATION: Chemically synthesized

<400> SEQUENCE: 175
uuaugcacgu gaacuugga                                                   19

<210> SEQ ID NO 176
<211> LENGTH: 19
<212> TYPE: RNA
<213> ORGANISM: Artificial sequence
<220> FEATURE:
<223> OTHER INFORMATION: Chemically synthesized

<400> SEQUENCE: 176
gguuguguua ugcacguga                                                   19

<210> SEQ ID NO 177
<211> LENGTH: 19
<212> TYPE: RNA
<213> ORGANISM: Artificial sequence
<220> FEATURE:
<223> OTHER INFORMATION: Chemically synthesized

<400> SEQUENCE: 177
gcgagguugu guuaugcac                                                   19

<210> SEQ ID NO 178
<211> LENGTH: 19
<212> TYPE: RNA
<213> ORGANISM: Artificial sequence
<220> FEATURE:
<223> OTHER INFORMATION: Chemically synthesized

<400> SEQUENCE: 178
aaagcaaacu aaacuuggu                                                   19

<210> SEQ ID NO 179
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 179
cuguuaugcu uacaaaaug                                              19

<210> SEQ ID NO 180
<211> LENGTH: 19
<212> TYPE: RNA
<213> ORGANISM: Artificial sequence
<220> FEATURE:
<223> OTHER INFORMATION: Chemically synthesized

<400> SEQUENCE: 180
uccuuuuucc acuaacagu                                              19

<210> SEQ ID NO 181
<211> LENGTH: 19
<212> TYPE: RNA
<213> ORGANISM: Artificial sequence
<220> FEATURE:
<223> OTHER INFORMATION: Chemically synthesized

<400> SEQUENCE: 181
caaucuuuau agaauuggg                                              19

<210> SEQ ID NO 182
<211> LENGTH: 19
<212> TYPE: RNA
<213> ORGANISM: Artificial sequence
<220> FEATURE:
<223> OTHER INFORMATION: Chemically synthesized

<400> SEQUENCE: 182
ccaaucuuua uagaauugg                                              19

<210> SEQ ID NO 183
<211> LENGTH: 19
<212> TYPE: RNA
<213> ORGANISM: Artificial sequence
<220> FEATURE:
<223> OTHER INFORMATION: Chemically synthesized

<400> SEQUENCE: 183
auacuacaaa gccaaucuu                                              19

<210> SEQ ID NO 184
<211> LENGTH: 19
<212> TYPE: RNA
<213> ORGANISM: Artificial sequence
<220> FEATURE:
<223> OTHER INFORMATION: Chemically synthesized

<400> SEQUENCE: 184
ccaguguucu aacaaacua                                              19

<210> SEQ ID NO 185
<211> LENGTH: 19
<212> TYPE: RNA
<213> ORGANISM: Artificial sequence
<220> FEATURE:
<223> OTHER INFORMATION: Chemically synthesized

<400> SEQUENCE: 185
```

```
acuguucaaa uuagccagu                                                    19

<210> SEQ ID NO 186
<211> LENGTH: 19
<212> TYPE: RNA
<213> ORGANISM: Artificial sequence
<220> FEATURE:
<223> OTHER INFORMATION: Chemically synthesized

<400> SEQUENCE: 186
ccuaaaaugu cacuguuca                                                    19

<210> SEQ ID NO 187
<211> LENGTH: 19
<212> TYPE: RNA
<213> ORGANISM: Artificial sequence
<220> FEATURE:
<223> OTHER INFORMATION: Chemically synthesized

<400> SEQUENCE: 187
ugaccuaaaa ugucacugu                                                    19

<210> SEQ ID NO 188
<211> LENGTH: 19
<212> TYPE: RNA
<213> ORGANISM: Artificial sequence
<220> FEATURE:
<223> OTHER INFORMATION: Chemically synthesized

<400> SEQUENCE: 188
uaagugaccu aaaauguca                                                    19

<210> SEQ ID NO 189
<211> LENGTH: 19
<212> TYPE: RNA
<213> ORGANISM: Artificial sequence
<220> FEATURE:
<223> OTHER INFORMATION: Chemically synthesized

<400> SEQUENCE: 189
cuauaaguga ccuaaaaug                                                    19

<210> SEQ ID NO 190
<211> LENGTH: 19
<212> TYPE: RNA
<213> ORGANISM: Artificial sequence
<220> FEATURE:
<223> OTHER INFORMATION: Chemically synthesized

<400> SEQUENCE: 190
gugugauccu guuacugau                                                    19

<210> SEQ ID NO 191
<211> LENGTH: 19
<212> TYPE: RNA
<213> ORGANISM: Artificial sequence
<220> FEATURE:
<223> OTHER INFORMATION: Chemically synthesized

<400> SEQUENCE: 191
ccacuucaca ugcuggaga                                                    19

<210> SEQ ID NO 192
<211> LENGTH: 19
<212> TYPE: RNA
```

<213> ORGANISM: Artificial sequence
<220> FEATURE:
<223> OTHER INFORMATION: Chemically synthesized

<400> SEQUENCE: 192
ggcuuucaua uccuugcug         19

<210> SEQ ID NO 193
<211> LENGTH: 19
<212> TYPE: RNA
<213> ORGANISM: Artificial sequence
<220> FEATURE:
<223> OTHER INFORMATION: Chemically synthesized

<400> SEQUENCE: 193
gcaaggcuuu cauauccuu         19

<210> SEQ ID NO 194
<211> LENGTH: 19
<212> TYPE: RNA
<213> ORGANISM: Artificial sequence
<220> FEATURE:
<223> OTHER INFORMATION: Chemically synthesized

<400> SEQUENCE: 194
cacucaacaa uguucaauu         19

<210> SEQ ID NO 195
<211> LENGTH: 19
<212> TYPE: RNA
<213> ORGANISM: Artificial sequence
<220> FEATURE:
<223> OTHER INFORMATION: Chemically synthesized

<400> SEQUENCE: 195
uagccuccac ucaacaaug         19

<210> SEQ ID NO 196
<211> LENGTH: 19
<212> TYPE: RNA
<213> ORGANISM: Artificial sequence
<220> FEATURE:
<223> OTHER INFORMATION: Chemically synthesized

<400> SEQUENCE: 196
guagaucauu aucucuuuc         19

<210> SEQ ID NO 197
<211> LENGTH: 19
<212> TYPE: RNA
<213> ORGANISM: Artificial sequence
<220> FEATURE:
<223> OTHER INFORMATION: Chemically synthesized

<400> SEQUENCE: 197
ccaccuugga uaccuguca         19

<210> SEQ ID NO 198
<211> LENGTH: 19
<212> TYPE: RNA
<213> ORGANISM: Artificial sequence
<220> FEATURE:
<223> OTHER INFORMATION: Chemically synthesized

<400> SEQUENCE: 198
augcaugcac ccagauuuu         19

```
<210> SEQ ID NO 199
<211> LENGTH: 19
<212> TYPE: RNA
<213> ORGANISM: Artificial sequence
<220> FEATURE:
<223> OTHER INFORMATION: Chemically synthesized

<400> SEQUENCE: 199
uugaaacggg ucaauuuac                                              19

<210> SEQ ID NO 200
<211> LENGTH: 19
<212> TYPE: RNA
<213> ORGANISM: Artificial sequence
<220> FEATURE:
<223> OTHER INFORMATION: Chemically synthesized

<400> SEQUENCE: 200
ucaacgaggu aauauuuga                                              19

<210> SEQ ID NO 201
<211> LENGTH: 19
<212> TYPE: RNA
<213> ORGANISM: Artificial sequence
<220> FEATURE:
<223> OTHER INFORMATION: Chemically synthesized

<400> SEQUENCE: 201
accucaacga gguaauauu                                              19

<210> SEQ ID NO 202
<211> LENGTH: 19
<212> TYPE: RNA
<213> ORGANISM: Artificial sequence
<220> FEATURE:
<223> OTHER INFORMATION: Chemically synthesized

<400> SEQUENCE: 202
ccaaccucaa cgagguaau                                              19

<210> SEQ ID NO 203
<211> LENGTH: 19
<212> TYPE: RNA
<213> ORGANISM: Artificial sequence
<220> FEATURE:
<223> OTHER INFORMATION: Chemically synthesized

<400> SEQUENCE: 203
gugcuuaauc ucagaugaa                                              19

<210> SEQ ID NO 204
<211> LENGTH: 19
<212> TYPE: RNA
<213> ORGANISM: Artificial sequence
<220> FEATURE:
<223> OTHER INFORMATION: Chemically synthesized

<400> SEQUENCE: 204
cuagucccuc ucugauuca                                              19

<210> SEQ ID NO 205
<211> LENGTH: 19
<212> TYPE: RNA
<213> ORGANISM: Artificial sequence
<220> FEATURE:
```

<223> OTHER INFORMATION: Chemically synthesized

<400> SEQUENCE: 205
augaauaccu gugaggaua                                                    19

<210> SEQ ID NO 206
<211> LENGTH: 19
<212> TYPE: RNA
<213> ORGANISM: Artificial sequence
<220> FEATURE:
<223> OTHER INFORMATION: Chemically synthesized

<400> SEQUENCE: 206
agaggggacu ccuaagaag                                                    19

<210> SEQ ID NO 207
<211> LENGTH: 19
<212> TYPE: RNA
<213> ORGANISM: Artificial sequence
<220> FEATURE:
<223> OTHER INFORMATION: Chemically synthesized

<400> SEQUENCE: 207
gauuacucuu ccauugagu                                                    19

<210> SEQ ID NO 208
<211> LENGTH: 19
<212> TYPE: RNA
<213> ORGANISM: Artificial sequence
<220> FEATURE:
<223> OTHER INFORMATION: Chemically synthesized

<400> SEQUENCE: 208
ugauuacucu uccauugag                                                    19

<210> SEQ ID NO 209
<211> LENGTH: 19
<212> TYPE: RNA
<213> ORGANISM: Artificial sequence
<220> FEATURE:
<223> OTHER INFORMATION: Chemically synthesized

<400> SEQUENCE: 209
uaguugauua cucuuccau                                                    19

<210> SEQ ID NO 210
<211> LENGTH: 19
<212> TYPE: RNA
<213> ORGANISM: Artificial sequence
<220> FEATURE:
<223> OTHER INFORMATION: Chemically synthesized

<400> SEQUENCE: 210
guaguugauu acucuucca                                                    19

<210> SEQ ID NO 211
<211> LENGTH: 19
<212> TYPE: RNA
<213> ORGANISM: Artificial sequence
<220> FEATURE:
<223> OTHER INFORMATION: Chemically synthesized

<400> SEQUENCE: 211
guguugaaua cugucuuua                                                    19

```
<210> SEQ ID NO 212
<211> LENGTH: 19
<212> TYPE: RNA
<213> ORGANISM: Artificial sequence
<220> FEATURE:
<223> OTHER INFORMATION: Chemically synthesized

<400> SEQUENCE: 212
aagcucaguu uccccuguu                                                   19

<210> SEQ ID NO 213
<211> LENGTH: 19
<212> TYPE: RNA
<213> ORGANISM: Artificial sequence
<220> FEATURE:
<223> OTHER INFORMATION: Chemically synthesized

<400> SEQUENCE: 213
accacggugu uguuuaga                                                    19

<210> SEQ ID NO 214
<211> LENGTH: 19
<212> TYPE: RNA
<213> ORGANISM: Artificial sequence
<220> FEATURE:
<223> OTHER INFORMATION: Chemically synthesized

<400> SEQUENCE: 214
gugccauuuc aguaaccac                                                   19

<210> SEQ ID NO 215
<211> LENGTH: 19
<212> TYPE: RNA
<213> ORGANISM: Artificial sequence
<220> FEATURE:
<223> OTHER INFORMATION: Chemically synthesized

<400> SEQUENCE: 215
ggugccauuu caguaacca                                                   19

<210> SEQ ID NO 216
<211> LENGTH: 19
<212> TYPE: RNA
<213> ORGANISM: Artificial sequence
<220> FEATURE:
<223> OTHER INFORMATION: Chemically synthesized

<400> SEQUENCE: 216
cugcuucacu guucuugg                                                    19

<210> SEQ ID NO 217
<211> LENGTH: 19
<212> TYPE: RNA
<213> ORGANISM: Artificial sequence
<220> FEATURE:
<223> OTHER INFORMATION: Chemically synthesized

<400> SEQUENCE: 217
aacugcuuca cuguuucuu                                                   19

<210> SEQ ID NO 218
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 218
caauaaugga acugcuuca                                                 19

<210> SEQ ID NO 219
<211> LENGTH: 19
<212> TYPE: RNA
<213> ORGANISM: Artificial sequence
<220> FEATURE:
<223> OTHER INFORMATION: Chemically synthesized

<400> SEQUENCE: 219
agguaagagu aaaugagaa                                                 19

<210> SEQ ID NO 220
<211> LENGTH: 19
<212> TYPE: RNA
<213> ORGANISM: Artificial sequence
<220> FEATURE:
<223> OTHER INFORMATION: Chemically synthesized

<400> SEQUENCE: 220
ggauuaagua ggugaguuu                                                 19

<210> SEQ ID NO 221
<211> LENGTH: 19
<212> TYPE: RNA
<213> ORGANISM: Artificial sequence
<220> FEATURE:
<223> OTHER INFORMATION: Chemically synthesized

<400> SEQUENCE: 221
gacucaaauu ugaaggguu                                                 19

<210> SEQ ID NO 222
<211> LENGTH: 19
<212> TYPE: RNA
<213> ORGANISM: Artificial sequence
<220> FEATURE:
<223> OTHER INFORMATION: Chemically synthesized

<400> SEQUENCE: 222
cagauuugcc uauuuugau                                                 19

<210> SEQ ID NO 223
<211> LENGTH: 19
<212> TYPE: RNA
<213> ORGANISM: Artificial sequence
<220> FEATURE:
<223> OTHER INFORMATION: Chemically synthesized

<400> SEQUENCE: 223
ccagauuugc cuauuuuga                                                 19

<210> SEQ ID NO 224
<211> LENGTH: 19
<212> TYPE: RNA
<213> ORGANISM: Artificial sequence
<220> FEATURE:
<223> OTHER INFORMATION: Chemically synthesized

<400> SEQUENCE: 224
auauaaacca gauuugccu                                                 19

<210> SEQ ID NO 225
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 225
ggcuugguaa uagacuaua                                                    19

<210> SEQ ID NO 226
<211> LENGTH: 19
<212> TYPE: RNA
<213> ORGANISM: Artificial sequence
<220> FEATURE:
<223> OTHER INFORMATION: Chemically synthesized

<400> SEQUENCE: 226
uuccacaauu ugguuucag                                                    19

<210> SEQ ID NO 227
<211> LENGTH: 19
<212> TYPE: RNA
<213> ORGANISM: Artificial sequence
<220> FEATURE:
<223> OTHER INFORMATION: Chemically synthesized

<400> SEQUENCE: 227
uuugauucca caauuuggu                                                    19

<210> SEQ ID NO 228
<211> LENGTH: 19
<212> TYPE: RNA
<213> ORGANISM: Artificial sequence
<220> FEATURE:
<223> OTHER INFORMATION: Chemically synthesized

<400> SEQUENCE: 228
ggaauaggua agcaaaagu                                                    19

<210> SEQ ID NO 229
<211> LENGTH: 19
<212> TYPE: RNA
<213> ORGANISM: Artificial sequence
<220> FEATURE:
<223> OTHER INFORMATION: Chemically synthesized

<400> SEQUENCE: 229
cagaauugaa ugggaugga                                                    19

<210> SEQ ID NO 230
<211> LENGTH: 19
<212> TYPE: RNA
<213> ORGANISM: Artificial sequence
<220> FEATURE:
<223> OTHER INFORMATION: Chemically synthesized

<400> SEQUENCE: 230
gaucccauuu uuguacaga                                                    19

<210> SEQ ID NO 231
<211> LENGTH: 19
<212> TYPE: RNA
<213> ORGANISM: Artificial sequence
<220> FEATURE:
<223> OTHER INFORMATION: Chemically synthesized

<400> SEQUENCE: 231
```

```
agaucccauu uuuguacag                                                    19

<210> SEQ ID NO 232
<211> LENGTH: 19
<212> TYPE: RNA
<213> ORGANISM: Artificial sequence
<220> FEATURE:
<223> OTHER INFORMATION: Chemically synthesized

<400> SEQUENCE: 232
guguagauuu ucugcauag                                                    19

<210> SEQ ID NO 233
<211> LENGTH: 19
<212> TYPE: RNA
<213> ORGANISM: Artificial sequence
<220> FEATURE:
<223> OTHER INFORMATION: Chemically synthesized

<400> SEQUENCE: 233
aggcugauuu ucuggccuu                                                    19

<210> SEQ ID NO 234
<211> LENGTH: 19
<212> TYPE: RNA
<213> ORGANISM: Artificial sequence
<220> FEATURE:
<223> OTHER INFORMATION: Chemically synthesized

<400> SEQUENCE: 234
cacauucaua gcaacugca                                                    19

<210> SEQ ID NO 235
<211> LENGTH: 19
<212> TYPE: RNA
<213> ORGANISM: Artificial sequence
<220> FEATURE:
<223> OTHER INFORMATION: Chemically synthesized

<400> SEQUENCE: 235
ccccaccugc ccuaaauaa                                                    19

<210> SEQ ID NO 236
<211> LENGTH: 19
<212> TYPE: RNA
<213> ORGANISM: Artificial sequence
<220> FEATURE:
<223> OTHER INFORMATION: Chemically synthesized

<400> SEQUENCE: 236
agcuaaaguc auuuguagu                                                    19

<210> SEQ ID NO 237
<211> LENGTH: 19
<212> TYPE: RNA
<213> ORGANISM: Artificial sequence
<220> FEATURE:
<223> OTHER INFORMATION: Chemically synthesized

<400> SEQUENCE: 237
ucagcuaaag ucauuugua                                                    19

<210> SEQ ID NO 238
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 238
cagcuaguca gcuaaaguc                                                19

<210> SEQ ID NO 239
<211> LENGTH: 19
<212> TYPE: RNA
<213> ORGANISM: Artificial sequence
<220> FEATURE:
<223> OTHER INFORMATION: Chemically synthesized

<400> SEQUENCE: 239
uggguaguaa aacuauuca                                                19

<210> SEQ ID NO 240
<211> LENGTH: 19
<212> TYPE: RNA
<213> ORGANISM: Artificial sequence
<220> FEATURE:
<223> OTHER INFORMATION: Chemically synthesized

<400> SEQUENCE: 240
gauuauuuca ugauugggu                                                19

<210> SEQ ID NO 241
<211> LENGTH: 19
<212> TYPE: RNA
<213> ORGANISM: Artificial sequence
<220> FEATURE:
<223> OTHER INFORMATION: Chemically synthesized

<400> SEQUENCE: 241
gguccuaaaa agggaaaau                                                19

<210> SEQ ID NO 242
<211> LENGTH: 19
<212> TYPE: RNA
<213> ORGANISM: Artificial sequence
<220> FEATURE:
<223> OTHER INFORMATION: Chemically synthesized

<400> SEQUENCE: 242
cagcauuuca gaauugcug                                                19

<210> SEQ ID NO 243
<211> LENGTH: 19
<212> TYPE: RNA
<213> ORGANISM: Artificial sequence
<220> FEATURE:
<223> OTHER INFORMATION: Chemically synthesized

<400> SEQUENCE: 243
gccagcauuu cagaauugc                                                19

<210> SEQ ID NO 244
<211> LENGTH: 19
<212> TYPE: RNA
<213> ORGANISM: Artificial sequence
<220> FEATURE:
<223> OTHER INFORMATION: Chemically synthesized

<400> SEQUENCE: 244
agaacucuga uccucagcu                                                19
```

```
<210> SEQ ID NO 245
<211> LENGTH: 19
<212> TYPE: RNA
<213> ORGANISM: Artificial sequence
<220> FEATURE:
<223> OTHER INFORMATION: Chemically synthesized

<400> SEQUENCE: 245
uaagaagcca ccugccugu                                               19

<210> SEQ ID NO 246
<211> LENGTH: 19
<212> TYPE: RNA
<213> ORGANISM: Artificial sequence
<220> FEATURE:
<223> OTHER INFORMATION: Chemically synthesized

<400> SEQUENCE: 246
cuccucuggu uucaggaga                                               19

<210> SEQ ID NO 247
<211> LENGTH: 19
<212> TYPE: RNA
<213> ORGANISM: Artificial sequence
<220> FEATURE:
<223> OTHER INFORMATION: Chemically synthesized

<400> SEQUENCE: 247
gggacuuuuu cuuuaguag                                               19

<210> SEQ ID NO 248
<211> LENGTH: 19
<212> TYPE: RNA
<213> ORGANISM: Artificial sequence
<220> FEATURE:
<223> OTHER INFORMATION: Chemically synthesized

<400> SEQUENCE: 248
agcuuacacu uguguuuaa                                               19

<210> SEQ ID NO 249
<211> LENGTH: 19
<212> TYPE: RNA
<213> ORGANISM: Artificial sequence
<220> FEATURE:
<223> OTHER INFORMATION: Chemically synthesized

<400> SEQUENCE: 249
gucguaccua cuuuugagc                                               19

<210> SEQ ID NO 250
<211> LENGTH: 19
<212> TYPE: RNA
<213> ORGANISM: Artificial sequence
<220> FEATURE:
<223> OTHER INFORMATION: Chemically synthesized

<400> SEQUENCE: 250
agcgucguac cuacuuuug                                               19

<210> SEQ ID NO 251
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 251
aagcuggaua ggauugugu                                              19

<210> SEQ ID NO 252
<211> LENGTH: 19
<212> TYPE: RNA
<213> ORGANISM: Artificial sequence
<220> FEATURE:
<223> OTHER INFORMATION: Chemically synthesized

<400> SEQUENCE: 252
uugcgagguu guguuaugc                                              19

<210> SEQ ID NO 253
<211> LENGTH: 19
<212> TYPE: RNA
<213> ORGANISM: Artificial sequence
<220> FEATURE:
<223> OTHER INFORMATION: Chemically synthesized

<400> SEQUENCE: 253
uugcucaaga uguccugcg                                              19

<210> SEQ ID NO 254
<211> LENGTH: 19
<212> TYPE: RNA
<213> ORGANISM: Artificial sequence
<220> FEATURE:
<223> OTHER INFORMATION: Chemically synthesized

<400> SEQUENCE: 254
acccagagaa uugcucaag                                              19

<210> SEQ ID NO 255
<211> LENGTH: 19
<212> TYPE: RNA
<213> ORGANISM: Artificial sequence
<220> FEATURE:
<223> OTHER INFORMATION: Chemically synthesized

<400> SEQUENCE: 255
ucaaagcaaa cuaaacuug                                              19

<210> SEQ ID NO 256
<211> LENGTH: 19
<212> TYPE: RNA
<213> ORGANISM: Artificial sequence
<220> FEATURE:
<223> OTHER INFORMATION: Chemically synthesized

<400> SEQUENCE: 256
uccaaaucaa agcaaacua                                              19

<210> SEQ ID NO 257
<211> LENGTH: 19
<212> TYPE: RNA
<213> ORGANISM: Artificial sequence
<220> FEATURE:
<223> OTHER INFORMATION: Chemically synthesized

<400> SEQUENCE: 257
auggaaggcu guuaaauua                                              19

<210> SEQ ID NO 258
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 258 cguccaaau caaagcaaa                                              19

<210> SEQ ID NO 259
<211> LENGTH: 19
<212> TYPE: RNA
<213> ORGANISM: Artificial sequence
<220> FEATURE:
<223> OTHER INFORMATION: Chemically synthesized

<400> SEQUENCE: 259
gucuguccaa aucaaagca                                             19

<210> SEQ ID NO 260
<211> LENGTH: 19
<212> TYPE: RNA
<213> ORGANISM: Artificial sequence
<220> FEATURE:
<223> OTHER INFORMATION: Chemically synthesized

<400> SEQUENCE: 260
guuaugcuua caaaauggu                                             19

<210> SEQ ID NO 261
<211> LENGTH: 19
<212> TYPE: RNA
<213> ORGANISM: Artificial sequence
<220> FEATURE:
<223> OTHER INFORMATION: Chemically synthesized

<400> SEQUENCE: 261
uugacucucu ugccuguua                                             19

<210> SEQ ID NO 262
<211> LENGTH: 19
<212> TYPE: RNA
<213> ORGANISM: Artificial sequence
<220> FEATURE:
<223> OTHER INFORMATION: Chemically synthesized

<400> SEQUENCE: 262
ccuuuuucca cuaacaguu                                             19

<210> SEQ ID NO 263
<211> LENGTH: 19
<212> TYPE: RNA
<213> ORGANISM: Artificial sequence
<220> FEATURE:
<223> OTHER INFORMATION: Chemically synthesized

<400> SEQUENCE: 263
gaacugucug uccaaauca                                             19

<210> SEQ ID NO 264
<211> LENGTH: 19
<212> TYPE: RNA
<213> ORGANISM: Artificial sequence
<220> FEATURE:
<223> OTHER INFORMATION: Chemically synthesized

<400> SEQUENCE: 264
```
ugggcaucga uguagaacu 19

<210> SEQ ID NO 265
<211> LENGTH: 19
<212> TYPE: RNA
<213> ORGANISM: Artificial sequence
<220> FEATURE:
<223> OTHER INFORMATION: Chemically synthesized

<400> SEQUENCE: 265
aaagguucac uguguuucu 19

<210> SEQ ID NO 266
<211> LENGTH: 19
<212> TYPE: RNA
<213> ORGANISM: Artificial sequence
<220> FEATURE:
<223> OTHER INFORMATION: Chemically synthesized

<400> SEQUENCE: 266
uccaaagguu cacuguguu 19

<210> SEQ ID NO 267
<211> LENGTH: 19
<212> TYPE: RNA
<213> ORGANISM: Artificial sequence
<220> FEATURE:
<223> OTHER INFORMATION: Chemically synthesized

<400> SEQUENCE: 267
gcaugucuau uguuaagcu 19

<210> SEQ ID NO 268
<211> LENGTH: 19
<212> TYPE: RNA
<213> ORGANISM: Artificial sequence
<220> FEATURE:
<223> OTHER INFORMATION: Chemically synthesized

<400> SEQUENCE: 268
ucaauguugu uuugcaugu 19

<210> SEQ ID NO 269
<211> LENGTH: 19
<212> TYPE: RNA
<213> ORGANISM: Artificial sequence
<220> FEATURE:
<223> OTHER INFORMATION: Chemically synthesized

<400> SEQUENCE: 269
uugggccaag auaaaucaa 19

<210> SEQ ID NO 270
<211> LENGTH: 19
<212> TYPE: RNA
<213> ORGANISM: Artificial sequence
<220> FEATURE:
<223> OTHER INFORMATION: Chemically synthesized

<400> SEQUENCE: 270
auugggccaa gauaaauca 19

<210> SEQ ID NO 271
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 271
caaagccaau cuuuauaga                                                19

<210> SEQ ID NO 272
<211> LENGTH: 19
<212> TYPE: RNA
<213> ORGANISM: Artificial sequence
<220> FEATURE:
<223> OTHER INFORMATION: Chemically synthesized

<400> SEQUENCE: 272
cuacaaagcc aaucuuuau                                                19

<210> SEQ ID NO 273
<211> LENGTH: 19
<212> TYPE: RNA
<213> ORGANISM: Artificial sequence
<220> FEATURE:
<223> OTHER INFORMATION: Chemically synthesized

<400> SEQUENCE: 273
acuaaacucu ucaaaugcu                                                19

<210> SEQ ID NO 274
<211> LENGTH: 19
<212> TYPE: RNA
<213> ORGANISM: Artificial sequence
<220> FEATURE:
<223> OTHER INFORMATION: Chemically synthesized

<400> SEQUENCE: 274
guguucuaac aaacuaaac                                                19

<210> SEQ ID NO 275
<211> LENGTH: 19
<212> TYPE: RNA
<213> ORGANISM: Artificial sequence
<220> FEATURE:
<223> OTHER INFORMATION: Chemically synthesized

<400> SEQUENCE: 275
ucacuguuca aauuagcca                                                19

<210> SEQ ID NO 276
<211> LENGTH: 19
<212> TYPE: RNA
<213> ORGANISM: Artificial sequence
<220> FEATURE:
<223> OTHER INFORMATION: Chemically synthesized

<400> SEQUENCE: 276
cuguuacuga uacuauaag                                                19

<210> SEQ ID NO 277
<211> LENGTH: 19
<212> TYPE: RNA
<213> ORGANISM: Artificial sequence
<220> FEATURE:
<223> OTHER INFORMATION: Chemically synthesized

<400> SEQUENCE: 277
uccuguuacu gauacuaua                                                19
```

<210> SEQ ID NO 278
<211> LENGTH: 19
<212> TYPE: RNA
<213> ORGANISM: Artificial sequence
<220> FEATURE:
<223> OTHER INFORMATION: Chemically synthesized

<400> SEQUENCE: 278
auccuguuac ugauacuau                                                19

<210> SEQ ID NO 279
<211> LENGTH: 19
<212> TYPE: RNA
<213> ORGANISM: Artificial sequence
<220> FEATURE:
<223> OTHER INFORMATION: Chemically synthesized

<400> SEQUENCE: 279
caggugugau ccuguuacu                                                19

<210> SEQ ID NO 280
<211> LENGTH: 19
<212> TYPE: RNA
<213> ORGANISM: Artificial sequence
<220> FEATURE:
<223> OTHER INFORMATION: Chemically synthesized

<400> SEQUENCE: 280
uagggacaga uguauucau                                                19

<210> SEQ ID NO 281
<211> LENGTH: 19
<212> TYPE: RNA
<213> ORGANISM: Artificial sequence
<220> FEATURE:
<223> OTHER INFORMATION: Chemically synthesized

<400> SEQUENCE: 281
gcuauuagcu ccacuucac                                                19

<210> SEQ ID NO 282
<211> LENGTH: 19
<212> TYPE: RNA
<213> ORGANISM: Artificial sequence
<220> FEATURE:
<223> OTHER INFORMATION: Chemically synthesized

<400> SEQUENCE: 282
gcccuagcua uuagcucca                                                19

<210> SEQ ID NO 283
<211> LENGTH: 19
<212> TYPE: RNA
<213> ORGANISM: Artificial sequence
<220> FEATURE:
<223> OTHER INFORMATION: Chemically synthesized

<400> SEQUENCE: 283
ucguggauaa ggagcuuau                                                19

<210> SEQ ID NO 284
<211> LENGTH: 19
<212> TYPE: RNA
<213> ORGANISM: Artificial sequence
<220> FEATURE:

<223> OTHER INFORMATION: Chemically synthesized

<400> SEQUENCE: 284
aaggcuuuca uauccuugc                                                         19

<210> SEQ ID NO 285
<211> LENGTH: 19
<212> TYPE: RNA
<213> ORGANISM: Artificial sequence
<220> FEATURE:
<223> OTHER INFORMATION: Chemically synthesized

<400> SEQUENCE: 285
ccacucaaca auguucaau                                                         19

<210> SEQ ID NO 286
<211> LENGTH: 19
<212> TYPE: RNA
<213> ORGANISM: Artificial sequence
<220> FEATURE:
<223> OTHER INFORMATION: Chemically synthesized

<400> SEQUENCE: 286
ccuccacuca acaauguuc                                                         19

<210> SEQ ID NO 287
<211> LENGTH: 19
<212> TYPE: RNA
<213> ORGANISM: Artificial sequence
<220> FEATURE:
<223> OTHER INFORMATION: Chemically synthesized

<400> SEQUENCE: 287
ggauaccugu cacuaggga                                                         19

<210> SEQ ID NO 288
<211> LENGTH: 19
<212> TYPE: RNA
<213> ORGANISM: Artificial sequence
<220> FEATURE:
<223> OTHER INFORMATION: Chemically synthesized

<400> SEQUENCE: 288
accuuggaua ccugucacu                                                         19

<210> SEQ ID NO 289
<211> LENGTH: 19
<212> TYPE: RNA
<213> ORGANISM: Artificial sequence
<220> FEATURE:
<223> OTHER INFORMATION: Chemically synthesized

<400> SEQUENCE: 289
ucaccgucca gauaaccau                                                         19

<210> SEQ ID NO 290
<211> LENGTH: 19
<212> TYPE: RNA
<213> ORGANISM: Artificial sequence
<220> FEATURE:
<223> OTHER INFORMATION: Chemically synthesized

<400> SEQUENCE: 290
aacucaccgu ccagauaac                                                         19

```
<210> SEQ ID NO 291
<211> LENGTH: 19
<212> TYPE: RNA
<213> ORGANISM: Artificial sequence
<220> FEATURE:
<223> OTHER INFORMATION: Chemically synthesized

<400> SEQUENCE: 291
gagauauggu uuauaguac                                               19

<210> SEQ ID NO 292
<211> LENGTH: 19
<212> TYPE: RNA
<213> ORGANISM: Artificial sequence
<220> FEATURE:
<223> OTHER INFORMATION: Chemically synthesized

<400> SEQUENCE: 292
gcauuggcua uggagauau                                               19

<210> SEQ ID NO 293
<211> LENGTH: 19
<212> TYPE: RNA
<213> ORGANISM: Artificial sequence
<220> FEATURE:
<223> OTHER INFORMATION: Chemically synthesized

<400> SEQUENCE: 293
aacgagguaa uauuugagg                                               19

<210> SEQ ID NO 294
<211> LENGTH: 19
<212> TYPE: RNA
<213> ORGANISM: Artificial sequence
<220> FEATURE:
<223> OTHER INFORMATION: Chemically synthesized

<400> SEQUENCE: 294
caacgaggua auauuugag                                               19

<210> SEQ ID NO 295
<211> LENGTH: 19
<212> TYPE: RNA
<213> ORGANISM: Artificial sequence
<220> FEATURE:
<223> OTHER INFORMATION: Chemically synthesized

<400> SEQUENCE: 295
cuguauacua ccacuuga                                                19

<210> SEQ ID NO 296
<211> LENGTH: 19
<212> TYPE: RNA
<213> ORGANISM: Artificial sequence
<220> FEATURE:
<223> OTHER INFORMATION: Chemically synthesized

<400> SEQUENCE: 296
uagcuguaua cuaccacuu                                               19

<210> SEQ ID NO 297
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 297
guagcuguau acuaccacu                                            19

<210> SEQ ID NO 298
<211> LENGTH: 19
<212> TYPE: RNA
<213> ORGANISM: Artificial sequence
<220> FEATURE:
<223> OTHER INFORMATION: Chemically synthesized

<400> SEQUENCE: 298
uggcaguguu aucucaucu                                            19

<210> SEQ ID NO 299
<211> LENGTH: 19
<212> TYPE: RNA
<213> ORGANISM: Artificial sequence
<220> FEATURE:
<223> OTHER INFORMATION: Chemically synthesized

<400> SEQUENCE: 299
ucucagauga accauuuca                                            19

<210> SEQ ID NO 300
<211> LENGTH: 19
<212> TYPE: RNA
<213> ORGANISM: Artificial sequence
<220> FEATURE:
<223> OTHER INFORMATION: Chemically synthesized

<400> SEQUENCE: 300
uaaucucaga ugaaccauu                                            19

<210> SEQ ID NO 301
<211> LENGTH: 19
<212> TYPE: RNA
<213> ORGANISM: Artificial sequence
<220> FEATURE:
<223> OTHER INFORMATION: Chemically synthesized

<400> SEQUENCE: 301
cccucucuga uucacuuag                                            19

<210> SEQ ID NO 302
<211> LENGTH: 19
<212> TYPE: RNA
<213> ORGANISM: Artificial sequence
<220> FEATURE:
<223> OTHER INFORMATION: Chemically synthesized

<400> SEQUENCE: 302
agucccucuc ugauucacu                                            19

<210> SEQ ID NO 303
<211> LENGTH: 19
<212> TYPE: RNA
<213> ORGANISM: Artificial sequence
<220> FEATURE:
<223> OTHER INFORMATION: Chemically synthesized

<400> SEQUENCE: 303
uagucccucu cugauucac                                            19

<210> SEQ ID NO 304
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 304
uugauuacuc uuccauuga                                                  19

<210> SEQ ID NO 305
<211> LENGTH: 19
<212> TYPE: RNA
<213> ORGANISM: Artificial sequence
<220> FEATURE:
<223> OTHER INFORMATION: Chemically synthesized

<400> SEQUENCE: 305
guguaguuga uuacucuuc                                                  19

<210> SEQ ID NO 306
<211> LENGTH: 19
<212> TYPE: RNA
<213> ORGANISM: Artificial sequence
<220> FEATURE:
<223> OTHER INFORMATION: Chemically synthesized

<400> SEQUENCE: 306
ccccuguucu uaaguguug                                                  19

<210> SEQ ID NO 307
<211> LENGTH: 19
<212> TYPE: RNA
<213> ORGANISM: Artificial sequence
<220> FEATURE:
<223> OTHER INFORMATION: Chemically synthesized

<400> SEQUENCE: 307
uuccccuguu cuuaagugu                                                  19

<210> SEQ ID NO 308
<211> LENGTH: 19
<212> TYPE: RNA
<213> ORGANISM: Artificial sequence
<220> FEATURE:
<223> OTHER INFORMATION: Chemically synthesized

<400> SEQUENCE: 308
caguuccccc uguucuuaa                                                  19

<210> SEQ ID NO 309
<211> LENGTH: 19
<212> TYPE: RNA
<213> ORGANISM: Artificial sequence
<220> FEATURE:
<223> OTHER INFORMATION: Chemically synthesized

<400> SEQUENCE: 309
gccuuuauaa gcucaguuu                                                  19

<210> SEQ ID NO 310
<211> LENGTH: 19
<212> TYPE: RNA
<213> ORGANISM: Artificial sequence
<220> FEATURE:
<223> OTHER INFORMATION: Chemically synthesized

<400> SEQUENCE: 310
```
guguuguuuu agaugccuu                              19

<210> SEQ ID NO 311
<211> LENGTH: 19
<212> TYPE: RNA
<213> ORGANISM: Artificial sequence
<220> FEATURE:
<223> OTHER INFORMATION: Chemically synthesized

<400> SEQUENCE: 311
acgguguugu uuagaugc                               19

<210> SEQ ID NO 312
<211> LENGTH: 19
<212> TYPE: RNA
<213> ORGANISM: Artificial sequence
<220> FEATURE:
<223> OTHER INFORMATION: Chemically synthesized

<400> SEQUENCE: 312
ccacgguguu guuuuagau                              19

<210> SEQ ID NO 313
<211> LENGTH: 19
<212> TYPE: RNA
<213> ORGANISM: Artificial sequence
<220> FEATURE:
<223> OTHER INFORMATION: Chemically synthesized

<400> SEQUENCE: 313
ucaguaacca cgguguugu                              19

<210> SEQ ID NO 314
<211> LENGTH: 19
<212> TYPE: RNA
<213> ORGANISM: Artificial sequence
<220> FEATURE:
<223> OTHER INFORMATION: Chemically synthesized

<400> SEQUENCE: 314
ccauuucagu aaccacggu                              19

<210> SEQ ID NO 315
<211> LENGTH: 19
<212> TYPE: RNA
<213> ORGANISM: Artificial sequence
<220> FEATURE:
<223> OTHER INFORMATION: Chemically synthesized

<400> SEQUENCE: 315
guaggauuaa guaggugag                              19

<210> SEQ ID NO 316
<211> LENGTH: 19
<212> TYPE: RNA
<213> ORGANISM: Artificial sequence
<220> FEATURE:
<223> OTHER INFORMATION: Chemically synthesized

<400> SEQUENCE: 316
gguaggauua aguagguga                              19

<210> SEQ ID NO 317
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 317
aaggguuuuu agacaggaa                                                  19

<210> SEQ ID NO 318
<211> LENGTH: 19
<212> TYPE: RNA
<213> ORGANISM: Artificial sequence
<220> FEATURE:
<223> OTHER INFORMATION: Chemically synthesized

<400> SEQUENCE: 318
uugaaggguu uuuagacag                                                  19

<210> SEQ ID NO 319
<211> LENGTH: 19
<212> TYPE: RNA
<213> ORGANISM: Artificial sequence
<220> FEATURE:
<223> OTHER INFORMATION: Chemically synthesized

<400> SEQUENCE: 319
caguuccuga cucaaauuu                                                  19

<210> SEQ ID NO 320
<211> LENGTH: 19
<212> TYPE: RNA
<213> ORGANISM: Artificial sequence
<220> FEATURE:
<223> OTHER INFORMATION: Chemically synthesized

<400> SEQUENCE: 320
accaguuccu gacucaaau                                                  19

<210> SEQ ID NO 321
<211> LENGTH: 19
<212> TYPE: RNA
<213> ORGANISM: Artificial sequence
<220> FEATURE:
<223> OTHER INFORMATION: Chemically synthesized

<400> SEQUENCE: 321 ccaucaaaa cuuccaaaa                                                   19

<210> SEQ ID NO 322
<211> LENGTH: 19
<212> TYPE: RNA
<213> ORGANISM: Artificial sequence
<220> FEATURE:
<223> OTHER INFORMATION: Chemically synthesized

<400> SEQUENCE: 322
ugcuaaguga uuuugacua                                                  19

<210> SEQ ID NO 323
<211> LENGTH: 19
<212> TYPE: RNA
<213> ORGANISM: Artificial sequence
<220> FEATURE:
<223> OTHER INFORMATION: Chemically synthesized

<400> SEQUENCE: 323
uccacaauuu gguuucagg                                                  19
```

<210> SEQ ID NO 324
<211> LENGTH: 19
<212> TYPE: RNA
<213> ORGANISM: Artificial sequence
<220> FEATURE:
<223> OTHER INFORMATION: Chemically synthesized

<400> SEQUENCE: 324
ugauuccaca auuugguuu                                               19

<210> SEQ ID NO 325
<211> LENGTH: 19
<212> TYPE: RNA
<213> ORGANISM: Artificial sequence
<220> FEATURE:
<223> OTHER INFORMATION: Chemically synthesized

<400> SEQUENCE: 325
auagauccca uuuuuguac                                               19

<210> SEQ ID NO 326
<211> LENGTH: 19
<212> TYPE: RNA
<213> ORGANISM: Artificial sequence
<220> FEATURE:
<223> OTHER INFORMATION: Chemically synthesized

<400> SEQUENCE: 326
cagagagccu gcuaaguga                                               19

<210> SEQ ID NO 327
<211> LENGTH: 19
<212> TYPE: RNA
<213> ORGANISM: Artificial sequence
<220> FEATURE:
<223> OTHER INFORMATION: Chemically synthesized

<400> SEQUENCE: 327
guagauuuuc ugcauagau                                               19

<210> SEQ ID NO 328
<211> LENGTH: 19
<212> TYPE: RNA
<213> ORGANISM: Artificial sequence
<220> FEATURE:
<223> OTHER INFORMATION: Chemically synthesized

<400> SEQUENCE: 328
uaguguagau uuucugcau                                               19

<210> SEQ ID NO 329
<211> LENGTH: 19
<212> TYPE: RNA
<213> ORGANISM: Artificial sequence
<220> FEATURE:
<223> OTHER INFORMATION: Chemically synthesized

<400> SEQUENCE: 329
auaguguaga uuuucugca                                               19

<210> SEQ ID NO 330
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 330
uguuucacau ucauagcaa                                                19

<210> SEQ ID NO 331
<211> LENGTH: 19
<212> TYPE: RNA
<213> ORGANISM: Artificial sequence
<220> FEATURE:
<223> OTHER INFORMATION: Chemically synthesized

<400> SEQUENCE: 331
caccugcccu aaauaagaa                                                19

<210> SEQ ID NO 332
<211> LENGTH: 19
<212> TYPE: RNA
<213> ORGANISM: Artificial sequence
<220> FEATURE:
<223> OTHER INFORMATION: Chemically synthesized

<400> SEQUENCE: 332
aaagucauuu guaguuugc                                                19

<210> SEQ ID NO 333
<211> LENGTH: 19
<212> TYPE: RNA
<213> ORGANISM: Artificial sequence
<220> FEATURE:
<223> OTHER INFORMATION: Chemically synthesized

<400> SEQUENCE: 333
gcuagucagc uaaagucau                                                19

<210> SEQ ID NO 334
<211> LENGTH: 19
<212> TYPE: RNA
<213> ORGANISM: Artificial sequence
<220> FEATURE:
<223> OTHER INFORMATION: Chemically synthesized

<400> SEQUENCE: 334
ucagcuaguc agcuaaagu                                                19

<210> SEQ ID NO 335
<211> LENGTH: 19
<212> TYPE: RNA
<213> ORGANISM: Artificial sequence
<220> FEATURE:
<223> OTHER INFORMATION: Chemically synthesized

<400> SEQUENCE: 335
ggguaguaaa acuauucag                                                19

<210> SEQ ID NO 336
<211> LENGTH: 19
<212> TYPE: RNA
<213> ORGANISM: Artificial sequence
<220> FEATURE:
<223> OTHER INFORMATION: Chemically synthesized

<400> SEQUENCE: 336
ccagcauuuc agaauugcu                                                19

<210> SEQ ID NO 337
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 337
cagcucagga uuucgacuu                                                       19

<210> SEQ ID NO 338
<211> LENGTH: 19
<212> TYPE: RNA
<213> ORGANISM: Artificial sequence
<220> FEATURE:
<223> OTHER INFORMATION: Chemically synthesized

<400> SEQUENCE: 338
gaacucugau ccucagcuc                                                       19

<210> SEQ ID NO 339
<211> LENGTH: 19
<212> TYPE: RNA
<213> ORGANISM: Artificial sequence
<220> FEATURE:
<223> OTHER INFORMATION: Chemically synthesized

<400> SEQUENCE: 339
cgcuucuccu cugguuuca                                                       19

<210> SEQ ID NO 340
<211> LENGTH: 19
<212> TYPE: RNA
<213> ORGANISM: Artificial sequence
<220> FEATURE:
<223> OTHER INFORMATION: Chemically synthesized

<400> SEQUENCE: 340 gacuuuucu uuaguagag                                                        19

<210> SEQ ID NO 341
<211> LENGTH: 19
<212> TYPE: RNA
<213> ORGANISM: Artificial sequence
<220> FEATURE:
<223> OTHER INFORMATION: Chemically synthesized

<400> SEQUENCE: 341
ucagggacuu uuucuuuag                                                       19

<210> SEQ ID NO 342
<211> LENGTH: 19
<212> TYPE: RNA
<213> ORGANISM: Artificial sequence
<220> FEATURE:
<223> OTHER INFORMATION: Chemically synthesized

<400> SEQUENCE: 342
uucagggacu uuuucuuua                                                       19

<210> SEQ ID NO 343
<211> LENGTH: 19
<212> TYPE: RNA
<213> ORGANISM: Artificial sequence
<220> FEATURE:
<223> OTHER INFORMATION: Chemically synthesized

<400> SEQUENCE: 343
```
cuuuugagcu uacacuugu                                    19

<210> SEQ ID NO 344
<211> LENGTH: 19
<212> TYPE: RNA
<213> ORGANISM: Artificial sequence
<220> FEATURE:
<223> OTHER INFORMATION: Chemically synthesized

<400> SEQUENCE: 344
uaccuacuuu ugagcuuac                                    19

<210> SEQ ID NO 345
<211> LENGTH: 19
<212> TYPE: RNA
<213> ORGANISM: Artificial sequence
<220> FEATURE:
<223> OTHER INFORMATION: Chemically synthesized

<400> SEQUENCE: 345
guaccuacuu uugagcuua                                    19

<210> SEQ ID NO 346
<211> LENGTH: 19
<212> TYPE: RNA
<213> ORGANISM: Artificial sequence
<220> FEATURE:
<223> OTHER INFORMATION: Chemically synthesized

<400> SEQUENCE: 346
gugaacuugg aaauugaaa                                    19

<210> SEQ ID NO 347
<211> LENGTH: 19
<212> TYPE: RNA
<213> ORGANISM: Artificial sequence
<220> FEATURE:
<223> OTHER INFORMATION: Chemically synthesized

<400> SEQUENCE: 347
gcacgugaac uuggaaauu                                    19

<210> SEQ ID NO 348
<211> LENGTH: 19
<212> TYPE: RNA
<213> ORGANISM: Artificial sequence
<220> FEATURE:
<223> OTHER INFORMATION: Chemically synthesized

<400> SEQUENCE: 348
ucccugagaa acugaccca                                    19

<210> SEQ ID NO 349
<211> LENGTH: 19
<212> TYPE: RNA
<213> ORGANISM: Artificial sequence
<220> FEATURE:
<223> OTHER INFORMATION: Chemically synthesized

<400> SEQUENCE: 349
agguccuugu cccugagaa                                    19

<210> SEQ ID NO 350
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 350
gcaaacuaaa cuugguugc                                                19

<210> SEQ ID NO 351
<211> LENGTH: 19
<212> TYPE: RNA
<213> ORGANISM: Artificial sequence
<220> FEATURE:
<223> OTHER INFORMATION: Chemically synthesized

<400> SEQUENCE: 351
guccaaauca aagcaaacu                                                19

<210> SEQ ID NO 352
<211> LENGTH: 19
<212> TYPE: RNA
<213> ORGANISM: Artificial sequence
<220> FEATURE:
<223> OTHER INFORMATION: Chemically synthesized

<400> SEQUENCE: 352
ucuguccaaa ucaaagcaa                                                19

<210> SEQ ID NO 353
<211> LENGTH: 19
<212> TYPE: RNA
<213> ORGANISM: Artificial sequence
<220> FEATURE:
<223> OTHER INFORMATION: Chemically synthesized

<400> SEQUENCE: 353
ccuguuaugc uuacaaaau                                                19

<210> SEQ ID NO 354
<211> LENGTH: 19
<212> TYPE: RNA
<213> ORGANISM: Artificial sequence
<220> FEATURE:
<223> OTHER INFORMATION: Chemically synthesized

<400> SEQUENCE: 354
gccuguuaug cuuacaaaa                                                19

<210> SEQ ID NO 355
<211> LENGTH: 19
<212> TYPE: RNA
<213> ORGANISM: Artificial sequence
<220> FEATURE:
<223> OTHER INFORMATION: Chemically synthesized

<400> SEQUENCE: 355
caguuaucuu ugacucucu                                                19

<210> SEQ ID NO 356
<211> LENGTH: 19
<212> TYPE: RNA
<213> ORGANISM: Artificial sequence
<220> FEATURE:
<223> OTHER INFORMATION: Chemically synthesized

<400> SEQUENCE: 356
cacuaacagu uaucuuuga                                                19
```

```
<210> SEQ ID NO 357
<211> LENGTH: 19
<212> TYPE: RNA
<213> ORGANISM: Artificial sequence
<220> FEATURE:
<223> OTHER INFORMATION: Chemically synthesized

<400> SEQUENCE: 357
uccacuaaca guuaucuuu                                                19

<210> SEQ ID NO 358
<211> LENGTH: 19
<212> TYPE: RNA
<213> ORGANISM: Artificial sequence
<220> FEATURE:
<223> OTHER INFORMATION: Chemically synthesized

<400> SEQUENCE: 358
agaacugucu guccaaauc                                                19

<210> SEQ ID NO 359
<211> LENGTH: 19
<212> TYPE: RNA
<213> ORGANISM: Artificial sequence
<220> FEATURE:
<223> OTHER INFORMATION: Chemically synthesized

<400> SEQUENCE: 359
ugacugggca aggcuucuu                                                19

<210> SEQ ID NO 360
<211> LENGTH: 19
<212> TYPE: RNA
<213> ORGANISM: Artificial sequence
<220> FEATURE:
<223> OTHER INFORMATION: Chemically synthesized

<400> SEQUENCE: 360
ucacuguguu ucugccgcu                                                19

<210> SEQ ID NO 361
<211> LENGTH: 19
<212> TYPE: RNA
<213> ORGANISM: Artificial sequence
<220> FEATURE:
<223> OTHER INFORMATION: Chemically synthesized

<400> SEQUENCE: 361
aagguucacu guguuucug                                                19

<210> SEQ ID NO 362
<211> LENGTH: 19
<212> TYPE: RNA
<213> ORGANISM: Artificial sequence
<220> FEATURE:
<223> OTHER INFORMATION: Chemically synthesized

<400> SEQUENCE: 362
ccaagauaaa ucaauguug                                                19

<210> SEQ ID NO 363
<211> LENGTH: 19
<212> TYPE: RNA
<213> ORGANISM: Artificial sequence
<220> FEATURE:
```

```
<223> OTHER INFORMATION: Chemically synthesized

<400> SEQUENCE: 363
gauacuacaa agccaaucu                                                      19

<210> SEQ ID NO 364
<211> LENGTH: 19
<212> TYPE: RNA
<213> ORGANISM: Artificial sequence
<220> FEATURE:
<223> OTHER INFORMATION: Chemically synthesized

<400> SEQUENCE: 364
aaagauacua caaagccaa                                                      19

<210> SEQ ID NO 365
<211> LENGTH: 19
<212> TYPE: RNA
<213> ORGANISM: Artificial sequence
<220> FEATURE:
<223> OTHER INFORMATION: Chemically synthesized

<400> SEQUENCE: 365
gaaagauacu acaaagcca                                                      19

<210> SEQ ID NO 366
<211> LENGTH: 19
<212> TYPE: RNA
<213> ORGANISM: Artificial sequence
<220> FEATURE:
<223> OTHER INFORMATION: Chemically synthesized

<400> SEQUENCE: 366
uggaaagaua cuacaaagc                                                      19

<210> SEQ ID NO 367
<211> LENGTH: 19
<212> TYPE: RNA
<213> ORGANISM: Artificial sequence
<220> FEATURE:
<223> OTHER INFORMATION: Chemically synthesized

<400> SEQUENCE: 367
uuggaaagau acuacaaag                                                      19

<210> SEQ ID NO 368
<211> LENGTH: 19
<212> TYPE: RNA
<213> ORGANISM: Artificial sequence
<220> FEATURE:
<223> OTHER INFORMATION: Chemically synthesized

<400> SEQUENCE: 368
ugcuuggaaa gauacuaca                                                      19

<210> SEQ ID NO 369
<211> LENGTH: 19
<212> TYPE: RNA
<213> ORGANISM: Artificial sequence
<220> FEATURE:
<223> OTHER INFORMATION: Chemically synthesized

<400> SEQUENCE: 369
augcuuggaa agauacuac                                                      19
```

<210> SEQ ID NO 370
<211> LENGTH: 19
<212> TYPE: RNA
<213> ORGANISM: Artificial sequence
<220> FEATURE:
<223> OTHER INFORMATION: Chemically synthesized

<400> SEQUENCE: 370
cuaaacucuu caaaugcuu                                                19

<210> SEQ ID NO 371
<211> LENGTH: 19
<212> TYPE: RNA
<213> ORGANISM: Artificial sequence
<220> FEATURE:
<223> OTHER INFORMATION: Chemically synthesized

<400> SEQUENCE: 371
aagugaccua aaaugucac                                                19

<210> SEQ ID NO 372
<211> LENGTH: 19
<212> TYPE: RNA
<213> ORGANISM: Artificial sequence
<220> FEATURE:
<223> OTHER INFORMATION: Chemically synthesized

<400> SEQUENCE: 372
ugauccuguu acugauacu                                                19

<210> SEQ ID NO 373
<211> LENGTH: 19
<212> TYPE: RNA
<213> ORGANISM: Artificial sequence
<220> FEATURE:
<223> OTHER INFORMATION: Chemically synthesized

<400> SEQUENCE: 373
acagguguga uccuguuac                                                19

<210> SEQ ID NO 374
<211> LENGTH: 19
<212> TYPE: RNA
<213> ORGANISM: Artificial sequence
<220> FEATURE:
<223> OTHER INFORMATION: Chemically synthesized

<400> SEQUENCE: 374
auccuggugu uacugaaaa                                                19

<210> SEQ ID NO 375
<211> LENGTH: 19
<212> TYPE: RNA
<213> ORGANISM: Artificial sequence
<220> FEATURE:
<223> OTHER INFORMATION: Chemically synthesized

<400> SEQUENCE: 375
ggacagaugu auucauccu                                                19

<210> SEQ ID NO 376
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 376
agcuccacuu cacaugcug                                              19

<210> SEQ ID NO 377
<211> LENGTH: 19
<212> TYPE: RNA
<213> ORGANISM: Artificial sequence
<220> FEATURE:
<223> OTHER INFORMATION: Chemically synthesized

<400> SEQUENCE: 377
agcuauuagc uccacuuca                                              19

<210> SEQ ID NO 378
<211> LENGTH: 19
<212> TYPE: RNA
<213> ORGANISM: Artificial sequence
<220> FEATURE:
<223> OTHER INFORMATION: Chemically synthesized

<400> SEQUENCE: 378
cuugccagaa uuugguuaa                                              19

<210> SEQ ID NO 379
<211> LENGTH: 19
<212> TYPE: RNA
<213> ORGANISM: Artificial sequence
<220> FEATURE:
<223> OTHER INFORMATION: Chemically synthesized

<400> SEQUENCE: 379
aaggagcuua uucagguuu                                              19

<210> SEQ ID NO 380
<211> LENGTH: 19
<212> TYPE: RNA
<213> ORGANISM: Artificial sequence
<220> FEATURE:
<223> OTHER INFORMATION: Chemically synthesized

<400> SEQUENCE: 380
gcuuucauau ccuugcugu                                              19

<210> SEQ ID NO 381
<211> LENGTH: 19
<212> TYPE: RNA
<213> ORGANISM: Artificial sequence
<220> FEATURE:
<223> OTHER INFORMATION: Chemically synthesized

<400> SEQUENCE: 381
ugagagaauu uagccucca                                              19

<210> SEQ ID NO 382
<211> LENGTH: 19
<212> TYPE: RNA
<213> ORGANISM: Artificial sequence
<220> FEATURE:
<223> OTHER INFORMATION: Chemically synthesized

<400> SEQUENCE: 382
augagagaau uuagccucc                                              19

<210> SEQ ID NO 383
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 383
ggaaucaacu ugccagaau                                            19

<210> SEQ ID NO 384
<211> LENGTH: 19
<212> TYPE: RNA
<213> ORGANISM: Artificial sequence
<220> FEATURE:
<223> OTHER INFORMATION: Chemically synthesized

<400> SEQUENCE: 384
uagggaauaa uaaaggccu                                            19

<210> SEQ ID NO 385
<211> LENGTH: 19
<212> TYPE: RNA
<213> ORGANISM: Artificial sequence
<220> FEATURE:
<223> OTHER INFORMATION: Chemically synthesized

<400> SEQUENCE: 385
ucacuaggga auaauaaag                                            19

<210> SEQ ID NO 386
<211> LENGTH: 19
<212> TYPE: RNA
<213> ORGANISM: Artificial sequence
<220> FEATURE:
<223> OTHER INFORMATION: Chemically synthesized

<400> SEQUENCE: 386
accugucacu agggaauaa                                            19

<210> SEQ ID NO 387
<211> LENGTH: 19
<212> TYPE: RNA
<213> ORGANISM: Artificial sequence
<220> FEATURE:
<223> OTHER INFORMATION: Chemically synthesized

<400> SEQUENCE: 387
auaccuguca cuagggaau                                            19

<210> SEQ ID NO 388
<211> LENGTH: 19
<212> TYPE: RNA
<213> ORGANISM: Artificial sequence
<220> FEATURE:
<223> OTHER INFORMATION: Chemically synthesized

<400> SEQUENCE: 388
uuggauaccu gucacuagg                                            19

<210> SEQ ID NO 389
<211> LENGTH: 19
<212> TYPE: RNA
<213> ORGANISM: Artificial sequence
<220> FEATURE:
<223> OTHER INFORMATION: Chemically synthesized

<400> SEQUENCE: 389
```
caccuuggau accugucac    19

<210> SEQ ID NO 390
<211> LENGTH: 19
<212> TYPE: RNA
<213> ORGANISM: Artificial sequence
<220> FEATURE:
<223> OTHER INFORMATION: Chemically synthesized

<400> SEQUENCE: 390
accguccaga uaaccaugc    19

<210> SEQ ID NO 391
<211> LENGTH: 19
<212> TYPE: RNA
<213> ORGANISM: Artificial sequence
<220> FEATURE:
<223> OTHER INFORMATION: Chemically synthesized

<400> SEQUENCE: 391
gaagucugca uuggcuaug    19

<210> SEQ ID NO 392
<211> LENGTH: 19
<212> TYPE: RNA
<213> ORGANISM: Artificial sequence
<220> FEATURE:
<223> OTHER INFORMATION: Chemically synthesized

<400> SEQUENCE: 392
gaauuauuga aacggguca    19

<210> SEQ ID NO 393
<211> LENGTH: 19
<212> TYPE: RNA
<213> ORGANISM: Artificial sequence
<220> FEATURE:
<223> OTHER INFORMATION: Chemically synthesized

<400> SEQUENCE: 393
uaguagcugu auacuacca    19

<210> SEQ ID NO 394
<211> LENGTH: 19
<212> TYPE: RNA
<213> ORGANISM: Artificial sequence
<220> FEATURE:
<223> OTHER INFORMATION: Chemically synthesized

<400> SEQUENCE: 394
ggguaguagc uguauacua    19

<210> SEQ ID NO 395
<211> LENGTH: 19
<212> TYPE: RNA
<213> ORGANISM: Artificial sequence
<220> FEATURE:
<223> OTHER INFORMATION: Chemically synthesized

<400> SEQUENCE: 395
gucaagggua guagcugua    19

<210> SEQ ID NO 396
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 396
ugaaguaucu cuccuuaac                                                 19

<210> SEQ ID NO 397
<211> LENGTH: 19
<212> TYPE: RNA
<213> ORGANISM: Artificial sequence
<220> FEATURE:
<223> OTHER INFORMATION: Chemically synthesized

<400> SEQUENCE: 397
uugaaguauc ucuccuuaa                                                 19

<210> SEQ ID NO 398
<211> LENGTH: 19
<212> TYPE: RNA
<213> ORGANISM: Artificial sequence
<220> FEATURE:
<223> OTHER INFORMATION: Chemically synthesized

<400> SEQUENCE: 398
gggaauugaa guaucucuc                                                 19

<210> SEQ ID NO 399
<211> LENGTH: 19
<212> TYPE: RNA
<213> ORGANISM: Artificial sequence
<220> FEATURE:
<223> OTHER INFORMATION: Chemically synthesized

<400> SEQUENCE: 399
ugggaauuga aguaucucu                                                 19

<210> SEQ ID NO 400
<211> LENGTH: 19
<212> TYPE: RNA
<213> ORGANISM: Artificial sequence
<220> FEATURE:
<223> OTHER INFORMATION: Chemically synthesized

<400> SEQUENCE: 400
ggcuuuucug ggaauugaa                                                 19

<210> SEQ ID NO 401
<211> LENGTH: 19
<212> TYPE: RNA
<213> ORGANISM: Artificial sequence
<220> FEATURE:
<223> OTHER INFORMATION: Chemically synthesized

<400> SEQUENCE: 401
cccaaccuca acgagguaa                                                 19

<210> SEQ ID NO 402
<211> LENGTH: 19
<212> TYPE: RNA
<213> ORGANISM: Artificial sequence
<220> FEATURE:
<223> OTHER INFORMATION: Chemically synthesized

<400> SEQUENCE: 402
gcaguguuau cucaucucu                                                 19
```

<210> SEQ ID NO 403
<211> LENGTH: 19
<212> TYPE: RNA
<213> ORGANISM: Artificial sequence
<220> FEATURE:
<223> OTHER INFORMATION: Chemically synthesized

<400> SEQUENCE: 403
cucagaugaa ccauuucac                                                    19

<210> SEQ ID NO 404
<211> LENGTH: 19
<212> TYPE: RNA
<213> ORGANISM: Artificial sequence
<220> FEATURE:
<223> OTHER INFORMATION: Chemically synthesized

<400> SEQUENCE: 404
cugaacccaa ccucaacga                                                    19

<210> SEQ ID NO 405
<211> LENGTH: 19
<212> TYPE: RNA
<213> ORGANISM: Artificial sequence
<220> FEATURE:
<223> OTHER INFORMATION: Chemically synthesized

<400> SEQUENCE: 405
cugauucacu uaguaaucu                                                    19

<210> SEQ ID NO 406
<211> LENGTH: 19
<212> TYPE: RNA
<213> ORGANISM: Artificial sequence
<220> FEATURE:
<223> OTHER INFORMATION: Chemically synthesized

<400> SEQUENCE: 406
cucugauuca cuuaguaau                                                    19

<210> SEQ ID NO 407
<211> LENGTH: 19
<212> TYPE: RNA
<213> ORGANISM: Artificial sequence
<220> FEATURE:
<223> OTHER INFORMATION: Chemically synthesized

<400> SEQUENCE: 407
ccucucugau ucacuuagu                                                    19

<210> SEQ ID NO 408
<211> LENGTH: 19
<212> TYPE: RNA
<213> ORGANISM: Artificial sequence
<220> FEATURE:
<223> OTHER INFORMATION: Chemically synthesized

<400> SEQUENCE: 408
aggaaacaga gccguugac                                                    19

<210> SEQ ID NO 409
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 409
uacucuucca uugagugaa                                                19

<210> SEQ ID NO 410
<211> LENGTH: 19
<212> TYPE: RNA
<213> ORGANISM: Artificial sequence
<220> FEATURE:
<223> OTHER INFORMATION: Chemically synthesized

<400> SEQUENCE: 410
guguguaguu gauuacucu                                                19

<210> SEQ ID NO 411
<211> LENGTH: 19
<212> TYPE: RNA
<213> ORGANISM: Artificial sequence
<220> FEATURE:
<223> OTHER INFORMATION: Chemically synthesized

<400> SEQUENCE: 411
gaacugauau uuuugugug                                                19

<210> SEQ ID NO 412
<211> LENGTH: 19
<212> TYPE: RNA
<213> ORGANISM: Artificial sequence
<220> FEATURE:
<223> OTHER INFORMATION: Chemically synthesized

<400> SEQUENCE: 412
aaguguugaa uacugucuu                                                19

<210> SEQ ID NO 413
<211> LENGTH: 19
<212> TYPE: RNA
<213> ORGANISM: Artificial sequence
<220> FEATURE:
<223> OTHER INFORMATION: Chemically synthesized

<400> SEQUENCE: 413
uccccuguuc uuaaguguu                                                19

<210> SEQ ID NO 414
<211> LENGTH: 19
<212> TYPE: RNA
<213> ORGANISM: Artificial sequence
<220> FEATURE:
<223> OTHER INFORMATION: Chemically synthesized

<400> SEQUENCE: 414
gcucaguuuc cccuguucu                                                19

<210> SEQ ID NO 415
<211> LENGTH: 19
<212> TYPE: RNA
<213> ORGANISM: Artificial sequence
<220> FEATURE:
<223> OTHER INFORMATION: Chemically synthesized

<400> SEQUENCE: 415
agcucaguuu ccccuguuc                                                19

<210> SEQ ID NO 416
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 416
ggauuauguu guuccugaa                                                   19

<210> SEQ ID NO 417
<211> LENGTH: 19
<212> TYPE: RNA
<213> ORGANISM: Artificial sequence
<220> FEATURE:
<223> OTHER INFORMATION: Chemically synthesized

<400> SEQUENCE: 417
uaagcucagu uuccccugu                                                   19

<210> SEQ ID NO 418
<211> LENGTH: 19
<212> TYPE: RNA
<213> ORGANISM: Artificial sequence
<220> FEATURE:
<223> OTHER INFORMATION: Chemically synthesized

<400> SEQUENCE: 418
ugccuuuaua agcucaguu                                                   19

<210> SEQ ID NO 419
<211> LENGTH: 19
<212> TYPE: RNA
<213> ORGANISM: Artificial sequence
<220> FEATURE:
<223> OTHER INFORMATION: Chemically synthesized

<400> SEQUENCE: 419
agaugccuuu auaagcuca                                                   19

<210> SEQ ID NO 420
<211> LENGTH: 19
<212> TYPE: RNA
<213> ORGANISM: Artificial sequence
<220> FEATURE:
<223> OTHER INFORMATION: Chemically synthesized

<400> SEQUENCE: 420
uuagaugccu uuauaagcu                                                   19

<210> SEQ ID NO 421
<211> LENGTH: 19
<212> TYPE: RNA
<213> ORGANISM: Artificial sequence
<220> FEATURE:
<223> OTHER INFORMATION: Chemically synthesized

<400> SEQUENCE: 421
cgguguuguu uuagaugcc                                                   19

<210> SEQ ID NO 422
<211> LENGTH: 19
<212> TYPE: RNA
<213> ORGANISM: Artificial sequence
<220> FEATURE:
<223> OTHER INFORMATION: Chemically synthesized

<400> SEQUENCE: 422
```
uaaccacggu guuguuuua                          19

<210> SEQ ID NO 423
<211> LENGTH: 19
<212> TYPE: RNA
<213> ORGANISM: Artificial sequence
<220> FEATURE:
<223> OTHER INFORMATION: Chemically synthesized

<400> SEQUENCE: 423
cuacugggau uauguuguu                          19

<210> SEQ ID NO 424
<211> LENGTH: 19
<212> TYPE: RNA
<213> ORGANISM: Artificial sequence
<220> FEATURE:
<223> OTHER INFORMATION: Chemically synthesized

<400> SEQUENCE: 424
acuacuggga uuauguugu                          19

<210> SEQ ID NO 425
<211> LENGTH: 19
<212> TYPE: RNA
<213> ORGANISM: Artificial sequence
<220> FEATURE:
<223> OTHER INFORMATION: Chemically synthesized

<400> SEQUENCE: 425
auggaacugc uucacuguu                          19

<210> SEQ ID NO 426
<211> LENGTH: 19
<212> TYPE: RNA
<213> ORGANISM: Artificial sequence
<220> FEATURE:
<223> OTHER INFORMATION: Chemically synthesized

<400> SEQUENCE: 426
uuacggcaau aauggaacu                          19

<210> SEQ ID NO 427
<211> LENGTH: 19
<212> TYPE: RNA
<213> ORGANISM: Artificial sequence
<220> FEATURE:
<223> OTHER INFORMATION: Chemically synthesized

<400> SEQUENCE: 427
aggugaguuu aauuaaagc                          19

<210> SEQ ID NO 428
<211> LENGTH: 19
<212> TYPE: RNA
<213> ORGANISM: Artificial sequence
<220> FEATURE:
<223> OTHER INFORMATION: Chemically synthesized

<400> SEQUENCE: 428
aggauuaagu aggugaguu                          19

<210> SEQ ID NO 429
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 429
acaggaaggu aggauuaag                                                19

<210> SEQ ID NO 430
<211> LENGTH: 19
<212> TYPE: RNA
<213> ORGANISM: Artificial sequence
<220> FEATURE:
<223> OTHER INFORMATION: Chemically synthesized

<400> SEQUENCE: 430
aggguuuuua gacaggaag                                                19

<210> SEQ ID NO 431
<211> LENGTH: 19
<212> TYPE: RNA
<213> ORGANISM: Artificial sequence
<220> FEATURE:
<223> OTHER INFORMATION: Chemically synthesized

<400> SEQUENCE: 431
gaaggguuuu uagacagga                                                19

<210> SEQ ID NO 432
<211> LENGTH: 19
<212> TYPE: RNA
<213> ORGANISM: Artificial sequence
<220> FEATURE:
<223> OTHER INFORMATION: Chemically synthesized

<400> SEQUENCE: 432
ugaaggguuu uuagacagg                                                19

<210> SEQ ID NO 433
<211> LENGTH: 19
<212> TYPE: RNA
<213> ORGANISM: Artificial sequence
<220> FEATURE:
<223> OTHER INFORMATION: Chemically synthesized

<400> SEQUENCE: 433
uuugaagggu uuuuagaca                                                19

<210> SEQ ID NO 434
<211> LENGTH: 19
<212> TYPE: RNA
<213> ORGANISM: Artificial sequence
<220> FEATURE:
<223> OTHER INFORMATION: Chemically synthesized

<400> SEQUENCE: 434
gugauuuuga cuacuggga                                                19

<210> SEQ ID NO 435
<211> LENGTH: 19
<212> TYPE: RNA
<213> ORGANISM: Artificial sequence
<220> FEATURE:
<223> OTHER INFORMATION: Chemically synthesized

<400> SEQUENCE: 435
uccugacuca aauuugaag                                                19
```

```
<210> SEQ ID NO 436
<211> LENGTH: 19
<212> TYPE: RNA
<213> ORGANISM: Artificial sequence
<220> FEATURE:
<223> OTHER INFORMATION: Chemically synthesized

<400> SEQUENCE: 436
ucucuaaguu uucagagga                                                19

<210> SEQ ID NO 437
<211> LENGTH: 19
<212> TYPE: RNA
<213> ORGANISM: Artificial sequence
<220> FEATURE:
<223> OTHER INFORMATION: Chemically synthesized

<400> SEQUENCE: 437
agguaggcuu gguaauaga                                                19

<210> SEQ ID NO 438
<211> LENGTH: 19
<212> TYPE: RNA
<213> ORGANISM: Artificial sequence
<220> FEATURE:
<223> OTHER INFORMATION: Chemically synthesized

<400> SEQUENCE: 438 acaauuggu uucagguag                                                 19

<210> SEQ ID NO 439
<211> LENGTH: 19
<212> TYPE: RNA
<213> ORGANISM: Artificial sequence
<220> FEATURE:
<223> OTHER INFORMATION: Chemically synthesized

<400> SEQUENCE: 439
guuuuacauu ugauuccac                                                19

<210> SEQ ID NO 440
<211> LENGTH: 19
<212> TYPE: RNA
<213> ORGANISM: Artificial sequence
<220> FEATURE:
<223> OTHER INFORMATION: Chemically synthesized

<400> SEQUENCE: 440
aagcccauuu gaguuuuac                                                19

<210> SEQ ID NO 441
<211> LENGTH: 19
<212> TYPE: RNA
<213> ORGANISM: Artificial sequence
<220> FEATURE:
<223> OTHER INFORMATION: Chemically synthesized

<400> SEQUENCE: 441
uagaagccca uuugaguuu                                                19

<210> SEQ ID NO 442
<211> LENGTH: 19
<212> TYPE: RNA
<213> ORGANISM: Artificial sequence
<220> FEATURE:
```

```
<223> OTHER INFORMATION: Chemically synthesized

<400> SEQUENCE: 442
aagcaaaagu agaagccca                                            19

<210> SEQ ID NO 443
<211> LENGTH: 19
<212> TYPE: RNA
<213> ORGANISM: Artificial sequence
<220> FEATURE:
<223> OTHER INFORMATION: Chemically synthesized

<400> SEQUENCE: 443
uagguaagca aaaguagaa                                            19

<210> SEQ ID NO 444
<211> LENGTH: 19
<212> TYPE: RNA
<213> ORGANISM: Artificial sequence
<220> FEATURE:
<223> OTHER INFORMATION: Chemically synthesized

<400> SEQUENCE: 444
gaauagguaa gcaaaagua                                            19

<210> SEQ ID NO 445
<211> LENGTH: 19
<212> TYPE: RNA
<213> ORGANISM: Artificial sequence
<220> FEATURE:
<223> OTHER INFORMATION: Chemically synthesized

<400> SEQUENCE: 445
ggauggaaua gguaagcaa                                            19

<210> SEQ ID NO 446
<211> LENGTH: 19
<212> TYPE: RNA
<213> ORGANISM: Artificial sequence
<220> FEATURE:
<223> OTHER INFORMATION: Chemically synthesized

<400> SEQUENCE: 446
gggauggaau agguaagca                                            19

<210> SEQ ID NO 447
<211> LENGTH: 19
<212> TYPE: RNA
<213> ORGANISM: Artificial sequence
<220> FEATURE:
<223> OTHER INFORMATION: Chemically synthesized

<400> SEQUENCE: 447
agaauugaau gggauggaa                                            19

<210> SEQ ID NO 448
<211> LENGTH: 19
<212> TYPE: RNA
<213> ORGANISM: Artificial sequence
<220> FEATURE:
<223> OTHER INFORMATION: Chemically synthesized

<400> SEQUENCE: 448
cugcauagau cccauuuuu                                            19
```

```
<210> SEQ ID NO 449
<211> LENGTH: 19
<212> TYPE: RNA
<213> ORGANISM: Artificial sequence
<220> FEATURE:
<223> OTHER INFORMATION: Chemically synthesized

<400> SEQUENCE: 449
uagauuuucu gcauagauc                                                  19

<210> SEQ ID NO 450
<211> LENGTH: 19
<212> TYPE: RNA
<213> ORGANISM: Artificial sequence
<220> FEATURE:
<223> OTHER INFORMATION: Chemically synthesized

<400> SEQUENCE: 450
ggccuuugga gaagugauu                                                  19

<210> SEQ ID NO 451
<211> LENGTH: 19
<212> TYPE: RNA
<213> ORGANISM: Artificial sequence
<220> FEATURE:
<223> OTHER INFORMATION: Chemically synthesized

<400> SEQUENCE: 451
acuguggcua ucacccaga                                                  19

<210> SEQ ID NO 452
<211> LENGTH: 19
<212> TYPE: RNA
<213> ORGANISM: Artificial sequence
<220> FEATURE:
<223> OTHER INFORMATION: Chemically synthesized

<400> SEQUENCE: 452
ggcugauuuu cuggccuuu                                                  19

<210> SEQ ID NO 453
<211> LENGTH: 19
<212> TYPE: RNA
<213> ORGANISM: Artificial sequence
<220> FEATURE:
<223> OTHER INFORMATION: Chemically synthesized

<400> SEQUENCE: 453
acaggcugau uuucuggcc                                                  19

<210> SEQ ID NO 454
<211> LENGTH: 19
<212> TYPE: RNA
<213> ORGANISM: Artificial sequence
<220> FEATURE:
<223> OTHER INFORMATION: Chemically synthesized

<400> SEQUENCE: 454
aacaggcuga uuuucuggc                                                  19

<210> SEQ ID NO 455
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 455
cugcagcuaa caggcugau                                                19

<210> SEQ ID NO 456
<211> LENGTH: 19
<212> TYPE: RNA
<213> ORGANISM: Artificial sequence
<220> FEATURE:
<223> OTHER INFORMATION: Chemically synthesized

<400> SEQUENCE: 456
agcaacugca gcuaacagg                                                19

<210> SEQ ID NO 457
<211> LENGTH: 19
<212> TYPE: RNA
<213> ORGANISM: Artificial sequence
<220> FEATURE:
<223> OTHER INFORMATION: Chemically synthesized

<400> SEQUENCE: 457
uagcaacugc agcuaacag                                                19

<210> SEQ ID NO 458
<211> LENGTH: 19
<212> TYPE: RNA
<213> ORGANISM: Artificial sequence
<220> FEATURE:
<223> OTHER INFORMATION: Chemically synthesized

<400> SEQUENCE: 458
ucauagcaac ugcagcuaa                                                19

<210> SEQ ID NO 459
<211> LENGTH: 19
<212> TYPE: RNA
<213> ORGANISM: Artificial sequence
<220> FEATURE:
<223> OTHER INFORMATION: Chemically synthesized

<400> SEQUENCE: 459
ucacauucau agcaacugc                                                19

<210> SEQ ID NO 460
<211> LENGTH: 19
<212> TYPE: RNA
<213> ORGANISM: Artificial sequence
<220> FEATURE:
<223> OTHER INFORMATION: Chemically synthesized

<400> SEQUENCE: 460
cagaauugcu ggacugugg                                                19

<210> SEQ ID NO 461
<211> LENGTH: 19
<212> TYPE: RNA
<213> ORGANISM: Artificial sequence
<220> FEATURE:
<223> OTHER INFORMATION: Chemically synthesized

<400> SEQUENCE: 461
gcccuaaaua agaaacccc                                                19

<210> SEQ ID NO 462
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 462
ccaccugccc uaaauaaga                                                   19

<210> SEQ ID NO 463
<211> LENGTH: 19
<212> TYPE: RNA
<213> ORGANISM: Artificial sequence
<220> FEATURE:
<223> OTHER INFORMATION: Chemically synthesized

<400> SEQUENCE: 463
gucauuugua guuugcccc                                                   19

<210> SEQ ID NO 464
<211> LENGTH: 19
<212> TYPE: RNA
<213> ORGANISM: Artificial sequence
<220> FEATURE:
<223> OTHER INFORMATION: Chemically synthesized

<400> SEQUENCE: 464
guaaaacuau ucagcuagu                                                   19

<210> SEQ ID NO 465
<211> LENGTH: 19
<212> TYPE: RNA
<213> ORGANISM: Artificial sequence
<220> FEATURE:
<223> OTHER INFORMATION: Chemically synthesized

<400> SEQUENCE: 465
uuggguagua aaacuauuc                                                   19

<210> SEQ ID NO 466
<211> LENGTH: 19
<212> TYPE: RNA
<213> ORGANISM: Artificial sequence
<220> FEATURE:
<223> OTHER INFORMATION: Chemically synthesized

<400> SEQUENCE: 466
ccucagcuca ggauuucga                                                   19

<210> SEQ ID NO 467
<211> LENGTH: 19
<212> TYPE: RNA
<213> ORGANISM: Artificial sequence
<220> FEATURE:
<223> OTHER INFORMATION: Chemically synthesized

<400> SEQUENCE: 467
ggagaacucu gauccucag                                                   19

<210> SEQ ID NO 468
<211> LENGTH: 19
<212> TYPE: RNA
<213> ORGANISM: Artificial sequence
<220> FEATURE:
<223> OTHER INFORMATION: Chemically synthesized

<400> SEQUENCE: 468
```
ucgcuucucc ucugguuuc                    19

<210> SEQ ID NO 469
<211> LENGTH: 19
<212> TYPE: RNA
<213> ORGANISM: Artificial sequence
<220> FEATURE:
<223> OTHER INFORMATION: Chemically synthesized

<400> SEQUENCE: 469
gucgcuucuc cucugguuu                    19

<210> SEQ ID NO 470
<211> LENGTH: 19
<212> TYPE: RNA
<213> ORGANISM: Artificial sequence
<220> FEATURE:
<223> OTHER INFORMATION: Chemically synthesized

<400> SEQUENCE: 470
ggacuuuuuc uuuaguaga                    19

<210> SEQ ID NO 471
<211> LENGTH: 19
<212> TYPE: RNA
<213> ORGANISM: Artificial sequence
<220> FEATURE:
<223> OTHER INFORMATION: Chemically synthesized

<400> SEQUENCE: 471
uggacuagcu ucagggacu                    19

<210> SEQ ID NO 472
<211> LENGTH: 19
<212> TYPE: RNA
<213> ORGANISM: Artificial sequence
<220> FEATURE:
<223> OTHER INFORMATION: Chemically synthesized

<400> SEQUENCE: 472
ugcucaugga cuagcuuca                    19

<210> SEQ ID NO 473
<211> LENGTH: 19
<212> TYPE: RNA
<213> ORGANISM: Artificial sequence
<220> FEATURE:
<223> OTHER INFORMATION: Chemically synthesized

<400> SEQUENCE: 473
accuacuuuu gagcuuaca                    19

<210> SEQ ID NO 474
<211> LENGTH: 19
<212> TYPE: RNA
<213> ORGANISM: Artificial sequence
<220> FEATURE:
<223> OTHER INFORMATION: Chemically synthesized

<400> SEQUENCE: 474
ucguaccuac uuuugagcu                    19

<210> SEQ ID NO 475
<211> LENGTH: 19
<212> TYPE: RNA
<213> ORGANISM: Artificial sequence
<220> FEATURE:
<223> OTHER INFORMATION: Chemically synthesized

<400> SEQUENCE: 475
cgucguaccu acuuugag                                                19

<210> SEQ ID NO 476
<211> LENGTH: 19
<212> TYPE: RNA
<213> ORGANISM: Artificial sequence
<220> FEATURE:
<223> OTHER INFORMATION: Chemically synthesized

<400> SEQUENCE: 476
cacgugaacu uggaaauug                                               19

<210> SEQ ID NO 477
<211> LENGTH: 19
<212> TYPE: RNA
<213> ORGANISM: Artificial sequence
<220> FEATURE:
<223> OTHER INFORMATION: Chemically synthesized

<400> SEQUENCE: 477
ugcgagguug uguuaugca                                               19

<210> SEQ ID NO 478
<211> LENGTH: 19
<212> TYPE: RNA
<213> ORGANISM: Artificial sequence
<220> FEATURE:
<223> OTHER INFORMATION: Chemically synthesized

<400> SEQUENCE: 478
uugucccuga gaaacugac                                               19

<210> SEQ ID NO 479
<211> LENGTH: 19
<212> TYPE: RNA
<213> ORGANISM: Artificial sequence
<220> FEATURE:
<223> OTHER INFORMATION: Chemically synthesized

<400> SEQUENCE: 479
uccuuguccc ugagaaacu                                               19

<210> SEQ ID NO 480
<211> LENGTH: 19
<212> TYPE: RNA
<213> ORGANISM: Artificial sequence
<220> FEATURE:
<223> OTHER INFORMATION: Chemically synthesized

<400> SEQUENCE: 480
ugaccauggu ugcaacugg                                               19

<210> SEQ ID NO 481
<211> LENGTH: 19
<212> TYPE: RNA
<213> ORGANISM: Artificial sequence
<220> FEATURE:
<223> OTHER INFORMATION: Chemically synthesized

<400> SEQUENCE: 481
aacuaaacuu gguugcuca                                               19

<210> SEQ ID NO 482
<211> LENGTH: 19
<212> TYPE: RNA
<213> ORGANISM: Artificial sequence
<220> FEATURE:
<223> OTHER INFORMATION: Chemically synthesized

<400> SEQUENCE: 482
agcaaacuaa acuugguug                                              19

<210> SEQ ID NO 483
<211> LENGTH: 19
<212> TYPE: RNA
<213> ORGANISM: Artificial sequence
<220> FEATURE:
<223> OTHER INFORMATION: Chemically synthesized

<400> SEQUENCE: 483
uguuaugcuu acaaaaugg                                              19

<210> SEQ ID NO 484
<211> LENGTH: 19
<212> TYPE: RNA
<213> ORGANISM: Artificial sequence
<220> FEATURE:
<223> OTHER INFORMATION: Chemically synthesized

<400> SEQUENCE: 484
acugucuguc caaucaaa                                               19

<210> SEQ ID NO 485
<211> LENGTH: 19
<212> TYPE: RNA
<213> ORGANISM: Artificial sequence
<220> FEATURE:
<223> OTHER INFORMATION: Chemically synthesized

<400> SEQUENCE: 485
cuaacaguua ucuuugacu                                              19

<210> SEQ ID NO 486
<211> LENGTH: 19
<212> TYPE: RNA
<213> ORGANISM: Artificial sequence
<220> FEATURE:
<223> OTHER INFORMATION: Chemically synthesized

<400> SEQUENCE: 486
gggcaucgau guagaacug                                              19

<210> SEQ ID NO 487
<211> LENGTH: 19
<212> TYPE: RNA
<213> ORGANISM: Artificial sequence
<220> FEATURE:
<223> OTHER INFORMATION: Chemically synthesized

<400> SEQUENCE: 487
uccuggaguu gucaccacu                                              19

<210> SEQ ID NO 488
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 488
uuguuaagcu ccaagguu                                                19

<210> SEQ ID NO 489
<211> LENGTH: 19
<212> TYPE: RNA
<213> ORGANISM: Artificial sequence
<220> FEATURE:
<223> OTHER INFORMATION: Chemically synthesized

<400> SEQUENCE: 489
uugcaugucu auuguuaag                                               19

<210> SEQ ID NO 490
<211> LENGTH: 19
<212> TYPE: RNA
<213> ORGANISM: Artificial sequence
<220> FEATURE:
<223> OTHER INFORMATION: Chemically synthesized

<400> SEQUENCE: 490
auguuguuuu gcaugucua                                               19

<210> SEQ ID NO 491
<211> LENGTH: 19
<212> TYPE: RNA
<213> ORGANISM: Artificial sequence
<220> FEATURE:
<223> OTHER INFORMATION: Chemically synthesized

<400> SEQUENCE: 491
aagauacuac aaagccaau                                               19

<210> SEQ ID NO 492
<211> LENGTH: 19
<212> TYPE: RNA
<213> ORGANISM: Artificial sequence
<220> FEATURE:
<223> OTHER INFORMATION: Chemically synthesized

<400> SEQUENCE: 492
cuuggaaaga uacuacaaa                                               19

<210> SEQ ID NO 493
<211> LENGTH: 19
<212> TYPE: RNA
<213> ORGANISM: Artificial sequence
<220> FEATURE:
<223> OTHER INFORMATION: Chemically synthesized

<400> SEQUENCE: 493
ugucacuguu caaauuagc                                               19

<210> SEQ ID NO 494
<211> LENGTH: 19
<212> TYPE: RNA
<213> ORGANISM: Artificial sequence
<220> FEATURE:
<223> OTHER INFORMATION: Chemically synthesized

<400> SEQUENCE: 494
ugauacuaua agugaccua                                               19

<210> SEQ ID NO 495
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 495
ccguugacca ugguugcaa                                                19

<210> SEQ ID NO 496
<211> LENGTH: 19
<212> TYPE: RNA
<213> ORGANISM: Artificial sequence
<220> FEATURE:
<223> OTHER INFORMATION: Chemically synthesized

<400> SEQUENCE: 496
guguuacuga aaacaggu                                                 19

<210> SEQ ID NO 497
<211> LENGTH: 19
<212> TYPE: RNA
<213> ORGANISM: Artificial sequence
<220> FEATURE:
<223> OTHER INFORMATION: Chemically synthesized

<400> SEQUENCE: 497
agggacagau guauucauc                                                19

<210> SEQ ID NO 498
<211> LENGTH: 19
<212> TYPE: RNA
<213> ORGANISM: Artificial sequence
<220> FEATURE:
<223> OTHER INFORMATION: Chemically synthesized

<400> SEQUENCE: 498
ggcguaggga cagauguau                                                19

<210> SEQ ID NO 499
<211> LENGTH: 19
<212> TYPE: RNA
<213> ORGANISM: Artificial sequence
<220> FEATURE:
<223> OTHER INFORMATION: Chemically synthesized

<400> SEQUENCE: 499
cuccacuuca caugcugga                                                19

<210> SEQ ID NO 500
<211> LENGTH: 19
<212> TYPE: RNA
<213> ORGANISM: Artificial sequence
<220> FEATURE:
<223> OTHER INFORMATION: Chemically synthesized

<400> SEQUENCE: 500
uuccugcccu agcuauuag                                                19

<210> SEQ ID NO 501
<211> LENGTH: 19
<212> TYPE: RNA
<213> ORGANISM: Artificial sequence
<220> FEATURE:
<223> OTHER INFORMATION: Chemically synthesized

<400> SEQUENCE: 501
```
aggagcuuau ucagguuuc                                                      19

<210> SEQ ID NO 502
<211> LENGTH: 19
<212> TYPE: RNA
<213> ORGANISM: Artificial sequence
<220> FEATURE:
<223> OTHER INFORMATION: Chemically synthesized

<400> SEQUENCE: 502
auaaggagcu uauucaggu                                                      19

<210> SEQ ID NO 503
<211> LENGTH: 19
<212> TYPE: RNA
<213> ORGANISM: Artificial sequence
<220> FEATURE:
<223> OTHER INFORMATION: Chemically synthesized

<400> SEQUENCE: 503
caacuugcca gaauuuggu                                                      19

<210> SEQ ID NO 504
<211> LENGTH: 19
<212> TYPE: RNA
<213> ORGANISM: Artificial sequence
<220> FEATURE:
<223> OTHER INFORMATION: Chemically synthesized

<400> SEQUENCE: 504
aauucagcaa ggcuuucau                                                      19

<210> SEQ ID NO 505
<211> LENGTH: 19
<212> TYPE: RNA
<213> ORGANISM: Artificial sequence
<220> FEATURE:
<223> OTHER INFORMATION: Chemically synthesized

<400> SEQUENCE: 505
ucaacaaugu ucaauucag                                                      19

<210> SEQ ID NO 506
<211> LENGTH: 19
<212> TYPE: RNA
<213> ORGANISM: Artificial sequence
<220> FEATURE:
<223> OTHER INFORMATION: Chemically synthesized

<400> SEQUENCE: 506
uccacucaac aauguucaa                                                      19

<210> SEQ ID NO 507
<211> LENGTH: 19
<212> TYPE: RNA
<213> ORGANISM: Artificial sequence
<220> FEATURE:
<223> OTHER INFORMATION: Chemically synthesized

<400> SEQUENCE: 507
uuccaacuaa guagaucau                                                      19

<210> SEQ ID NO 508
<211> LENGTH: 19
<212> TYPE: RNA

<213> ORGANISM: Artificial sequence
<220> FEATURE:
<223> OTHER INFORMATION: Chemically synthesized

<400> SEQUENCE: 508
agggaauaau aaaggccuu                                               19

<210> SEQ ID NO 509
<211> LENGTH: 19
<212> TYPE: RNA
<213> ORGANISM: Artificial sequence
<220> FEATURE:
<223> OTHER INFORMATION: Chemically synthesized

<400> SEQUENCE: 509
cacuagggaa uauaaagg                                                19

<210> SEQ ID NO 510
<211> LENGTH: 19
<212> TYPE: RNA
<213> ORGANISM: Artificial sequence
<220> FEATURE:
<223> OTHER INFORMATION: Chemically synthesized

<400> SEQUENCE: 510
gaggaaucaa cuugccaga                                               19

<210> SEQ ID NO 511
<211> LENGTH: 19
<212> TYPE: RNA
<213> ORGANISM: Artificial sequence
<220> FEATURE:
<223> OTHER INFORMATION: Chemically synthesized

<400> SEQUENCE: 511
ccugucacua gggaauaau                                               19

<210> SEQ ID NO 512
<211> LENGTH: 19
<212> TYPE: RNA
<213> ORGANISM: Artificial sequence
<220> FEATURE:
<223> OTHER INFORMATION: Chemically synthesized

<400> SEQUENCE: 512
caugcaugca cccagauuu                                               19

<210> SEQ ID NO 513
<211> LENGTH: 19
<212> TYPE: RNA
<213> ORGANISM: Artificial sequence
<220> FEATURE:
<223> OTHER INFORMATION: Chemically synthesized

<400> SEQUENCE: 513
guccagauaa ccaugcaug                                               19

<210> SEQ ID NO 514
<211> LENGTH: 19
<212> TYPE: RNA
<213> ORGANISM: Artificial sequence
<220> FEATURE:
<223> OTHER INFORMATION: Chemically synthesized

<400> SEQUENCE: 514
ccguccagau aaccaugca                                               19

```
<210> SEQ ID NO 515
<211> LENGTH: 19
<212> TYPE: RNA
<213> ORGANISM: Artificial sequence
<220> FEATURE:
<223> OTHER INFORMATION: Chemically synthesized

<400> SEQUENCE: 515
gaaugaaacu caccgucca                                              19

<210> SEQ ID NO 516
<211> LENGTH: 19
<212> TYPE: RNA
<213> ORGANISM: Artificial sequence
<220> FEATURE:
<223> OTHER INFORMATION: Chemically synthesized

<400> SEQUENCE: 516
gagaaugaaa cucaccguc                                              19

<210> SEQ ID NO 517
<211> LENGTH: 19
<212> TYPE: RNA
<213> ORGANISM: Artificial sequence
<220> FEATURE:
<223> OTHER INFORMATION: Chemically synthesized

<400> SEQUENCE: 517
acagccuaga gaaugaaac                                              19

<210> SEQ ID NO 518
<211> LENGTH: 19
<212> TYPE: RNA
<213> ORGANISM: Artificial sequence
<220> FEATURE:
<223> OTHER INFORMATION: Chemically synthesized

<400> SEQUENCE: 518
cugcauuggc uauggagau                                              19

<210> SEQ ID NO 519
<211> LENGTH: 19
<212> TYPE: RNA
<213> ORGANISM: Artificial sequence
<220> FEATURE:
<223> OTHER INFORMATION: Chemically synthesized

<400> SEQUENCE: 519
agucugcauu ggcuaugga                                              19

<210> SEQ ID NO 520
<211> LENGTH: 19
<212> TYPE: RNA
<213> ORGANISM: Artificial sequence
<220> FEATURE:
<223> OTHER INFORMATION: Chemically synthesized

<400> SEQUENCE: 520
aagucugcau uggcuaugg                                              19

<210> SEQ ID NO 521
<211> LENGTH: 19
<212> TYPE: RNA
<213> ORGANISM: Artificial sequence
<220> FEATURE:
```

<223> OTHER INFORMATION: Chemically synthesized

<400> SEQUENCE: 521
uugaauuauu gaaacgggu                                                    19

<210> SEQ ID NO 522
<211> LENGTH: 19
<212> TYPE: RNA
<213> ORGANISM: Artificial sequence
<220> FEATURE:
<223> OTHER INFORMATION: Chemically synthesized

<400> SEQUENCE: 522
gcuguauacu accacuuug                                                    19

<210> SEQ ID NO 523
<211> LENGTH: 19
<212> TYPE: RNA
<213> ORGANISM: Artificial sequence
<220> FEATURE:
<223> OTHER INFORMATION: Chemically synthesized

<400> SEQUENCE: 523
aaggguagua gcuguauac                                                    19

<210> SEQ ID NO 524
<211> LENGTH: 19
<212> TYPE: RNA
<213> ORGANISM: Artificial sequence
<220> FEATURE:
<223> OTHER INFORMATION: Chemically synthesized

<400> SEQUENCE: 524
gaaguaucuc uccuuaacc                                                    19

<210> SEQ ID NO 525
<211> LENGTH: 19
<212> TYPE: RNA
<213> ORGANISM: Artificial sequence
<220> FEATURE:
<223> OTHER INFORMATION: Chemically synthesized

<400> SEQUENCE: 525
uucugggaau ugaaguauc                                                    19

<210> SEQ ID NO 526
<211> LENGTH: 19
<212> TYPE: RNA
<213> ORGANISM: Artificial sequence
<220> FEATURE:
<223> OTHER INFORMATION: Chemically synthesized

<400> SEQUENCE: 526
aacccaaccu caacgaggu                                                    19

<210> SEQ ID NO 527
<211> LENGTH: 19
<212> TYPE: RNA
<213> ORGANISM: Artificial sequence
<220> FEATURE:
<223> OTHER INFORMATION: Chemically synthesized

<400> SEQUENCE: 527
augaaccauu ucaccaugg                                                    19

```
<210> SEQ ID NO 528
<211> LENGTH: 19
<212> TYPE: RNA
<213> ORGANISM: Artificial sequence
<220> FEATURE:
<223> OTHER INFORMATION: Chemically synthesized

<400> SEQUENCE: 528
agaugaacca uuucaccau                                                  19

<210> SEQ ID NO 529
<211> LENGTH: 19
<212> TYPE: RNA
<213> ORGANISM: Artificial sequence
<220> FEATURE:
<223> OTHER INFORMATION: Chemically synthesized

<400> SEQUENCE: 529
aaucucagau gaaccauuu                                                  19

<210> SEQ ID NO 530
<211> LENGTH: 19
<212> TYPE: RNA
<213> ORGANISM: Artificial sequence
<220> FEATURE:
<223> OTHER INFORMATION: Chemically synthesized

<400> SEQUENCE: 530
ugugcuuaau cucagauga                                                  19

<210> SEQ ID NO 531
<211> LENGTH: 19
<212> TYPE: RNA
<213> ORGANISM: Artificial sequence
<220> FEATURE:
<223> OTHER INFORMATION: Chemically synthesized

<400> SEQUENCE: 531
augugcuuaa ucucagaug                                                  19

<210> SEQ ID NO 532
<211> LENGTH: 19
<212> TYPE: RNA
<213> ORGANISM: Artificial sequence
<220> FEATURE:
<223> OTHER INFORMATION: Chemically synthesized

<400> SEQUENCE: 532
acaugugcuu aaucucaga                                                  19

<210> SEQ ID NO 533
<211> LENGTH: 19
<212> TYPE: RNA
<213> ORGANISM: Artificial sequence
<220> FEATURE:
<223> OTHER INFORMATION: Chemically synthesized

<400> SEQUENCE: 533
uacaugugcu uaaucucag                                                  19

<210> SEQ ID NO 534
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 534
ccucuuuuca guauuacau                                              19

<210> SEQ ID NO 535
<211> LENGTH: 19
<212> TYPE: RNA
<213> ORGANISM: Artificial sequence
<220> FEATURE:
<223> OTHER INFORMATION: Chemically synthesized

<400> SEQUENCE: 535
cucucugauu cacuuagua                                              19

<210> SEQ ID NO 536
<211> LENGTH: 19
<212> TYPE: RNA
<213> ORGANISM: Artificial sequence
<220> FEATURE:
<223> OTHER INFORMATION: Chemically synthesized

<400> SEQUENCE: 536
auguuguucc ugaacccaa                                              19

<210> SEQ ID NO 537
<211> LENGTH: 19
<212> TYPE: RNA
<213> ORGANISM: Artificial sequence
<220> FEATURE:
<223> OTHER INFORMATION: Chemically synthesized

<400> SEQUENCE: 537
cccuguucuu aaguguuga                                              19

<210> SEQ ID NO 538
<211> LENGTH: 19
<212> TYPE: RNA
<213> ORGANISM: Artificial sequence
<220> FEATURE:
<223> OTHER INFORMATION: Chemically synthesized

<400> SEQUENCE: 538
augccuuuau aagcucagu                                              19

<210> SEQ ID NO 539
<211> LENGTH: 19
<212> TYPE: RNA
<213> ORGANISM: Artificial sequence
<220> FEATURE:
<223> OTHER INFORMATION: Chemically synthesized

<400> SEQUENCE: 539
cugggauuau guuguuccu                                              19

<210> SEQ ID NO 540
<211> LENGTH: 19
<212> TYPE: RNA
<213> ORGANISM: Artificial sequence
<220> FEATURE:
<223> OTHER INFORMATION: Chemically synthesized

<400> SEQUENCE: 540
cuaauguuuu aaagaggca                                              19

<210> SEQ ID NO 541
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 541
uugacuacug ggauuaugu                                              19

<210> SEQ ID NO 542
<211> LENGTH: 19
<212> TYPE: RNA
<213> ORGANISM: Artificial sequence
<220> FEATURE:
<223> OTHER INFORMATION: Chemically synthesized

<400> SEQUENCE: 542
ugagaaauau uacggcaau                                              19

<210> SEQ ID NO 543
<211> LENGTH: 19
<212> TYPE: RNA
<213> ORGANISM: Artificial sequence
<220> FEATURE:
<223> OTHER INFORMATION: Chemically synthesized

<400> SEQUENCE: 543
augagaaaua uuacggcaa                                              19

<210> SEQ ID NO 544
<211> LENGTH: 19
<212> TYPE: RNA
<213> ORGANISM: Artificial sequence
<220> FEATURE:
<223> OTHER INFORMATION: Chemically synthesized

<400> SEQUENCE: 544
gguaagagua aaugagaaa                                              19

<210> SEQ ID NO 545
<211> LENGTH: 19
<212> TYPE: RNA
<213> ORGANISM: Artificial sequence
<220> FEATURE:
<223> OTHER INFORMATION: Chemically synthesized

<400> SEQUENCE: 545
cuagguaaga guaaaugag                                              19

<210> SEQ ID NO 546
<211> LENGTH: 19
<212> TYPE: RNA
<213> ORGANISM: Artificial sequence
<220> FEATURE:
<223> OTHER INFORMATION: Chemically synthesized

<400> SEQUENCE: 546
aacccuaggu aagaguaaa                                              19

<210> SEQ ID NO 547
<211> LENGTH: 19
<212> TYPE: RNA
<213> ORGANISM: Artificial sequence
<220> FEATURE:
<223> OTHER INFORMATION: Chemically synthesized

<400> SEQUENCE: 547
```
ggugaguuua auuaaagcu                                             19

<210> SEQ ID NO 548
<211> LENGTH: 19
<212> TYPE: RNA
<213> ORGANISM: Artificial sequence
<220> FEATURE:
<223> OTHER INFORMATION: Chemically synthesized

<400> SEQUENCE: 548
uagacaggaa gguaggauu                                             19

<210> SEQ ID NO 549
<211> LENGTH: 19
<212> TYPE: RNA
<213> ORGANISM: Artificial sequence
<220> FEATURE:
<223> OTHER INFORMATION: Chemically synthesized

<400> SEQUENCE: 549
ugacucaaau uugaagggu                                             19

<210> SEQ ID NO 550
<211> LENGTH: 19
<212> TYPE: RNA
<213> ORGANISM: Artificial sequence
<220> FEATURE:
<223> OTHER INFORMATION: Chemically synthesized

<400> SEQUENCE: 550
cugacucaaa uuugaaggg                                             19

<210> SEQ ID NO 551
<211> LENGTH: 19
<212> TYPE: RNA
<213> ORGANISM: Artificial sequence
<220> FEATURE:
<223> OTHER INFORMATION: Chemically synthesized

<400> SEQUENCE: 551
caccaguucc ugacucaaa                                             19

<210> SEQ ID NO 552
<211> LENGTH: 19
<212> TYPE: RNA
<213> ORGANISM: Artificial sequence
<220> FEATURE:
<223> OTHER INFORMATION: Chemically synthesized

<400> SEQUENCE: 552
accaccaguu ccugacuca                                             19

<210> SEQ ID NO 553
<211> LENGTH: 19
<212> TYPE: RNA
<213> ORGANISM: Artificial sequence
<220> FEATURE:
<223> OTHER INFORMATION: Chemically synthesized

<400> SEQUENCE: 553
aaagcccaca ccaccaguu                                             19

<210> SEQ ID NO 554
<211> LENGTH: 19
<212> TYPE: RNA
<213> ORGANISM: Artificial sequence
<220> FEATURE:
<223> OTHER INFORMATION: Chemically synthesized

<400> SEQUENCE: 554
uaggcuuggu aauagacua                                              19

<210> SEQ ID NO 555
<211> LENGTH: 19
<212> TYPE: RNA
<213> ORGANISM: Artificial sequence
<220> FEATURE:
<223> OTHER INFORMATION: Chemically synthesized

<400> SEQUENCE: 555
caauuugguu ucagguagg                                              19

<210> SEQ ID NO 556
<211> LENGTH: 19
<212> TYPE: RNA
<213> ORGANISM: Artificial sequence
<220> FEATURE:
<223> OTHER INFORMATION: Chemically synthesized

<400> SEQUENCE: 556
agcccauuug aguuuuaca                                              19

<210> SEQ ID NO 557
<211> LENGTH: 19
<212> TYPE: RNA
<213> ORGANISM: Artificial sequence
<220> FEATURE:
<223> OTHER INFORMATION: Chemically synthesized

<400> SEQUENCE: 557
gccugcuaag ugauuuuga                                              19

<210> SEQ ID NO 558
<211> LENGTH: 19
<212> TYPE: RNA
<213> ORGANISM: Artificial sequence
<220> FEATURE:
<223> OTHER INFORMATION: Chemically synthesized

<400> SEQUENCE: 558
agcaaaagua gaagcccau                                              19

<210> SEQ ID NO 559
<211> LENGTH: 19
<212> TYPE: RNA
<213> ORGANISM: Artificial sequence
<220> FEATURE:
<223> OTHER INFORMATION: Chemically synthesized

<400> SEQUENCE: 559
guaagcaaaa guagaagcc                                              19

<210> SEQ ID NO 560
<211> LENGTH: 19
<212> TYPE: RNA
<213> ORGANISM: Artificial sequence
<220> FEATURE:
<223> OTHER INFORMATION: Chemically synthesized

<400> SEQUENCE: 560
gagagccugc uaagugauu                                              19

<210> SEQ ID NO 561
<211> LENGTH: 19
<212> TYPE: RNA
<213> ORGANISM: Artificial sequence
<220> FEATURE:
<223> OTHER INFORMATION: Chemically synthesized

<400> SEQUENCE: 561
gcauagaucc cauuuuugu					19

<210> SEQ ID NO 562
<211> LENGTH: 19
<212> TYPE: RNA
<213> ORGANISM: Artificial sequence
<220> FEATURE:
<223> OTHER INFORMATION: Chemically synthesized

<400> SEQUENCE: 562
aguguagauu uucugcaua					19

<210> SEQ ID NO 563
<211> LENGTH: 19
<212> TYPE: RNA
<213> ORGANISM: Artificial sequence
<220> FEATURE:
<223> OTHER INFORMATION: Chemically synthesized

<400> SEQUENCE: 563
uggagaagug auucaaaau					19

<210> SEQ ID NO 564
<211> LENGTH: 19
<212> TYPE: RNA
<213> ORGANISM: Artificial sequence
<220> FEATURE:
<223> OTHER INFORMATION: Chemically synthesized

<400> SEQUENCE: 564
acugcagcua acaggcuga					19

<210> SEQ ID NO 565
<211> LENGTH: 19
<212> TYPE: RNA
<213> ORGANISM: Artificial sequence
<220> FEATURE:
<223> OTHER INFORMATION: Chemically synthesized

<400> SEQUENCE: 565
cuguguuuca cauucauag					19

<210> SEQ ID NO 566
<211> LENGTH: 19
<212> TYPE: RNA
<213> ORGANISM: Artificial sequence
<220> FEATURE:
<223> OTHER INFORMATION: Chemically synthesized

<400> SEQUENCE: 566
uucuguguuu cacauucau					19

<210> SEQ ID NO 567
<211> LENGTH: 19
<212> TYPE: RNA
<213> ORGANISM: Artificial sequence
<220> FEATURE:
<223> OTHER INFORMATION: Chemically synthesized

<400> SEQUENCE: 567
cccaaaugua gucucuuuu          19

<210> SEQ ID NO 568
<211> LENGTH: 19
<212> TYPE: RNA
<213> ORGANISM: Artificial sequence
<220> FEATURE:
<223> OTHER INFORMATION: Chemically synthesized

<400> SEQUENCE: 568
ccccaaaugu agucucuuu          19

<210> SEQ ID NO 569
<211> LENGTH: 19
<212> TYPE: RNA
<213> ORGANISM: Artificial sequence
<220> FEATURE:
<223> OTHER INFORMATION: Chemically synthesized

<400> SEQUENCE: 569
aaccccaaau guagucucu          19

<210> SEQ ID NO 570
<211> LENGTH: 19
<212> TYPE: RNA
<213> ORGANISM: Artificial sequence
<220> FEATURE:
<223> OTHER INFORMATION: Chemically synthesized

<400> SEQUENCE: 570
cugcccuaaa uaagaaacc          19

<210> SEQ ID NO 571
<211> LENGTH: 19
<212> TYPE: RNA
<213> ORGANISM: Artificial sequence
<220> FEATURE:
<223> OTHER INFORMATION: Chemically synthesized

<400> SEQUENCE: 571
accugcccua aauaagaaa          19

<210> SEQ ID NO 572
<211> LENGTH: 19
<212> TYPE: RNA
<213> ORGANISM: Artificial sequence
<220> FEATURE:
<223> OTHER INFORMATION: Chemically synthesized

<400> SEQUENCE: 572
cccaccugcc cuaaauaag          19

<210> SEQ ID NO 573
<211> LENGTH: 19
<212> TYPE: RNA
<213> ORGANISM: Artificial sequence
<220> FEATURE:
<223> OTHER INFORMATION: Chemically synthesized

<400> SEQUENCE: 573
cucacugauu ggaacaaca          19

<210> SEQ ID NO 574

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 574
cucaggauuu cgacuuguu                                                   19

<210> SEQ ID NO 575
<211> LENGTH: 19
<212> TYPE: RNA
<213> ORGANISM: Artificial sequence
<220> FEATURE:
<223> OTHER INFORMATION: Chemically synthesized

<400> SEQUENCE: 575
gcucaggauu ucgacuugu                                                   19

<210> SEQ ID NO 576
<211> LENGTH: 19
<212> TYPE: RNA
<213> ORGANISM: Artificial sequence
<220> FEATURE:
<223> OTHER INFORMATION: Chemically synthesized

<400> SEQUENCE: 576
agcucaggau uucgacuug                                                   19

<210> SEQ ID NO 577
<211> LENGTH: 19
<212> TYPE: RNA
<213> ORGANISM: Artificial sequence
<220> FEATURE:
<223> OTHER INFORMATION: Chemically synthesized

<400> SEQUENCE: 577
aggagaacuc ugauccuca                                                   19

<210> SEQ ID NO 578
<211> LENGTH: 19
<212> TYPE: RNA
<213> ORGANISM: Artificial sequence
<220> FEATURE:
<223> OTHER INFORMATION: Chemically synthesized

<400> SEQUENCE: 578
ggcaguuuga gcagcaaga                                                   19

<210> SEQ ID NO 579
<211> LENGTH: 19
<212> TYPE: RNA
<213> ORGANISM: Artificial sequence
<220> FEATURE:
<223> OTHER INFORMATION: Chemically synthesized

<400> SEQUENCE: 579
ugagcuuaca cuuguguuu                                                   19

<210> SEQ ID NO 580
<211> LENGTH: 19
<212> TYPE: RNA
<213> ORGANISM: Artificial sequence
<220> FEATURE:
<223> OTHER INFORMATION: Chemically synthesized

<400> SEQUENCE: 580
```
uuugagcuua cacugugu                                                19

<210> SEQ ID NO 581
<211> LENGTH: 19
<212> TYPE: RNA
<213> ORGANISM: Artificial sequence
<220> FEATURE:
<223> OTHER INFORMATION: Chemically synthesized

<400> SEQUENCE: 581
gugugugauu cuagcgucg                                               19

<210> SEQ ID NO 582
<211> LENGTH: 19
<212> TYPE: RNA
<213> ORGANISM: Artificial sequence
<220> FEATURE:
<223> OTHER INFORMATION: Chemically synthesized

<400> SEQUENCE: 582
uuguguguga uucuagcgu                                               19

<210> SEQ ID NO 583
<211> LENGTH: 19
<212> TYPE: RNA
<213> ORGANISM: Artificial sequence
<220> FEATURE:
<223> OTHER INFORMATION: Chemically synthesized

<400> SEQUENCE: 583
uggauaggau uguguguga                                               19

<210> SEQ ID NO 584
<211> LENGTH: 19
<212> TYPE: RNA
<213> ORGANISM: Artificial sequence
<220> FEATURE:
<223> OTHER INFORMATION: Chemically synthesized

<400> SEQUENCE: 584
aaaagcugga uaggauugu                                               19

<210> SEQ ID NO 585
<211> LENGTH: 19
<212> TYPE: RNA
<213> ORGANISM: Artificial sequence
<220> FEATURE:
<223> OTHER INFORMATION: Chemically synthesized

<400> SEQUENCE: 585
guauguaaaa agcuggaua                                               19

<210> SEQ ID NO 586
<211> LENGTH: 19
<212> TYPE: RNA
<213> ORGANISM: Artificial sequence
<220> FEATURE:
<223> OTHER INFORMATION: Chemically synthesized

<400> SEQUENCE: 586
auguauguaa aaagcugga                                               19

<210> SEQ ID NO 587
<211> LENGTH: 19
<212> TYPE: RNA

<213> ORGANISM: Artificial sequence
<220> FEATURE:
<223> OTHER INFORMATION: Chemically synthesized

<400> SEQUENCE: 587
cugacccaga gaauugcuc                                                    19

<210> SEQ ID NO 588
<211> LENGTH: 19
<212> TYPE: RNA
<213> ORGANISM: Artificial sequence
<220> FEATURE:
<223> OTHER INFORMATION: Chemically synthesized

<400> SEQUENCE: 588
augguugcaa cuggcaguu                                                    19

<210> SEQ ID NO 589
<211> LENGTH: 19
<212> TYPE: RNA
<213> ORGANISM: Artificial sequence
<220> FEATURE:
<223> OTHER INFORMATION: Chemically synthesized

<400> SEQUENCE: 589
uggaaggcug uuaaauuaa                                                    19

<210> SEQ ID NO 590
<211> LENGTH: 19
<212> TYPE: RNA
<213> ORGANISM: Artificial sequence
<220> FEATURE:
<223> OTHER INFORMATION: Chemically synthesized

<400> SEQUENCE: 590
gcuuauggaa ggcuguuaa                                                    19

<210> SEQ ID NO 591
<211> LENGTH: 19
<212> TYPE: RNA
<213> ORGANISM: Artificial sequence
<220> FEATURE:
<223> OTHER INFORMATION: Chemically synthesized

<400> SEQUENCE: 591
cugucugucc aaaucaaag                                                    19

<210> SEQ ID NO 592
<211> LENGTH: 19
<212> TYPE: RNA
<213> ORGANISM: Artificial sequence
<220> FEATURE:
<223> OTHER INFORMATION: Chemically synthesized

<400> SEQUENCE: 592
auguagaacu guuguccuu                                                    19

<210> SEQ ID NO 593
<211> LENGTH: 19
<212> TYPE: RNA
<213> ORGANISM: Artificial sequence
<220> FEATURE:
<223> OTHER INFORMATION: Chemically synthesized

<400> SEQUENCE: 593
gcaucgaugu agaacuguu                                                    19

<210> SEQ ID NO 594
<211> LENGTH: 19
<212> TYPE: RNA
<213> ORGANISM: Artificial sequence
<220> FEATURE:
<223> OTHER INFORMATION: Chemically synthesized

<400> SEQUENCE: 594
aauguuguuu ugcaugucu                                                    19

<210> SEQ ID NO 595
<211> LENGTH: 19
<212> TYPE: RNA
<213> ORGANISM: Artificial sequence
<220> FEATURE:
<223> OTHER INFORMATION: Chemically synthesized

<400> SEQUENCE: 595
ugggccaaga uaaaucaau                                                    19

<210> SEQ ID NO 596
<211> LENGTH: 19
<212> TYPE: RNA
<213> ORGANISM: Artificial sequence
<220> FEATURE:
<223> OTHER INFORMATION: Chemically synthesized

<400> SEQUENCE: 596
gaauugggcc aagauaaau                                                    19

<210> SEQ ID NO 597
<211> LENGTH: 19
<212> TYPE: RNA
<213> ORGANISM: Artificial sequence
<220> FEATURE:
<223> OTHER INFORMATION: Chemically synthesized

<400> SEQUENCE: 597
agaauugggc caagauaaa                                                    19

<210> SEQ ID NO 598
<211> LENGTH: 19
<212> TYPE: RNA
<213> ORGANISM: Artificial sequence
<220> FEATURE:
<223> OTHER INFORMATION: Chemically synthesized

<400> SEQUENCE: 598
cucuucaaau gcuuggaaa                                                    19

<210> SEQ ID NO 599
<211> LENGTH: 19
<212> TYPE: RNA
<213> ORGANISM: Artificial sequence
<220> FEATURE:
<223> OTHER INFORMATION: Chemically synthesized

<400> SEQUENCE: 599
acucuucaaa ugcuuggaa                                                    19

<210> SEQ ID NO 600
<211> LENGTH: 19
<212> TYPE: RNA
<213> ORGANISM: Artificial sequence
<220> FEATURE:

<223> OTHER INFORMATION: Chemically synthesized

<400> SEQUENCE: 600
gucacuguuc aaauuagcc                                                19

<210> SEQ ID NO 601
<211> LENGTH: 19
<212> TYPE: RNA
<213> ORGANISM: Artificial sequence
<220> FEATURE:
<223> OTHER INFORMATION: Chemically synthesized

<400> SEQUENCE: 601
gugaccuaaa augcacug                                                 19

<210> SEQ ID NO 602
<211> LENGTH: 19
<212> TYPE: RNA
<213> ORGANISM: Artificial sequence
<220> FEATURE:
<223> OTHER INFORMATION: Chemically synthesized

<400> SEQUENCE: 602
cugauacuau aagugaccu                                                19

<210> SEQ ID NO 603
<211> LENGTH: 19
<212> TYPE: RNA
<213> ORGANISM: Artificial sequence
<220> FEATURE:
<223> OTHER INFORMATION: Chemically synthesized

<400> SEQUENCE: 603
acugauacua uaagugacc                                                19

<210> SEQ ID NO 604
<211> LENGTH: 19
<212> TYPE: RNA
<213> ORGANISM: Artificial sequence
<220> FEATURE:
<223> OTHER INFORMATION: Chemically synthesized

<400> SEQUENCE: 604
uacugauacu auaagugac                                                19

<210> SEQ ID NO 605
<211> LENGTH: 19
<212> TYPE: RNA
<213> ORGANISM: Artificial sequence
<220> FEATURE:
<223> OTHER INFORMATION: Chemically synthesized

<400> SEQUENCE: 605
gauccuguua cugauacua                                                19

<210> SEQ ID NO 606
<211> LENGTH: 19
<212> TYPE: RNA
<213> ORGANISM: Artificial sequence
<220> FEATURE:
<223> OTHER INFORMATION: Chemically synthesized

<400> SEQUENCE: 606
ggugugaucc uguuacuga                                                19

```
<210> SEQ ID NO 607
<211> LENGTH: 19
<212> TYPE: RNA
<213> ORGANISM: Artificial sequence
<220> FEATURE:
<223> OTHER INFORMATION: Chemically synthesized

<400> SEQUENCE: 607
cugaaaaaca ggugugauc                                                19

<210> SEQ ID NO 608
<211> LENGTH: 19
<212> TYPE: RNA
<213> ORGANISM: Artificial sequence
<220> FEATURE:
<223> OTHER INFORMATION: Chemically synthesized

<400> SEQUENCE: 608
ugguguuacu gaaaaacag                                                19

<210> SEQ ID NO 609
<211> LENGTH: 19
<212> TYPE: RNA
<213> ORGANISM: Artificial sequence
<220> FEATURE:
<223> OTHER INFORMATION: Chemically synthesized

<400> SEQUENCE: 609
cugguguuac ugaaaaaca                                                19

<210> SEQ ID NO 610
<211> LENGTH: 19
<212> TYPE: RNA
<213> ORGANISM: Artificial sequence
<220> FEATURE:
<223> OTHER INFORMATION: Chemically synthesized

<400> SEQUENCE: 610
uccuggaguu acugaaaaa                                                19

<210> SEQ ID NO 611
<211> LENGTH: 19
<212> TYPE: RNA
<213> ORGANISM: Artificial sequence
<220> FEATURE:
<223> OTHER INFORMATION: Chemically synthesized

<400> SEQUENCE: 611
acagauguau ucauccugg                                                19

<210> SEQ ID NO 612
<211> LENGTH: 19
<212> TYPE: RNA
<213> ORGANISM: Artificial sequence
<220> FEATURE:
<223> OTHER INFORMATION: Chemically synthesized

<400> SEQUENCE: 612
gacagaugua uucauccug                                                19

<210> SEQ ID NO 613
<211> LENGTH: 19
<212> TYPE: RNA
<213> ORGANISM: Artificial sequence
<220> FEATURE:
<223> OTHER INFORMATION: Chemically synthesized
```

<400> SEQUENCE: 613
gcguagggac agauguauu					19

<210> SEQ ID NO 614
<211> LENGTH: 19
<212> TYPE: RNA
<213> ORGANISM: Artificial sequence
<220> FEATURE:
<223> OTHER INFORMATION: Chemically synthesized

<400> SEQUENCE: 614
uccugcccua gcuauuagc					19

<210> SEQ ID NO 615
<211> LENGTH: 19
<212> TYPE: RNA
<213> ORGANISM: Artificial sequence
<220> FEATURE:
<223> OTHER INFORMATION: Chemically synthesized

<400> SEQUENCE: 615
guggauaagg agcuuauuc					19

<210> SEQ ID NO 616
<211> LENGTH: 19
<212> TYPE: RNA
<213> ORGANISM: Artificial sequence
<220> FEATURE:
<223> OTHER INFORMATION: Chemically synthesized

<400> SEQUENCE: 616
ugcugugggu cguggauaa					19

<210> SEQ ID NO 617
<211> LENGTH: 19
<212> TYPE: RNA
<213> ORGANISM: Artificial sequence
<220> FEATURE:
<223> OTHER INFORMATION: Chemically synthesized

<400> SEQUENCE: 617
gaaucaacuu gccagaauu					19

<210> SEQ ID NO 618
<211> LENGTH: 19
<212> TYPE: RNA
<213> ORGANISM: Artificial sequence
<220> FEATURE:
<223> OTHER INFORMATION: Chemically synthesized

<400> SEQUENCE: 618
ccaacuaagu agaucauua					19

<210> SEQ ID NO 619
<211> LENGTH: 19
<212> TYPE: RNA
<213> ORGANISM: Artificial sequence
<220> FEATURE:
<223> OTHER INFORMATION: Chemically synthesized

<400> SEQUENCE: 619
aaaggccuua uuuuuguc					19

<210> SEQ ID NO 620
<211> LENGTH: 19

```
<212> TYPE: RNA
<213> ORGANISM: Artificial sequence
<220> FEATURE:
<223> OTHER INFORMATION: Chemically synthesized

<400> SEQUENCE: 620
ggaauaauaa aggccuuau                                                  19

<210> SEQ ID NO 621
<211> LENGTH: 19
<212> TYPE: RNA
<213> ORGANISM: Artificial sequence
<220> FEATURE:
<223> OTHER INFORMATION: Chemically synthesized

<400> SEQUENCE: 621
gggaauaaua aaggccuua                                                  19

<210> SEQ ID NO 622
<211> LENGTH: 19
<212> TYPE: RNA
<213> ORGANISM: Artificial sequence
<220> FEATURE:
<223> OTHER INFORMATION: Chemically synthesized

<400> SEQUENCE: 622
aaccaugcau gcacccaga                                                  19

<210> SEQ ID NO 623
<211> LENGTH: 19
<212> TYPE: RNA
<213> ORGANISM: Artificial sequence
<220> FEATURE:
<223> OTHER INFORMATION: Chemically synthesized

<400> SEQUENCE: 623
cagauaacca ugcaugcac                                                  19

<210> SEQ ID NO 624
<211> LENGTH: 19
<212> TYPE: RNA
<213> ORGANISM: Artificial sequence
<220> FEATURE:
<223> OTHER INFORMATION: Chemically synthesized

<400> SEQUENCE: 624
cucaccgucc agauaacca                                                  19

<210> SEQ ID NO 625
<211> LENGTH: 19
<212> TYPE: RNA
<213> ORGANISM: Artificial sequence
<220> FEATURE:
<223> OTHER INFORMATION: Chemically synthesized

<400> SEQUENCE: 625
augaaacuca ccguccaga                                                  19

<210> SEQ ID NO 626
<211> LENGTH: 19
<212> TYPE: RNA
<213> ORGANISM: Artificial sequence
<220> FEATURE:
<223> OTHER INFORMATION: Chemically synthesized

<400> SEQUENCE: 626
```
agagaaugaa acucaccgu                                          19

<210> SEQ ID NO 627
<211> LENGTH: 19
<212> TYPE: RNA
<213> ORGANISM: Artificial sequence
<220> FEATURE:
<223> OTHER INFORMATION: Chemically synthesized

<400> SEQUENCE: 627
guacagccua gagaaugaa                                          19

<210> SEQ ID NO 628
<211> LENGTH: 19
<212> TYPE: RNA
<213> ORGANISM: Artificial sequence
<220> FEATURE:
<223> OTHER INFORMATION: Chemically synthesized

<400> SEQUENCE: 628
augguuuaua guacagccu                                          19

<210> SEQ ID NO 629
<211> LENGTH: 19
<212> TYPE: RNA
<213> ORGANISM: Artificial sequence
<220> FEATURE:
<223> OTHER INFORMATION: Chemically synthesized

<400> SEQUENCE: 629
auggagauau gguuuauag                                          19

<210> SEQ ID NO 630
<211> LENGTH: 19
<212> TYPE: RNA
<213> ORGANISM: Artificial sequence
<220> FEATURE:
<223> OTHER INFORMATION: Chemically synthesized

<400> SEQUENCE: 630
uggcuaugga gauaugguu                                          19

<210> SEQ ID NO 631
<211> LENGTH: 19
<212> TYPE: RNA
<213> ORGANISM: Artificial sequence
<220> FEATURE:
<223> OTHER INFORMATION: Chemically synthesized

<400> SEQUENCE: 631
ugcauuggcu auggagaua                                          19

<210> SEQ ID NO 632
<211> LENGTH: 19
<212> TYPE: RNA
<213> ORGANISM: Artificial sequence
<220> FEATURE:
<223> OTHER INFORMATION: Chemically synthesized

<400> SEQUENCE: 632
guauacuacc acuuugaau                                          19

<210> SEQ ID NO 633
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 633
agcuguauac uaccacuuu                                                  19

<210> SEQ ID NO 634
<211> LENGTH: 19
<212> TYPE: RNA
<213> ORGANISM: Artificial sequence
<220> FEATURE:
<223> OTHER INFORMATION: Chemically synthesized

<400> SEQUENCE: 634
gguaguagcu guauacuac                                                  19

<210> SEQ ID NO 635
<211> LENGTH: 19
<212> TYPE: RNA
<213> ORGANISM: Artificial sequence
<220> FEATURE:
<223> OTHER INFORMATION: Chemically synthesized

<400> SEQUENCE: 635 caagguagu agcuguaua                                                   19

<210> SEQ ID NO 636
<211> LENGTH: 19
<212> TYPE: RNA
<213> ORGANISM: Artificial sequence
<220> FEATURE:
<223> OTHER INFORMATION: Chemically synthesized

<400> SEQUENCE: 636
uccuuaaccc caauuguca                                                  19

<210> SEQ ID NO 637
<211> LENGTH: 19
<212> TYPE: RNA
<213> ORGANISM: Artificial sequence
<220> FEATURE:
<223> OTHER INFORMATION: Chemically synthesized

<400> SEQUENCE: 637
aaguaucucu ccuuaaccc                                                  19

<210> SEQ ID NO 638
<211> LENGTH: 19
<212> TYPE: RNA
<213> ORGANISM: Artificial sequence
<220> FEATURE:
<223> OTHER INFORMATION: Chemically synthesized

<400> SEQUENCE: 638
ucugggaauu gaaguaucu                                                  19

<210> SEQ ID NO 639
<211> LENGTH: 19
<212> TYPE: RNA
<213> ORGANISM: Artificial sequence
<220> FEATURE:
<223> OTHER INFORMATION: Chemically synthesized

<400> SEQUENCE: 639 uuucuggaa uugaaguau                                                   19
```

<210> SEQ ID NO 640
<211> LENGTH: 19
<212> TYPE: RNA
<213> ORGANISM: Artificial sequence
<220> FEATURE:
<223> OTHER INFORMATION: Chemically synthesized

<400> SEQUENCE: 640
ggcaguguua ucucaucuc                                                19

<210> SEQ ID NO 641
<211> LENGTH: 19
<212> TYPE: RNA
<213> ORGANISM: Artificial sequence
<220> FEATURE:
<223> OTHER INFORMATION: Chemically synthesized

<400> SEQUENCE: 641
auggcagugu uaucucauc                                                19

<210> SEQ ID NO 642
<211> LENGTH: 19
<212> TYPE: RNA
<213> ORGANISM: Artificial sequence
<220> FEATURE:
<223> OTHER INFORMATION: Chemically synthesized

<400> SEQUENCE: 642
caccauggca guguuaucu                                                19

<210> SEQ ID NO 643
<211> LENGTH: 19
<212> TYPE: RNA
<213> ORGANISM: Artificial sequence
<220> FEATURE:
<223> OTHER INFORMATION: Chemically synthesized

<400> SEQUENCE: 643
ugcuuaaucu cagaugaac                                                19

<210> SEQ ID NO 644
<211> LENGTH: 19
<212> TYPE: RNA
<213> ORGANISM: Artificial sequence
<220> FEATURE:
<223> OTHER INFORMATION: Chemically synthesized

<400> SEQUENCE: 644
caugugcuua aucucagau                                                19

<210> SEQ ID NO 645
<211> LENGTH: 19
<212> TYPE: RNA
<213> ORGANISM: Artificial sequence
<220> FEATURE:
<223> OTHER INFORMATION: Chemically synthesized

<400> SEQUENCE: 645
uuacaugugc uuaaucuca                                                19

<210> SEQ ID NO 646
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 646
caguauuaca ugugcuuaa                                              19

<210> SEQ ID NO 647
<211> LENGTH: 19
<212> TYPE: RNA
<213> ORGANISM: Artificial sequence
<220> FEATURE:
<223> OTHER INFORMATION: Chemically synthesized

<400> SEQUENCE: 647
ucacuuagua aucuauccu                                              19

<210> SEQ ID NO 648
<211> LENGTH: 19
<212> TYPE: RNA
<213> ORGANISM: Artificial sequence
<220> FEATURE:
<223> OTHER INFORMATION: Chemically synthesized

<400> SEQUENCE: 648
cugugaggau aggaaauua                                              19

<210> SEQ ID NO 649
<211> LENGTH: 19
<212> TYPE: RNA
<213> ORGANISM: Artificial sequence
<220> FEATURE:
<223> OTHER INFORMATION: Chemically synthesized

<400> SEQUENCE: 649
aguguugaau acugucuuu                                              19

<210> SEQ ID NO 650
<211> LENGTH: 19
<212> TYPE: RNA
<213> ORGANISM: Artificial sequence
<220> FEATURE:
<223> OTHER INFORMATION: Chemically synthesized

<400> SEQUENCE: 650
uaaguguuga auacugucu                                              19

<210> SEQ ID NO 651
<211> LENGTH: 19
<212> TYPE: RNA
<213> ORGANISM: Artificial sequence
<220> FEATURE:
<223> OTHER INFORMATION: Chemically synthesized

<400> SEQUENCE: 651
cuguucuuaa guguugaau                                              19

<210> SEQ ID NO 652
<211> LENGTH: 19
<212> TYPE: RNA
<213> ORGANISM: Artificial sequence
<220> FEATURE:
<223> OTHER INFORMATION: Chemically synthesized

<400> SEQUENCE: 652
ccuguucuua aguguugaa                                              19

<210> SEQ ID NO 653
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 653
gaugccuuua uaagcucag                                                  19

<210> SEQ ID NO 654
<211> LENGTH: 19
<212> TYPE: RNA
<213> ORGANISM: Artificial sequence
<220> FEATURE:
<223> OTHER INFORMATION: Chemically synthesized

<400> SEQUENCE: 654
uagaugccuu uauaagcuc                                                  19

<210> SEQ ID NO 655
<211> LENGTH: 19
<212> TYPE: RNA
<213> ORGANISM: Artificial sequence
<220> FEATURE:
<223> OTHER INFORMATION: Chemically synthesized

<400> SEQUENCE: 655
gguguuguuu uagaugccu                                                  19

<210> SEQ ID NO 656
<211> LENGTH: 19
<212> TYPE: RNA
<213> ORGANISM: Artificial sequence
<220> FEATURE:
<223> OTHER INFORMATION: Chemically synthesized

<400> SEQUENCE: 656
uaaagaggca acaaaagcu                                                  19

<210> SEQ ID NO 657
<211> LENGTH: 19
<212> TYPE: RNA
<213> ORGANISM: Artificial sequence
<220> FEATURE:
<223> OTHER INFORMATION: Chemically synthesized

<400> SEQUENCE: 657
guuuuaaaga ggcaacaaa                                                  19

<210> SEQ ID NO 658
<211> LENGTH: 19
<212> TYPE: RNA
<213> ORGANISM: Artificial sequence
<220> FEATURE:
<223> OTHER INFORMATION: Chemically synthesized

<400> SEQUENCE: 658
auguuuuaaa gaggcaaca                                                  19

<210> SEQ ID NO 659
<211> LENGTH: 19
<212> TYPE: RNA
<213> ORGANISM: Artificial sequence
<220> FEATURE:
<223> OTHER INFORMATION: Chemically synthesized

<400> SEQUENCE: 659
```
gcuucacugu uucuuggug                                           19

<210> SEQ ID NO 660
<211> LENGTH: 19
<212> TYPE: RNA
<213> ORGANISM: Artificial sequence
<220> FEATURE:
<223> OTHER INFORMATION: Chemically synthesized

<400> SEQUENCE: 660
gagaaauauu acggcaaua                                           19

<210> SEQ ID NO 661
<211> LENGTH: 19
<212> TYPE: RNA
<213> ORGANISM: Artificial sequence
<220> FEATURE:
<223> OTHER INFORMATION: Chemically synthesized

<400> SEQUENCE: 661
acucaaauuu gaagguuu                                            19

<210> SEQ ID NO 662
<211> LENGTH: 19
<212> TYPE: RNA
<213> ORGANISM: Artificial sequence
<220> FEATURE:
<223> OTHER INFORMATION: Chemically synthesized

<400> SEQUENCE: 662
aagugauuuu gacuacugg                                           19

<210> SEQ ID NO 663
<211> LENGTH: 19
<212> TYPE: RNA
<213> ORGANISM: Artificial sequence
<220> FEATURE:
<223> OTHER INFORMATION: Chemically synthesized

<400> SEQUENCE: 663
uaagugauuu ugacuacug                                           19

<210> SEQ ID NO 664
<211> LENGTH: 19
<212> TYPE: RNA
<213> ORGANISM: Artificial sequence
<220> FEATURE:
<223> OTHER INFORMATION: Chemically synthesized

<400> SEQUENCE: 664
cacagaauca uacuaaaug                                           19

<210> SEQ ID NO 665
<211> LENGTH: 19
<212> TYPE: RNA
<213> ORGANISM: Artificial sequence
<220> FEATURE:
<223> OTHER INFORMATION: Chemically synthesized

<400> SEQUENCE: 665
gcuaagugau uuugacuac                                           19

<210> SEQ ID NO 666
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 666
cagguaggcu ugguaauag                                               19

<210> SEQ ID NO 667
<211> LENGTH: 19
<212> TYPE: RNA
<213> ORGANISM: Artificial sequence
<220> FEATURE:
<223> OTHER INFORMATION: Chemically synthesized

<400> SEQUENCE: 667
ugggauggaa uagguaagc                                               19

<210> SEQ ID NO 668
<211> LENGTH: 19
<212> TYPE: RNA
<213> ORGANISM: Artificial sequence
<220> FEATURE:
<223> OTHER INFORMATION: Chemically synthesized

<400> SEQUENCE: 668
augggaugga auagguaag                                               19

<210> SEQ ID NO 669
<211> LENGTH: 19
<212> TYPE: RNA
<213> ORGANISM: Artificial sequence
<220> FEATURE:
<223> OTHER INFORMATION: Chemically synthesized

<400> SEQUENCE: 669
uagucucuuu ucuuucugu                                               19

<210> SEQ ID NO 670
<211> LENGTH: 19
<212> TYPE: RNA
<213> ORGANISM: Artificial sequence
<220> FEATURE:
<223> OTHER INFORMATION: Chemically synthesized

<400> SEQUENCE: 670
aagaaacccc aaauguagu                                               19

<210> SEQ ID NO 671
<211> LENGTH: 19
<212> TYPE: RNA
<213> ORGANISM: Artificial sequence
<220> FEATURE:
<223> OTHER INFORMATION: Chemically synthesized

<400> SEQUENCE: 671
cccuaaauaa gaaacccca                                               19

<210> SEQ ID NO 672
<211> LENGTH: 19
<212> TYPE: RNA
<213> ORGANISM: Artificial sequence
<220> FEATURE:
<223> OTHER INFORMATION: Chemically synthesized

<400> SEQUENCE: 672
gaacaacagu gauugaagg                                               19
```

<210> SEQ ID NO 673
<211> LENGTH: 19
<212> TYPE: RNA
<213> ORGANISM: Artificial sequence
<220> FEATURE:
<223> OTHER INFORMATION: Chemically synthesized

<400> SEQUENCE: 673
cugauuggaa caacaguga                                                    19

<210> SEQ ID NO 674
<211> LENGTH: 19
<212> TYPE: RNA
<213> ORGANISM: Artificial sequence
<220> FEATURE:
<223> OTHER INFORMATION: Chemically synthesized

<400> SEQUENCE: 674
gauccucagc ucaggauuu                                                    19

<210> SEQ ID NO 675
<211> LENGTH: 19
<212> TYPE: RNA
<213> ORGANISM: Artificial sequence
<220> FEATURE:
<223> OTHER INFORMATION: Chemically synthesized

<400> SEQUENCE: 675
uucaggagaa cucugaucc                                                    19

<210> SEQ ID NO 676
<211> LENGTH: 19
<212> TYPE: RNA
<213> ORGANISM: Artificial sequence
<220> FEATURE:
<223> OTHER INFORMATION: Chemically synthesized

<400> SEQUENCE: 676
uaguagaggu cgcuucucc                                                    19

<210> SEQ ID NO 677
<211> LENGTH: 19
<212> TYPE: RNA
<213> ORGANISM: Artificial sequence
<220> FEATURE:
<223> OTHER INFORMATION: Chemically synthesized

<400> SEQUENCE: 677
gcuucaggga cuuuuucuu                                                    19

<210> SEQ ID NO 678
<211> LENGTH: 19
<212> TYPE: RNA
<213> ORGANISM: Artificial sequence
<220> FEATURE:
<223> OTHER INFORMATION: Chemically synthesized

<400> SEQUENCE: 678
aagcaggaga acugcucau                                                    19

<210> SEQ ID NO 679
<211> LENGTH: 19
<212> TYPE: RNA
<213> ORGANISM: Artificial sequence
<220> FEATURE:

<223> OTHER INFORMATION: Chemically synthesized

<400> SEQUENCE: 679
gagcuuacac uuguguuua    19

<210> SEQ ID NO 680
<211> LENGTH: 19
<212> TYPE: RNA
<213> ORGANISM: Artificial sequence
<220> FEATURE:
<223> OTHER INFORMATION: Chemically synthesized

<400> SEQUENCE: 680
gugugauucu agcgucgua    19

<210> SEQ ID NO 681
<211> LENGTH: 19
<212> TYPE: RNA
<213> ORGANISM: Artificial sequence
<220> FEATURE:
<223> OTHER INFORMATION: Chemically synthesized

<400> SEQUENCE: 681
aggauugugu gugauucua    19

<210> SEQ ID NO 682
<211> LENGTH: 19
<212> TYPE: RNA
<213> ORGANISM: Artificial sequence
<220> FEATURE:
<223> OTHER INFORMATION: Chemically synthesized

<400> SEQUENCE: 682
gguccuuguc ccugagaaa    19

<210> SEQ ID NO 683
<211> LENGTH: 19
<212> TYPE: RNA
<213> ORGANISM: Artificial sequence
<220> FEATURE:
<223> OTHER INFORMATION: Chemically synthesized

<400> SEQUENCE: 683
acaaaauggu gauggcuua    19

<210> SEQ ID NO 684
<211> LENGTH: 19
<212> TYPE: RNA
<213> ORGANISM: Artificial sequence
<220> FEATURE:
<223> OTHER INFORMATION: Chemically synthesized

<400> SEQUENCE: 684
cucucuugcc uguuaugcu    19

<210> SEQ ID NO 685
<211> LENGTH: 19
<212> TYPE: RNA
<213> ORGANISM: Artificial sequence
<220> FEATURE:
<223> OTHER INFORMATION: Chemically synthesized

<400> SEQUENCE: 685
aucuuugacu cucuugccu    19

```
<210> SEQ ID NO 686
<211> LENGTH: 19
<212> TYPE: RNA
<213> ORGANISM: Artificial sequence
<220> FEATURE:
<223> OTHER INFORMATION: Chemically synthesized

<400> SEQUENCE: 686
uuccacuaac aguuaucuu                                                19

<210> SEQ ID NO 687
<211> LENGTH: 19
<212> TYPE: RNA
<213> ORGANISM: Artificial sequence
<220> FEATURE:
<223> OTHER INFORMATION: Chemically synthesized

<400> SEQUENCE: 687
ucgauguaga acuguuguc                                                19

<210> SEQ ID NO 688
<211> LENGTH: 19
<212> TYPE: RNA
<213> ORGANISM: Artificial sequence
<220> FEATURE:
<223> OTHER INFORMATION: Chemically synthesized

<400> SEQUENCE: 688
ucuugggcau cgauguaga                                                19

<210> SEQ ID NO 689
<211> LENGTH: 19
<212> TYPE: RNA
<213> ORGANISM: Artificial sequence
<220> FEATURE:
<223> OTHER INFORMATION: Chemically synthesized

<400> SEQUENCE: 689
aaggcuucuu gggcaucga                                                19

<210> SEQ ID NO 690
<211> LENGTH: 19
<212> TYPE: RNA
<213> ORGANISM: Artificial sequence
<220> FEATURE:
<223> OTHER INFORMATION: Chemically synthesized

<400> SEQUENCE: 690
gucuauuguu aagcuccaa                                                19

<210> SEQ ID NO 691
<211> LENGTH: 19
<212> TYPE: RNA
<213> ORGANISM: Artificial sequence
<220> FEATURE:
<223> OTHER INFORMATION: Chemically synthesized

<400> SEQUENCE: 691
ugucuauugu uaagcucca                                                19

<210> SEQ ID NO 692
<211> LENGTH: 19
<212> TYPE: RNA
<213> ORGANISM: Artificial sequence
<220> FEATURE:
<223> OTHER INFORMATION: Chemically synthesized
```

<400> SEQUENCE: 692
ugcaugucua uuguuaagc                                           19

<210> SEQ ID NO 693
<211> LENGTH: 19
<212> TYPE: RNA
<213> ORGANISM: Artificial sequence
<220> FEATURE:
<223> OTHER INFORMATION: Chemically synthesized

<400> SEQUENCE: 693
uguuuugcau gucuauugu                                           19

<210> SEQ ID NO 694
<211> LENGTH: 19
<212> TYPE: RNA
<213> ORGANISM: Artificial sequence
<220> FEATURE:
<223> OTHER INFORMATION: Chemically synthesized

<400> SEQUENCE: 694
uuguuuugca ugucuauug                                           19

<210> SEQ ID NO 695
<211> LENGTH: 19
<212> TYPE: RNA
<213> ORGANISM: Artificial sequence
<220> FEATURE:
<223> OTHER INFORMATION: Chemically synthesized

<400> SEQUENCE: 695
agugaccuaa aaugucacu                                           19

<210> SEQ ID NO 696
<211> LENGTH: 19
<212> TYPE: RNA
<213> ORGANISM: Artificial sequence
<220> FEATURE:
<223> OTHER INFORMATION: Chemically synthesized

<400> SEQUENCE: 696
guuacugaua cuauaagug                                           19

<210> SEQ ID NO 697
<211> LENGTH: 19
<212> TYPE: RNA
<213> ORGANISM: Artificial sequence
<220> FEATURE:
<223> OTHER INFORMATION: Chemically synthesized

<400> SEQUENCE: 697
aaacaggugu gauccuguu                                           19

<210> SEQ ID NO 698
<211> LENGTH: 19
<212> TYPE: RNA
<213> ORGANISM: Artificial sequence
<220> FEATURE:
<223> OTHER INFORMATION: Chemically synthesized

<400> SEQUENCE: 698
ucauccuggu guuacugaa                                           19

<210> SEQ ID NO 699
<211> LENGTH: 19

```
<212> TYPE: RNA
<213> ORGANISM: Artificial sequence
<220> FEATURE:
<223> OTHER INFORMATION: Chemically synthesized

<400> SEQUENCE: 699
gauguauuca uccuggugu                                                   19

<210> SEQ ID NO 700
<211> LENGTH: 19
<212> TYPE: RNA
<213> ORGANISM: Artificial sequence
<220> FEATURE:
<223> OTHER INFORMATION: Chemically synthesized

<400> SEQUENCE: 700
cuagcuauua gcuccacuu                                                   19

<210> SEQ ID NO 701
<211> LENGTH: 19
<212> TYPE: RNA
<213> ORGANISM: Artificial sequence
<220> FEATURE:
<223> OTHER INFORMATION: Chemically synthesized

<400> SEQUENCE: 701
uaaggagcuu auucagguu                                                   19

<210> SEQ ID NO 702
<211> LENGTH: 19
<212> TYPE: RNA
<213> ORGANISM: Artificial sequence
<220> FEATURE:
<223> OTHER INFORMATION: Chemically synthesized

<400> SEQUENCE: 702
gucguggaua aggagcuua                                                   19

<210> SEQ ID NO 703
<211> LENGTH: 19
<212> TYPE: RNA
<213> ORGANISM: Artificial sequence
<220> FEATURE:
<223> OTHER INFORMATION: Chemically synthesized

<400> SEQUENCE: 703
ugugggucgu ggauaagga                                                   19

<210> SEQ ID NO 704
<211> LENGTH: 19
<212> TYPE: RNA
<213> ORGANISM: Artificial sequence
<220> FEATURE:
<223> OTHER INFORMATION: Chemically synthesized

<400> SEQUENCE: 704
uucauauccu ugcuguggg                                                   19

<210> SEQ ID NO 705
<211> LENGTH: 19
<212> TYPE: RNA
<213> ORGANISM: Artificial sequence
<220> FEATURE:
<223> OTHER INFORMATION: Chemically synthesized

<400> SEQUENCE: 705
```
uaaugagaga auuuagccu 19

<210> SEQ ID NO 706
<211> LENGTH: 19
<212> TYPE: RNA
<213> ORGANISM: Artificial sequence
<220> FEATURE:
<223> OTHER INFORMATION: Chemically synthesized

<400> SEQUENCE: 706
guuaaugaga gaauuuagc 19

<210> SEQ ID NO 707
<211> LENGTH: 19
<212> TYPE: RNA
<213> ORGANISM: Artificial sequence
<220> FEATURE:
<223> OTHER INFORMATION: Chemically synthesized

<400> SEQUENCE: 707
cuuauuccaa cuaaguaga 19

<210> SEQ ID NO 708
<211> LENGTH: 19
<212> TYPE: RNA
<213> ORGANISM: Artificial sequence
<220> FEATURE:
<223> OTHER INFORMATION: Chemically synthesized

<400> SEQUENCE: 708
uugucuuauu ccaacuaag 19

<210> SEQ ID NO 709
<211> LENGTH: 19
<212> TYPE: RNA
<213> ORGANISM: Artificial sequence
<220> FEATURE:
<223> OTHER INFORMATION: Chemically synthesized

<400> SEQUENCE: 709
gucacuaggg aauaauaaa 19

<210> SEQ ID NO 710
<211> LENGTH: 19
<212> TYPE: RNA
<213> ORGANISM: Artificial sequence
<220> FEATURE:
<223> OTHER INFORMATION: Chemically synthesized

<400> SEQUENCE: 710
cugucacuag ggaauaaua 19

<210> SEQ ID NO 711
<211> LENGTH: 19
<212> TYPE: RNA
<213> ORGANISM: Artificial sequence
<220> FEATURE:
<223> OTHER INFORMATION: Chemically synthesized

<400> SEQUENCE: 711
cguccagaua accaugcau 19

<210> SEQ ID NO 712
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 712
uagagaauga aacucaccg                                              19

<210> SEQ ID NO 713
<211> LENGTH: 19
<212> TYPE: RNA
<213> ORGANISM: Artificial sequence
<220> FEATURE:
<223> OTHER INFORMATION: Chemically synthesized

<400> SEQUENCE: 713
cuaccacuuu gaauuauug                                              19

<210> SEQ ID NO 714
<211> LENGTH: 19
<212> TYPE: RNA
<213> ORGANISM: Artificial sequence
<220> FEATURE:
<223> OTHER INFORMATION: Chemically synthesized

<400> SEQUENCE: 714
ugucaagggu aguagcugu                                              19

<210> SEQ ID NO 715
<211> LENGTH: 19
<212> TYPE: RNA
<213> ORGANISM: Artificial sequence
<220> FEATURE:
<223> OTHER INFORMATION: Chemically synthesized

<400> SEQUENCE: 715
cucuccuuaa ccccaauug                                              19

<210> SEQ ID NO 716
<211> LENGTH: 19
<212> TYPE: RNA
<213> ORGANISM: Artificial sequence
<220> FEATURE:
<223> OTHER INFORMATION: Chemically synthesized

<400> SEQUENCE: 716
gaugaaccau uucaccaug                                              19

<210> SEQ ID NO 717
<211> LENGTH: 19
<212> TYPE: RNA
<213> ORGANISM: Artificial sequence
<220> FEATURE:
<223> OTHER INFORMATION: Chemically synthesized

<400> SEQUENCE: 717
uuucaguauu acaugugcu                                              19

<210> SEQ ID NO 718
<211> LENGTH: 19
<212> TYPE: RNA
<213> ORGANISM: Artificial sequence
<220> FEATURE:
<223> OTHER INFORMATION: Chemically synthesized

<400> SEQUENCE: 718
uuccugaacc caaccucaa                                              19
```

```
<210> SEQ ID NO 719
<211> LENGTH: 19
<212> TYPE: RNA
<213> ORGANISM: Artificial sequence
<220> FEATURE:
<223> OTHER INFORMATION: Chemically synthesized

<400> SEQUENCE: 719
guaaucuauc cucuuuuca                                                   19

<210> SEQ ID NO 720
<211> LENGTH: 19
<212> TYPE: RNA
<213> ORGANISM: Artificial sequence
<220> FEATURE:
<223> OTHER INFORMATION: Chemically synthesized

<400> SEQUENCE: 720
uuguuccuga acccaaccu                                                   19

<210> SEQ ID NO 721
<211> LENGTH: 19
<212> TYPE: RNA
<213> ORGANISM: Artificial sequence
<220> FEATURE:
<223> OTHER INFORMATION: Chemically synthesized

<400> SEQUENCE: 721
ggaaauuagu ucugagauc                                                   19

<210> SEQ ID NO 722
<211> LENGTH: 19
<212> TYPE: RNA
<213> ORGANISM: Artificial sequence
<220> FEATURE:
<223> OTHER INFORMATION: Chemically synthesized

<400> SEQUENCE: 722
aggauaggaa auuaguucu                                                   19

<210> SEQ ID NO 723
<211> LENGTH: 19
<212> TYPE: RNA
<213> ORGANISM: Artificial sequence
<220> FEATURE:
<223> OTHER INFORMATION: Chemically synthesized

<400> SEQUENCE: 723
ugugaggaua ggaaauuag                                                   19

<210> SEQ ID NO 724
<211> LENGTH: 19
<212> TYPE: RNA
<213> ORGANISM: Artificial sequence
<220> FEATURE:
<223> OTHER INFORMATION: Chemically synthesized

<400> SEQUENCE: 724
ccugugagga uaggaaauu                                                   19

<210> SEQ ID NO 725
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 725
cugauauuuu uguguguag                                                19

<210> SEQ ID NO 726
<211> LENGTH: 19
<212> TYPE: RNA
<213> ORGANISM: Artificial sequence
<220> FEATURE:
<223> OTHER INFORMATION: Chemically synthesized

<400> SEQUENCE: 726
guucuuaagu guugaauac                                                19

<210> SEQ ID NO 727
<211> LENGTH: 19
<212> TYPE: RNA
<213> ORGANISM: Artificial sequence
<220> FEATURE:
<223> OTHER INFORMATION: Chemically synthesized

<400> SEQUENCE: 727
acugggauua uguuguucc                                                19

<210> SEQ ID NO 728
<211> LENGTH: 19
<212> TYPE: RNA
<213> ORGANISM: Artificial sequence
<220> FEATURE:
<223> OTHER INFORMATION: Chemically synthesized

<400> SEQUENCE: 728
ggugacuucc ucacucuaa                                                19

<210> SEQ ID NO 729
<211> LENGTH: 19
<212> TYPE: RNA
<213> ORGANISM: Artificial sequence
<220> FEATURE:
<223> OTHER INFORMATION: Chemically synthesized

<400> SEQUENCE: 729
uuggugacuu ccucacucu                                                19

<210> SEQ ID NO 730
<211> LENGTH: 19
<212> TYPE: RNA
<213> ORGANISM: Artificial sequence
<220> FEATURE:
<223> OTHER INFORMATION: Chemically synthesized

<400> SEQUENCE: 730
cacuguuucu uggugacuu                                                19

<210> SEQ ID NO 731
<211> LENGTH: 19
<212> TYPE: RNA
<213> ORGANISM: Artificial sequence
<220> FEATURE:
<223> OTHER INFORMATION: Chemically synthesized

<400> SEQUENCE: 731
cuucacuguu ucuuggugA                                                19

<210> SEQ ID NO 732
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 732
uauuacggca auaauggaa                                              19

<210> SEQ ID NO 733
<211> LENGTH: 19
<212> TYPE: RNA
<213> ORGANISM: Artificial sequence
<220> FEATURE:
<223> OTHER INFORMATION: Chemically synthesized

<400> SEQUENCE: 733
uagguaagag uaaaugaga                                              19

<210> SEQ ID NO 734
<211> LENGTH: 19
<212> TYPE: RNA
<213> ORGANISM: Artificial sequence
<220> FEATURE:
<223> OTHER INFORMATION: Chemically synthesized

<400> SEQUENCE: 734
cccuagguaa gaguaaaug                                              19

<210> SEQ ID NO 735
<211> LENGTH: 19
<212> TYPE: RNA
<213> ORGANISM: Artificial sequence
<220> FEATURE:
<223> OTHER INFORMATION: Chemically synthesized

<400> SEQUENCE: 735
uuagacagga agguaggau                                              19

<210> SEQ ID NO 736
<211> LENGTH: 19
<212> TYPE: RNA
<213> ORGANISM: Artificial sequence
<220> FEATURE:
<223> OTHER INFORMATION: Chemically synthesized

<400> SEQUENCE: 736
cuaagugauu uugacuacu                                              19

<210> SEQ ID NO 737
<211> LENGTH: 19
<212> TYPE: RNA
<213> ORGANISM: Artificial sequence
<220> FEATURE:
<223> OTHER INFORMATION: Chemically synthesized

<400> SEQUENCE: 737
agaagcccau uugaguuuu                                              19

<210> SEQ ID NO 738
<211> LENGTH: 19
<212> TYPE: RNA
<213> ORGANISM: Artificial sequence
<220> FEATURE:
<223> OTHER INFORMATION: Chemically synthesized

<400> SEQUENCE: 738
```
guagaagccc auuugaguu                                               19

<210> SEQ ID NO 739
<211> LENGTH: 19
<212> TYPE: RNA
<213> ORGANISM: Artificial sequence
<220> FEATURE:
<223> OTHER INFORMATION: Chemically synthesized

<400> SEQUENCE: 739
aaguagaagc ccauuugag                                               19

<210> SEQ ID NO 740
<211> LENGTH: 19
<212> TYPE: RNA
<213> ORGANISM: Artificial sequence
<220> FEATURE:
<223> OTHER INFORMATION: Chemically synthesized

<400> SEQUENCE: 740
caaaaguaga agcccauuu                                               19

<210> SEQ ID NO 741
<211> LENGTH: 19
<212> TYPE: RNA
<213> ORGANISM: Artificial sequence
<220> FEATURE:
<223> OTHER INFORMATION: Chemically synthesized

<400> SEQUENCE: 741
agccugcuaa gugauuuug                                               19

<210> SEQ ID NO 742
<211> LENGTH: 19
<212> TYPE: RNA
<213> ORGANISM: Artificial sequence
<220> FEATURE:
<223> OTHER INFORMATION: Chemically synthesized

<400> SEQUENCE: 742
gguaagcaaa aguagaagc                                               19

<210> SEQ ID NO 743
<211> LENGTH: 19
<212> TYPE: RNA
<213> ORGANISM: Artificial sequence
<220> FEATURE:
<223> OTHER INFORMATION: Chemically synthesized

<400> SEQUENCE: 743
agguaagcaa aaguagaag                                               19

<210> SEQ ID NO 744
<211> LENGTH: 19
<212> TYPE: RNA
<213> ORGANISM: Artificial sequence
<220> FEATURE:
<223> OTHER INFORMATION: Chemically synthesized

<400> SEQUENCE: 744
uggaauaggu aagcaaaag                                               19

<210> SEQ ID NO 745
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 745 auggauagg uaagcaaaa                                                19

<210> SEQ ID NO 746
<211> LENGTH: 19
<212> TYPE: RNA
<213> ORGANISM: Artificial sequence
<220> FEATURE:
<223> OTHER INFORMATION: Chemically synthesized

<400> SEQUENCE: 746
uugaauggga uggaauagg                                               19

<210> SEQ ID NO 747
<211> LENGTH: 19
<212> TYPE: RNA
<213> ORGANISM: Artificial sequence
<220> FEATURE:
<223> OTHER INFORMATION: Chemically synthesized

<400> SEQUENCE: 747
agagccugcu aagugauuu                                               19

<210> SEQ ID NO 748
<211> LENGTH: 19
<212> TYPE: RNA
<213> ORGANISM: Artificial sequence
<220> FEATURE:
<223> OTHER INFORMATION: Chemically synthesized

<400> SEQUENCE: 748
ucugcauaga ucccauuuu                                               19

<210> SEQ ID NO 749
<211> LENGTH: 19
<212> TYPE: RNA
<213> ORGANISM: Artificial sequence
<220> FEATURE:
<223> OTHER INFORMATION: Chemically synthesized

<400> SEQUENCE: 749
uucuggccuu uggagaagu                                               19

<210> SEQ ID NO 750
<211> LENGTH: 19
<212> TYPE: RNA
<213> ORGANISM: Artificial sequence
<220> FEATURE:
<223> OTHER INFORMATION: Chemically synthesized

<400> SEQUENCE: 750
uuucuguguu ucacauuca                                               19

<210> SEQ ID NO 751
<211> LENGTH: 19
<212> TYPE: RNA
<213> ORGANISM: Artificial sequence
<220> FEATURE:
<223> OTHER INFORMATION: Chemically synthesized

<400> SEQUENCE: 751
guagucucuu uucuuucug                                               19
```

<210> SEQ ID NO 752
<211> LENGTH: 19
<212> TYPE: RNA
<213> ORGANISM: Artificial sequence
<220> FEATURE:
<223> OTHER INFORMATION: Chemically synthesized

<400> SEQUENCE: 752 gaaacccaa auguagucu                                                   19

<210> SEQ ID NO 753
<211> LENGTH: 19
<212> TYPE: RNA
<213> ORGANISM: Artificial sequence
<220> FEATURE:
<223> OTHER INFORMATION: Chemically synthesized

<400> SEQUENCE: 753
guaguaaaac uauucagcu                                                  19

<210> SEQ ID NO 754
<211> LENGTH: 19
<212> TYPE: RNA
<213> ORGANISM: Artificial sequence
<220> FEATURE:
<223> OTHER INFORMATION: Chemically synthesized

<400> SEQUENCE: 754
gguaguaaaa cuauucagc                                                  19

<210> SEQ ID NO 755
<211> LENGTH: 19
<212> TYPE: RNA
<213> ORGANISM: Artificial sequence
<220> FEATURE:
<223> OTHER INFORMATION: Chemically synthesized

<400> SEQUENCE: 755
gauuggaaca acagugauu                                                  19

<210> SEQ ID NO 756
<211> LENGTH: 19
<212> TYPE: RNA
<213> ORGANISM: Artificial sequence
<220> FEATURE:
<223> OTHER INFORMATION: Chemically synthesized

<400> SEQUENCE: 756
uacucacuga uuggaacaa                                                  19

<210> SEQ ID NO 757
<211> LENGTH: 19
<212> TYPE: RNA
<213> ORGANISM: Artificial sequence
<220> FEATURE:
<223> OTHER INFORMATION: Chemically synthesized

<400> SEQUENCE: 757
gauuucgacu uguuaagaa                                                  19

<210> SEQ ID NO 758
<211> LENGTH: 19
<212> TYPE: RNA
<213> ORGANISM: Artificial sequence
<220> FEATURE:

<223> OTHER INFORMATION: Chemically synthesized

<400> SEQUENCE: 758
aggauuucga cuuguuaag                      19

<210> SEQ ID NO 759
<211> LENGTH: 19
<212> TYPE: RNA
<213> ORGANISM: Artificial sequence
<220> FEATURE:
<223> OTHER INFORMATION: Chemically synthesized

<400> SEQUENCE: 759
ucaggagaac ucugauccu                      19

<210> SEQ ID NO 760
<211> LENGTH: 19
<212> TYPE: RNA
<213> ORGANISM: Artificial sequence
<220> FEATURE:
<223> OTHER INFORMATION: Chemically synthesized

<400> SEQUENCE: 760
ggacuagcuu cagggacuu                      19

<210> SEQ ID NO 761
<211> LENGTH: 19
<212> TYPE: RNA
<213> ORGANISM: Artificial sequence
<220> FEATURE:
<223> OTHER INFORMATION: Chemically synthesized

<400> SEQUENCE: 761
cucauggacu agcuucagg                      19

<210> SEQ ID NO 762
<211> LENGTH: 19
<212> TYPE: RNA
<213> ORGANISM: Artificial sequence
<220> FEATURE:
<223> OTHER INFORMATION: Chemically synthesized

<400> SEQUENCE: 762
gagaacugcu cauggacua                      19

<210> SEQ ID NO 763
<211> LENGTH: 19
<212> TYPE: RNA
<213> ORGANISM: Artificial sequence
<220> FEATURE:
<223> OTHER INFORMATION: Chemically synthesized

<400> SEQUENCE: 763
ggagaacugc ucauggacu                      19

<210> SEQ ID NO 764
<211> LENGTH: 19
<212> TYPE: RNA
<213> ORGANISM: Artificial sequence
<220> FEATURE:
<223> OTHER INFORMATION: Chemically synthesized

<400> SEQUENCE: 764
caggagaacu gcucaugga                      19

```
<210> SEQ ID NO 765
<211> LENGTH: 19
<212> TYPE: RNA
<213> ORGANISM: Artificial sequence
<220> FEATURE:
<223> OTHER INFORMATION: Chemically synthesized

<400> SEQUENCE: 765
gcuuacacuu guguuuaag                                                19

<210> SEQ ID NO 766
<211> LENGTH: 19
<212> TYPE: RNA
<213> ORGANISM: Artificial sequence
<220> FEATURE:
<223> OTHER INFORMATION: Chemically synthesized

<400> SEQUENCE: 766
ggauugugug ugauucuag                                                19

<210> SEQ ID NO 767
<211> LENGTH: 19
<212> TYPE: RNA
<213> ORGANISM: Artificial sequence
<220> FEATURE:
<223> OTHER INFORMATION: Chemically synthesized

<400> SEQUENCE: 767
ggauaggauu gugugugau                                                19

<210> SEQ ID NO 768
<211> LENGTH: 19
<212> TYPE: RNA
<213> ORGANISM: Artificial sequence
<220> FEATURE:
<223> OTHER INFORMATION: Chemically synthesized

<400> SEQUENCE: 768
gguugcaacu ggcaguuug                                                19

<210> SEQ ID NO 769
<211> LENGTH: 19
<212> TYPE: RNA
<213> ORGANISM: Artificial sequence
<220> FEATURE:
<223> OTHER INFORMATION: Chemically synthesized

<400> SEQUENCE: 769
uaaacuuggu ugcucaaag                                                19

<210> SEQ ID NO 770
<211> LENGTH: 19
<212> TYPE: RNA
<213> ORGANISM: Artificial sequence
<220> FEATURE:
<223> OTHER INFORMATION: Chemically synthesized

<400> SEQUENCE: 770
ggcuuaugga aggcuguua                                                19

<210> SEQ ID NO 771
<211> LENGTH: 19
<212> TYPE: RNA
<213> ORGANISM: Artificial sequence
<220> FEATURE:
<223> OTHER INFORMATION: Chemically synthesized
```

<400> SEQUENCE: 771
aaauggugau ggcuuaugg                                                19

<210> SEQ ID NO 772
<211> LENGTH: 19
<212> TYPE: RNA
<213> ORGANISM: Artificial sequence
<220> FEATURE:
<223> OTHER INFORMATION: Chemically synthesized

<400> SEQUENCE: 772
ucucuugccu guuaugcuu                                                19

<210> SEQ ID NO 773
<211> LENGTH: 19
<212> TYPE: RNA
<213> ORGANISM: Artificial sequence
<220> FEATURE:
<223> OTHER INFORMATION: Chemically synthesized

<400> SEQUENCE: 773 uucuuggggca ucgauguag                                               19

<210> SEQ ID NO 774
<211> LENGTH: 19
<212> TYPE: RNA
<213> ORGANISM: Artificial sequence
<220> FEATURE:
<223> OTHER INFORMATION: Chemically synthesized

<400> SEQUENCE: 774
aagcuccaaa gguucacug                                                19

<210> SEQ ID NO 775
<211> LENGTH: 19
<212> TYPE: RNA
<213> ORGANISM: Artificial sequence
<220> FEATURE:
<223> OTHER INFORMATION: Chemically synthesized

<400> SEQUENCE: 775
ucuauuguua agcuccaaa                                                19

<210> SEQ ID NO 776
<211> LENGTH: 19
<212> TYPE: RNA
<213> ORGANISM: Artificial sequence
<220> FEATURE:
<223> OTHER INFORMATION: Chemically synthesized

<400> SEQUENCE: 776
gggccaagau aaaucaaug                                                19

<210> SEQ ID NO 777
<211> LENGTH: 19
<212> TYPE: RNA
<213> ORGANISM: Artificial sequence
<220> FEATURE:
<223> OTHER INFORMATION: Chemically synthesized

<400> SEQUENCE: 777
uagaauuggg ccaagauaa                                                19

<210> SEQ ID NO 778
<211> LENGTH: 19

```
<212> TYPE: RNA
<213> ORGANISM: Artificial sequence
<220> FEATURE:
<223> OTHER INFORMATION: Chemically synthesized

<400> SEQUENCE: 778
ggaaagauac uacaaagcc                                              19

<210> SEQ ID NO 779
<211> LENGTH: 19
<212> TYPE: RNA
<213> ORGANISM: Artificial sequence
<220> FEATURE:
<223> OTHER INFORMATION: Chemically synthesized

<400> SEQUENCE: 779
ucaaaugcuu ggaaagaua                                              19

<210> SEQ ID NO 780
<211> LENGTH: 19
<212> TYPE: RNA
<213> ORGANISM: Artificial sequence
<220> FEATURE:
<223> OTHER INFORMATION: Chemically synthesized

<400> SEQUENCE: 780
guuacugaaa aacaggugu                                              19

<210> SEQ ID NO 781
<211> LENGTH: 19
<212> TYPE: RNA
<213> ORGANISM: Artificial sequence
<220> FEATURE:
<223> OTHER INFORMATION: Chemically synthesized

<400> SEQUENCE: 781
auguauucau ccugguguu                                              19

<210> SEQ ID NO 782
<211> LENGTH: 19
<212> TYPE: RNA
<213> ORGANISM: Artificial sequence
<220> FEATURE:
<223> OTHER INFORMATION: Chemically synthesized

<400> SEQUENCE: 782
cagauguauu cauccuggu                                              19

<210> SEQ ID NO 783
<211> LENGTH: 19
<212> TYPE: RNA
<213> ORGANISM: Artificial sequence
<220> FEATURE:
<223> OTHER INFORMATION: Chemically synthesized

<400> SEQUENCE: 783
ugcccuagcu auuagcucc                                              19

<210> SEQ ID NO 784
<211> LENGTH: 19
<212> TYPE: RNA
<213> ORGANISM: Artificial sequence
<220> FEATURE:
<223> OTHER INFORMATION: Chemically synthesized

<400> SEQUENCE: 784
```

```
gagcuuauuc agguuuccu                                           19

<210> SEQ ID NO 785
<211> LENGTH: 19
<212> TYPE: RNA
<213> ORGANISM: Artificial sequence
<220> FEATURE:
<223> OTHER INFORMATION: Chemically synthesized

<400> SEQUENCE: 785
ggagcuuauu cagguuucc                                           19

<210> SEQ ID NO 786
<211> LENGTH: 19
<212> TYPE: RNA
<213> ORGANISM: Artificial sequence
<220> FEATURE:
<223> OTHER INFORMATION: Chemically synthesized

<400> SEQUENCE: 786
ucauauccuu gcugugggu                                           19

<210> SEQ ID NO 787
<211> LENGTH: 19
<212> TYPE: RNA
<213> ORGANISM: Artificial sequence
<220> FEATURE:
<223> OTHER INFORMATION: Chemically synthesized

<400> SEQUENCE: 787
guucaauuca gcaaggcuu                                           19

<210> SEQ ID NO 788
<211> LENGTH: 19
<212> TYPE: RNA
<213> ORGANISM: Artificial sequence
<220> FEATURE:
<223> OTHER INFORMATION: Chemically synthesized

<400> SEQUENCE: 788
caacaauguu caauucagc                                           19

<210> SEQ ID NO 789
<211> LENGTH: 19
<212> TYPE: RNA
<213> ORGANISM: Artificial sequence
<220> FEATURE:
<223> OTHER INFORMATION: Chemically synthesized

<400> SEQUENCE: 789
gucuuauucc aacuaagua                                           19

<210> SEQ ID NO 790
<211> LENGTH: 19
<212> TYPE: RNA
<213> ORGANISM: Artificial sequence
<220> FEATURE:
<223> OTHER INFORMATION: Chemically synthesized

<400> SEQUENCE: 790
cuagggaaua auaaaggcc                                           19

<210> SEQ ID NO 791
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 791
uaaccaugca ugcacccag                                    19

<210> SEQ ID NO 792
<211> LENGTH: 19
<212> TYPE: RNA
<213> ORGANISM: Artificial sequence
<220> FEATURE:
<223> OTHER INFORMATION: Chemically synthesized

<400> SEQUENCE: 792
agauaaccau gcaugcacc                                    19

<210> SEQ ID NO 793
<211> LENGTH: 19
<212> TYPE: RNA
<213> ORGANISM: Artificial sequence
<220> FEATURE:
<223> OTHER INFORMATION: Chemically synthesized

<400> SEQUENCE: 793
agccuagaga augaaacuc                                    19

<210> SEQ ID NO 794
<211> LENGTH: 19
<212> TYPE: RNA
<213> ORGANISM: Artificial sequence
<220> FEATURE:
<223> OTHER INFORMATION: Chemically synthesized

<400> SEQUENCE: 794
uuauaguaca gccuagaga                                    19

<210> SEQ ID NO 795
<211> LENGTH: 19
<212> TYPE: RNA
<213> ORGANISM: Artificial sequence
<220> FEATURE:
<223> OTHER INFORMATION: Chemically synthesized

<400> SEQUENCE: 795
gcuauggaga uaugguuua                                    19

<210> SEQ ID NO 796
<211> LENGTH: 19
<212> TYPE: RNA
<213> ORGANISM: Artificial sequence
<220> FEATURE:
<223> OTHER INFORMATION: Chemically synthesized

<400> SEQUENCE: 796
ucucuccuua accccaauu                                    19

<210> SEQ ID NO 797
<211> LENGTH: 19
<212> TYPE: RNA
<213> ORGANISM: Artificial sequence
<220> FEATURE:
<223> OTHER INFORMATION: Chemically synthesized

<400> SEQUENCE: 797
aucucuccuu aaccccaau                                    19
```

<210> SEQ ID NO 798
<211> LENGTH: 19
<212> TYPE: RNA
<213> ORGANISM: Artificial sequence
<220> FEATURE:
<223> OTHER INFORMATION: Chemically synthesized

<400> SEQUENCE: 798
cugggcuuuu cugggaauu                                                     19

<210> SEQ ID NO 799
<211> LENGTH: 19
<212> TYPE: RNA
<213> ORGANISM: Artificial sequence
<220> FEATURE:
<223> OTHER INFORMATION: Chemically synthesized

<400> SEQUENCE: 799
aaccauuuca ccauggcag                                                     19

<210> SEQ ID NO 800
<211> LENGTH: 19
<212> TYPE: RNA
<213> ORGANISM: Artificial sequence
<220> FEATURE:
<223> OTHER INFORMATION: Chemically synthesized

<400> SEQUENCE: 800
uucaguauua caugugcuu                                                     19

<210> SEQ ID NO 801
<211> LENGTH: 19
<212> TYPE: RNA
<213> ORGANISM: Artificial sequence
<220> FEATURE:
<223> OTHER INFORMATION: Chemically synthesized

<400> SEQUENCE: 801
uccucuuuuc aguauuaca                                                     19

<210> SEQ ID NO 802
<211> LENGTH: 19
<212> TYPE: RNA
<213> ORGANISM: Artificial sequence
<220> FEATURE:
<223> OTHER INFORMATION: Chemically synthesized

<400> SEQUENCE: 802
auccucuuuu caguauuac                                                     19

<210> SEQ ID NO 803
<211> LENGTH: 19
<212> TYPE: RNA
<213> ORGANISM: Artificial sequence
<220> FEATURE:
<223> OTHER INFORMATION: Chemically synthesized

<400> SEQUENCE: 803
cuauccucuu uucaguauu                                                     19

<210> SEQ ID NO 804
<211> LENGTH: 19
<212> TYPE: RNA
<213> ORGANISM: Artificial sequence
<220> FEATURE:
<223> OTHER INFORMATION: Chemically synthesized -continued

```
<400> SEQUENCE: 804
aaucuauccu cuuuucagu                                                    19

<210> SEQ ID NO 805
<211> LENGTH: 19
<212> TYPE: RNA
<213> ORGANISM: Artificial sequence
<220> FEATURE:
<223> OTHER INFORMATION: Chemically synthesized

<400> SEQUENCE: 805
uucacuuagu aaucuaucc                                                    19

<210> SEQ ID NO 806
<211> LENGTH: 19
<212> TYPE: RNA
<213> ORGANISM: Artificial sequence
<220> FEATURE:
<223> OTHER INFORMATION: Chemically synthesized

<400> SEQUENCE: 806
uaggaaauua guucugaga                                                    19

<210> SEQ ID NO 807
<211> LENGTH: 19
<212> TYPE: RNA
<213> ORGANISM: Artificial sequence
<220> FEATURE:
<223> OTHER INFORMATION: Chemically synthesized

<400> SEQUENCE: 807
ggauaggaaa uuaguucug                                                    19

<210> SEQ ID NO 808
<211> LENGTH: 19
<212> TYPE: RNA
<213> ORGANISM: Artificial sequence
<220> FEATURE:
<223> OTHER INFORMATION: Chemically synthesized

<400> SEQUENCE: 808
gaggauagga aauuaguuc                                                    19

<210> SEQ ID NO 809
<211> LENGTH: 19
<212> TYPE: RNA
<213> ORGANISM: Artificial sequence
<220> FEATURE:
<223> OTHER INFORMATION: Chemically synthesized

<400> SEQUENCE: 809
gugaggauag gaaauuagu                                                    19

<210> SEQ ID NO 810
<211> LENGTH: 19
<212> TYPE: RNA
<213> ORGANISM: Artificial sequence
<220> FEATURE:
<223> OTHER INFORMATION: Chemically synthesized

<400> SEQUENCE: 810
guaggcuugg uaauagacu                                                    19

<210> SEQ ID NO 811
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 811
ccugcuaagu gauuuugac                                              19

<210> SEQ ID NO 812
<211> LENGTH: 19
<212> TYPE: RNA
<213> ORGANISM: Artificial sequence
<220> FEATURE:
<223> OTHER INFORMATION: Chemically synthesized

<400> SEQUENCE: 812
ugcauagauc ccauuuuug                                              19

<210> SEQ ID NO 813
<211> LENGTH: 19
<212> TYPE: RNA
<213> ORGANISM: Artificial sequence
<220> FEATURE:
<223> OTHER INFORMATION: Chemically synthesized

<400> SEQUENCE: 813
uucuuucugu guuucacau                                              19

<210> SEQ ID NO 814
<211> LENGTH: 19
<212> TYPE: RNA
<213> ORGANISM: Artificial sequence
<220> FEATURE:
<223> OTHER INFORMATION: Chemically synthesized

<400> SEQUENCE: 814
caaauguagu cucuuuucu                                              19

<210> SEQ ID NO 815
<211> LENGTH: 19
<212> TYPE: RNA
<213> ORGANISM: Artificial sequence
<220> FEATURE:
<223> OTHER INFORMATION: Chemically synthesized

<400> SEQUENCE: 815
aaaccccaaa uguagucuc                                              19

<210> SEQ ID NO 816
<211> LENGTH: 19
<212> TYPE: RNA
<213> ORGANISM: Artificial sequence
<220> FEATURE:
<223> OTHER INFORMATION: Chemically synthesized

<400> SEQUENCE: 816
ugcccuaaau aagaaaccc                                              19

<210> SEQ ID NO 817
<211> LENGTH: 19
<212> TYPE: RNA
<213> ORGANISM: Artificial sequence
<220> FEATURE:
<223> OTHER INFORMATION: Chemically synthesized

<400> SEQUENCE: 817
```

```
aaacuauuca gcuagucag                                                  19

<210> SEQ ID NO 818
<211> LENGTH: 19
<212> TYPE: RNA
<213> ORGANISM: Artificial sequence
<220> FEATURE:
<223> OTHER INFORMATION: Chemically synthesized

<400> SEQUENCE: 818
gugauugaag gguccuaaa                                                  19

<210> SEQ ID NO 819
<211> LENGTH: 19
<212> TYPE: RNA
<213> ORGANISM: Artificial sequence
<220> FEATURE:
<223> OTHER INFORMATION: Chemically synthesized

<400> SEQUENCE: 819
ucaggauuuc gacuuguua                                                  19

<210> SEQ ID NO 820
<211> LENGTH: 19
<212> TYPE: RNA
<213> ORGANISM: Artificial sequence
<220> FEATURE:
<223> OTHER INFORMATION: Chemically synthesized

<400> SEQUENCE: 820
uagaggucgc uucuccucu                                                  19

<210> SEQ ID NO 821
<211> LENGTH: 19
<212> TYPE: RNA
<213> ORGANISM: Artificial sequence
<220> FEATURE:
<223> OTHER INFORMATION: Chemically synthesized

<400> SEQUENCE: 821
aacugcucau ggacuagcu                                                  19

<210> SEQ ID NO 822
<211> LENGTH: 19
<212> TYPE: RNA
<213> ORGANISM: Artificial sequence
<220> FEATURE:
<223> OTHER INFORMATION: Chemically synthesized

<400> SEQUENCE: 822
ggugauggcu uauggaagg                                                  19

<210> SEQ ID NO 823
<211> LENGTH: 19
<212> TYPE: RNA
<213> ORGANISM: Artificial sequence
<220> FEATURE:
<223> OTHER INFORMATION: Chemically synthesized

<400> SEQUENCE: 823
aggcuucuug ggcaucgau                                                  19

<210> SEQ ID NO 824
<211> LENGTH: 19
<212> TYPE: RNA
```

```
<213> ORGANISM: Artificial sequence
<220> FEATURE:
<223> OTHER INFORMATION: Chemically synthesized

<400> SEQUENCE: 824
uaagcuccaa agguucacu                                                 19

<210> SEQ ID NO 825
<211> LENGTH: 19
<212> TYPE: RNA
<213> ORGANISM: Artificial sequence
<220> FEATURE:
<223> OTHER INFORMATION: Chemically synthesized

<400> SEQUENCE: 825
ggccaagaua aaucaaugu                                                 19

<210> SEQ ID NO 826
<211> LENGTH: 19
<212> TYPE: RNA
<213> ORGANISM: Artificial sequence
<220> FEATURE:
<223> OTHER INFORMATION: Chemically synthesized

<400> SEQUENCE: 826
uucaaaugcu uggaaagau                                                 19

<210> SEQ ID NO 827
<211> LENGTH: 19
<212> TYPE: RNA
<213> ORGANISM: Artificial sequence
<220> FEATURE:
<223> OTHER INFORMATION: Chemically synthesized

<400> SEQUENCE: 827
gggacagaug uauucaucc                                                 19

<210> SEQ ID NO 828
<211> LENGTH: 19
<212> TYPE: RNA
<213> ORGANISM: Artificial sequence
<220> FEATURE:
<223> OTHER INFORMATION: Chemically synthesized

<400> SEQUENCE: 828
agcuuauuca gguuuccug                                                 19

<210> SEQ ID NO 829
<211> LENGTH: 19
<212> TYPE: RNA
<213> ORGANISM: Artificial sequence
<220> FEATURE:
<223> OTHER INFORMATION: Chemically synthesized

<400> SEQUENCE: 829
auuccaacua aguagauca                                                 19

<210> SEQ ID NO 830
<211> LENGTH: 19
<212> TYPE: RNA
<213> ORGANISM: Artificial sequence
<220> FEATURE:
<223> OTHER INFORMATION: Chemically synthesized

<400> SEQUENCE: 830
aguacagccu agagaauga                                                 19
```

<210> SEQ ID NO 831
<211> LENGTH: 19
<212> TYPE: RNA
<213> ORGANISM: Artificial sequence
<220> FEATURE:
<223> OTHER INFORMATION: Chemically synthesized

<400> SEQUENCE: 831
auaguacagc cuagagaau                                           19

<210> SEQ ID NO 832
<211> LENGTH: 19
<212> TYPE: RNA
<213> ORGANISM: Artificial sequence
<220> FEATURE:
<223> OTHER INFORMATION: Chemically synthesized

<400> SEQUENCE: 832
gguuuauagu acagccuag                                           19

<210> SEQ ID NO 833
<211> LENGTH: 19
<212> TYPE: RNA
<213> ORGANISM: Artificial sequence
<220> FEATURE:
<223> OTHER INFORMATION: Chemically synthesized

<400> SEQUENCE: 833
gauaugguuu auaguacag                                           19

<210> SEQ ID NO 834
<211> LENGTH: 19
<212> TYPE: RNA
<213> ORGANISM: Artificial sequence
<220> FEATURE:
<223> OTHER INFORMATION: Chemically synthesized

<400> SEQUENCE: 834
ggagauaugg uuuauagua                                           19

<210> SEQ ID NO 835
<211> LENGTH: 19
<212> TYPE: RNA
<213> ORGANISM: Artificial sequence
<220> FEATURE:
<223> OTHER INFORMATION: Chemically synthesized

<400> SEQUENCE: 835
aaccccaauu gucaagggu                                           19

<210> SEQ ID NO 836
<211> LENGTH: 19
<212> TYPE: RNA
<213> ORGANISM: Artificial sequence
<220> FEATURE:
<223> OTHER INFORMATION: Chemically synthesized

<400> SEQUENCE: 836
uaucucuccu uaaccccaa                                           19

<210> SEQ ID NO 837
<211> LENGTH: 19
<212> TYPE: RNA
<213> ORGANISM: Artificial sequence
<220> FEATURE:

```
<223> OTHER INFORMATION: Chemically synthesized

<400> SEQUENCE: 837
guaucucucc uuaacccca                                                    19

<210> SEQ ID NO 838
<211> LENGTH: 19
<212> TYPE: RNA
<213> ORGANISM: Artificial sequence
<220> FEATURE:
<223> OTHER INFORMATION: Chemically synthesized

<400> SEQUENCE: 838
ucugggcuuu ucugggaau                                                    19

<210> SEQ ID NO 839
<211> LENGTH: 19
<212> TYPE: RNA
<213> ORGANISM: Artificial sequence
<220> FEATURE:
<223> OTHER INFORMATION: Chemically synthesized

<400> SEQUENCE: 839
gaaccauuuc accauggca                                                    19

<210> SEQ ID NO 840
<211> LENGTH: 19
<212> TYPE: RNA
<213> ORGANISM: Artificial sequence
<220> FEATURE:
<223> OTHER INFORMATION: Chemically synthesized

<400> SEQUENCE: 840 ucuaccucu uuucaguau                                                     19

<210> SEQ ID NO 841
<211> LENGTH: 19
<212> TYPE: RNA
<213> ORGANISM: Artificial sequence
<220> FEATURE:
<223> OTHER INFORMATION: Chemically synthesized

<400> SEQUENCE: 841
uguguguagu ugauuacuc                                                    19

<210> SEQ ID NO 842
<211> LENGTH: 19
<212> TYPE: RNA
<213> ORGANISM: Artificial sequence
<220> FEATURE:
<223> OTHER INFORMATION: Chemically synthesized

<400> SEQUENCE: 842
cuuaaguguu gaauacugu                                                    19

<210> SEQ ID NO 843
<211> LENGTH: 19
<212> TYPE: RNA
<213> ORGANISM: Artificial sequence
<220> FEATURE:
<223> OTHER INFORMATION: Chemically synthesized

<400> SEQUENCE: 843
ucuuaagugu ugaauacug                                                    19
```

```
<210> SEQ ID NO 844
<211> LENGTH: 19
<212> TYPE: RNA
<213> ORGANISM: Artificial sequence
<220> FEATURE:
<223> OTHER INFORMATION: Chemically synthesized

<400> SEQUENCE: 844
aaaccagauu ugccuauuu                                                  19

<210> SEQ ID NO 845
<211> LENGTH: 19
<212> TYPE: RNA
<213> ORGANISM: Artificial sequence
<220> FEATURE:
<223> OTHER INFORMATION: Chemically synthesized

<400> SEQUENCE: 845
ccuuuggaga agugauuca                                                  19

<210> SEQ ID NO 846
<211> LENGTH: 19
<212> TYPE: RNA
<213> ORGANISM: Artificial sequence
<220> FEATURE:
<223> OTHER INFORMATION: Chemically synthesized

<400> SEQUENCE: 846
uggccuuugg agaagugau                                                  19

<210> SEQ ID NO 847
<211> LENGTH: 19
<212> TYPE: RNA
<213> ORGANISM: Artificial sequence
<220> FEATURE:
<223> OTHER INFORMATION: Chemically synthesized

<400> SEQUENCE: 847
uguagucucu uuucuuucu                                                  19

<210> SEQ ID NO 848
<211> LENGTH: 19
<212> TYPE: RNA
<213> ORGANISM: Artificial sequence
<220> FEATURE:
<223> OTHER INFORMATION: Chemically synthesized

<400> SEQUENCE: 848
cuaaauaaga aaccccaaa                                                  19

<210> SEQ ID NO 849
<211> LENGTH: 19
<212> TYPE: RNA
<213> ORGANISM: Artificial sequence
<220> FEATURE:
<223> OTHER INFORMATION: Chemically synthesized

<400> SEQUENCE: 849
ccugcccuaa auaagaaac                                                  19

<210> SEQ ID NO 850
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 850
aaacuuuacu cacugauug                                           19

<210> SEQ ID NO 851
<211> LENGTH: 19
<212> TYPE: RNA
<213> ORGANISM: Artificial sequence
<220> FEATURE:
<223> OTHER INFORMATION: Chemically synthesized

<400> SEQUENCE: 851
gaaaaaacuu uacucacug                                           19

<210> SEQ ID NO 852
<211> LENGTH: 19
<212> TYPE: RNA
<213> ORGANISM: Artificial sequence
<220> FEATURE:
<223> OTHER INFORMATION: Chemically synthesized

<400> SEQUENCE: 852
ggauuucgac uuguuaaga                                           19

<210> SEQ ID NO 853
<211> LENGTH: 19
<212> TYPE: RNA
<213> ORGANISM: Artificial sequence
<220> FEATURE:
<223> OTHER INFORMATION: Chemically synthesized

<400> SEQUENCE: 853
caggauuucg acuuguuaa                                           19

<210> SEQ ID NO 854
<211> LENGTH: 19
<212> TYPE: RNA
<213> ORGANISM: Artificial sequence
<220> FEATURE:
<223> OTHER INFORMATION: Chemically synthesized

<400> SEQUENCE: 854
cuggcaguuu gagcagcaa                                           19

<210> SEQ ID NO 855
<211> LENGTH: 19
<212> TYPE: RNA
<213> ORGANISM: Artificial sequence
<220> FEATURE:
<223> OTHER INFORMATION: Chemically synthesized

<400> SEQUENCE: 855
acuggcaguu ugagcagca                                           19

<210> SEQ ID NO 856
<211> LENGTH: 19
<212> TYPE: RNA
<213> ORGANISM: Artificial sequence
<220> FEATURE:
<223> OTHER INFORMATION: Chemically synthesized

<400> SEQUENCE: 856
uaggauugug ugugauucu                                           19

<210> SEQ ID NO 857
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 857
cuggauagga uugugugug                                                 19

<210> SEQ ID NO 858
<211> LENGTH: 19
<212> TYPE: RNA
<213> ORGANISM: Artificial sequence
<220> FEATURE:
<223> OTHER INFORMATION: Chemically synthesized

<400> SEQUENCE: 858
caaagguccu ugcccuga                                                  19

<210> SEQ ID NO 859
<211> LENGTH: 19
<212> TYPE: RNA
<213> ORGANISM: Artificial sequence
<220> FEATURE:
<223> OTHER INFORMATION: Chemically synthesized

<400> SEQUENCE: 859
guugcucaaa gguccuugu                                                 19

<210> SEQ ID NO 860
<211> LENGTH: 19
<212> TYPE: RNA
<213> ORGANISM: Artificial sequence
<220> FEATURE:
<223> OTHER INFORMATION: Chemically synthesized

<400> SEQUENCE: 860
aaacuugguu gcucaaagg                                                 19

<210> SEQ ID NO 861
<211> LENGTH: 19
<212> TYPE: RNA
<213> ORGANISM: Artificial sequence
<220> FEATURE:
<223> OTHER INFORMATION: Chemically synthesized

<400> SEQUENCE: 861
uggugauggc uuauggaag                                                 19

<210> SEQ ID NO 862
<211> LENGTH: 19
<212> TYPE: RNA
<213> ORGANISM: Artificial sequence
<220> FEATURE:
<223> OTHER INFORMATION: Chemically synthesized

<400> SEQUENCE: 862
ggaguuguca ccacugacu                                                 19

<210> SEQ ID NO 863
<211> LENGTH: 19
<212> TYPE: RNA
<213> ORGANISM: Artificial sequence
<220> FEATURE:
<223> OTHER INFORMATION: Chemically synthesized

<400> SEQUENCE: 863
```
acaauguuca auucagcaa                                                 19

<210> SEQ ID NO 864
<211> LENGTH: 19
<212> TYPE: RNA
<213> ORGANISM: Artificial sequence
<220> FEATURE:
<223> OTHER INFORMATION: Chemically synthesized

<400> SEQUENCE: 864
ugaggaauca acuugccag                                                 19

<210> SEQ ID NO 865
<211> LENGTH: 19
<212> TYPE: RNA
<213> ORGANISM: Artificial sequence
<220> FEATURE:
<223> OTHER INFORMATION: Chemically synthesized

<400> SEQUENCE: 865
uggagauaug guuuauagu                                                 19

<210> SEQ ID NO 866
<211> LENGTH: 19
<212> TYPE: RNA
<213> ORGANISM: Artificial sequence
<220> FEATURE:
<223> OTHER INFORMATION: Chemically synthesized

<400> SEQUENCE: 866
cuauggagau augguuuau                                                 19

<210> SEQ ID NO 867
<211> LENGTH: 19
<212> TYPE: RNA
<213> ORGANISM: Artificial sequence
<220> FEATURE:
<223> OTHER INFORMATION: Chemically synthesized

<400> SEQUENCE: 867
ccccaauugu caaggguag                                                 19

<210> SEQ ID NO 868
<211> LENGTH: 19
<212> TYPE: RNA
<213> ORGANISM: Artificial sequence
<220> FEATURE:
<223> OTHER INFORMATION: Chemically synthesized

<400> SEQUENCE: 868
uaaccccaau ugucaaggg                                                 19

<210> SEQ ID NO 869
<211> LENGTH: 19
<212> TYPE: RNA
<213> ORGANISM: Artificial sequence
<220> FEATURE:
<223> OTHER INFORMATION: Chemically synthesized

<400> SEQUENCE: 869
acuuaguaau cuauccucu                                                 19

<210> SEQ ID NO 870
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 870
cacuuaguaa ucuauccuc                                              19

<210> SEQ ID NO 871
<211> LENGTH: 19
<212> TYPE: RNA
<213> ORGANISM: Artificial sequence
<220> FEATURE:
<223> OTHER INFORMATION: Chemically synthesized

<400> SEQUENCE: 871
aggaaauuag uucugagau                                              19

<210> SEQ ID NO 872
<211> LENGTH: 19
<212> TYPE: RNA
<213> ORGANISM: Artificial sequence
<220> FEATURE:
<223> OTHER INFORMATION: Chemically synthesized

<400> SEQUENCE: 872
uggugacuuc cucacucua                                              19

<210> SEQ ID NO 873
<211> LENGTH: 19
<212> TYPE: RNA
<213> ORGANISM: Artificial sequence
<220> FEATURE:
<223> OTHER INFORMATION: Chemically synthesized

<400> SEQUENCE: 873
guuucaggua ggcuuggua                                              19

<210> SEQ ID NO 874
<211> LENGTH: 19
<212> TYPE: RNA
<213> ORGANISM: Artificial sequence
<220> FEATURE:
<223> OTHER INFORMATION: Chemically synthesized

<400> SEQUENCE: 874
auagguaagc aaaaguaga                                              19

<210> SEQ ID NO 875
<211> LENGTH: 19
<212> TYPE: RNA
<213> ORGANISM: Artificial sequence
<220> FEATURE:
<223> OTHER INFORMATION: Chemically synthesized

<400> SEQUENCE: 875
acaacaguga uugaagggu                                              19

<210> SEQ ID NO 876
<211> LENGTH: 19
<212> TYPE: RNA
<213> ORGANISM: Artificial sequence
<220> FEATURE:
<223> OTHER INFORMATION: Chemically synthesized

<400> SEQUENCE: 876
gaacugcuca uggacuagc                                              19
```

```
<210> SEQ ID NO 877
<211> LENGTH: 19
<212> TYPE: RNA
<213> ORGANISM: Artificial sequence
<220> FEATURE:
<223> OTHER INFORMATION: Chemically synthesized

<400> SEQUENCE: 877
guguuuaagc aggagaacu                                               19

<210> SEQ ID NO 878
<211> LENGTH: 19
<212> TYPE: RNA
<213> ORGANISM: Artificial sequence
<220> FEATURE:
<223> OTHER INFORMATION: Chemically synthesized

<400> SEQUENCE: 878
gagaaacuga cccagagaa                                               19

<210> SEQ ID NO 879
<211> LENGTH: 19
<212> TYPE: RNA
<213> ORGANISM: Artificial sequence
<220> FEATURE:
<223> OTHER INFORMATION: Chemically synthesized

<400> SEQUENCE: 879
caauguucaa uucagcaag                                               19

<210> SEQ ID NO 880
<211> LENGTH: 19
<212> TYPE: RNA
<213> ORGANISM: Artificial sequence
<220> FEATURE:
<223> OTHER INFORMATION: Chemically synthesized

<400> SEQUENCE: 880
ggcuauggag auaugguuu                                               19

<210> SEQ ID NO 881
<211> LENGTH: 19
<212> TYPE: RNA
<213> ORGANISM: Artificial sequence
<220> FEATURE:
<223> OTHER INFORMATION: Chemically synthesized

<400> SEQUENCE: 881
auaggaaauu aguucugag                                               19

<210> SEQ ID NO 882
<211> LENGTH: 19
<212> TYPE: RNA
<213> ORGANISM: Artificial sequence
<220> FEATURE:
<223> OTHER INFORMATION: Chemically synthesized

<400> SEQUENCE: 882
gauaggaaau uaguucuga                                               19

<210> SEQ ID NO 883
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 883
auaaaccaga uuugccuau                                            19

<210> SEQ ID NO 884
<211> LENGTH: 19
<212> TYPE: RNA
<213> ORGANISM: Artificial sequence
<220> FEATURE:
<223> OTHER INFORMATION: Chemically synthesized

<400> SEQUENCE: 884
caacagugau ugaaggguc                                            19

<210> SEQ ID NO 885
<211> LENGTH: 19
<212> TYPE: RNA
<213> ORGANISM: Artificial sequence
<220> FEATURE:
<223> OTHER INFORMATION: Chemically synthesized

<400> SEQUENCE: 885
ugguugcuca aagguccuu                                            19

<210> SEQ ID NO 886
<211> LENGTH: 19
<212> TYPE: RNA
<213> ORGANISM: Artificial sequence
<220> FEATURE:
<223> OTHER INFORMATION: Chemically synthesized

<400> SEQUENCE: 886
uugguugcuc aaagguccu                                            19

<210> SEQ ID NO 887
<211> LENGTH: 19
<212> TYPE: RNA
<213> ORGANISM: Artificial sequence
<220> FEATURE:
<223> OTHER INFORMATION: Chemically synthesized

<400> SEQUENCE: 887
augcuuacaa aauggugau                                            19

<210> SEQ ID NO 888
<211> LENGTH: 19
<212> TYPE: RNA
<213> ORGANISM: Artificial sequence
<220> FEATURE:
<223> OTHER INFORMATION: Chemically synthesized

<400> SEQUENCE: 888
cuggaguugu caccacuga                                            19

<210> SEQ ID NO 889
<211> LENGTH: 19
<212> TYPE: RNA
<213> ORGANISM: Artificial sequence
<220> FEATURE:
<223> OTHER INFORMATION: Chemically synthesized

<400> SEQUENCE: 889
cuccaaaggu ucacugugu                                            19

<210> SEQ ID NO 890
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 890
gagguaauau uugaggaau                                                 19

<210> SEQ ID NO 891
<211> LENGTH: 19
<212> TYPE: RNA
<213> ORGANISM: Artificial sequence
<220> FEATURE:
<223> OTHER INFORMATION: Chemically synthesized

<400> SEQUENCE: 891
acgagguaau auuugagga                                                 19

<210> SEQ ID NO 892
<211> LENGTH: 19
<212> TYPE: RNA
<213> ORGANISM: Artificial sequence
<220> FEATURE:
<223> OTHER INFORMATION: Chemically synthesized

<400> SEQUENCE: 892
guuccugacu caaauuuga                                                 19

<210> SEQ ID NO 893
<211> LENGTH: 19
<212> TYPE: RNA
<213> ORGANISM: Artificial sequence
<220> FEATURE:
<223> OTHER INFORMATION: Chemically synthesized

<400> SEQUENCE: 893
cugauccuca gcucaggau                                                 19

<210> SEQ ID NO 894
<211> LENGTH: 19
<212> TYPE: RNA
<213> ORGANISM: Artificial sequence
<220> FEATURE:
<223> OTHER INFORMATION: Chemically synthesized

<400> SEQUENCE: 894
agguaauauu ugaggaauc                                                 19

<210> SEQ ID NO 895
<211> LENGTH: 19
<212> TYPE: RNA
<213> ORGANISM: Artificial sequence
<220> FEATURE:
<223> OTHER INFORMATION: Chemically synthesized

<400> SEQUENCE: 895
cgagguaaua uuugaggaa                                                 19

<210> SEQ ID NO 896
<211> LENGTH: 19
<212> TYPE: RNA
<213> ORGANISM: Artificial sequence
<220> FEATURE:
<223> OTHER INFORMATION: Chemically synthesized

<400> SEQUENCE: 896
```

-continued aucaaaacuu ccaaaagcc                                        19

<210> SEQ ID NO 897
<211> LENGTH: 19
<212> TYPE: RNA
<213> ORGANISM: Artificial sequence
<220> FEATURE:
<223> OTHER INFORMATION: Chemically synthesized

<400> SEQUENCE: 897
uaucaaaacu uccaaaagc                                        19

<210> SEQ ID NO 898
<211> LENGTH: 19
<212> TYPE: RNA
<213> ORGANISM: Artificial sequence
<220> FEATURE:
<223> OTHER INFORMATION: Chemically synthesized

<400> SEQUENCE: 898
cugauuuucu ggccuuugg                                        19

<210> SEQ ID NO 899
<211> LENGTH: 19
<212> TYPE: RNA
<213> ORGANISM: Artificial sequence
<220> FEATURE:
<223> OTHER INFORMATION: Chemically synthesized

<400> SEQUENCE: 899
cacuuguguu uaagcagga                                        19

<210> SEQ ID NO 900
<211> LENGTH: 19
<212> TYPE: RNA
<213> ORGANISM: Artificial sequence
<220> FEATURE:
<223> OTHER INFORMATION: Chemically synthesized

<400> SEQUENCE: 900
uaugcuuaca aaaugguga                                        19

<210> SEQ ID NO 901
<211> LENGTH: 19
<212> TYPE: RNA
<213> ORGANISM: Artificial sequence
<220> FEATURE:
<223> OTHER INFORMATION: Chemically synthesized

<400> SEQUENCE: 901
gaauugaagu aucucuccu                                        19

<210> SEQ ID NO 902
<211> LENGTH: 19
<212> TYPE: RNA
<213> ORGANISM: Artificial sequence
<220> FEATURE:
<223> OTHER INFORMATION: Chemically synthesized

<400> SEQUENCE: 902
uuccugacuc aaauuugaa                                        19

<210> SEQ ID NO 903
<211> LENGTH: 19
<212> TYPE: RNA

<213> ORGANISM: Artificial sequence
<220> FEATURE:
<223> OTHER INFORMATION: Chemically synthesized

<400> SEQUENCE: 903
uucucuaagu uuucagagg                                              19

<210> SEQ ID NO 904
<211> LENGTH: 19
<212> TYPE: RNA
<213> ORGANISM: Artificial sequence
<220> FEATURE:
<223> OTHER INFORMATION: Chemically synthesized

<400> SEQUENCE: 904
ugaaugggau ggauaggu                                               19

<210> SEQ ID NO 905
<211> LENGTH: 19
<212> TYPE: RNA
<213> ORGANISM: Artificial sequence
<220> FEATURE:
<223> OTHER INFORMATION: Chemically synthesized

<400> SEQUENCE: 905
gaagugauuc aaaauagug                                              19

<210> SEQ ID NO 906
<211> LENGTH: 19
<212> TYPE: RNA
<213> ORGANISM: Artificial sequence
<220> FEATURE:
<223> OTHER INFORMATION: Chemically synthesized

<400> SEQUENCE: 906
uugaaggguc cuaaaaagg                                              19

<210> SEQ ID NO 907
<211> LENGTH: 19
<212> TYPE: RNA
<213> ORGANISM: Artificial sequence
<220> FEATURE:
<223> OTHER INFORMATION: Chemically synthesized

<400> SEQUENCE: 907
cgacuuguua agaaaaaac                                              19

<210> SEQ ID NO 908
<211> LENGTH: 19
<212> TYPE: RNA
<213> ORGANISM: Artificial sequence
<220> FEATURE:
<223> OTHER INFORMATION: Chemically synthesized

<400> SEQUENCE: 908 uuuguuuaa gcaggagaa                                               19

<210> SEQ ID NO 909
<211> LENGTH: 19
<212> TYPE: RNA
<213> ORGANISM: Artificial sequence
<220> FEATURE:
<223> OTHER INFORMATION: Chemically synthesized

<400> SEQUENCE: 909
acacuugugu uuaagcagg                                              19

<210> SEQ ID NO 910
<211> LENGTH: 19
<212> TYPE: RNA
<213> ORGANISM: Artificial sequence
<220> FEATURE:
<223> OTHER INFORMATION: Chemically synthesized

<400> SEQUENCE: 910
uuacacuugu guuuaagca                                              19

<210> SEQ ID NO 911
<211> LENGTH: 19
<212> TYPE: RNA
<213> ORGANISM: Artificial sequence
<220> FEATURE:
<223> OTHER INFORMATION: Chemically synthesized

<400> SEQUENCE: 911
agaaacugac ccagagaau                                              19

<210> SEQ ID NO 912
<211> LENGTH: 19
<212> TYPE: RNA
<213> ORGANISM: Artificial sequence
<220> FEATURE:
<223> OTHER INFORMATION: Chemically synthesized

<400> SEQUENCE: 912
ccauggcagu guuaucuca                                              19

<210> SEQ ID NO 913
<211> LENGTH: 19
<212> TYPE: RNA
<213> ORGANISM: Artificial sequence
<220> FEATURE:
<223> OTHER INFORMATION: Chemically synthesized

<400> SEQUENCE: 913
auugaagggu ccuaaaaag                                              19

<210> SEQ ID NO 914
<211> LENGTH: 19
<212> TYPE: RNA
<213> ORGANISM: Artificial sequence
<220> FEATURE:
<223> OTHER INFORMATION: Chemically synthesized

<400> SEQUENCE: 914
uggaacaaca gugauugaa                                              19

<210> SEQ ID NO 915
<211> LENGTH: 19
<212> TYPE: RNA
<213> ORGANISM: Artificial sequence
<220> FEATURE:
<223> OTHER INFORMATION: Chemically synthesized

<400> SEQUENCE: 915
gcaacuggca guuugagca                                              19

<210> SEQ ID NO 916
<211> LENGTH: 19
<212> TYPE: RNA
<213> ORGANISM: Artificial sequence
<220> FEATURE:

```
<223> OTHER INFORMATION: Chemically synthesized

<400> SEQUENCE: 916
gguaauauuu gaggaauca                                                  19

<210> SEQ ID NO 917
<211> LENGTH: 19
<212> TYPE: RNA
<213> ORGANISM: Artificial sequence
<220> FEATURE:
<223> OTHER INFORMATION: Chemically synthesized

<400> SEQUENCE: 917
cugagaaacu gacccagag                                                  19

<210> SEQ ID NO 918
<211> LENGTH: 19
<212> TYPE: RNA
<213> ORGANISM: Artificial sequence
<220> FEATURE:
<223> OTHER INFORMATION: Chemically synthesized

<400> SEQUENCE: 918
cucugggcuu uucugggaa                                                  19

<210> SEQ ID NO 919
<211> LENGTH: 19
<212> TYPE: RNA
<213> ORGANISM: Artificial sequence
<220> FEATURE:
<223> OTHER INFORMATION: Chemically synthesized

<400> SEQUENCE: 919
uuggaacaac agugauuga                                                  19

<210> SEQ ID NO 920
<211> LENGTH: 19
<212> TYPE: RNA
<213> ORGANISM: Artificial sequence
<220> FEATURE:
<223> OTHER INFORMATION: Chemically synthesized

<400> SEQUENCE: 920
ugauggcuua uggaaggcu                                                  19

<210> SEQ ID NO 921
<211> LENGTH: 19
<212> TYPE: RNA
<213> ORGANISM: Artificial sequence
<220> FEATURE:
<223> OTHER INFORMATION: Chemically synthesized

<400> SEQUENCE: 921
gugauggcuu auggaaggc                                                  19

<210> SEQ ID NO 922
<211> LENGTH: 19
<212> TYPE: RNA
<213> ORGANISM: Artificial sequence
<220> FEATURE:
<223> OTHER INFORMATION: Chemically synthesized

<400> SEQUENCE: 922
uuggcuaugg agauauggu                                                  19
```

```
<210> SEQ ID NO 923
<211> LENGTH: 19
<212> TYPE: RNA
<213> ORGANISM: Artificial sequence
<220> FEATURE:
<223> OTHER INFORMATION: Chemically synthesized

<400> SEQUENCE: 923
cucuuuucuu ucuguguuu                                                      19

<210> SEQ ID NO 924
<211> LENGTH: 19
<212> TYPE: RNA
<213> ORGANISM: Artificial sequence
<220> FEATURE:
<223> OTHER INFORMATION: Chemically synthesized

<400> SEQUENCE: 924
ggaacaacag ugauugaag                                                      19

<210> SEQ ID NO 925
<211> LENGTH: 19
<212> TYPE: RNA
<213> ORGANISM: Artificial sequence
<220> FEATURE:
<223> OTHER INFORMATION: Chemically synthesized

<400> SEQUENCE: 925
ucucugggcu uuucuggga                                                      19

<210> SEQ ID NO 926
<211> LENGTH: 19
<212> TYPE: RNA
<213> ORGANISM: Artificial sequence
<220> FEATURE:
<223> OTHER INFORMATION: Chemically synthesized

<400> SEQUENCE: 926
ucucuuuucu uucuguguu                                                      19

<210> SEQ ID NO 927
<211> LENGTH: 19
<212> TYPE: RNA
<213> ORGANISM: Artificial sequence
<220> FEATURE:
<223> OTHER INFORMATION: Chemically synthesized

<400> SEQUENCE: 927
gucucuuuuc uuucugugu                                                      19

<210> SEQ ID NO 928
<211> LENGTH: 19
<212> TYPE: RNA
<213> ORGANISM: Artificial sequence
<220> FEATURE:
<223> OTHER INFORMATION: Chemically synthesized

<400> SEQUENCE: 928
aguuuguuag aacacuggc                                                      19

<210> SEQ ID NO 929
<211> LENGTH: 19
<212> TYPE: RNA
<213> ORGANISM: Artificial sequence
<220> FEATURE:
<223> OTHER INFORMATION: Chemically synthesized
```

<400> SEQUENCE: 929
uuuguuagaa cacuggcua                                            19

<210> SEQ ID NO 930
<211> LENGTH: 19
<212> TYPE: RNA
<213> ORGANISM: Artificial sequence
<220> FEATURE:
<223> OTHER INFORMATION: Chemically synthesized

<400> SEQUENCE: 930
auuagaguga ggaagucac                                            19

<210> SEQ ID NO 931
<211> LENGTH: 19
<212> TYPE: RNA
<213> ORGANISM: Artificial sequence
<220> FEATURE:
<223> OTHER INFORMATION: Chemically synthesized

<400> SEQUENCE: 931 guuguuaga acacuggcu                                             19

<210> SEQ ID NO 932
<211> LENGTH: 19
<212> TYPE: RNA
<213> ORGANISM: Artificial sequence
<220> FEATURE:
<223> OTHER INFORMATION: Chemically synthesized

<400> SEQUENCE: 932
agguauucau cauucacuc                                            19

<210> SEQ ID NO 933
<211> LENGTH: 19
<212> TYPE: RNA
<213> ORGANISM: Artificial sequence
<220> FEATURE:
<223> OTHER INFORMATION: Chemically synthesized

<400> SEQUENCE: 933
acauuagagu gaggaaguc                                            19

<210> SEQ ID NO 934
<211> LENGTH: 19
<212> TYPE: RNA
<213> ORGANISM: Artificial sequence
<220> FEATURE:
<223> OTHER INFORMATION: Chemically synthesized

<400> SEQUENCE: 934
gaguuuaguu uguuagaac                                            19

<210> SEQ ID NO 935
<211> LENGTH: 19
<212> TYPE: RNA
<213> ORGANISM: Artificial sequence
<220> FEATURE:
<223> OTHER INFORMATION: Chemically synthesized

<400> SEQUENCE: 935
ucacagguau ucaucauuc                                            19

<210> SEQ ID NO 936
<211> LENGTH: 19

```
<212> TYPE: RNA
<213> ORGANISM: Artificial sequence
<220> FEATURE:
<223> OTHER INFORMATION: Chemically synthesized

<400> SEQUENCE: 936
uaaaacauua gagugagga                                                      19

<210> SEQ ID NO 937
<211> LENGTH: 19
<212> TYPE: RNA
<213> ORGANISM: Artificial sequence
<220> FEATURE:
<223> OTHER INFORMATION: Chemically synthesized

<400> SEQUENCE: 937
auuuuaacca aauucuggc                                                      19

<210> SEQ ID NO 938
<211> LENGTH: 19
<212> TYPE: RNA
<213> ORGANISM: Artificial sequence
<220> FEATURE:
<223> OTHER INFORMATION: Chemically synthesized

<400> SEQUENCE: 938
acuucguaaa uugacccgu                                                      19

<210> SEQ ID NO 939
<211> LENGTH: 19
<212> TYPE: RNA
<213> ORGANISM: Artificial sequence
<220> FEATURE:
<223> OTHER INFORMATION: Chemically synthesized

<400> SEQUENCE: 939
ucaucauuca cucaaugga                                                      19

<210> SEQ ID NO 940
<211> LENGTH: 19
<212> TYPE: RNA
<213> ORGANISM: Artificial sequence
<220> FEATURE:
<223> OTHER INFORMATION: Chemically synthesized

<400> SEQUENCE: 940
aaaacauuag agugaggaa                                                      19

<210> SEQ ID NO 941
<211> LENGTH: 19
<212> TYPE: RNA
<213> ORGANISM: Artificial sequence
<220> FEATURE:
<223> OTHER INFORMATION: Chemically synthesized

<400> SEQUENCE: 941
guggaaaaaa ucugggugc                                                      19

<210> SEQ ID NO 942
<211> LENGTH: 19
<212> TYPE: RNA
<213> ORGANISM: Artificial sequence
<220> FEATURE:
<223> OTHER INFORMATION: Chemically synthesized

<400> SEQUENCE: 942
```

-continued guuacugaaa uggcaccac                                                19

<210> SEQ ID NO 943
<211> LENGTH: 19
<212> TYPE: RNA
<213> ORGANISM: Artificial sequence
<220> FEATURE:
<223> OTHER INFORMATION: Chemically synthesized

<400> SEQUENCE: 943
uuaaaacauu agagugagg                                                19

<210> SEQ ID NO 944
<211> LENGTH: 19
<212> TYPE: RNA
<213> ORGANISM: Artificial sequence
<220> FEATURE:
<223> OTHER INFORMATION: Chemically synthesized

<400> SEQUENCE: 944
aaacauuaga gugaggaag                                                19

<210> SEQ ID NO 945
<211> LENGTH: 19
<212> TYPE: RNA
<213> ORGANISM: Artificial sequence
<220> FEATURE:
<223> OTHER INFORMATION: Chemically synthesized

<400> SEQUENCE: 945
acuuagagaa aaaaaagcc                                                19

<210> SEQ ID NO 946
<211> LENGTH: 19
<212> TYPE: RNA
<213> ORGANISM: Artificial sequence
<220> FEATURE:
<223> OTHER INFORMATION: Chemically synthesized

<400> SEQUENCE: 946
auucuguaca aaaauggga                                                19

<210> SEQ ID NO 947
<211> LENGTH: 19
<212> TYPE: RNA
<213> ORGANISM: Artificial sequence
<220> FEATURE:
<223> OTHER INFORMATION: Chemically synthesized

<400> SEQUENCE: 947
cuauuuugaa ucacuucuc                                                19

<210> SEQ ID NO 948
<211> LENGTH: 19
<212> TYPE: RNA
<213> ORGANISM: Artificial sequence
<220> FEATURE:
<223> OTHER INFORMATION: Chemically synthesized

<400> SEQUENCE: 948
uauuuugaau cacuucucc                                                19

<210> SEQ ID NO 949
<211> LENGTH: 19
<212> TYPE: RNA
<213> ORGANISM: Artificial sequence
<220> FEATURE:
<223> OTHER INFORMATION: Chemically synthesized

<400> SEQUENCE: 949
acaaaugacu uuagcugac                                                19

<210> SEQ ID NO 950
<211> LENGTH: 19
<212> TYPE: RNA
<213> ORGANISM: Artificial sequence
<220> FEATURE:
<223> OTHER INFORMATION: Chemically synthesized

<400> SEQUENCE: 950
auucugaaau gcuggccgg                                                19

<210> SEQ ID NO 951
<211> LENGTH: 19
<212> TYPE: RNA
<213> ORGANISM: Artificial sequence
<220> FEATURE:
<223> OTHER INFORMATION: Chemically synthesized

<400> SEQUENCE: 951
acagacaguu cuccagcau                                                19

<210> SEQ ID NO 952
<211> LENGTH: 19
<212> TYPE: RNA
<213> ORGANISM: Artificial sequence
<220> FEATURE:
<223> OTHER INFORMATION: Chemically synthesized

<400> SEQUENCE: 952
agacaguucu ccagcauuu                                                19

<210> SEQ ID NO 953
<211> LENGTH: 19
<212> TYPE: RNA
<213> ORGANISM: Artificial sequence
<220> FEATURE:
<223> OTHER INFORMATION: Chemically synthesized

<400> SEQUENCE: 953
uucuccagca uuuuaacca                                                19

<210> SEQ ID NO 954
<211> LENGTH: 19
<212> TYPE: RNA
<213> ORGANISM: Artificial sequence
<220> FEATURE:
<223> OTHER INFORMATION: Chemically synthesized

<400> SEQUENCE: 954
ucuccagcau uuuaaccaa                                                19

<210> SEQ ID NO 955
<211> LENGTH: 19
<212> TYPE: RNA
<213> ORGANISM: Artificial sequence
<220> FEATURE:
<223> OTHER INFORMATION: Chemically synthesized

<400> SEQUENCE: 955
agcaugugaa guggagcua                                                19

-continued

```
<210> SEQ ID NO 956
<211> LENGTH: 19
<212> TYPE: RNA
<213> ORGANISM: Artificial sequence
<220> FEATURE:
<223> OTHER INFORMATION: Chemically synthesized

<400> SEQUENCE: 956
acauuguuga guggaggcu                                                     19

<210> SEQ ID NO 957
<211> LENGTH: 19
<212> TYPE: RNA
<213> ORGANISM: Artificial sequence
<220> FEATURE:
<223> OTHER INFORMATION: Chemically synthesized

<400> SEQUENCE: 957
agguggaaaa aaucugggu                                                     19

<210> SEQ ID NO 958
<211> LENGTH: 19
<212> TYPE: RNA
<213> ORGANISM: Artificial sequence
<220> FEATURE:
<223> OTHER INFORMATION: Chemically synthesized

<400> SEQUENCE: 958
uggaaaaaau cugggugca                                                     19

<210> SEQ ID NO 959
<211> LENGTH: 19
<212> TYPE: RNA
<213> ORGANISM: Artificial sequence
<220> FEATURE:
<223> OTHER INFORMATION: Chemically synthesized

<400> SEQUENCE: 959
uucguaaauu gacccguuu                                                     19

<210> SEQ ID NO 960
<211> LENGTH: 19
<212> TYPE: RNA
<213> ORGANISM: Artificial sequence
<220> FEATURE:
<223> OTHER INFORMATION: Chemically synthesized

<400> SEQUENCE: 960
ccucacaggu auucaucau                                                     19

<210> SEQ ID NO 961
<211> LENGTH: 19
<212> TYPE: RNA
<213> ORGANISM: Artificial sequence
<220> FEATURE:
<223> OTHER INFORMATION: Chemically synthesized

<400> SEQUENCE: 961
guauucauca uucacucaa                                                     19

<210> SEQ ID NO 962
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 962
agcaguucca uuauugccg                                                19

<210> SEQ ID NO 963
<211> LENGTH: 19
<212> TYPE: RNA
<213> ORGANISM: Artificial sequence
<220> FEATURE:
<223> OTHER INFORMATION: Chemically synthesized

<400> SEQUENCE: 963
uuuggaaguu uugauaggc                                                19

<210> SEQ ID NO 964
<211> LENGTH: 19
<212> TYPE: RNA
<213> ORGANISM: Artificial sequence
<220> FEATURE:
<223> OTHER INFORMATION: Chemically synthesized

<400> SEQUENCE: 964
cuuagagaaa aaaaagcca                                                19

<210> SEQ ID NO 965
<211> LENGTH: 19
<212> TYPE: RNA
<213> ORGANISM: Artificial sequence
<220> FEATURE:
<223> OTHER INFORMATION: Chemically synthesized

<400> SEQUENCE: 965
auguaaaacu caaaugggc                                                19

<210> SEQ ID NO 966
<211> LENGTH: 19
<212> TYPE: RNA
<213> ORGANISM: Artificial sequence
<220> FEATURE:
<223> OTHER INFORMATION: Chemically synthesized

<400> SEQUENCE: 966
caauucugaa augcuggcc                                                19

<210> SEQ ID NO 967
<211> LENGTH: 19
<212> TYPE: RNA
<213> ORGANISM: Artificial sequence
<220> FEATURE:
<223> OTHER INFORMATION: Chemically synthesized

<400> SEQUENCE: 967
aauucugaaa ugcuggccg                                                19

<210> SEQ ID NO 968
<211> LENGTH: 19
<212> TYPE: RNA
<213> ORGANISM: Artificial sequence
<220> FEATURE:
<223> OTHER INFORMATION: Chemically synthesized

<400> SEQUENCE: 968
ucaaaaguag guacgacgc                                                19

<210> SEQ ID NO 969
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 969
aaaaguaggu acgacgcua                                                   19

<210> SEQ ID NO 970
<211> LENGTH: 19
<212> TYPE: RNA
<213> ORGANISM: Artificial sequence
<220> FEATURE:
<223> OTHER INFORMATION: Chemically synthesized

<400> SEQUENCE: 970
uuuccaaguu cacgugcau                                                   19

<210> SEQ ID NO 971
<211> LENGTH: 19
<212> TYPE: RNA
<213> ORGANISM: Artificial sequence
<220> FEATURE:
<223> OTHER INFORMATION: Chemically synthesized

<400> SEQUENCE: 971
guuaguggaa aaaggacaa                                                   19

<210> SEQ ID NO 972
<211> LENGTH: 19
<212> TYPE: RNA
<213> ORGANISM: Artificial sequence
<220> FEATURE:
<223> OTHER INFORMATION: Chemically synthesized

<400> SEQUENCE: 972
uuaguggaaa aaggacaac                                                   19

<210> SEQ ID NO 973
<211> LENGTH: 19
<212> TYPE: RNA
<213> ORGANISM: Artificial sequence
<220> FEATURE:
<223> OTHER INFORMATION: Chemically synthesized

<400> SEQUENCE: 973
aguggaaaaa ggacaacag                                                   19

<210> SEQ ID NO 974
<211> LENGTH: 19
<212> TYPE: RNA
<213> ORGANISM: Artificial sequence
<220> FEATURE:
<223> OTHER INFORMATION: Chemically synthesized

<400> SEQUENCE: 974
uggacagaca guucuccag                                                   19

<210> SEQ ID NO 975
<211> LENGTH: 19
<212> TYPE: RNA
<213> ORGANISM: Artificial sequence
<220> FEATURE:
<223> OTHER INFORMATION: Chemically synthesized

<400> SEQUENCE: 975
```
caauucuaua aagauuggc                                                        19

<210> SEQ ID NO 976
<211> LENGTH: 19
<212> TYPE: RNA
<213> ORGANISM: Artificial sequence
<220> FEATURE:
<223> OTHER INFORMATION: Chemically synthesized

<400> SEQUENCE: 976
aacacuggcu aauugaac                                                         19

<210> SEQ ID NO 977
<211> LENGTH: 19
<212> TYPE: RNA
<213> ORGANISM: Artificial sequence
<220> FEATURE:
<223> OTHER INFORMATION: Chemically synthesized

<400> SEQUENCE: 977
uuuuaaccaa auucuggca                                                        19

<210> SEQ ID NO 978
<211> LENGTH: 19
<212> TYPE: RNA
<213> ORGANISM: Artificial sequence
<220> FEATURE:
<223> OTHER INFORMATION: Chemically synthesized

<400> SEQUENCE: 978
aagguggaaa aaaucuggg                                                        19

<210> SEQ ID NO 979
<211> LENGTH: 19
<212> TYPE: RNA
<213> ORGANISM: Artificial sequence
<220> FEATURE:
<223> OTHER INFORMATION: Chemically synthesized

<400> SEQUENCE: 979
gguggaaaaa aucugggug                                                        19

<210> SEQ ID NO 980
<211> LENGTH: 19
<212> TYPE: RNA
<213> ORGANISM: Artificial sequence
<220> FEATURE:
<223> OTHER INFORMATION: Chemically synthesized

<400> SEQUENCE: 980
augcagacuu cguaaauug                                                        19

<210> SEQ ID NO 981
<211> LENGTH: 19
<212> TYPE: RNA
<213> ORGANISM: Artificial sequence
<220> FEATURE:
<223> OTHER INFORMATION: Chemically synthesized

<400> SEQUENCE: 981
agacuucgua aauugaccc                                                        19

<210> SEQ ID NO 982
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 982
cuucguaaau ugacccguu                                               19

<210> SEQ ID NO 983
<211> LENGTH: 19
<212> TYPE: RNA
<213> ORGANISM: Artificial sequence
<220> FEATURE:
<223> OTHER INFORMATION: Chemically synthesized

<400> SEQUENCE: 983
cguaaauuga cccguuuca                                               19

<210> SEQ ID NO 984
<211> LENGTH: 19
<212> TYPE: RNA
<213> ORGANISM: Artificial sequence
<220> FEATURE:
<223> OTHER INFORMATION: Chemically synthesized

<400> SEQUENCE: 984
gguuacugaa auggcacca                                               19

<210> SEQ ID NO 985
<211> LENGTH: 19
<212> TYPE: RNA
<213> ORGANISM: Artificial sequence
<220> FEATURE:
<223> OTHER INFORMATION: Chemically synthesized

<400> SEQUENCE: 985
aaacagugaa gcaguucca                                               19

<210> SEQ ID NO 986
<211> LENGTH: 19
<212> TYPE: RNA
<213> ORGANISM: Artificial sequence
<220> FEATURE:
<223> OTHER INFORMATION: Chemically synthesized

<400> SEQUENCE: 986
accuacuuaa uccuaccuu                                               19

<210> SEQ ID NO 987
<211> LENGTH: 19
<212> TYPE: RNA
<213> ORGANISM: Artificial sequence
<220> FEATURE:
<223> OTHER INFORMATION: Chemically synthesized

<400> SEQUENCE: 987
acuuaauccu accuuccug                                               19

<210> SEQ ID NO 988
<211> LENGTH: 19
<212> TYPE: RNA
<213> ORGANISM: Artificial sequence
<220> FEATURE:
<223> OTHER INFORMATION: Chemically synthesized

<400> SEQUENCE: 988
uuggaaguuu ugauaggcu                                               19
```

<210> SEQ ID NO 989
<211> LENGTH: 19
<212> TYPE: RNA
<213> ORGANISM: Artificial sequence
<220> FEATURE:
<223> OTHER INFORMATION: Chemically synthesized

<400> SEQUENCE: 989
aaaauaggca aaucugguu                                                  19

<210> SEQ ID NO 990
<211> LENGTH: 19
<212> TYPE: RNA
<213> ORGANISM: Artificial sequence
<220> FEATURE:
<223> OTHER INFORMATION: Chemically synthesized

<400> SEQUENCE: 990
aucccauuca auucuguac                                                  19

<210> SEQ ID NO 991
<211> LENGTH: 19
<212> TYPE: RNA
<213> ORGANISM: Artificial sequence
<220> FEATURE:
<223> OTHER INFORMATION: Chemically synthesized

<400> SEQUENCE: 991
uucuguacaa aaaugggau                                                  19

<210> SEQ ID NO 992
<211> LENGTH: 19
<212> TYPE: RNA
<213> ORGANISM: Artificial sequence
<220> FEATURE:
<223> OTHER INFORMATION: Chemically synthesized

<400> SEQUENCE: 992
cuacaaauga cuuuagcug                                                  19

<210> SEQ ID NO 993
<211> LENGTH: 19
<212> TYPE: RNA
<213> ORGANISM: Artificial sequence
<220> FEATURE:
<223> OTHER INFORMATION: Chemically synthesized

<400> SEQUENCE: 993
aguuuuacua cccaaucau                                                  19

<210> SEQ ID NO 994
<211> LENGTH: 19
<212> TYPE: RNA
<213> ORGANISM: Artificial sequence
<220> FEATURE:
<223> OTHER INFORMATION: Chemically synthesized

<400> SEQUENCE: 994 uuuccuuuu uaggacccu                                                   19

<210> SEQ ID NO 995
<211> LENGTH: 19
<212> TYPE: RNA
<213> ORGANISM: Artificial sequence
<220> FEATURE:

```
<223> OTHER INFORMATION: Chemically synthesized

<400> SEQUENCE: 995
ucaauuucca aguucacgu                                                     19

<210> SEQ ID NO 996
<211> LENGTH: 19
<212> TYPE: RNA
<213> ORGANISM: Artificial sequence
<220> FEATURE:
<223> OTHER INFORMATION: Chemically synthesized

<400> SEQUENCE: 996
aggacaucuu gagcaauuc                                                     19

<210> SEQ ID NO 997
<211> LENGTH: 19
<212> TYPE: RNA
<213> ORGANISM: Artificial sequence
<220> FEATURE:
<223> OTHER INFORMATION: Chemically synthesized

<400> SEQUENCE: 997
gacaucuuga gcaauucuc                                                     19

<210> SEQ ID NO 998
<211> LENGTH: 19
<212> TYPE: RNA
<213> ORGANISM: Artificial sequence
<220> FEATURE:
<223> OTHER INFORMATION: Chemically synthesized

<400> SEQUENCE: 998
acaucuugag caauucucu                                                     19

<210> SEQ ID NO 999
<211> LENGTH: 19
<212> TYPE: RNA
<213> ORGANISM: Artificial sequence
<220> FEATURE:
<223> OTHER INFORMATION: Chemically synthesized

<400> SEQUENCE: 999
aucuugagca auucucugg                                                     19

<210> SEQ ID NO 1000
<211> LENGTH: 19
<212> TYPE: RNA
<213> ORGANISM: Artificial sequence
<220> FEATURE:
<223> OTHER INFORMATION: Chemically synthesized

<400> SEQUENCE: 1000
ucuugagcaa uucucuggg                                                     19

<210> SEQ ID NO 1001
<211> LENGTH: 19
<212> TYPE: RNA
<213> ORGANISM: Artificial sequence
<220> FEATURE:
<223> OTHER INFORMATION: Chemically synthesized

<400> SEQUENCE: 1001
uugauuugga cagacaguu                                                     19
```

```
<210> SEQ ID NO 1002
<211> LENGTH: 19
<212> TYPE: RNA
<213> ORGANISM: Artificial sequence
<220> FEATURE:
<223> OTHER INFORMATION: Chemically synthesized

<400> SEQUENCE: 1002
uguuagugga aaaaggaca                                                  19

<210> SEQ ID NO 1003
<211> LENGTH: 19
<212> TYPE: RNA
<213> ORGANISM: Artificial sequence
<220> FEATURE:
<223> OTHER INFORMATION: Chemically synthesized

<400> SEQUENCE: 1003
ggaaaaagga caacaguuc                                                  19

<210> SEQ ID NO 1004
<211> LENGTH: 19
<212> TYPE: RNA
<213> ORGANISM: Artificial sequence
<220> FEATURE:
<223> OTHER INFORMATION: Chemically synthesized

<400> SEQUENCE: 1004
uuuggacaga caguucucc                                                  19

<210> SEQ ID NO 1005
<211> LENGTH: 19
<212> TYPE: RNA
<213> ORGANISM: Artificial sequence
<220> FEATURE:
<223> OTHER INFORMATION: Chemically synthesized

<400> SEQUENCE: 1005
uuaguuuguu agaacacug                                                  19

<210> SEQ ID NO 1006
<211> LENGTH: 19
<212> TYPE: RNA
<213> ORGANISM: Artificial sequence
<220> FEATURE:
<223> OTHER INFORMATION: Chemically synthesized

<400> SEQUENCE: 1006
uuagaacacu ggcuaauuu                                                  19

<210> SEQ ID NO 1007
<211> LENGTH: 19
<212> TYPE: RNA
<213> ORGANISM: Artificial sequence
<220> FEATURE:
<223> OTHER INFORMATION: Chemically synthesized

<400> SEQUENCE: 1007
aacagugaca uuuuagguc                                                  19

<210> SEQ ID NO 1008
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1008
uuuaaccaaa uucuggcaa                                                19

<210> SEQ ID NO 1009
<211> LENGTH: 19
<212> TYPE: RNA
<213> ORGANISM: Artificial sequence
<220> FEATURE:
<223> OTHER INFORMATION: Chemically synthesized

<400> SEQUENCE: 1009
ugaauaagcu ccuuaucca                                                19

<210> SEQ ID NO 1010
<211> LENGTH: 19
<212> TYPE: RNA
<213> ORGANISM: Artificial sequence
<220> FEATURE:
<223> OTHER INFORMATION: Chemically synthesized

<400> SEQUENCE: 1010
aggauaugaa agccuugcu                                                19

<210> SEQ ID NO 1011
<211> LENGTH: 19
<212> TYPE: RNA
<213> ORGANISM: Artificial sequence
<220> FEATURE:
<223> OTHER INFORMATION: Chemically synthesized

<400> SEQUENCE: 1011
ugaacauugu ugaguggag                                                19

<210> SEQ ID NO 1012
<211> LENGTH: 19
<212> TYPE: RNA
<213> ORGANISM: Artificial sequence
<220> FEATURE:
<223> OTHER INFORMATION: Chemically synthesized

<400> SEQUENCE: 1012
auuguugagu ggaggcuaa                                                19

<210> SEQ ID NO 1013
<211> LENGTH: 19
<212> TYPE: RNA
<213> ORGANISM: Artificial sequence
<220> FEATURE:
<223> OTHER INFORMATION: Chemically synthesized

<400> SEQUENCE: 1013
aguggaggcu aaauucucu                                                19

<210> SEQ ID NO 1014
<211> LENGTH: 19
<212> TYPE: RNA
<213> ORGANISM: Artificial sequence
<220> FEATURE:
<223> OTHER INFORMATION: Chemically synthesized

<400> SEQUENCE: 1014
aggaaagaga uaaugaucu                                                19

<210> SEQ ID NO 1015
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1015
uaagacaaaa aauaaggcc                                                   19

<210> SEQ ID NO 1016
<211> LENGTH: 19
<212> TYPE: RNA
<213> ORGANISM: Artificial sequence
<220> FEATURE:
<223> OTHER INFORMATION: Chemically synthesized

<400> SEQUENCE: 1016
ccaaggugga aaaaucug                                                    19

<210> SEQ ID NO 1017
<211> LENGTH: 19
<212> TYPE: RNA
<213> ORGANISM: Artificial sequence
<220> FEATURE:
<223> OTHER INFORMATION: Chemically synthesized

<400> SEQUENCE: 1017
caagguggaa aaaucugg                                                    19

<210> SEQ ID NO 1018
<211> LENGTH: 19
<212> TYPE: RNA
<213> ORGANISM: Artificial sequence
<220> FEATURE:
<223> OTHER INFORMATION: Chemically synthesized

<400> SEQUENCE: 1018
ugaguuucau ucucuaggc                                                   19

<210> SEQ ID NO 1019
<211> LENGTH: 19
<212> TYPE: RNA
<213> ORGANISM: Artificial sequence
<220> FEATURE:
<223> OTHER INFORMATION: Chemically synthesized

<400> SEQUENCE: 1019
agccaaugca gacuucgua                                                   19

<210> SEQ ID NO 1020
<211> LENGTH: 19
<212> TYPE: RNA
<213> ORGANISM: Artificial sequence
<220> FEATURE:
<223> OTHER INFORMATION: Chemically synthesized

<400> SEQUENCE: 1020
gacuucguaa auugacccg                                                   19

<210> SEQ ID NO 1021
<211> LENGTH: 19
<212> TYPE: RNA
<213> ORGANISM: Artificial sequence
<220> FEATURE:
<223> OTHER INFORMATION: Chemically synthesized

<400> SEQUENCE: 1021
```

```
ucguaaauug acccguuuc                                              19

<210> SEQ ID NO 1022
<211> LENGTH: 19
<212> TYPE: RNA
<213> ORGANISM: Artificial sequence
<220> FEATURE:
<223> OTHER INFORMATION: Chemically synthesized

<400> SEQUENCE: 1022
aagugaauca gagagggac                                              19

<210> SEQ ID NO 1023
<211> LENGTH: 19
<212> TYPE: RNA
<213> ORGANISM: Artificial sequence
<220> FEATURE:
<223> OTHER INFORMATION: Chemically synthesized

<400> SEQUENCE: 1023
uucuuaggag uccccucuc                                              19

<210> SEQ ID NO 1024
<211> LENGTH: 19
<212> TYPE: RNA
<213> ORGANISM: Artificial sequence
<220> FEATURE:
<223> OTHER INFORMATION: Chemically synthesized

<400> SEQUENCE: 1024
ccuacuuaau ccuaccuuc                                              19

<210> SEQ ID NO 1025
<211> LENGTH: 19
<212> TYPE: RNA
<213> ORGANISM: Artificial sequence
<220> FEATURE:
<223> OTHER INFORMATION: Chemically synthesized

<400> SEQUENCE: 1025
uggaaguuuu gauaggcua                                              19

<210> SEQ ID NO 1026
<211> LENGTH: 19
<212> TYPE: RNA
<213> ORGANISM: Artificial sequence
<220> FEATURE:
<223> OTHER INFORMATION: Chemically synthesized

<400> SEQUENCE: 1026
caauucugua caaaaaugg                                              19

<210> SEQ ID NO 1027
<211> LENGTH: 19
<212> TYPE: RNA
<213> ORGANISM: Artificial sequence
<220> FEATURE:
<223> OTHER INFORMATION: Chemically synthesized

<400> SEQUENCE: 1027
uguacaaaaa ugggaucua                                              19

<210> SEQ ID NO 1028
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 1028
aaaucagccu guuagcugc                                              19

<210> SEQ ID NO 1029
<211> LENGTH: 19
<212> TYPE: RNA
<213> ORGANISM: Artificial sequence
<220> FEATURE:
<223> OTHER INFORMATION: Chemically synthesized

<400> SEQUENCE: 1029
ugcuaugaau gugaaacac                                              19

<210> SEQ ID NO 1030
<211> LENGTH: 19
<212> TYPE: RNA
<213> ORGANISM: Artificial sequence
<220> FEATURE:
<223> OTHER INFORMATION: Chemically synthesized

<400> SEQUENCE: 1030
uauuuucccu uuuuaggac                                              19

<210> SEQ ID NO 1031
<211> LENGTH: 19
<212> TYPE: RNA
<213> ORGANISM: Artificial sequence
<220> FEATURE:
<223> OTHER INFORMATION: Chemically synthesized

<400> SEQUENCE: 1031
uuuucccuuu uuaggaccc                                              19

<210> SEQ ID NO 1032
<211> LENGTH: 19
<212> TYPE: RNA
<213> ORGANISM: Artificial sequence
<220> FEATURE:
<223> OTHER INFORMATION: Chemically synthesized

<400> SEQUENCE: 1032
uucccuuuuu aggacccuu                                              19

<210> SEQ ID NO 1033
<211> LENGTH: 19
<212> TYPE: RNA
<213> ORGANISM: Artificial sequence
<220> FEATURE:
<223> OTHER INFORMATION: Chemically synthesized

<400> SEQUENCE: 1033
acuaaagaaa aagucccug                                              19

<210> SEQ ID NO 1034
<211> LENGTH: 19
<212> TYPE: RNA
<213> ORGANISM: Artificial sequence
<220> FEATURE:
<223> OTHER INFORMATION: Chemically synthesized

<400> SEQUENCE: 1034
auuuccaagu ucacgugca                                              19
```

<210> SEQ ID NO 1035
<211> LENGTH: 19
<212> TYPE: RNA
<213> ORGANISM: Artificial sequence
<220> FEATURE:
<223> OTHER INFORMATION: Chemically synthesized

<400> SEQUENCE: 1035
aaguucacgu gcauaacac                                                  19

<210> SEQ ID NO 1036
<211> LENGTH: 19
<212> TYPE: RNA
<213> ORGANISM: Artificial sequence
<220> FEATURE:
<223> OTHER INFORMATION: Chemically synthesized

<400> SEQUENCE: 1036
uucacgugca uaacacaac                                                  19

<210> SEQ ID NO 1037
<211> LENGTH: 19
<212> TYPE: RNA
<213> ORGANISM: Artificial sequence
<220> FEATURE:
<223> OTHER INFORMATION: Chemically synthesized

<400> SEQUENCE: 1037
acgugcauaa cacaaccuc                                                  19

<210> SEQ ID NO 1038
<211> LENGTH: 19
<212> TYPE: RNA
<213> ORGANISM: Artificial sequence
<220> FEATURE:
<223> OTHER INFORMATION: Chemically synthesized

<400> SEQUENCE: 1038
uugagcaauu cucuggguc                                                  19

<210> SEQ ID NO 1039
<211> LENGTH: 19
<212> TYPE: RNA
<213> ORGANISM: Artificial sequence
<220> FEATURE:
<223> OTHER INFORMATION: Chemically synthesized

<400> SEQUENCE: 1039
aaccaaguuu aguuugcuu                                                  19

<210> SEQ ID NO 1040
<211> LENGTH: 19
<212> TYPE: RNA
<213> ORGANISM: Artificial sequence
<220> FEATURE:
<223> OTHER INFORMATION: Chemically synthesized

<400> SEQUENCE: 1040
uuaguuugcu uugauuugg                                                  19

<210> SEQ ID NO 1041
<211> LENGTH: 19
<212> TYPE: RNA
<213> ORGANISM: Artificial sequence
<220> FEATURE:
<223> OTHER INFORMATION: Chemically synthesized -continued

<400> SEQUENCE: 1041
auuaauuuaa cagccuucc					19

<210> SEQ ID NO 1042
<211> LENGTH: 19
<212> TYPE: RNA
<213> ORGANISM: Artificial sequence
<220> FEATURE:
<223> OTHER INFORMATION: Chemically synthesized

<400> SEQUENCE: 1042
uuuguaagca uaacaggca					19

<210> SEQ ID NO 1043
<211> LENGTH: 19
<212> TYPE: RNA
<213> ORGANISM: Artificial sequence
<220> FEATURE:
<223> OTHER INFORMATION: Chemically synthesized

<400> SEQUENCE: 1043
uuguaagcau aacaggcaa					19

<210> SEQ ID NO 1044
<211> LENGTH: 19
<212> TYPE: RNA
<213> ORGANISM: Artificial sequence
<220> FEATURE:
<223> OTHER INFORMATION: Chemically synthesized

<400> SEQUENCE: 1044
auaacaggca agagaguca					19

<210> SEQ ID NO 1045
<211> LENGTH: 19
<212> TYPE: RNA
<213> ORGANISM: Artificial sequence
<220> FEATURE:
<223> OTHER INFORMATION: Chemically synthesized

<400> SEQUENCE: 1045
cuguuagugg aaaaaggac					19

<210> SEQ ID NO 1046
<211> LENGTH: 19
<212> TYPE: RNA
<213> ORGANISM: Artificial sequence
<220> FEATURE:
<223> OTHER INFORMATION: Chemically synthesized

<400> SEQUENCE: 1046
aaaaaggaca acaguucua					19

<210> SEQ ID NO 1047
<211> LENGTH: 19
<212> TYPE: RNA
<213> ORGANISM: Artificial sequence
<220> FEATURE:
<223> OTHER INFORMATION: Chemically synthesized

<400> SEQUENCE: 1047
aaaaggacaa caguucuac					19

<210> SEQ ID NO 1048

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1048
auuuggacag acaguucuc                                                  19

<210> SEQ ID NO 1049
<211> LENGTH: 19
<212> TYPE: RNA
<213> ORGANISM: Artificial sequence
<220> FEATURE:
<223> OTHER INFORMATION: Chemically synthesized

<400> SEQUENCE: 1049
aacauugauu uaucuuggc                                                  19

<210> SEQ ID NO 1050
<211> LENGTH: 19
<212> TYPE: RNA
<213> ORGANISM: Artificial sequence
<220> FEATURE:
<223> OTHER INFORMATION: Chemically synthesized

<400> SEQUENCE: 1050
cuauaaagau uggcuuugu                                                  19

<210> SEQ ID NO 1051
<211> LENGTH: 19
<212> TYPE: RNA
<213> ORGANISM: Artificial sequence
<220> FEATURE:
<223> OTHER INFORMATION: Chemically synthesized

<400> SEQUENCE: 1051
cuaauuugaa cagugacau                                                  19

<210> SEQ ID NO 1052
<211> LENGTH: 19
<212> TYPE: RNA
<213> ORGANISM: Artificial sequence
<220> FEATURE:
<223> OTHER INFORMATION: Chemically synthesized

<400> SEQUENCE: 1052
guaucaguaa caggaucac                                                  19

<210> SEQ ID NO 1053
<211> LENGTH: 19
<212> TYPE: RNA
<213> ORGANISM: Artificial sequence
<220> FEATURE:
<223> OTHER INFORMATION: Chemically synthesized

<400> SEQUENCE: 1053
cagcauuuua accaaauuc                                                  19

<210> SEQ ID NO 1054
<211> LENGTH: 19
<212> TYPE: RNA
<213> ORGANISM: Artificial sequence
<220> FEATURE:
<223> OTHER INFORMATION: Chemically synthesized

<400> SEQUENCE: 1054
```
agcaaggaua ugaaagccu                                                    19

<210> SEQ ID NO 1055
<211> LENGTH: 19
<212> TYPE: RNA
<213> ORGANISM: Artificial sequence
<220> FEATURE:
<223> OTHER INFORMATION: Chemically synthesized

<400> SEQUENCE: 1055
ggauaugaaa gccuugcug                                                    19

<210> SEQ ID NO 1056
<211> LENGTH: 19
<212> TYPE: RNA
<213> ORGANISM: Artificial sequence
<220> FEATURE:
<223> OTHER INFORMATION: Chemically synthesized

<400> SEQUENCE: 1056
aacauuguug aguggaggc                                                    19

<210> SEQ ID NO 1057
<211> LENGTH: 19
<212> TYPE: RNA
<213> ORGANISM: Artificial sequence
<220> FEATURE:
<223> OTHER INFORMATION: Chemically synthesized

<400> SEQUENCE: 1057
uugaguggag gcuaaauuc                                                    19

<210> SEQ ID NO 1058
<211> LENGTH: 19
<212> TYPE: RNA
<213> ORGANISM: Artificial sequence
<220> FEATURE:
<223> OTHER INFORMATION: Chemically synthesized

<400> SEQUENCE: 1058
guggaggcua aauucucuc                                                    19

<210> SEQ ID NO 1059
<211> LENGTH: 19
<212> TYPE: RNA
<213> ORGANISM: Artificial sequence
<220> FEATURE:
<223> OTHER INFORMATION: Chemically synthesized

<400> SEQUENCE: 1059
ggaaagagau aaugaucua                                                    19

<210> SEQ ID NO 1060
<211> LENGTH: 19
<212> TYPE: RNA
<213> ORGANISM: Artificial sequence
<220> FEATURE:
<223> OTHER INFORMATION: Chemically synthesized

<400> SEQUENCE: 1060
aagacaaaaa auaaggccu                                                    19

<210> SEQ ID NO 1061
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1061
agacaaaaaa uaaggccuu                                                   19

<210> SEQ ID NO 1062
<211> LENGTH: 19
<212> TYPE: RNA
<213> ORGANISM: Artificial sequence
<220> FEATURE:
<223> OTHER INFORMATION: Chemically synthesized

<400> SEQUENCE: 1062
aaaaaaucug ggugcaugc                                                   19

<210> SEQ ID NO 1063
<211> LENGTH: 19
<212> TYPE: RNA
<213> ORGANISM: Artificial sequence
<220> FEATURE:
<223> OTHER INFORMATION: Chemically synthesized

<400> SEQUENCE: 1063
cagacuucgu aaauugacc                                                   19

<210> SEQ ID NO 1064
<211> LENGTH: 19
<212> TYPE: RNA
<213> ORGANISM: Artificial sequence
<220> FEATURE:
<223> OTHER INFORMATION: Chemically synthesized

<400> SEQUENCE: 1064
ucaauuccca gaaaagccc                                                   19

<210> SEQ ID NO 1065
<211> LENGTH: 19
<212> TYPE: RNA
<213> ORGANISM: Artificial sequence
<220> FEATURE:
<223> OTHER INFORMATION: Chemically synthesized

<400> SEQUENCE: 1065
uuccuauccu cacagguau                                                   19

<210> SEQ ID NO 1066
<211> LENGTH: 19
<212> TYPE: RNA
<213> ORGANISM: Artificial sequence
<220> FEATURE:
<223> OTHER INFORMATION: Chemically synthesized

<400> SEQUENCE: 1066
auucacucaa uggaagagu                                                   19

<210> SEQ ID NO 1067
<211> LENGTH: 19
<212> TYPE: RNA
<213> ORGANISM: Artificial sequence
<220> FEATURE:
<223> OTHER INFORMATION: Chemically synthesized

<400> SEQUENCE: 1067
ucaggaacaa cauaauccc                                                   19
```

```
<210> SEQ ID NO 1068
<211> LENGTH: 19
<212> TYPE: RNA
<213> ORGANISM: Artificial sequence
<220> FEATURE:
<223> OTHER INFORMATION: Chemically synthesized

<400> SEQUENCE: 1068
cgugguuacu gaaauggca                                                   19

<210> SEQ ID NO 1069
<211> LENGTH: 19
<212> TYPE: RNA
<213> ORGANISM: Artificial sequence
<220> FEATURE:
<223> OTHER INFORMATION: Chemically synthesized

<400> SEQUENCE: 1069
uuacugaaau ggcaccaca                                                   19

<210> SEQ ID NO 1070
<211> LENGTH: 19
<212> TYPE: RNA
<213> ORGANISM: Artificial sequence
<220> FEATURE:
<223> OTHER INFORMATION: Chemically synthesized

<400> SEQUENCE: 1070
ugaaauggca ccacaagcu                                                   19

<210> SEQ ID NO 1071
<211> LENGTH: 19
<212> TYPE: RNA
<213> ORGANISM: Artificial sequence
<220> FEATURE:
<223> OTHER INFORMATION: Chemically synthesized

<400> SEQUENCE: 1071
ccucuuuaaa acauuagag                                                   19

<210> SEQ ID NO 1072
<211> LENGTH: 19
<212> TYPE: RNA
<213> ORGANISM: Artificial sequence
<220> FEATURE:
<223> OTHER INFORMATION: Chemically synthesized

<400> SEQUENCE: 1072
agaaacagug aagcaguuc                                                   19

<210> SEQ ID NO 1073
<211> LENGTH: 19
<212> TYPE: RNA
<213> ORGANISM: Artificial sequence
<220> FEATURE:
<223> OTHER INFORMATION: Chemically synthesized

<400> SEQUENCE: 1073
gaaacaguga agcaguucc                                                   19

<210> SEQ ID NO 1074
<211> LENGTH: 19
<212> TYPE: RNA
<213> ORGANISM: Artificial sequence
<220> FEATURE:
```

<223> OTHER INFORMATION: Chemically synthesized

<400> SEQUENCE: 1074
gcaguuccau uauugccgu                                                      19

<210> SEQ ID NO 1075
<211> LENGTH: 19
<212> TYPE: RNA
<213> ORGANISM: Artificial sequence
<220> FEATURE:
<223> OTHER INFORMATION: Chemically synthesized

<400> SEQUENCE: 1075
auuuacucuu accagggu                                                       19

<210> SEQ ID NO 1076
<211> LENGTH: 19
<212> TYPE: RNA
<213> ORGANISM: Artificial sequence
<220> FEATURE:
<223> OTHER INFORMATION: Chemically synthesized

<400> SEQUENCE: 1076
auccucugaa aacuuagag                                                      19

<210> SEQ ID NO 1077
<211> LENGTH: 19
<212> TYPE: RNA
<213> ORGANISM: Artificial sequence
<220> FEATURE:
<223> OTHER INFORMATION: Chemically synthesized

<400> SEQUENCE: 1077
auauagucua uuaccaagc                                                      19

<210> SEQ ID NO 1078
<211> LENGTH: 19
<212> TYPE: RNA
<213> ORGANISM: Artificial sequence
<220> FEATURE:
<223> OTHER INFORMATION: Chemically synthesized

<400> SEQUENCE: 1078
auagucuauu accaagccu                                                      19

<210> SEQ ID NO 1079
<211> LENGTH: 19
<212> TYPE: RNA
<213> ORGANISM: Artificial sequence
<220> FEATURE:
<223> OTHER INFORMATION: Chemically synthesized

<400> SEQUENCE: 1079
ggaaucaaau guaaaacuc                                                      19

<210> SEQ ID NO 1080
<211> LENGTH: 19
<212> TYPE: RNA
<213> ORGANISM: Artificial sequence
<220> FEATURE:
<223> OTHER INFORMATION: Chemically synthesized

<400> SEQUENCE: 1080
uaaaacucaa augggcuuc                                                      19

```
<210> SEQ ID NO 1081
<211> LENGTH: 19
<212> TYPE: RNA
<213> ORGANISM: Artificial sequence
<220> FEATURE:
<223> OTHER INFORMATION: Chemically synthesized

<400> SEQUENCE: 1081
aaaaucacuu agcaggcuc                                                    19

<210> SEQ ID NO 1082
<211> LENGTH: 19
<212> TYPE: RNA
<213> ORGANISM: Artificial sequence
<220> FEATURE:
<223> OTHER INFORMATION: Chemically synthesized

<400> SEQUENCE: 1082
ucccauucaa uucuguaca                                                    19

<210> SEQ ID NO 1083
<211> LENGTH: 19
<212> TYPE: RNA
<213> ORGANISM: Artificial sequence
<220> FEATURE:
<223> OTHER INFORMATION: Chemically synthesized

<400> SEQUENCE: 1083
cccauucaau ucuguacaa                                                    19

<210> SEQ ID NO 1084
<211> LENGTH: 19
<212> TYPE: RNA
<213> ORGANISM: Artificial sequence
<220> FEATURE:
<223> OTHER INFORMATION: Chemically synthesized

<400> SEQUENCE: 1084
cuacacuauu uugaaucac                                                    19

<210> SEQ ID NO 1085
<211> LENGTH: 19
<212> TYPE: RNA
<213> ORGANISM: Artificial sequence
<220> FEATURE:
<223> OTHER INFORMATION: Chemically synthesized

<400> SEQUENCE: 1085
uuuugaauca cuucuccaa                                                    19

<210> SEQ ID NO 1086
<211> LENGTH: 19
<212> TYPE: RNA
<213> ORGANISM: Artificial sequence
<220> FEATURE:
<223> OTHER INFORMATION: Chemically synthesized

<400> SEQUENCE: 1086
aggccagaaa aucagccug                                                    19

<210> SEQ ID NO 1087
<211> LENGTH: 19
<212> TYPE: RNA
<213> ORGANISM: Artificial sequence
<220> FEATURE:
<223> OTHER INFORMATION: Chemically synthesized
```

-continued

<400> SEQUENCE: 1087
agaaaaucag ccuguuagc                                                19

<210> SEQ ID NO 1088
<211> LENGTH: 19
<212> TYPE: RNA
<213> ORGANISM: Artificial sequence
<220> FEATURE:
<223> OTHER INFORMATION: Chemically synthesized

<400> SEQUENCE: 1088
aacuacaaau gacuuuagc                                                19

<210> SEQ ID NO 1089
<211> LENGTH: 19
<212> TYPE: RNA
<213> ORGANISM: Artificial sequence
<220> FEATURE:
<223> OTHER INFORMATION: Chemically synthesized

<400> SEQUENCE: 1089
aaaugacuuu agcugacua                                                19

<210> SEQ ID NO 1090
<211> LENGTH: 19
<212> TYPE: RNA
<213> ORGANISM: Artificial sequence
<220> FEATURE:
<223> OTHER INFORMATION: Chemically synthesized

<400> SEQUENCE: 1090
aaugacuuua gcugacuag                                                19

<210> SEQ ID NO 1091
<211> LENGTH: 19
<212> TYPE: RNA
<213> ORGANISM: Artificial sequence
<220> FEATURE:
<223> OTHER INFORMATION: Chemically synthesized

<400> SEQUENCE: 1091
uaguuuuacu acccaauca                                                19

<210> SEQ ID NO 1092
<211> LENGTH: 19
<212> TYPE: RNA
<213> ORGANISM: Artificial sequence
<220> FEATURE:
<223> OTHER INFORMATION: Chemically synthesized

<400> SEQUENCE: 1092
uccagcaauu cugaaaugc                                                19

<210> SEQ ID NO 1093
<211> LENGTH: 19
<212> TYPE: RNA
<213> ORGANISM: Artificial sequence
<220> FEATURE:
<223> OTHER INFORMATION: Chemically synthesized

<400> SEQUENCE: 1093
ucccuuuuua ggacccuuc                                                19

<210> SEQ ID NO 1094
<211> LENGTH: 19

```
<212> TYPE: RNA
<213> ORGANISM: Artificial sequence
<220> FEATURE:
<223> OTHER INFORMATION: Chemically synthesized

<400> SEQUENCE: 1094
ucagaguucu ccugaaacc                                              19

<210> SEQ ID NO 1095
<211> LENGTH: 19
<212> TYPE: RNA
<213> ORGANISM: Artificial sequence
<220> FEATURE:
<223> OTHER INFORMATION: Chemically synthesized

<400> SEQUENCE: 1095
uucuccugaa accagagga                                              19

<210> SEQ ID NO 1096
<211> LENGTH: 19
<212> TYPE: RNA
<213> ORGANISM: Artificial sequence
<220> FEATURE:
<223> OTHER INFORMATION: Chemically synthesized

<400> SEQUENCE: 1096
uacuaaagaa aaagucccu                                              19

<210> SEQ ID NO 1097
<211> LENGTH: 19
<212> TYPE: RNA
<213> ORGANISM: Artificial sequence
<220> FEATURE:
<223> OTHER INFORMATION: Chemically synthesized

<400> SEQUENCE: 1097
aguguaagcu caaaaguag                                              19

<210> SEQ ID NO 1098
<211> LENGTH: 19
<212> TYPE: RNA
<213> ORGANISM: Artificial sequence
<220> FEATURE:
<223> OTHER INFORMATION: Chemically synthesized

<400> SEQUENCE: 1098
aaaguaggua cgacgcuag                                              19

<210> SEQ ID NO 1099
<211> LENGTH: 19
<212> TYPE: RNA
<213> ORGANISM: Artificial sequence
<220> FEATURE:
<223> OTHER INFORMATION: Chemically synthesized

<400> SEQUENCE: 1099
auccuaucca gcuuuuuac                                              19

<210> SEQ ID NO 1100
<211> LENGTH: 19
<212> TYPE: RNA
<213> ORGANISM: Artificial sequence
<220> FEATURE:
<223> OTHER INFORMATION: Chemically synthesized

<400> SEQUENCE: 1100
```

| | |
|---|---|
| uccaaguuca cgugcauaa | 19 |

```
<210> SEQ ID NO 1101
<211> LENGTH: 19
<212> TYPE: RNA
<213> ORGANISM: Artificial sequence
<220> FEATURE:
<223> OTHER INFORMATION: Chemically synthesized

<400> SEQUENCE: 1101
```

| | |
|---|---|
| ucacgugcau aacacaacc | 19 |

```
<210> SEQ ID NO 1102
<211> LENGTH: 19
<212> TYPE: RNA
<213> ORGANISM: Artificial sequence
<220> FEATURE:
<223> OTHER INFORMATION: Chemically synthesized

<400> SEQUENCE: 1102
```

| | |
|---|---|
| gugcauaaca caaccucgc | 19 |

```
<210> SEQ ID NO 1103
<211> LENGTH: 19
<212> TYPE: RNA
<213> ORGANISM: Artificial sequence
<220> FEATURE:
<223> OTHER INFORMATION: Chemically synthesized

<400> SEQUENCE: 1103
```

| | |
|---|---|
| accaaguuua guuugcuuu | 19 |

```
<210> SEQ ID NO 1104
<211> LENGTH: 19
<212> TYPE: RNA
<213> ORGANISM: Artificial sequence
<220> FEATURE:
<223> OTHER INFORMATION: Chemically synthesized

<400> SEQUENCE: 1104
```

| | |
|---|---|
| cauuuuguaa gcauaacag | 19 |

```
<210> SEQ ID NO 1105
<211> LENGTH: 19
<212> TYPE: RNA
<213> ORGANISM: Artificial sequence
<220> FEATURE:
<223> OTHER INFORMATION: Chemically synthesized

<400> SEQUENCE: 1105
```

| | |
|---|---|
| acuguuagug gaaaaagga | 19 |

```
<210> SEQ ID NO 1106
<211> LENGTH: 19
<212> TYPE: RNA
<213> ORGANISM: Artificial sequence
<220> FEATURE:
<223> OTHER INFORMATION: Chemically synthesized

<400> SEQUENCE: 1106
```

| | |
|---|---|
| cccaauucua uaaagauug | 19 |

```
<210> SEQ ID NO 1107
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 1107
ccaauucuau aaagauugg                                              19

<210> SEQ ID NO 1108
<211> LENGTH: 19
<212> TYPE: RNA
<213> ORGANISM: Artificial sequence
<220> FEATURE:
<223> OTHER INFORMATION: Chemically synthesized

<400> SEQUENCE: 1108
aagauuggcu uguaguau                                               19

<210> SEQ ID NO 1109
<211> LENGTH: 19
<212> TYPE: RNA
<213> ORGANISM: Artificial sequence
<220> FEATURE:
<223> OTHER INFORMATION: Chemically synthesized

<400> SEQUENCE: 1109
uaguuuguua gaacacugg                                              19

<210> SEQ ID NO 1110
<211> LENGTH: 19
<212> TYPE: RNA
<213> ORGANISM: Artificial sequence
<220> FEATURE:
<223> OTHER INFORMATION: Chemically synthesized

<400> SEQUENCE: 1110
acuggcuaau uugaacagu                                              19

<210> SEQ ID NO 1111
<211> LENGTH: 19
<212> TYPE: RNA
<213> ORGANISM: Artificial sequence
<220> FEATURE:
<223> OTHER INFORMATION: Chemically synthesized

<400> SEQUENCE: 1111
ugaacaguga cauuuuagg                                              19

<210> SEQ ID NO 1112
<211> LENGTH: 19
<212> TYPE: RNA
<213> ORGANISM: Artificial sequence
<220> FEATURE:
<223> OTHER INFORMATION: Chemically synthesized

<400> SEQUENCE: 1112
acagugacau uuuagguca                                              19

<210> SEQ ID NO 1113
<211> LENGTH: 19
<212> TYPE: RNA
<213> ORGANISM: Artificial sequence
<220> FEATURE:
<223> OTHER INFORMATION: Chemically synthesized

<400> SEQUENCE: 1113
ugacauuuua ggucacuua                                              19
```

```
<210> SEQ ID NO 1114
<211> LENGTH: 19
<212> TYPE: RNA
<213> ORGANISM: Artificial sequence
<220> FEATURE:
<223> OTHER INFORMATION: Chemically synthesized

<400> SEQUENCE: 1114 cauuuaggu cacuuauag                                                 19

<210> SEQ ID NO 1115
<211> LENGTH: 19
<212> TYPE: RNA
<213> ORGANISM: Artificial sequence
<220> FEATURE:
<223> OTHER INFORMATION: Chemically synthesized

<400> SEQUENCE: 1115
aucaguaaca ggaucacac                                                19

<210> SEQ ID NO 1116
<211> LENGTH: 19
<212> TYPE: RNA
<213> ORGANISM: Artificial sequence
<220> FEATURE:
<223> OTHER INFORMATION: Chemically synthesized

<400> SEQUENCE: 1116
ucuccagcau gugaagugg                                                19

<210> SEQ ID NO 1117
<211> LENGTH: 19
<212> TYPE: RNA
<213> ORGANISM: Artificial sequence
<220> FEATURE:
<223> OTHER INFORMATION: Chemically synthesized

<400> SEQUENCE: 1117
cagcaaggau augaaagcc                                                19

<210> SEQ ID NO 1118
<211> LENGTH: 19
<212> TYPE: RNA
<213> ORGANISM: Artificial sequence
<220> FEATURE:
<223> OTHER INFORMATION: Chemically synthesized

<400> SEQUENCE: 1118
aaggauauga aagccuugc                                                19

<210> SEQ ID NO 1119
<211> LENGTH: 19
<212> TYPE: RNA
<213> ORGANISM: Artificial sequence
<220> FEATURE:
<223> OTHER INFORMATION: Chemically synthesized

<400> SEQUENCE: 1119
aauugaacau uguugagug                                                19

<210> SEQ ID NO 1120
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1120
cauuguugag uggaggcua                                           19

<210> SEQ ID NO 1121
<211> LENGTH: 19
<212> TYPE: RNA
<213> ORGANISM: Artificial sequence
<220> FEATURE:
<223> OTHER INFORMATION: Chemically synthesized

<400> SEQUENCE: 1121
gaaagagaua augaucuac                                           19

<210> SEQ ID NO 1122
<211> LENGTH: 19
<212> TYPE: RNA
<213> ORGANISM: Artificial sequence
<220> FEATURE:
<223> OTHER INFORMATION: Chemically synthesized

<400> SEQUENCE: 1122
ugacagguau ccaaggugg                                           19

<210> SEQ ID NO 1123
<211> LENGTH: 19
<212> TYPE: RNA
<213> ORGANISM: Artificial sequence
<220> FEATURE:
<223> OTHER INFORMATION: Chemically synthesized

<400> SEQUENCE: 1123
aaaaucuggg ugcaugcau                                           19

<210> SEQ ID NO 1124
<211> LENGTH: 19
<212> TYPE: RNA
<213> ORGANISM: Artificial sequence
<220> FEATURE:
<223> OTHER INFORMATION: Chemically synthesized

<400> SEQUENCE: 1124
guaaauugac ccguuucaa                                           19

<210> SEQ ID NO 1125
<211> LENGTH: 19
<212> TYPE: RNA
<213> ORGANISM: Artificial sequence
<220> FEATURE:
<223> OTHER INFORMATION: Chemically synthesized

<400> SEQUENCE: 1125
ucaaauauua ccucguuga                                           19

<210> SEQ ID NO 1126
<211> LENGTH: 19
<212> TYPE: RNA
<213> ORGANISM: Artificial sequence
<220> FEATURE:
<223> OTHER INFORMATION: Chemically synthesized

<400> SEQUENCE: 1126
aauauuaccu cguugaggu                                           19

<210> SEQ ID NO 1127
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1127
auuaccucgu ugagguugg                                                     19

<210> SEQ ID NO 1128
<211> LENGTH: 19
<212> TYPE: RNA
<213> ORGANISM: Artificial sequence
<220> FEATURE:
<223> OTHER INFORMATION: Chemically synthesized

<400> SEQUENCE: 1128
uucaucugag auuaagcac                                                     19

<210> SEQ ID NO 1129
<211> LENGTH: 19
<212> TYPE: RNA
<213> ORGANISM: Artificial sequence
<220> FEATURE:
<223> OTHER INFORMATION: Chemically synthesized

<400> SEQUENCE: 1129
ugaaucagag agggacuag                                                     19

<210> SEQ ID NO 1130
<211> LENGTH: 19
<212> TYPE: RNA
<213> ORGANISM: Artificial sequence
<220> FEATURE:
<223> OTHER INFORMATION: Chemically synthesized

<400> SEQUENCE: 1130
uauccucaca gguauucau                                                     19

<210> SEQ ID NO 1131
<211> LENGTH: 19
<212> TYPE: RNA
<213> ORGANISM: Artificial sequence
<220> FEATURE:
<223> OTHER INFORMATION: Chemically synthesized

<400> SEQUENCE: 1131
cuucuuagga gucccucu                                                      19

<210> SEQ ID NO 1132
<211> LENGTH: 19
<212> TYPE: RNA
<213> ORGANISM: Artificial sequence
<220> FEATURE:
<223> OTHER INFORMATION: Chemically synthesized

<400> SEQUENCE: 1132
acucaaugga agaguaauc                                                     19

<210> SEQ ID NO 1133
<211> LENGTH: 19
<212> TYPE: RNA
<213> ORGANISM: Artificial sequence
<220> FEATURE:
<223> OTHER INFORMATION: Chemically synthesized

<400> SEQUENCE: 1133
```
cucaauggaa gaguaauca                                                    19

<210> SEQ ID NO 1134
<211> LENGTH: 19
<212> TYPE: RNA
<213> ORGANISM: Artificial sequence
<220> FEATURE:
<223> OTHER INFORMATION: Chemically synthesized

<400> SEQUENCE: 1134
auggaagagu aaucaacua                                                    19

<210> SEQ ID NO 1135
<211> LENGTH: 19
<212> TYPE: RNA
<213> ORGANISM: Artificial sequence
<220> FEATURE:
<223> OTHER INFORMATION: Chemically synthesized

<400> SEQUENCE: 1135
uggaagagua aucaacuac                                                    19

<210> SEQ ID NO 1136
<211> LENGTH: 19
<212> TYPE: RNA
<213> ORGANISM: Artificial sequence
<220> FEATURE:
<223> OTHER INFORMATION: Chemically synthesized

<400> SEQUENCE: 1136
uaaagacagu auucaacac                                                    19

<210> SEQ ID NO 1137
<211> LENGTH: 19
<212> TYPE: RNA
<213> ORGANISM: Artificial sequence
<220> FEATURE:
<223> OTHER INFORMATION: Chemically synthesized

<400> SEQUENCE: 1137
aacaggggaa acugagcuu                                                    19

<210> SEQ ID NO 1138
<211> LENGTH: 19
<212> TYPE: RNA
<213> ORGANISM: Artificial sequence
<220> FEATURE:
<223> OTHER INFORMATION: Chemically synthesized

<400> SEQUENCE: 1138
ucuaaaacaa caccguggu                                                    19

<210> SEQ ID NO 1139
<211> LENGTH: 19
<212> TYPE: RNA
<213> ORGANISM: Artificial sequence
<220> FEATURE:
<223> OTHER INFORMATION: Chemically synthesized

<400> SEQUENCE: 1139
gugguuacug aaauggcac                                                    19

<210> SEQ ID NO 1140
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1140
ugguuacuga aauggcacc                                                  19

<210> SEQ ID NO 1141
<211> LENGTH: 19
<212> TYPE: RNA
<213> ORGANISM: Artificial sequence
<220> FEATURE:
<223> OTHER INFORMATION: Chemically synthesized

<400> SEQUENCE: 1141
ccaagaaaca gugaagcag                                                  19

<210> SEQ ID NO 1142
<211> LENGTH: 19
<212> TYPE: RNA
<213> ORGANISM: Artificial sequence
<220> FEATURE:
<223> OTHER INFORMATION: Chemically synthesized

<400> SEQUENCE: 1142
aagaaacagu gaagcaguu                                                  19

<210> SEQ ID NO 1143
<211> LENGTH: 19
<212> TYPE: RNA
<213> ORGANISM: Artificial sequence
<220> FEATURE:
<223> OTHER INFORMATION: Chemically synthesized

<400> SEQUENCE: 1143
ugaagcaguu ccauuauug                                                  19

<210> SEQ ID NO 1144
<211> LENGTH: 19
<212> TYPE: RNA
<213> ORGANISM: Artificial sequence
<220> FEATURE:
<223> OTHER INFORMATION: Chemically synthesized

<400> SEQUENCE: 1144
uucucauuua cucuuaccu                                                  19

<210> SEQ ID NO 1145
<211> LENGTH: 19
<212> TYPE: RNA
<213> ORGANISM: Artificial sequence
<220> FEATURE:
<223> OTHER INFORMATION: Chemically synthesized

<400> SEQUENCE: 1145
aaacucaccu acuuaaucc                                                  19

<210> SEQ ID NO 1146
<211> LENGTH: 19
<212> TYPE: RNA
<213> ORGANISM: Artificial sequence
<220> FEATURE:
<223> OTHER INFORMATION: Chemically synthesized

<400> SEQUENCE: 1146
aacccuucaa auuugaguc                                                  19
```

<210> SEQ ID NO 1147
<211> LENGTH: 19
<212> TYPE: RNA
<213> ORGANISM: Artificial sequence
<220> FEATURE:
<223> OTHER INFORMATION: Chemically synthesized

<400> SEQUENCE: 1147
aucaaaauag gcaaaucug                                              19

<210> SEQ ID NO 1148
<211> LENGTH: 19
<212> TYPE: RNA
<213> ORGANISM: Artificial sequence
<220> FEATURE:
<223> OTHER INFORMATION: Chemically synthesized

<400> SEQUENCE: 1148
ucaaaauagg caaaucugg                                              19

<210> SEQ ID NO 1149
<211> LENGTH: 19
<212> TYPE: RNA
<213> ORGANISM: Artificial sequence
<220> FEATURE:
<223> OTHER INFORMATION: Chemically synthesized

<400> SEQUENCE: 1149
aggcaaaucu gguuuauau                                              19

<210> SEQ ID NO 1150
<211> LENGTH: 19
<212> TYPE: RNA
<213> ORGANISM: Artificial sequence
<220> FEATURE:
<223> OTHER INFORMATION: Chemically synthesized

<400> SEQUENCE: 1150
uauagucuau uaccaagcc                                              19

<210> SEQ ID NO 1151
<211> LENGTH: 19
<212> TYPE: RNA
<213> ORGANISM: Artificial sequence
<220> FEATURE:
<223> OTHER INFORMATION: Chemically synthesized

<400> SEQUENCE: 1151
cugaaaccaa auuguggaa                                              19

<210> SEQ ID NO 1152
<211> LENGTH: 19
<212> TYPE: RNA
<213> ORGANISM: Artificial sequence
<220> FEATURE:
<223> OTHER INFORMATION: Chemically synthesized

<400> SEQUENCE: 1152
accaaauugu ggaaucaaa                                              19

<210> SEQ ID NO 1153
<211> LENGTH: 19
<212> TYPE: RNA
<213> ORGANISM: Artificial sequence
<220> FEATURE:

<223> OTHER INFORMATION: Chemically synthesized

<400> SEQUENCE: 1153
acuuuugcuu accuauucc                                                19

<210> SEQ ID NO 1154
<211> LENGTH: 19
<212> TYPE: RNA
<213> ORGANISM: Artificial sequence
<220> FEATURE:
<223> OTHER INFORMATION: Chemically synthesized

<400> SEQUENCE: 1154
uccaucccau ucaauucug                                                19

<210> SEQ ID NO 1155
<211> LENGTH: 19
<212> TYPE: RNA
<213> ORGANISM: Artificial sequence
<220> FEATURE:
<223> OTHER INFORMATION: Chemically synthesized

<400> SEQUENCE: 1155
ucuguacaaa aaugggauc                                                19

<210> SEQ ID NO 1156
<211> LENGTH: 19
<212> TYPE: RNA
<213> ORGANISM: Artificial sequence
<220> FEATURE:
<223> OTHER INFORMATION: Chemically synthesized

<400> SEQUENCE: 1156 cguacaaaa augggaucu                                                 19

<210> SEQ ID NO 1157
<211> LENGTH: 19
<212> TYPE: RNA
<213> ORGANISM: Artificial sequence
<220> FEATURE:
<223> OTHER INFORMATION: Chemically synthesized

<400> SEQUENCE: 1157
cuaugcagaa aaucuacac                                                19

<210> SEQ ID NO 1158
<211> LENGTH: 19
<212> TYPE: RNA
<213> ORGANISM: Artificial sequence
<220> FEATURE:
<223> OTHER INFORMATION: Chemically synthesized

<400> SEQUENCE: 1158
aaggccagaa aaucagccu                                                19

<210> SEQ ID NO 1159
<211> LENGTH: 19
<212> TYPE: RNA
<213> ORGANISM: Artificial sequence
<220> FEATURE:
<223> OTHER INFORMATION: Chemically synthesized

<400> SEQUENCE: 1159
ugcaguugcu augaaugug                                                19

```
<210> SEQ ID NO 1160
<211> LENGTH: 19
<212> TYPE: RNA
<213> ORGANISM: Artificial sequence
<220> FEATURE:
<223> OTHER INFORMATION: Chemically synthesized

<400> SEQUENCE: 1160
uuauuuaggg caggugggg                                                      19

<210> SEQ ID NO 1161
<211> LENGTH: 19
<212> TYPE: RNA
<213> ORGANISM: Artificial sequence
<220> FEATURE:
<223> OTHER INFORMATION: Chemically synthesized

<400> SEQUENCE: 1161
acuacaaaug acuuuagcu                                                      19

<210> SEQ ID NO 1162
<211> LENGTH: 19
<212> TYPE: RNA
<213> ORGANISM: Artificial sequence
<220> FEATURE:
<223> OTHER INFORMATION: Chemically synthesized

<400> SEQUENCE: 1162
uacaaaugac uuuagcuga                                                      19

<210> SEQ ID NO 1163
<211> LENGTH: 19
<212> TYPE: RNA
<213> ORGANISM: Artificial sequence
<220> FEATURE:
<223> OTHER INFORMATION: Chemically synthesized

<400> SEQUENCE: 1163
gacuuuagcu gacuagcug                                                      19

<210> SEQ ID NO 1164
<211> LENGTH: 19
<212> TYPE: RNA
<213> ORGANISM: Artificial sequence
<220> FEATURE:
<223> OTHER INFORMATION: Chemically synthesized

<400> SEQUENCE: 1164
ugaauaguuu uacuaccca                                                      19

<210> SEQ ID NO 1165
<211> LENGTH: 19
<212> TYPE: RNA
<213> ORGANISM: Artificial sequence
<220> FEATURE:
<223> OTHER INFORMATION: Chemically synthesized

<400> SEQUENCE: 1165
acccaaucau gaaauaauc                                                      19

<210> SEQ ID NO 1166
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1166 auuuuccuu uuuaggacc                                                    19

<210> SEQ ID NO 1167
<211> LENGTH: 19
<212> TYPE: RNA
<213> ORGANISM: Artificial sequence
<220> FEATURE:
<223> OTHER INFORMATION: Chemically synthesized

<400> SEQUENCE: 1167
cagcaauucu gaaaugcug                                                   19

<210> SEQ ID NO 1168
<211> LENGTH: 19
<212> TYPE: RNA
<213> ORGANISM: Artificial sequence
<220> FEATURE:
<223> OTHER INFORMATION: Chemically synthesized

<400> SEQUENCE: 1168
gcaauucuga aaugcuggc                                                   19

<210> SEQ ID NO 1169
<211> LENGTH: 19
<212> TYPE: RNA
<213> ORGANISM: Artificial sequence
<220> FEATURE:
<223> OTHER INFORMATION: Chemically synthesized

<400> SEQUENCE: 1169
agcugaggau cagaguucu                                                   19

<210> SEQ ID NO 1170
<211> LENGTH: 19
<212> TYPE: RNA
<213> ORGANISM: Artificial sequence
<220> FEATURE:
<223> OTHER INFORMATION: Chemically synthesized

<400> SEQUENCE: 1170
acaggcaggu ggcuucuua                                                   19

<210> SEQ ID NO 1171
<211> LENGTH: 19
<212> TYPE: RNA
<213> ORGANISM: Artificial sequence
<220> FEATURE:
<223> OTHER INFORMATION: Chemically synthesized

<400> SEQUENCE: 1171
ucuccugaaa ccagaggag                                                   19

<210> SEQ ID NO 1172
<211> LENGTH: 19
<212> TYPE: RNA
<213> ORGANISM: Artificial sequence
<220> FEATURE:
<223> OTHER INFORMATION: Chemically synthesized

<400> SEQUENCE: 1172
cuacuaaaga aaaagucccc                                                  19

<210> SEQ ID NO 1173
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1173
uuaaacacaa guguaagcu                                                    19

<210> SEQ ID NO 1174
<211> LENGTH: 19
<212> TYPE: RNA
<213> ORGANISM: Artificial sequence
<220> FEATURE:
<223> OTHER INFORMATION: Chemically synthesized

<400> SEQUENCE: 1174
gcucaaaagu agguacgac                                                    19

<210> SEQ ID NO 1175
<211> LENGTH: 19
<212> TYPE: RNA
<213> ORGANISM: Artificial sequence
<220> FEATURE:
<223> OTHER INFORMATION: Chemically synthesized

<400> SEQUENCE: 1175
caaaaguagg uacgacgcu                                                    19

<210> SEQ ID NO 1176
<211> LENGTH: 19
<212> TYPE: RNA
<213> ORGANISM: Artificial sequence
<220> FEATURE:
<223> OTHER INFORMATION: Chemically synthesized

<400> SEQUENCE: 1176
acacaauccu auccagcuu                                                    19

<210> SEQ ID NO 1177
<211> LENGTH: 19
<212> TYPE: RNA
<213> ORGANISM: Artificial sequence
<220> FEATURE:
<223> OTHER INFORMATION: Chemically synthesized

<400> SEQUENCE: 1177
gcauaacaca accucgcaa                                                    19

<210> SEQ ID NO 1178
<211> LENGTH: 19
<212> TYPE: RNA
<213> ORGANISM: Artificial sequence
<220> FEATURE:
<223> OTHER INFORMATION: Chemically synthesized

<400> SEQUENCE: 1178
cgcaggacau cuugagcaa                                                    19

<210> SEQ ID NO 1179
<211> LENGTH: 19
<212> TYPE: RNA
<213> ORGANISM: Artificial sequence
<220> FEATURE:
<223> OTHER INFORMATION: Chemically synthesized

<400> SEQUENCE: 1179
```
cuugagcaau ucucugggu                                              19

<210> SEQ ID NO 1180
<211> LENGTH: 19
<212> TYPE: RNA
<213> ORGANISM: Artificial sequence
<220> FEATURE:
<223> OTHER INFORMATION: Chemically synthesized

<400> SEQUENCE: 1180
caaguuuagu uugcuuuga                                              19

<210> SEQ ID NO 1181
<211> LENGTH: 19
<212> TYPE: RNA
<213> ORGANISM: Artificial sequence
<220> FEATURE:
<223> OTHER INFORMATION: Chemically synthesized

<400> SEQUENCE: 1181
uaguuugcuu ugauuugga                                              19

<210> SEQ ID NO 1182
<211> LENGTH: 19
<212> TYPE: RNA
<213> ORGANISM: Artificial sequence
<220> FEATURE:
<223> OTHER INFORMATION: Chemically synthesized

<400> SEQUENCE: 1182
uaauuuaaca gccuuccau                                              19

<210> SEQ ID NO 1183
<211> LENGTH: 19
<212> TYPE: RNA
<213> ORGANISM: Artificial sequence
<220> FEATURE:
<223> OTHER INFORMATION: Chemically synthesized

<400> SEQUENCE: 1183
uuugcuuuga uuuggacag                                              19

<210> SEQ ID NO 1184
<211> LENGTH: 19
<212> TYPE: RNA
<213> ORGANISM: Artificial sequence
<220> FEATURE:
<223> OTHER INFORMATION: Chemically synthesized

<400> SEQUENCE: 1184
ugcuuugauu uggacagac                                              19

<210> SEQ ID NO 1185
<211> LENGTH: 19
<212> TYPE: RNA
<213> ORGANISM: Artificial sequence
<220> FEATURE:
<223> OTHER INFORMATION: Chemically synthesized

<400> SEQUENCE: 1185
accauuuugu aagcauaac                                              19

<210> SEQ ID NO 1186
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 1186
uaacaggcaa gagagucaa                                                19

<210> SEQ ID NO 1187
<211> LENGTH: 19
<212> TYPE: RNA
<213> ORGANISM: Artificial sequence
<220> FEATURE:
<223> OTHER INFORMATION: Chemically synthesized

<400> SEQUENCE: 1187
aacuguuagu ggaaaaagg                                                19

<210> SEQ ID NO 1188
<211> LENGTH: 19
<212> TYPE: RNA
<213> ORGANISM: Artificial sequence
<220> FEATURE:
<223> OTHER INFORMATION: Chemically synthesized

<400> SEQUENCE: 1188
ugauuuggac agacaguuc                                                19

<210> SEQ ID NO 1189
<211> LENGTH: 19
<212> TYPE: RNA
<213> ORGANISM: Artificial sequence
<220> FEATURE:
<223> OTHER INFORMATION: Chemically synthesized

<400> SEQUENCE: 1189
aguucuacau cgaugccca                                                19

<210> SEQ ID NO 1190
<211> LENGTH: 19
<212> TYPE: RNA
<213> ORGANISM: Artificial sequence
<220> FEATURE:
<223> OTHER INFORMATION: Chemically synthesized

<400> SEQUENCE: 1190
agaaacacag ugaaccuuu                                                19

<210> SEQ ID NO 1191
<211> LENGTH: 19
<212> TYPE: RNA
<213> ORGANISM: Artificial sequence
<220> FEATURE:
<223> OTHER INFORMATION: Chemically synthesized

<400> SEQUENCE: 1191
aacacaguga accuuugga                                                19

<210> SEQ ID NO 1192
<211> LENGTH: 19
<212> TYPE: RNA
<213> ORGANISM: Artificial sequence
<220> FEATURE:
<223> OTHER INFORMATION: Chemically synthesized

<400> SEQUENCE: 1192
agcuuaacaa uagacaugc                                                19
```

<210> SEQ ID NO 1193
<211> LENGTH: 19
<212> TYPE: RNA
<213> ORGANISM: Artificial sequence
<220> FEATURE:
<223> OTHER INFORMATION: Chemically synthesized

<400> SEQUENCE: 1193
acaugcaaaa caacauuga                                                  19

<210> SEQ ID NO 1194
<211> LENGTH: 19
<212> TYPE: RNA
<213> ORGANISM: Artificial sequence
<220> FEATURE:
<223> OTHER INFORMATION: Chemically synthesized

<400> SEQUENCE: 1194
uugauuuauc uuggcccaa                                                  19

<210> SEQ ID NO 1195
<211> LENGTH: 19
<212> TYPE: RNA
<213> ORGANISM: Artificial sequence
<220> FEATURE:
<223> OTHER INFORMATION: Chemically synthesized

<400> SEQUENCE: 1195
ugauuuaucu uggcccaau                                                  19

<210> SEQ ID NO 1196
<211> LENGTH: 19
<212> TYPE: RNA
<213> ORGANISM: Artificial sequence
<220> FEATURE:
<223> OTHER INFORMATION: Chemically synthesized

<400> SEQUENCE: 1196
ucuauaaaga uuggcuuug                                                  19

<210> SEQ ID NO 1197
<211> LENGTH: 19
<212> TYPE: RNA
<213> ORGANISM: Artificial sequence
<220> FEATURE:
<223> OTHER INFORMATION: Chemically synthesized

<400> SEQUENCE: 1197
auaaagauug gcuuuguag                                                  19

<210> SEQ ID NO 1198
<211> LENGTH: 19
<212> TYPE: RNA
<213> ORGANISM: Artificial sequence
<220> FEATURE:
<223> OTHER INFORMATION: Chemically synthesized

<400> SEQUENCE: 1198
agcauuugaa gaguuuagu                                                  19

<210> SEQ ID NO 1199
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 1199
guuuaguuug uuagaacac                                             19

<210> SEQ ID NO 1200
<211> LENGTH: 19
<212> TYPE: RNA
<213> ORGANISM: Artificial sequence
<220> FEATURE:
<223> OTHER INFORMATION: Chemically synthesized

<400> SEQUENCE: 1200
uggcuaauuu gaacaguga                                             19

<210> SEQ ID NO 1201
<211> LENGTH: 19
<212> TYPE: RNA
<213> ORGANISM: Artificial sequence
<220> FEATURE:
<223> OTHER INFORMATION: Chemically synthesized

<400> SEQUENCE: 1201
cuuauaguau caguaacag                                             19

<210> SEQ ID NO 1202
<211> LENGTH: 19
<212> TYPE: RNA
<213> ORGANISM: Artificial sequence
<220> FEATURE:
<223> OTHER INFORMATION: Chemically synthesized

<400> SEQUENCE: 1202
uauaguauca guaacagga                                             19

<210> SEQ ID NO 1203
<211> LENGTH: 19
<212> TYPE: RNA
<213> ORGANISM: Artificial sequence
<220> FEATURE:
<223> OTHER INFORMATION: Chemically synthesized

<400> SEQUENCE: 1203
auaguaucag uaacaggau                                             19

<210> SEQ ID NO 1204
<211> LENGTH: 19
<212> TYPE: RNA
<213> ORGANISM: Artificial sequence
<220> FEATURE:
<223> OTHER INFORMATION: Chemically synthesized

<400> SEQUENCE: 1204
aguaacagga ucacaccug                                             19

<210> SEQ ID NO 1205
<211> LENGTH: 19
<212> TYPE: RNA
<213> ORGANISM: Artificial sequence
<220> FEATURE:
<223> OTHER INFORMATION: Chemically synthesized

<400> SEQUENCE: 1205
augaauacau cugucccua                                             19

<210> SEQ ID NO 1206
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1206
gugaagugga gcuaauagc                                                    19

<210> SEQ ID NO 1207
<211> LENGTH: 19
<212> TYPE: RNA
<213> ORGANISM: Artificial sequence
<220> FEATURE:
<223> OTHER INFORMATION: Chemically synthesized

<400> SEQUENCE: 1207
uggagcuaau agcuagggc                                                    19

<210> SEQ ID NO 1208
<211> LENGTH: 19
<212> TYPE: RNA
<213> ORGANISM: Artificial sequence
<220> FEATURE:
<223> OTHER INFORMATION: Chemically synthesized

<400> SEQUENCE: 1208
auaagcuccu uauccacga                                                    19

<210> SEQ ID NO 1209
<211> LENGTH: 19
<212> TYPE: RNA
<213> ORGANISM: Artificial sequence
<220> FEATURE:
<223> OTHER INFORMATION: Chemically synthesized

<400> SEQUENCE: 1209
gcaaggauau gaaagccuu                                                    19

<210> SEQ ID NO 1210
<211> LENGTH: 19
<212> TYPE: RNA
<213> ORGANISM: Artificial sequence
<220> FEATURE:
<223> OTHER INFORMATION: Chemically synthesized

<400> SEQUENCE: 1210
auugaacauu guugagugg                                                    19

<210> SEQ ID NO 1211
<211> LENGTH: 19
<212> TYPE: RNA
<213> ORGANISM: Artificial sequence
<220> FEATURE:
<223> OTHER INFORMATION: Chemically synthesized

<400> SEQUENCE: 1211
gaacauuguu gaguggagg                                                    19

<210> SEQ ID NO 1212
<211> LENGTH: 19
<212> TYPE: RNA
<213> ORGANISM: Artificial sequence
<220> FEATURE:
<223> OTHER INFORMATION: Chemically synthesized

<400> SEQUENCE: 1212
```
ucccuaguga cagguaucc                                            19

<210> SEQ ID NO 1213
<211> LENGTH: 19
<212> TYPE: RNA
<213> ORGANISM: Artificial sequence
<220> FEATURE:
<223> OTHER INFORMATION: Chemically synthesized

<400> SEQUENCE: 1213
agugacaggu auccaaggu                                            19

<210> SEQ ID NO 1214
<211> LENGTH: 19
<212> TYPE: RNA
<213> ORGANISM: Artificial sequence
<220> FEATURE:
<223> OTHER INFORMATION: Chemically synthesized

<400> SEQUENCE: 1214
augguuaucu ggacgguga                                            19

<210> SEQ ID NO 1215
<211> LENGTH: 19
<212> TYPE: RNA
<213> ORGANISM: Artificial sequence
<220> FEATURE:
<223> OTHER INFORMATION: Chemically synthesized

<400> SEQUENCE: 1215
guuaucugga cggugaguu                                            19

<210> SEQ ID NO 1216
<211> LENGTH: 19
<212> TYPE: RNA
<213> ORGANISM: Artificial sequence
<220> FEATURE:
<223> OTHER INFORMATION: Chemically synthesized

<400> SEQUENCE: 1216
guacuauaaa ccauaucuc                                            19

<210> SEQ ID NO 1217
<211> LENGTH: 19
<212> TYPE: RNA
<213> ORGANISM: Artificial sequence
<220> FEATURE:
<223> OTHER INFORMATION: Chemically synthesized

<400> SEQUENCE: 1217
auaucuccau agccaaugc                                            19

<210> SEQ ID NO 1218
<211> LENGTH: 19
<212> TYPE: RNA
<213> ORGANISM: Artificial sequence
<220> FEATURE:
<223> OTHER INFORMATION: Chemically synthesized

<400> SEQUENCE: 1218
ccucaaauau uaccucguu                                            19

<210> SEQ ID NO 1219
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1219
cucaaauauu accucguug                                                      19

<210> SEQ ID NO 1220
<211> LENGTH: 19
<212> TYPE: RNA
<213> ORGANISM: Artificial sequence
<220> FEATURE:
<223> OTHER INFORMATION: Chemically synthesized

<400> SEQUENCE: 1220 ucaaagggu aguauacag                                                       19

<210> SEQ ID NO 1221
<211> LENGTH: 19
<212> TYPE: RNA
<213> ORGANISM: Artificial sequence
<220> FEATURE:
<223> OTHER INFORMATION: Chemically synthesized

<400> SEQUENCE: 1221
aagugguagu auacagcua                                                      19

<210> SEQ ID NO 1222
<211> LENGTH: 19
<212> TYPE: RNA
<213> ORGANISM: Artificial sequence
<220> FEATURE:
<223> OTHER INFORMATION: Chemically synthesized

<400> SEQUENCE: 1222
agugguagua uacagcuac                                                      19

<210> SEQ ID NO 1223
<211> LENGTH: 19
<212> TYPE: RNA
<213> ORGANISM: Artificial sequence
<220> FEATURE:
<223> OTHER INFORMATION: Chemically synthesized

<400> SEQUENCE: 1223
agaugagaua acacugcca                                                      19

<210> SEQ ID NO 1224
<211> LENGTH: 19
<212> TYPE: RNA
<213> ORGANISM: Artificial sequence
<220> FEATURE:
<223> OTHER INFORMATION: Chemically synthesized

<400> SEQUENCE: 1224 ugaaagguu caucugaga                                                       19

<210> SEQ ID NO 1225
<211> LENGTH: 19
<212> TYPE: RNA
<213> ORGANISM: Artificial sequence
<220> FEATURE:
<223> OTHER INFORMATION: Chemically synthesized

<400> SEQUENCE: 1225 aauggucau cugagauua                                                       19
```

```
<210> SEQ ID NO 1226
<211> LENGTH: 19
<212> TYPE: RNA
<213> ORGANISM: Artificial sequence
<220> FEATURE:
<223> OTHER INFORMATION: Chemically synthesized

<400> SEQUENCE: 1226
cuaagugaau cagagaggg                                               19

<210> SEQ ID NO 1227
<211> LENGTH: 19
<212> TYPE: RNA
<213> ORGANISM: Artificial sequence
<220> FEATURE:
<223> OTHER INFORMATION: Chemically synthesized

<400> SEQUENCE: 1227
agugaaucag agagggacu                                               19

<210> SEQ ID NO 1228
<211> LENGTH: 19
<212> TYPE: RNA
<213> ORGANISM: Artificial sequence
<220> FEATURE:
<223> OTHER INFORMATION: Chemically synthesized

<400> SEQUENCE: 1228
gugaaucaga gagggacua                                               19

<210> SEQ ID NO 1229
<211> LENGTH: 19
<212> TYPE: RNA
<213> ORGANISM: Artificial sequence
<220> FEATURE:
<223> OTHER INFORMATION: Chemically synthesized

<400> SEQUENCE: 1229
ucaauggaag aguaaucaa                                               19

<210> SEQ ID NO 1230
<211> LENGTH: 19
<212> TYPE: RNA
<213> ORGANISM: Artificial sequence
<220> FEATURE:
<223> OTHER INFORMATION: Chemically synthesized

<400> SEQUENCE: 1230
gaagaguaau caacuacac                                               19

<210> SEQ ID NO 1231
<211> LENGTH: 19
<212> TYPE: RNA
<213> ORGANISM: Artificial sequence
<220> FEATURE:
<223> OTHER INFORMATION: Chemically synthesized

<400> SEQUENCE: 1231
caacacuuaa gaacagggg                                               19

<210> SEQ ID NO 1232
<211> LENGTH: 19
<212> TYPE: RNA
<213> ORGANISM: Artificial sequence
<220> FEATURE:
```

```
<223> OTHER INFORMATION: Chemically synthesized

<400> SEQUENCE: 1232
acacuuaaga acaggggaa                                                19

<210> SEQ ID NO 1233
<211> LENGTH: 19
<212> TYPE: RNA
<213> ORGANISM: Artificial sequence
<220> FEATURE:
<223> OTHER INFORMATION: Chemically synthesized

<400> SEQUENCE: 1233
uuaagaacag gggaaacug                                                19

<210> SEQ ID NO 1234
<211> LENGTH: 19
<212> TYPE: RNA
<213> ORGANISM: Artificial sequence
<220> FEATURE:
<223> OTHER INFORMATION: Chemically synthesized

<400> SEQUENCE: 1234
aaacugagcu uauaaaggc                                                19

<210> SEQ ID NO 1235
<211> LENGTH: 19
<212> TYPE: RNA
<213> ORGANISM: Artificial sequence
<220> FEATURE:
<223> OTHER INFORMATION: Chemically synthesized

<400> SEQUENCE: 1235
aaggcaucua aaacaacac                                                19

<210> SEQ ID NO 1236
<211> LENGTH: 19
<212> TYPE: RNA
<213> ORGANISM: Artificial sequence
<220> FEATURE:
<223> OTHER INFORMATION: Chemically synthesized

<400> SEQUENCE: 1236
gcaucuaaaa caacaccgu                                                19

<210> SEQ ID NO 1237
<211> LENGTH: 19
<212> TYPE: RNA
<213> ORGANISM: Artificial sequence
<220> FEATURE:
<223> OTHER INFORMATION: Chemically synthesized

<400> SEQUENCE: 1237
aucuaaaaca caccgugg                                                 19

<210> SEQ ID NO 1238
<211> LENGTH: 19
<212> TYPE: RNA
<213> ORGANISM: Artificial sequence
<220> FEATURE:
<223> OTHER INFORMATION: Chemically synthesized

<400> SEQUENCE: 1238
acaacaccgu gguuacuga                                                19
```

```
<210> SEQ ID NO 1239
<211> LENGTH: 19
<212> TYPE: RNA
<213> ORGANISM: Artificial sequence
<220> FEATURE:
<223> OTHER INFORMATION: Chemically synthesized

<400> SEQUENCE: 1239
accgugguua cugaaaugg                                                19

<210> SEQ ID NO 1240
<211> LENGTH: 19
<212> TYPE: RNA
<213> ORGANISM: Artificial sequence
<220> FEATURE:
<223> OTHER INFORMATION: Chemically synthesized

<400> SEQUENCE: 1240
cucaccuacu uaauccuac                                                19

<210> SEQ ID NO 1241
<211> LENGTH: 19
<212> TYPE: RNA
<213> ORGANISM: Artificial sequence
<220> FEATURE:
<223> OTHER INFORMATION: Chemically synthesized

<400> SEQUENCE: 1241
ucaccuacuu aauccuacc                                                19

<210> SEQ ID NO 1242
<211> LENGTH: 19
<212> TYPE: RNA
<213> ORGANISM: Artificial sequence
<220> FEATURE:
<223> OTHER INFORMATION: Chemically synthesized

<400> SEQUENCE: 1242
uuccugucua aaaacccuu                                                19

<210> SEQ ID NO 1243
<211> LENGTH: 19
<212> TYPE: RNA
<213> ORGANISM: Artificial sequence
<220> FEATURE:
<223> OTHER INFORMATION: Chemically synthesized

<400> SEQUENCE: 1243
cugucuaaaa acccuucaa                                                19

<210> SEQ ID NO 1244
<211> LENGTH: 19
<212> TYPE: RNA
<213> ORGANISM: Artificial sequence
<220> FEATURE:
<223> OTHER INFORMATION: Chemically synthesized

<400> SEQUENCE: 1244
aaauuugagu caggaacug                                                19

<210> SEQ ID NO 1245
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1245
auuugaguca ggaacuggu                                          19

<210> SEQ ID NO 1246
<211> LENGTH: 19
<212> TYPE: RNA
<213> ORGANISM: Artificial sequence
<220> FEATURE:
<223> OTHER INFORMATION: Chemically synthesized

<400> SEQUENCE: 1246
uuuuggaagu uuugauagg                                          19

<210> SEQ ID NO 1247
<211> LENGTH: 19
<212> TYPE: RNA
<213> ORGANISM: Artificial sequence
<220> FEATURE:
<223> OTHER INFORMATION: Chemically synthesized

<400> SEQUENCE: 1247
uagucaaaau cacuuagca                                          19

<210> SEQ ID NO 1248
<211> LENGTH: 19
<212> TYPE: RNA
<213> ORGANISM: Artificial sequence
<220> FEATURE:
<223> OTHER INFORMATION: Chemically synthesized

<400> SEQUENCE: 1248
ccugaaacca aauugugga                                          19

<210> SEQ ID NO 1249
<211> LENGTH: 19
<212> TYPE: RNA
<213> ORGANISM: Artificial sequence
<220> FEATURE:
<223> OTHER INFORMATION: Chemically synthesized

<400> SEQUENCE: 1249
aaaccaaauu guggaauca                                          19

<210> SEQ ID NO 1250
<211> LENGTH: 19
<212> TYPE: RNA
<213> ORGANISM: Artificial sequence
<220> FEATURE:
<223> OTHER INFORMATION: Chemically synthesized

<400> SEQUENCE: 1250
guacaaaaau gggaucuau                                          19

<210> SEQ ID NO 1251
<211> LENGTH: 19
<212> TYPE: RNA
<213> ORGANISM: Artificial sequence
<220> FEATURE:
<223> OTHER INFORMATION: Chemically synthesized

<400> SEQUENCE: 1251
ucacuuagca ggcucucug                                          19

<210> SEQ ID NO 1252
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1252
aucuaugcag aaaaucuac                                              19

<210> SEQ ID NO 1253
<211> LENGTH: 19
<212> TYPE: RNA
<213> ORGANISM: Artificial sequence
<220> FEATURE:
<223> OTHER INFORMATION: Chemically synthesized

<400> SEQUENCE: 1253
augcagaaaa ucuacacua                                              19

<210> SEQ ID NO 1254
<211> LENGTH: 19
<212> TYPE: RNA
<213> ORGANISM: Artificial sequence
<220> FEATURE:
<223> OTHER INFORMATION: Chemically synthesized

<400> SEQUENCE: 1254
ugcagaaaau cuacacuau                                              19

<210> SEQ ID NO 1255
<211> LENGTH: 19
<212> TYPE: RNA
<213> ORGANISM: Artificial sequence
<220> FEATURE:
<223> OTHER INFORMATION: Chemically synthesized

<400> SEQUENCE: 1255
uugcuaugaa ugugaaaca                                              19

<210> SEQ ID NO 1256
<211> LENGTH: 19
<212> TYPE: RNA
<213> ORGANISM: Artificial sequence
<220> FEATURE:
<223> OTHER INFORMATION: Chemically synthesized

<400> SEQUENCE: 1256
uucuuauuua gggcaggug                                              19

<210> SEQ ID NO 1257
<211> LENGTH: 19
<212> TYPE: RNA
<213> ORGANISM: Artificial sequence
<220> FEATURE:
<223> OTHER INFORMATION: Chemically synthesized

<400> SEQUENCE: 1257
gcaaacuaca aaugacuuu                                              19

<210> SEQ ID NO 1258
<211> LENGTH: 19
<212> TYPE: RNA
<213> ORGANISM: Artificial sequence
<220> FEATURE:
<223> OTHER INFORMATION: Chemically synthesized

<400> SEQUENCE: 1258
```

```
augacuuuag cugacuagc                                         19

<210> SEQ ID NO 1259
<211> LENGTH: 19
<212> TYPE: RNA
<213> ORGANISM: Artificial sequence
<220> FEATURE:
<223> OTHER INFORMATION: Chemically synthesized

<400> SEQUENCE: 1259
acuuuagcug acuagcuga                                         19

<210> SEQ ID NO 1260
<211> LENGTH: 19
<212> TYPE: RNA
<213> ORGANISM: Artificial sequence
<220> FEATURE:
<223> OTHER INFORMATION: Chemically synthesized

<400> SEQUENCE: 1260
cugaauaguu uuacuaccc                                         19

<210> SEQ ID NO 1261
<211> LENGTH: 19
<212> TYPE: RNA
<213> ORGANISM: Artificial sequence
<220> FEATURE:
<223> OTHER INFORMATION: Chemically synthesized

<400> SEQUENCE: 1261
agcaauucug aaaugcugg                                         19

<210> SEQ ID NO 1262
<211> LENGTH: 19
<212> TYPE: RNA
<213> ORGANISM: Artificial sequence
<220> FEATURE:
<223> OTHER INFORMATION: Chemically synthesized

<400> SEQUENCE: 1262
aagucgaaau ccugagcug                                         19

<210> SEQ ID NO 1263
<211> LENGTH: 19
<212> TYPE: RNA
<213> ORGANISM: Artificial sequence
<220> FEATURE:
<223> OTHER INFORMATION: Chemically synthesized

<400> SEQUENCE: 1263
gagcugagga ucagaguuc                                         19

<210> SEQ ID NO 1264
<211> LENGTH: 19
<212> TYPE: RNA
<213> ORGANISM: Artificial sequence
<220> FEATURE:
<223> OTHER INFORMATION: Chemically synthesized

<400> SEQUENCE: 1264
ugaaaccaga ggagaagcg                                         19

<210> SEQ ID NO 1265
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 1265
cucuacuaaa gaaaaaguc                                                19

<210> SEQ ID NO 1266
<211> LENGTH: 19
<212> TYPE: RNA
<213> ORGANISM: Artificial sequence
<220> FEATURE:
<223> OTHER INFORMATION: Chemically synthesized

<400> SEQUENCE: 1266
cuaaagaaaa agucccuga                                                19

<210> SEQ ID NO 1267
<211> LENGTH: 19
<212> TYPE: RNA
<213> ORGANISM: Artificial sequence
<220> FEATURE:
<223> OTHER INFORMATION: Chemically synthesized

<400> SEQUENCE: 1267
uaaagaaaaa gucccugaa                                                19

<210> SEQ ID NO 1268
<211> LENGTH: 19
<212> TYPE: RNA
<213> ORGANISM: Artificial sequence
<220> FEATURE:
<223> OTHER INFORMATION: Chemically synthesized

<400> SEQUENCE: 1268
acaaguguaa gcucaaaag                                                19

<210> SEQ ID NO 1269
<211> LENGTH: 19
<212> TYPE: RNA
<213> ORGANISM: Artificial sequence
<220> FEATURE:
<223> OTHER INFORMATION: Chemically synthesized

<400> SEQUENCE: 1269
guaagcucaa aaguaggua                                                19

<210> SEQ ID NO 1270
<211> LENGTH: 19
<212> TYPE: RNA
<213> ORGANISM: Artificial sequence
<220> FEATURE:
<223> OTHER INFORMATION: Chemically synthesized

<400> SEQUENCE: 1270
uaagcucaaa aguagguac                                                19

<210> SEQ ID NO 1271
<211> LENGTH: 19
<212> TYPE: RNA
<213> ORGANISM: Artificial sequence
<220> FEATURE:
<223> OTHER INFORMATION: Chemically synthesized

<400> SEQUENCE: 1271
uuucaauuuc caaguucac                                                19
```

```
<210> SEQ ID NO 1272
<211> LENGTH: 19
<212> TYPE: RNA
<213> ORGANISM: Artificial sequence
<220> FEATURE:
<223> OTHER INFORMATION: Chemically synthesized

<400> SEQUENCE: 1272
aauuuccaag uucacgugc                                                19

<210> SEQ ID NO 1273
<211> LENGTH: 19
<212> TYPE: RNA
<213> ORGANISM: Artificial sequence
<220> FEATURE:
<223> OTHER INFORMATION: Chemically synthesized

<400> SEQUENCE: 1273
ugggucaguu ucucaggga                                                19

<210> SEQ ID NO 1274
<211> LENGTH: 19
<212> TYPE: RNA
<213> ORGANISM: Artificial sequence
<220> FEATURE:
<223> OTHER INFORMATION: Chemically synthesized

<400> SEQUENCE: 1274
uucucaggga caaggaccu                                                19

<210> SEQ ID NO 1275
<211> LENGTH: 19
<212> TYPE: RNA
<213> ORGANISM: Artificial sequence
<220> FEATURE:
<223> OTHER INFORMATION: Chemically synthesized

<400> SEQUENCE: 1275
gcaaccaagu uuaguuugc                                                19

<210> SEQ ID NO 1276
<211> LENGTH: 19
<212> TYPE: RNA
<213> ORGANISM: Artificial sequence
<220> FEATURE:
<223> OTHER INFORMATION: Chemically synthesized

<400> SEQUENCE: 1276
aguuugcuuu gauuuggac                                                19

<210> SEQ ID NO 1277
<211> LENGTH: 19
<212> TYPE: RNA
<213> ORGANISM: Artificial sequence
<220> FEATURE:
<223> OTHER INFORMATION: Chemically synthesized

<400> SEQUENCE: 1277
uugcuuugau uuggacaga                                                19

<210> SEQ ID NO 1278
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1278
auuuuguaag cauaacagg                                              19

<210> SEQ ID NO 1279
<211> LENGTH: 19
<212> TYPE: RNA
<213> ORGANISM: Artificial sequence
<220> FEATURE:
<223> OTHER INFORMATION: Chemically synthesized

<400> SEQUENCE: 1279
uuuuguaagc auaacaggc                                              19

<210> SEQ ID NO 1280
<211> LENGTH: 19
<212> TYPE: RNA
<213> ORGANISM: Artificial sequence
<220> FEATURE:
<223> OTHER INFORMATION: Chemically synthesized

<400> SEQUENCE: 1280
agagagucaa agauaacug                                              19

<210> SEQ ID NO 1281
<211> LENGTH: 19
<212> TYPE: RNA
<213> ORGANISM: Artificial sequence
<220> FEATURE:
<223> OTHER INFORMATION: Chemically synthesized

<400> SEQUENCE: 1281
ucaaagauaa cuguuagug                                              19

<210> SEQ ID NO 1282
<211> LENGTH: 19
<212> TYPE: RNA
<213> ORGANISM: Artificial sequence
<220> FEATURE:
<223> OTHER INFORMATION: Chemically synthesized

<400> SEQUENCE: 1282
aaagauaacu guuagugga                                              19

<210> SEQ ID NO 1283
<211> LENGTH: 19
<212> TYPE: RNA
<213> ORGANISM: Artificial sequence
<220> FEATURE:
<223> OTHER INFORMATION: Chemically synthesized

<400> SEQUENCE: 1283
gauuuggaca gacaguucu                                              19

<210> SEQ ID NO 1284
<211> LENGTH: 19
<212> TYPE: RNA
<213> ORGANISM: Artificial sequence
<220> FEATURE:
<223> OTHER INFORMATION: Chemically synthesized

<400> SEQUENCE: 1284
aagaagccuu gcccaguca                                              19

<210> SEQ ID NO 1285
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1285
agcggcagaa acacaguga                                              19

<210> SEQ ID NO 1286
<211> LENGTH: 19
<212> TYPE: RNA
<213> ORGANISM: Artificial sequence
<220> FEATURE:
<223> OTHER INFORMATION: Chemically synthesized

<400> SEQUENCE: 1286
cagaaacaca gugaaccuu                                              19

<210> SEQ ID NO 1287
<211> LENGTH: 19
<212> TYPE: RNA
<213> ORGANISM: Artificial sequence
<220> FEATURE:
<223> OTHER INFORMATION: Chemically synthesized

<400> SEQUENCE: 1287
caacauugau uuaucuugg                                              19

<210> SEQ ID NO 1288
<211> LENGTH: 19
<212> TYPE: RNA
<213> ORGANISM: Artificial sequence
<220> FEATURE:
<223> OTHER INFORMATION: Chemically synthesized

<400> SEQUENCE: 1288
agauuggcuu uguaguauc                                              19

<210> SEQ ID NO 1289
<211> LENGTH: 19
<212> TYPE: RNA
<213> ORGANISM: Artificial sequence
<220> FEATURE:
<223> OTHER INFORMATION: Chemically synthesized

<400> SEQUENCE: 1289
uuggcuuugu aguaucuuu                                              19

<210> SEQ ID NO 1290
<211> LENGTH: 19
<212> TYPE: RNA
<213> ORGANISM: Artificial sequence
<220> FEATURE:
<223> OTHER INFORMATION: Chemically synthesized

<400> SEQUENCE: 1290
uggcuuugua guaucuuuc                                              19

<210> SEQ ID NO 1291
<211> LENGTH: 19
<212> TYPE: RNA
<213> ORGANISM: Artificial sequence
<220> FEATURE:
<223> OTHER INFORMATION: Chemically synthesized

<400> SEQUENCE: 1291
``` gcuuguagu aucuuucca                                                   19

<210> SEQ ID NO 1292
<211> LENGTH: 19
<212> TYPE: RNA
<213> ORGANISM: Artificial sequence
<220> FEATURE:
<223> OTHER INFORMATION: Chemically synthesized

<400> SEQUENCE: 1292 cuuguagua ucuuuccaa                                                   19

<210> SEQ ID NO 1293
<211> LENGTH: 19
<212> TYPE: RNA
<213> ORGANISM: Artificial sequence
<220> FEATURE:
<223> OTHER INFORMATION: Chemically synthesized

<400> SEQUENCE: 1293
uguaguaucu uuccaagca                                                  19

<210> SEQ ID NO 1294
<211> LENGTH: 19
<212> TYPE: RNA
<213> ORGANISM: Artificial sequence
<220> FEATURE:
<223> OTHER INFORMATION: Chemically synthesized

<400> SEQUENCE: 1294
guaguaucuu uccaagcau                                                  19

<210> SEQ ID NO 1295
<211> LENGTH: 19
<212> TYPE: RNA
<213> ORGANISM: Artificial sequence
<220> FEATURE:
<223> OTHER INFORMATION: Chemically synthesized

<400> SEQUENCE: 1295
aagcauuuga agaguuuag                                                  19

<210> SEQ ID NO 1296
<211> LENGTH: 19
<212> TYPE: RNA
<213> ORGANISM: Artificial sequence
<220> FEATURE:
<223> OTHER INFORMATION: Chemically synthesized

<400> SEQUENCE: 1296
gugacauuuu aggucacuu                                                  19

<210> SEQ ID NO 1297
<211> LENGTH: 19
<212> TYPE: RNA
<213> ORGANISM: Artificial sequence
<220> FEATURE:
<223> OTHER INFORMATION: Chemically synthesized

<400> SEQUENCE: 1297
aguaucagua acaggauca                                                  19

<210> SEQ ID NO 1298
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1298
guaacaggau cacaccugu                                                    19

<210> SEQ ID NO 1299
<211> LENGTH: 19
<212> TYPE: RNA
<213> ORGANISM: Artificial sequence
<220> FEATURE:
<223> OTHER INFORMATION: Chemically synthesized

<400> SEQUENCE: 1299
uuuucaguaa caccaggau                                                    19

<210> SEQ ID NO 1300
<211> LENGTH: 19
<212> TYPE: RNA
<213> ORGANISM: Artificial sequence
<220> FEATURE:
<223> OTHER INFORMATION: Chemically synthesized

<400> SEQUENCE: 1300
aggaugaaua caucugucc                                                    19

<210> SEQ ID NO 1301
<211> LENGTH: 19
<212> TYPE: RNA
<213> ORGANISM: Artificial sequence
<220> FEATURE:
<223> OTHER INFORMATION: Chemically synthesized

<400> SEQUENCE: 1301
cagcauguga aguggagcu                                                    19

<210> SEQ ID NO 1302
<211> LENGTH: 19
<212> TYPE: RNA
<213> ORGANISM: Artificial sequence
<220> FEATURE:
<223> OTHER INFORMATION: Chemically synthesized

<400> SEQUENCE: 1302
ugaaguggag cuaauagcu                                                    19

<210> SEQ ID NO 1303
<211> LENGTH: 19
<212> TYPE: RNA
<213> ORGANISM: Artificial sequence
<220> FEATURE:
<223> OTHER INFORMATION: Chemically synthesized

<400> SEQUENCE: 1303
uuaaccaaau ucuggcaag                                                    19

<210> SEQ ID NO 1304
<211> LENGTH: 19
<212> TYPE: RNA
<213> ORGANISM: Artificial sequence
<220> FEATURE:
<223> OTHER INFORMATION: Chemically synthesized

<400> SEQUENCE: 1304
aaaccugaau aagcuccuu                                                    19
```

<210> SEQ ID NO 1305
<211> LENGTH: 19
<212> TYPE: RNA
<213> ORGANISM: Artificial sequence
<220> FEATURE:
<223> OTHER INFORMATION: Chemically synthesized

<400> SEQUENCE: 1305
acagcaagga uaugaaagc                                                  19

<210> SEQ ID NO 1306
<211> LENGTH: 19
<212> TYPE: RNA
<213> ORGANISM: Artificial sequence
<220> FEATURE:
<223> OTHER INFORMATION: Chemically synthesized

<400> SEQUENCE: 1306
uggaggcuaa auucucuca                                                  19

<210> SEQ ID NO 1307
<211> LENGTH: 19
<212> TYPE: RNA
<213> ORGANISM: Artificial sequence
<220> FEATURE:
<223> OTHER INFORMATION: Chemically synthesized

<400> SEQUENCE: 1307
ggaggcuaaa uucucucau                                                  19

<210> SEQ ID NO 1308
<211> LENGTH: 19
<212> TYPE: RNA
<213> ORGANISM: Artificial sequence
<220> FEATURE:
<223> OTHER INFORMATION: Chemically synthesized

<400> SEQUENCE: 1308
auucuggcaa guugauucc                                                  19

<210> SEQ ID NO 1309
<211> LENGTH: 19
<212> TYPE: RNA
<213> ORGANISM: Artificial sequence
<220> FEATURE:
<223> OTHER INFORMATION: Chemically synthesized

<400> SEQUENCE: 1309
aggccuuuau uauucccua                                                  19

<210> SEQ ID NO 1310
<211> LENGTH: 19
<212> TYPE: RNA
<213> ORGANISM: Artificial sequence
<220> FEATURE:
<223> OTHER INFORMATION: Chemically synthesized

<400> SEQUENCE: 1310
cuuuauuauu cccaguga                                                   19

<210> SEQ ID NO 1311
<211> LENGTH: 19
<212> TYPE: RNA
<213> ORGANISM: Artificial sequence
<220> FEATURE:

```
<223> OTHER INFORMATION: Chemically synthesized

<400> SEQUENCE: 1311
uuauucccua gugacaggu                                              19

<210> SEQ ID NO 1312
<211> LENGTH: 19
<212> TYPE: RNA
<213> ORGANISM: Artificial sequence
<220> FEATURE:
<223> OTHER INFORMATION: Chemically synthesized

<400> SEQUENCE: 1312
auucccuagu gacagguau                                              19

<210> SEQ ID NO 1313
<211> LENGTH: 19
<212> TYPE: RNA
<213> ORGANISM: Artificial sequence
<220> FEATURE:
<223> OTHER INFORMATION: Chemically synthesized

<400> SEQUENCE: 1313
ccuagugaca gguauccaa                                              19

<210> SEQ ID NO 1314
<211> LENGTH: 19
<212> TYPE: RNA
<213> ORGANISM: Artificial sequence
<220> FEATURE:
<223> OTHER INFORMATION: Chemically synthesized

<400> SEQUENCE: 1314
gugacaggua uccaaggug                                              19

<210> SEQ ID NO 1315
<211> LENGTH: 19
<212> TYPE: RNA
<213> ORGANISM: Artificial sequence
<220> FEATURE:
<223> OTHER INFORMATION: Chemically synthesized

<400> SEQUENCE: 1315
gcaugguuau cuggacggu                                              19

<210> SEQ ID NO 1316
<211> LENGTH: 19
<212> TYPE: RNA
<213> ORGANISM: Artificial sequence
<220> FEATURE:
<223> OTHER INFORMATION: Chemically synthesized

<400> SEQUENCE: 1316
cauagccaau gcagacuuc                                              19

<210> SEQ ID NO 1317
<211> LENGTH: 19
<212> TYPE: RNA
<213> ORGANISM: Artificial sequence
<220> FEATURE:
<223> OTHER INFORMATION: Chemically synthesized

<400> SEQUENCE: 1317
ugacccguuu caauaauuc                                              19
```

```
<210> SEQ ID NO 1318
<211> LENGTH: 19
<212> TYPE: RNA
<213> ORGANISM: Artificial sequence
<220> FEATURE:
<223> OTHER INFORMATION: Chemically synthesized

<400> SEQUENCE: 1318
ugguaguaua cagcuacua                                                    19

<210> SEQ ID NO 1319
<211> LENGTH: 19
<212> TYPE: RNA
<213> ORGANISM: Artificial sequence
<220> FEATURE:
<223> OTHER INFORMATION: Chemically synthesized

<400> SEQUENCE: 1319
uaguauacag cuacuaccc                                                    19

<210> SEQ ID NO 1320
<211> LENGTH: 19
<212> TYPE: RNA
<213> ORGANISM: Artificial sequence
<220> FEATURE:
<223> OTHER INFORMATION: Chemically synthesized

<400> SEQUENCE: 1320
uacagcuacu acccuugac                                                    19

<210> SEQ ID NO 1321
<211> LENGTH: 19
<212> TYPE: RNA
<213> ORGANISM: Artificial sequence
<220> FEATURE:
<223> OTHER INFORMATION: Chemically synthesized

<400> SEQUENCE: 1321
guuaaggaga gauacuuca                                                    19

<210> SEQ ID NO 1322
<211> LENGTH: 19
<212> TYPE: RNA
<213> ORGANISM: Artificial sequence
<220> FEATURE:
<223> OTHER INFORMATION: Chemically synthesized

<400> SEQUENCE: 1322
uuaaggagag auacuucaa                                                    19

<210> SEQ ID NO 1323
<211> LENGTH: 19
<212> TYPE: RNA
<213> ORGANISM: Artificial sequence
<220> FEATURE:
<223> OTHER INFORMATION: Chemically synthesized

<400> SEQUENCE: 1323
gagagauacu ucaauuccc                                                    19

<210> SEQ ID NO 1324
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1324
agagauacuu caauuccca                                                  19

<210> SEQ ID NO 1325
<211> LENGTH: 19
<212> TYPE: RNA
<213> ORGANISM: Artificial sequence
<220> FEATURE:
<223> OTHER INFORMATION: Chemically synthesized

<400> SEQUENCE: 1325
uucaauuccc agaaaagcc                                                  19

<210> SEQ ID NO 1326
<211> LENGTH: 19
<212> TYPE: RNA
<213> ORGANISM: Artificial sequence
<220> FEATURE:
<223> OTHER INFORMATION: Chemically synthesized

<400> SEQUENCE: 1326
uuaccucguu gagguuggg                                                  19

<210> SEQ ID NO 1327
<211> LENGTH: 19
<212> TYPE: RNA
<213> ORGANISM: Artificial sequence
<220> FEATURE:
<223> OTHER INFORMATION: Chemically synthesized

<400> SEQUENCE: 1327
agagaugaga uaacacugc                                                  19

<210> SEQ ID NO 1328
<211> LENGTH: 19
<212> TYPE: RNA
<213> ORGANISM: Artificial sequence
<220> FEATURE:
<223> OTHER INFORMATION: Chemically synthesized

<400> SEQUENCE: 1328
gugaaauggu ucaucugag                                                  19

<210> SEQ ID NO 1329
<211> LENGTH: 19
<212> TYPE: RNA
<213> ORGANISM: Artificial sequence
<220> FEATURE:
<223> OTHER INFORMATION: Chemically synthesized

<400> SEQUENCE: 1329
ucguugaggu uggguucag                                                  19

<210> SEQ ID NO 1330
<211> LENGTH: 19
<212> TYPE: RNA
<213> ORGANISM: Artificial sequence
<220> FEATURE:
<223> OTHER INFORMATION: Chemically synthesized

<400> SEQUENCE: 1330
agauuacuaa gugaaucag                                                  19

<210> SEQ ID NO 1331
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1331
auuacuaagu gaaucagag                                                  19

<210> SEQ ID NO 1332
<211> LENGTH: 19
<212> TYPE: RNA
<213> ORGANISM: Artificial sequence
<220> FEATURE:
<223> OTHER INFORMATION: Chemically synthesized

<400> SEQUENCE: 1332
acuaagugaa ucagagagg                                                  19

<210> SEQ ID NO 1333
<211> LENGTH: 19
<212> TYPE: RNA
<213> ORGANISM: Artificial sequence
<220> FEATURE:
<223> OTHER INFORMATION: Chemically synthesized

<400> SEQUENCE: 1333
gucaacggcu cuguuccu                                                   19

<210> SEQ ID NO 1334
<211> LENGTH: 19
<212> TYPE: RNA
<213> ORGANISM: Artificial sequence
<220> FEATURE:
<223> OTHER INFORMATION: Chemically synthesized

<400> SEQUENCE: 1334
uucacucaau ggaagagua                                                  19

<210> SEQ ID NO 1335
<211> LENGTH: 19
<212> TYPE: RNA
<213> ORGANISM: Artificial sequence
<220> FEATURE:
<223> OTHER INFORMATION: Chemically synthesized

<400> SEQUENCE: 1335
agaguaauca acuacacac                                                  19

<210> SEQ ID NO 1336
<211> LENGTH: 19
<212> TYPE: RNA
<213> ORGANISM: Artificial sequence
<220> FEATURE:
<223> OTHER INFORMATION: Chemically synthesized

<400> SEQUENCE: 1336
cacacaaaaa uaucaguuc                                                  19

<210> SEQ ID NO 1337
<211> LENGTH: 19
<212> TYPE: RNA
<213> ORGANISM: Artificial sequence
<220> FEATURE:
<223> OTHER INFORMATION: Chemically synthesized

<400> SEQUENCE: 1337
```

```
aagacaguau ucaacacuu                                              19

<210> SEQ ID NO 1338
<211> LENGTH: 19
<212> TYPE: RNA
<213> ORGANISM: Artificial sequence
<220> FEATURE:
<223> OTHER INFORMATION: Chemically synthesized

<400> SEQUENCE: 1338
aacacuuaag aacagggga                                              19

<210> SEQ ID NO 1339
<211> LENGTH: 19
<212> TYPE: RNA
<213> ORGANISM: Artificial sequence
<220> FEATURE:
<223> OTHER INFORMATION: Chemically synthesized

<400> SEQUENCE: 1339
agaacagggg aaacugagc                                              19

<210> SEQ ID NO 1340
<211> LENGTH: 19
<212> TYPE: RNA
<213> ORGANISM: Artificial sequence
<220> FEATURE:
<223> OTHER INFORMATION: Chemically synthesized

<400> SEQUENCE: 1340
gaacagggga aacugagcu                                              19

<210> SEQ ID NO 1341
<211> LENGTH: 19
<212> TYPE: RNA
<213> ORGANISM: Artificial sequence
<220> FEATURE:
<223> OTHER INFORMATION: Chemically synthesized

<400> SEQUENCE: 1341
uucaggaaca acauaaucc                                              19

<210> SEQ ID NO 1342
<211> LENGTH: 19
<212> TYPE: RNA
<213> ORGANISM: Artificial sequence
<220> FEATURE:
<223> OTHER INFORMATION: Chemically synthesized

<400> SEQUENCE: 1342 acagggaaa cugagcuua                                               19

<210> SEQ ID NO 1343
<211> LENGTH: 19
<212> TYPE: RNA
<213> ORGANISM: Artificial sequence
<220> FEATURE:
<223> OTHER INFORMATION: Chemically synthesized

<400> SEQUENCE: 1343
aacugagcuu auaaaggca                                              19

<210> SEQ ID NO 1344
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 1344
ugagcuuaua aaggcaucu                                                    19

<210> SEQ ID NO 1345
<211> LENGTH: 19
<212> TYPE: RNA
<213> ORGANISM: Artificial sequence
<220> FEATURE:
<223> OTHER INFORMATION: Chemically synthesized

<400> SEQUENCE: 1345
agcuuauaaa ggcaucuaa                                                    19

<210> SEQ ID NO 1346
<211> LENGTH: 19
<212> TYPE: RNA
<213> ORGANISM: Artificial sequence
<220> FEATURE:
<223> OTHER INFORMATION: Chemically synthesized

<400> SEQUENCE: 1346
ggcaucuaaa acaacaccg                                                    19

<210> SEQ ID NO 1347
<211> LENGTH: 19
<212> TYPE: RNA
<213> ORGANISM: Artificial sequence
<220> FEATURE:
<223> OTHER INFORMATION: Chemically synthesized

<400> SEQUENCE: 1347
uaaaacaaca ccgugguua                                                    19

<210> SEQ ID NO 1348
<211> LENGTH: 19
<212> TYPE: RNA
<213> ORGANISM: Artificial sequence
<220> FEATURE:
<223> OTHER INFORMATION: Chemically synthesized

<400> SEQUENCE: 1348
aacaacauaa ucccaguag                                                    19

<210> SEQ ID NO 1349
<211> LENGTH: 19
<212> TYPE: RNA
<213> ORGANISM: Artificial sequence
<220> FEATURE:
<223> OTHER INFORMATION: Chemically synthesized

<400> SEQUENCE: 1349
acaacauaau cccaguagu                                                    19

<210> SEQ ID NO 1350
<211> LENGTH: 19
<212> TYPE: RNA
<213> ORGANISM: Artificial sequence
<220> FEATURE:
<223> OTHER INFORMATION: Chemically synthesized

<400> SEQUENCE: 1350
aacagugaag caguuccau                                                    19
```

<210> SEQ ID NO 1351
<211> LENGTH: 19
<212> TYPE: RNA
<213> ORGANISM: Artificial sequence
<220> FEATURE:
<223> OTHER INFORMATION: Chemically synthesized

<400> SEQUENCE: 1351
aguuccauua uugccguaa                                              19

<210> SEQ ID NO 1352
<211> LENGTH: 19
<212> TYPE: RNA
<213> ORGANISM: Artificial sequence
<220> FEATURE:
<223> OTHER INFORMATION: Chemically synthesized

<400> SEQUENCE: 1352
gcuuuaauua aacucaccu                                              19

<210> SEQ ID NO 1353
<211> LENGTH: 19
<212> TYPE: RNA
<213> ORGANISM: Artificial sequence
<220> FEATURE:
<223> OTHER INFORMATION: Chemically synthesized

<400> SEQUENCE: 1353
aacucaccua cuuaauccu                                              19

<210> SEQ ID NO 1354
<211> LENGTH: 19
<212> TYPE: RNA
<213> ORGANISM: Artificial sequence
<220> FEATURE:
<223> OTHER INFORMATION: Chemically synthesized

<400> SEQUENCE: 1354
cuuaauccua ccuuccugu                                              19

<210> SEQ ID NO 1355
<211> LENGTH: 19
<212> TYPE: RNA
<213> ORGANISM: Artificial sequence
<220> FEATURE:
<223> OTHER INFORMATION: Chemically synthesized

<400> SEQUENCE: 1355
cuuccugucu aaaaacccu                                              19

<210> SEQ ID NO 1356
<211> LENGTH: 19
<212> TYPE: RNA
<213> ORGANISM: Artificial sequence
<220> FEATURE:
<223> OTHER INFORMATION: Chemically synthesized

<400> SEQUENCE: 1356
uccugucuaa aaacccuuc                                              19

<210> SEQ ID NO 1357
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 1357
ccugucuaaa aacccuuca                                              19

<210> SEQ ID NO 1358
<211> LENGTH: 19
<212> TYPE: RNA
<213> ORGANISM: Artificial sequence
<220> FEATURE:
<223> OTHER INFORMATION: Chemically synthesized

<400> SEQUENCE: 1358
ugucuaaaaa cccuucaaa                                              19

<210> SEQ ID NO 1359
<211> LENGTH: 19
<212> TYPE: RNA
<213> ORGANISM: Artificial sequence
<220> FEATURE:
<223> OTHER INFORMATION: Chemically synthesized

<400> SEQUENCE: 1359
ucccaguagu caaaaucac                                              19

<210> SEQ ID NO 1360
<211> LENGTH: 19
<212> TYPE: RNA
<213> ORGANISM: Artificial sequence
<220> FEATURE:
<223> OTHER INFORMATION: Chemically synthesized

<400> SEQUENCE: 1360
cuucaaauuu gagucagga                                              19

<210> SEQ ID NO 1361
<211> LENGTH: 19
<212> TYPE: RNA
<213> ORGANISM: Artificial sequence
<220> FEATURE:
<223> OTHER INFORMATION: Chemically synthesized

<400> SEQUENCE: 1361
uccucugaaa acuuagaga                                              19

<210> SEQ ID NO 1362
<211> LENGTH: 19
<212> TYPE: RNA
<213> ORGANISM: Artificial sequence
<220> FEATURE:
<223> OTHER INFORMATION: Chemically synthesized

<400> SEQUENCE: 1362
ucuauuacca agccuaccu                                              19

<210> SEQ ID NO 1363
<211> LENGTH: 19
<212> TYPE: RNA
<213> ORGANISM: Artificial sequence
<220> FEATURE:
<223> OTHER INFORMATION: Chemically synthesized

<400> SEQUENCE: 1363
cuaccugaaa ccaaauugu                                              19

<210> SEQ ID NO 1364
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1364
guggaaucaa auguaaaac                                                        19

<210> SEQ ID NO 1365
<211> LENGTH: 19
<212> TYPE: RNA
<213> ORGANISM: Artificial sequence
<220> FEATURE:
<223> OTHER INFORMATION: Chemically synthesized

<400> SEQUENCE: 1365
guaaaacuca aaugggcuu                                                        19

<210> SEQ ID NO 1366
<211> LENGTH: 19
<212> TYPE: RNA
<213> ORGANISM: Artificial sequence
<220> FEATURE:
<223> OTHER INFORMATION: Chemically synthesized

<400> SEQUENCE: 1366
aaacucaaau gggcuucua                                                        19

<210> SEQ ID NO 1367
<211> LENGTH: 19
<212> TYPE: RNA
<213> ORGANISM: Artificial sequence
<220> FEATURE:
<223> OTHER INFORMATION: Chemically synthesized

<400> SEQUENCE: 1367
ugggcuucua cuuuugcuu                                                        19

<210> SEQ ID NO 1368
<211> LENGTH: 19
<212> TYPE: RNA
<213> ORGANISM: Artificial sequence
<220> FEATURE:
<223> OTHER INFORMATION: Chemically synthesized

<400> SEQUENCE: 1368
uucuacuuuu gcuuaccua                                                        19

<210> SEQ ID NO 1369
<211> LENGTH: 19
<212> TYPE: RNA
<213> ORGANISM: Artificial sequence
<220> FEATURE:
<223> OTHER INFORMATION: Chemically synthesized

<400> SEQUENCE: 1369
uacuuuugcu uaccuauuc                                                        19

<210> SEQ ID NO 1370
<211> LENGTH: 19
<212> TYPE: RNA
<213> ORGANISM: Artificial sequence
<220> FEATURE:
<223> OTHER INFORMATION: Chemically synthesized

<400> SEQUENCE: 1370
```
uugcuuaccu auccaucc 19

<210> SEQ ID NO 1371
<211> LENGTH: 19
<212> TYPE: RNA
<213> ORGANISM: Artificial sequence
<220> FEATURE:
<223> OTHER INFORMATION: Chemically synthesized

<400> SEQUENCE: 1371
ugcuuaccua uuccaucc 19

<210> SEQ ID NO 1372
<211> LENGTH: 19
<212> TYPE: RNA
<213> ORGANISM: Artificial sequence
<220> FEATURE:
<223> OTHER INFORMATION: Chemically synthesized

<400> SEQUENCE: 1372
uuccauccca uucaauucu 19

<210> SEQ ID NO 1373
<211> LENGTH: 19
<212> TYPE: RNA
<213> ORGANISM: Artificial sequence
<220> FEATURE:
<223> OTHER INFORMATION: Chemically synthesized

<400> SEQUENCE: 1373
aaaaauggga ucuaugcag 19

<210> SEQ ID NO 1374
<211> LENGTH: 19
<212> TYPE: RNA
<213> ORGANISM: Artificial sequence
<220> FEATURE:
<223> OTHER INFORMATION: Chemically synthesized

<400> SEQUENCE: 1374
gaucuaugca gaaaaucua 19

<210> SEQ ID NO 1375
<211> LENGTH: 19
<212> TYPE: RNA
<213> ORGANISM: Artificial sequence
<220> FEATURE:
<223> OTHER INFORMATION: Chemically synthesized

<400> SEQUENCE: 1375
aaucacuucu ccaaaggcc 19

<210> SEQ ID NO 1376
<211> LENGTH: 19
<212> TYPE: RNA
<213> ORGANISM: Artificial sequence
<220> FEATURE:
<223> OTHER INFORMATION: Chemically synthesized

<400> SEQUENCE: 1376
ucugggugau agccacagu 19

<210> SEQ ID NO 1377
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1377
aaaggccaga aaaucagcc                                                   19

<210> SEQ ID NO 1378
<211> LENGTH: 19
<212> TYPE: RNA
<213> ORGANISM: Artificial sequence
<220> FEATURE:
<223> OTHER INFORMATION: Chemically synthesized

<400> SEQUENCE: 1378
ggccagaaaa ucagccugu                                                   19

<210> SEQ ID NO 1379
<211> LENGTH: 19
<212> TYPE: RNA
<213> ORGANISM: Artificial sequence
<220> FEATURE:
<223> OTHER INFORMATION: Chemically synthesized

<400> SEQUENCE: 1379
gccagaaaau cagccuguu                                                   19

<210> SEQ ID NO 1380
<211> LENGTH: 19
<212> TYPE: RNA
<213> ORGANISM: Artificial sequence
<220> FEATURE:
<223> OTHER INFORMATION: Chemically synthesized

<400> SEQUENCE: 1380
aucagccugu uagcugcag                                                   19

<210> SEQ ID NO 1381
<211> LENGTH: 19
<212> TYPE: RNA
<213> ORGANISM: Artificial sequence
<220> FEATURE:
<223> OTHER INFORMATION: Chemically synthesized

<400> SEQUENCE: 1381
ccuguuagcu gcaguugcu                                                   19

<210> SEQ ID NO 1382
<211> LENGTH: 19
<212> TYPE: RNA
<213> ORGANISM: Artificial sequence
<220> FEATURE:
<223> OTHER INFORMATION: Chemically synthesized

<400> SEQUENCE: 1382 cguuagcug caguugcua                                                    19

<210> SEQ ID NO 1383
<211> LENGTH: 19
<212> TYPE: RNA
<213> ORGANISM: Artificial sequence
<220> FEATURE:
<223> OTHER INFORMATION: Chemically synthesized

<400> SEQUENCE: 1383
uuagcugcag uugcuauga                                                   19
```

<210> SEQ ID NO 1384
<211> LENGTH: 19
<212> TYPE: RNA
<213> ORGANISM: Artificial sequence
<220> FEATURE:
<223> OTHER INFORMATION: Chemically synthesized

<400> SEQUENCE: 1384
gcaguugcua ugaauguga                                                  19

<210> SEQ ID NO 1385
<211> LENGTH: 19
<212> TYPE: RNA
<213> ORGANISM: Artificial sequence
<220> FEATURE:
<223> OTHER INFORMATION: Chemically synthesized

<400> SEQUENCE: 1385
ccacagucca gcaauucug                                                  19

<210> SEQ ID NO 1386
<211> LENGTH: 19
<212> TYPE: RNA
<213> ORGANISM: Artificial sequence
<220> FEATURE:
<223> OTHER INFORMATION: Chemically synthesized

<400> SEQUENCE: 1386
ggggutucuu auuuagggc                                                  19

<210> SEQ ID NO 1387
<211> LENGTH: 19
<212> TYPE: RNA
<213> ORGANISM: Artificial sequence
<220> FEATURE:
<223> OTHER INFORMATION: Chemically synthesized

<400> SEQUENCE: 1387
ucuuauuuag ggcaggugg                                                  19

<210> SEQ ID NO 1388
<211> LENGTH: 19
<212> TYPE: RNA
<213> ORGANISM: Artificial sequence
<220> FEATURE:
<223> OTHER INFORMATION: Chemically synthesized

<400> SEQUENCE: 1388
ggggcaaacu acaaaugac                                                  19

<210> SEQ ID NO 1389
<211> LENGTH: 19
<212> TYPE: RNA
<213> ORGANISM: Artificial sequence
<220> FEATURE:
<223> OTHER INFORMATION: Chemically synthesized

<400> SEQUENCE: 1389
acuagcugaa uaguuuuac                                                  19

<210> SEQ ID NO 1390
<211> LENGTH: 19
<212> TYPE: RNA
<213> ORGANISM: Artificial sequence
<220> FEATURE:

```
<223> OTHER INFORMATION: Chemically synthesized

<400> SEQUENCE: 1390
gaauaguuuu acuacccaa                                                    19

<210> SEQ ID NO 1391
<211> LENGTH: 19
<212> TYPE: RNA
<213> ORGANISM: Artificial sequence
<220> FEATURE:
<223> OTHER INFORMATION: Chemically synthesized

<400> SEQUENCE: 1391
ucgaaauccu gagcugagg                                                    19

<210> SEQ ID NO 1392
<211> LENGTH: 19
<212> TYPE: RNA
<213> ORGANISM: Artificial sequence
<220> FEATURE:
<223> OTHER INFORMATION: Chemically synthesized

<400> SEQUENCE: 1392
cugaggauca gaguucucc                                                    19

<210> SEQ ID NO 1393
<211> LENGTH: 19
<212> TYPE: RNA
<213> ORGANISM: Artificial sequence
<220> FEATURE:
<223> OTHER INFORMATION: Chemically synthesized

<400> SEQUENCE: 1393
gaaaccagag gagaagcga                                                    19

<210> SEQ ID NO 1394
<211> LENGTH: 19
<212> TYPE: RNA
<213> ORGANISM: Artificial sequence
<220> FEATURE:
<223> OTHER INFORMATION: Chemically synthesized

<400> SEQUENCE: 1394
aaaccagagg agaagcgac                                                    19

<210> SEQ ID NO 1395
<211> LENGTH: 19
<212> TYPE: RNA
<213> ORGANISM: Artificial sequence
<220> FEATURE:
<223> OTHER INFORMATION: Chemically synthesized

<400> SEQUENCE: 1395
ucuacuaaag aaaaagucc                                                    19

<210> SEQ ID NO 1396
<211> LENGTH: 19
<212> TYPE: RNA
<213> ORGANISM: Artificial sequence
<220> FEATURE:
<223> OTHER INFORMATION: Chemically synthesized

<400> SEQUENCE: 1396
agucccugaa gcuagucca                                                    19
```

```
<210> SEQ ID NO 1397
<211> LENGTH: 19
<212> TYPE: RNA
<213> ORGANISM: Artificial sequence
<220> FEATURE:
<223> OTHER INFORMATION: Chemically synthesized

<400> SEQUENCE: 1397
ugaagcuagu ccaugagca                                              19

<210> SEQ ID NO 1398
<211> LENGTH: 19
<212> TYPE: RNA
<213> ORGANISM: Artificial sequence
<220> FEATURE:
<223> OTHER INFORMATION: Chemically synthesized

<400> SEQUENCE: 1398
uguaagcuca aaaguaggu                                              19

<210> SEQ ID NO 1399
<211> LENGTH: 19
<212> TYPE: RNA
<213> ORGANISM: Artificial sequence
<220> FEATURE:
<223> OTHER INFORMATION: Chemically synthesized

<400> SEQUENCE: 1399
agcucaaaag uagguacga                                              19

<210> SEQ ID NO 1400
<211> LENGTH: 19
<212> TYPE: RNA
<213> ORGANISM: Artificial sequence
<220> FEATURE:
<223> OTHER INFORMATION: Chemically synthesized

<400> SEQUENCE: 1400
cucaaaagua gguacgacg                                              19

<210> SEQ ID NO 1401
<211> LENGTH: 19
<212> TYPE: RNA
<213> ORGANISM: Artificial sequence
<220> FEATURE:
<223> OTHER INFORMATION: Chemically synthesized

<400> SEQUENCE: 1401
caauuuccaa guucacgug                                              19

<210> SEQ ID NO 1402
<211> LENGTH: 19
<212> TYPE: RNA
<213> ORGANISM: Artificial sequence
<220> FEATURE:
<223> OTHER INFORMATION: Chemically synthesized

<400> SEQUENCE: 1402
ugcauaacac aaccucgca                                              19

<210> SEQ ID NO 1403
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1403
gucaguuucu cagggacaa                                                19

<210> SEQ ID NO 1404
<211> LENGTH: 19
<212> TYPE: RNA
<213> ORGANISM: Artificial sequence
<220> FEATURE:
<223> OTHER INFORMATION: Chemically synthesized

<400> SEQUENCE: 1404
aguuucucag ggacaagga                                                19

<210> SEQ ID NO 1405
<211> LENGTH: 19
<212> TYPE: RNA
<213> ORGANISM: Artificial sequence
<220> FEATURE:
<223> OTHER INFORMATION: Chemically synthesized

<400> SEQUENCE: 1405
ccaguugcaa ccaugguca                                                19

<210> SEQ ID NO 1406
<211> LENGTH: 19
<212> TYPE: RNA
<213> ORGANISM: Artificial sequence
<220> FEATURE:
<223> OTHER INFORMATION: Chemically synthesized

<400> SEQUENCE: 1406
ugagcaacca aguuuaguu                                                19

<210> SEQ ID NO 1407
<211> LENGTH: 19
<212> TYPE: RNA
<213> ORGANISM: Artificial sequence
<220> FEATURE:
<223> OTHER INFORMATION: Chemically synthesized

<400> SEQUENCE: 1407
caaccaaguu uaguuugcu                                                19

<210> SEQ ID NO 1408
<211> LENGTH: 19
<212> TYPE: RNA
<213> ORGANISM: Artificial sequence
<220> FEATURE:
<223> OTHER INFORMATION: Chemically synthesized

<400> SEQUENCE: 1408
ccauuuugua agcauaaca                                                19

<210> SEQ ID NO 1409
<211> LENGTH: 19
<212> TYPE: RNA
<213> ORGANISM: Artificial sequence
<220> FEATURE:
<223> OTHER INFORMATION: Chemically synthesized

<400> SEQUENCE: 1409
uuugauuugg acagacagu                                                19

<210> SEQ ID NO 1410
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1410
agucaaagau aacuguuag                                                19

<210> SEQ ID NO 1411
<211> LENGTH: 19
<212> TYPE: RNA
<213> ORGANISM: Artificial sequence
<220> FEATURE:
<223> OTHER INFORMATION: Chemically synthesized

<400> SEQUENCE: 1411
caguucuaca ucgaugccc                                                19

<210> SEQ ID NO 1412
<211> LENGTH: 19
<212> TYPE: RNA
<213> ORGANISM: Artificial sequence
<220> FEATURE:
<223> OTHER INFORMATION: Chemically synthesized

<400> SEQUENCE: 1412
aguggugaca acuccagga                                                19

<210> SEQ ID NO 1413
<211> LENGTH: 19
<212> TYPE: RNA
<213> ORGANISM: Artificial sequence
<220> FEATURE:
<223> OTHER INFORMATION: Chemically synthesized

<400> SEQUENCE: 1413
aaccuuugga gcuuaacaa                                                19

<210> SEQ ID NO 1414
<211> LENGTH: 19
<212> TYPE: RNA
<213> ORGANISM: Artificial sequence
<220> FEATURE:
<223> OTHER INFORMATION: Chemically synthesized

<400> SEQUENCE: 1414
cuuaacaaua gacaugcaa                                                19

<210> SEQ ID NO 1415
<211> LENGTH: 19
<212> TYPE: RNA
<213> ORGANISM: Artificial sequence
<220> FEATURE:
<223> OTHER INFORMATION: Chemically synthesized

<400> SEQUENCE: 1415
uagacaugca aaacaacau                                                19

<210> SEQ ID NO 1416
<211> LENGTH: 19
<212> TYPE: RNA
<213> ORGANISM: Artificial sequence
<220> FEATURE:
<223> OTHER INFORMATION: Chemically synthesized

<400> SEQUENCE: 1416
```
auuggcuuug uaguaucuu                                                 19

<210> SEQ ID NO 1417
<211> LENGTH: 19
<212> TYPE: RNA
<213> ORGANISM: Artificial sequence
<220> FEATURE:
<223> OTHER INFORMATION: Chemically synthesized

<400> SEQUENCE: 1417
uuuguaguau cuuccaag                                                  19

<210> SEQ ID NO 1418
<211> LENGTH: 19
<212> TYPE: RNA
<213> ORGANISM: Artificial sequence
<220> FEATURE:
<223> OTHER INFORMATION: Chemically synthesized

<400> SEQUENCE: 1418
gcuaauuuga acagugaca                                                 19

<210> SEQ ID NO 1419
<211> LENGTH: 19
<212> TYPE: RNA
<213> ORGANISM: Artificial sequence
<220> FEATURE:
<223> OTHER INFORMATION: Chemically synthesized

<400> SEQUENCE: 1419
uaggucacuu auaguauca                                                 19

<210> SEQ ID NO 1420
<211> LENGTH: 19
<212> TYPE: RNA
<213> ORGANISM: Artificial sequence
<220> FEATURE:
<223> OTHER INFORMATION: Chemically synthesized

<400> SEQUENCE: 1420
uugcaaccau ggucaacgg                                                 19

<210> SEQ ID NO 1421
<211> LENGTH: 19
<212> TYPE: RNA
<213> ORGANISM: Artificial sequence
<220> FEATURE:
<223> OTHER INFORMATION: Chemically synthesized

<400> SEQUENCE: 1421
accuguuuuu caguaacac                                                 19

<210> SEQ ID NO 1422
<211> LENGTH: 19
<212> TYPE: RNA
<213> ORGANISM: Artificial sequence
<220> FEATURE:
<223> OTHER INFORMATION: Chemically synthesized

<400> SEQUENCE: 1422
gaugaauaca ucugucccu                                                 19

<210> SEQ ID NO 1423
<211> LENGTH: 19
<212> TYPE: RNA
<213> ORGANISM: Artificial sequence
<220> FEATURE:
<223> OTHER INFORMATION: Chemically synthesized

<400> SEQUENCE: 1423
auacaucugu cccuacgcc         19

<210> SEQ ID NO 1424
<211> LENGTH: 19
<212> TYPE: RNA
<213> ORGANISM: Artificial sequence
<220> FEATURE:
<223> OTHER INFORMATION: Chemically synthesized

<400> SEQUENCE: 1424
uccagcaugu gaagggag         19

<210> SEQ ID NO 1425
<211> LENGTH: 19
<212> TYPE: RNA
<213> ORGANISM: Artificial sequence
<220> FEATURE:
<223> OTHER INFORMATION: Chemically synthesized

<400> SEQUENCE: 1425
cuaauagcua gggcaggaa         19

<210> SEQ ID NO 1426
<211> LENGTH: 19
<212> TYPE: RNA
<213> ORGANISM: Artificial sequence
<220> FEATURE:
<223> OTHER INFORMATION: Chemically synthesized

<400> SEQUENCE: 1426
gaaaccugaa uaagcuccu         19

<210> SEQ ID NO 1427
<211> LENGTH: 19
<212> TYPE: RNA
<213> ORGANISM: Artificial sequence
<220> FEATURE:
<223> OTHER INFORMATION: Chemically synthesized

<400> SEQUENCE: 1427
accugaauaa gcuccuuau         19

<210> SEQ ID NO 1428
<211> LENGTH: 19
<212> TYPE: RNA
<213> ORGANISM: Artificial sequence
<220> FEATURE:
<223> OTHER INFORMATION: Chemically synthesized

<400> SEQUENCE: 1428
accaaauucu ggcaaguug         19

<210> SEQ ID NO 1429
<211> LENGTH: 19
<212> TYPE: RNA
<213> ORGANISM: Artificial sequence
<220> FEATURE:
<223> OTHER INFORMATION: Chemically synthesized

<400> SEQUENCE: 1429
augaaagccu ugcugaauu         19

<210> SEQ ID NO 1430
<211> LENGTH: 19
<212> TYPE: RNA
<213> ORGANISM: Artificial sequence
<220> FEATURE:
<223> OTHER INFORMATION: Chemically synthesized

<400> SEQUENCE: 1430
cugaauugaa cauuguuga                                               19

<210> SEQ ID NO 1431
<211> LENGTH: 19
<212> TYPE: RNA
<213> ORGANISM: Artificial sequence
<220> FEATURE:
<223> OTHER INFORMATION: Chemically synthesized

<400> SEQUENCE: 1431
uugaacauug uugagugga                                               19

<210> SEQ ID NO 1432
<211> LENGTH: 19
<212> TYPE: RNA
<213> ORGANISM: Artificial sequence
<220> FEATURE:
<223> OTHER INFORMATION: Chemically synthesized

<400> SEQUENCE: 1432
augaucuacu uaguuggaa                                               19

<210> SEQ ID NO 1433
<211> LENGTH: 19
<212> TYPE: RNA
<213> ORGANISM: Artificial sequence
<220> FEATURE:
<223> OTHER INFORMATION: Chemically synthesized

<400> SEQUENCE: 1433
aaggccuuua uuauucccu                                               19

<210> SEQ ID NO 1434
<211> LENGTH: 19
<212> TYPE: RNA
<213> ORGANISM: Artificial sequence
<220> FEATURE:
<223> OTHER INFORMATION: Chemically synthesized

<400> SEQUENCE: 1434
ccuuuauuau ucccuagug                                               19

<210> SEQ ID NO 1435
<211> LENGTH: 19
<212> TYPE: RNA
<213> ORGANISM: Artificial sequence
<220> FEATURE:
<223> OTHER INFORMATION: Chemically synthesized

<400> SEQUENCE: 1435
ucuggcaagu ugauccuc                                                19

<210> SEQ ID NO 1436
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 1436
auuauucccu agugacagg                                                19

<210> SEQ ID NO 1437
<211> LENGTH: 19
<212> TYPE: RNA
<213> ORGANISM: Artificial sequence
<220> FEATURE:
<223> OTHER INFORMATION: Chemically synthesized

<400> SEQUENCE: 1437
aaaucugggu gcaugcaug                                                19

<210> SEQ ID NO 1438
<211> LENGTH: 19
<212> TYPE: RNA
<213> ORGANISM: Artificial sequence
<220> FEATURE:
<223> OTHER INFORMATION: Chemically synthesized

<400> SEQUENCE: 1438
caugcauggu uaucuggac                                                19

<210> SEQ ID NO 1439
<211> LENGTH: 19
<212> TYPE: RNA
<213> ORGANISM: Artificial sequence
<220> FEATURE:
<223> OTHER INFORMATION: Chemically synthesized

<400> SEQUENCE: 1439
ugcaugguua ucuggacgg                                                19

<210> SEQ ID NO 1440
<211> LENGTH: 19
<212> TYPE: RNA
<213> ORGANISM: Artificial sequence
<220> FEATURE:
<223> OTHER INFORMATION: Chemically synthesized

<400> SEQUENCE: 1440
uggacggugu guuucauuc                                                19

<210> SEQ ID NO 1441
<211> LENGTH: 19
<212> TYPE: RNA
<213> ORGANISM: Artificial sequence
<220> FEATURE:
<223> OTHER INFORMATION: Chemically synthesized

<400> SEQUENCE: 1441
gacggugagu uucauucuc                                                19

<210> SEQ ID NO 1442
<211> LENGTH: 19
<212> TYPE: RNA
<213> ORGANISM: Artificial sequence
<220> FEATURE:
<223> OTHER INFORMATION: Chemically synthesized

<400> SEQUENCE: 1442
guuucauucu cuaggcugu                                                19

<210> SEQ ID NO 1443
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1443
aucuccauag ccaaugcag                                            19

<210> SEQ ID NO 1444
<211> LENGTH: 19
<212> TYPE: RNA
<213> ORGANISM: Artificial sequence
<220> FEATURE:
<223> OTHER INFORMATION: Chemically synthesized

<400> SEQUENCE: 1444
uccauagcca augcagacu                                            19

<210> SEQ ID NO 1445
<211> LENGTH: 19
<212> TYPE: RNA
<213> ORGANISM: Artificial sequence
<220> FEATURE:
<223> OTHER INFORMATION: Chemically synthesized

<400> SEQUENCE: 1445
ccauagccaa ugcagacuu                                            19

<210> SEQ ID NO 1446
<211> LENGTH: 19
<212> TYPE: RNA
<213> ORGANISM: Artificial sequence
<220> FEATURE:
<223> OTHER INFORMATION: Chemically synthesized

<400> SEQUENCE: 1446
acccguuuca auaauucaa                                            19

<210> SEQ ID NO 1447
<211> LENGTH: 19
<212> TYPE: RNA
<213> ORGANISM: Artificial sequence
<220> FEATURE:
<223> OTHER INFORMATION: Chemically synthesized

<400> SEQUENCE: 1447
caaaguggua guauacagc                                            19

<210> SEQ ID NO 1448
<211> LENGTH: 19
<212> TYPE: RNA
<213> ORGANISM: Artificial sequence
<220> FEATURE:
<223> OTHER INFORMATION: Chemically synthesized

<400> SEQUENCE: 1448
guauacagcu acucccuu                                             19

<210> SEQ ID NO 1449
<211> LENGTH: 19
<212> TYPE: RNA
<213> ORGANISM: Artificial sequence
<220> FEATURE:
<223> OTHER INFORMATION: Chemically synthesized

<400> SEQUENCE: 1449
```
gguuaaggag agauacuuc                                          19

<210> SEQ ID NO 1450
<211> LENGTH: 19
<212> TYPE: RNA
<213> ORGANISM: Artificial sequence
<220> FEATURE:
<223> OTHER INFORMATION: Chemically synthesized

<400> SEQUENCE: 1450
gauacuucaa uucccagaa                                          19

<210> SEQ ID NO 1451
<211> LENGTH: 19
<212> TYPE: RNA
<213> ORGANISM: Artificial sequence
<220> FEATURE:
<223> OTHER INFORMATION: Chemically synthesized

<400> SEQUENCE: 1451
accucguuga gguuggguu                                          19

<210> SEQ ID NO 1452
<211> LENGTH: 19
<212> TYPE: RNA
<213> ORGANISM: Artificial sequence
<220> FEATURE:
<223> OTHER INFORMATION: Chemically synthesized

<400> SEQUENCE: 1452
ccauggugaa augguucau                                          19

<210> SEQ ID NO 1453
<211> LENGTH: 19
<212> TYPE: RNA
<213> ORGANISM: Artificial sequence
<220> FEATURE:
<223> OTHER INFORMATION: Chemically synthesized

<400> SEQUENCE: 1453
auggugaaau gguucaucu                                          19

<210> SEQ ID NO 1454
<211> LENGTH: 19
<212> TYPE: RNA
<213> ORGANISM: Artificial sequence
<220> FEATURE:
<223> OTHER INFORMATION: Chemically synthesized

<400> SEQUENCE: 1454
aaaugguuca ucugagauu                                          19

<210> SEQ ID NO 1455
<211> LENGTH: 19
<212> TYPE: RNA
<213> ORGANISM: Artificial sequence
<220> FEATURE:
<223> OTHER INFORMATION: Chemically synthesized

<400> SEQUENCE: 1455
ucaucugaga uuaagcaca                                          19

<210> SEQ ID NO 1456
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1456
caucugagau uaagcacau                                              19

<210> SEQ ID NO 1457
<211> LENGTH: 19
<212> TYPE: RNA
<213> ORGANISM: Artificial sequence
<220> FEATURE:
<223> OTHER INFORMATION: Chemically synthesized

<400> SEQUENCE: 1457
ucugagauua agcacaugu                                              19

<210> SEQ ID NO 1458
<211> LENGTH: 19
<212> TYPE: RNA
<213> ORGANISM: Artificial sequence
<220> FEATURE:
<223> OTHER INFORMATION: Chemically synthesized

<400> SEQUENCE: 1458
cugagauuaa gcacaugua                                              19

<210> SEQ ID NO 1459
<211> LENGTH: 19
<212> TYPE: RNA
<213> ORGANISM: Artificial sequence
<220> FEATURE:
<223> OTHER INFORMATION: Chemically synthesized

<400> SEQUENCE: 1459
auguaauacu gaaaagagg                                              19

<210> SEQ ID NO 1460
<211> LENGTH: 19
<212> TYPE: RNA
<213> ORGANISM: Artificial sequence
<220> FEATURE:
<223> OTHER INFORMATION: Chemically synthesized

<400> SEQUENCE: 1460
uacuaaguga aucagagag                                              19

<210> SEQ ID NO 1461
<211> LENGTH: 19
<212> TYPE: RNA
<213> ORGANISM: Artificial sequence
<220> FEATURE:
<223> OTHER INFORMATION: Chemically synthesized

<400> SEQUENCE: 1461
uuggguucag gaacaacau                                              19

<210> SEQ ID NO 1462
<211> LENGTH: 19
<212> TYPE: RNA
<213> ORGANISM: Artificial sequence
<220> FEATURE:
<223> OTHER INFORMATION: Chemically synthesized

<400> SEQUENCE: 1462
ucaacacuua agaacaggg                                              19
```

```
<210> SEQ ID NO 1463
<211> LENGTH: 19
<212> TYPE: RNA
<213> ORGANISM: Artificial sequence
<220> FEATURE:
<223> OTHER INFORMATION: Chemically synthesized

<400> SEQUENCE: 1463
acugagcuua uaaaggcau                                               19

<210> SEQ ID NO 1464
<211> LENGTH: 19
<212> TYPE: RNA
<213> ORGANISM: Artificial sequence
<220> FEATURE:
<223> OTHER INFORMATION: Chemically synthesized

<400> SEQUENCE: 1464
aggaacaaca uaaucccag                                               19

<210> SEQ ID NO 1465
<211> LENGTH: 19
<212> TYPE: RNA
<213> ORGANISM: Artificial sequence
<220> FEATURE:
<223> OTHER INFORMATION: Chemically synthesized

<400> SEQUENCE: 1465
ugccucuuua aaacauuag                                               19

<210> SEQ ID NO 1466
<211> LENGTH: 19
<212> TYPE: RNA
<213> ORGANISM: Artificial sequence
<220> FEATURE:
<223> OTHER INFORMATION: Chemically synthesized

<400> SEQUENCE: 1466
acauaauccc aguagucaa                                               19

<210> SEQ ID NO 1467
<211> LENGTH: 19
<212> TYPE: RNA
<213> ORGANISM: Artificial sequence
<220> FEATURE:
<223> OTHER INFORMATION: Chemically synthesized

<400> SEQUENCE: 1467
auugccguaa uauuucuca                                               19

<210> SEQ ID NO 1468
<211> LENGTH: 19
<212> TYPE: RNA
<213> ORGANISM: Artificial sequence
<220> FEATURE:
<223> OTHER INFORMATION: Chemically synthesized

<400> SEQUENCE: 1468
uugccguaau auuucucau                                               19

<210> SEQ ID NO 1469
<211> LENGTH: 19
<212> TYPE: RNA
<213> ORGANISM: Artificial sequence
<220> FEATURE:
```

```
<223> OTHER INFORMATION: Chemically synthesized

<400> SEQUENCE: 1469
uuucucauuu acucuuacc                                                19

<210> SEQ ID NO 1470
<211> LENGTH: 19
<212> TYPE: RNA
<213> ORGANISM: Artificial sequence
<220> FEATURE:
<223> OTHER INFORMATION: Chemically synthesized

<400> SEQUENCE: 1470
cucauuuacu cuuaccuag                                                19

<210> SEQ ID NO 1471
<211> LENGTH: 19
<212> TYPE: RNA
<213> ORGANISM: Artificial sequence
<220> FEATURE:
<223> OTHER INFORMATION: Chemically synthesized

<400> SEQUENCE: 1471
uuuacucuua ccuaggguu                                                19

<210> SEQ ID NO 1472
<211> LENGTH: 19
<212> TYPE: RNA
<213> ORGANISM: Artificial sequence
<220> FEATURE:
<223> OTHER INFORMATION: Chemically synthesized

<400> SEQUENCE: 1472
agcuuuaauu aaacucacc                                                19

<210> SEQ ID NO 1473
<211> LENGTH: 19
<212> TYPE: RNA
<213> ORGANISM: Artificial sequence
<220> FEATURE:
<223> OTHER INFORMATION: Chemically synthesized

<400> SEQUENCE: 1473
aauccuaccu uccugucua                                                19

<210> SEQ ID NO 1474
<211> LENGTH: 19
<212> TYPE: RNA
<213> ORGANISM: Artificial sequence
<220> FEATURE:
<223> OTHER INFORMATION: Chemically synthesized

<400> SEQUENCE: 1474
acccuucaaa uuugaguca                                                19

<210> SEQ ID NO 1475
<211> LENGTH: 19
<212> TYPE: RNA
<213> ORGANISM: Artificial sequence
<220> FEATURE:
<223> OTHER INFORMATION: Chemically synthesized

<400> SEQUENCE: 1475
cccuucaaau uugagucag                                                19
```

<210> SEQ ID NO 1476
<211> LENGTH: 19
<212> TYPE: RNA
<213> ORGANISM: Artificial sequence
<220> FEATURE:
<223> OTHER INFORMATION: Chemically synthesized

<400> SEQUENCE: 1476
uuugagucag gaacuggug                                              19

<210> SEQ ID NO 1477
<211> LENGTH: 19
<212> TYPE: RNA
<213> ORGANISM: Artificial sequence
<220> FEATURE:
<223> OTHER INFORMATION: Chemically synthesized

<400> SEQUENCE: 1477
ugagucagga acugguggu                                              19

<210> SEQ ID NO 1478
<211> LENGTH: 19
<212> TYPE: RNA
<213> ORGANISM: Artificial sequence
<220> FEATURE:
<223> OTHER INFORMATION: Chemically synthesized

<400> SEQUENCE: 1478
aacugguggu gugggcuuu                                              19

<210> SEQ ID NO 1479
<211> LENGTH: 19
<212> TYPE: RNA
<213> ORGANISM: Artificial sequence
<220> FEATURE:
<223> OTHER INFORMATION: Chemically synthesized

<400> SEQUENCE: 1479
uagucuauua ccaagccua                                              19

<210> SEQ ID NO 1480
<211> LENGTH: 19
<212> TYPE: RNA
<213> ORGANISM: Artificial sequence
<220> FEATURE:
<223> OTHER INFORMATION: Chemically synthesized

<400> SEQUENCE: 1480
ccuaccugaa accaaauug                                              19

<210> SEQ ID NO 1481
<211> LENGTH: 19
<212> TYPE: RNA
<213> ORGANISM: Artificial sequence
<220> FEATURE:
<223> OTHER INFORMATION: Chemically synthesized

<400> SEQUENCE: 1481
uguaaaacuc aaaugggcu                                              19

<210> SEQ ID NO 1482
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 1482
ucaaaaucac uuagcaggc                                              19

<210> SEQ ID NO 1483
<211> LENGTH: 19
<212> TYPE: RNA
<213> ORGANISM: Artificial sequence
<220> FEATURE:
<223> OTHER INFORMATION: Chemically synthesized

<400> SEQUENCE: 1483
augggcuucu acuuuugcu                                              19

<210> SEQ ID NO 1484
<211> LENGTH: 19
<212> TYPE: RNA
<213> ORGANISM: Artificial sequence
<220> FEATURE:
<223> OTHER INFORMATION: Chemically synthesized

<400> SEQUENCE: 1484
ggcuucuacu uuugcuuac                                              19

<210> SEQ ID NO 1485
<211> LENGTH: 19
<212> TYPE: RNA
<213> ORGANISM: Artificial sequence
<220> FEATURE:
<223> OTHER INFORMATION: Chemically synthesized

<400> SEQUENCE: 1485
aaucacuuag caggcucuc                                              19

<210> SEQ ID NO 1486
<211> LENGTH: 19
<212> TYPE: RNA
<213> ORGANISM: Artificial sequence
<220> FEATURE:
<223> OTHER INFORMATION: Chemically synthesized

<400> SEQUENCE: 1486 acaaaaugg gaucuaugc                                               19

<210> SEQ ID NO 1487
<211> LENGTH: 19
<212> TYPE: RNA
<213> ORGANISM: Artificial sequence
<220> FEATURE:
<223> OTHER INFORMATION: Chemically synthesized

<400> SEQUENCE: 1487
uaugcagaaa aucuacacu                                              19

<210> SEQ ID NO 1488
<211> LENGTH: 19
<212> TYPE: RNA
<213> ORGANISM: Artificial sequence
<220> FEATURE:
<223> OTHER INFORMATION: Chemically synthesized

<400> SEQUENCE: 1488
auuuugaauc acuucucca                                              19

<210> SEQ ID NO 1489
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1489
ucagccuguu agcugcagu                                                        19

<210> SEQ ID NO 1490
<211> LENGTH: 19
<212> TYPE: RNA
<213> ORGANISM: Artificial sequence
<220> FEATURE:
<223> OTHER INFORMATION: Chemically synthesized

<400> SEQUENCE: 1490
cuaugaaugu gaaacacag                                                        19

<210> SEQ ID NO 1491
<211> LENGTH: 19
<212> TYPE: RNA
<213> ORGANISM: Artificial sequence
<220> FEATURE:
<223> OTHER INFORMATION: Chemically synthesized

<400> SEQUENCE: 1491
augaauguga aacacagaa                                                        19

<210> SEQ ID NO 1492
<211> LENGTH: 19
<212> TYPE: RNA
<213> ORGANISM: Artificial sequence
<220> FEATURE:
<223> OTHER INFORMATION: Chemically synthesized

<400> SEQUENCE: 1492
aaaagagacu acauuuggg                                                        19

<210> SEQ ID NO 1493
<211> LENGTH: 19
<212> TYPE: RNA
<213> ORGANISM: Artificial sequence
<220> FEATURE:
<223> OTHER INFORMATION: Chemically synthesized

<400> SEQUENCE: 1493
aaagagacua cauuuggggu                                                       19

<210> SEQ ID NO 1494
<211> LENGTH: 19
<212> TYPE: RNA
<213> ORGANISM: Artificial sequence
<220> FEATURE:
<223> OTHER INFORMATION: Chemically synthesized

<400> SEQUENCE: 1494
agagacuaca uuugggguu                                                        19

<210> SEQ ID NO 1495
<211> LENGTH: 19
<212> TYPE: RNA
<213> ORGANISM: Artificial sequence
<220> FEATURE:
<223> OTHER INFORMATION: Chemically synthesized

<400> SEQUENCE: 1495
```

```
gguuucuuau uuagggcag                                                   19

<210> SEQ ID NO 1496
<211> LENGTH: 19
<212> TYPE: RNA
<213> ORGANISM: Artificial sequence
<220> FEATURE:
<223> OTHER INFORMATION: Chemically synthesized

<400> SEQUENCE: 1496
uuucuuauuu agggcaggu                                                   19

<210> SEQ ID NO 1497
<211> LENGTH: 19
<212> TYPE: RNA
<213> ORGANISM: Artificial sequence
<220> FEATURE:
<223> OTHER INFORMATION: Chemically synthesized

<400> SEQUENCE: 1497
cuuauuuagg gcagguggg                                                   19

<210> SEQ ID NO 1498
<211> LENGTH: 19
<212> TYPE: RNA
<213> ORGANISM: Artificial sequence
<220> FEATURE:
<223> OTHER INFORMATION: Chemically synthesized

<400> SEQUENCE: 1498
uguuguucca aucagugag                                                   19

<210> SEQ ID NO 1499
<211> LENGTH: 19
<212> TYPE: RNA
<213> ORGANISM: Artificial sequence
<220> FEATURE:
<223> OTHER INFORMATION: Chemically synthesized

<400> SEQUENCE: 1499
aacaagucga aauccugag                                                   19

<210> SEQ ID NO 1500
<211> LENGTH: 19
<212> TYPE: RNA
<213> ORGANISM: Artificial sequence
<220> FEATURE:
<223> OTHER INFORMATION: Chemically synthesized

<400> SEQUENCE: 1500
acaagucgaa auccugagc                                                   19

<210> SEQ ID NO 1501
<211> LENGTH: 19
<212> TYPE: RNA
<213> ORGANISM: Artificial sequence
<220> FEATURE:
<223> OTHER INFORMATION: Chemically synthesized

<400> SEQUENCE: 1501
caagucgaaa uccugagcu                                                   19

<210> SEQ ID NO 1502
<211> LENGTH: 19
<212> TYPE: RNA
<213> ORGANISM: Artificial sequence
```

```
<220> FEATURE:
<223> OTHER INFORMATION: Chemically synthesized

<400> SEQUENCE: 1502
ugaggaucag aguucuccu                                              19

<210> SEQ ID NO 1503
<211> LENGTH: 19
<212> TYPE: RNA
<213> ORGANISM: Artificial sequence
<220> FEATURE:
<223> OTHER INFORMATION: Chemically synthesized

<400> SEQUENCE: 1503
ucuugcugcu caaacugcc                                              19

<210> SEQ ID NO 1504
<211> LENGTH: 19
<212> TYPE: RNA
<213> ORGANISM: Artificial sequence
<220> FEATURE:
<223> OTHER INFORMATION: Chemically synthesized

<400> SEQUENCE: 1504
aaacacaagu guaagcuca                                              19

<210> SEQ ID NO 1505
<211> LENGTH: 19
<212> TYPE: RNA
<213> ORGANISM: Artificial sequence
<220> FEATURE:
<223> OTHER INFORMATION: Chemically synthesized

<400> SEQUENCE: 1505
acacaagugu aagcucaaa                                              19

<210> SEQ ID NO 1506
<211> LENGTH: 19
<212> TYPE: RNA
<213> ORGANISM: Artificial sequence
<220> FEATURE:
<223> OTHER INFORMATION: Chemically synthesized

<400> SEQUENCE: 1506
cgacgcuaga aucacacac                                              19

<210> SEQ ID NO 1507
<211> LENGTH: 19
<212> TYPE: RNA
<213> ORGANISM: Artificial sequence
<220> FEATURE:
<223> OTHER INFORMATION: Chemically synthesized

<400> SEQUENCE: 1507
acgcuagaau cacacacaa                                              19

<210> SEQ ID NO 1508
<211> LENGTH: 19
<212> TYPE: RNA
<213> ORGANISM: Artificial sequence
<220> FEATURE:
<223> OTHER INFORMATION: Chemically synthesized

<400> SEQUENCE: 1508
ucacacacaa uccuaucca                                              19
```

<210> SEQ ID NO 1509
<211> LENGTH: 19
<212> TYPE: RNA
<213> ORGANISM: Artificial sequence
<220> FEATURE:
<223> OTHER INFORMATION: Chemically synthesized

<400> SEQUENCE: 1509
acaauccuau ccagcuuuu                                                19

<210> SEQ ID NO 1510
<211> LENGTH: 19
<212> TYPE: RNA
<213> ORGANISM: Artificial sequence
<220> FEATURE:
<223> OTHER INFORMATION: Chemically synthesized

<400> SEQUENCE: 1510
uauccagcuu uuuacauac                                                19

<210> SEQ ID NO 1511
<211> LENGTH: 19
<212> TYPE: RNA
<213> ORGANISM: Artificial sequence
<220> FEATURE:
<223> OTHER INFORMATION: Chemically synthesized

<400> SEQUENCE: 1511
uccagcuuuu uacauacau                                                19

<210> SEQ ID NO 1512
<211> LENGTH: 19
<212> TYPE: RNA
<213> ORGANISM: Artificial sequence
<220> FEATURE:
<223> OTHER INFORMATION: Chemically synthesized

<400> SEQUENCE: 1512
gagcaauucu cugggucag                                                19

<210> SEQ ID NO 1513
<211> LENGTH: 19
<212> TYPE: RNA
<213> ORGANISM: Artificial sequence
<220> FEATURE:
<223> OTHER INFORMATION: Chemically synthesized

<400> SEQUENCE: 1513
aacugccagu ugcaaccau                                                19

<210> SEQ ID NO 1514
<211> LENGTH: 19
<212> TYPE: RNA
<213> ORGANISM: Artificial sequence
<220> FEATURE:
<223> OTHER INFORMATION: Chemically synthesized

<400> SEQUENCE: 1514
uuaauuuaac agccuucca                                                19

<210> SEQ ID NO 1515
<211> LENGTH: 19
<212> TYPE: RNA
<213> ORGANISM: Artificial sequence
<220> FEATURE:
<223> OTHER INFORMATION: Chemically synthesized

<400> SEQUENCE: 1515
uuaacagccu uccauaagc                                                    19

<210> SEQ ID NO 1516
<211> LENGTH: 19
<212> TYPE: RNA
<213> ORGANISM: Artificial sequence
<220> FEATURE:
<223> OTHER INFORMATION: Chemically synthesized

<400> SEQUENCE: 1516
cuuugauuug gacagacag                                                    19

<210> SEQ ID NO 1517
<211> LENGTH: 19
<212> TYPE: RNA
<213> ORGANISM: Artificial sequence
<220> FEATURE:
<223> OTHER INFORMATION: Chemically synthesized

<400> SEQUENCE: 1517
aaggacaaca guucuacau                                                    19

<210> SEQ ID NO 1518
<211> LENGTH: 19
<212> TYPE: RNA
<213> ORGANISM: Artificial sequence
<220> FEATURE:
<223> OTHER INFORMATION: Chemically synthesized

<400> SEQUENCE: 1518
aacaguucua caucgaugc                                                    19

<210> SEQ ID NO 1519
<211> LENGTH: 19
<212> TYPE: RNA
<213> ORGANISM: Artificial sequence
<220> FEATURE:
<223> OTHER INFORMATION: Chemically synthesized

<400> SEQUENCE: 1519
agacaugcaa aacaacauu                                                    19

<210> SEQ ID NO 1520
<211> LENGTH: 19
<212> TYPE: RNA
<213> ORGANISM: Artificial sequence
<220> FEATURE:
<223> OTHER INFORMATION: Chemically synthesized

<400> SEQUENCE: 1520
auugauuuau cuuggccca                                                    19

<210> SEQ ID NO 1521
<211> LENGTH: 19
<212> TYPE: RNA
<213> ORGANISM: Artificial sequence
<220> FEATURE:
<223> OTHER INFORMATION: Chemically synthesized

<400> SEQUENCE: 1521
auuuaucuug gcccaauuc                                                    19

<210> SEQ ID NO 1522

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1522
uuuaucuugg cccaauucu                                                   19

<210> SEQ ID NO 1523
<211> LENGTH: 19
<212> TYPE: RNA
<213> ORGANISM: Artificial sequence
<220> FEATURE:
<223> OTHER INFORMATION: Chemically synthesized

<400> SEQUENCE: 1523
uuuccaagca uuugaagag                                                   19

<210> SEQ ID NO 1524
<211> LENGTH: 19
<212> TYPE: RNA
<213> ORGANISM: Artificial sequence
<220> FEATURE:
<223> OTHER INFORMATION: Chemically synthesized

<400> SEQUENCE: 1524
uuccaagcau uugaagagu                                                   19

<210> SEQ ID NO 1525
<211> LENGTH: 19
<212> TYPE: RNA
<213> ORGANISM: Artificial sequence
<220> FEATURE:
<223> OTHER INFORMATION: Chemically synthesized

<400> SEQUENCE: 1525
ggcuaauuug aacagugac                                                   19

<210> SEQ ID NO 1526
<211> LENGTH: 19
<212> TYPE: RNA
<213> ORGANISM: Artificial sequence
<220> FEATURE:
<223> OTHER INFORMATION: Chemically synthesized

<400> SEQUENCE: 1526
cagugacauu uuaggucac                                                   19

<210> SEQ ID NO 1527
<211> LENGTH: 19
<212> TYPE: RNA
<213> ORGANISM: Artificial sequence
<220> FEATURE:
<223> OTHER INFORMATION: Chemically synthesized

<400> SEQUENCE: 1527
aggucacuua uaguaucag                                                   19

<210> SEQ ID NO 1528
<211> LENGTH: 19
<212> TYPE: RNA
<213> ORGANISM: Artificial sequence
<220> FEATURE:
<223> OTHER INFORMATION: Chemically synthesized

<400> SEQUENCE: 1528
```

```
ggucacuuau aguaucagu                                              19

<210> SEQ ID NO 1529
<211> LENGTH: 19
<212> TYPE: RNA
<213> ORGANISM: Artificial sequence
<220> FEATURE:
<223> OTHER INFORMATION: Chemically synthesized

<400> SEQUENCE: 1529
gucacuuaua guaucagua                                              19

<210> SEQ ID NO 1530
<211> LENGTH: 19
<212> TYPE: RNA
<213> ORGANISM: Artificial sequence
<220> FEATURE:
<223> OTHER INFORMATION: Chemically synthesized

<400> SEQUENCE: 1530
uaguaucagu aacaggauc                                              19

<210> SEQ ID NO 1531
<211> LENGTH: 19
<212> TYPE: RNA
<213> ORGANISM: Artificial sequence
<220> FEATURE:
<223> OTHER INFORMATION: Chemically synthesized

<400> SEQUENCE: 1531
ucaguaacag gaucacacc                                              19

<210> SEQ ID NO 1532
<211> LENGTH: 19
<212> TYPE: RNA
<213> ORGANISM: Artificial sequence
<220> FEATURE:
<223> OTHER INFORMATION: Chemically synthesized

<400> SEQUENCE: 1532
gaucacaccu guuuucag                                               19

<210> SEQ ID NO 1533
<211> LENGTH: 19
<212> TYPE: RNA
<213> ORGANISM: Artificial sequence
<220> FEATURE:
<223> OTHER INFORMATION: Chemically synthesized

<400> SEQUENCE: 1533 cuguuuuca guaacacca                                               19

<210> SEQ ID NO 1534
<211> LENGTH: 19
<212> TYPE: RNA
<213> ORGANISM: Artificial sequence
<220> FEATURE:
<223> OTHER INFORMATION: Chemically synthesized

<400> SEQUENCE: 1534 uguuuucag uaacaccag                                               19

<210> SEQ ID NO 1535
<211> LENGTH: 19
<212> TYPE: RNA
```

```
<213> ORGANISM: Artificial sequence
<220> FEATURE:
<223> OTHER INFORMATION: Chemically synthesized

<400> SEQUENCE: 1535
uuuuucagua acaccagga                                                    19

<210> SEQ ID NO 1536
<211> LENGTH: 19
<212> TYPE: RNA
<213> ORGANISM: Artificial sequence
<220> FEATURE:
<223> OTHER INFORMATION: Chemically synthesized

<400> SEQUENCE: 1536
ccaggaugaa uacaucugu                                                    19

<210> SEQ ID NO 1537
<211> LENGTH: 19
<212> TYPE: RNA
<213> ORGANISM: Artificial sequence
<220> FEATURE:
<223> OTHER INFORMATION: Chemically synthesized

<400> SEQUENCE: 1537
caggaugaau acaucuguc                                                    19

<210> SEQ ID NO 1538
<211> LENGTH: 19
<212> TYPE: RNA
<213> ORGANISM: Artificial sequence
<220> FEATURE:
<223> OTHER INFORMATION: Chemically synthesized

<400> SEQUENCE: 1538
aauacaucug ucccuacgc                                                    19

<210> SEQ ID NO 1539
<211> LENGTH: 19
<212> TYPE: RNA
<213> ORGANISM: Artificial sequence
<220> FEATURE:
<223> OTHER INFORMATION: Chemically synthesized

<400> SEQUENCE: 1539
gcuaauagcu agggcagga                                                    19

<210> SEQ ID NO 1540
<211> LENGTH: 19
<212> TYPE: RNA
<213> ORGANISM: Artificial sequence
<220> FEATURE:
<223> OTHER INFORMATION: Chemically synthesized

<400> SEQUENCE: 1540
gaauaagcuc cuuauccac                                                    19

<210> SEQ ID NO 1541
<211> LENGTH: 19
<212> TYPE: RNA
<213> ORGANISM: Artificial sequence
<220> FEATURE:
<223> OTHER INFORMATION: Chemically synthesized

<400> SEQUENCE: 1541
uuauccacga cccacagca                                                    19
```

```
<210> SEQ ID NO 1542
<211> LENGTH: 19
<212> TYPE: RNA
<213> ORGANISM: Artificial sequence
<220> FEATURE:
<223> OTHER INFORMATION: Chemically synthesized

<400> SEQUENCE: 1542
aauucuggca aguugauuc                                               19

<210> SEQ ID NO 1543
<211> LENGTH: 19
<212> TYPE: RNA
<213> ORGANISM: Artificial sequence
<220> FEATURE:
<223> OTHER INFORMATION: Chemically synthesized

<400> SEQUENCE: 1543
uaaugaucua cuuaguugg                                               19

<210> SEQ ID NO 1544
<211> LENGTH: 19
<212> TYPE: RNA
<213> ORGANISM: Artificial sequence
<220> FEATURE:
<223> OTHER INFORMATION: Chemically synthesized

<400> SEQUENCE: 1544
gacaaaaaau aaggccuuu                                               19

<210> SEQ ID NO 1545
<211> LENGTH: 19
<212> TYPE: RNA
<213> ORGANISM: Artificial sequence
<220> FEATURE:
<223> OTHER INFORMATION: Chemically synthesized

<400> SEQUENCE: 1545
auaaggccuu uauuauucc                                               19

<210> SEQ ID NO 1546
<211> LENGTH: 19
<212> TYPE: RNA
<213> ORGANISM: Artificial sequence
<220> FEATURE:
<223> OTHER INFORMATION: Chemically synthesized

<400> SEQUENCE: 1546
uaaggccuuu auuauuccc                                               19

<210> SEQ ID NO 1547
<211> LENGTH: 19
<212> TYPE: RNA
<213> ORGANISM: Artificial sequence
<220> FEATURE:
<223> OTHER INFORMATION: Chemically synthesized

<400> SEQUENCE: 1547
ucugggugca ugcaugguu                                               19

<210> SEQ ID NO 1548
<211> LENGTH: 19
<212> TYPE: RNA
<213> ORGANISM: Artificial sequence
<220> FEATURE:
```

<223> OTHER INFORMATION: Chemically synthesized

<400> SEQUENCE: 1548
gugcaugcau gguuaucug					19

<210> SEQ ID NO 1549
<211> LENGTH: 19
<212> TYPE: RNA
<213> ORGANISM: Artificial sequence
<220> FEATURE:
<223> OTHER INFORMATION: Chemically synthesized

<400> SEQUENCE: 1549
ugguuaucug gacggugag					19

<210> SEQ ID NO 1550
<211> LENGTH: 19
<212> TYPE: RNA
<213> ORGANISM: Artificial sequence
<220> FEATURE:
<223> OTHER INFORMATION: Chemically synthesized

<400> SEQUENCE: 1550
ucuggacggu gaguuucau					19

<210> SEQ ID NO 1551
<211> LENGTH: 19
<212> TYPE: RNA
<213> ORGANISM: Artificial sequence
<220> FEATURE:
<223> OTHER INFORMATION: Chemically synthesized

<400> SEQUENCE: 1551
acggugaguu ucauucucu					19

<210> SEQ ID NO 1552
<211> LENGTH: 19
<212> TYPE: RNA
<213> ORGANISM: Artificial sequence
<220> FEATURE:
<223> OTHER INFORMATION: Chemically synthesized

<400> SEQUENCE: 1552
uucauucucu aggcuguac					19

<210> SEQ ID NO 1553
<211> LENGTH: 19
<212> TYPE: RNA
<213> ORGANISM: Artificial sequence
<220> FEATURE:
<223> OTHER INFORMATION: Chemically synthesized

<400> SEQUENCE: 1553
aggcuguacu auaaaccau					19

<210> SEQ ID NO 1554
<211> LENGTH: 19
<212> TYPE: RNA
<213> ORGANISM: Artificial sequence
<220> FEATURE:
<223> OTHER INFORMATION: Chemically synthesized

<400> SEQUENCE: 1554
cuauaaacca uaucuccau					19

```
<210> SEQ ID NO 1555
<211> LENGTH: 19
<212> TYPE: RNA
<213> ORGANISM: Artificial sequence
<220> FEATURE:
<223> OTHER INFORMATION: Chemically synthesized

<400> SEQUENCE: 1555
aaccauaucu ccauagcca                                              19

<210> SEQ ID NO 1556
<211> LENGTH: 19
<212> TYPE: RNA
<213> ORGANISM: Artificial sequence
<220> FEATURE:
<223> OTHER INFORMATION: Chemically synthesized

<400> SEQUENCE: 1556
uaucuccaua gccaaugca                                              19

<210> SEQ ID NO 1557
<211> LENGTH: 19
<212> TYPE: RNA
<213> ORGANISM: Artificial sequence
<220> FEATURE:
<223> OTHER INFORMATION: Chemically synthesized

<400> SEQUENCE: 1557
auucaaagug guaguauac                                              19

<210> SEQ ID NO 1558
<211> LENGTH: 19
<212> TYPE: RNA
<213> ORGANISM: Artificial sequence
<220> FEATURE:
<223> OTHER INFORMATION: Chemically synthesized

<400> SEQUENCE: 1558
aaagugguag uauacagcu                                              19

<210> SEQ ID NO 1559
<211> LENGTH: 19
<212> TYPE: RNA
<213> ORGANISM: Artificial sequence
<220> FEATURE:
<223> OTHER INFORMATION: Chemically synthesized

<400> SEQUENCE: 1559
guaguauaca gcuacuacc                                              19

<210> SEQ ID NO 1560
<211> LENGTH: 19
<212> TYPE: RNA
<213> ORGANISM: Artificial sequence
<220> FEATURE:
<223> OTHER INFORMATION: Chemically synthesized

<400> SEQUENCE: 1560
uauacagcua cuacccuug                                              19

<210> SEQ ID NO 1561
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1561
ugacaauugg gguuaagga                                                19

<210> SEQ ID NO 1562
<211> LENGTH: 19
<212> TYPE: RNA
<213> ORGANISM: Artificial sequence
<220> FEATURE:
<223> OTHER INFORMATION: Chemically synthesized

<400> SEQUENCE: 1562
ggguuaagga gagauacuu                                                19

<210> SEQ ID NO 1563
<211> LENGTH: 19
<212> TYPE: RNA
<213> ORGANISM: Artificial sequence
<220> FEATURE:
<223> OTHER INFORMATION: Chemically synthesized

<400> SEQUENCE: 1563
agauacuuca auucccaga                                                19

<210> SEQ ID NO 1564
<211> LENGTH: 19
<212> TYPE: RNA
<213> ORGANISM: Artificial sequence
<220> FEATURE:
<223> OTHER INFORMATION: Chemically synthesized

<400> SEQUENCE: 1564
auacuucaau ucccagaaa                                                19

<210> SEQ ID NO 1565
<211> LENGTH: 19
<212> TYPE: RNA
<213> ORGANISM: Artificial sequence
<220> FEATURE:
<223> OTHER INFORMATION: Chemically synthesized

<400> SEQUENCE: 1565
gagaugagau aacacugcc                                                19

<210> SEQ ID NO 1566
<211> LENGTH: 19
<212> TYPE: RNA
<213> ORGANISM: Artificial sequence
<220> FEATURE:
<223> OTHER INFORMATION: Chemically synthesized

<400> SEQUENCE: 1566
gaugagauaa cacugccau                                                19

<210> SEQ ID NO 1567
<211> LENGTH: 19
<212> TYPE: RNA
<213> ORGANISM: Artificial sequence
<220> FEATURE:
<223> OTHER INFORMATION: Chemically synthesized

<400> SEQUENCE: 1567
agauaacacu gccauggug                                                19

<210> SEQ ID NO 1568
<211> LENGTH: 19
```

-continued

```
<212> TYPE: RNA
<213> ORGANISM: Artificial sequence
<220> FEATURE:
<223> OTHER INFORMATION: Chemically synthesized

<400> SEQUENCE: 1568
guucaucuga gauuaagca                                                      19

<210> SEQ ID NO 1569
<211> LENGTH: 19
<212> TYPE: RNA
<213> ORGANISM: Artificial sequence
<220> FEATURE:
<223> OTHER INFORMATION: Chemically synthesized

<400> SEQUENCE: 1569
aucugagauu aagcacaug                                                      19

<210> SEQ ID NO 1570
<211> LENGTH: 19
<212> TYPE: RNA
<213> ORGANISM: Artificial sequence
<220> FEATURE:
<223> OTHER INFORMATION: Chemically synthesized

<400> SEQUENCE: 1570
ugagauuaag cacauguaa                                                      19

<210> SEQ ID NO 1571
<211> LENGTH: 19
<212> TYPE: RNA
<213> ORGANISM: Artificial sequence
<220> FEATURE:
<223> OTHER INFORMATION: Chemically synthesized

<400> SEQUENCE: 1571
uuaagcacau guaauacug                                                      19

<210> SEQ ID NO 1572
<211> LENGTH: 19
<212> TYPE: RNA
<213> ORGANISM: Artificial sequence
<220> FEATURE:
<223> OTHER INFORMATION: Chemically synthesized

<400> SEQUENCE: 1572
aggauagauu acuaaguga                                                      19

<210> SEQ ID NO 1573
<211> LENGTH: 19
<212> TYPE: RNA
<213> ORGANISM: Artificial sequence
<220> FEATURE:
<223> OTHER INFORMATION: Chemically synthesized

<400> SEQUENCE: 1573
uaauuuccua uccucacag                                                      19

<210> SEQ ID NO 1574
<211> LENGTH: 19
<212> TYPE: RNA
<213> ORGANISM: Artificial sequence
<220> FEATURE:
<223> OTHER INFORMATION: Chemically synthesized

<400> SEQUENCE: 1574
```
aaagacagua uucaacacu            19

<210> SEQ ID NO 1575
<211> LENGTH: 19
<212> TYPE: RNA
<213> ORGANISM: Artificial sequence
<220> FEATURE:
<223> OTHER INFORMATION: Chemically synthesized

<400> SEQUENCE: 1575
agacaguauu caacacuua            19

<210> SEQ ID NO 1576
<211> LENGTH: 19
<212> TYPE: RNA
<213> ORGANISM: Artificial sequence
<220> FEATURE:
<223> OTHER INFORMATION: Chemically synthesized

<400> SEQUENCE: 1576
auucaacacu uaagaacag            19

<210> SEQ ID NO 1577
<211> LENGTH: 19
<212> TYPE: RNA
<213> ORGANISM: Artificial sequence
<220> FEATURE:
<223> OTHER INFORMATION: Chemically synthesized

<400> SEQUENCE: 1577
uucaacacuu aagaacagg            19

<210> SEQ ID NO 1578
<211> LENGTH: 19
<212> TYPE: RNA
<213> ORGANISM: Artificial sequence
<220> FEATURE:
<223> OTHER INFORMATION: Chemically synthesized

<400> SEQUENCE: 1578
cugagcuuau aaaggcauc            19

<210> SEQ ID NO 1579
<211> LENGTH: 19
<212> TYPE: RNA
<213> ORGANISM: Artificial sequence
<220> FEATURE:
<223> OTHER INFORMATION: Chemically synthesized

<400> SEQUENCE: 1579
gagcuuauaa aggcaucua            19

<210> SEQ ID NO 1580
<211> LENGTH: 19
<212> TYPE: RNA
<213> ORGANISM: Artificial sequence
<220> FEATURE:
<223> OTHER INFORMATION: Chemically synthesized

<400> SEQUENCE: 1580
aggcaucuaa aacaacacc            19

<210> SEQ ID NO 1581
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 1581
agcuuuuguu gccucuuua                                              19

<210> SEQ ID NO 1582
<211> LENGTH: 19
<212> TYPE: RNA
<213> ORGANISM: Artificial sequence
<220> FEATURE:
<223> OTHER INFORMATION: Chemically synthesized

<400> SEQUENCE: 1582
uuuguugccu cuuuaaaac                                              19

<210> SEQ ID NO 1583
<211> LENGTH: 19
<212> TYPE: RNA
<213> ORGANISM: Artificial sequence
<220> FEATURE:
<223> OTHER INFORMATION: Chemically synthesized

<400> SEQUENCE: 1583
uguugccucu uuaaaacau                                              19

<210> SEQ ID NO 1584
<211> LENGTH: 19
<212> TYPE: RNA
<213> ORGANISM: Artificial sequence
<220> FEATURE:
<223> OTHER INFORMATION: Chemically synthesized

<400> SEQUENCE: 1584
caccaagaaa cagugaagc                                              19

<210> SEQ ID NO 1585
<211> LENGTH: 19
<212> TYPE: RNA
<213> ORGANISM: Artificial sequence
<220> FEATURE:
<223> OTHER INFORMATION: Chemically synthesized

<400> SEQUENCE: 1585
uauugccgua auauuucuc                                              19

<210> SEQ ID NO 1586
<211> LENGTH: 19
<212> TYPE: RNA
<213> ORGANISM: Artificial sequence
<220> FEATURE:
<223> OTHER INFORMATION: Chemically synthesized

<400> SEQUENCE: 1586
aaacccuuca aauuugagu                                              19

<210> SEQ ID NO 1587
<211> LENGTH: 19
<212> TYPE: RNA
<213> ORGANISM: Artificial sequence
<220> FEATURE:
<223> OTHER INFORMATION: Chemically synthesized

<400> SEQUENCE: 1587
ccaguaguca aaaucacuu                                              19
```

<210> SEQ ID NO 1588
<211> LENGTH: 19
<212> TYPE: RNA
<213> ORGANISM: Artificial sequence
<220> FEATURE:
<223> OTHER INFORMATION: Chemically synthesized

<400> SEQUENCE: 1588
caguagucaa aaucacuua                                                19

<210> SEQ ID NO 1589
<211> LENGTH: 19
<212> TYPE: RNA
<213> ORGANISM: Artificial sequence
<220> FEATURE:
<223> OTHER INFORMATION: Chemically synthesized

<400> SEQUENCE: 1589
cauuuaguau gauucugug                                                19

<210> SEQ ID NO 1590
<211> LENGTH: 19
<212> TYPE: RNA
<213> ORGANISM: Artificial sequence
<220> FEATURE:
<223> OTHER INFORMATION: Chemically synthesized

<400> SEQUENCE: 1590
guagucaaaa ucacuuagc                                                19

<210> SEQ ID NO 1591
<211> LENGTH: 19
<212> TYPE: RNA
<213> ORGANISM: Artificial sequence
<220> FEATURE:
<223> OTHER INFORMATION: Chemically synthesized

<400> SEQUENCE: 1591
cuauuaccaa gccuaccug                                                19

<210> SEQ ID NO 1592
<211> LENGTH: 19
<212> TYPE: RNA
<213> ORGANISM: Artificial sequence
<220> FEATURE:
<223> OTHER INFORMATION: Chemically synthesized

<400> SEQUENCE: 1592
gcuuaccuau uccauccca                                                19

<210> SEQ ID NO 1593
<211> LENGTH: 19
<212> TYPE: RNA
<213> ORGANISM: Artificial sequence
<220> FEATURE:
<223> OTHER INFORMATION: Chemically synthesized

<400> SEQUENCE: 1593
cuuaccuauu ccaucccau                                                19

<210> SEQ ID NO 1594
<211> LENGTH: 19
<212> TYPE: RNA
<213> ORGANISM: Artificial sequence
<220> FEATURE:
<223> OTHER INFORMATION: Chemically synthesized

<400> SEQUENCE: 1594
acagaaagaa aagagacua                                                19

<210> SEQ ID NO 1595
<211> LENGTH: 19
<212> TYPE: RNA
<213> ORGANISM: Artificial sequence
<220> FEATURE:
<223> OTHER INFORMATION: Chemically synthesized

<400> SEQUENCE: 1595
acuacauuug ggguuucuu                                                19

<210> SEQ ID NO 1596
<211> LENGTH: 19
<212> TYPE: RNA
<213> ORGANISM: Artificial sequence
<220> FEATURE:
<223> OTHER INFORMATION: Chemically synthesized

<400> SEQUENCE: 1596 uggguuucu uauuuaggg                                                 19

<210> SEQ ID NO 1597
<211> LENGTH: 19
<212> TYPE: RNA
<213> ORGANISM: Artificial sequence
<220> FEATURE:
<223> OTHER INFORMATION: Chemically synthesized

<400> SEQUENCE: 1597
ccuucaauca cuguuguuc                                                19

<210> SEQ ID NO 1598
<211> LENGTH: 19
<212> TYPE: RNA
<213> ORGANISM: Artificial sequence
<220> FEATURE:
<223> OTHER INFORMATION: Chemically synthesized

<400> SEQUENCE: 1598
ucacuguugu uccaaucag                                                19

<210> SEQ ID NO 1599
<211> LENGTH: 19
<212> TYPE: RNA
<213> ORGANISM: Artificial sequence
<220> FEATURE:
<223> OTHER INFORMATION: Chemically synthesized

<400> SEQUENCE: 1599
aaauccugag cugaggauc                                                19

<210> SEQ ID NO 1600
<211> LENGTH: 19
<212> TYPE: RNA
<213> ORGANISM: Artificial sequence
<220> FEATURE:
<223> OTHER INFORMATION: Chemically synthesized

<400> SEQUENCE: 1600
ggaucagagu ucuccugaa                                                19

<210> SEQ ID NO 1601

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1601
ggagaagcga ccucuacua                                                 19

<210> SEQ ID NO 1602
<211> LENGTH: 19
<212> TYPE: RNA
<213> ORGANISM: Artificial sequence
<220> FEATURE:
<223> OTHER INFORMATION: Chemically synthesized

<400> SEQUENCE: 1602
aagaaaaagu cccugaagc                                                 19

<210> SEQ ID NO 1603
<211> LENGTH: 19
<212> TYPE: RNA
<213> ORGANISM: Artificial sequence
<220> FEATURE:
<223> OTHER INFORMATION: Chemically synthesized

<400> SEQUENCE: 1603
augagcaguu cuccugcuu                                                 19

<210> SEQ ID NO 1604
<211> LENGTH: 19
<212> TYPE: RNA
<213> ORGANISM: Artificial sequence
<220> FEATURE:
<223> OTHER INFORMATION: Chemically synthesized

<400> SEQUENCE: 1604
uaaacacaag uguaagcuc                                                 19

<210> SEQ ID NO 1605
<211> LENGTH: 19
<212> TYPE: RNA
<213> ORGANISM: Artificial sequence
<220> FEATURE:
<223> OTHER INFORMATION: Chemically synthesized

<400> SEQUENCE: 1605
uacgacgcua gaaucacac                                                 19

<210> SEQ ID NO 1606
<211> LENGTH: 19
<212> TYPE: RNA
<213> ORGANISM: Artificial sequence
<220> FEATURE:
<223> OTHER INFORMATION: Chemically synthesized

<400> SEQUENCE: 1606
uagaaucaca cacaauccu                                                 19

<210> SEQ ID NO 1607
<211> LENGTH: 19
<212> TYPE: RNA
<213> ORGANISM: Artificial sequence
<220> FEATURE:
<223> OTHER INFORMATION: Chemically synthesized

<400> SEQUENCE: 1607
```
uuucucaggg acaaggacc 19

<210> SEQ ID NO 1608
<211> LENGTH: 19
<212> TYPE: RNA
<213> ORGANISM: Artificial sequence
<220> FEATURE:
<223> OTHER INFORMATION: Chemically synthesized

<400> SEQUENCE: 1608
uaagccauca ccauuuugu 19

<210> SEQ ID NO 1609
<211> LENGTH: 19
<212> TYPE: RNA
<213> ORGANISM: Artificial sequence
<220> FEATURE:
<223> OTHER INFORMATION: Chemically synthesized

<400> SEQUENCE: 1609
agcauaacag gcaagagag 19

<210> SEQ ID NO 1610
<211> LENGTH: 19
<212> TYPE: RNA
<213> ORGANISM: Artificial sequence
<220> FEATURE:
<223> OTHER INFORMATION: Chemically synthesized

<400> SEQUENCE: 1610
aggcaagaga gucaaagau 19

<210> SEQ ID NO 1611
<211> LENGTH: 19
<212> TYPE: RNA
<213> ORGANISM: Artificial sequence
<220> FEATURE:
<223> OTHER INFORMATION: Chemically synthesized

<400> SEQUENCE: 1611
aagauaacug uuaguggaa 19

<210> SEQ ID NO 1612
<211> LENGTH: 19
<212> TYPE: RNA
<213> ORGANISM: Artificial sequence
<220> FEATURE:
<223> OTHER INFORMATION: Chemically synthesized

<400> SEQUENCE: 1612
gacaacaguu cuacaucga 19

<210> SEQ ID NO 1613
<211> LENGTH: 19
<212> TYPE: RNA
<213> ORGANISM: Artificial sequence
<220> FEATURE:
<223> OTHER INFORMATION: Chemically synthesized

<400> SEQUENCE: 1613
ucuacaucga ugcccaaga 19

<210> SEQ ID NO 1614
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1614
ucgaugccca agaagccuu                                                    19

<210> SEQ ID NO 1615
<211> LENGTH: 19
<212> TYPE: RNA
<213> ORGANISM: Artificial sequence
<220> FEATURE:
<223> OTHER INFORMATION: Chemically synthesized

<400> SEQUENCE: 1615
uuggagcuua acaauagac                                                    19

<210> SEQ ID NO 1616
<211> LENGTH: 19
<212> TYPE: RNA
<213> ORGANISM: Artificial sequence
<220> FEATURE:
<223> OTHER INFORMATION: Chemically synthesized

<400> SEQUENCE: 1616
uggagcuuaa caauagaca                                                    19

<210> SEQ ID NO 1617
<211> LENGTH: 19
<212> TYPE: RNA
<213> ORGANISM: Artificial sequence
<220> FEATURE:
<223> OTHER INFORMATION: Chemically synthesized

<400> SEQUENCE: 1617
gcuuaacaau agacaugca                                                    19

<210> SEQ ID NO 1618
<211> LENGTH: 19
<212> TYPE: RNA
<213> ORGANISM: Artificial sequence
<220> FEATURE:
<223> OTHER INFORMATION: Chemically synthesized

<400> SEQUENCE: 1618
acaauagaca ugcaaaaca                                                    19

<210> SEQ ID NO 1619
<211> LENGTH: 19
<212> TYPE: RNA
<213> ORGANISM: Artificial sequence
<220> FEATURE:
<223> OTHER INFORMATION: Chemically synthesized

<400> SEQUENCE: 1619
caauagacau gcaaaacaa                                                    19

<210> SEQ ID NO 1620
<211> LENGTH: 19
<212> TYPE: RNA
<213> ORGANISM: Artificial sequence
<220> FEATURE:
<223> OTHER INFORMATION: Chemically synthesized

<400> SEQUENCE: 1620
agugacauuu uaggucacu                                                    19
```

<210> SEQ ID NO 1621
<211> LENGTH: 19
<212> TYPE: RNA
<213> ORGANISM: Artificial sequence
<220> FEATURE:
<223> OTHER INFORMATION: Chemically synthesized

<400> SEQUENCE: 1621
cacuuauagu aucaguaac                                              19

<210> SEQ ID NO 1622
<211> LENGTH: 19
<212> TYPE: RNA
<213> ORGANISM: Artificial sequence
<220> FEATURE:
<223> OTHER INFORMATION: Chemically synthesized

<400> SEQUENCE: 1622
aacaggauca caccuguuu                                              19

<210> SEQ ID NO 1623
<211> LENGTH: 19
<212> TYPE: RNA
<213> ORGANISM: Artificial sequence
<220> FEATURE:
<223> OTHER INFORMATION: Chemically synthesized

<400> SEQUENCE: 1623
uucaguaaca ccaggauga                                              19

<210> SEQ ID NO 1624
<211> LENGTH: 19
<212> TYPE: RNA
<213> ORGANISM: Artificial sequence
<220> FEATURE:
<223> OTHER INFORMATION: Chemically synthesized

<400> SEQUENCE: 1624
acaccaggau gaauacauc                                              19

<210> SEQ ID NO 1625
<211> LENGTH: 19
<212> TYPE: RNA
<213> ORGANISM: Artificial sequence
<220> FEATURE:
<223> OTHER INFORMATION: Chemically synthesized

<400> SEQUENCE: 1625
aaguggagcu aauagcuag                                              19

<210> SEQ ID NO 1626
<211> LENGTH: 19
<212> TYPE: RNA
<213> ORGANISM: Artificial sequence
<220> FEATURE:
<223> OTHER INFORMATION: Chemically synthesized

<400> SEQUENCE: 1626
aaccugaaua agcuccuua                                              19

<210> SEQ ID NO 1627
<211> LENGTH: 19
<212> TYPE: RNA
<213> ORGANISM: Artificial sequence
<220> FEATURE:

```
<223> OTHER INFORMATION: Chemically synthesized

<400> SEQUENCE: 1627
uaagcuccuu auccacgac                                                    19

<210> SEQ ID NO 1628
<211> LENGTH: 19
<212> TYPE: RNA
<213> ORGANISM: Artificial sequence
<220> FEATURE:
<223> OTHER INFORMATION: Chemically synthesized

<400> SEQUENCE: 1628
uccuuaucca cgacccaca                                                    19

<210> SEQ ID NO 1629
<211> LENGTH: 19
<212> TYPE: RNA
<213> ORGANISM: Artificial sequence
<220> FEATURE:
<223> OTHER INFORMATION: Chemically synthesized

<400> SEQUENCE: 1629
cccacagcaa ggauaugaa                                                    19

<210> SEQ ID NO 1630
<211> LENGTH: 19
<212> TYPE: RNA
<213> ORGANISM: Artificial sequence
<220> FEATURE:
<223> OTHER INFORMATION: Chemically synthesized

<400> SEQUENCE: 1630
aggcuaaauu cucucauua                                                    19

<210> SEQ ID NO 1631
<211> LENGTH: 19
<212> TYPE: RNA
<213> ORGANISM: Artificial sequence
<220> FEATURE:
<223> OTHER INFORMATION: Chemically synthesized

<400> SEQUENCE: 1631
gcuaaauucu cucauuaac                                                    19

<210> SEQ ID NO 1632
<211> LENGTH: 19
<212> TYPE: RNA
<213> ORGANISM: Artificial sequence
<220> FEATURE:
<223> OTHER INFORMATION: Chemically synthesized

<400> SEQUENCE: 1632
ucuacuuagu uggaauaag                                                    19

<210> SEQ ID NO 1633
<211> LENGTH: 19
<212> TYPE: RNA
<213> ORGANISM: Artificial sequence
<220> FEATURE:
<223> OTHER INFORMATION: Chemically synthesized

<400> SEQUENCE: 1633
cuuaguugga auaagacaa                                                    19
```

<210> SEQ ID NO 1634
<211> LENGTH: 19
<212> TYPE: RNA
<213> ORGANISM: Artificial sequence
<220> FEATURE:
<223> OTHER INFORMATION: Chemically synthesized

<400> SEQUENCE: 1634
uuuauuauuc ccuagugac                                           19

<210> SEQ ID NO 1635
<211> LENGTH: 19
<212> TYPE: RNA
<213> ORGANISM: Artificial sequence
<220> FEATURE:
<223> OTHER INFORMATION: Chemically synthesized

<400> SEQUENCE: 1635
uauuauuccc uagugacag                                           19

<210> SEQ ID NO 1636
<211> LENGTH: 19
<212> TYPE: RNA
<213> ORGANISM: Artificial sequence
<220> FEATURE:
<223> OTHER INFORMATION: Chemically synthesized

<400> SEQUENCE: 1636
augcaugguu aucuggacg                                           19

<210> SEQ ID NO 1637
<211> LENGTH: 19
<212> TYPE: RNA
<213> ORGANISM: Artificial sequence
<220> FEATURE:
<223> OTHER INFORMATION: Chemically synthesized

<400> SEQUENCE: 1637
cggugaguuu cauucucua                                           19

<210> SEQ ID NO 1638
<211> LENGTH: 19
<212> TYPE: RNA
<213> ORGANISM: Artificial sequence
<220> FEATURE:
<223> OTHER INFORMATION: Chemically synthesized

<400> SEQUENCE: 1638
caauaauuca aaguggua g                                          19

<210> SEQ ID NO 1639
<211> LENGTH: 19
<212> TYPE: RNA
<213> ORGANISM: Artificial sequence
<220> FEATURE:
<223> OTHER INFORMATION: Chemically synthesized

<400> SEQUENCE: 1639
acagcuacua cccuugaca                                           19

<210> SEQ ID NO 1640
<211> LENGTH: 19
<212> TYPE: RNA
<213> ORGANISM: Artificial sequence
<220> FEATURE:
<223> OTHER INFORMATION: Chemically synthesized

<400> SEQUENCE: 1640
caauuggggu uaaggagag					19

<210> SEQ ID NO 1641
<211> LENGTH: 19
<212> TYPE: RNA
<213> ORGANISM: Artificial sequence
<220> FEATURE:
<223> OTHER INFORMATION: Chemically synthesized

<400> SEQUENCE: 1641
cauggugaaa ugguucauc					19

<210> SEQ ID NO 1642
<211> LENGTH: 19
<212> TYPE: RNA
<213> ORGANISM: Artificial sequence
<220> FEATURE:
<223> OTHER INFORMATION: Chemically synthesized

<400> SEQUENCE: 1642
agcacaugua auacugaaa					19

<210> SEQ ID NO 1643
<211> LENGTH: 19
<212> TYPE: RNA
<213> ORGANISM: Artificial sequence
<220> FEATURE:
<223> OTHER INFORMATION: Chemically synthesized

<400> SEQUENCE: 1643
uugagguugg guucaggaa					19

<210> SEQ ID NO 1644
<211> LENGTH: 19
<212> TYPE: RNA
<213> ORGANISM: Artificial sequence
<220> FEATURE:
<223> OTHER INFORMATION: Chemically synthesized

<400> SEQUENCE: 1644
ugaaaagagg auagauuac					19

<210> SEQ ID NO 1645
<211> LENGTH: 19
<212> TYPE: RNA
<213> ORGANISM: Artificial sequence
<220> FEATURE:
<223> OTHER INFORMATION: Chemically synthesized

<400> SEQUENCE: 1645
agguuggguu caggaacaa					19

<210> SEQ ID NO 1646
<211> LENGTH: 19
<212> TYPE: RNA
<213> ORGANISM: Artificial sequence
<220> FEATURE:
<223> OTHER INFORMATION: Chemically synthesized

<400> SEQUENCE: 1646
gaucucagaa cuaauuccc					19

<210> SEQ ID NO 1647
<211> LENGTH: 19

```
<212> TYPE: RNA
<213> ORGANISM: Artificial sequence
<220> FEATURE:
<223> OTHER INFORMATION: Chemically synthesized

<400> SEQUENCE: 1647
agaacuaauu uccuauccu                                                    19

<210> SEQ ID NO 1648
<211> LENGTH: 19
<212> TYPE: RNA
<213> ORGANISM: Artificial sequence
<220> FEATURE:
<223> OTHER INFORMATION: Chemically synthesized

<400> SEQUENCE: 1648
cuaauuuccu auccucaca                                                    19

<210> SEQ ID NO 1649
<211> LENGTH: 19
<212> TYPE: RNA
<213> ORGANISM: Artificial sequence
<220> FEATURE:
<223> OTHER INFORMATION: Chemically synthesized

<400> SEQUENCE: 1649 aauuccuau ccucacagg                                                     19

<210> SEQ ID NO 1650
<211> LENGTH: 19
<212> TYPE: RNA
<213> ORGANISM: Artificial sequence
<220> FEATURE:
<223> OTHER INFORMATION: Chemically synthesized

<400> SEQUENCE: 1650
cuacacacaa aaauaucag                                                    19

<210> SEQ ID NO 1651
<211> LENGTH: 19
<212> TYPE: RNA
<213> ORGANISM: Artificial sequence
<220> FEATURE:
<223> OTHER INFORMATION: Chemically synthesized

<400> SEQUENCE: 1651
guauucaaca cuuaagaac                                                    19

<210> SEQ ID NO 1652
<211> LENGTH: 19
<212> TYPE: RNA
<213> ORGANISM: Artificial sequence
<220> FEATURE:
<223> OTHER INFORMATION: Chemically synthesized

<400> SEQUENCE: 1652
ggaacaacau aaucccagu                                                    19

<210> SEQ ID NO 1653
<211> LENGTH: 19
<212> TYPE: RNA
<213> ORGANISM: Artificial sequence
<220> FEATURE:
<223> OTHER INFORMATION: Chemically synthesized

<400> SEQUENCE: 1653
```
uuagagugag gaagucacc                                               19

<210> SEQ ID NO 1654
<211> LENGTH: 19
<212> TYPE: RNA
<213> ORGANISM: Artificial sequence
<220> FEATURE:
<223> OTHER INFORMATION: Chemically synthesized

<400> SEQUENCE: 1654
agagugagga agucaccaa                                               19

<210> SEQ ID NO 1655
<211> LENGTH: 19
<212> TYPE: RNA
<213> ORGANISM: Artificial sequence
<220> FEATURE:
<223> OTHER INFORMATION: Chemically synthesized

<400> SEQUENCE: 1655
aagucaccaa gaaacagug                                               19

<210> SEQ ID NO 1656
<211> LENGTH: 19
<212> TYPE: RNA
<213> ORGANISM: Artificial sequence
<220> FEATURE:
<223> OTHER INFORMATION: Chemically synthesized

<400> SEQUENCE: 1656
ucaccaagaa acagugaag                                               19

<210> SEQ ID NO 1657
<211> LENGTH: 19
<212> TYPE: RNA
<213> ORGANISM: Artificial sequence
<220> FEATURE:
<223> OTHER INFORMATION: Chemically synthesized

<400> SEQUENCE: 1657
uuccauuauu gccguaaua                                               19

<210> SEQ ID NO 1658
<211> LENGTH: 19
<212> TYPE: RNA
<213> ORGANISM: Artificial sequence
<220> FEATURE:
<223> OTHER INFORMATION: Chemically synthesized

<400> SEQUENCE: 1658
ucucauuuac ucuuaccua                                               19

<210> SEQ ID NO 1659
<211> LENGTH: 19
<212> TYPE: RNA
<213> ORGANISM: Artificial sequence
<220> FEATURE:
<223> OTHER INFORMATION: Chemically synthesized

<400> SEQUENCE: 1659
cauuuacucu uaccuaggg                                               19

<210> SEQ ID NO 1660
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 1660
auccuaccuu ccugucuaa                                                19

<210> SEQ ID NO 1661
<211> LENGTH: 19
<212> TYPE: RNA
<213> ORGANISM: Artificial sequence
<220> FEATURE:
<223> OTHER INFORMATION: Chemically synthesized

<400> SEQUENCE: 1661
aguagucaaa aucacuuag                                                19

<210> SEQ ID NO 1662
<211> LENGTH: 19
<212> TYPE: RNA
<213> ORGANISM: Artificial sequence
<220> FEATURE:
<223> OTHER INFORMATION: Chemically synthesized

<400> SEQUENCE: 1662
aaaacucaaa ugggcuucu                                                19

<210> SEQ ID NO 1663
<211> LENGTH: 19
<212> TYPE: RNA
<213> ORGANISM: Artificial sequence
<220> FEATURE:
<223> OTHER INFORMATION: Chemically synthesized

<400> SEQUENCE: 1663
aacucaaaug ggcuucuac                                                19

<210> SEQ ID NO 1664
<211> LENGTH: 19
<212> TYPE: RNA
<213> ORGANISM: Artificial sequence
<220> FEATURE:
<223> OTHER INFORMATION: Chemically synthesized

<400> SEQUENCE: 1664
cucaaauggg cuucuacuu                                                19

<210> SEQ ID NO 1665
<211> LENGTH: 19
<212> TYPE: RNA
<213> ORGANISM: Artificial sequence
<220> FEATURE:
<223> OTHER INFORMATION: Chemically synthesized

<400> SEQUENCE: 1665
aaaugggcuu cuacuuug                                                 19

<210> SEQ ID NO 1666
<211> LENGTH: 19
<212> TYPE: RNA
<213> ORGANISM: Artificial sequence
<220> FEATURE:
<223> OTHER INFORMATION: Chemically synthesized

<400> SEQUENCE: 1666 caaaucacu uagcaggcu                                                 19
```

<210> SEQ ID NO 1667
<211> LENGTH: 19
<212> TYPE: RNA
<213> ORGANISM: Artificial sequence
<220> FEATURE:
<223> OTHER INFORMATION: Chemically synthesized

<400> SEQUENCE: 1667
gcuucuacuu uugcuuacc                                                19

<210> SEQ ID NO 1668
<211> LENGTH: 19
<212> TYPE: RNA
<213> ORGANISM: Artificial sequence
<220> FEATURE:
<223> OTHER INFORMATION: Chemically synthesized

<400> SEQUENCE: 1668
cuucuacuuu ugcuuaccu                                                19

<210> SEQ ID NO 1669
<211> LENGTH: 19
<212> TYPE: RNA
<213> ORGANISM: Artificial sequence
<220> FEATURE:
<223> OTHER INFORMATION: Chemically synthesized

<400> SEQUENCE: 1669
cuuuugcuua ccuauucca                                                19

<210> SEQ ID NO 1670
<211> LENGTH: 19
<212> TYPE: RNA
<213> ORGANISM: Artificial sequence
<220> FEATURE:
<223> OTHER INFORMATION: Chemically synthesized

<400> SEQUENCE: 1670
uuuugcuuac cuauuccau                                                19

<210> SEQ ID NO 1671
<211> LENGTH: 19
<212> TYPE: RNA
<213> ORGANISM: Artificial sequence
<220> FEATURE:
<223> OTHER INFORMATION: Chemically synthesized

<400> SEQUENCE: 1671
ccuauuccau cccauucaa                                                19

<210> SEQ ID NO 1672
<211> LENGTH: 19
<212> TYPE: RNA
<213> ORGANISM: Artificial sequence
<220> FEATURE:
<223> OTHER INFORMATION: Chemically synthesized

<400> SEQUENCE: 1672
aaaucacuua gcaggcucu                                                19

<210> SEQ ID NO 1673
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 1673
aaaaugggau cuaugcaga                                                  19

<210> SEQ ID NO 1674
<211> LENGTH: 19
<212> TYPE: RNA
<213> ORGANISM: Artificial sequence
<220> FEATURE:
<223> OTHER INFORMATION: Chemically synthesized

<400> SEQUENCE: 1674
acuucuccaa aggccagaa                                                  19

<210> SEQ ID NO 1675
<211> LENGTH: 19
<212> TYPE: RNA
<213> ORGANISM: Artificial sequence
<220> FEATURE:
<223> OTHER INFORMATION: Chemically synthesized

<400> SEQUENCE: 1675
ugaaugugaa acacagaaa                                                  19

<210> SEQ ID NO 1676
<211> LENGTH: 19
<212> TYPE: RNA
<213> ORGANISM: Artificial sequence
<220> FEATURE:
<223> OTHER INFORMATION: Chemically synthesized

<400> SEQUENCE: 1676
cagaaagaaa agagacuac                                                  19

<210> SEQ ID NO 1677
<211> LENGTH: 19
<212> TYPE: RNA
<213> ORGANISM: Artificial sequence
<220> FEATURE:
<223> OTHER INFORMATION: Chemically synthesized

<400> SEQUENCE: 1677
agacuacauu uggguuuc                                                   19

<210> SEQ ID NO 1678
<211> LENGTH: 19
<212> TYPE: RNA
<213> ORGANISM: Artificial sequence
<220> FEATURE:
<223> OTHER INFORMATION: Chemically synthesized

<400> SEQUENCE: 1678
agcugaauag uuuuacuac                                                  19

<210> SEQ ID NO 1679
<211> LENGTH: 19
<212> TYPE: RNA
<213> ORGANISM: Artificial sequence
<220> FEATURE:
<223> OTHER INFORMATION: Chemically synthesized

<400> SEQUENCE: 1679
gcugaauagu uuacuacc                                                   19

<210> SEQ ID NO 1680
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1680
aaucacuguu guuccaauc                                                  19

<210> SEQ ID NO 1681
<211> LENGTH: 19
<212> TYPE: RNA
<213> ORGANISM: Artificial sequence
<220> FEATURE:
<223> OTHER INFORMATION: Chemically synthesized

<400> SEQUENCE: 1681
uuguuccaau cagugagua                                                  19

<210> SEQ ID NO 1682
<211> LENGTH: 19
<212> TYPE: RNA
<213> ORGANISM: Artificial sequence
<220> FEATURE:
<223> OTHER INFORMATION: Chemically synthesized

<400> SEQUENCE: 1682
uucuuaacaa gucgaaauc                                                  19

<210> SEQ ID NO 1683
<211> LENGTH: 19
<212> TYPE: RNA
<213> ORGANISM: Artificial sequence
<220> FEATURE:
<223> OTHER INFORMATION: Chemically synthesized

<400> SEQUENCE: 1683
cuuaacaagu cgaaauccu                                                  19

<210> SEQ ID NO 1684
<211> LENGTH: 19
<212> TYPE: RNA
<213> ORGANISM: Artificial sequence
<220> FEATURE:
<223> OTHER INFORMATION: Chemically synthesized

<400> SEQUENCE: 1684
aggaucagag uucuccuga                                                  19

<210> SEQ ID NO 1685
<211> LENGTH: 19
<212> TYPE: RNA
<213> ORGANISM: Artificial sequence
<220> FEATURE:
<223> OTHER INFORMATION: Chemically synthesized

<400> SEQUENCE: 1685
aagucccuga agcuagucc                                                  19

<210> SEQ ID NO 1686
<211> LENGTH: 19
<212> TYPE: RNA
<213> ORGANISM: Artificial sequence
<220> FEATURE:
<223> OTHER INFORMATION: Chemically synthesized

<400> SEQUENCE: 1686
```
ccugaagcua guccaugag					19

<210> SEQ ID NO 1687
<211> LENGTH: 19
<212> TYPE: RNA
<213> ORGANISM: Artificial sequence
<220> FEATURE:
<223> OTHER INFORMATION: Chemically synthesized

<400> SEQUENCE: 1687
uaguccauga gcaguucuc					19

<210> SEQ ID NO 1688
<211> LENGTH: 19
<212> TYPE: RNA
<213> ORGANISM: Artificial sequence
<220> FEATURE:
<223> OTHER INFORMATION: Chemically synthesized

<400> SEQUENCE: 1688
aguccaugag caguucucc					19

<210> SEQ ID NO 1689
<211> LENGTH: 19
<212> TYPE: RNA
<213> ORGANISM: Artificial sequence
<220> FEATURE:
<223> OTHER INFORMATION: Chemically synthesized

<400> SEQUENCE: 1689
uccaugagca guucuccug					19

<210> SEQ ID NO 1690
<211> LENGTH: 19
<212> TYPE: RNA
<213> ORGANISM: Artificial sequence
<220> FEATURE:
<223> OTHER INFORMATION: Chemically synthesized

<400> SEQUENCE: 1690
cuuaaacaca aguguaagc					19

<210> SEQ ID NO 1691
<211> LENGTH: 19
<212> TYPE: RNA
<213> ORGANISM: Artificial sequence
<220> FEATURE:
<223> OTHER INFORMATION: Chemically synthesized

<400> SEQUENCE: 1691
cuagaaucac acacaaucc					19

<210> SEQ ID NO 1692
<211> LENGTH: 19
<212> TYPE: RNA
<213> ORGANISM: Artificial sequence
<220> FEATURE:
<223> OTHER INFORMATION: Chemically synthesized

<400> SEQUENCE: 1692
aucacacaca auccuaucc					19

<210> SEQ ID NO 1693
<211> LENGTH: 19
<212> TYPE: RNA

<213> ORGANISM: Artificial sequence
<220> FEATURE:
<223> OTHER INFORMATION: Chemically synthesized

<400> SEQUENCE: 1693
caaacugcca guugcaacc                                                      19

<210> SEQ ID NO 1694
<211> LENGTH: 19
<212> TYPE: RNA
<213> ORGANISM: Artificial sequence
<220> FEATURE:
<223> OTHER INFORMATION: Chemically synthesized

<400> SEQUENCE: 1694
cuuugagcaa ccaaguuua                                                      19

<210> SEQ ID NO 1695
<211> LENGTH: 19
<212> TYPE: RNA
<213> ORGANISM: Artificial sequence
<220> FEATURE:
<223> OTHER INFORMATION: Chemically synthesized

<400> SEQUENCE: 1695
uaacagccuu ccauaagcc                                                      19

<210> SEQ ID NO 1696
<211> LENGTH: 19
<212> TYPE: RNA
<213> ORGANISM: Artificial sequence
<220> FEATURE:
<223> OTHER INFORMATION: Chemically synthesized

<400> SEQUENCE: 1696
ccauaagcca ucaccauuu                                                      19

<210> SEQ ID NO 1697
<211> LENGTH: 19
<212> TYPE: RNA
<213> ORGANISM: Artificial sequence
<220> FEATURE:
<223> OTHER INFORMATION: Chemically synthesized

<400> SEQUENCE: 1697
aagcauaaca ggcaagaga                                                      19

<210> SEQ ID NO 1698
<211> LENGTH: 19
<212> TYPE: RNA
<213> ORGANISM: Artificial sequence
<220> FEATURE:
<223> OTHER INFORMATION: Chemically synthesized

<400> SEQUENCE: 1698
cuacaucgau gcccaagaa                                                      19

<210> SEQ ID NO 1699
<211> LENGTH: 19
<212> TYPE: RNA
<213> ORGANISM: Artificial sequence
<220> FEATURE:
<223> OTHER INFORMATION: Chemically synthesized

<400> SEQUENCE: 1699
cagugaaccu uuggagcuu                                                      19

<210> SEQ ID NO 1700
<211> LENGTH: 19
<212> TYPE: RNA
<213> ORGANISM: Artificial sequence
<220> FEATURE:
<223> OTHER INFORMATION: Chemically synthesized

<400> SEQUENCE: 1700
uuuggagcuu aacaauaga                                              19

<210> SEQ ID NO 1701
<211> LENGTH: 19
<212> TYPE: RNA
<213> ORGANISM: Artificial sequence
<220> FEATURE:
<223> OTHER INFORMATION: Chemically synthesized

<400> SEQUENCE: 1701
cauugauuua ucuuggccc                                              19

<210> SEQ ID NO 1702
<211> LENGTH: 19
<212> TYPE: RNA
<213> ORGANISM: Artificial sequence
<220> FEATURE:
<223> OTHER INFORMATION: Chemically synthesized

<400> SEQUENCE: 1702
uuaucuuggc ccaauucua                                              19

<210> SEQ ID NO 1703
<211> LENGTH: 19
<212> TYPE: RNA
<213> ORGANISM: Artificial sequence
<220> FEATURE:
<223> OTHER INFORMATION: Chemically synthesized

<400> SEQUENCE: 1703
ggcuuuguag uaucuuucc                                              19

<210> SEQ ID NO 1704
<211> LENGTH: 19
<212> TYPE: RNA
<213> ORGANISM: Artificial sequence
<220> FEATURE:
<223> OTHER INFORMATION: Chemically synthesized

<400> SEQUENCE: 1704
uaucuuucca agcauuuga                                              19

<210> SEQ ID NO 1705
<211> LENGTH: 19
<212> TYPE: RNA
<213> ORGANISM: Artificial sequence
<220> FEATURE:
<223> OTHER INFORMATION: Chemically synthesized

<400> SEQUENCE: 1705
acaccuguuu uucaguaac                                              19

<210> SEQ ID NO 1706
<211> LENGTH: 19
<212> TYPE: RNA
<213> ORGANISM: Artificial sequence
<220> FEATURE:

<223> OTHER INFORMATION: Chemically synthesized

<400> SEQUENCE: 1706
aacaccagga ugaauacau                                                    19

<210> SEQ ID NO 1707
<211> LENGTH: 19
<212> TYPE: RNA
<213> ORGANISM: Artificial sequence
<220> FEATURE:
<223> OTHER INFORMATION: Chemically synthesized

<400> SEQUENCE: 1707
accaggauga auacaucug                                                    19

<210> SEQ ID NO 1708
<211> LENGTH: 19
<212> TYPE: RNA
<213> ORGANISM: Artificial sequence
<220> FEATURE:
<223> OTHER INFORMATION: Chemically synthesized

<400> SEQUENCE: 1708
ggagcuaaua gcuagggca                                                    19

<210> SEQ ID NO 1709
<211> LENGTH: 19
<212> TYPE: RNA
<213> ORGANISM: Artificial sequence
<220> FEATURE:
<223> OTHER INFORMATION: Chemically synthesized

<400> SEQUENCE: 1709
aggaaaccug aauaagcuc                                                    19

<210> SEQ ID NO 1710
<211> LENGTH: 19
<212> TYPE: RNA
<213> ORGANISM: Artificial sequence
<220> FEATURE:
<223> OTHER INFORMATION: Chemically synthesized

<400> SEQUENCE: 1710
ggaaaccuga auaagcucc                                                    19

<210> SEQ ID NO 1711
<211> LENGTH: 19
<212> TYPE: RNA
<213> ORGANISM: Artificial sequence
<220> FEATURE:
<223> OTHER INFORMATION: Chemically synthesized

<400> SEQUENCE: 1711
acccacagca aggauauga                                                    19

<210> SEQ ID NO 1712
<211> LENGTH: 19
<212> TYPE: RNA
<213> ORGANISM: Artificial sequence
<220> FEATURE:
<223> OTHER INFORMATION: Chemically synthesized

<400> SEQUENCE: 1712
aagccuugcu gaauugaac                                                    19

```
<210> SEQ ID NO 1713
<211> LENGTH: 19
<212> TYPE: RNA
<213> ORGANISM: Artificial sequence
<220> FEATURE:
<223> OTHER INFORMATION: Chemically synthesized

<400> SEQUENCE: 1713
gcugaauuga acauuguug                                                    19

<210> SEQ ID NO 1714
<211> LENGTH: 19
<212> TYPE: RNA
<213> ORGANISM: Artificial sequence
<220> FEATURE:
<223> OTHER INFORMATION: Chemically synthesized

<400> SEQUENCE: 1714
uacuuaguug gaauaagac                                                    19

<210> SEQ ID NO 1715
<211> LENGTH: 19
<212> TYPE: RNA
<213> ORGANISM: Artificial sequence
<220> FEATURE:
<223> OTHER INFORMATION: Chemically synthesized

<400> SEQUENCE: 1715
ggccuuuauu auucccuag                                                    19

<210> SEQ ID NO 1716
<211> LENGTH: 19
<212> TYPE: RNA
<213> ORGANISM: Artificial sequence
<220> FEATURE:
<223> OTHER INFORMATION: Chemically synthesized

<400> SEQUENCE: 1716
cugggugcau gcauggugga                                                   19

<210> SEQ ID NO 1717
<211> LENGTH: 19
<212> TYPE: RNA
<213> ORGANISM: Artificial sequence
<220> FEATURE:
<223> OTHER INFORMATION: Chemically synthesized

<400> SEQUENCE: 1717
ggugcaugca ugguuaucu                                                    19

<210> SEQ ID NO 1718
<211> LENGTH: 19
<212> TYPE: RNA
<213> ORGANISM: Artificial sequence
<220> FEATURE:
<223> OTHER INFORMATION: Chemically synthesized

<400> SEQUENCE: 1718
gaguuucauu cucuaggcu                                                    19

<210> SEQ ID NO 1719
<211> LENGTH: 19
<212> TYPE: RNA
<213> ORGANISM: Artificial sequence
<220> FEATURE:
<223> OTHER INFORMATION: Chemically synthesized
```

```
<400> SEQUENCE: 1719
ucucuaggcu guacuauaa                                                    19

<210> SEQ ID NO 1720
<211> LENGTH: 19
<212> TYPE: RNA
<213> ORGANISM: Artificial sequence
<220> FEATURE:
<223> OTHER INFORMATION: Chemically synthesized

<400> SEQUENCE: 1720
uaaaccauau cuccauagc                                                    19

<210> SEQ ID NO 1721
<211> LENGTH: 19
<212> TYPE: RNA
<213> ORGANISM: Artificial sequence
<220> FEATURE:
<223> OTHER INFORMATION: Chemically synthesized

<400> SEQUENCE: 1721
aauugggguu aaggagaga                                                    19

<210> SEQ ID NO 1722
<211> LENGTH: 19
<212> TYPE: RNA
<213> ORGANISM: Artificial sequence
<220> FEATURE:
<223> OTHER INFORMATION: Chemically synthesized

<400> SEQUENCE: 1722 auuggguua aggagagau                                                     19

<210> SEQ ID NO 1723
<211> LENGTH: 19
<212> TYPE: RNA
<213> ORGANISM: Artificial sequence
<220> FEATURE:
<223> OTHER INFORMATION: Chemically synthesized

<400> SEQUENCE: 1723
aauucccaga aaagcccag                                                    19

<210> SEQ ID NO 1724
<211> LENGTH: 19
<212> TYPE: RNA
<213> ORGANISM: Artificial sequence
<220> FEATURE:
<223> OTHER INFORMATION: Chemically synthesized

<400> SEQUENCE: 1724
cugccauggu gaaaugguu                                                    19

<210> SEQ ID NO 1725
<211> LENGTH: 19
<212> TYPE: RNA
<213> ORGANISM: Artificial sequence
<220> FEATURE:
<223> OTHER INFORMATION: Chemically synthesized

<400> SEQUENCE: 1725
aagcacaugu aauacugaa                                                    19

<210> SEQ ID NO 1726
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1726
uguaauacug aaaagagga                                                      19

<210> SEQ ID NO 1727
<211> LENGTH: 19
<212> TYPE: RNA
<213> ORGANISM: Artificial sequence
<220> FEATURE:
<223> OTHER INFORMATION: Chemically synthesized

<400> SEQUENCE: 1727
guaauacuga aaagaggau                                                      19

<210> SEQ ID NO 1728
<211> LENGTH: 19
<212> TYPE: RNA
<213> ORGANISM: Artificial sequence
<220> FEATURE:
<223> OTHER INFORMATION: Chemically synthesized

<400> SEQUENCE: 1728
aauacugaaa agaggauag                                                      19

<210> SEQ ID NO 1729
<211> LENGTH: 19
<212> TYPE: RNA
<213> ORGANISM: Artificial sequence
<220> FEATURE:
<223> OTHER INFORMATION: Chemically synthesized

<400> SEQUENCE: 1729
acugaaaaga ggauagauu                                                      19

<210> SEQ ID NO 1730
<211> LENGTH: 19
<212> TYPE: RNA
<213> ORGANISM: Artificial sequence
<220> FEATURE:
<223> OTHER INFORMATION: Chemically synthesized

<400> SEQUENCE: 1730
ggauagauua cuaagugaa                                                      19

<210> SEQ ID NO 1731
<211> LENGTH: 19
<212> TYPE: RNA
<213> ORGANISM: Artificial sequence
<220> FEATURE:
<223> OTHER INFORMATION: Chemically synthesized

<400> SEQUENCE: 1731
ucucagaacu aauuuccua                                                      19

<210> SEQ ID NO 1732
<211> LENGTH: 19
<212> TYPE: RNA
<213> ORGANISM: Artificial sequence
<220> FEATURE:
<223> OTHER INFORMATION: Chemically synthesized

<400> SEQUENCE: 1732
```
cagaacuaau uuccuaucc                                                    19

<210> SEQ ID NO 1733
<211> LENGTH: 19
<212> TYPE: RNA
<213> ORGANISM: Artificial sequence
<220> FEATURE:
<223> OTHER INFORMATION: Chemically synthesized

<400> SEQUENCE: 1733
gaacuaauuu ccuauccuc                                                    19

<210> SEQ ID NO 1734
<211> LENGTH: 19
<212> TYPE: RNA
<213> ORGANISM: Artificial sequence
<220> FEATURE:
<223> OTHER INFORMATION: Chemically synthesized

<400> SEQUENCE: 1734
acuaauuucc uauccucac                                                    19

<210> SEQ ID NO 1735
<211> LENGTH: 19
<212> TYPE: RNA
<213> ORGANISM: Artificial sequence
<220> FEATURE:
<223> OTHER INFORMATION: Chemically synthesized

<400> SEQUENCE: 1735
agucuauuac caagccuac                                                    19

<210> SEQ ID NO 1736
<211> LENGTH: 19
<212> TYPE: RNA
<213> ORGANISM: Artificial sequence
<220> FEATURE:
<223> OTHER INFORMATION: Chemically synthesized

<400> SEQUENCE: 1736
gucaaaauca cuuagcagg                                                    19

<210> SEQ ID NO 1737
<211> LENGTH: 19
<212> TYPE: RNA
<213> ORGANISM: Artificial sequence
<220> FEATURE:
<223> OTHER INFORMATION: Chemically synthesized

<400> SEQUENCE: 1737
caaaaauggg aucuaugca                                                    19

<210> SEQ ID NO 1738
<211> LENGTH: 19
<212> TYPE: RNA
<213> ORGANISM: Artificial sequence
<220> FEATURE:
<223> OTHER INFORMATION: Chemically synthesized

<400> SEQUENCE: 1738
augugaaaca cagaaagaa                                                    19

<210> SEQ ID NO 1739
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 1739
agaaaagaga cuacauuug                                                19

<210> SEQ ID NO 1740
<211> LENGTH: 19
<212> TYPE: RNA
<213> ORGANISM: Artificial sequence
<220> FEATURE:
<223> OTHER INFORMATION: Chemically synthesized

<400> SEQUENCE: 1740
gagacuacau uuggguuu                                                 19

<210> SEQ ID NO 1741
<211> LENGTH: 19
<212> TYPE: RNA
<213> ORGANISM: Artificial sequence
<220> FEATURE:
<223> OTHER INFORMATION: Chemically synthesized

<400> SEQUENCE: 1741
ggguuucuua uuuagggca                                                19

<210> SEQ ID NO 1742
<211> LENGTH: 19
<212> TYPE: RNA
<213> ORGANISM: Artificial sequence
<220> FEATURE:
<223> OTHER INFORMATION: Chemically synthesized

<400> SEQUENCE: 1742
cugacuagcu gaauaguuu                                                19

<210> SEQ ID NO 1743
<211> LENGTH: 19
<212> TYPE: RNA
<213> ORGANISM: Artificial sequence
<220> FEATURE:
<223> OTHER INFORMATION: Chemically synthesized

<400> SEQUENCE: 1743
uuuaggaccc uucaaucac                                                19

<210> SEQ ID NO 1744
<211> LENGTH: 19
<212> TYPE: RNA
<213> ORGANISM: Artificial sequence
<220> FEATURE:
<223> OTHER INFORMATION: Chemically synthesized

<400> SEQUENCE: 1744
uaacaagucg aaauccuga                                                19

<210> SEQ ID NO 1745
<211> LENGTH: 19
<212> TYPE: RNA
<213> ORGANISM: Artificial sequence
<220> FEATURE:
<223> OTHER INFORMATION: Chemically synthesized

<400> SEQUENCE: 1745
agaggagaag cgaccucua                                                19
```

<210> SEQ ID NO 1746
<211> LENGTH: 19
<212> TYPE: RNA
<213> ORGANISM: Artificial sequence
<220> FEATURE:
<223> OTHER INFORMATION: Chemically synthesized

<400> SEQUENCE: 1746
agcuagucca ugagcaguu                                                   19

<210> SEQ ID NO 1747
<211> LENGTH: 19
<212> TYPE: RNA
<213> ORGANISM: Artificial sequence
<220> FEATURE:
<223> OTHER INFORMATION: Chemically synthesized

<400> SEQUENCE: 1747
ccuuccauaa gccaucacc                                                   19

<210> SEQ ID NO 1748
<211> LENGTH: 19
<212> TYPE: RNA
<213> ORGANISM: Artificial sequence
<220> FEATURE:
<223> OTHER INFORMATION: Chemically synthesized

<400> SEQUENCE: 1748
aucgaugccc aagaagccu                                                   19

<210> SEQ ID NO 1749
<211> LENGTH: 19
<212> TYPE: RNA
<213> ORGANISM: Artificial sequence
<220> FEATURE:
<223> OTHER INFORMATION: Chemically synthesized

<400> SEQUENCE: 1749
agugaaccuu uggagcuua                                                   19

<210> SEQ ID NO 1750
<211> LENGTH: 19
<212> TYPE: RNA
<213> ORGANISM: Artificial sequence
<220> FEATURE:
<223> OTHER INFORMATION: Chemically synthesized

<400> SEQUENCE: 1750
acauugauuu aucuuggcc                                                   19

<210> SEQ ID NO 1751
<211> LENGTH: 19
<212> TYPE: RNA
<213> ORGANISM: Artificial sequence
<220> FEATURE:
<223> OTHER INFORMATION: Chemically synthesized

<400> SEQUENCE: 1751
aucuuuccaa gcauuugaa                                                   19

<210> SEQ ID NO 1752
<211> LENGTH: 19
<212> TYPE: RNA
<213> ORGANISM: Artificial sequence
<220> FEATURE:
<223> OTHER INFORMATION: Chemically synthesized -continued

```
<400> SEQUENCE: 1752
ggaugaauac aucuguccc                                                    19

<210> SEQ ID NO 1753
<211> LENGTH: 19
<212> TYPE: RNA
<213> ORGANISM: Artificial sequence
<220> FEATURE:
<223> OTHER INFORMATION: Chemically synthesized

<400> SEQUENCE: 1753
caggaaaccu gaauaagcu                                                    19

<210> SEQ ID NO 1754
<211> LENGTH: 19
<212> TYPE: RNA
<213> ORGANISM: Artificial sequence
<220> FEATURE:
<223> OTHER INFORMATION: Chemically synthesized

<400> SEQUENCE: 1754
ugaucuacuu aguuggaau                                                    19

<210> SEQ ID NO 1755
<211> LENGTH: 19
<212> TYPE: RNA
<213> ORGANISM: Artificial sequence
<220> FEATURE:
<223> OTHER INFORMATION: Chemically synthesized

<400> SEQUENCE: 1755
ucauucucua ggcuguacu                                                    19

<210> SEQ ID NO 1756
<211> LENGTH: 19
<212> TYPE: RNA
<213> ORGANISM: Artificial sequence
<220> FEATURE:
<223> OTHER INFORMATION: Chemically synthesized

<400> SEQUENCE: 1756
auucucuagg cuguacuau                                                    19

<210> SEQ ID NO 1757
<211> LENGTH: 19
<212> TYPE: RNA
<213> ORGANISM: Artificial sequence
<220> FEATURE:
<223> OTHER INFORMATION: Chemically synthesized

<400> SEQUENCE: 1757
cuaggcugua cuauaaacc                                                    19

<210> SEQ ID NO 1758
<211> LENGTH: 19
<212> TYPE: RNA
<213> ORGANISM: Artificial sequence
<220> FEATURE:
<223> OTHER INFORMATION: Chemically synthesized

<400> SEQUENCE: 1758
cuguacuaua aaccauauc                                                    19

<210> SEQ ID NO 1759
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1759
uacuauaaac cauaucucc                                          19

<210> SEQ ID NO 1760
<211> LENGTH: 19
<212> TYPE: RNA
<213> ORGANISM: Artificial sequence
<220> FEATURE:
<223> OTHER INFORMATION: Chemically synthesized

<400> SEQUENCE: 1760
acccuugaca auuggggun                                          19

<210> SEQ ID NO 1761
<211> LENGTH: 19
<212> TYPE: RNA
<213> ORGANISM: Artificial sequence
<220> FEATURE:
<223> OTHER INFORMATION: Chemically synthesized

<400> SEQUENCE: 1761
uuggggunaa ggagagaua                                          19

<210> SEQ ID NO 1762
<211> LENGTH: 19
<212> TYPE: RNA
<213> ORGANISM: Artificial sequence
<220> FEATURE:
<223> OTHER INFORMATION: Chemically synthesized

<400> SEQUENCE: 1762
uggggunaag gagagauac                                          19

<210> SEQ ID NO 1763
<211> LENGTH: 19
<212> TYPE: RNA
<213> ORGANISM: Artificial sequence
<220> FEATURE:
<223> OTHER INFORMATION: Chemically synthesized

<400> SEQUENCE: 1763
auucccagaa aagcccaga                                          19

<210> SEQ ID NO 1764
<211> LENGTH: 19
<212> TYPE: RNA
<213> ORGANISM: Artificial sequence
<220> FEATURE:
<223> OTHER INFORMATION: Chemically synthesized

<400> SEQUENCE: 1764
ugccauggug aaaugguuc                                          19

<210> SEQ ID NO 1765
<211> LENGTH: 19
<212> TYPE: RNA
<213> ORGANISM: Artificial sequence
<220> FEATURE:
<223> OTHER INFORMATION: Chemically synthesized

<400> SEQUENCE: 1765
```
auacugaaaa gaggauaga                                                19

<210> SEQ ID NO 1766
<211> LENGTH: 19
<212> TYPE: RNA
<213> ORGANISM: Artificial sequence
<220> FEATURE:
<223> OTHER INFORMATION: Chemically synthesized

<400> SEQUENCE: 1766
gaguaaucaa cuacacaca                                                19

<210> SEQ ID NO 1767
<211> LENGTH: 19
<212> TYPE: RNA
<213> ORGANISM: Artificial sequence
<220> FEATURE:
<223> OTHER INFORMATION: Chemically synthesized

<400> SEQUENCE: 1767
acaguauuca acacuuaag                                                19

<210> SEQ ID NO 1768
<211> LENGTH: 19
<212> TYPE: RNA
<213> ORGANISM: Artificial sequence
<220> FEATURE:
<223> OTHER INFORMATION: Chemically synthesized

<400> SEQUENCE: 1768
caguauucaa cacuuaaga                                                19

<210> SEQ ID NO 1769
<211> LENGTH: 19
<212> TYPE: RNA
<213> ORGANISM: Artificial sequence
<220> FEATURE:
<223> OTHER INFORMATION: Chemically synthesized

<400> SEQUENCE: 1769
aaauaggcaa aucugguuu                                                19

<210> SEQ ID NO 1770
<211> LENGTH: 19
<212> TYPE: RNA
<213> ORGANISM: Artificial sequence
<220> FEATURE:
<223> OTHER INFORMATION: Chemically synthesized

<400> SEQUENCE: 1770
ugaaucacuu cuccaaagg                                                19

<210> SEQ ID NO 1771
<211> LENGTH: 19
<212> TYPE: RNA
<213> ORGANISM: Artificial sequence
<220> FEATURE:
<223> OTHER INFORMATION: Chemically synthesized

<400> SEQUENCE: 1771
aucacuucuc caaaggcca                                                19

<210> SEQ ID NO 1772
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1772
agaaagaaaa gagacuaca                                                    19

<210> SEQ ID NO 1773
<211> LENGTH: 19
<212> TYPE: RNA
<213> ORGANISM: Artificial sequence
<220> FEATURE:
<223> OTHER INFORMATION: Chemically synthesized

<400> SEQUENCE: 1773
uuugggguuu cuuauuuag                                                    19

<210> SEQ ID NO 1774
<211> LENGTH: 19
<212> TYPE: RNA
<213> ORGANISM: Artificial sequence
<220> FEATURE:
<223> OTHER INFORMATION: Chemically synthesized

<400> SEQUENCE: 1774
guuucuuauu uagggcagg                                                    19

<210> SEQ ID NO 1775
<211> LENGTH: 19
<212> TYPE: RNA
<213> ORGANISM: Artificial sequence
<220> FEATURE:
<223> OTHER INFORMATION: Chemically synthesized

<400> SEQUENCE: 1775
caaucaguga guaaaguuu                                                    19

<210> SEQ ID NO 1776
<211> LENGTH: 19
<212> TYPE: RNA
<213> ORGANISM: Artificial sequence
<220> FEATURE:
<223> OTHER INFORMATION: Chemically synthesized

<400> SEQUENCE: 1776
cagugaguaa aguuuuuuc                                                    19

<210> SEQ ID NO 1777
<211> LENGTH: 19
<212> TYPE: RNA
<213> ORGANISM: Artificial sequence
<220> FEATURE:
<223> OTHER INFORMATION: Chemically synthesized

<400> SEQUENCE: 1777
ucuuaacaag ucgaaaucc                                                    19

<210> SEQ ID NO 1778
<211> LENGTH: 19
<212> TYPE: RNA
<213> ORGANISM: Artificial sequence
<220> FEATURE:
<223> OTHER INFORMATION: Chemically synthesized

<400> SEQUENCE: 1778
uuaacaaguc gaaauccug                                                    19
```

<210> SEQ ID NO 1779
<211> LENGTH: 19
<212> TYPE: RNA
<213> ORGANISM: Artificial sequence
<220> FEATURE:
<223> OTHER INFORMATION: Chemically synthesized

<400> SEQUENCE: 1779
uugcugcuca aacugccag                                              19

<210> SEQ ID NO 1780
<211> LENGTH: 19
<212> TYPE: RNA
<213> ORGANISM: Artificial sequence
<220> FEATURE:
<223> OTHER INFORMATION: Chemically synthesized

<400> SEQUENCE: 1780
ugcugcucaa acugccagu                                              19

<210> SEQ ID NO 1781
<211> LENGTH: 19
<212> TYPE: RNA
<213> ORGANISM: Artificial sequence
<220> FEATURE:
<223> OTHER INFORMATION: Chemically synthesized

<400> SEQUENCE: 1781
agaaucacac acaauccua                                              19

<210> SEQ ID NO 1782
<211> LENGTH: 19
<212> TYPE: RNA
<213> ORGANISM: Artificial sequence
<220> FEATURE:
<223> OTHER INFORMATION: Chemically synthesized

<400> SEQUENCE: 1782
cacacacaau ccuauccag                                              19

<210> SEQ ID NO 1783
<211> LENGTH: 19
<212> TYPE: RNA
<213> ORGANISM: Artificial sequence
<220> FEATURE:
<223> OTHER INFORMATION: Chemically synthesized

<400> SEQUENCE: 1783
ucagggacaa ggaccuuug                                              19

<210> SEQ ID NO 1784
<211> LENGTH: 19
<212> TYPE: RNA
<213> ORGANISM: Artificial sequence
<220> FEATURE:
<223> OTHER INFORMATION: Chemically synthesized

<400> SEQUENCE: 1784
acaaggaccu uugagcaac                                              19

<210> SEQ ID NO 1785
<211> LENGTH: 19
<212> TYPE: RNA
<213> ORGANISM: Artificial sequence
<220> FEATURE:

<223> OTHER INFORMATION: Chemically synthesized

<400> SEQUENCE: 1785
ccuuugagca accaaguuu                                                        19

<210> SEQ ID NO 1786
<211> LENGTH: 19
<212> TYPE: RNA
<213> ORGANISM: Artificial sequence
<220> FEATURE:
<223> OTHER INFORMATION: Chemically synthesized

<400> SEQUENCE: 1786
cuuccauaag ccaucacca                                                        19

<210> SEQ ID NO 1787
<211> LENGTH: 19
<212> TYPE: RNA
<213> ORGANISM: Artificial sequence
<220> FEATURE:
<223> OTHER INFORMATION: Chemically synthesized

<400> SEQUENCE: 1787
agucaguggu gacaacucc                                                        19

<210> SEQ ID NO 1788
<211> LENGTH: 19
<212> TYPE: RNA
<213> ORGANISM: Artificial sequence
<220> FEATURE:
<223> OTHER INFORMATION: Chemically synthesized

<400> SEQUENCE: 1788
uugcugaauu gaacauugu                                                        19

<210> SEQ ID NO 1789
<211> LENGTH: 19
<212> TYPE: RNA
<213> ORGANISM: Artificial sequence
<220> FEATURE:
<223> OTHER INFORMATION: Chemically synthesized

<400> SEQUENCE: 1789
cuggcaaguu gauuccuca                                                        19

<210> SEQ ID NO 1790
<211> LENGTH: 19
<212> TYPE: RNA
<213> ORGANISM: Artificial sequence
<220> FEATURE:
<223> OTHER INFORMATION: Chemically synthesized

<400> SEQUENCE: 1790
acuauaaacc auaucucca                                                        19

<210> SEQ ID NO 1791
<211> LENGTH: 19
<212> TYPE: RNA
<213> ORGANISM: Artificial sequence
<220> FEATURE:
<223> OTHER INFORMATION: Chemically synthesized

<400> SEQUENCE: 1791
auaaaccaua ucuccauag                                                        19

<210> SEQ ID NO 1792
<211> LENGTH: 19
<212> TYPE: RNA
<213> ORGANISM: Artificial sequence
<220> FEATURE:
<223> OTHER INFORMATION: Chemically synthesized

<400> SEQUENCE: 1792
cuacccuuga caauggggg                                                19

<210> SEQ ID NO 1793
<211> LENGTH: 19
<212> TYPE: RNA
<213> ORGANISM: Artificial sequence
<220> FEATURE:
<223> OTHER INFORMATION: Chemically synthesized

<400> SEQUENCE: 1793
cccuugacaa uuggguua                                                 19

<210> SEQ ID NO 1794
<211> LENGTH: 19
<212> TYPE: RNA
<213> ORGANISM: Artificial sequence
<220> FEATURE:
<223> OTHER INFORMATION: Chemically synthesized

<400> SEQUENCE: 1794
agaggauaga uuacuaagu                                                19

<210> SEQ ID NO 1795
<211> LENGTH: 19
<212> TYPE: RNA
<213> ORGANISM: Artificial sequence
<220> FEATURE:
<223> OTHER INFORMATION: Chemically synthesized

<400> SEQUENCE: 1795
gaggauagau uacuaagug                                                19

<210> SEQ ID NO 1796
<211> LENGTH: 19
<212> TYPE: RNA
<213> ORGANISM: Artificial sequence
<220> FEATURE:
<223> OTHER INFORMATION: Chemically synthesized

<400> SEQUENCE: 1796
aucucagaac uaauuuccu                                                19

<210> SEQ ID NO 1797
<211> LENGTH: 19
<212> TYPE: RNA
<213> ORGANISM: Artificial sequence
<220> FEATURE:
<223> OTHER INFORMATION: Chemically synthesized

<400> SEQUENCE: 1797
uagagugagg aagucacca                                                19

<210> SEQ ID NO 1798
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 1798
uaccaagccu accugaaac                                            19

<210> SEQ ID NO 1799
<211> LENGTH: 19
<212> TYPE: RNA
<213> ORGANISM: Artificial sequence
<220> FEATURE:
<223> OTHER INFORMATION: Chemically synthesized

<400> SEQUENCE: 1799
ucuacuuuug cuuaccuau                                            19

<210> SEQ ID NO 1800
<211> LENGTH: 19
<212> TYPE: RNA
<213> ORGANISM: Artificial sequence
<220> FEATURE:
<223> OTHER INFORMATION: Chemically synthesized

<400> SEQUENCE: 1800
acccuucaau cacuguugu                                            19

<210> SEQ ID NO 1801
<211> LENGTH: 19
<212> TYPE: RNA
<213> ORGANISM: Artificial sequence
<220> FEATURE:
<223> OTHER INFORMATION: Chemically synthesized

<400> SEQUENCE: 1801
gcuaguccau gagcaguuc                                            19

<210> SEQ ID NO 1802
<211> LENGTH: 19
<212> TYPE: RNA
<213> ORGANISM: Artificial sequence
<220> FEATURE:
<223> OTHER INFORMATION: Chemically synthesized

<400> SEQUENCE: 1802 aguucccug cuuaaacac                                             19

<210> SEQ ID NO 1803
<211> LENGTH: 19
<212> TYPE: RNA
<213> ORGANISM: Artificial sequence
<220> FEATURE:
<223> OTHER INFORMATION: Chemically synthesized

<400> SEQUENCE: 1803
uucucugggu caguuucuc                                            19

<210> SEQ ID NO 1804
<211> LENGTH: 19
<212> TYPE: RNA
<213> ORGANISM: Artificial sequence
<220> FEATURE:
<223> OTHER INFORMATION: Chemically synthesized

<400> SEQUENCE: 1804
cuugcugaau ugaacauug                                            19

<210> SEQ ID NO 1805
<211> LENGTH: 19
```

```
<212> TYPE: RNA
<213> ORGANISM: Artificial sequence
<220> FEATURE:
<223> OTHER INFORMATION: Chemically synthesized

<400> SEQUENCE: 1805
aaaccauauc uccauagcc                                                  19

<210> SEQ ID NO 1806
<211> LENGTH: 19
<212> TYPE: RNA
<213> ORGANISM: Artificial sequence
<220> FEATURE:
<223> OTHER INFORMATION: Chemically synthesized

<400> SEQUENCE: 1806
cucagaacua auuccuau                                                   19

<210> SEQ ID NO 1807
<211> LENGTH: 19
<212> TYPE: RNA
<213> ORGANISM: Artificial sequence
<220> FEATURE:
<223> OTHER INFORMATION: Chemically synthesized

<400> SEQUENCE: 1807
ucagaacuaa uuccuauc                                                   19

<210> SEQ ID NO 1808
<211> LENGTH: 19
<212> TYPE: RNA
<213> ORGANISM: Artificial sequence
<220> FEATURE:
<223> OTHER INFORMATION: Chemically synthesized

<400> SEQUENCE: 1808
auaggcaaau cugguuuau                                                  19

<210> SEQ ID NO 1809
<211> LENGTH: 19
<212> TYPE: RNA
<213> ORGANISM: Artificial sequence
<220> FEATURE:
<223> OTHER INFORMATION: Chemically synthesized

<400> SEQUENCE: 1809
gacccuucaa ucacuguug                                                  19

<210> SEQ ID NO 1810
<211> LENGTH: 19
<212> TYPE: RNA
<213> ORGANISM: Artificial sequence
<220> FEATURE:
<223> OTHER INFORMATION: Chemically synthesized

<400> SEQUENCE: 1810
aaggaccuuu gagcaacca                                                  19

<210> SEQ ID NO 1811
<211> LENGTH: 19
<212> TYPE: RNA
<213> ORGANISM: Artificial sequence
<220> FEATURE:
<223> OTHER INFORMATION: Chemically synthesized

<400> SEQUENCE: 1811
```

-continued aggaccuuug agcaaccaa                                        19

<210> SEQ ID NO 1812
<211> LENGTH: 19
<212> TYPE: RNA
<213> ORGANISM: Artificial sequence
<220> FEATURE:
<223> OTHER INFORMATION: Chemically synthesized

<400> SEQUENCE: 1812
aucaccauuu uguaagcau                                        19

<210> SEQ ID NO 1813
<211> LENGTH: 19
<212> TYPE: RNA
<213> ORGANISM: Artificial sequence
<220> FEATURE:
<223> OTHER INFORMATION: Chemically synthesized

<400> SEQUENCE: 1813
ucagugguga caacuccag                                        19

<210> SEQ ID NO 1814
<211> LENGTH: 19
<212> TYPE: RNA
<213> ORGANISM: Artificial sequence
<220> FEATURE:
<223> OTHER INFORMATION: Chemically synthesized

<400> SEQUENCE: 1814
acacagugaa ccuuuggag                                        19

<210> SEQ ID NO 1815
<211> LENGTH: 19
<212> TYPE: RNA
<213> ORGANISM: Artificial sequence
<220> FEATURE:
<223> OTHER INFORMATION: Chemically synthesized

<400> SEQUENCE: 1815
auuccucaaa uauuaccuc                                        19

<210> SEQ ID NO 1816
<211> LENGTH: 19
<212> TYPE: RNA
<213> ORGANISM: Artificial sequence
<220> FEATURE:
<223> OTHER INFORMATION: Chemically synthesized

<400> SEQUENCE: 1816
uccucaaaua uuaccucgu                                        19

<210> SEQ ID NO 1817
<211> LENGTH: 19
<212> TYPE: RNA
<213> ORGANISM: Artificial sequence
<220> FEATURE:
<223> OTHER INFORMATION: Chemically synthesized

<400> SEQUENCE: 1817
ucaaauuuga gucaggaac                                        19

<210> SEQ ID NO 1818
<211> LENGTH: 19
<212> TYPE: RNA
<213> ORGANISM: Artificial sequence

```
<220> FEATURE:
<223> OTHER INFORMATION: Chemically synthesized

<400> SEQUENCE: 1818
auccugagcu gaggaucag                                                19

<210> SEQ ID NO 1819
<211> LENGTH: 19
<212> TYPE: RNA
<213> ORGANISM: Artificial sequence
<220> FEATURE:
<223> OTHER INFORMATION: Chemically synthesized

<400> SEQUENCE: 1819
gauuccucaa auauuaccu                                                19

<210> SEQ ID NO 1820
<211> LENGTH: 19
<212> TYPE: RNA
<213> ORGANISM: Artificial sequence
<220> FEATURE:
<223> OTHER INFORMATION: Chemically synthesized

<400> SEQUENCE: 1820
uuccucaaau auuaccucg                                                19

<210> SEQ ID NO 1821
<211> LENGTH: 19
<212> TYPE: RNA
<213> ORGANISM: Artificial sequence
<220> FEATURE:
<223> OTHER INFORMATION: Chemically synthesized

<400> SEQUENCE: 1821
ggcuuuugga aguuuugau                                                19

<210> SEQ ID NO 1822
<211> LENGTH: 19
<212> TYPE: RNA
<213> ORGANISM: Artificial sequence
<220> FEATURE:
<223> OTHER INFORMATION: Chemically synthesized

<400> SEQUENCE: 1822
gcuuuuggaa guuugaua                                                 19

<210> SEQ ID NO 1823
<211> LENGTH: 19
<212> TYPE: RNA
<213> ORGANISM: Artificial sequence
<220> FEATURE:
<223> OTHER INFORMATION: Chemically synthesized

<400> SEQUENCE: 1823
ccaaaggcca gaaaucag                                                 19

<210> SEQ ID NO 1824
<211> LENGTH: 19
<212> TYPE: RNA
<213> ORGANISM: Artificial sequence
<220> FEATURE:
<223> OTHER INFORMATION: Chemically synthesized

<400> SEQUENCE: 1824
uccugcuuaa acacaagug                                                19
```

<210> SEQ ID NO 1825
<211> LENGTH: 19
<212> TYPE: RNA
<213> ORGANISM: Artificial sequence
<220> FEATURE:
<223> OTHER INFORMATION: Chemically synthesized

<400> SEQUENCE: 1825
ucaccauuuu guaagcaua                                                    19

<210> SEQ ID NO 1826
<211> LENGTH: 19
<212> TYPE: RNA
<213> ORGANISM: Artificial sequence
<220> FEATURE:
<223> OTHER INFORMATION: Chemically synthesized

<400> SEQUENCE: 1826
aggagagaua cuucaauuc                                                    19

<210> SEQ ID NO 1827
<211> LENGTH: 19
<212> TYPE: RNA
<213> ORGANISM: Artificial sequence
<220> FEATURE:
<223> OTHER INFORMATION: Chemically synthesized

<400> SEQUENCE: 1827
uucaaauuug agucaggaa                                                    19

<210> SEQ ID NO 1828
<211> LENGTH: 19
<212> TYPE: RNA
<213> ORGANISM: Artificial sequence
<220> FEATURE:
<223> OTHER INFORMATION: Chemically synthesized

<400> SEQUENCE: 1828
ccucugaaaa cuuagagaa                                                    19

<210> SEQ ID NO 1829
<211> LENGTH: 19
<212> TYPE: RNA
<213> ORGANISM: Artificial sequence
<220> FEATURE:
<223> OTHER INFORMATION: Chemically synthesized

<400> SEQUENCE: 1829
accuauucca ucccauuca                                                    19

<210> SEQ ID NO 1830
<211> LENGTH: 19
<212> TYPE: RNA
<213> ORGANISM: Artificial sequence
<220> FEATURE:
<223> OTHER INFORMATION: Chemically synthesized

<400> SEQUENCE: 1830
cacuauuuug aaucacuuc                                                    19

<210> SEQ ID NO 1831
<211> LENGTH: 19
<212> TYPE: RNA
<213> ORGANISM: Artificial sequence
<220> FEATURE:
<223> OTHER INFORMATION: Chemically synthesized

```
<400> SEQUENCE: 1831
ccuuuuuagg acccuucaa                                                19

<210> SEQ ID NO 1832
<211> LENGTH: 19
<212> TYPE: RNA
<213> ORGANISM: Artificial sequence
<220> FEATURE:
<223> OTHER INFORMATION: Chemically synthesized

<400> SEQUENCE: 1832 guuuuucuu aacaagucg                                                 19

<210> SEQ ID NO 1833
<211> LENGTH: 19
<212> TYPE: RNA
<213> ORGANISM: Artificial sequence
<220> FEATURE:
<223> OTHER INFORMATION: Chemically synthesized

<400> SEQUENCE: 1833
uucuccugcu uaaacacaa                                                19

<210> SEQ ID NO 1834
<211> LENGTH: 19
<212> TYPE: RNA
<213> ORGANISM: Artificial sequence
<220> FEATURE:
<223> OTHER INFORMATION: Chemically synthesized

<400> SEQUENCE: 1834
ccugcuuaaa cacaagugu                                                19

<210> SEQ ID NO 1835
<211> LENGTH: 19
<212> TYPE: RNA
<213> ORGANISM: Artificial sequence
<220> FEATURE:
<223> OTHER INFORMATION: Chemically synthesized

<400> SEQUENCE: 1835
ugcuuaaaca caaguguaa                                                19

<210> SEQ ID NO 1836
<211> LENGTH: 19
<212> TYPE: RNA
<213> ORGANISM: Artificial sequence
<220> FEATURE:
<223> OTHER INFORMATION: Chemically synthesized

<400> SEQUENCE: 1836
auucucuggg ucaguuucu                                                19

<210> SEQ ID NO 1837
<211> LENGTH: 19
<212> TYPE: RNA
<213> ORGANISM: Artificial sequence
<220> FEATURE:
<223> OTHER INFORMATION: Chemically synthesized

<400> SEQUENCE: 1837
ugagauaaca cugccaugg                                                19

<210> SEQ ID NO 1838
```

```
<211> LENGTH: 19
<212> TYPE: RNA
<213> ORGANISM: Artificial sequence
<220> FEATURE:
<223> OTHER INFORMATION: Chemically synthesized

<400> SEQUENCE: 1838
cuuuuuagga cccuucaau                                              19

<210> SEQ ID NO 1839
<211> LENGTH: 19
<212> TYPE: RNA
<213> ORGANISM: Artificial sequence
<220> FEATURE:
<223> OTHER INFORMATION: Chemically synthesized

<400> SEQUENCE: 1839
uucaaucacu guuguucca                                              19

<210> SEQ ID NO 1840
<211> LENGTH: 19
<212> TYPE: RNA
<213> ORGANISM: Artificial sequence
<220> FEATURE:
<223> OTHER INFORMATION: Chemically synthesized

<400> SEQUENCE: 1840
ugcucaaacu gccaguugc                                              19

<210> SEQ ID NO 1841
<211> LENGTH: 19
<212> TYPE: RNA
<213> ORGANISM: Artificial sequence
<220> FEATURE:
<223> OTHER INFORMATION: Chemically synthesized

<400> SEQUENCE: 1841 ugauccuca aauauuacc                                               19

<210> SEQ ID NO 1842
<211> LENGTH: 19
<212> TYPE: RNA
<213> ORGANISM: Artificial sequence
<220> FEATURE:
<223> OTHER INFORMATION: Chemically synthesized

<400> SEQUENCE: 1842
cucuggguca guuucucag                                              19

<210> SEQ ID NO 1843
<211> LENGTH: 19
<212> TYPE: RNA
<213> ORGANISM: Artificial sequence
<220> FEATURE:
<223> OTHER INFORMATION: Chemically synthesized

<400> SEQUENCE: 1843
uucccagaaa agcccagag                                              19

<210> SEQ ID NO 1844
<211> LENGTH: 19
<212> TYPE: RNA
<213> ORGANISM: Artificial sequence
<220> FEATURE:
<223> OTHER INFORMATION: Chemically synthesized

<400> SEQUENCE: 1844
```
ucaaucacug uuguuccaa                                               19

<210> SEQ ID NO 1845
<211> LENGTH: 19
<212> TYPE: RNA
<213> ORGANISM: Artificial sequence
<220> FEATURE:
<223> OTHER INFORMATION: Chemically synthesized

<400> SEQUENCE: 1845
agccuuccau aagccauca                                               19

<210> SEQ ID NO 1846
<211> LENGTH: 19
<212> TYPE: RNA
<213> ORGANISM: Artificial sequence
<220> FEATURE:
<223> OTHER INFORMATION: Chemically synthesized

<400> SEQUENCE: 1846
gccuuccaua agccaucac                                               19

<210> SEQ ID NO 1847
<211> LENGTH: 19
<212> TYPE: RNA
<213> ORGANISM: Artificial sequence
<220> FEATURE:
<223> OTHER INFORMATION: Chemically synthesized

<400> SEQUENCE: 1847
accauaucuc cauagccaa                                               19

<210> SEQ ID NO 1848
<211> LENGTH: 19
<212> TYPE: RNA
<213> ORGANISM: Artificial sequence
<220> FEATURE:
<223> OTHER INFORMATION: Chemically synthesized

<400> SEQUENCE: 1848
aaacacagaa agaaaagag                                               19

<210> SEQ ID NO 1849
<211> LENGTH: 19
<212> TYPE: RNA
<213> ORGANISM: Artificial sequence
<220> FEATURE:
<223> OTHER INFORMATION: Chemically synthesized

<400> SEQUENCE: 1849
cuucaaucac uguuguucc                                               19

<210> SEQ ID NO 1850
<211> LENGTH: 19
<212> TYPE: RNA
<213> ORGANISM: Artificial sequence
<220> FEATURE:
<223> OTHER INFORMATION: Chemically synthesized

<400> SEQUENCE: 1850
ucccagaaaa gcccagaga                                               19

<210> SEQ ID NO 1851
<211> LENGTH: 19
<212> TYPE: RNA

```
<213> ORGANISM: Artificial sequence
<220> FEATURE:
<223> OTHER INFORMATION: Chemically synthesized

<400> SEQUENCE: 1851
aacacagaaa gaaaagaga                                            19

<210> SEQ ID NO 1852
<211> LENGTH: 19
<212> TYPE: RNA
<213> ORGANISM: Artificial sequence
<220> FEATURE:
<223> OTHER INFORMATION: Chemically synthesized

<400> SEQUENCE: 1852
acacagaaag aaaagagac                                            19
```

THERAPEUTIC USES OF INHIBITORS OF RTP801L

This application is a continuation of U.S. Ser. No. 13/218,053, filed Aug. 25, 2011, which is a continuation of U.S. Ser. No. 12/589,972, filed Oct. 29, 2009, now U.S. Pat. No. 8,017,764, issued Sep. 13, 2011, which is a continuation of U.S. Ser. No. 11/811,112, filed Jun. 8, 2007, now U.S. Pat. No. 7,626,015, issued Dec. 1, 2009, which claims the benefit of U.S. provisional patent application No. 60/812,229 filed on Jun. 9, 2006, the contents of each of which are hereby incorporated by reference in their entirety into this application.

This application incorporates-by-reference nucleotide and/or amino acid sequences which are present in the file named "130424_2094_76494-AAZA_SequenceListing_LC.txt" which is 361 KB in size, and which was created Apr. 23, 2013, and which is contained in the text file filed Apr. 24, 2013.

FIELD OF THE INVENTION

The present invention relates to novel siRNA molecules which inhibit the RTP801L gene and to the use of such molecules to treat respiratory disorders of all types (including pulmonary disorders), eye diseases and conditions, microvascular disorders, angiogenesis- and apoptosis-related conditions, and hearing impairments.

BACKGROUND OF THE INVENTION

Chronic Obstructive Pulmonary Disease (COPD)

Chronic obstructive pulmonary disease (COPD), affects more than 16 million Americans and is the fourth highest cause of death in the United States. Cigarette smoking causes most occurrences of the debilitating disease but other environmental factors cannot be excluded (Petty T L. 2003. *Definition, epidemiology, course, and prognosis of COPD*. Clin. Cornerstone, 5-10).

Pulmonary emphysema is a major manifestation of COPD. Permanent destruction of peripheral air spaces, distal to terminal bronchioles, is the hallmark of emphysema (Tuder R M, et al. *Oxidative stress and apoptosis interact and cause emphysema due to vascular endothelial growth factor blocade. Am J Respir Cell Mol Biol,* 29:88-97; 2003.). Emphysema is also characterized by accumulation of inflammatory cells such as macrophages and neutrophils in bronchioles and alveolar structures (Petty, 2003).

The pathogenesis of emphysema is complex and multifactorial. In humans, a deficiency of inhibitors of proteases produced by inflammatory cells, such as alpha1-antitrypsin, has been shown to contribute to protease/antiprotease imbalance, thereby favoring destruction of alveolar extracellular matrix in cigarette-smoke (CS) induced emphysema (Eriksson, S. 1964. *Pulmonary Emphysema and Alpha1-Antitrypsin Deficiency. Acta Med Scand* 175:197-205. Joos, L., Pare, P. D., and Sandford, A. J. 2002. *Genetic risk factors of chronic obstructive pulmonary disease. Swiss Med Wkly* 132:27-37). Matrix metalloproteinases (MMPs) play a central role in experimental emphysema, as documented by resistance of macrophage metalloelastase knockout mice against emphysema caused by chronic inhalation of CS (Hautamaki, et al: *Requirement for macrophage elastase for cigarette smoke-induced emphysema in mice. Science* 277:2002-2004). Moreover, pulmonary overexpression of interleukin-13 in transgenic mice results in MMP- and cathepsin-dependent emphysema (Zheng, T., et al 2000. *Inducible targeting of IL-13 to the adult lung causes matrix metalloproteinase-and cathepsin-dependent emphysema. J Clin Invest* 106:1081-1093). Recent works describe involvement of septal cell apoptosis in lung tissue destruction leading to emphysema (Rangasami T, et al. *Genetic ablation of Nrf2 enhances susceptibility to cigarette smoke-iduced emphysema in mice. Submitted to Journal of Clinincal Investigation.*; Tuder R M et al. *Oxidative stress and apoptosis interact and cause emphysema due to vascular endothelial growth factor blocade. Am J Respir Cell Mol Biol,* 29:88-97; 2003.; Yokohori N, Aoshiba K, Nagai A, *Increased levels of cell death and proliferation in alveolar wall cells in patients with pulmonary emphysema. Chest.* 2004 February; 125(2):626-32.; Aoshiba K, Yokohori N, Nagai A., *Alveolar wall apoptosis causes lung destruction and emphysematous changes. Am J Respir Cell Mol. Biol.* 2003 May; 28(5): 555-62.).

Among the mechanisms that underlie both pathways of lung destruction in emphysema, excessive formation of reactive oxygen species (ROS) should be first of all mentioned. It is well established that prooxidant/antioxidant imbalance exists in the blood and in the lung tissue of smokers (Hulea S A, et al: *Cigarette smoking causes biochemical changes in blood that are suggestive of oxidative stress: a case-control study. J Environ Pathol Toxicol Oncol.* 1995; 14(3-4):173-80.; Rahman I, MacNee W. *Lung glutathione and oxidative stress: implications in cigarette smoke-induced airway disease. Am J Physiol.* 1999 December; 277(6 Pt 1):L1067-88.; MacNee W. Oxidants/antioxidants and COPD. Chest. 2000 May; 117(5 Suppl 1):303S-17S.; Marwick J A, Kirkham P, Gilmour P S, Donaldson K, MacNEE W, Rahman I. *Cigarette smoke-induced oxidative stress and TGF-beta1 increase p21waf1/cip1 expression in alveolar epithelial cells. Ann N Y Acad. Sci.* 2002 November; 973:278-83.; Aoshiba K, Koinuma M, Yokohori N, Nagai A. *Immunohistochemical evaluation of oxidative stress in murine lungs after cigarette smoke exposure. Inhal Toxicol.* 2003 September; 15(10):1029-38.; Dekhuijzen P N. *Antioxidant properties of N-acetylcysteine: their relevance in relation to chronic obstructive pulmonary disease. Eur Respir J.* 2004 April; 23(4):629-36.; Tuder R M, Zhen L, Cho C Y, Taraseviciene-Stewart L, Kasahara Y, Salvemini D, Voelkel N F, and Flores S C. *Oxidative stress and apoptosis interact and cause emphysema due to vascular endothelial growth factor blocade. Am J Respir Cell Mol Biol,* 29:88-97; 2003.). After one hour exposure of mice to CS, there is a dramatic increase of 8-hydroxy-2'-deoxyguanosine (8-OHdG) in the alveolar epithelial cells, particularly of type II (see *Inhal Toxicol.* 2003 September; 15(10):1029-38. above).

Overproduced reactive oxygen species are known for their cytotoxic activity, which stems from a direct DNA damaging effect and from the activation of apoptotic signal transduction pathways (Takahashi A, Masuda A, Sun M, Centonze V E, Herman B. *Oxidative stress-induced apoptosis is associated with alterations in mitochondrial caspase activity and Bcl-2-dependent alterations in mitochondrial pH (pHm). Brain Res Bull.* 2004 Feb. 15; 62(6):497-504.; Taniyama Y, Griendling K K. *Reactive oxygen species in the vasculature: molecular and cellular mechanisms. Hypertension.* 2003 December; 42(6):1075-81. Epub 2003 Oct. 27.; Higuchi Y. *Chromosomal DNA fragmentation in apoptosis and necrosis induced by oxidative stress. Biochem Pharmacol.* 2003 Oct. 15; 66(8): 1527-35.; Punj V, Chakrabarty A M. *Redox proteins in mammalian cell death: an evolutionarily conserved function in mitochondria and prokaryotes. Cell Microbiol.* 2003 April; 5(4):225-31.; Ueda S, Masutani H, Nakamura H, Tanaka T, Ueno M, Yodoi J. *Redox control of cell death. Antioxid Redox Signal.* 2002 June; 4(3):405-14.).

ROS's are not only cytotoxic per se but are also proinflammatory stimuli, being prominent activators of redox-sensitive transcription factors NFkB and AP-1 (reviewed in Rahman I. *Oxidative stress and gene transcription in asthma and chronic obstructive pulmonary disease: antioxidant therapeutic targets. Curr Drug Targets Inflamm Allergy.* 2002 September; 1(3):291-315.). Both transcription factors are, in turn, strongly implicated in stimulation of transcription of proinflammatory cytokines (reviewed in Renard P, Raes M. *The proinflammatory transcription factor NFkappaB: a potential target for novel therapeutical strategies. Cell Biol Toxicol.* 1999; 15(6):341-4.; Lentsch A B, Ward P A. The NFkappaBb/IkappaB system in acute inflammation. *Arch Immunol Ther Exp* (Warsz). 2000; 48(2):59-63) and matrix degrading proteinases (Andela V B, Gordon A H, Zotalis G, Rosier R N, Goater J J, Lewis G D, Schwarz E M, Puzas J E, O'Keefe R J. NFkappaB: *a pivotal transcription factor in prostate cancer metastasis to bone. Clin Orthop.* 2003 October; (415 Suppl):S75-85.; Fleenor D L, Pang I H, Clark A F. *Involvement of AP-1 in interleukin-1 alpha-stimulated MMP-3 expression in human trabecular meshwork cells. Invest Ophthalmol Vis Sci.* 2003 August; 44(8):3494-501.; Ruhul Amin A R, Senga T, Oo M L, Thant A A, Hamaguchi M. *Secretion of matrix metalloproteinase-9 by the proinflammatory cytokine, IL-1 beta: a role for the dual signalling pathways, Akt and Erk. Genes Cells.* 2003 June; 8(6):515-23.). Proinflammatory cytokines, in turn, serve as attractors of inflammatory cells that also secrete matrix degrading enzymes, cytokines and reactive oxygen species. Thus, it appears that a pathogenic factor, like e.g. CS, triggers a pathological network where reactive oxygen species act as major mediators of lung destruction.

Both reactive oxygen species (ROS) from inhaled cigarette smoke and those endogenously formed by inflammatory cells contribute to an increased intrapulmonary oxidant burden.

One additional pathogenic factor with regards to COPD pathogenesis is the observed decreased expression of VEGF and VEGFRII in lungs of emphysematous patients (Yasunori Kasahara, Rubin M. Tuder, Carlyne D. Cool, David A. Lynch, Sonia C. Flores, and Norbert F. Voelkel. *Endothelial Cell Death and Decreased Expression of Vascular Endothelial Growth Factor and Vascular Endothelial Growth Factor Receptor 2 in Emphysema. Am J Respir Crit. Care Med Vol* 163. pp 737-744, 2001). Moreover, inhibition of VEGF signaling using chemical VEGFR inhibitor leads to alveolar septal endothelial and then to epithelial cell apoptosis, probably due to disruption of intimate structural/functional connection of both types of cells within alveoli (Yasunori Kasahara, Rubin M. Tuder, Laimute Taraseviciene-Stewart, Timothy D. Le Cras, Steven Abman, Peter K. Hirth, Johannes Waltenberger, and Norbert F. Voelkel. *Inhibition of VEGF receptors causes lung cell apoptosis and emphysema. J. Clin. Invest.* 106:1311-1319 (2000).; Voelkel N F, Cool C D. *Pulmonary vascular involvement in chronic obstructive pulmonary disease. Eur Respir J. Suppl.* 2003 November; 46:28s-32s).

Macular Degeneration

The most common cause of decreased best-corrected vision in individuals over 65 years of age in the US is the retinal disorder known as age-related macular degeneration (AMD). As AMD progresses, the disease is characterized by loss of sharp, central vision. The area of the eye affected by AMD is the Macula—a small area in the center of the retina, composed primarily of photoreceptor cells. So-called "dry" AMD, accounting for about 85%-90% of AMD patients, involves alterations in eye pigment distribution, loss of photoreceptors and diminished retinal function due to overall atrophy of cells. So-called "wet" AMD involves proliferation of abnormal choroidal vessels leading to clots or scars in the sub-retinal space. Thus, the onset of wet AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, *Age-related Macular degeneration—a new viewpoint, Frontiers in Bioscience,* e305-314, May 2003). CNV occurs not only in wet AMD but also in other ocular pathologies such as ocular histoplasmosis syndrome, angiod streaks, ruptures in Bruch's membrane, myopic degeneration, ocular tumors and some retinal degenerative diseases.

Various studies conducted have determined several risk factors for AMD, such as smoking, aging, family history (Milton, *Am J Ophthalmol* 88, 269 (1979); Mitchell et al., *Ophthalmology* 102, 1450-1460 (1995); Smith et al., *Ophthalmology* 108, 697-704 (2001)) sex (7-fold higher likelihood in females: Klein et al., *Ophthalmology* 99, 933-943 (1992) and race (whites are most susceptible). Additional risk factors may include eye characteristics such as farsightedness (hyperopia) and light-colored eyes, as well as cardiovascular disease and hypertension. Evidence of genetic involvement in the onset progression of the disease has also been documented (see Hamdi & Kenney above).

Two companies, Acuity Pharmaceuticals and Sirna Therapeutics, have both recently filed an IND for siRNA molecules inhibiting VEGF and VEGF-R1 (Flt-1), respectively, for treatment of AMD. These molecules are termed Candy inhibitor and 027 inhibitor respectively.

Glaucoma

Glaucoma is one of the leading causes of blindness in the world. It affects approximately 66.8 million people worldwide. At least 12,000 Americans are blinded by this disease each year (Kahn and Milton, Am J. Epidemiol. 1980 111(6): 769-76). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular meshwork (TM), causing IOP elevation and eventual optic nerve damage.

Microvascular Disorders

Microvascular disorders are composed of a broad group of conditions that primarily affect the microscopic capillaries and lymphatics and are therefore outside the scope of direct surgical intervention. Microvascular disease can be broadly grouped into the vasospastic, the vasculitis and lymphatic occlusive. Additionally, many of the known vascular conditions have a microvascular element to them.

Vasospastic Disease—Vasospastic diseases are a group of relatively common conditions where, for unknown reasons, the peripheral vasoconstrictive reflexes are hypersensitive. This results in inappropriate vasoconstriction and tissue ischaemia, even to the point of tissue loss. Vasospastic symptoms are usually related to temperature or the use of vibrating machinery but may be secondary to other conditions.

Vasculitic Disease—Vasculitic diseases are those that involve a primary inflammatory process in the microcirculation. Vasculitis is usually a component of an autoimmune or connective tissue disorder and is not generally amenable to surgical treatment but requires immunosuppressive treatment if the symptoms are severe.

Lymphatic Occlusive Disease—Chronic swelling of the lower or upper limb (lymphoedema) is the result of peripheral lymphatic occlusion. This is a relatively rare condition that has a large number of causes, some inherited, some acquired. The mainstays of treatment are correctly fitted compression garments and the use of intermittent compression devices.

Microvascular Pathologies Associated with Diabetes

Diabetes is the leading cause of blindness, the number one cause of amputations and impotence, and one of the most frequently occurring chronic childhood diseases. Diabetes is also the leading cause of end-stage renal disease in the United States, with a prevalence rate of 31% compared with other renal diseases. Diabetes is also the most frequent indication for kidney transplantation, accounting for 22% of all transplantation operations.

In general, diabetic complications can be classified broadly as microvascular or macrovascular disease. Microvascular complications include neuropathy (nerve damage), nephropathy (kidney disease) and vision disorders (eg retinopathy, glaucoma, cataract and corneal disease). In the retina, glomerulus, and vasa nervorum, similar pathophysiologic features characterize diabetes-specific microvascular disease.

Microvascular pathologies associated with diabetes are defined as a disease of the smallest blood vessels (capillaries) that may occur e.g. in people who have had diabetes for a long time. The walls of the vessels become abnormally thick but weak. They, therefore, bleed, leak protein and slow the flow of blood through the body.

Clinical and animal model data indicate that chronic hyperglycemia is the central initiating factor for all types of diabetic microvascular disease. Duration and magnitude of hyperglycemia are both strongly correlated with the extent and rate of progression of diabetic microvascular disease. Although all diabetic cells are exposed to elevated levels of plasma glucose, hyperglycemic damage is limited to those cell types (e.g., endothelial cells) that develop intracellular hyperglycemia. Endothelial cells develop intracellular hyperglycemia because, unlike many other cells, they cannot down-regulate glucose transport when exposed to extracellular hyperglycemia. That intracellular hyperglycemia is necessary and sufficient for the development of diabetic pathology is further demonstrated by the fact that overexpression of the GLUT1 glucose transporter in mesangial cells cultured in a normal glucose milieu mimics the diabetic phenotype, inducing the same increases in collagen type IV, collagen type I, and fibronectin gene expression as diabetic hyperglycemia.

Abnormal Endothelial Cell Function:

Early in the course of diabetes mellitus, before structural changes are evident, hyperglycemia causes abnormalities in blood flow and vascular permeability in the retina, glomerulus, and peripheral nerve vasa nervorum. The increase in blood flow and intracapillary pressure is thought to reflect hyperglycemia-induced decreased nitric oxide (NO) production on the efferent side of capillary beds, and possibly an increased sensitivity to angiotensin II. As a consequence of increased intracapillary pressure and endothelial cell dysfunction, retinal capillaries exhibit increased leakage of fluorescein and glomerular capillaries have an elevated albumin excretion rate (AER). Comparable changes occur in the vasa vasorum of peripheral nerve. Early in the course of diabetes, increased permeability is reversible; as time progresses, however, it becomes irreversible.

Increased Vessel Wall Protein Accumulation

The common pathophysiologic feature of diabetic microvascular disease is progressive narrowing and eventual occlusion of vascular lumina, which results in inadequate perfusion and function of the affected tissues. Early hyperglycemia-induced microvascular hypertension and increased vascular permeability contribute to irreversible microvessel occlusion by three processes:

The first is an abnormal leakage of periodic acid—Schiff (PAS)-positive, carbohydrate-containing plasma proteins, which are deposited in the capillary wall and which may stimulate perivascular cells such as pericytes and mesangial cells to elaborate growth factors and extracellular matrix.

The second is extravasation of growth factors, such as transforming growth factor β1 (TGF-β1), which directly stimulates overproduction of extracellular matrix components, and may induce apoptosis in certain complication-relevant cell types.

The third is hypertension-induced stimulation of pathologic gene expression by endothelial cells and supporting cells, which include glut-1 glucose transporters, growth factors, growth factor receptors, extracellular matrix components, and adhesion molecules that can activate circulating leukocytes. The observation that unilateral reduction in the severity of diabetic microvascular disease occurs on the side with ophthalmic or renal artery stenosis is consistent with this concept.

Microvascular Cell Loss and Vessel Occlusion

The progressive narrowing and occlusion of diabetic microvascular lumina are also accompanied by microvascular cell loss. In the retina, diabetes mellitus induces programmed cell death of Müller cells and ganglion cells, pericytes, and endothelial cells. In the glomerulus, declining renal function is associated with widespread capillary occlusion and podocyte loss, but the mechanisms underlying glomerular cell loss are not yet known. In the vasa nervorum, endothelial cell and pericyte degeneration occur, and these microvascular changes appear to precede the development of diabetic peripheral neuropathy. The multifocal distribution of axonal degeneration in diabetes supports a causal role for microvascular occlusion, but hyperglycemia-induced decreases in neurotrophins may contribute by preventing normal axonal repair and regeneration.

Another common feature of diabetic microvascular disease has been termed hyperglycemic memory, or the persistence or progression of hyperglycemia-induced microvascular alterations during subsequent periods of normal glucose homeostasis. The most striking example of this phenomenon is the development of severe retinopathy in histologically normal eyes of diabetic dogs that occurred entirely during a 2.5-year period of normalized blood glucose that followed 2.5 years of hyperglycemia. Hyperglycemia-induced increases in selected matrix gene transcription also persist for weeks after restoration of normoglycemia in vivo, and a less pronounced, but qualitatively similar, prolongation of hyperglycemia-induced increase in selected matrix gene transcription occurs in cultured endothelial cells.

For further information, see "Shared pathophysiologic features of microvascular complications of diabetes" (Larsen: Williams Textbook of Endocrinology, 10th ed., Copyright © 2003 Elsevier).

Microvascular complications occur not only in overt diabetes but are also due to Impaired Glucose Tolerance (IGT). Microvascular complications of IGT: neuropathy, retinopathy, and renal microproteinuria.

Diabetic Neuropathy

Diabetic neuropathies are neuropathic disorders (peripheral nerve damage) that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy and the most common form, peripheral neuropathy, which mainly affects the feet and legs. There are four factors involved in the development of diabetic neuropathy: microvascular disease, advanced glycated end products, protein kinase C, and the polyol pathway.

Microvascular Disease in Diabetic Neuropathy

Vascular and neural diseases are closely related and intertwined. Blood vessels depend on normal nerve function, and nerves depends on adequate blood flow. The first pathological change in the microvasculature is vasoconstriction. As the disease progresses, neuronal dysfunction correlates closely with the development of vascular abnormalities, such as capillary basement membrane thickening and endothelial hyperplasia, which contribute to diminished oxygen tension and hypoxia. Neuronal ischemia is a well-established characteristic of diabetic neuropathy. Vasodilator agents (e.g., angiotensin-converting-enzyme inhibitors, alpha1-antagonists) can lead to substantial improvements in neuronal blood flow, with corresponding improvements in nerve conduction velocities. Thus, microvascular dysfunction occurs early in diabetes, parallels the progression of neural dysfunction, and may be sufficient to support the severity of structural, functional, and clinical changes observed in diabetic neuropathy. Peripheral neuropathy (legs), sensorimotor neuropathy is a significant component in the pathogenesis of leg ulcers in diabetes.

Neuropathy is a common complication of diabetes occurring over time in more than half of patients with type 2 diabetes. Nerve conduction studies demonstrate that neuropathy is already present in 10-18% of patients at the time of diabetes diagnosis, suggesting that peripheral nerve injury occurs at early stages of disease and with milder glycemic dysregulation. The concept that neuropathy is an early clinical sign of diabetes was proposed >40 years ago, and most studies report an association between IGT and neuropathy. Most patients with IGT and associated neuropathy have a symmetric, distal sensory polyneuropathy with prominent neuropathic pain. IGT neuropathy (*Microvascular complications of impaired glucose tolerance—Perspectives in Diabetes*, J. Robinson Singleton, in *Diabetes* Dec. 1, 2003) is phenotypically similar to early diabetic neuropathy, which also causes sensory symptoms, including pain, and autonomic dysfunction. In a survey of 669 patients with early diabetic neuropathy, sensory symptoms were present in >60%, impotence in nearly 40%, and other autonomic involvement in 33%, but evidence of motor involvement in only 12%. These clinical findings suggest prominent early involvement of the small unmyelinated nerve fibers that carry pain, temperature, and autonomic signals. Direct quantitation of unmyelinated intraepidermal nerve fibers from skin biopsies shows similar fiber loss and altered morphology in patients with neuropathy associated with IGT and early diabetes.

Autonomic dysfunction, particularly erectile dysfunction and altered cardiac vagal response, are common early features of neuropathic injury in diabetes. Work with IGT patients also suggests prevalent vagal dysautonoinia: separate studies have found abnormal heart rate recovery following exercise, blunted R—R interval variability to deep breathing, and reduced expiration to inspiration ratio (all measures of vagal dysautonomia) in a greater fraction of IGT patients than age-matched normoglycemic control subjects.

Nerve damage in diabetes affects the motor, sensory, and autonomic fibers. Motor neuropathy causes muscle weakness, atrophy, and paresis. Sensory neuropathy leads to loss of the protective sensations of pain, pressure, and heat. The absence of pain leads to many problems in the insensate foot, including ulceration, unperceived trauma, and Charcot neuroarthropathy. The patient may not seek treatment until after the wound has advanced. A combination of sensory and motor dysfunction can cause the patient to place abnormal stresses on the foot, resulting in trauma, which may lead to infection. Autonomic sympathetic neuropathy causes vasodilation and decreased sweating, which results in warm, overly dry feet that are particularly prone to skin breakdown, as well as functional alterations in microvascular flow. Autonomic dysfunction (and denervation of dermal structures) also results in loss of skin integrity, which provides an ideal site for microbial invasion. The neuropathic foot does not ulcerate spontaneously; rather, it is the combination of some form of trauma accompanied by neuropathy.

Microvascular dysfunction occurs early in diabetes, parallels the progression of neural dysfunction, and may be sufficient to support the severity of structural, functional, and clinical changes observed in diabetic neuropathy.

Advanced Glycated End Products

Elevated intracellular levels of glucose cause a non-enzymatic covalent bonding with proteins, which alters their structure and destroys their function. Certain of these glycated proteins are implicated in the pathology of diabetic neuropathy and other long term complications of diabetes.

Protein Kinase C (PKC)

PKC is implicated in the pathology of diabetic neuropathy. Increased levels of glucose cause an increase in intracellular diacylglycerol, which activates PKC. PKC inhibitors in animal models will increase nerve conduction velocity by increasing neuronal blood flow.

Sensorimotor Polyneuropathy

Longer nerve fibers are affected to a greater degree than shorter ones, because nerve conduction velocity is slowed in proportion to a nerve's length. In this syndrome, decreased sensation and loss of reflexes occurs first in the toes bilaterally, then extends upward. It is usually described as glove-stocking distribution of numbness, sensory loss, dysesthesia and nighttime pain. The pain can feel like burning, pricking sensation, achy or dull. Pins and needles sensation is common. Loss of proprioception, that is, the sense of where a limb is in space, is affected early. These patients cannot feel when they are stepping on a foreign body, like a splinter, or when they are developing a callous from an ill-fitting shoe. Consequently, they are at risk for developing ulcers and infections on the feet and legs, which can lead to amputation. Similarly, these patients can get multiple fractures of the knee, ankle or foot, and develop a Charcot joint. Loss of motor function results on dorsiflexion contractures of the toes, so called hammertoes. These contractures occur not only in the foot but also in the hand.

Autonomic Neuropathy

The autonomic nervous system is composed of nerves serving the heart, GI tract and urinary system. Autonomic neuropathy can affect any of these organ systems. The most commonly recognized autonomic dysfuction in diabetics is orthostatic hypotension, or the uncomfortable sensation of fainting when a patient stands up. In the case of diabetic autonomic neuropathy, it is due to the failure of the heart and arteries to appropriately adjust heart rate and vascular tone to keep blood continually and fully flowing to the brain. This symptom is usually accompanied by a loss of sinus respiratory variation, that is, the usual change in heart rate seen with normal breathing. When these two findings are present, cardiac autonomic neuropathy is present.

GI tract manifestations include delayed gastric emptying, gastroparesis, nausea, bloating, and diarrhea. Because many diabetics take oral medication for their diabetes, absorption of these medicines is greatly affected by the delayed gastric emptying. This can lead to hypoglycemia when an oral diabetic agent is taken before a meal and does not get absorbed until hours, or sometimes days later, when there is normal or low blood sugar already. Sluggish movement of the small instestine can cause bacterial overgrowth, made worse by the presence of hyperglycemia. This leads to bloating, gas and diarrhea.

Urinary symptoms include urinary frequency, urgency, incontinence and retention. Again, because of the retention of sweet urine, urinary tract infections are frequent. Urinary retention can lead to bladder diverticula, stones, reflux nephropathy.

Cranial Neuropathy

When cranial nerves are affected, oculomotor (3rd) neuropathies are most common. The oculomotor nerve controls all of the muscles that move the eye with the exception of the lateral rectus and superior oblique muscles. It also serves to constrict the pupil and open the eyelid. The onset of a diabetic third nerve palsy is usually abrupt, beginning with frontal or periorbital pain and then diplopia. All of the oculomotor muscles innervated by the third nerve may be affected, except for those that control pupil size. The sixth nerve, the abducens nerve, which innervates the lateral rectus muscle of the eye (moves the eye laterally), is also commonly affected but fourth nerve, the trochlear nerve, (innervates the superior oblique muscle, which moves the eye downward) involvement is unusual. Mononeuropathies of the thoracic or lumbar spinal nerves can occur and lead to painful syndromes that mimic myocardial infarction, cholecystitis or appendicitis. Diabetics have a higher incidence of entrapment neuropathies, such as carpal tunnel syndrome.

Diabetic Limb Ischemia and Diabetic Foot Ulcers

Diabetes and pressure can impair microvascular circulation and lead to changes in the skin on the lower extremities, which in turn, can lead to formation of ulcers and subsequent infection. Microvascular changes lead to limb muscle microangiopathy, as well as a predisposition to develop peripheral ischemia and a reduced angiogenesis compensatory response to ischemic events. Microvascular pathology exacerbates Peripheral Vascular Disease (PVD) (or Peripheral Arterial Disease (PAD) or Lower Extremity Arterial Disease (LEAD)—a MACROvascular complication—narrowing of the arteries in the legs due to atherosclerosis. PVD occurs earlier in diabetics, is more severe and widespread, and often involves intercurrent microcirculatory problems affecting the legs, eyes, and kidneys.

Foot ulcers and gangrene are frequent comorbid conditions of PAD. Concurrent peripheral neuropathy with impaired sensation make the foot susceptible to trauma, ulceration, and infection. The progression of PAD in diabetes is compounded by such comorbidity as peripheral neuropathy and insensitivity of the feet and lower extremities to pain and trauma. With impaired circulation and impaired sensation, ulceration and infection occur. Progression to osteomyelitis and gangrene may necessitate amputation.

Persons with diabetes are up to 25 times more likely than nondiabetic persons to sustain a lower limb amputation, underscoring the need to prevent foot ulcers and subsequent limb loss.

Diabetic foot ulcers may occur not only in conjunction with PAD but may also be associated with neuropathy, venous insufficiency (varicose veins), trauma, and infection. PAD contributes to these other conditions in producing or precipitating foot ulcers. Foot ulcers do not necessarily represent progression of PAD, as they may occur in the presence of adequate clinical peripheral arterial perfusion. Patient-based studies indicate an increased risk of foot ulceration in diabetic patients who have peripheral neuropathy and a high plantar foot pressure. The prevalence of a history of ulcers or sores on the foot or ankles was 15% of all diabetic patients in the population-based study in southern Wisconsin. The prevalence was higher for diabetic individuals diagnosed at age <30 years, was slightly higher in men (16%) than in women (13%), and was greater in insulin-treated diabetic patients (17%) than in patients not taking insulin (10%). The prevalence increased with age, especially in diabetic patients diagnosed at age <30 years. In patient studies from Europe, prevalence of foot ulcers in diabetic patients was 3% in those age <50 years, 7% in those age <60 years, and 14% in those age <80 years. Prevalence was greater in males than in females at age 70 years.

In diabetic patients, foot ischemia and infection are serious and even life-threatening occurrences; however, neuropathy is the most difficult condition to treat. The medical and surgical literature concerning all aspects of the clinical and pathological manifestations of the diabetic foot is overwhelming. Neuropathy, angiopathy, retinopathy, and nephropathy, alone or in combination and in varying degrees of severity, may influence the treatment of the diabetic foot.

Every year, 82,000 limb amputations are performed in patients with diabetes mellitus. The majority of these amputations are performed in the elderly population. Amputations resulting from diabetes may arise from multiple etiologies, including foot ulcers, ischemia, venous leg ulcers (ie, those secondary to venous reflux), and heel ulcers (ie, those resulting from untreated pressure ulcers in the heel). The majority of these amputations originate from ulcers. The prevalence of foot ulcers among patients with diabetes is 12%. In addition, the 20-year cumulative incidence of lower-extremity ulcers in patients with type 1 diabetes is 9.9%. Diabetes-induced limb amputations result in a 5-year mortality rate of 39% to 68% and are associated with an increased risk of additional amputations. The length of hospital stay is approximately 60% longer among patients with diabetic foot ulcers, as compared with those without ulcers.

Diabetic neuropathy impairs the nerve axon reflex that depends on healthy C-fiber nociceptor function and causes local vasodilation in response to a painful stimulus. This condition further compromises the vasodilatory response present in conditions of stress, such as injury or inflammation, in the diabetic neuropathic foot. This impairment may partially explain why some ulcers in the diabetic neuropathic foot are either slow to heal or fail to heal at all, despite successful lower-extremity revascularization.

The most common causal pathway to diabetic foot ulceration can thus be identified as the combination of neuropathy (sensory loss), deformity (eg, prominent metatarsal heads), and trauma (eg, ill-fitting footwear).

Most surgeons prefer to perform popliteal or tibial arterial bypass because of inferior rates of limb salvage and patency compared with more proximal procedures. If popliteal or tibial arterial bypass is unable to restore a palpable foot pulse, pedal bypass has been reported to provide a more durable and effective limb-salvage procedure for patients with diabetes and ischemic foot wounds]. Even extensive multisegment occlusive disease in patients with diabetes does not present an impediment to foot salvage. Whereas serious wound complications may have disastrous results, they are uncommon after pedal bypass grafting. Adequate control of preexisting foot infection and careful graft tunneling have been shown to be effective in avoiding further complications. Angioplasty in the lower extremity is becoming more progressively utilized. However, it must be emphasized that for angioplasty to be effective, a distal vessel or feeding vessel must be patent if the more proximal angioplasty is to succeed.

While diabetic ulcers/limb pathologies may be managed in some patients (by Debridement, antibiotic treatment, use of preparations to stimulate granulation tissue (new collagen and angiogenesis) and reduction of bacterial burden in the wound), it would be beneficial to have a pharmaceutical composition that could better treat these conditions and/or alleviate the symptoms.

For further information, see American Journal of Surgery, Volume 187•Number 5 Suppl 1•May 1, 2004, Copyright © 2004 Elsevier.

Coronary Microvascular Dysfunction in Diabetes

The correlation between histopathology and microcirculatory dysfunction in diabetes is well known from old experimental studies and from autopsy, where thickening of the basal membrane, perivascular fibrosis, vascular rarefication, and capillary hemorrhage are frequently found. It remains difficult to confirm these data in vivo, although a recent paper demonstrated a correlation between pathology and ocular micorovascular dysfunction (Am J Physiol 2003; 285). A large amount of clinical studies, however, indicate that not only overt diabetes but also impaired metabolic control may affect coronary microcirculation (Hypert Res 2002; 25:893). Werner alluded to the important paper by Sambuceti et al (Circulation 2001; 104:1129) showing the persistence of microvascular dysfunction in patients after successful reopening of the infarct related artery, and which may explain the increased cardiovascular morbidity and mortality in these patients. There is mounting evidence from large acute reperfusion studies that morbidity and mortality are unrelated to the reopening itself of the infarct related artery, but much more dependent on the TIMI flow+/−myocardial blush (Stone 2002; Feldmann Circulation 2003). Herrmann indicated, among others, that the integrity of the coronary microcirculation is probably the most important clincal and prognostic factor in this context (Circulation 2001). The neutral effect of protection devices (no relevant change for TIMI flow, for ST resolution, or for MACE) may indicate that a functional impairment of microcirculation is the major determinant of prognosis. There is also increasing evidence that coronary microvascular dysfunction plays a major role in non obstructive CAD. Coronary endothelial dysfunction remains a strong prognostic predictor in these patients.

Diabetic Nephropathy (Renal Dysfunction in Patients with Diabetes)

Diabetic nephropathy encompasses microalbuminuria (a microvascular disease effect), proteinuria and ESRD. Diabetes is the most common cause of kidney failure, accounting for more than 40 percent of new cases. Even when drugs and diet are able to control diabetes, the disease can lead to nephropathy and kidney failure. Most people with diabetes do not develop nephropathy that is severe enough to cause kidney failure. About 16 million people in the United States have diabetes, and about 100,000 people have kidney failure as a result of diabetes.

Diabetic Retinopathy

In the diabetic state, hyperglycemia leads to decreased retinal blood flow, retinal hyperpermeability, delays in photoreceptor nerve conduction, and retinal neuronal cell death. In short duration diabetes, neuronal cell death has been identified within the inner nuclear layer of the retina. Specifically, apoptosis has been localized to glial cells such as Mueller cells and astrocytes and has been shown to occur within 1 month of diabetes in the STZ-induced diabetic rat model. The cause of these events is multi-factorial including activation of the diacylglycerol/PKC pathway, oxidative stress, and non-enzymatic glycosylation. The combination of these events renders the retina hypoxic and ultimately leads to the development of diabetic retinopathy. One possible connection between retinal ischemia and the early changes in the diabetic retina is the hypoxia-induced production of growth factors such as VEGF. The master regulator of the hypoxic response has been identified as hypoxia inducible factor-1 (HIF-1), which controls genes that regulate cellular proliferation and angiogenesis. Prior studies have demonstrated that inhibition of HIF-1 ubiquitination leads to binding with hypoxia responsive elements (HRE) and production of VEGF mRNA.

Diabetic Retinopathy is defined as the progressive dysfunction of the retinal vasculature caused by chronic hyperglycemia. Key features of diabetic retinopathy include microaneurysms, retinal hemorrhages, retinal lipid exudates, cotton-wool spots, capillary nonperfusion, macular edema and neovascularization. Associated features include vitreous hemorrhage, retinal detachment, neovascular glaucoma, premature cataract and cranial nerve palsies.

There are 16 million people in the US with Type 1 and Type 2 diabetes. Within 15 years, 80% of Type 1 patients have developed diabetic retinopathy while 84% of Type 2 diabetic patients develop retinopathy within 19 years. These numbers constitute a significant market for therapeutic agents aimed at ocular diseases of neovasculature. The development of diabetic retinopathy is time-dependent. Despite optimal blood sugar control, patients with long-standing disease can be expected to eventually develop some form of retinopathy. The National Society to Prevent Blindness has estimated that 4 to 6 million diabetics in the U.S. have diabetic retinopathy. The estimated annual incidence of new cases of proliferative diabetic retinopathy and diabetic macular edema are 65,000 and 75,000, respectively, with a prevalence of 700,000 and 500, 000 respectively. Diabetic retinopathy causes from 12,000 to 24,000 new cases of blindness in the US every year. Retinopathy is treated by surgical methods, effective in reducing severe vision loss, but the lasered portions of the retina are irreversibly destroyed. There are no drug treatments available.

A microvascular disease that primarily affects the capillaries, diabetes mellitus affects the eye by destroying the vasculature in the conjunctiva, retina and central nervous system. Patients may present with histories of long-standing injected bulbar conjunctivae along with systemic complaints of weight loss despite larger than normal appetite (polyphasia), abnormal thirst (polydypsia) and abnormally frequent urination (polyuria).

Fluctuating visual acuity secondary to unstable blood sugar is a common ocular sign. Swelling within the crystalline lens results in large sudden shifts in refraction as well as premature cataract formation. Changes in visual acuity will depend upon the severity and stage of the disease.

In the retina, weakening of the arterioles and capillaries may result in the characteristic appearance of intraretinal dot and blot hemorrhages, exudates, intraretinal microvascular abnormalities (IRMA) microaneurysms, edema and cotton wool infarcts. Proliferative diabetic retinopathy is the result of severe vascular compromise and is visible as neovascularization of the disc (NVD), neovascularization elsewhere (NVE) and neovascularization of the iris (NVI, or rubeosis irides). Neurological complications include palsies of the third, fourth and sixth cranial nerves as well as diabetic papillitis and facial nerve paralysis.

Diabetes mellitus is a genetically influenced group of diseases that share glucose intolerance. It is characterized as a disorder of metabolic regulation as a result of deficient or malfunctioning insulin or deficient or malfunctioning cellular insulin receptors.

Biochemistry involving the formation of sorbitol plays a role in the destruction of pericytes, which are cells that support the vascular endothelium. As the supportive pericytes perish, capillary endothelium becomes compromised, resulting in the vascular leakage of blood, protein and lipid. This, in combination with thickened, glucose-laden blood, produces vascular insufficiency, capillary nonperfusion, retinal hypoxia, altered structure and decreased function. The formation and release of vasoproliferative factors which play a role in the genesis of retinal neovascularization are poorly understood.

Most non-vision threatening sequelae of diabetes resolve spontaneously over the course of weeks to months following medical control. In cases where there are large refractive changes, patients may require a temporary spectacle prescription until the refraction stabilizes. When retinopathy threatens the macula or when new blood vessels proliferate, the patient may be referred for laser photocoagulation. The Diabetic Retinopathy Study (DRS) has conclusively proven that panretinal photocoagulation was successful in reducing the risk of severe vision loss in high-risk patients. It defined the high-risk characteristics as: (1) Neovascularization of the optic disc (NVD) one-quarter to one-third of a disc diameter in size and (2) Neovascularization elsewhere (NVE) with any vitreous hemorrhage.

Diabetic Macular Edema (DME)

DME is a complication of diabetic retinopathy, a disease affecting the blood vessels of the retina. Diabetic retinopathy results in multiple abnormalities in the retina, including retinal thickening and edema, hemorrhages, impeded blood flow, excessive leakage of fluid from blood vessels and, in the final stages, abnormal blood vessel growth. This blood vessel growth can lead to large hemorrhages and severe retinal damage. When the blood vessel leakage of diabetic retinopathy causes swelling in the macula, it is referred to as DME. The principal symptom of DME is a loss of central vision. Risk factors associated with DME include poorly controlled blood glucose levels, high blood pressure, abnormal kidney function causing fluid retention, high cholesterol levels and other general systemic factors.

According to the World Health Organization, diabetic retinopathy is the leading cause of blindness in working age adults and a leading cause of vision loss in diabetics. The American Diabetes Association reports that there are approximately 18 million diabetics in the United States and approximately 1.3 million newly diagnosed cases of diabetes in the United States each year. Prevent Blindness America and the National Eye Institute estimate that in the United States there are over 5.3 million people aged 18 or older with diabetic retinopathy, including approximately 500,000 with DME. The CDC estimates that there are approximately 75,000 new cases of DME in the United States each year.

Additional Neuropathies

In addition to diabetes, the common causes of neuropathy are herpes zoster infection, chronic or acute trauma (including surgery) and various neurotoxins. Neuropathic pain is common in cancer as a direct result of the cancer on peripheral nerves (e.g., compression by a tumor) and as a side effect of many chemotherapy drugs.

Microvascular Disease

Vascular and neural diseases are closely related and intertwined. Blood vessels depend on normal nerve function, and nerves depends on adequate blood flow. The first pathological change in the microvasculature is vasoconstriction. As the disease progresses, neuronal dysfunction correlates closely with the development of vascular abnormalities, such as capillary basement membrane thickening and endothelial hyperplasia, which contribute to diminished oxygen tension and hypoxia. Vasodilator agents (e.g., angiotensin-converting-enzyme inhibitors, $\alpha$1-antagonists) can lead to substantial improvements in neuronal blood flow, with corresponding improvements in nerve conduction velocities.

Clinical Manifestations

Neuropathy affects all peripheral nerves: pain fibers, motor neurons, autonomic nerves. It therefore necessarily can affect all organs and systems since all are innervated. There are several distinct syndromes based on the organ systems and members affected, but these are by no means exclusive. A patient can have sensorimotor and autonomic neuropathy or any other combination.

Despite advances in the understanding of the metabolic causes of neuropathy, treatments aimed at interrupting these pathological processes have been limited by side effects and lack of efficacy. Thus, treatments are symptomatic and do not address the underlying problems. Agents for pain caused by sensorimotor neuropathy include tricyclic antidepressants (TCAs), serotonin reuptake inhibitors (SSRIs) and antiepileptic drugs (AEDs). None of these agents reverse the pathological processes leading to diabetic neuropathy and none alter the relentless course of the illness. Thus, it would be useful to have a pharmaceutical composition that could better treat these conditions and/or alleviate the symptoms.

Additional Retinopathies

Retinal Microvasculopathy (AIDS Retinopathy)

Retinal microvasculopathy is seen in 100% of AIDS patients. It is characterized by intraretinal hemorrhages, microaneurysms, Roth spots, cotton-wool spots (microinfarctions of the nerve fiber layer) and perivascular sheathing. The etiology of the retinopathy is unknown though it has been thought to be due to circulating immune complexes, local release of cytotoxic substances, abnormal hemorheology, and HIV infection of endothelial cells. AIDS retinopathy is now so common that cotton wool spots in a patient without diabetes or hypertension but at risk for HIV should prompt the physician to consider viral testing. There is no specific treatment for AIDS retinopathy but its continued presence may prompt a physician to reexamine the efficacy of the HIV therapy and patient compliance.

Bone Marrow Transplantation (BMT) Retinopathy

Bone marrow transplantation retinopathy was first reported in 1983. It typically occurs within six months, but it can occur as late as 62 months after BMT. Risk factors such as diabetes and hypertension may facilitate the development of BMT retinopathy by heightening the ischemic microvasculopathy. There is no known age, gender or race predilection for development of BMT retinopathy. Patients present with decreased visual acuity and/or visual field deficit. Posterior segment findings are typically bilateral and symmetric. Clinical manifestations include multiple cotton wool spots, telangiectasia, microaneurysms, macular edema, hard exudates and retinal hemorrhages. Fluorescein angiography demonstrates capillary nonperfusion and dropout, intraretinal microvascular abnormalities, microaneurysms and macular edema. Although the precise etiology of BMT retinopathy has not been elucidated, it appears to be affected by several factors: cyclosporine toxicity, total body irradiation (TBI), and chemotherapeutic agents. Cyclosporine is a powerful immunomodulatory agent that suppresses graft-versus-host immune response. It may lead to endothelial cell injury and neurologic side effects, and as a result, it has been suggested as the cause of BMT retinopathy. However, BMT retinopathy can develop in the absence of cyclosporine use, and cyclosporine has not been shown to cause BMT retinopathy in autologous or syngeneic bone marrow recipients. Cyclosporine does not, therefore, appear to be the sole cause of BMT retinopathy. Total body irradiation (TBI) has also been implicated as the cause of BMT retinopathy. Radiation injures the retinal microvasculature and leads to ischemic vasculopathy. Variables such as the total dose of radiation and the time interval between radiation and bone marrow ablation appear to be important. However, BMT retinopathy can occur in patients who did not receive TBI, and BMT retinopathy is not observed in solid organ transplant recipients who received similar doses of radiation. Thus, TBI is not the sole cause, but it is another contributing factor in development of BMT retinopathy. Chemotherapeutic agents have been suggested as a potential contributing factor in BMT retinopathy. Medications such as cisplatin, carmustine, and cyclophosphamide can cause ocular side effects including papilledema, optic neuritis, visual field deficit and cortical blindness. It has been suggested that these chemotherapeutic drugs may predispose patients to radiation-induced retinal damages and enhance the deleterious effect of radiation. In general, patients with BMT retinopathy have a good prognosis. The retinopathy usually resolves within two to four months after stopping or lowering the dosage of cyclosporine. In one report, 69 percent of patients experienced complete resolution of the retinal findings, and 46 percent of patients fully recovered their baseline visual acuity. Because of the favorable prognosis and relatively non-progressive nature of BMT retinopathy, aggressive intervention is usually not necessary.

Ischemic Conditions

Ischemia can be divided into 2 categories: the first involves the accelerated atherosclerosis that occurs commonly in patients with diabetes, i.e., in the femoral, popliteal, and posterior tibial arteries. These vessels, often only 1 or 2 cm in diameter, can develop atherosclerotic plaque, which seriously decreases blood flow. After large vessels become completely occluded, stroke, myocardial infarction, ischemia, and non-healing diabetic foot ulcers can occur. This form of ischemia is essentially a large-vessel disease.

Post Stroke Dementia

25% of people have dementia after a stroke with many others developing dementia over the following 5 to 10 years. In addition, many individuals experience more subtle impairments of their higher brain functions (such as planning skills and speed of processing information) and are at very high risk of subsequently developing dementia. Very small strokes in the deep parts of the brain in this process (called microvascular disease) seem to be essential in the process leading to an identified pattern of brain atrophy specific to post-stroke dementia.

Ocular Ischemic Syndrome

Patients suffering from ocular ischemic syndrome (OIS) are generally elderly, ranging in age from the 50s to 80s. Males are affected twice as commonly as females. The patient is only rarely asymptomatic. Decreased vision occurs at presentation in 90 percent of cases, and 40 percent of patients have attendant eye pain. There may also be an attendant or antecedent history of transient ischemic attacks or amaurosis fugax. Patients also have significant known or unknown systemic disease at the time of presentation. The most commonly encountered systemic diseases are hypertension, diabetes, ischemic heart disease, stroke, and peripheral vascular disease. To a lesser extent, patients manifest OIS as a result of giant cell arteritis (GCA).

Unilateral findings are present in 80 percent of cases. Common findings may include advanced unilateral cataract, anterior segment inflammation, asymptomatic anterior chamber reaction, macular edema, dilated but non-tortuous retinal veins, mid-peripheral dot and blot hemorrhages, cotton wool spots, exudates, and neovascularization of the disc and retina. There may also be spontaneous arterial pulsation, elevated intraocular pressure, and neovascularization of the iris and angle with neovascular glaucoma (NVG). While the patient may exhibit anterior segment neovascularization, ocular hypotony may occur due to low arterial perfusion to the ciliary body. Occasionally, there is visible retinal emboli (Hollenhorst plaques).

The findings in OIS are caused by internal carotid artery atheromatous ulceration and stenosis at the bifurcation of the common carotid artery. Five percent of patients with internal artery stenosis develop OIS. However, OIS only occurs if the degree of stenosis exceeds 90 percent. Stenosis of the carotid artery reduces perfusion pressure to the eye, resulting in the above-mentioned ischemic phenomena. Once stenosis reaches 90 percent, the perfusion pressure in the central retinal artery (CRA) drops only to 50 percent. Often, the reduced arterial pressure manifests as spontaneous pulsation of the CRA. The findings are variable and may include any or all of the above findings.

Patients with OIS have significant systemic disease that must be assessed. Cardiac death is the primary cause of mortality in patients with OIS—the five-year mortality rate is 40 percent. For this reason, patients with OIS must be referred to a cardiologist for complete serology, EKG, ECG, and carotid evaluation.

Microvascular Diseases of the Kidney

The kidney is involved in a number of discreet clinico-pathologic conditions that affect systemic and renal microvasculature. Certain of these conditions are characterized by primary injury to endothelial cells, such as:

hemolytic-uremic syndrome (HUS) and thrombotic thrombocytopenic purpura (TTP) HUS and TTP are closely related diseases characterized by microangiopathic hemolytic anemia and variable organ impairment Traditionally, the diagnosis of HUS is made when renal failure is a predominant feature of the syndrome, as is common in children. In adults, neurologic impairment frequently predominates and the syndrome is then referred to as TTP. Thrombotic microangiopathy is the underlying pathologic lesion in both syndromes, and the clinical and laboratory findings in patients with either HUS or TTP overlap to a large extent. This has prompted several investigators to regard the two syndromes as a continuum of a single disease entity. Pathogenesis: Experimental data strongly suggest that endothelial cell injury is the primary event in the pathogenesis of HUS/TTP. Endothelial damage triggers a cascade of events that includes local intravascular coagulation, fibrin deposition, and platelet activation and aggregation. The end result is the histopathologic finding of thrombotic microangiopathy common to the different forms of the HUS/TTP syndrome. If HUS/TTP is left untreated, the mortality rate approaches 90%. Supportive therapy—including dialysis, antihypertensive medications, blood transfusions, and management of neurologic complications—contributes to the improved survival of patients with HUS/TTP. Adequate fluid balance and bowel rest are important in treating typical HUS associated with diarrhea.

radiation nephritis—The long-term consequences of renal irradiation in excess of 2500 rad can be divided into five clinical syndromes:
(i) Acute radiation nephritis occurs in approximately 40% of patients after a latency period of 6 to 13 months. It is characterized clinically by abrupt onset of hypertension, proteinuria, edema, and progressive renal failure in most cases leading to end-stage kidneys.
(ii) Chronic radiation nephritis, conversely, has a latency period that varies between 18 months and 14 years after the initial insult. It is insidious in onset and is characterized by hypertension, proteinuria, and gradual loss of renal function.
(iii) The third syndrome manifests 5 to 19 years after exposure to radiation as benign proteinuria with normal renal function
(iv) A fourth group of patients exhibits only benign hypertension 2 to 5 years later and may have variable proteinuria. Late malignant hypertension arises 18 months to 11 years after irradiation in patients with either chronic radiation nephritis or benign hypertension. Removal of the affected kidney reversed the hypertension. Radiation-induced damage to the renal arteries with subsequent renovascular hypertension has been reported.
(v) A syndrome of renal insufficiency analogous to acute radiation nephritis has been observed in bone marrow transplantation (BMT) patients who were treated with total-body irradiation (TBI).

It has been reported that irradiation causes endothelial dysfunction but spares vascular smooth muscle cells in the early postradiation phase. Radiation could directly damage DNA, leading to decreased regeneration of these cells and denudement of the basement membrane in the glomerular capillaries and tubules. How this initial insult eventually leads to glomerulosclerosis, tubule atrophy, and interstitial fibrosis is unclear. It is postulated that degeneration of the endothelial cell layer may result in intravascular thrombosis in capillaries and smaller arterioles. This intrarenal angiopathy would then explain the progressive renal fibrosis and the hypertension that characterize radiation nephritis. A recent study of irradiated mouse kidneys showed a dose-dependent increase in leukocytes in the renal cortex, suggesting a role for inflammatory processes in radiation-induced nephritis.

In other kidney diseases, the microvasculature of the kidney is involved in autoimmune disorders, such as systemic sclerosis (scleroderma). Kidney involvement in systemic sclerosis manifests as a slowly progressing chronic renal disease or as scleroderma renal crisis (SRC), which is characterized by malignant hypertension and acute azotemia. It is postulated that SRC is caused by a Raynaud-like phenomenon in the kidney. Severe vasospasm leads to cortical ischemia and enhanced production of renin and angiotensin II, which in turn perpetuate renal vasoconstriction. Hormonal changes (pregnancy), physical and emotional stress, or cold temperature may trigger the Raynaud-like arterial vasospasm. The role of the renin-angiotensin system in perpetuating renal ischemia is underscored by the significant benefit of ACE inhibitors in treating SRC. In patients with SRC who progress to severe renal insufficiency despite antihypertensive treatment, dialysis becomes a necessity. Both peritoneal dialysis and hemodialysis have been employed. The End-Stage Renal Disease (ESRD) Network report on 311 patients with systemic sclerosis-induced ESRD dialyzed between 1983 and 1985 revealed a 33% survival rate at 3 years.

The renal microcirculation can also be affected in sickle cell disease, to which the kidney is particularly susceptible because of the low oxygen tension attained in the deep vessels of the renal medulla as a result of countercurrent transfer of oxygen along the vasa recta. The smaller renal arteries and arterioles can also be the site of thromboembolic injury from cholesterol-containing material dislodged from the walls of the large vessels.

Taken as a group, diseases that cause transient or permanent occlusion of renal microvasculature uniformly result in disruption of glomerular perfusion, and hence of the glomerular filtration rate, thereby constituting a serious threat to systemic homeostasis.

Acute Renal Failure (ARF)

ARF can be caused by microvascular or macrovascular disease (major renal artery occlusion or severe abdominal aortic disease). The classic microvascular diseases often present with microangiopathic hemolysis and acute renal failure occurring because of glomerular capillary thrombosis or occlusion, often with accompanying thrombocytopenia. Typical examples of these diseases include:
a) Thrombotic thrombocytopenic purpura—The classic pentad in thrombotic thrombocytopenic purpura includes fever, neurologic changes, renal failure, microangiopathic hemolytic anemia and thrombocytopenia.
b) Hemolytic uremic syndrome—Hemolytic uremic syndrome is similar to thrombotic thrombocytopenic purpura but does not present with neurologic changes.
c) HELLP syndrome (hemolysis, elevated liver enzymes and low platelets). HELLP syndrome is a type of hemolytic uremic syndrome that occurs in pregnant women with the addition of transaminase elevations.

Acute renal failure can present in all medical settings but is predominantly acquired in hospitals. The condition develops in 5 percent of hospitalized patients, and approximately 0.5 percent of hospitalized patients require dialysis. Over the past 40 years, the survival rate for acute renal failure has not improved, primarily because affected patients are now older and have more comorbid conditions. Infection accounts for 75 percent of deaths in patients with acute renal failure, and cardio-respiratory complications are the second most common cause of death. Depending on the severity of renal failure, the mortality rate can range from 7 percent to as high as 80 percent. Acute renal failure can be divided into three categories: Prerenal, intrinsic and postrenal ARF. Intrinsic ARF is subdivided into four categories: tubular disease, glomerular disease, vascular disease (includes microvascular) and interstitial disease.

Progressive Renal Disease

There is evidence that progressive renal disease is characterized by a progressive loss of the microvasculature. The loss of the microvasculature correlates directly with the development of glomerular and tubulointerstitial scarring. The mechanism is mediated in part by a reduction in the endothelial proliferative response, and this impairment in capillary repair is mediated by alteration in the local expression of both angiogenic (vascular endothelial growth factor) and antiangiogenic (thrombospondin 1) factors in the kidney. The alteration in balance of angiogenic growth factors is mediated by both macrophage-associated cytokines (interleukin-1β) and vasoactive mediators. Finally, there is intriguing evidence that stimulation of angiogenesis and/or capillary repair may stabilize renal function and slow progression and that this benefit occurs independently of effects on BP or proteinuria.

For further information see Brenner & Rector's The Kidney, 7th ed., Copyright © 2004 Elsevier: Chapter 33—*Microvascular diseases of the kidney* and also Tiwari and Vikrant Journal of Indian Academy of Clinical Medicine Vol. 5, No. 1 *Review Article—Sepsis and the Kidney.*

Hearing Disorders

Chemical-Induced Ototoxicity

The toxic effects of various ototoxic therapeutic drugs on auditory cells and spiral ganglion neurons are often the limiting factor for their therapeutic usefulness. Main ototoxic drugs include the widely used chemotherapeutic agent cisplatin and its analogs, commonly used aminoglycoside antibiotics, e.g. gentamicin, for the treatment of infections caused by gram-negative bacteria, quinine and its analogs, salicylate and its analogs, and loop-diuretics.

For example, antibacterial aminoglycosides such as gentamicins, streptomycins, kanamycins, tobramycins, and the like are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-(1980)). Clearly, ototoxicity is a dose-limiting side-effect of antibiotic administration. From 4 to 15% of patients receiving 1 gram per day for greater than 1 week develop measurable hearing loss, which slowly becomes worse and can lead to complete permanent deafness if treatment continues.

Ototoxicity is also a serious dose-limiting side-effect for cisplatin, a platinum coordination complex, that has proven effective on a variety of human cancers including testicular, ovarian, bladder, and head and neck cancer. Cisplatin (Platinol®) damages auditory and vestibular systems. Salicylates, such as aspirin, are the most commonly used therapeutic drugs for their anti-inflammatory, analgesic, anti-pyretic and anti-thrombotic effects. Unfortunately, they too have ototoxic side effects. They often lead to tinnitus ("ringing in the ears") and temporary hearing loss. Moreover, if the drug is used at high doses for a prolonged time, the hearing impairment can become persistent and irreversible.

Accordingly, there exists a need for means to prevent, reduce or treat the incidence and/or severity of inner ear disorders and hearing impairments involving inner ear tissue, particularly inner ear hair cells. Of particular interest are those conditions arising as an unwanted side-effect of ototoxic therapeutic drugs including cisplatin and its analogs, aminoglycoside antibiotics, salicylate and its analogs, or loop diuretics. In addition, there exits a need for methods which will allow higher and thus more effective dosing with these ototoxicity-inducing pharmaceutical drugs, while concomitantly preventing or reducing ototoxic effects caused by these drugs. What is needed is a method that provides a safe, effective, and prolonged means for prophylactic or curative treatment of hearing impairments related to inner ear tissue damage, loss, or degeneration, particularly ototoxin-induced and particularly involving inner ear hair cells. In addition, there is required a method and composition for the treatment of damage and deafness resulting from inner ear trauma (acoustic trauma).

Without being bound by theory, it is believed that cisplatin drugs and other drugs that induce ototoxicity (such as aminoglycoside antibiotics) may induce the ototoxic effects via programmed cell death or apoptosis in inner ear tissue, particularly inner ear hair cells (Zhang et al., Neuroscience 120 (2003) 191-205; Wang et al., J. Neuroscience 23((24):8596-8607). In mammals, auditory hair cells are produced only during embryonic development and do not regenerate if lost during postnatal life, therefore, a loss of hair cells will result in profound and irreversible deafness. Unfortunately, at present, there are no effective therapies to treat the cochlea and reverse this condition. Thus, an effective therapy to prevent cell death of auditory hair cells would be of great therapeutic value.

Pressure Sores

Pressure sores or pressure ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's position.

Pressure sores are wounds which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Ischemic Conditions

Ischemic injury is the most common clinical expression of cell injury by oxygen deprivation. The most useful models for studying ischemic injury involve complete occlusion of one of the end-arteries to an organ (e.g., a coronary artery) and examination of the tissue (e.g., cardiac muscle) in areas supplied by the artery. Complex pathologic changes occur in diverse cellular systems during ischemia. Up to a certain point, for a duration that varies among different types of cells, the injury may be amenable to repair, and the affected cells may recover if oxygen and metabolic substrates are again made available by restoration of blood flow. With further extension of the ischemic duration, cell structure continues to deteriorate, owing to relentless progression of ongoing injury mechanisms. With time, the energetic machinery of the cell—the mitochondrial oxidative powerhouse and the glycolytic pathway—becomes irreparably damaged, and restoration of blood flow (reperfusion) cannot rescue the damaged cell. Even if the cellular energetic machinery were to remain intact, irreparable damage to the genome or to cellular membranes will ensure a lethal outcome regardless of reperfusion. This irreversible injury is usually manifested as necrosis, but apoptosis may also play a role. Under certain circumstances, when blood flow is restored to cells that have been previously made ischemic but have not died, injury is often paradoxically exacerbated and proceeds at an accelerated pace—this is reperfusion injury.

Ischemia and Reperfusion Injury Following Lung Transplantation

Lung transplantation, the only definitive therapy for many patients with end stage lung disease, has poor survival rates in all solid allograft recipients. Ischemia reperfusion injury is one of the leading causes of death in lung allograft recipients.

Reperfusion injury may occur in a variety of conditions, especially during medical intervention, including but not limited to angioplasty, cardiac surgery or thrombolysis; organ transplant; as a result of plastic surgery; during severe compartment syndrome; during re-attachment of severed limbs; as a result of multiorgan failure syndrome; in the brain as a result of stroke or brain trauma; in connection with chronic wounds such as pressure sores, venous ulcers and diabetic ulcers; during skeletal muscle ischemia or limb transplantation; as a result of mesenteric ischemia or acute ischemic bowel disease; respiratory failure as a result of lower torso ischemia, leading to pulmonary hypertension, hypoxemia, and noncardiogenic pulmonary edema; acute renal failure as observed after renal transplantation, major surgery, trauma, and septic as well as hemorrhagic shock; Sepsis; Retinal ischemia occurring as a result of acute vascular occlusion, leading to loss of vision in a number of ocular diseases such as acute glaucoma, diabetic retinopathy, hypertensive retinopathy, and retinal vascular occlusion; Cochlear ischemia; flap failure in microvascular surgery for head and neck defects; Raynaud's phenomenon and the associated digital ischemic lesions in scleroderma; spinal cord injury; vascular surgery; Traumatic rhabdomyolysis (crush syndrome); and myoglobinuria.

Further, ischemia/reperfusion may be involved in the following conditions: hypertension, hypertensive cerebral vascular disease, rupture of aneurysm, a constriction or obstruction of a blood vessel—as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor; and diseases such as stroke, Parkinson's disease, epilepsy, depression, ALS, Alzheimer's disease, Huntington's disease and any other disease-induced dementia (such as HIV induced dementia for example).

Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracarnial hematoma or edema). Similarly, traumatic constriction or compression can arise from the presence of a mass of abnormal tissue, such as a metastatic or primary tumor.

Spinal Cord Injury

Spinal cord injury or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

Acute Respiratory Distress Syndrome

Acute respiratory distress syndrome (ARDS), also known as respiratory distress syndrome (RDS) or adult respiratory distress syndrome (in contrast with infant respiratory distress syndrome, IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

In conclusion, current modes of therapy for the prevention and/or treatment of COPD, macular degeneration microvascular diseases and ototoxic conditions are unsatisfactory and there is a need therefore to develop novel compounds for this purpose. There is also a need to develop a therapy and a medicament which can treat the ototoxic effects currently associated with certain drugs and conditions, in particular with cisplatin chemotherapeutics and certain antibiotics without sacrificing the effectiveness of the drugs. Additionally, there is a need to develop a therapy and medicament which can treat the ototoxic effects associated with acoustic trauma or mechanical trauma within the inner ear. Furthermore, there is a need to develop a therapy and a medicament for the treatment of pressure sores, ischemia and ischemia-reperfusion related conditions. All the diseases and indications disclosed herein above, as well as other diseases and conditions described herein such as MI may also be treated by the novel compounds of this invention.

RTP801L

Gene RTP801, was first reported by the assignee of the instant application. U.S. Pat. Nos. 6,455,674, 6,555,667, and 6740738, all assigned to the assignee of the instant application, disclose and claim per se the RTP801 polynucleotide and polypeptide, and antibodies directed toward the polypeptide. RTP801 represents a unique gene target for hypoxia-inducible factor-1 (HIF-1) that may regulate hypoxia-induced pathogenesis independent of growth factors such as VEGF. Further discoveries relating to gene RTP801, as discovered by the assignee of the instant application, were reported in: Tzipora Shoshani, et al. *Identification of a Novel Hypoxia-Inducible Factor 1—Responsive Gene, RTP801, Involved in Apoptosis. MOLECULAR AND CELLULAR BIOLOGY*, April 2002, p. 2283-2293; this paper, co-authored by the inventor of the present invention, details the discovery of the RTP801 gene. Gene RTP801L, so named because of its resemblance to RTP801, was also first reported by the assignee of the instant application, and given Pubmed accession No. NM_145244 subsequent to said report.

It has been demonstrated that RTP801/Redd1 and RTP801L/Redd2 potently inhibit signaling through mTOR, by working downstream of AKT and upstream of TSC2 to inhibit mammalian target of rapamycin (mTOR) functions. mTOR is a serine/threonine kinase that plays an essential role in cell growth control. mTOR stimulates cell growth by phosphorylating p70 ribosomal S6 kinase (S6K) and eukaryote initiation factor 4E-binding protein 1 (4EBP1). The mTOR pathway is regulated by a wide variety of cellular signals, including mitogenic growth factors, nutrients, cellular energy levels, and stress conditions. (Corradetti et al, The stress-inducted proteins RTP801 and RTP801L are negative regulators of the mammalian target of rapamycin pathway. J Biol. Chem. 2005 Mar. 18; 280(11):9769-72. Epub 2005 Jan. 4.)

Also reported under the name "SMHS1", RTP801L was found to be upregulated in rat soleus muscle atrophied by restriction of activity. (Pisani et al., SMHS1 is involved in oxidative/glycolytic-energy metabolism balance of muscle fibers. Biochem Biophys Res Commun 2005 Jan. 28; 326(4): 788-93.). While the RTP801L amino acid sequence shares 65% similarity with RTP801—which is a cellular stress response protein regulated by HIF-1, RTP801L expression was demonstrated to be independent of HIF-1. RTP801L was found to be mainly expressed in skeletal muscle, and comparisons of its expression in atrophied versus hypertrophied muscles and in oxidative versus glycolytic muscles suggested that RTP801L contributes to the muscle energy metabolism phenotypes.

Further, the RTP801L gene was found to be was strongly up-regulated as THP-1 macrophages are converted to foam cells. Treatment of HMDM with desferrioxamine, a molecule that mimics the effect of hypoxia, increased expression of RTP801L in a concentration-dependent fashion. Transfection of U-937 and HMEC cells with a RTP801L expression vector increased the sensitivity of the cells for oxLDL-induced cytotoxicity, by inducing a shift from apoptosis toward necrosis. In contrast, suppression of mRNA expression using siRNA approach resulted in increased resistance to oxLDL treatment. Thus, it has been demonstrated that stimulation of RTP801L expression in macrophages increases oxLDL-induced cell death, suggesting that RTP801L gene might play an important role in arterial pathology. (Cuaz-perolin et al., REDD2 gene is upregulated by modified LDL or hypoxia and mediates human macrophage cell death. Arterioscler Thromb Vasc Biol. 2004 October; 24(10):1830-5. Epub 2004 Aug. 12.).

Additionally, Sofer et al (Regulation of mTOR and cell growth in response to energy stress by REDD1.; Mol Cell Biol. 2005 July; 25(14):5834-45.) have shown that RTP801 and RTP801L have non-overlappong expression patterns in adult tissues, and that RTP801L mRNA is absent in immortalized MEFs+/−Glucose and 2DG, thus demonstrating that RTP801 may function independently of RTP801L.

While RTP801 and RTP801L share sequence homology of about 65% at the amino acid level, indicating a possible similarity of function, and while the assignee of the present invention has found that both RTP801 and RTP801L interact with TSC2 and affect the mTOR pathway, the inventors of the present invention have found that the embryological expression pattern of the two polypeptides differs, and that, contrary to RTP801, RTP801L is not induced by hypoxia in all conditions which induce RTP801 expression; it is, however, induced in MEFs as a result of H2O2 treatment (hypoxia treatment), and the induction follows kinetics similar to those of RTP801 expression induction under the same conditions. Additionally, the inventors of the present invention have found that RTP801 polypeptide is more abundantly expressed than RTP801L. Thus, RTP801L may be used as a target in the treatment of conditions for which RTP801 is a target, and may have the added benefit of a similar—yet different—target.

Thus, the inventor of the instant invention has made discoveries leading to the novel concept of inhibiting gene RTP801L with the purpose of improving various disorders as detailed herein.

The following patent applications and publications give aspects of background information.

Patent application/publication Nos. EP1580263, WO2003029271, WO2001096391, WO2003087768, WO2004048938, WO2005044981, WO2003025138, WO2002068579, EP1104808 and CA2343602 all disclose a nucleic acid or polypeptide which is homologous to RTP801L.

Tzipora Shoshani, et al. *Identification of a Novel Hypoxia-Inducible Factor* 1—Responsive Gene, RTP801, *Involved in Apoptosis. MOLECULAR AND CELLULAR BIOLOGY*, April 2002, p. 2283-2293; this paper, co-authored by the inventor of the present invention, details the discovery of the RTP801L gene (a then novel HIF-1-dependent gene).

Anat Brafman, et al Inhibition of Oxygen-Induced Retinopathy in RTP801L-Deficient Mice. Invest Ophthalmol V is Sci. 2004 October; 45 (10): 3796-805; also co-authored by the inventor of the present invention, this paper demonstrates that in RTP801 knock out mice, hyperoxia does not cause degeneration of the retinal capillary network.

Leif W. Ellisen, et al. *REDD1, a Developmentally Regulated Transcriptional Target of p63 and p53, Links p63 to Regulation of Reactive Oxygen Species*. Molecular Cell, Vol. 10, 995-1005, November, 2002; this paper demonstrates that overexpression of RTP801 (referred to therein as REDD1) leads to increased production of reactive oxygen species.

Richard D R, Berra E, and Pouyssegur J. *Non-hypoxic pathway mediates the induction of hypoxia-inducible factor 1 alpha in vascular smooth muscle cells*. J. Biol. Chem. 2000, Sepl; 275(35): 26765-71 this paper demonstrates that HIF-1-dependent transcription may be induced by excessive production of reactive oxygen species.

Rangasami T, et al., *Genetic ablation of Nrf2 enhances susceptibility to cigarette smoke-induced emphysema in mice*. Submitted to Journal of Clinical Investigation. This work relates to mice with a compromised antoxidant defence (due to a germline inactivation of RTP801).

Corradetti et al, The stress-inducted proteins RTP801 and RTP801L are negative regulators of the mammalian target of rapamycin pathway. J Biol. Chem. 2005 Mar. 18; 280(11): 9769-72. Epub 2005 Jan. 4.

Pisani et al., SMHS1 is involved in oxidative/glycolytic-energy metabolism balance of muscle fibers. Biochem Biophys Res Commun 2005 Jan. 28; 326(4):788-93.).

Cuaz-perolin et al., REDD2 gene is upregulated by modified LDL or hypoxia and mediates human macrophage cell death. Arterioscler Thromb Vasc Biol. 2004 October; 24(10): 1830-5. Epub 2004 Aug. 12.).

Sofer et al., Regulation of mTOR and cell growth in response to energy stress by REDD1. Mol Cell Biol. 2005 July; 25(14):5834-45.

SUMMARY OF THE INVENTION

The present invention provides novel methods and compositions for treating microvascular disorders, macular degeneration, respiratory disorders, and spinal cord injury or disease.

In one aspect, novel molecules which inhibit RTP801L and can be used to treat various diseases and indications are provided.

In various embodiments, the present invention provides a compound having structure A:

wherein each N and N' is a ribonucleotide selected from the group consisting of a modified ribonucleotide or an unmodified ribonucleotide and each of $(N)_x$ and $(N')_y$ is an oligomer in which each consecutive N or N' is joined to the next N or N' by a covalent bond;

wherein each of x and y is an integer between 18 and 40;

wherein each of Z and Z' may be present or absent, but if present is dTdT and is covalently attached at the 3' terminus of the strand in which it is present;

and wherein the sequence of $(N)_x$ comprises an antisense sequence having substantial identity to about 18 to about 40 consecutive ribonucleotides in the mRNA transcribed from the RTP801L gene.

The compound may be phosphorylated at one or both ends. In some embodiments x=y=19 and Z and Z' are absent.

Preferred sense and antisense strands are set forth in Table A. According to one embodiment the compound consists of an antisense strand having an oligomer sequence set forth in SEQ ID NO:1000 and a sense strand having an oligomer sequence set forth in SEQ ID NO:75.

In another aspect the present invention provides a pharmaceutical composition comprising an 801L inhibitor of the invention; and a pharmaceutically acceptable excipient. In various embodiments the 801L inhibitor is selected from the group consisting of an siRNA molecule, an antisense molecule, an antibody (such as a neutralizing antibody), a dominant negative peptide, an aptamer and a ribozyme.

In preferred embodiments the 801L inhibitor is siRNA.

In another aspect, the present invention provides a method of treating a patient suffering from a microvascular disorder, macular degeneration or a respiratory disorder, comprising administering to the patient a pharmaceutical composition comprising an RTP801 L inhibitor.

Another embodiment of the present invention concerns a method for treating a patient suffering from COPD, comprising administering to the patient a pharmaceutical composition comprising a therapeutically effective amount of an RTP801L inhibitor. In one embodiment the inhibitor is selected from the group consisting of an siRNA molecule, an antisense molecule, an antibody (such as a neutralizing antibody), a dominant negative peptide, an aptamer and a ribozyme.

Another embodiment of the present invention concerns a method for treating a patient suffering from Acute Lung Injury (ALI), comprising administering to the patient a pharmaceutical composition comprising a therapeutically effective amount of an RTP801L inhibitor. In one embodiment the inhibitor selected from the group consisting of an siRNA molecule, an antisense molecule, an antibody (such as a neutralizing antibody), a dominant negative peptide, an aptamer and a ribozyme.

Another embodiment of the present invention concerns a method for treating a patient suffering from macular degeneration, comprising administering to the patient a pharmaceutical composition comprising a therapeutically effective amount of an RTP801L inhibitor. In one embodiment the inhibitor is an siRNA molecule, an antisense molecule, an antibody (such as a neutralizing antibody), a dominant negative peptide or a ribozyme.

Another embodiment of the present invention concerns a method for treating a patient suffering from a microvascular disorder, comprising administering to the patient a pharmaceutical composition comprising a therapeutically effective amount of an RTP801L inhibitor. In one embodiment the inhibitor is an siRNA molecule, an antisense molecule, an antibody (such as a neutralizing antibody), a dominant negative peptide or a ribozyme.

An additional embodiment of the present invention provides for the use of a therapeutically effective amount of an RTP801L inhibitor for the preparation of a medicament for promoting recovery in a patient suffering from a respiratory disorder. In one embodiment the respiratory disorder is COPD and the inhibitor is preferably an siRNA. In another embodiment the respiratory disorder is ALI and the inhibitor is preferably an siRNA.

An additional embodiment of the present invention provides for the use of a therapeutically effective dose of an RTP801L inhibitor for the preparation of a medicament for promoting recovery in a patient suffering from macular degeneration. In one embodiment the macular degeneration is AMD and the inhibitor is preferably an siRNA.

An additional embodiment of the present invention provides for the use of a therapeutically effective dose of an RTP801L inhibitor for the preparation of a medicament for promoting recovery in a patient suffering from glaucoma. In one embodiment the inhibitor is preferably an siRNA.

An additional embodiment of the present invention provides for the use of a therapeutically effective amount of an RTP801L inhibitor for the preparation of a medicament for promoting recovery in a patient suffering from a microvascular disorder. In one embodiment the microvascular disorder is diabetic retinopathy and the inhibitor is preferably an siRNA. In another embodiment the disorder is Acute Renal Failure and the inhibitor is preferably an siRNA.

The present invention also relates generally to methods and compositions for treating or preventing the incidence or severity of hearing impairment (or balance impairment), particularly hearing impairment associated with cell death of the inner ear hair cells. The methods and compositions involve administering to a mammal in need of such treatment a prophylactically or therapeutically effective amount of one or more compounds which down-regulate expression of the RTP801L gene, particularly novel small interfering RNAs (siRNAs).

More specifically, the present invention provides methods and compositions for treating a patient suffering from hearing impairment, or other oto-pathologies associated with cell death of inner ear hair cells. Such oto-pathologies may be the result of acoustic trauma, mechanical trauma, age (presbycusis) or ototoxin-induced hearing loss. The methods of the invention comprising administering to the patient one or more compounds which down-regulate expression of the RTP801L gene, particularly siRNAs that inhibit RTP801L typically as a pharmaceutical composition, in a therapeutically effective dose so as to thereby treat the patient.

In one embodiment, the present invention provides for improved compositions and methods for treatments requiring administration of a pharmaceutical drug having an ototoxic, hearing-impairing side-effect, in combination with a therapeutically effective amount of one or more siRNA molecules that inhibit RTP801L, to treat or prevent the ototoxicity induced by the pharmaceutical drug. The compositions of the invention can be administered at a suitable interval(s) either prior to, subsequent to, or substantially concurrent with the administration of the ototoxic, hearing-impairing drug that induces inner ear apoptotic tissue damage.

Accordingly, it is an object of the invention to provide an improved composition containing a therapeutically effective amount of one or more siRNA molecules that inhibit RTP801L in combination with an ototoxic, hearing-impairing pharmaceutical drug for administration to a mammal. Said combination drugs may be administered separately; the siRNA molecules that inhibit RTP801L would then be administered locally while the ototoxic, hearing-impairing pharmaceutical drug is administered systemically. The siRNA molecules may be administered prior to, simultaneously with or subsequent to the ototoxic drug. Such combination compositions can further contain a pharmaceutically acceptable carrier. The pharmaceutical composition will have lower ototoxicity than the ototoxic pharmaceutical alone, and preferably, will have a higher dosage of the ototoxic pharmaceutical than typically used. Examples of such improved compositions include cisplatin or other ototoxic neoplastic agent or an aminoglycoside antibiotic(s) in combination with the therapeutically effective amount of one or more siRNA molecules that inhibit RTP801L.

Still further, the invention relates to the use of the compositions of the invention in cases where diuretics are needed. The present invention provides a solution to the art that has long sought a therapy and a medicament which can treat the ototoxic effects currently associated with certain diuretics, and particular with the more popular and commonly used loop-diuretics, without sacrificing their diuretic effectiveness.

Still further, the invention relates to the use of the compositions of the invention in cases where quinine or quinine-like compounds are needed. The present invention provides a solution to the art that has long sought a therapy and a medicament which can treat the ototoxic effects currently associated with certain quinines without sacrificing their effectiveness.

The present invention further relates to methods and compositions for treating or preventing the incidence or severity of pressure sores. The methods and compositions involve administering to a mammal in need of such treatment a prophylactically or therapeutically effective amount of one or more compounds which down-regulate expression of the RTP801L gene, particularly novel small interfering RNAs (siRNAs).

Further, the present invention relates to methods and compositions for the treatment of any ischemic or ischemia-reperfuson injuries or conditions, as described herein. Said methods and compositions involve administering to a mammal in need of such treatment a prophylactically or therapeutically effective amount of one or more compounds which down-regulate expression of the RTP801L gene, particularly novel small interfering RNAs (siRNAs).

DETAILED DESCRIPTION OF THE INVENTION

The present invention, in some of its embodiments, concerns inhibition of the RTP801L gene or polypeptide for the treatment of eye diseases, respiratory disorders, microvascular disorders, hearing disorders and ischemic conditions, inter alia. As will be described herein, the preferred inhibitors to be used with the present invention are biological molecules.

Without being bound by theory, the inventors of the present invention have found that RTP801L is involved in various disease states including microvascular disorders, eye diseases, respiratory disorders, hearing disorders, pressure sores, ischemic conditions and spinal cord injury and disease, and it would be beneficial to inhibit RTP801L in order to treat any of said diseases or disorders. Methods, molecules and compositions which inhibit RTP801L are discussed herein at length, and any of said molecules and/or compositions may be beneficially employed in the treatment of a patient suffering from any of said conditions.

The present invention provides methods and compositions for inhibiting expression of the RTP801L gene in vivo. In general, the method includes administering oligoribonucleotides, such as small interfering RNAs (i.e., siRNAs) that are targeted to a particular mRNA and hybridise to it, or nucleic acid material that can produce siRNAs in a cell, in an amount sufficient to down-regulate expression of a target gene by an RNA interference mechanism. In particular, the subject method can be used to inhibit expression of the RTP801L gene for treatment of respiratory disorders, microvascular disorders, eye disorders and hearing impairments.

Thus, in one embodiment the present invention provides for a method of treating a patient suffering from a microvascular disorder, an eye disease a respiratory disorder, a hearing disorder or a spinal cord injury or other wound, comprising administering to the patient a pharmaceutical composition comprising an RTP801L inhibitor in a therapeutically effective amount so as to thereby treat the patient. The invention further provides a method of treating a patient suffering from a microvascular disorder, an eye disease, a respiratory disorder, a hearing disorder or a spinal cord injury or other wound, comprising administering to the patient a pharmaceutical composition comprising an RTP801L inhibitor, in a dosage and over a period of time sufficient to promote recovery. The eye disease may be macular degeneration such as age-related macular degeneration (AMD), or glaucoma, inter alia. The microvascular disorder may be diabetic retinopathy or acute renal failure, inter alia. The respiratory disorder may be chronic obstructive pulmonary disease (COPD), acute lung injury (ALI), emphysema, chronic bronchitis, asthma and lung cancer, inter alia. The hearing disorder may be trauma-induced deafness, age-related deafness or cisplatin-induced deafness, inter alia. The RTP801L inhibitor may be selected from a large variety of molecules, including but not limited to compounds such as polynucleotides, AS fragments, RNA molecules which target the RTP801L gene mRNA such as ribozymes or siRNAs (such as the siRNAs of Table A, or expression vectors comprising them; polypeptides such as dominant negatives, antibodies (such as an antibody which specifically binds to an epitope present within a polypeptide which comprises consecutive amino acids, the sequence of which is set forth in FIG. 2 (SEQ ID No:2), or, in some cases, enzymes. Additionally, the RTP801L inhibitor may be a chemical inhibitor such as a small molecule, e.g., chemical molecules with a low molecular weight e.g. a molecular weight below 2000 daltons. Specific RTP801L inhibitors are given below.

The present invention further provides a method for treating a patient suffering from macular degeneration, glaucoma, COPD, ALI, diabetic retinopathy, age-related deafness or cisplatin-induced deafness, comprising administering to the patient a pharmaceutical composition comprising a therapeutically effective dose of an RTP801L inhibitor comprising a polynucleotide which specifically hybridizes to mRNA transcribed from the RTP801L gene and/or down regulates the expression of the RTP801L gene so as to thereby treat the patient. The polynucleotide may be an siRNA comprising consecutive nucleotides having a sequence identical to any one of the sequences set forth in Table A (SEQ ID NOs:3-1852).

Further, an additional embodiment of the present invention concerns a method for treating a patient suffering from a microvascular disorder, an eye disease, a respiratory disorder, a hearing disorder or a spinal cord injury or other wound, comprising administering to the patient a pharmaceutical composition comprising a therapeutically effective dose of an RTP801L inhibitor comprising an siRNA molecule, optionally an siRNA molecule detailed in any one of Table A, in a dosage and over a period of time so as to thereby treat the patient.

An additional method for treating a patient suffering from a microvascular disorder, an eye disease, a respiratory disorder, a hearing disorder or a spinal cord injury or other wound is provided, comprising administering to the patient a pharmaceutical composition comprising a therapeutically effective dose of an RNA molecule which targets the RTP801L gene mRNA in a dosage and over a period of time so as to thereby treat the patient. The RNA molecule may be an siRNA molecule, such as an siRNA molecule detailed in Table A, preferably siRNA Nos:72 or 73, or a ribozyme or an AS molecule.

The present invention further provides a method for treating a patient suffering from a microvascular disorder, an eye disease, a respiratory disorder, a hearing disorder or a spinal cord injury or other wound or any of the conditions disclosed herein, comprising administering to the patient a pharmaceutical composition comprising a therapeutically effective dose of an siRNA molecule which targets the RTP801L gene mRNA, optionally an siRNA molecule detailed in Table A, in a dosage and over a period of time so as to thereby treat the patient. Further, the eye disease may be macular degeneration such as age-related macular degeneration (AMD) or glaucoma; the microvascular disorder may be diabetic retinopathy or acute renal failure; the respiratory disorder may be COPD or ALI; and the hearing disorder may be noise—induced deafness, chemically induced deafness such as cisplatin-induced deafness or age-related deafness.

The present invention additionally relates to the use of the novel siRNAs disclosed herein in the treatment of hearing impairment in which inhibition of RTP801L expression is beneficial. In one embodiment, the present invention constitutes a method for treating a mammal having or prone to a hearing (or balance) impairment or treating a mammal prophylactically in conditions where inhibition of RTP801L expression is beneficial. The method of this embodiment of the present invention would prevent or reduce the occurrence or severity of a hearing (or balance) impairment that would result from inner ear cell injury, loss, or degeneration, in particular caused by an ototoxic agent or by aging. In this embodiment, the method of the invention includes administering a therapeutically effective amount of one or more compounds which down-regulate expression of the RTP801L gene, particularly the novel siRNAs of the present invention.

In one embodiment, it is the object of the present invention to provide a method for treating a mammal, to prevent, reduce, or treat a hearing impairment, disorder or imbalance, preferably an ototoxin-induced hearing condition, by administering to a mammal in need of such treatment a composition of the invention. One embodiment is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds. These methods are especially effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2. The methods of the invention are also effective when the ototoxic compound is a neoplastic agent such as vincristine, vinblastine, cisplatin and cisplatin-like compounds and taxol and taxol-like compounds In some embodiments aimed at treating or preventing a hearing disorder, the composition of the invention is co-administered with an ototoxin. For example, an improved method is provided for treatment of infection of a mammal by administration of an aminoglycoside antibiotic, the improvement comprising administering a therapeutically effective amount of one or more compounds which down-regulate expression of the RTP801L gene particularly novel siRNAs, to the patient in need of such treatment to reduce or prevent ototoxin-induced hearing impairment associated with the antibiotic. The compounds which reduce or prevent the ototoxin-induced hearing impairment, particularly the novel siRNAs are preferably administered locally within the inner ear.

In yet another embodiment is provided an improved method for treatment of cancer in a mammal by administration of a chemotherapeutic compound, the improvement comprises administering a therapeutically effective amount of a composition of the invention to the patient in need of such treatment to reduce or prevent ototoxin-induced hearing impairment associated with the chemotherapeutic drug. In another embodiment the methods of treatment are applied to hearing impairments resulting from the administration of a chemotherapeutic agent to treat its ototoxic side-effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas. Cisplatin-like compounds include carboplatin (Paraplatin®), tetraplatin, oxaliplatin, aroplatin and transplatin inter alia. In another embodiment the methods of the invention are applied to hearing impairments resulting from the administration of quinine and its synthetic substitutes, typically used in the treatment of malaria, to treat its ototoxic side-effect. In another embodiment the methods of the invention are applied to hearing impairments resulting from administration of a diuretic. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics are also used in nonedematous states for example hypertension, hypercalcemia, idiopathic hypercalciuria, and nephrogenic diabetes insipidus.

In another embodiment, the methods of the invention are applied to treating or preventing the incidence or severity of pressure sores. The methods and compositions involve administering to a mammal in need of such treatment a prophylactically or therapeutically effective amount of one or more compounds which down-regulate expression of the RTP801L gene, particularly novel small interfering RNAs (siRNAs). The compounds which treat or prevent the incidence or severity of pressure sores, particularly the novel siRNAs are preferably administered locally within the damaged area. The methods and compositions of the present invention are effective in the treatment and prevention of pressure sores or pressure ulcers developed when sustained pressure (usually from a bed or wheelchair) cuts off circulation to vulnerable parts of the body. The methods and compositions are effective in patients with diminished or absent sensation or who are debilitated, emaciated, paralyzed, or long bedridden. The compositions of the present invention are effective also in improving the healing of pressure sores using the compositions. The compositions may be used at any particular stage in the healing process including the stage before any healing has initiated or even before a specific sore is made (prophylactic treatment).

Other kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions.

The methods and compositions of the present invention are also effective in the treatment and prevention of any chronic wounds including inter alia pressure sores, venous ulcers, and diabetic ulcers. In all these chronic wound types, the underlying precipitating event is a period of ischemia followed by a period of reperfusion. These ischemia-reperfusion events are usually repetitive, which means the deleterious effects of ischemia-reperfusion are potentiated and eventually sufficient to cause ulceration. For both pressure sores and diabetic foot ulcers, the ischemic event is the result of prolonged pressure sufficient to prevent tissue perfusion, and when the pressure is finally relieved, the reperfusion injury occurs. The present compositions are effective in inhibiting the damage caused by ischemia-reperfusion in chronic wounds.

The present compositions are also effective in other conditions associated with ischemia-reperfusion such as but not limited to: organ transplantation, intestinal and colon anastamoses, operations on large blood vessels, stitching detached limbs, balloon angioplasty or any cardiac surgery, stroke or brain trauma, limb transplantation, pulmonary hypertension, hypoxemia, and noncardiogenic pulmonary edema, acute renal failure, acute glaucoma, diabetic retinopathy, hypertensive retinopathy, and retinal vascular occlusion, cochlear ischemia, microvascular surgery and ischemic lesions in scleroderma.

The methods and compositions of the present invention are also effective in the treatment of accoustic trauma or mechanical trauma, preferably accoustic or mechanical trauma that leads to inner ear hair cell loss. Accoustic trauma to be treated in the present invention may be caused by a single exposure to an extremely loud sound, or following long-term exposure to everyday loud sounds above 85 decibels. Mechanical inner ear trauma to be treated in the present invention is for example the inner ear trauma following an operation of electronic device insertion in the inner ear. The compositions of the present invention prevent or minimize the damage to inner ear hair cells associated with the operation. The compounds which reduce or prevent the ototoxin-induced hearing impairment, particularly the novel siRNAs are preferably administered locally within the inner ear.

Additionally, as detailed above, the compound of the present invention can be used to treat any condition in which ischemia is involved, optionally ischemia-reperfusion. Such condition include ischmia or ischemia-reperfusion resulting from an angioplasty, cardiac surgery or thrombolysis; organ transplant; as a result of plastic surgery; during severe compartment syndrome; during re-attachment of severed limbs; as a result of multiorgan failure syndrome; in the brain as a result of stroke or brain trauma; in connection with chronic wounds such as pressure sores, venous ulcers and diabetic ulcers; during skeletal muscle ischemia or limb transplantation; as a result of mesenteric ischemia or acute ischemic bowel disease; respiratory failure as a result of lower torso ischemia, leading to pulmonary hypertension, hypoxemia, and noncardiogenic pulmonary edema; acute renal failure as observed after renal transplantation, major surgery, trauma, and septic as well as hemorrhagic shock; Sepsis; Retinal ischemia occurring as a result of acute vascular occlusion, leading to loss of vision in a number of ocular diseases such as acute glaucoma, diabetic retinopathy, hypertensive retinopathy, and retinal vascular occlusion; Cochlear ischemia; flap failure in microvascular surgery for head and neck defects; Raynaud's phenomenon and the associated digital ischemic lesions in scleroderma; spinal cord injury; vascular surgery; Traumatic rhabdomyolysis (crush syndrome); and myoglobinuria. Further, ischemia/reperfusion may be involved in the following conditions: hypertension, hypertensive cerebral vascular disease, rupture of aneurysm, a constriction or obstruction of a blood vessel—as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor; and diseases such as stroke, Parkinson's disease, epilepsy, depression, ALS, Alzheimer's disease, Huntington's disease and any other disease-induced dementia (such as HIV induced dementia for example). Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracarnial hematoma or edema). Similarly, traumatic constriction or compression can arise from the presence of a mass of abnormal tissue, such as a metastatic or primary tumor.

"Treating a disease" refers to administering a therapeutic substance effective to ameliorate symptoms associated with a disease, to lessen the severity or cure the disease, or to prevent the disease from occurring. "Treatment" refers to both therapeutic treatment and prophylactic or preventative measures, wherein the object is to prevent or slow down (lessen) a disease or disorder.

A "therapeutically effective dose" refers to an amount of a pharmaceutical compound or composition which is effective to achieve an improvement in a patient or his physiological systems including, but not limited to, improved survival rate, more rapid recovery, or improvement or elimination of symptoms, and other indicators as are selected as appropriate determining measures by those skilled in the art.

The methods of treating the diseases disclosed herein and included in the present invention may include administering an RTP801L inhibitor in conjunction with an additional RTP801L inhibitor, a substance which improves the pharmacological properties of the active ingredient as detailed below, or an additional compound known to be effective in the treatment of the disease to be treated, such as macular degeneration, glaucoma, COPD, ALI, ARF, DR, cisplatin-induced deafness, and age-related deafness, inter alia. By "in conjunction with" is meant prior to, simultaneously or subsequent to. Further detail on exemplary conjoined therapies is given below.

In another embodiment, the present invention provides for the use of a therapeutically effective dose of an RTP801L inhibitor for the preparation of a medicament for promoting recovery in a patient suffering from macular degeneration, glaucoma, COPD, ALI, ARF, DR, cisplatin-induced deafness, age-related deafness or any eye disease, microvascular or respiratory condition or hearing disorder as detailed above, and the use of a therapeutically effective dose of an RTP801L inhibitor for the preparation of a medicament for treating said diseases and conditions. In this embodiment, the RTP801L inhibitor may comprise a polynucleotide which comprises consecutive nucleotides having a sequence which comprises an antisense sequence to the sequence set forth in FIG. 1 (SEQ ID No: 1). Additionally, the RTP801L inhibitor may be an expression vector comprising a polynucleotide having a sequence which is an antisense sequence to the sequence set forth in FIG. 1 (SEQ ID No:1). The RTP801L inhibitor according to said uses may also be an antibody, such as a neutralizing antibody which specifically binds to an epitope present within a polypeptide which comprises consecutive amino acids, the sequence of which is set forth in FIG. 2 (SEQ ID No:2). Additionally, the RTP801L inhibitor may be an RNA molecule which targets the RTP801L gene mRNA such as a ribozyme or an siRNA, optionally an siRNA comprising consecutive nucleotides having a sequence identical to any one of the sequences set forth in Table A (SEQ ID NOs:3-1852) and preferably, siRNA Nos:72 and 73 of Table A.

Thus, according to the information disclosed herein, the RTP801L inhibitor to be used with any of the methods disclosed herein, in any of the uses disclosed herein and in any of the pharmaceutical compositions disclosed herein, may be selected from the group consisting of an siRNA molecule, a vector comprising an siRNA molecule, a vector which can express an siRNA molecule and any molecule which is endogenously processed into an siRNA molecule. As detailed herein, said siRNA molecule is preferably an siRNA comprising consecutive nucleotides having a sequence identical to any one of the sequences set forth in Table A and preferably siRNA Nos:72 and 73 of Table A.

"Respiratory disorder" refers to conditions, diseases or syndromes of the respiratory system including but not limited to pulmonary disorders of all types including chronic obstructive pulmonary disease (COPD), acute lung injury (ALI), emphysema, chronic bronchitis, asthma and lung cancer, inter alia. Emphysema and chronic bronchitis may occur as part of COPD or independently.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, anterior ischemic optic neuropathy, optic neuritis (primary or secondary to autoimmune diseases), glaucoma, von hippel lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, Birdshot retinochoroidopathy, long-standing retinal detachment; systemic conditions such as Diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, neuropathies, nephropathies, microvascular diseases of the kidney, acute renal failure and ischemic microvascular conditions, inter alia Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. All these neovascular conditions may be treated using the compounds and pharmaceutical compositions of the present invention.

"Eye disease" refers to refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases, glaucoma, and retinal vein occlusion (RVO). Some conditions disclosed herein, such as DR, which may be treated according to the methods of the present invention have been regarded as either a microvascular disorder and an eye disease, or both, under the definitions presented herein. Hearing impairments relevant to the invention may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than 85 decibels (db) that damages the inner ear. Preferably, the hearing loss is caused by aging (presbycusis) or an ototoxic drug that affects the auditory portion of the inner ear, particularly inner ear hair cells. Incorporated herein by reference are Chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Hearing disorders or impairments (or balance impairment) to be treated or prevented in the context of the present invention are preferably, without being bound by theory, trauma-induced deafness, age-related deafness and ototoxin-induced inner ear hair cells apoptotic damage. Those in need of treatment include those already experiencing a hearing impairment, those prone to having the impairment, and those in which the impairment is to be prevented. Without being bound by theory, the hearing impairments may be due to apoptotic inner ear hair cell damage or loss, wherein the damage or loss is caused by infection, mechanical injury, loud sound, aging, or, in particular, chemical-induced ototoxicity.

Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

The hearing impairment may be induced by chemotherapy. In more detail, hearing impairment may be caused by chemotherapeutic agents such as etoposide, 5-FU (5-fluorouracil), cis-platinum, doxorubicin, a vinca alkaloid, vincristine, vinblastine, vinorelbine, taxol, cyclophosphamide, ifosfamide, chlorambucil, busulfan, mechlorethamine, mitomycin, dacarbazine, carboplatinum, thiotepa, daunorubicin, idarubicin, mitoxantrone, bleomycin, esperamicin A1, dactinomycin, plicamycin, carmustine, lomustine, tauromustine, streptozocin, melphalan, dactinomycin, procarbazine, dexamethasone, prednisone, 2-chlorodeoxyadenosine, cytarabine, docetaxel, fludarabine, gemcitabine, herceptin, hydroxyurea, irinotecan, methotrexate, oxaliplatin, rituxin, semustine, epirubicin, etoposide, tomudex and topotecan, or a chemical analog of one of these chemotherapeutic agents. The chemotherapeutic agents most likely to cause hearing impairment is cis-platinum(cisplatin) and cisplatin-like compounds By "ototoxin" in the context of the present invention is meant a substance that through its chemical action injures, impairs or inhibits the activity of the sound receptors of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin and cisplatin-like compounds, taxol and taxol-like compounds, dideoxy-compounds, e.g., dideoxyinosine; alcohol; metals; industrial toxins involved in occupational or environmental exposure; contaminants of food or medicinals; and over-doses of vitamins or therapeutic drugs, e.g., antibiotics such as penicillin or chloramphenicol, and megadoses of vitamins A, D, or B6, salicylates, quinines and loop diuretics. By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e g., aerial or aqueous exposure.

"RTP801L gene" refers to the RTP801L coding sequence open reading frame, as shown in FIG. 1 (SEQ ID NO:1), or any homologous sequence thereof preferably having at least 70% identity, more preferable 80% identity, even more preferably 90% or 95% identity. This encompasses any sequences derived from SEQ ID NO:1 which have undergone mutations, alterations or modifications as described herein. Thus, in a preferred embodiment RTP801L is encoded by a nucleic acid sequence according to SEQ. ID. NO. 1. It is also within the present invention that the nucleic acids according to the present invention are only complementary and identical, respectively, to a part of the nucleic acid coding for RTP801L as, preferably, the first stretch and first strand is typically shorter than the nucleic acid according to the present invention. It is also to be acknowledged that based on the amino acid sequence of RTP801L any nucleic acid sequence coding for such amino acid sequence can be perceived by the one skilled in the art based on the genetic code. However, due to the assumed mode of action of the nucleic acids according to the present invention, it is most preferred that the nucleic acid coding for RTP801L, preferably the mRNA thereof, is the one present in the organism, tissue and/or cell, respectively, where the expression of RTP801L is to be reduced.

"RTP801L polypeptide" refers to the polypeptide of the RTP801L gene, and is understood to include, for the purposes of the instant invention, the terms "RTP777", "DDIT4L" "REDD2", and "SMHS1", derived from any organism, optionally man, splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the RTP801L coding sequence, such as, inter alia, point mutations, substitutions, deletions and insertions which may cause a difference in a few amino acids between the resultant polypeptide and the naturally occurring RTP801L. Polypeptides encoded by nucleic acid sequences which bind to the RTP801L coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified RTP801L or chemically modified fragments of RTP801L are also included in the term, so long as the biological activity is retained. RTP801L preferably has or comprises an amino acid sequence according to SEQ. ID. NO. 2. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention. Particular fragments of RTP801L include amino acids 1-50, 51-100, 101-150 and 151-193 of the sequence shown in FIG. 2. Further particular fragments of RTP801L include amino acids 25-74, 75-124, 125-174 and 175-193 of the sequence shown in FIG. 2.

Without being bound by theory, RTP801L may be a factor acting in fine-tuning of cell response to energy disbalance. As such, it is a target suitable for treatment of any disease where cells should be rescued from apoptosis due to stressful conditions (e.g. diseases accompanied by death of normal cells) or where cells, which are adapted to stressful conditions due to changes in RTP801L expression (e.g. cancer cells), should be killed. In the latter case, RTP801L may be viewed as a survival factor for cancer cells and its inhibitors may treat cancer as a monotherapy or as sensitising drugs in combination with chemotherapy or radiotherapy. The assignee of the present invention has previously discovered gene RTP801 (see above) and molecules effective in inhibiting gene RTP801 (see co-assigned PCT publication No. WO06/023544A2 and PCT Application No. PCT/US2007/01468, hereby incorporated by reference in their entirety). Although RTP801L shares sequence and functional homology with RTP801, the assignee of the present invention has discovered that inhibition of RTP801 does not cause simultaneous inhibition of RTP801L, and vice versa. Therefore, RTP801L is an excellent target for inhibition in the conditions disclosed herein, and its inhibition is gene-specific. Tandem therapies which inhibit both RTP801 and RTP801L can have additional advantages and are discussed herein blow.

The term "polynucleotide" refers to any molecule composed of DNA nucleotides, RNA nucleotides or a combination of both types, i.e. that comprises two or more of the bases guanidine, cytosine, thymidine, adenine, uracil or inosine, inter alia. A polynucleotide may include natural nucleotides, chemically modified nucleotides and synthetic nucleotides, or chemical analogs thereof. The term includes "oligonucleotides" and encompasses "nucleic acids".

The term "amino acid" refers to a molecule which consists of any one of the 20 naturally occurring amino acids, amino acids which have been chemically modified (see below), or synthetic amino acids.

The term "polypeptide" refers to a molecule composed of two or more amino acids residues. The term includes peptides, polypeptides, proteins and peptidomimetics.

A "peptidomimetic" is a compound containing non-peptidic structural elements that is capable of mimicking the biological action(s) of a natural parent peptide. Some of the classical peptide characteristics such as enzymatically scissile peptidic bonds are normally not present in a peptidomimetic.

By the term "dominant negative peptide" is meant a polypeptide encoded by a cDNA fragment that encodes for a part of a protein (see Herskowitz I.: *Functional inactivation of genes by dominant negative mutations. Nature.* 1987 Sep. 17-23; 329(6136):219-22. Review; Roninson I B et al., *Genetic suppressor elements: new tools for molecular oncology*—thirteenth Cornelius P. Rhoads Memorial Award Lecture. *Cancer Res.* 1995 Sep. 15; 55(18):4023). This peptide can have a different function from the protein from which it was derived. It can interact with the full protein and inhibit its activity or it can interact with other proteins and inhibit their activity in response to the full-length (parent) protein. Dominant negative means that the peptide is able to overcome the natural parent protein and inhibit its activity to give the cell a different characteristic, such as resistance or sensitization to death or any cellular phenotype of interest. For therapeutic intervention the peptide itself may be delivered as the active ingredient of a pharmaceutical composition, or the cDNA can be delivered to the cell utilizing known methods.

Preparation of Peptides and Polypeptides

Polypeptides may be produced via several methods, for example:

1) Synthetically:

Synthetic polypeptides can be made using a commercially available machine, using the known sequence of RTP801L or a portion thereof.

2) Recombinant Methods:

A preferred method of making the RTP801L polypeptides or fragments thereof is to clone a polynucleotide comprising the cDNA of the RTP801L gene into an expression vector and culture the cell harboring the vector so as to express the encoded polypeptide, and then purify the resulting polypeptide, all performed using methods known in the art as described in, for example, Marshak et al., "*Strategies for Protein Purification and Characterization. A laboratory course manual.*" CSHL Press (1996). (in addition, see *Bibl Haematol.* 1965; 23:1165-74 *Appl Microbiol.* 1967 July; 15(4):851-6; *Can J. Biochem.* 1968 May; 46(5):441-4; *Biochemistry.* 1968 July; 7(7):2574-80; *Arch Biochem Biophys.* 1968 Sep. 10; 126(3): 746-72; *Biochem Biophys Res Commun.* 1970 Feb. 20; 38(4):825-30;).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al. (1986).

3) Purification from Natural Sources:

RTP801L polypeptide, or naturally occurring fragments thereof, can be purified from natural sources (such as tissues) using many methods known to one of ordinary skill in the art, such as for example: immuno-precipitation with anti-RTP801L antibody, or matrix-bound affinity chromatography with any molecule known to bind RTP801L. Protein purification is practiced as is known in the art as described in, for example, Marshak et al., "*Strategies for Protein Purification and Characterization. A laboratory course manual.*" CSHL Press (1996).

By "biological effect of RTP801L" or "RTP801L biological activity" is meant, without being bound by theory, the effect of RTP801L on apoptosis, such as apoptosis of alveolar cells in respiratory disorders; apoptosis of inner ear hair cells in hearing disorders, apoptosis of macular cells in macular degeneration, apoptosis of cells related to ischemia in any diseases or conditions, inter alia. The effect of RTP801L on apoptosis may be direct or indirect, and includes, without being bound by theory, any effect of RTP801L of induced by hypoxic or hyperoxic conditions. The indirect effect includes, but is not limited to, RTP801L binding to or having an effect on one of several molecules, which are involved in a signal transduction cascade resulting in apoptosis.

"Apoptosis" refers to a physiological type of cell death which results from activation of some cellular mechanisms, i.e. death that is controlled by the machinery of the cell. Apoptosis may, for example, be the result of activation of the cell machinery by an external trigger, e.g. a cytokine or anti-FAS antibody, which leads to cell death or by an internal signal. The term "programmed cell death" may also be used interchangeably with "apoptosis".

"Apoptosis-related disease" refers to a disease whose etiology is related either wholly or partially to the process of apoptosis. The disease may be caused either by a malfunction of the apoptotic process (such as in cancer or an autoimmune disease) or by overactivity of the apoptotic process (such as in certain neurodegenerative diseases). Many diseases in which RTP801L is involved are apoptosis-related diseases. For example, apoptosis is a significant mechanism in dry AMD, whereby slow atrophy of photoreceptor and pigment epithelium cells, primarily in the central (macular) region of retina takes place. Neuroretinal apoptosis is also a significant mechanism in diabetic retinopathy.

An "inhibitor" is a compound which is capable of inhibiting the activity of a gene or the product of such gene to an extent sufficient to achieve a desired biological or physiological effect. An "RTP801L inhibitor" is a compound which is capable of inhibiting the activity of the RTP801L gene or RTP801L gene product, particularly the human RTP801L gene or gene product. Such inhibitors include substances that affect the transcription or translation of the gene as well as substances that affect the activity of the gene product. An RTP801L inhibitor may also be an inhibitor of the RTP801L promoter. Examples of such inhibitors may include, inter alia: polynucleotides such as AS fragments, siRNA, or vectors comprising them; polypeptides such as dominant negatives, antibodies, and enzymes; catalytic RNAs such as ribozymes; and chemical molecules with a low molecular weight e.g. a molecular weight below 2000 daltons. Specific RTP801L inhibitors are given below.

"Expression vector" refers to a vector that has the ability to incorporate and express heterologous DNA fragments in a foreign cell. Many prokaryotic and eukaryotic expression vectors are known and/or commercially available. Selection of appropriate expression vectors is within the knowledge of those having skill in the art.

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;
(2) (Fab')$_2$, the fragment of the antibody that can be obtained by treating whole antibody with the enzyme pepsin without subsequent reduction; F(ab'$_2$) is a dimer of two Fab fragments held together by two disulfide bonds;
(3) Fv, defined as a genetically engineered fragment containing the variable region of the light chain and the variable region of the heavy chain expressed as two chains; and
(4) Single chain antibody (SCA), defined as a genetically engineered molecule containing the variable region of the light chain and the variable region of the heavy chain linked by a suitable polypeptide linker as a genetically fused single chain molecule.

By the term "epitope" as used in this invention is meant an antigenic determinant on an antigen to which the antibody binds. Epitopic determinants usually consist of chemically active surface groupings of molecules such as amino acids or sugar side chains and usually have specific three-dimensional structural characteristics, as well as specific charge characteristics.

Preparation of Anti-RTP801L Antibodies

Antibodies which bind to RTP801L or a fragment derived therefrom may be prepared using an intact polypeptide or fragments containing smaller polypeptides as the immunizing antigen. For example, it may be desirable to produce antibodies that specifically bind to the N- or C-terminal or any other suitable domains of the RTP801L. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, *Current Protocols in Immunology*, Wiley Interscience, 1994).

Methods for making antibodies of all types, including fragments, are known in the art (See for example, Harlow and Lane, *Antibodies: A Laboratory Manual*, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP239, 400: PCT publication WO.91/09967; U.S. Pat. Nos. 5,225, 539; 5,530,101; and 5,585,089, veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

The terms "chemical compound", "small molecule", "chemical molecule" "small chemical molecule" and "small chemical compound" are used interchangeably herein and are understood to refer to chemical moieties of any particular type which may be synthetically produced or obtained from natural sources and usually have a molecular weight of less than 2000 daltons, less than 1000 daltons or even less than 600 daltons.

The present invention also relates to functional nucleic acids comprising a double-stranded structure, their use for the manufacture of a medicament, a pharmaceutical composition comprising such functional nucleic acids and a method for the treatment of a patient.

Hypoxia has been recognised as a key element in the patho-mechanism of quite a number of diseases such as stroke, emphysema and infarct which are associated with sub-optimum oxygen availability and tissue damaging responses to the hypoxia conditions. In fast-growing tissues, including tumor, a sub-optimum oxygen availability is compensated by undesired neo-angiogenesis. Therefore, at least in case of cancer diseases, the growth of vasculature is undesired.

In view of this, the inhibition of angiogenesis and vascular growth, respectively, is subject to intense research. Already today some compounds are available which inhibit undesired angiogenesis and vascular growth. Some of the more prominent compounds are those inhibiting VEGF and the VEGF receptor. In both cases, the effect of VEGF is avoided by either blocking VEGF as such, for example by using an antibody directed against VEGF such as pursued by Genentech's AVASTIN (monoclonal AB specific for VEGF) (Ferrara N.; Endocr Rev. 2004 August; 25(4):581-611), or by blocking the corresponding receptor, i.e. the VEGF receptor (Traxler P; Cancer Res. 2004 Jul. 15; 64(14):4931-41; or Stadler W M et al., Clin Cancer Res. 2004 May 15; 10(10):3365-70).

As, however, angiogenesis and the growth of vasculature is a very basic and vital process in any animal and human being, the effect of this kind of compound has to be focused at the particular site where angiogenesis and vascular growth is actually undesired which renders appropriate targeting or delivery a critical issue in connection with this kind of therapeutic approach.

It is thus an objective of the present invention to provide further means for the treatment of diseases involving undesired growth of vasculature and angiogenesis, respectively.

By "small interfering RNA" (siRNA) is meant an RNA molecule which decreases or silences (prevents) the expression of a gene/mRNA of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs) (Fire al, 1998, Nature 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, Genes Dev., 15, 188). For recent information on these terms and proposed mechanisms, see Bernstein E., Denli A M., Hannon G J: *The rest is silence. RNA.* 2001 November; 7(11):1509-21; and Nishikura K.: *A short primer on RNAi: RNA-directed RNA polymerase acts as a key catalyst. Cell.* 2001 Nov. 16; 107(4):415-8. Examples of siRNA molecules which may be used in the present invention are given in Tables A.

During recent years, RNAi has emerged as one of the most efficient methods for inactivation of genes (Nature Reviews, 2002, v. 3, p. 737-47; Nature, 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (Nature, 2001, v. 409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v. 3, p. 737-47; Curr Opin Mol. Ther. 2003 June; 5(3):217-24).

For disclosure on how to design and prepare siRNA to known genes see for example Chalk A M, Wahlestedt C, Sonnhammer E L. *Improved and automated prediction of effective siRNA* Biochem. Biophys. Res. Commun. 2004 Jun. 18; 319(1):264-74; Sioud M, Leirdal M., *Potential design rules and enzymatic synthesis of siRNAs*, Methods Mol Biol. 2004; 252:457-69; Levenkova N, Gu Q, Rux J J.: Gene specific siRNA selector Bioinformatics. 2004 Feb. 12; 20(3): 430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference* Nucleic Acids Res. 2004 Feb. 9; 32(3):936-48. See also Liu Y, Braasch D A, Nulf C J, Corey D R. *Efficient and isoform-selective inhibition of cellular gene expression by peptide nucleic acids* Biochemistry, 2004 Feb. 24; 43(7):1921-7. See also PCT publications WO 2004/015107 (Atugen) and WO 02/44321 (Tuschl et al), and also Chiu Y L, Rana T M. siRNA function in RNAi: a chemical modification analysis, RNA 2003 September; 9(9):1034-48 and U.S. Pat. Nos. 5,898,031 and 6,107,094 (Crooke) for production of modified/more stable siRNAs.

DNA-based vectors capable of generating siRNA within cells have been developed. The method generally involves transcription of short hairpin RNAs that are efficiently processed to form siRNAs within cells. Paddison et al. *PNAS* 2002, 99:1443-1448; Paddison et al. Genes & Dev 2002, 16:948-958; Sui et al. *PNAS* 2002, 8:5515-5520; and Brummelkamp et al. *Science* 2002, 296:550-553. These reports describe methods to generate siRNAs capable of specifically targeting numerous endogenously and exogenously expressed genes.

For delivery of siRNAs, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 pp 132-138.

siRNAs of the Present Invention

General Specifications of siRNAs of the Present Invention

In some embodiments the oligoribonucleotide according to the present invention comprises modified siRNA. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid, and the second strand comprises ribonucleotide sequence at least partially complementary to the first strand and wherein said first strand and/or said second strand comprises a plurality of groups of modified ribonucleotides having a modification at the 2'-position of the sugar moiety whereby within each strand each group of modified ribonucleotides is flanked on one or both sides by a group of flanking ribonucleotides whereby each ribonucleotide forming the group of flanking ribonucleotides is selected from an unmodified ribonucleotide or a ribonucleotide having a modification different from the modification of the groups of modified ribonucleotides.

The group of modified ribonucleotides and/or the group of flanking ribonucleotides comprise a number of ribonucleotides selected from the group consisting of an integer from 1 to 10. Accordingly, the group thus comprises one nucleotide, two nucleotides, three nucleotides, four nucleotides, five nucleotides, six nucleotides, seven nucleotides, eight nucleotides, nine nucleotides or ten nucleotides.

The groups of modified nucleotides and flanking nucleotides may be organized in a pattern on at least one of the strands.

In some embodiments the first and second strands comprise a pattern of modified nucleotides. In various embodiments the pattern of modified nucleotides of said first strand is identical relative to the pattern of modified nucleotides of the second strand.

In other embodiments the pattern of modified nucleotides of said first strand is shifted by one or more nucleotides relative to the pattern of modified nucleotides of the second strand.

In some preferred embodiments the middle ribonucleotide in the antisense strand is an unmodified nucleotide. For example, in a 19-oligomer antisense strand, ribonucleotide number 10 is unmodified; in a 21-oligomer antisense strand, ribonucleotide number 11 is unmodified; and in a 23-oligomer antisense strand, ribonucleotide number 12 is unmodified. The modifications or pattern of modification, if any, of the siRNA must be planned to allow for this.

The modifications on the 2' moiety of the sugar residue include amino, fluoro, methoxy alkoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

In some embodiments the siRNA is blunt ended, on one or both ends. More specifically, the siRNA may be blunt ended on the end defined by the 5'-terminus of the first strand and the 3'-terminus of the second strand, or the end defined by the 3'-terminus of the first strand and the 5'-terminus of the second strand.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 4 nucleotides The length of RNA duplex is from about 18 to about 40 ribonucleotides, preferably 19 or 23 ribonucleotides. Further, the length of each strand may independently have a length selected from the group consisting of about 15 to about 40 bases, preferably 18 to 23 bases and more preferably 19, 20 or 21 ribonucleotides.

Additionally, the complementarity between said first strand and the target nucleic acid may be perfect. In some embodiments, the strands are substantially complementary, i.e. having one, two or up to three mismatches between said first strand and the target nucleic acid.

In some embodiments the first strand and the second strand each comprise at least one group of modified ribonucleotides and at least one group of flanking ribonucleotides, whereby each group of modified ribonucleotides comprises at least one ribonucleotide and whereby each group of flanking ribonucleotides comprises at least one ribonucleotide, wherein each group of modified ribonucleotides of the first strand is aligned with a group of flanking ribonucleotides on the second strand, and wherein the 5' most terminal ribonucleotide is selected from a group of modified ribonucleotides, and the 3' most terminal ribonucleotide of the second strand is a selected from the group of flanking ribonucleotide. In some embodiments each group of modified ribonucleotides consists of a single ribonucleotide and each group of flanking ribonucleotides consists of a single nucleotide In yet other embodiments the ribonucleotide forming the group of flanking ribonucleotides on the first strand is an unmodified ribonucleotide arranged in a 3' direction relative to the ribonucleotide forming the group of modified ribonucleotides, and the ribonucleotide forming the group of modified ribonucleotides on the second strand is a modified ribonucleotide which is arranged in 5' direction relative to the ribonucleotide forming the group of flanking ribonucleotides.

In some embodiments the first strand of the siRNA comprises five to about twenty, eight to twelve, preferably nine to eleven, groups of modified ribonucleotides, and the second strand comprises seven to eleven, preferably eight to ten, groups of modified ribonucleotides.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides. Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 10-2000 nucleobases, preferably about 3 to about 50 nucleobases.

In various embodiments, the present invention provides a compound having structure A:

```
5'    (N)_x - Z 3'      (antisense strand)

3'  Z'-(N')_y 5'         (sense strand)
``` wherein each N and N' is a ribonucleotide selected from the group consisting of a modified ribonucleotide or an unmodified ribonucleotide and each of $(N)_x$ and $(N')_y$ is an oligomer in which each consecutive N or N' is joined to the next N or N' by a covalent bond;

wherein each of x and y is an integer between 18 and 40;

wherein each of Z and Z' may be present or absent, but if present is dTdT and is covalently attached at the 3' terminus of the strand in which it is present;

and wherein the sequence of $(N)_x$ comprises an antisense sequence having substantial identity to about 18 to about 40 consecutive ribonucleotides in the mRNA transcribed from the RTP801L gene.

In preferred embodiments the antisense sequence is selected from a sequence presented in Table A.

It will be readily understood by those skilled in the art that the compounds of the present invention consist of a plurality of ribonucleotides, which are linked through covalent linkages. Each such covalent linkage may be a phosphodiester linkage, a phosphothioate linkage, or a combination of both, along the length of the ribonucleotide sequence of the individual strand. Other possible backbone modifications are described inter alia in U.S. Pat. Nos. 5,587,361; 6,242,589; 6,277,967; 6,326,358; 5,399,676; 5,489,677; and 5,596,086.

In particular embodiments, x and y are independently an integer between about 18 to about 40, preferably from about 19 to about 23. In a particular embodiment, x is equal to y (i.e. x=y) and in preferred embodiments x=y=19, x=y=20 or x=y=21. In a particularly preferred embodiment x=y=19.

In one embodiment of the compound of the invention, Z and Z' are both absent; in another embodiment one of Z or Z' is present.

In one embodiment all of the ribonucleotides of the compound are unmodified in their sugar residues.

In preferred embodiments at least one ribonucleotide is modified in its sugar residue, preferably by the addition of a moiety at the 2' position. A preferred moiety is selected from the group consisting of amino, fluoro, methoxy, alkoxy and alkyl groups. In a presently preferred embodiment the moiety at the 2' position is methoxy (2'-O-Me).

In preferred embodiments of the invention, alternating ribonucleotides are modified in both the antisense and the sense strands of the compound. In particular the exemplified siRNA has been modified such that a 2'-O-methyl (Me) group was present on the first, third, fifth, seventh, ninth, eleventh, thirteenth, fifteenth, seventeenth and nineteenth nucleotide of the antisense strand, whereby the very same modification, i.e. a 2'-O-Me group, was present at the second, fourth, sixth, eighth, tenth, twelfth, fourteenth, sixteenth and eighteenth nucleotide of the sense strand. Additionally, it is to be noted that these particular siRNA compounds are also blunt ended.

In preferred embodiments of the compounds of the invention having alternating ribonucleotides modified in both the antisense and the sense strands of the compound, for 19 mers and 23 mers the ribonucleotides at the 5' and 3' termini of the antisense strand are modified in their sugar residues, and the ribonucleotides at the 5' and 3' termini of the sense strand are unmodified in their sugar residues. For 21 mers the ribonucleotides at the 5' and 3' termini of the sense strand are modified in their sugar residues, and the ribonucleotides at the 5' and 3' termini of the antisense strand are unmodified in their sugar residues. As mentioned above, it is preferred that the middle nucleotide of the antisense strand is unmodified.

In a particularly preferred embodiment the ribonucleic acid sequence is one of Table A, preferably of the sequences having ID Nos. 72 and 73.

Thus, in a particularly preferred embodiment, the present invention comprises a compound having the structure

```
5' UCUUGAGCAAUUCUCUGGG 3' antisense strand (SEQ ID NO: 1000)
   |||||||||||||||||||
3' AGAACUCGUUAAGAGACCC 5' sense strand     (SEQ ID NO: 75)
``` wherein alternating ribonucleotides in the antisense and the sense strands are modified to result in a 2'-O-methyl modification in the sugar residue of the ribonucleotides; wherein the ribonucleotides at the 5' and 3' termini of the antisense strand are modified to result in the 2'-O-methyl modification; wherein the ribonucleotides at the 5' and 3' termini of the sense strand are unmodified; and wherein the antisense and the sense strands are non-phosphorylated at the 3' and 5' termini.

And a compound having the structure

```
5' UCUUGAGCAAUUCUCUGGG 3' antisense strand (SEQ ID NO: 1000)
   |||||||||||||||||||
3' AGAACUCGUUAAGAGACCC 5' sense strand     (SEQ ID NO: 75)
``` wherein alternating ribonucleotides in the antisense and the sense strands are modified to result in a 2'-O-methyl modification in the sugar residue of the ribonucleotides; wherein the ribonucleotides at the 5' and 3' termini of the antisense strand are modified to result in the 2'-O-methyl modification; wherein the ribonucleotides at the 5' and 3' termini of the sense strand are unmodified; and wherein the antisense and the sense strands are phosphorylated at the 3' termini.

And a compound having the structure

```
5' AUCUUGAGCAAUUCUCUGG 3' antisense strand (SEQ ID NO: 999)
   |||||||||||||||||||
3' UAGAACUCGUUAAGAGACC 5' sense strand     (SEQ ID NO: 74)
``` wherein alternating ribonucleotides in the antisense and the sense strands are modified to result in a 2'-O-methyl modification in the sugar residue of the ribonucleotides; wherein the ribonucleotides at the 5' and 3' termini of the antisense strand are modified to result in the 2'-O-methyl modification; wherein the ribonucleotides at the 5' and 3' termini of the sense strand are unmodified; and wherein the antisense and the sense strands are non-phosphorylated at the 3' and 5' termini.

And a compound having the structure

```
5' AUCUUGAGCAAUUCUCUGG 3' antisense strand (SEQ ID NO: 999)
   |||||||||||||||||||
3' UAGAACUCGUUAAGAGACC 5' sense strand     (SEQ ID NO: 74)
``` wherein alternating ribonucleotides in the antisense and the sense strands are modified to result in a 2'-O-methyl modification in the sugar residue of the ribonucleotides; wherein the ribonucleotides at the 5' and 3' termini of the antisense strand are modified to result in the 2'-O-methyl modification; wherein the ribonucleotides at the 5' and 3' termini of the sense strand are unmodified; and wherein the antisense and the sense strands are phosphorylated at the 3' termini.

Further, the present invention comprises a pharmaceutical composition comprising any one of the above compounds and a pharmaceutically acceptable excipient.

These compounds and pharmaceuticals may be used to treat a patient suffering from any one of the diseases or conditions disclosed herein; further, any of the siRNAs in Table A may be used in the same manner.

According to one preferred embodiment of the invention, the antisense and the sense strands of the siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

The invention further provides a vector capable of expressing any of the aforementioned oligoribonucleotides in unmodified form in a cell after which appropriate modification may be made. In preferred embodiment the cell is a mammalian cell, preferably a human cell.

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different siRNAs.

The invention further provides a pharmaceutical composition comprising at least one compound of the invention covalently or non-covalently bound to one or more compounds of the invention in an amount effective to inhibit the RTP801L gene; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to down-regulate expression in a cell of the human RTP801L gene of the present invention, the compound comprising a sequence substantially complementary to the sequence of $(N)_x$ Substantially complementary refers to complementarity of greater than about 84% to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, the invention provides a method of down-regulating the expression of the RTP801L gene by at least 50% as compared to a control comprising contacting an mRNA transcript of the RTP801L gene with one or more of the compounds of the invention.

In one embodiment the oligoribonucleotide is down-regulating the RTP801L gene, whereby the down-regulation is selected from the group comprising down-regulation of gene function, down-regulation of polypeptide and down-regulation of mRNA expression.

In one embodiment the compound is down-regulating the RTP801L polypeptide, whereby the down-regulation is selected from the group comprising down-regulation of function (which may be examined by an enzymatic assay or a binding assay with a known interactor of the native gene/polypeptide, inter alia), down-regulation of protein (which may be examined by Western blotting, ELISA or immunoprecipitation, inter alia) and down-regulation of mRNA expression (which may be examined by Northern blotting, quantitative RT-PCR, in-situ hybridization or microarray hybridisation, inter alia).

In additional embodiments the invention provides a method of treating a patient suffering from a disease accompanied by an elevated level of RTP801L, the method comprising administering to the patient a compound of the invention in a therapeutically effective dose thereby treating the patient.

More particularly, the invention provides an oligoribonucleotide wherein one strand comprises consecutive nucleotides having, from 5' to 3', the sequence set forth in Table A, or a homolog thereof wherein in up to two of the ribonucleotides in each terminal region is altered.

The terminal region of the oligoribonucleotide refers to bases 1-4 and/or 16-19 in the 19-mer sequence and to bases 1-4 and/or 18-21 in the 21-mer sequence.

Additionally, the invention provides oligoribonucleotides wherein one strand comprises consecutive nucleotides having, from 5' to 3', the sequence set forth in Table A or a homolog thereof wherein in up to two of the ribonucleotides in each terminal region is altered.

The presently most preferred compound of the invention is a blunt-ended 19-mer siRNA, i.e. x=y=19 and Z and Z' are both absent. The siRNA is either phosphorylated at 3' termini of both sense and anti-sense strands, or non-phosphorylated at all (both phosphorylated and non-phosphorylated molecules have similar activity); or having the 5' most ribonucleotide in the on the sense strand specifically modified to abolish any possibility of in vivo 5'-phosphorylation. The alternating ribonucleotides are modified at the 2' position of the sugar residue in both the antisense and the sense strands, wherein the moiety at the 2' position is methoxy (2'-O-methyl) and wherein the ribonucleotides at the 5' and 3' termini of the antisense strand are modified in their sugar residues, and the ribonucleotides at the 5' and 3' termini of the sense strand are unmodified in their sugar residues.

Additionally, further nucleic acids according to the present invention comprise at least 14 contiguous nucleotides of any one of the polynucleotides in Table A and more preferably 14 contiguous nucleotide base pairs at any end of the double-stranded structure comprised of the first strand and second strand as described above.

Additionally, further nucleic acids according to the present invention comprise at least 14 contiguous nucleotides of any one of the sequences of Table A, and more preferably 14 contiguous nucleotide base pairs at any end of the double-stranded structure comprised of the first stretch and second stretch as described above. It will be understood by one skilled in the art that given the potential length of the nucleic acid according to the present invention and particularly of the individual stretches forming such nucleic acid according to the present invention, some shifts relative to the coding sequence of the RTP801L gene to each side is possible, whereby such shifts can be up to 1, 2, 3, 4, 5 and 6 nucleotides in both directions, and whereby the thus generated double-stranded nucleic acid molecules shall also be within the present invention.

An additional aspect of the present invention provides for a pharmaceutical composition comprising a compound of the above structure (A) for the treatment of any of the diseases and conditions mentioned herein.

Further, this aspect provides for a pharmaceutical composition comprising two or more compounds of the above structure (A) for the treatment of any of the diseases and conditions mentioned herein, whereby said two compounds may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. Such siRNA molecules are therefore comprised of a double-stranded nucleic acid structure as described herein, whereby two siRNA sequences selected from Table A, optionally siRNA Nos: 72 and 73 are covalently or non-covalently bound or joined by a linker to form a tandem siRNA molecule. Such tandem siRNA molecules comprising two siRNA sequences would typically be of 38-150 nucleotides in length, more preferably 38 or 40-60 nucleotides in length, and longer accordingly if more than two siRNA sequences are included in the tandem molecule. A longer tandem molecule comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention, and further information concerning them is given below.

Said combined or tandem structures have the advantage that toxicity and/or off-target effects of each siRNA are minimized, while the efficacy is increased.

In particular the siRNA used in the Examples has been such modified that a 2' O-Me group was present on the first, third, fifth, seventh, ninth, eleventh, thirteenth, fifteenth, seventeenth and nineteenth nucleotide of the antisense strand, whereby the very same modification, i.e. a 2'-O-Me group was present at the second, fourth, sixth, eighth, tenth, twelfth, fourteenth, sixteenth and eighteenth nucleotide of the sense strand. Additionally, it is to be noted that in the case of these particular nucleic acids according to the present invention the first stretch is identical to the first strand and the second stretch is identical to the second strand and these nucleic acids are also blunt ended.

The terminal region of the oligonucleotide refers to bases 1-4 and/or 16-19 in the 19-mer sequences (Table A below).

Additionally, the siRNAs used in the present invention are oligoribonucleotides wherein one strand comprises consecutive nucleotides having, from 5' to 3', the sequence set forth SEQ ID NOS: 928-1852 (antisense strands) or a homolog thereof wherein in up to 2 of the nucleotides in each terminal region a base is altered.

In one embodiment the first strand of the siRNA comprises a sequence of at least 14 contiguous nucleotides of an oligonucleotide, whereby such oligonucleotide is selected from the group comprising SEQ. ID. Nos. 3-1852, optionally from the group comprising the oligoribonucleotides of having the sequence of any of the serial numbers 72 and 73 of Table A. Additional specifications of the siRNA molecules used in the present invention may provide an oligoribonucleotide wherein the dinucleotide dTdT is covalently attached to the 3' terminus, and/or in at least one nucleotide a sugar residue is modified, possibly with a modification comprising a 2'-O-methyl modification. Further, the 2' OH group may be replaced by a group or moiety selected from the group comprising —H—OCH$_3$, —OCH$_2$CH$_3$, —OCH$_2$CH$_2$CH$_3$, —NH$_2$, and F. Further, the preferable compounds of the present invention as disclosed above may be phosphorylated or non-phosphorylated, and both have essentially equal activity.

Additionally, the siRNA used in the present invention may be an oligoribonucleotide wherein in alternating nucleotides modified sugars are located in both strands. Particularly, the oligoribonucleotide may comprise one of the sense strands wherein the sugar is unmodified in the terminal 5' and 3' nucleotides, or one of the antisense strands wherein the sugar is modified in the terminal 5' and 3' nucleotides.

This application discloses that a nucleic acid comprising a double-stranded structure which is specific for RTP801L is a suitable means of inhibiting angiogenesis/growth of vasculature and vascular leakage, (both from the existing vasculature and from growing vasculature). Additionally, this application discloses (without being bound by theory) that RTP801L being a stress-inducible protein (induced by hypoxia, oxidative stress, thermal stress, ER stress) is a factor acting in fine-tuning of cell response to energy disbalance. Thus inhibition of RTP801L by such double-stranded nucleic acid is suitable for treatment of any disease where cells should be rescued from apoptosis due to stressful conditions (e.g. diseases accompanied by death of normal cells) or where cells adapted to stressful conditions due to changes in RTP801L expression, should be killed (e.g. tumor cells). In the latter case, upon inhibiting RTP801L through such double-stranded nucleic acid, this survival factor with anti-apoptotic function in hypoxic cells, more particularly hypoxic cancer cells, is made ineffective thus allowing the cells devoid of RTP801L-mediated protection to be driven into apoptosis. This can additionally occur when other apoptosis promoting factors are present Such other apoptosis promoting factors include, among others, chemotherapy and radiation therapy. In other words, the double-stranded nucleic acid according to the present invention may be effective alone in cancer treatment (monotherapy) and also as a supplementary therapy.

It is to be understood that the nucleic acid according to the present invention is preferably a functional nucleic acid. As used herein, the term functional nucleic acid preferably means a nucleic acid the function of which is different from being active in the cell as a template for the transcription of any hnRNA, mRNA, or any other transcription product, whereby either said hnRNA, mRNA or any other transcription product, respectively, or the nucleic acid according to the present invention is subject to a translation process, preferably a cellular translation process, resulting in a biologically active RTP801L protein. It is to be acknowledged that a functional nucleic acid as preferably used herein is capable of reducing the expression of a target nucleic acid. More preferably, such reduction is based on a post-transcriptional gene silencing process of the target nucleic acid. Even more preferably such reduction is based on RNA interference. A most preferred form of the functional nucleic acid is an siRNA molecule or any further molecule having the same effect as an siRNA molecule. Such further molecule is selected from the group comprising siRNAs, synthetic siRNAs, shRNAs and synthetic shRNAs. As used herein siRNAs may additionally comprise expression vector derived siRNAs, whereby the expression vector is in a preferred embodiment a virus such as Adenoviruses, Adenoassociated viruses, Herpes viruses and Lentiviruses. As used herein shRNA preferably means short hairpin RNAs. Such shRNA can be made synthetically or can be generated using vector encoded expression systems, preferably using RNA polymerase III promoters. In connection therewith it is to be acknowledged that the functional nucleic acid according to the present invention is directed to RTP801L which is also preferably referred to herein as the target and the nucleic acid coding for said target as the target nucleic acid.

As preferably used herein, the double-stranded structure of the nucleic acid according to the present invention comprises any double-stranded structure, whereby such double-stranded structure is preferably generated by the first stretch and the second stretch provided by the nucleic acid having the basic design. The double-stranded structure may comprise one or several mismatches. Such double-stranded structure is formed by Watson-Crick-base pairing and/or Hoogsteen base pairing and/or similar base pairing mechanisms. Based on the basic design of the nucleic acid according to the present invention it is preferred that one stretch, is in antisense orientation to a nucleic acid sequence coding for RTP801L or a part thereof, whereas the other stretch is in the sense orientation to a nucleic acid sequence coding for RTP801L or a part thereof. Because of this, one stretch is complementary to a nucleic acid sequence coding for RTP801L or a part thereof, and the other stretch is identical to a nucleic acid sequence coding for RTP801L or a part thereof. In connection therewith it is to be acknowledged that the term identical, of course, means also partially identical, whereby the identity, expressed as homology, is at least 80%, preferably 90%, more preferably 95%, 96%, 97%, 98%, 99% or 100%. Similar to the definition of identity, complementarity can be defined in terms of homology, whereby such homology is of the same range as the identity if the complementary strand would be translated into the identical strand according to Watson-Crick base pairing rules. In an alternative embodiment, one stretch is identical to a nucleic acid sequence coding for RTP801L or a part thereof and the other stretch is complementary to a nucleic acid sequence coding for RTP801L or a part thereof.

In a preferred embodiment, the nucleic acid according to the present invention is down-regulating RTP801L function. Down-regulation of RTP801L function preferably happens by reduction in the level of expression at the protein level and/or the mRNA level, whereby such reduced level of expression, preferably at the protein level, can be as little as 5% and be as high as 100%, with reference to an expression under conditions where the nucleic acid according to the present invention is not administered or is not functionally active. Such conditions are preferably the conditions of or as present in an expression system, preferably an expression system for RTP801L. Such expression system is preferably a translation system which can be an in vitro translation system, more preferably a cell, organ and/or organism. It is more preferred that the organism is a multicellular organism, more preferably a mammal, whereby such mammal is preferably selected from the group comprising man, monkey, mouse, rat, guinea pig, rabbit, cat, dog, sheep, cow, horse, cattle and pig. In connection with the down-regulation it is to be acknowledged that said down-regulation may be a function of time, i.e. the down-regulation effect is not necessarily observed immediately upon administration or functional activation of the nucleic acids according to the present invention, but may be deferred in time as well as in space, i.e. in various cells, tissues and/or organs. Such deferment may range from 5%-100%, preferably 10 to 50%. It will be acknowledged by the ones skilled in the art that a 5% reduction for a longer time period might be as effective as a 100% reduction over a shorter time period. It will also be acknowledged by the ones skilled in the art that such deferment strongly depends on the particular functional nucleic acid actually used, as well as on the target cell population and thus, ultimately, on the disease to be treated and/or prevented according to the technical teaching of the present application. Insofar, a 5% reduction over a longer time period might be as effective as 100% reduction over a shorter time period. It will also be acknowledged by the ones skilled in the art that the deferment can occur at any level as outlined above, i.e. a deferment in function, whereby such function is any function exhibited by RTP801L, a deferment in protein expression or a deferment at mRNA expression level.

In a preferred embodiment the first stretch comprises at least 14 nucleotides, preferably 14 contiguous nucleotides. It will be acknowledged by the one skilled in the art that the first stretch should have a length which is suitable to allow for specifically addressing a nucleic acid sequence coding for RTP801L and more specifically the nucleic acid coding for RTP801L as present in the translation system where the expression of RTP801L is to be reduced. Again without wishing to be bound by any theory or any mode of action of the nucleic acid according to the present invention, it seems that there is an interaction between the nucleic acid according to the present invention and the nucleic acid sequence coding for RTP801L, preferably at the transcript level, i.e. upon generation of an mRNA from the respective nucleic acid sequence coding for RTP801L. Due to the likelihood of any sequence of the nucleic acid according to the present invention being identical to or complementary to a sequence contained in the genome or transcriptome of the translation system, the length of the first stretch should thus be as long as to make sure that, under the assumption that some kind of base pairing between the nucleic acid coding for RTP801L and one of the strands of the nucleic acid according to the present invention actually occurs, only the sequence coding for RTP801L but no other coding sequence, preferably no other essential coding sequence, of the genome or the transcriptome is addressed for or by such base pairing. By this length, the occurrence of off-target effects can be reduced and preferably eliminated. To increase the stringency of this kind of specifically addressing RTP801L and the nucleic acid sequence coding therefor, the first stretch preferably has a length of at least 18 or 19 nucleotides. The upper limit for the length of the first stretch is preferably less than 50 nucleotides, however, the length can be significantly longer and can comprise 100, 200 or even 500 nucleotides or any length in-between. Apart from this, one skilled in the art will prefer to have a rather short first stretch, particularly in case the nucleic acid according to the present invention is chemically synthesised as the shorter the sequence is, the less time and material consuming the synthesis thereof will be and the lower will be the rate at which incorrect nucleotides are inserted into the respective sequence. Another factor which is to be taken into consideration in connection with fixing the length of the first stretch is the fact that, typically at a length beyond 50 or more nucleotides, an unspecific interferon response may be observed. It depends on the particular condition to be treated whether this kind of unspecific interferon response is to be tolerated or not. For example, an interferon response could be tolerated if the interferon response and/or the expression of the interferon genes can be limited to the pathogenic cells.

In view of this, more preferred lengths of the first stretch are from about 14 to 40 nucleotides, 18 to 30 nucleotides, 19 to 27 nucleotides, 21 to 25 nucleotides and 19 to 23 nucleotides.

The same considerations as outlined above for the first stretch are applicable to the second stretch which may thus comprise any length as described herein in connection with the first stretch. It is also within the present invention that the length of the first stretch is different from the length of the second stretch, however, it is preferred that both stretches have the same length.

According to the basic design of the nucleic acid, the first stretch and second stretch are parts of the first strand and second strand, respectively, of the nucleic acid according to the present invention. It will be acknowledged that at either end, i.e. at the 5' end as well as the 3' end the first strand and/or second strand may comprise one or several nucleotides, preferably additional nucleotides, at any combination.

In connection therewith it is to be acknowledged that those nucleotides of the individual strand going beyond the end(s) of the stretch corresponding to the respective strand can be used to further contribute to the complementarity and identity, respectively, of the stretch and thus to the specific addressing of the nucleic acid sequence coding for RTP801L.

It will be acknowledged that, basically, based on the technical teaching provided herein, the nucleic acid according to the present invention can address any part of the nucleic acid sequence coding for RTP801L, preferably coding for RTP801L in the translation system where the expression of RTP801L is to be reduced. Insofar, the present invention comprises any nucleic acid having the characteristics as defined herein, whereby the complementary and identical strands and stretches of the nucleic acid according to the present invention can basically start from any nucleotide of the nucleic acid sequence coding for RTP801L. Accordingly, under the proviso that the first stretch of the nucleic acid according to the present invention is complementary to the nucleic acid sequence coding for RTP801L, i.e. is the antisense strand thereof or is in antisense orientation thereto, the first nucleotide of said stretch, i.e. the most 5' terminal nucleotide corresponds, i.e. aligns to the last nucleotide of the sequence coding for RTP801L at the 3' end. In a further embodiment such most 5' terminal nucleotide corresponds to the penultimate nucleotide of the nucleic acid coding for RTP801L and so on until the last position is reached which, given the length of the antisense stretch, still allows that the antisense strand of the nucleic acid according to the present invention is complementary to the nucleic acid sequence coding for RTP801L. Insofar, any nucleic acid according to the present invention is within the present invention which could be generated by scanning the nucleic acid sequence coding for RTP801L starting from the most 5' terminal nucleotide thereof and laying over the basic design of the nucleic acid according to the present invention and realising the characteristics for such nucleic acid according to the present invention. The same considerations are applicable to the embodiments disclosed herein where the complementarity and identity of the nucleic acid according to the present invention is not only provided by the first stretch and second stretch, respectively, but such complementarity and identity also involves one or more nucleotides beyond the first stretch and second stretch, respectively, then being part of the first strand and second strand, respectively.

It is to be noted that those nucleic acids according to the present invention which can be used in both human and an animal model such as rat and/or mouse and/or chinchilla are particularly useful. The surprising advantage of these particular nucleic acids according to the present invention resides in the fact that they are effective both in human and in an animal model which means that the test results obtained in the animal model can be immediately transferred from the animal model to the human being and more particularly without the necessity to make any changes to the human sequence which would otherwise become necessary in case the nucleic acid according to the present invention was designed such as to comprise (a) sequence(s) which differ(s) between the species, more particularly the species used for animal model testing and man as the ultimate preferred organisms or patient. It is further preferred that these nucleic acids have a modification pattern as also described in the examples.

However, it is also within the present invention that any of the sequences according to SEQ. ID. NOs. 3-1852 and respective combinations resulting in the nucleic acid molecules according to the present invention only partially contained in a further nucleic acid according to the present invention. Preferably, the further nucleic acids according to the present invention comprise at least 14 contiguous nucleotides of the SEQ. ID. NOs. 3-1852, and more preferably 14 contiguous nucleotide base pairs at any end of the double-stranded structure comprised of the first stretch and second stretch as outlined in the preceding table. It will be understood by the ones skilled in the art that given the potential length of the nucleic acid according to the present invention and particularly of the individual stretches forming such nucleic acid according to the present invention, some shifts relative to the coding sequence of RTP801L to each side is possible, whereby such shifts can be up to 1, 2, 3, 4, 5 and 6 nucleotides in both directions, and whereby the thus generated double-stranded nucleic acid molecules shall also be within the present invention.

In a preferred embodiment of the present invention the first stretch and the first strand have the same length. Likewise it is preferred that the second strand has the same length as the second stretch, whereby it is even more preferred that the first stretch and the second stretch have the same length. In a still more preferred embodiment, the first strand only comprises the first stretch and the second strand only comprises the second stretch. In an even more preferred embodiment neither the first stretch, and thus the first strand, nor the second stretch, and thus the second strand, comprise an overhang. In other words, it is also within the present invention that the double-stranded nucleic acids according to the present invention are blunt ended, preferably at each end of the double-stranded structure of the nucleic acids according to the present invention. Such blunt ended structure can be realized in connection with any other embodiments of the nucleic acids according to the present invention, particularly those embodiments where the nucleic acids according to the present invention have a modification pattern, more preferably a modification pattern as described herein.

In a further aspect, the nucleic acid according to the present invention has thus a basic design which provides for blunt ends at both ends of the double-stranded structure of the nucleic acid according to the present invention. However, it is also within the present invention that there is a overhang, i.e. a stretch of one or more nucleotides protruding from the double-stranded structure. The overhang can be, in principle, at the 5' end of the antisense strand, at the 3' end of the antisense strand, at the 5' end of the sense strand and/or the 3' end of the sense strand. It is to be noted that realising any single of said options as well as any combination thereof is within the present invention. More preferred is a combination, whereby the overhang is located at the 3' end of the antisense strand and at the 3' end of the sense strand. It is also within the present invention that the overhang is at the 5' end of the antisense strand and at the 5' end of the sense strand. Furthermore it is within the present invention that the overhang is located only at the antisense strand of double-stranded structure, more preferably at the 3' end of the antisense strand of the double-stranded structure.

In connection with the overhangs, it is to be noted that the overhang plus the stretch preferably form the strand and the lengths provided for the stretches herein apply also to these embodiments. The individual overhang can, independent of its location, consist of at least one nucleotide. However, the individual overhang can comprise as many as 10 and is preferably two nucleotides long. It is within the present invention that the respective nucleotide(s) forming the overhang(s) is/are also complementary to the nucleic acid sequence coding for RTP801L in case of the first strand being complementary to said nucleic acid sequence coding for RTP801L, and the overhang being at the 3' or 5' end of the antisense strand, or that the overhang(s) is/are identical to the nucleic acid sequence coding for RTP801L in case the first strand is identical to the nucleic acid sequence coding for RTP801L. The same applies to any overhang located at the second stretch of the basic design of the nucleic acid according to the present invention, whereby it is to be acknowledged that the overhang design at the second stretch can be independent from the overhang design of the first stretch.

It is also within the present invention that the overhang forming nucleotides are neither complementary nor identical to the corresponding nucleotides of the nucleic acid sequence coding for RTP801L. As used herein, and preferably in this embodiment, "corresponding" means the respective nucleotides which follow at the 5' end and/or the 3' end of the stretch having a nucleotide counterpart on the nucleic acid coding for RTP801L.

Preferably, the first strand comprises at its 3' end two nucleotides, preferably deoxynucleotides and more preferably two TT and/or this kind of nucleotides also at the 3' end of the second strand, whereby more preferably the length of the first stretch and the second stretch is 19 nucleotides. The strands are thus comprised of the stretch and the overhang. In this embodiment the double-stranded structure consists of 19 base pairs and an overhang of two nucleotides at each end of 3' end of the individual stretch.

In a preferred embodiment, the first stretch and/or the first strand comprise(s) ribonucleotides, whereby it is particularly preferred that the first stretch consists in its entirety of ribonucleotides. The same applies to the second stretch and the second strand, respectively. In connection therewith, however, each and any of the nucleotides of the first stretch and second stretch, respectively, is modified in a preferred embodiment. The same applies to the first strand and second strand, respectively. Particularly the terminal nucleotides, irrespective whether they are ribonucleotides or deoxyribonucleotides, can have an OH-group which as such can be modified. Such OH— group may stem from either the sugar moiety of the nucleotide, more preferably from the 5' position in case of the 5'OH-group and/or from the 3' position in case of the 3'OH-group, or from a phosphate group attached to the sugar moiety of the respective terminal nucleotide. The phosphate group may in principle be attached to any OH-group of the sugar moiety of the nucleotide. Preferably, the phosphate group is attached to the 5'OH-group of the sugar moiety in case of the free 5'OH-group and/or to the 3'OH-group of the sugar moiety in case of the free 3' OH-group still providing what is referred to herein as free 5' or 3' OH-group.

As used herein with any strategy for the design of RNAi or any embodiment of RNAi disclosed herein, the term end modification means a chemical entity added to the most 5' or 3' nucleotide of the first and/or second strand. Examples for such end modifications include, but are not limited to, 3' or 5' phosphate, inverted (deoxy) abasics, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocloalkaryl; aminoalkylamino; polyalkylamino or substituted silyl, as, among others, described in European patents EP 0 586 520 B1 or EP 0 618 925 B1.

As used herein, alkyl or any term comprising "alkyl" preferably means any carbon atom chain comprising 1 to 12, preferably 1 to 6 and more, preferably 1 to 2 C atoms.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications. The polypeptide or protein may confer further characteristics to the nucleic acid molecules according to the present invention. Among others the polypeptide or protein may act as a ligand to another molecule. If said other molecule is a receptor the receptor's function and activity may be activated by the binding ligand. The receptor may show an internalization activity which allows an effective transfection of the ligand bound nucleic acid molecules according to the present invention. An example for the ligand to be coupled to the inventive nucleic acid molecule is VEGF and the corresponding receptor is the VEGF receptor.

Various possible embodiments of the RNAi of the present invention having different kinds of end modification(s) are presented in the following Table 1.

TABLE 1

VARIOUS EMBODIMENTS OF THE INTERFERING RIBONUCLEIC ACID ACCORDING TO THE PRESENT INVENTION

| | | $1^{st}$ strand/$1^{st}$ stretch | $2^{nd}$ strand/2nd stretch |
|---|---|---|---|
| 1.) | 5'-end | free OH | free OH |
| | 3'-end | free OH | free OH |
| 2.) | 5'-end | free OH | free OH |
| | 3'-end | end modification | end modification |
| 3.) | 5'-end | free OH | free OH |
| | 3'-end | free OH | end modification |
| 4.) | 5'-end | free OH | free OH |
| | 3'-end | end modification | free OH |
| 5.) | 5'-end | free OH | end modification |
| | 3'-end | free OH | free OH |
| 6.) | 5'-end | free OH | end modification |
| | 3'-end | end modification | free OH |
| 7.) | 5'-end | free OH | end modification |
| | 3'-end | free OH | end modification |
| 8.) | 5'-end | free OH | end modification |
| | 3'-end | end modification | end modification |

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasics are nucleotides, either desoxyribonucleotides or ribonucleotides which do not have a nucleobase moiety. This kind of compound is, among others, described in Sternberger, M., Schmiedeknecht, A., Kretschmer, A., Gebhardt, F., Leenders, F., Czauderna, F., Von Carlowitz, I., Engle, M., Giese, K., Beigelman, L. & Klippel, A. (2002). Antisense Nucleic Acid Drug Dev, 12, 131-43

Any of the aforementioned end modifications may be used in connection with the various embodiments of RNAi depicted in Table 1; it is to be noted that the 5' end modifications mentioned above are usually only present in the sense strand of the siRNA molecule Further modifications can be related to the nucleobase moiety, the sugar moiety or the phosphate moiety of the individual nucleotide.

Such modification of the nucleobase moiety can be such that the derivatives of adenine, guanine, cytosine and thymidine and uracil, respectively, are modified. Particularly preferred modified nucleobases are selected from the group comprising inosine, xanthine, hypoxanthine, 2-aminoadenine, 6-methyl, 2-propyl and other alkyladenines, 5-halo uracil, 5-halocytosine, 5-halo cytosine, 6-azacytosine, 6-aza thymine, pseudo-uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanine, 8-hydroxylguanine and other substituted guanines, other aza- and deaza adenines, other aza- and deaza guanines, 5-trifluoromethyl uracil and 5-trifluoro cytosine.

In another preferred embodiment, the sugar moiety of the nucleotide is modified, whereby such modification preferably is at the 2' position of the ribose and desoxyribose moiety, respectively, of the nucleotide. More preferably, the 2' OH group is replaced by a group or moiety selected from the group comprising amino, fluoro, alkoxy and alkyl. Preferably, alkoxy is either methoxy or ethoxy. Also preferably alkyl means methyl, ethyl, propyl, isobutyl, butyl and isobutyl. It is even more preferred that, regardless of the type of modification, the nucleotide is preferably a ribonucleotide.

The modification of the phosphate moiety is preferably selected from the group comprising phosphothioates.

It will be acknowledged by the one skilled in the art that the nucleic acid of the present invention which consists of a multitude of nucleotides may thus be formed by nucleotides which are linked through a phosphodiester linkage or through a phosphothioate linkage, or a combination of both along the length of the nucleotide sequence of the individual strand and stretch, respectively.

A further form of nucleotides used may be siNA which is, among others, described in international patent application WO 03/070918.

The nucleotides forming the first stretch and first strand, respectively, of the nucleic acid according to the present invention can comprise one or more modified nucleotides, whereby the individual modified nucleotide has a modification which is preferably a modification as disclosed herein. In addition to the particular modification, the modification can be or comprise some sort of label, whereby the label is selected from the group chemiluminescent labels, fluorescent labels and radio labels. These kinds of labels are known to the one skilled in the art and, e.g., described in Ausubel et al., Current Protocols in Molecular Biology, John Wiley and Sons, Baltimore, Md., 1998. The thus labelled nucleic acid according to the present invention may be used also for diagnostic purposes or for monitoring the site of action as well as for the staging of any treatment, preferably related to any of the diseases disclosed herein.

In a preferred embodiment, the nucleic acid according to the present invention is modified such that the pyrimidine nucleotides in the sense stretch or strand are 2' O-methylpyrimidine nucleotides and, either additionally or alternatively, the purine nucleotides in the sense stretch or strand are 2'-deoxypurine nucleotides. In a further embodiment the pyrimidine nucleotides present in the sense stretch or sense strand are 2'-deoxy-2'-fluoro pyrimidine nucleotides.

In an alternative embodiment, the modification is not based on the chemistry of the nucleotide, i.e. the modification depends on whether the nucleotide to be modified is either a purine nucleotide or a pyrimidine nucleotide, but is predominantly based on the individual nucleotide's spatial arrangement in the overall double-stranded structure of the basic design of the nucleic acid according to the present invention.

More particularly, either the first strand and first stretch, respectively, or the second strand and second stretch, respectively, show a spatial pattern of modification of the nucleotides forming said stretches and strands, respectively.

Focusing on the first stretch first, there is a pattern of groups of modified nucleotides and groups of non-modified nucleotides. These groups of non-modified nucleotides are also referred to herein as flanking groups of nucleotides. More preferably, the pattern consists of groups of modified nucleotides and non-modified nucleotides. Even more preferably, the pattern is a regular pattern and even more preferably an alternating pattern along the length of the first stretch of the nucleic acid according to the present invention. The group of modified nucleotides may either consist of one or of several nucleotides which are modified and which are preferably nucleotides which are modified at the 2' position, i.e. have a modification at the sugar moiety. More preferably, this modification is a 2'-O-Me modification.

The group of non-modified nucleotides may either consist of one or of several nucleotides which are either not modified, whereby the not-modified nucleotides are preferably ribonucleotides, or the not modified nucleotides are nucleotides having a modification, whereby such modification is different from the modification shown by the nucleotides forming the group of modified nucleotides. Even more preferably, the not modified nucleotides are ribonucleotides. It is to be noted that the term not modified and non-modified nucleotide are used in an interchangeable manner if not indicated to the contrary. The first stretch of the nucleic acid according to the present invention may either start with a group of modified nucleotides or start with a group of non-modified nucleotides as defined herein. However, it is preferred that the first stretch starts with a group of modified nucleotides. Most preferably, the group of modified nucleotides consists of a single nucleotide. In connection with this embodiment the first stretch is preferably in antisense orientation to the nucleic acid coding for RTP801L. It is also within the present invention that the modification as exhibited by the nucleotides forming the group of modified nucleotides is the same for all groups of modified nucleotides present on the first stretch. However, it is also within the present invention that some group of modified nucleotides have a different modification than one or several groups of modified nucleotides present on the first stretch.

On the second strand of the nucleic acid according to the present invention, a pattern as described for the first stretch can also be realised. The same characteristics as described in connection with the first stretch can be realized in an embodiment on the second stretch as well, whereby it is preferred that, under the proviso that the second stretch is in sense orientation relative to the nucleic acid sequence coding for RTP801L, the second strand of the nucleic acid according to the present invention starts with a group of non-modified nucleotides.

The nucleic acid according to the present invention comprising a double-stranded structure may comprise a first stretch having the modification pattern as described herein. Alternatively, the double-stranded nucleic acid according to the present invention may comprise a second stretch having the modification pattern as outlined above. It is, however, most preferred that the double-stranded nucleic acid according to the present invention consists of a first stretch and a second stretch, whereby both the first stretch and the second stretch have a spatial modification pattern as described herein.

It is within the present invention that the characteristics of the spatial modification pattern is the same on both stretches in terms of size of the groups of modified nucleotides and groups of non-modified nucleotides and the kind of modifications actually used. Preferably, the spatial pattern of modification on the first stretch is shifted such that a group of modified nucleotides on the first stretch is opposing a group of non-modified nucleotides on the second stretch and vice versa. However, it is also with the present invention that the patterns are exactly aligned, i.e. that a group of modified nucleotides on the first stretch is opposing a group of non-modified nucleotides on the second stretch and a group of non-modified nucleotides on the first stretch is opposing a group of non-modified nucleotides on the second stretch. It is still within the present invention that the spatial pattern of modification on the first stretch and the second stretch is shifted relative to each other so that only a first portion of a group of modified nucleotides on one stretch is opposing a portion of a group of non-modified nucleotides on the other stretch, whereas the second portion of the group of modified nucleotides is opposing another group of modified nucleotides. It is within the present invention that the disclosure provided herein on the spatial modification pattern of the stretch(es) of the nucleic acid according to the present invention applies also to the strand(s) of the nucleic acid according to the present invention. However, it is preferred that the stretches of the nucleic acid comprise the spatial modification pattern and the strands comprise such stretches and one or more overhang(s) as disclosed herein. It is particularly preferred that there is a phosphate group at the 3' end of either the antisense strand, or the sense strand or both strands, whereby it is more preferred that the phosphate group is at the 3' end of both the antisense strand and the sense strand. In an even more preferred embodiment, the phosphate group is a phosphate group as defined herein.

It is also within the present invention that the nucleic acid according to the present invention may exhibit a linker connecting the first and the second strand. Such linker is preferably a polymer. The polymer can be any synthetic or natural polymer. Possible synthetic linkers are, among others, PEG or a polynucleotide. Such linker is preferably designed such as to allow the either partial or complete folding back of the first stretch onto the second stretch and vice versa.

Finally, it is within the present invention that the nucleic acid according to the present invention is a synthetic one, a chemically synthesised one, an isolated one, or one derived from any natural sources such as, for example, prepared by means of recombinant technology. In connection with the preparation of any nucleic acid according to the present invention any modification as disclosed herein can be introduced either prior, during or subsequent to the preparation of the respective nucleic acid according to the present invention as known to the ones skilled in the art.

The vector according to the present invention comprises a nucleic acid according to the present invention. Additionally, the vector may include elements to control targeting, expression and transcription of said nucleic acid in a cell selective manner as is known in the art. The plasmid can include a promoter for controlling transcription of the heterologous material, i.e. the nucleic acid according to the present invention, and can be either a constitutive or an inducible promoter to allow selective transcription. Enhancers that may be required to obtain necessary transcription levels can optionally be included. Enhancers are generally any non-translated DNA sequences which work contiguously with the coding sequence, thus in cis, to change the basal transcription level dictated by the promoter. The expression of such constructs is known to the one skilled in the art and may be done, e.g., by providing a respective tandem construct or by having different promoters transcribing for the first and second strand and first and second stretch, respectively, of the nucleic acid according to the present invention.

When the nucleic acid according to the present invention is manufactured or expressed, preferably expressed in vivo, more preferably in a patient who is in need of the nucleic acid according to the present invention, such manufacture or expression preferably uses an expression vector, preferably a mammalian expression vector. Expression vectors are known in the art and preferably comprise plasmids, cosmids, viral expression systems. Preferred viral expression systems include, but are not limited to, adenovirus, retrovirus and lentivirus.

Methods are known in the art to introduce the vectors into cells or tissues. Such methods can be found generally described in Sambrook et al., Molecular cloning: A Laboratory Manual, Cold Springs Harbour Laboratory, New York (1983, 1992), or in Ausubel et al., Current Protocols in Molecular Biology, John Wiley and Sons, Baltimore, Md., 1998.

Suitable methods comprise, among others, transfection, lipofection, electroporation and infection with recombinant viral vectors. In connection with the present invention, an additional feature of the vector is in one embodiment an expression limiting feature such as a promoter and regulatory element, respectively, that are specific for the desired cell type thus allowing the expression of the nucleic acid sequence according to the present invention only once the background is provided which allows the desired expression.

In a further aspect the present invention is related to a pharmaceutical composition comprising a nucleic acid according to the present invention and/or a vector according to the present invention and, optionally, a pharmaceutically acceptable carrier, diluent or adjuvants or other vehicle(s). Preferably, such carrier, diluents, adjuvants and vehicles are inert, and non-toxic. The pharmaceutical composition is in its various embodiments adapted for administration in various ways. Such administration comprises systemic and local administration as well as oral, subcutaneous, parenteral, intravenous, intraarterial, intramuscular, intraperitoneal, intranasal, and intrategral.

It will be acknowledged by the ones skilled in the art that the amount of the pharmaceutical composition and the respective nucleic acid and vector, respectively, depends on the clinical condition of the individual patient, the site and method of administration, scheduling of administration, patient age, sex, bodyweight and other factors known to medical practitioners. The pharmaceutically effective amount for purposes of prevention and/or treatment is thus determined by such considerations as are known in the medical arts. Preferably, the amount is effective to achieve improvement including but limited to improve the diseased condition or to provide for a more rapid recovery, improvement or elimination of symptoms and other indicators as are selected as appropriate measures by those skilled in the medical arts.

In a preferred embodiment, the pharmaceutical composition according to the present invention may comprise other pharmaceutically active compounds. Preferably, such other pharmaceutically active compounds are selected from the group comprising compounds which allow for uptake intracellular cell delivery, compounds which allow for endosomal release, compounds which allow for, longer circulation time and compounds which allow for targeting of endothelial cells or pathogenic cells. Preferred compounds for endosomal release are chloroquine, and inhibitors of ATP dependent H+ pumps.

The pharmaceutical composition is preferably formulated so as to provide for a single dosage administration or a multi-dosage administration.

It will be acknowledged that the pharmaceutical composition according to the present invention can be used for any disease which involves undesired development or growth of vasculature including angiogenesis, as well as any of the diseases and conditions described herein. Preferably, these kind of diseases are tumor diseases. Among tumor diseases, the following tumors are most preferred: endometrial cancer, colorectal carcinomas, gliomas, endometrial cancers, adenocarcinomas, endometrial hyperplasias, Cowden's syndrome, hereditary non-polyposis colorectal carcinoma, Li-Fraumene's syndrome, breast-ovarian cancer, prostate cancer (Ali, I. U., Journal of the National Cancer Institute, Vol. 92, no. 11, Jun. 7, 2000, page 861-863), Bannayan-Zonana syndrome, LDD (Lhermitte-Duklos' syndrome) (Macleod, K., supra) hamartoma-macrocephaly diseases including Cow disease (CD) and Bannayan-Ruvalcaba-Rily syndrome (BRR), mucocutaneous lesions (e.g. trichilemmonmas), macrocephaly, mental retardation, gastrointestinal harmatomas, lipomas, thyroid adenomas, fibrocystic disease of the breast, cerebellar dysplastic gangliocytoma and breast and thyroid malignancies (Vazquez, F., Sellers, W. R., supra).

It is to be acknowledged that any of the tumor disease to be treated with the pharmaceutical composition according to the present invention is preferably a late stage tumor disease. In another embodiment, the tumor disease involves cells which are tumor suppressor negative, whereby more preferably the tumor suppressor is PTEN.

The pharmaceutical composition according to the present invention can also be used in a method for preventing and/or treating a disease as disclosed herein, whereby the method comprises the administration of a nucleic acid according to the present invention, a vector according to the present invention or a pharmaceutical composition or medicament according to the present invention for any of the diseases described herein.

In a further aspect, the present invention is related to a method for designing or screening a nucleic acid which is suitable to down-regulate RTP801L, more particularly to down-regulate RTP801L function. This method comprises the use of a nucleic acid sequence as disclosed herein and the assessment of such nucleic acid in a suitable assay. Such assay is known in the art and, for example, described in the example part of this application. In a further step, a double-stranded nucleic acid is designed, preferably according to the design principles as laid down herein, which is suitable to down-regulate RTP801L, preferably in connection with a post transcriptional gene silencing mechanism such as RNA interference. Also the thus obtained, i.e. designed or screened, nucleic acid is assessed in the respective assay and the result, i.e. the effect of both the nucleic acid according to the present invention as well as the newly designed or screened nucleic acid in such assay compared. Preferably, the designed or screened nucleic acid is more suitable in case it is either more stable or more effective, preferably both. It will be acknowledged that the method will be particularly effective if any of the nucleic acids according to the present invention is used as a starting point. It is thus within the present invention that new nucleic acid molecules will be designed based on the principles disclosed herein, whereby the target sequence on the RTP801L mRNA will be slightly shifted relative to the target sequence on the RTP801L mRNA for the corresponding nucleic acid according to the present invention. Preferably the new nucleic acid will be shifted by at least one or more nucleotides relative to the stretch on the target mRNA in either the 5' or the 3' direction of the mRNA coding for RTP801L. It is however with in the present invention that the shift occurs in both directions simultaneously which means that the new nucleic acid incorporates the nucleic acid according to the present invention used as a starting point. It is also within the present invention that the elongation of the nucleic acid according to the present invention and used as a starting point is biased to either the 3' end or the 5' end. In case of such as bias either the 3' end or the 5' end of the new nucleic acid is longer, i.e more extended than the other end. When the new nucleic acid molecule is generated by extending either the 3' end of the 5' end of the antisense strand and/or the sense strand, the following sequence of steps is typically applied. If the shift is to the 5' end of the mRNA of RTP801L, the 3' end of the antisense strand has to be extended by the number of the nucleotides by which the 5' end of the mRNA of RTP801L is shifted. The nucleotide(s) thus to be added to the 3' end of the antisense strand of the new nucleic acid is/are complementary to those nucleotides following at the 5' end of the target sequence on the RTP801L mRNA used for the nucleic acid molecule according to the present invention used as a starting point. The same has to be done to the sense strand. However the nucleotides to be added to the sense strand have to correspond, i.e. be complementary to the nucleotides newly added to the 3' end of the antisense strand which means that they have to be added to the 5' end of the sense strand. The latter step on the sense strand, however has to be done only to the extent that apart from the antisense strand also the sense strand shall be shifted, which is the case in preferred embodiments of the present invention. Although this shifting can be done to an extent defined by the ones skilled in the art, more preferably the shift shall be done such that also the new nucleic acid still contains a strech of at least 14 nucleotides, preferably 14 contiguous nucleotides as exhibited by any of the nucleic acid molecules disclosed herein.

The synthesis of any of the nucleic acids described herein is within the skills of the one of the art. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313, the synthesis of thioates is, among others, described in Eckstein F., Annu Rev. Biochem. 1985; 54: 367-402, the synthesis of RNA molecules is described in Sproat B., in Humana Press 2005 Edited by Herdewijn P.; Kap. 2: 17-31 and respective downstream processes are, among others, described in Pingoud A. et. al., in IRL Press 1989 Edited by Oliver R. W. A.; Kap. 7: 183-208 and Sproat B., in Humana Press 2005 Edited by Herdewijn P.; Kap. 2: 17-31 (supra).

siRNA for RTP801L can be made using methods known in the art as described above, based on the known sequence of RTP801L (SEQ ID NO:1), and can be made stable by various modifications as described above. For further information, see Example 5.

Further, in relation to the methods of the present invention as described herein, additional RNA molecules may be used with said methods e g inhibitory RNA molecules of the present invention include single stranded oligoribonucleotides preferably comprising stretches of at least 7-10 consecutive nucleotides present in the sequences detailed in Table A, said oligoribonucleotides being capable of forming [and/or comprising] double stranded regions in particular conformations that are recognized by intracellular complexes, leading to the degradation of said oligoribonucleotides into smaller RNA molecules that are capable of exerting inhibition of their corresponding endogenous gene, and DNA molecules encoding such RNA molecules. The corresponding endogenous gene is preferably the 801L gene and may additionally be the RTP801 gene (described in U.S. Pat. No. 6,555,667), the VEGF gene and/or the VEGF-R1 gene. The invention also provides a composition comprising the above single stranded oligoribonucleotide in a carrier, preferably a pharmaceutically acceptable carrier.

Additionally, the present invention provides for combination therapy for all the conditions disclosed herein and in particular conditions involving choroidal neovascularization. In said combination therapy, both the RTP801L and VEGFR genes are inhibited in order to ameliorate the symptoms of the disease being treated. These genes may be inhibited with a combination of siRNAs or antibodies (including aptamer antibodies) or both. The present invention therefore also provides for a novel pharmaceutical composition comprising an RTP801L inhibitor and a VEGF or VEGFR-1 inhibitor, the RTP801L inhibitor preferable being an siRNA, more preferably an siRNA molecule detailed in Table A, optionally-selected from the group consisting of siRNAs Nos: 72 and 73, and the VEGF/VEGFR-1 inhibitor optionally being an antibody or aptamer. The combined use of said compounds (I.e., RTP801L siRNA and VEGF antibody or any other combined example disclosed herein) in the preparation of a medicament is also part of the present invention.

Thus, RTP801L siRNA such as an siRNA molecule detailed in Table A and optionally siRNA Nos: 72 and 73, may be administered in conjunction with agents which target VEGF or VEGF receptor 1 (VEGFR1). Such agents currently exist on the market or in various stages of approval and work through different mechanisms. Antibodies and antibody fragments such as ranibizumab (Lucentis, Genentech) attach to released VEGF to inhibit binding of VEGF to active receptors. An aptamer which can act like a ligand/antibody (Macugen, Eyetech/Pfizer, approved recently by the FDA for wet AMD) is also a possibility. Macugen bonds with extracellular VEGF to block its activity. These drugs are administered locally by intravitreal injection. Anti-VEGF siRNA based compounds (such as Acuity's Cand5 inhibitor of VEGF or SIRNA's 027 inhibitor of VEGFR-1) are also available. Additionally, the small molecule aminosterol Squalamine (Genaera) which is administered systemically reportedly interferes in multiple facets of the angiogenic process, including inhibiting VEGF and other growth factor signaling in endothelial cells.

The conjoined administration of an RTP801L inhibitor, preferably an siRNA, and any of the above VEGF/VEGFR-1 inhibitory agents can have an additive or even synergistic effect whereby said combined treatment is more effective than treatment by any of these individual compositions, irrespective of dosage in the single therapy option. RTP801L siRNA has a different mechanism of action and is potentially additive or even synergistic with VEGF-VEGFR inhibitors.

It is to be understood that, in the context of the present invention, any of the siRNA molecules disclosed herein, or any long double-stranded RNA molecules (typically 25-500 nucleotides in length) which are processed by endogenous cellular complexes (such as DICER—see above) to form the siRNA molecules disclosed herein, or molecules which comprise the siRNA molecules disclosed herein, can be employed in the treatment of the diseases or disorders described herein.

Additional disorders which can be treated by the molecules and compositions of the present invention include all types of choroidal neovascularization (CNV), which occurs not only in wet AMD but also in other ocular pathologies such as ocular histoplasmosis syndrome, angiod streaks, ruptures in Bruch's membrane, myopic degeneration, ocular tumors and some retinal degenerative diseases.

An additional aspect of the present invention provides for methods of treating an apoptosis related disease. Methods for therapy of diseases or disorders associated with uncontrolled, pathological cell growth, e.g. cancer, psoriasis, autoimmune diseases, inter alia, and methods for therapy of diseases associated with ischemia and lack of proper blood flow, e.g. myocardial infarction (MI) and stroke, are provided. "Cancer" or "Tumor" refers to an uncontrolled growing mass of abnormal cells. These terms include both primary tumors, which may be benign or malignant, as well as secondary tumors, or metastases which have spread to other sites in the body. Examples of cancer-type diseases include, inter alia: carcinoma (e.g.: breast, colon and lung), leukemia such as B cell leukemia, lymphoma such as B-cell lymphoma, blastoma such as neuroblastoma and melanoma and sarcoma.

The invention also provides a composition comprising one or more of the compounds of the invention in a carrier, preferably a pharmaceutically acceptable carrier. This composition may comprise a mixture of two or more siRNAs for different genes or different siRNAs for the same gene. A composition comprising siRNA for the RTP801L gene and siRNA for the VEGF gene and/or the VEGF-R1 gene is envisaged.

Another compound of the invention comprises the above compound of the invention (structure A) covalently or non-covalently bound to one or more compounds of the invention (structure A). This compound may be delivered in a carrier, preferably a pharmaceutically acceptable carrier, and may be processed intracellularly by endogenous cellular complexes to produce one or more siRNAs of the invention. Another compound of the invention comprises the above compound of the invention (structure A) covalently or non-covalently bound to an siRNA for another gene, especially the VEGF gene and/or the VEGF-R1 gene.

This invention also comprises a novel chemical entity which is an RTP801L inhibitor, preferably an siRNA, chemically bound, covalently or non-covalently, to any of the above VEGF/VEGFR-1 inhibitory agents. A particular chemical entity envisaged is an siRNA RTP801L inhibitor covalently bound to an antibody to VEGF or VEGF receptor-1. Methods of production of such novel chemical entities are known to those skilled in the art.

This invention also comprises a tandem double-stranded structure which comprises two or more siRNA sequences, which is processed intracellularly to form two or more different siRNAs, one inhibiting 801 and a second inhibiting VEGF/VEGFR-1 In a related aspect, this invention also comprises a tandem double-stranded structure which comprises two or more siRNA sequences, which is degraded intracellularly to form two or more different siRNAs, both inhibiting 801.

In particular, it is envisaged that a long oligonucleotide (typically about 80-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an 801 gene. In particular, it is envisaged that this oligonucleotide comprises sense and antisense siRNA sequences as depicted in Table A. Alternatively, the tandem shRNA construct may comprise sense and complementary antisense siRNA sequence corresponding to an 801L gene and additionally sense and complementary antisense siRNA sequence corresponding to a different gene such as 801, VEGF or VEGF-R1.

As mentioned herein, siRNA against RTP801L may be the main active component in a pharmaceutical composition, or may be one active component of a pharmaceutical composition containing two or more siRNAs (or molecules which encode or endogenously produce two or more siRNAs, be it a mixture of molecules or one or more tandem molecule which encodes two or more siRNAs), said pharmaceutical composition further being comprised of one or more additional siRNA molecule which targets one or more additional gene. Simultaneous inhibition of RTP801L and said additional gene(s) has an additive or synergistic effect for treatment of the diseases disclosed herein, according to the following:

Acute Renal Failure (ARF) and other microvascular disorders: the pharmaceutical composition for treatment of ARF may be comprised of the following compound combinations: 1) RTP801L siRNA and p53 siRNA dimers; 2) RTP801L and Fas siRNA dimers; 3) RTP801L and Bax siRNA dimers; 4) p53 and Fas siRNA dimers; 5) RTP801L and Bax siRNA dimers; 6) RTP801L and Noxa siRNA dimers; 7) RTP801L and Puma siRNA dimers; 8) RTP801L (REDD1) and RTP801LL (REDD2) siRNA dimers; 9) RTP801LsiRNA, Fas siRNA and any of RTP801LL siRNA p53 siRNA, Bax siRNA, Noxa siRNA or Puma siRNA to form trimers or polymers (i.e., tandem molecules which encode three siRNAs).

Macular degeneration (MD), diabetic retinopathy (DR), spinal cord injury: pharmaceutical compositions for treatment of MD, DR and spinal cord injury may be comprised of the following compound combinations: 1) RTP801L siRNA combined with either of VEGF siRNA, VEGF-R1 siRNA, VEGF R2 siRNA, PKCbeta siRNA, MCPJ siRNA, eNOS siRNA, KLF2 siRNA, RTP801 siRNA (either physically mixed or in a tandem molecule); 2) RTP801L siRNA in combination with two or more siRNAs of the above list (physically mixed or in a tandem molecule encodimg three siRNAs, or a combination thereof).

COPD and respiratory disorders: the pharmaceutical composition for treatment of respiratory disorders may be comprised of the following compound combinations: RTP801L siRNA combined with siRNA against one or more of the following genes: elastases, matrix metalloproteases, phospholipases, caspases, sphingomyelinase, RTP801 and ceramide synthase.

Further, a combination (tandem) siRNA directed against both RTP801 and RTP801L can be used to treat any of the conditions disclosed herein. For Example, the siRNA directed against RTP801 termed REDD14 (sense sequence: 5' GUGCCAACCUGAUGCAGCU 3' and antisense sequence 5' AGCUGCAUCAGGUUGGCAC 3') can be joined in tandem with any of the RTP801L siRNAs disclosed herein, such as siRNA Nos. 72 or 73 in Table A, or any other siRNA present in Table A Additionally, RTP801L siRNA or any nucleic acid molecule comprising or encoding RTP801L siRNA can be linked (covalently or non-covalently) to antibodies, in order to achieve enhanced targeting for treatment of the diseases disclosed herein, according to the following:

ARF: Anti-Fas Antibody (Preferably Neutralizing Antibodies).

Macular degeneration, diabetic retinopathy, spinal cord injury: anti-Fas antibody, anti-MCP1 antibody, anti-VEGFR1 and anti-VEGFR2 antibody. The antibodies should be preferably be neutralizing antibodies.

Any molecules, such as, for example, antisense DNA molecules which comprise the siRNA sequences disclosed herein (with the appropriate nucleic acid modifications) are particularly desirable and may be used in the same capacity as their corresponding siRNAs for all uses and methods disclosed herein.

The invention also comprises a method of treating a patient suffering from a disorder such as the disorders described herein comprising administering to the patient the above composition or compound in a therapeutically effective dose so as to thereby treat the patient.

Antisense Molecules

By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene. An AS polynucleotide is a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its enormous therapeutic potential (Aboul-Fadl T., Curr Med. Chem. 2005; 12(19):2193-214; Crooke S T, Curr Mol. Med. 2004 August; 4(5):465-87; Crooke S T, Annu Rev Med. 2004; 55:61-95; Vacek M et al., Cell Mol Life Sci. 2003 May; 60(5):825-33; Cho-Chung Y S, Arch Pharm Res. 2003 March; 26(3):183-91. There are further reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this technology. Antisense intervention in the expression of specific genes can be achieved by the use of synthetic AS oligonucleotide sequences (for recent reports see Lefebvre-d'Hellencourt et al, 1995; Agrawal, 1996; LevLehman et al, 1997).

AS oligonucleotide sequences may be short sequences of DNA, typically 15-30 mer but may be as small as 7 mer (Wagner et al, 1996), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996 Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation [Anazodo et al., 19961. For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitution do not substantially affect function.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for the glial fibrillary acidic protein (GFAP), for the establishment of tectal plate formation in chick (Galileo et al., 1991) and for the N-myc protein, responsible for the maintenance of cellular heterogeneity in neuroectodermal cultures (ephithelial vs. neuroblastic cells, which differ in their colony forming abilities, tumorigenicity and adherence) (Rosolen et al., 1990; Whitesell et al, 1991). Antisense oligonucleotide inhibition of basic fibroblast growth factor (bFgF), having mitogenic and angiogenic properties, suppressed 80% of growth in glioma cells (Morrison, 1991) in a saturable and specific manner. Being hydrophobic, antisense oligonucleotides interact well with phospholipid membranes (Akhter et al., 1991). Following their interaction with the cellular plasma membrane, they are actively (or passively) transported into living cells (Loke et al., 1989), in a saturable mechanism predicted to involve specific receptors (Yakubov et al., 1989).

Ribozymes

A "ribozyme" is an RNA molecule that possesses RNA catalytic ability (see Cech for review) and cleaves a specific site in a target RNA. In accordance with the present invention, ribozymes which cleave mRNA may be utilized as inhibitors. This may be necessary in cases where antisense therapy is limited by stoichiometric considerations (Sarver et al., 1990, *Gene Regulation and Aids*, pp. 305-325). Ribozymes can then be used that will target the a gene associated with a bone marrow disease. The number of RNA molecules that are cleaved by a ribozyme is greater than the number predicted by stochiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

It will be noted that all the polynucleotides to be used in the present invention may undergo modifications so as to possess improved therapeutic properties. Modifications or analogs of nucleotides can be introduced to improve the therapeutic properties of polynucleotides. Improved properties include increased nuclease resistance and/or increased ability to permeate cell membranes. Nuclease resistance, where needed, is provided by any method known in the art that does not interfere with biological activity of the AS polynucleotide, siRNA, cDNA and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include modifying the phosphorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Other modifications known in the art may be used where the biological activity is retained, but the stability to nucleases is substantially increased.

All analogues of, or modifications to, a polynucleotide may be employed with the present invention, provided that said analogue or modification does not substantially affect the function of the polynucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones, as well as LNA ("locked nucleic acid").

The polypeptides employed in the present invention may also be modified, optionally chemically modified, in order to improve their therapeutic activity. "Chemically modified"— when referring to the polypeptides, means a polypeptide where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiquitination, or any similar process.

Additional possible polypeptide modifications (such as those resulting from nucleic acid sequence alteration) include the following:

"Conservative substitution"—refers to the substitution of an amino acid in one class by an amino acid of the same class, where a class is defined by common physicochemical amino acid side chain properties and high substitution frequencies in homologous polypeptides found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class III residue such as Asp, Asn, Glu, or Gln.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

In an additional embodiment of the present invention, the RTP801L polypeptide or polynucleotide may be used to diagnose or detect macular degeneration in a subject. A detection method would typically comprise assaying for RTP801L mRNA or RTP801L polypeptide in a sample derived from a subject.

"Detection"—refers to a method of detection of a disease. This term may refer to detection of a predisposition to a disease, or to the detection of the severity of the disease.

By "homolog/homology", as utilized in the present invention, is meant at least about 70%, preferably at least about 75% homology, advantageously at least about 80% homology, more advantageously at least about 90% homology, even more advantageously at least about 95%, e.g., at least about 97%, about 98%, about 99% or even about 100% homology. The invention also comprehends that these polynucleotides and polypeptides can be used in the same fashion as the herein or aforementioned polynucleotides and polypeptides.

Alternatively or additionally, "homology", with respect to sequences, can refer to the number of positions with identical nucleotides or amino acid residues, divided by the number of nucleotides or amino acid residues in the shorter of the two sequences, wherein alignment of the two sequences can be determined in accordance with the Wilbur and Lipman algorithm ((1983) Proc. Natl. Acad. Sci. USA 80:726); for instance, using a window size of 20 nucleotides, a word length of 4 nucleotides, and a gap penalty of 4, computer-assisted analysis and interpretation of the sequence data, including alignment, can be conveniently performed using commercially available programs (e.g., Intelligenetics™ Suite, Intelligenetics Inc., CA). When RNA sequences are said to be similar, or to have a degree of sequence identity or homology with DNA sequences, thymidine (T) in the DNA sequence is considered equal to uracil (U) in the RNA sequence. RNA sequences within the scope of the invention can be derived from DNA sequences or their complements, by substituting thymidine (T) in the DNA sequence with uracil (U).

Additionally or alternatively, amino acid sequence similarity or homology can be determined, for instance, using the BlastP program (Altschul et al., Nucl. Acids Res. 25:3389-3402) and available at NCBI. The following references provide algorithms for comparing the relative identity or homology of amino acid residues of two polypeptides, and additionally, or alternatively, with respect to the foregoing, the teachings in these references can be used for determining percent homology: Smith et al., (1981) Adv. Appl. Math. 2:482-489; Smith et al., (1983) Nucl. Acids Res. 11:2205-2220; Devereux et al., (1984) Nucl. Acids Res. 12:387-395; Feng et al., (1987) J. Molec. Evol. 25:351-360; Higgins et al., (1989) CABIOS 5:151-153; and Thompson et al., (1994) Nucl. Acids Res. 22:4673-4680.

"Having at least X % homolgy"—with respect to two amino acid or nucleotide sequences, refers to the percentage of residues that are identical in the two sequences when the sequences are optimally aligned. Thus, 90% amino acid sequence identity means that 90% of the amino acids in two or more optimally aligned polypeptide sequences are identical.

An additional embodiment of the present invention concerns a pharmaceutical composition comprising an RTP801L inhibitor in a therapeutically affective amount as an active ingredient and a pharmaceutically acceptable carrier. The inhibitor may be a biological inhibitor, an organic molecule, a chemical molecule, etc. said pharmaceutical composition may comprise an RTP801L inhibitor which is a polynucleotide which comprises consecutive nucleotides having a sequence which is an antisense sequence to the sequence set forth in FIG. 1 (SEQ ID No: 1). Further, the RTP801L inhibitor may be a vector comprising these polynucleotides. Additionally, the RTP801L inhibitor may be a monoclonal antibody which specifically binds to an epitope comprising 4-25 amino acids set forth in FIG. 2 (SEQ ID No:2), or an RNA molecule which targets the RTP801L gene mRNA such as an siRNA molecule (optionally depicted in Table A) or a ribozyme.

The active ingredients of the pharmaceutical composition can include oligonucleotides that are nuclease resistant needed for the practice of the invention or a fragment thereof shown to have the same effect targeted against the appropriate sequence(s) and/or ribozymes. Combinations of active ingredients as disclosed in the present invention can be used, including combinations of antisense sequences.

An additional embodiment of the present invention provides for the use of a therapeutically effective dose of an RTP801L inhibitor for the preparation of a medicament for promoting recovery in a patient suffering from any of the diseases or conditions described herein eg spinal cord disease or injury. In one embodiment the inhibitor is preferably an siRNA. In another embodiment the inhibitor is preferably Structure A depicted herein.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

BRIEF DESCRIPTION OF THE FIGURES

FIG. 1 details the coding sequence of the RTP801L gene (SEQ ID NO:1);

FIG. 2 details the amino acid sequence of the RTP801L polypeptide (SEQ ID NO:2);

EXAMPLES

Figure 3:
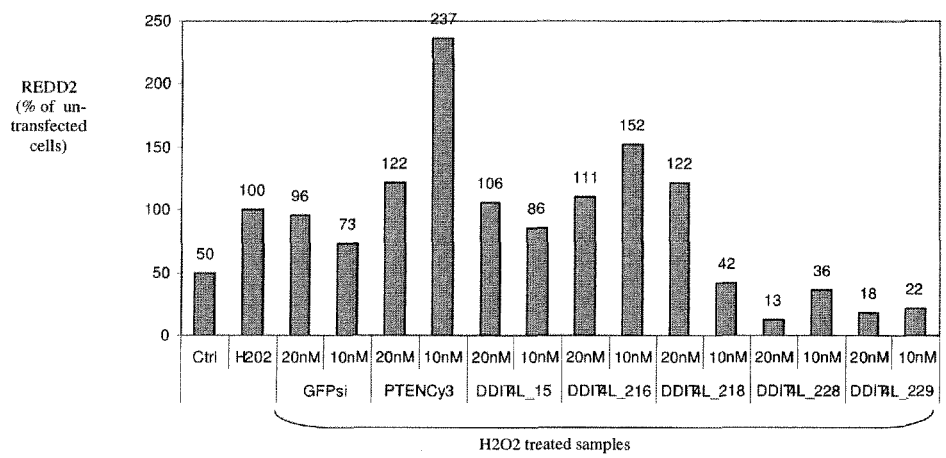
FIG. 3 details the activity results of REDD2 siRNAs on the endogenous REDD2 gene in wt MEF cells following H2O2 treatment.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988).

Standard organic synthesis protocols known in the art not specifically described herein are generally followed essentially as in *Organic syntheses: Vol.* 1-79, editors vary, J. Wiley, New York, (1941-2003); Gewert et al., *Organic synthesis workbook*, Wiley-VCH, Weinheim (2000); Smith & March, *Advanced Organic Chemistry*, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

The features of the present invention disclosed in the specification, the claims and/or the drawings may both separately and in any combination thereof be material for realizing the invention in various forms thereof.

Example 1

General Materials and Methods

If not indicated to the contrary, the following materials and methods were used in Examples 1-5:

Cell Culture

The first human cell line, namely HeLa cells (American Type Culture Collection) were cultured as follows: Hela cells (American Type Culture Collection) were cultured as described in Czauderna F et al. (Czauderna, F., Fechtner, M., Aygun, H., Arnold, W., Klippel, A., Giese, K. & Kaufmann, J. (2003). Nucleic Acids Res, 31, 670-82).

The second human cell line was a human keratinozyte cell line which was cultivated as follows: Human keratinocytes were cultured at 37° C. in Dulbecco's modified Eagle medium (DMEM) containing 10% FCS.

The mouse cell line was B16V (American Type Culture Collection) cultured at 37° C. in Dulbecco's modified Eagle medium (DMEM) containing 10% FCS. Culture conditions were as described in Methods Find Exp Clin Pharmacol. 1997 May; 19(4):231-9:

In each case, the cells were subject to the experiments as described herein at a density of about 50,000 cells per well and the double-stranded nucleic acid according to the present invention was added at 20 nM, whereby the double-stranded nucleic acid was complexed using 1 µg/ml of a proprietary lipid.

Induction of Hypoxia-Like Condition

The cells were treated with $CoCl_2$ for inducing a hypoxia-like condition as follows: siRNA transfections were carried out in 10-cm plates (30-50% confluency) as described by (Czauderna et al., 2003; Kretschmer et al., 2003). Briefly, siRNA were transfected by adding a preformed 10× concentrated complex of GB and lipid in serum-free medium to cells in complete medium. The total transfection volume was 10 ml. The final lipid concentration was 1.0 µg/ml; the final siRNA concentration was 20 nM unless otherwise stated. Induction of the hypoxic responses was carried out by adding $CoCl_2$ (100 µM) directly to the tissue culture medium 24 h before lysis.

Preparation of Cell Extracts and Immuno Blotting

The preparation of cell extracts and immuno blot analysis were carried out essentially as described by Klippel et al. (Klippel, A., Escobedo, M. A., Wachowicz, M. S., Apell, G., Brown, T. W., Giedlin, M. A., Kavanaugh, W. M. & Williams, L. T. (1998). Mol Cell Biol, 18, 5699-711; Klippel, A., Reinhard, C., Kavanaugh, W. M., Apell, G., Escobedo, M. A. & Williams, L. T. (1996). Mol Cell Biol, 16, 4117-27). Polyclonal antibodies against full length RTP801L were generated by immunising rabbits with recombinant RTP801L protein producing bacteria from pET19-b expression vector (Merck Biosciences GmbH, Schwalbach, Germany). The murine monoclonal anti-p110a and anti-p85 antibodies have been described by Klippel et al. (supra).

Example 2

Experimental Models, Methods and Results Relating to Macular Degeneration

The compounds of the present invention are tested in the following animal model of Choroidal neovascularization (CNV). This hallmark of wet AMD is induced in model animals by laser treatment.

A) Mouse Model

Choroidal Neovascularization (CNV) Induction

Choroid neovascularization (CNV), a hallmark of wet AMD, is triggered by laser photocoagulation (532 nm, 200 mW, 100 ms, 75 µm) (OcuLight GL, Iridex, Mountain View, Calif.) performed on both eyes of each mouse on day 0 by a single individual masked to drug group assignment. Laser spots are applied in a standardized fashion around the optic nerve, using a slit lamp delivery system and a cover slip as a contact lens.

Treatment Groups

CNV is induced in the following groups of mice (males 6-8 weeks of age):
(1) 12 WT mice;
(2) 12 RTP801L Knock-Out mice;
(3) 12 WT mice injected with 0.25 µg of synthetic stabilized active anti-RTP801L siRNA (REDD14) in one eye and inactive anti-RTP801L siRNA (REDD8-negative control) in the fellow eye, at days 0 and 7;

(4) 12 WT mice injected with 0.25 µg of synthetic stabilized active anti-RTP801L siRNA (REDD14) in one eye and inactive anti-GFP siRNA (negative control) in the fellow eye at days 0 and 7;

(5) 12 WT mice injected with either 0.1 µg of synthetic stabilized active anti-RTP801L siRNA (REDD14) in one eye and PBS (negative control) in the fellow eye at days 0 and 7;

(6) 12 WT mice injected with either 0.05 µg of synthetic stabilized active anti-RTP801L siRNA (REDD14) in one eye and PBS (negative control) in the fellow eye at days 0 and 7.

Both eyes of each mouse are laser-treated.

Evaluation

1. The experiment is terminated at day 14. For evaluation, the eyes are enucleated and fixed with 4% paraformaldehyde for 30 min at 4° C. The neurosensory retina is detached and severed from the optic nerve. The remaining RPE-choroid-sclera complex is flat mounted in Immu-Mount (Vectashield Mounting Medium, Vector) and coverslipped. Flat mounts are examined with a scanning laser confocal microscope (TCS SP, Leica, Germany). Vessels are visualized by exciting with blue argon laser. Horizontal optical sections (1 µm step) are obtained from the surface of the RPE-choroid-sclera complex. The deepest focal plane in which the surrounding choroidal vascular network connecting to the lesion can be identified is judged to be the floor of the lesion. Any vessel in the laser treated area and superficial to this reference plane is judged as CNV. Images of each section are digitally stored. The area of CNV-related fluorescence is measured by computerized image analysis using the Leica TCS SP software. The summation of whole fluorescent area in each horizontal section is used as an index for the volume of CNV.

2. Separate WT mice are used for evaluating RTP801L mRNA expression in CNV (as well as the expression of other genes relevant to AMD) (untreated and treated with siRNA) using real-time PCR on RNA extracted from RPE/choroids, or from neural retina.

Expression profiling conducted in the mouse model of CNV revealed that the RTP801L transcript level is gradually increased in mouse Retina following CNV induction, thus indicating that RTP801L is a good target for inhibition in the treatment of AMD and other conditions which involve choroidal neovascularization.

B) Non-Human Primate Model

CNV Induction

Choroidal neovascularization (CNV) is induced by perimacular laser treatment of both eyes prior to doseadministration. Nine lesions are placed in the macula with a laser [OcuLight GL (532 nm) Laser Photo-coagulator with an IRIS Medical® Portable Slit Lamp Adaptor], and laser spots in the right eye mirror the placement in the left eye. The approximate laser parameters are as follows: spot size: 50-100 µm diameter; laser power: 300-700 milliwatts; exposure time: 0.1 seconds.

Treatment

Immediately following laser treatment, both eyes of all animals are subjected to a single intravitreal injection. Left eye is typically dosed with 350 ug of synthetic stabilized siRNA against RTP801L in the final volume of 50 ul, whereas the contralateral eye receives 50 ul of PBS (vehicle).

Evaluation

1. All the animals are subjected to daily examination of food consumption and body weight measurements.

2. two monkeys are euthanized at day 6 following CNV induction. Their eyes are enucleated and the posterior pole is flattened. Then the fovea region is excised and separated into choroids and neuroretina which are separately (for every animal) frozen in liquid nitrogen to be subsequently used for RNA extraction and real time PCR evaluation of RTP801L expression.

3. Fluorescein angiograms are performed pre-study, and at the end of weeks 1, 2, and 3 following CNV induction. Photographs are taken, using a fundus camera (TRC-50EX Retina Camera). Images are captured using the TOPCON IMAGEnet™ system. Fluorescein dye (10% fluorescein sodium, approximately 0.1 mL/kg) is injected via vascular access ports. Photographs are taken at several timepoints following dye injection, to include the arterial phase, early arteriovenous phase and several late arteriovenous phases in order to evaluate neovascularization snd to monitor leakage of fluorescein associated with CNV lesions. Interpretation and analysis of the fluorescein angiograms is independently conducted by two ophthalmologists.

Neovascularization (NV) is assessed in early angiograms and every spot is graded according to the following scheme:
0—no signs of NV
0.5—suspicious spot
1—"hot" spot
2—NV in the laser burn
3—evident NV Leakage is assessed according to the following scheme:
0—no leakage
0.5—suspicious spot
1—evident small spot leakage
2—leakage growing with time
3—leakage greater than previous borders (evidently)

In addition, the size of every spot is compared between the early and the late angiograms using morphometric measurements, and the increase in the spot's size resulting from the leakage is calculated.

4. Electroretinograms (ERGs) are recorded using an Epic 2000 electroretinograph according to Sierra's SOPs and the study-specific SOP, including the use of the Ganzfield apparatus, at prestudy and in the end of week 3. The tabulated ERG data are evaluated by a veterinary ophthalmologist.

C) Efficacy of Combination Therapy of RTP801L siRNA (Redd14) and Anti-VEGF Antibody The efficacy of combination therapy of RTP801L siRNA (REDD14) and anti-VEGF antibody or aptamer (such as macugen) in the treatment of diseases in which CNV occurs is tested in the above mouse CNV model.

A) CNV Volume Studies

The volume of choroidal neovascularization (CNV) 3 weeks after laser injury is computed byconfocal fluorescence microscopy as previously described (Sakurai et al. *IOVS* 2003; 44: 3578-85 & Sakurai et al. *IOVS* 2003; 44: 2743-2749).

In previous studies the assignee of the present invention found that anti-VEGF-A antibody (Ab) reduced CNV volume in a dose dependent fashion. A dose of 1 ng of VEGF-A Ab was chosen for the RTP801L siRNA+VEGF-A Ab combination studies because this dose had an intermediate inhibitory effect: VEGF-A Ab (1 ng) reduced the size of CNV by 26±6%.

In a study conducted with siRNA against RTP801, The principal findings were:
  The addition of RTP801 siRNA at the lower 0.05 µg dose reduced the size of CNV by 27±4% compared to VEGF-A Ab alone.
  The addition of RTP801 siRNA at the higher 0.25 µg dose reduced the size of CNV by 55±3% compared to VEGF-A Ab alone.
B) CNV Leakage Studies
Experiment 1
This experiment was designed in order to identify a potential additive or synergistic therapeutic effect of inhibition of VEGF and RTP801L in the model of laser-induced choroid neovascularization in mice
Materials:
  RTP801L siRNA
  negative control
  Anti-VEGF antibodies or macugen
  negative control CNV is induced on day zero as described above; the test material is injected to the subjects on day zero and day 7.
  The results are evaluated by Fluorescein angiography on weeks 1, 2, 3, and by CNV volume measurement on week 3.
Experimental Groups:
  VEGF Ab or macugen 0.5 ng/eye
  VEGF Ab or macugen 1 ng/eye
  VEGF Ab or macugen 2 ng/eye
  VEGF Ab 4 or macugen ng/eye
  RTP801L siRNA 0.05 ug/eye
  RTP801L siRNA 0.1 ug/eye
  RTP801L siRNA 0.25 ug/eye
  RTP801L siRNA 0.05 ug/eye+VEGF Ab or macugen 1 ng/eye
  RTP801L siRNA 0.1 ug/eye+VEGF Ab or macugen 1 ng/eye
  RTP801L siRNA 0.25 ug/eye+VEGF Ab or macugen 1 ng/eye
Control Groups
  PBS
  Non-specific IgG 2 ng/eye
  negative control 0.1 ug/eye
  negative control 0.1 ug/eye+VEGF Ab or macugen 1 ng/eye
The results show an additive or synergistic therapeutic effect of inhibition of VEGF and RTP801L
Experiment 2
This experiment was designed in order to study the effect of RTP801L siRNA on gene expression in RPE and neural retina.
Experimental Design
Groups:
  PBS
  RTP801L siRNA 0.25 mg
  CNV is induced by laser treatment as described above on day zero; the test material is also injected on day zero, and the effect evaluated by qPCR analysis of gene expression in RPE and neural retina on days zero and 5.
Results Obtained with RTP801a Functionally Homologous Gene:
  Simultaneous inhibition of RTP801L and VEGF has enhanced inhibitory effect on choroid neovascularization and neovascular leakage.
  Inhibition of RTP801 expression by REDD14 (siRNA to 801) not only prevents PEDF downregulation in the CNV model but enhances its expression compared to the baseline.
  Inhibition of RTP801 expression leads to concomitant downregulation of MCP1 which should have an anti-inflammatory effect.
  Without being bound by theory, the increase of PEDF expression by REDD14 may underlie the observed cooperative effect of simultaneous inhibition of VEGF and RTP801
  (Note: PEDF is a well-known antiangiogenic and neuroprotective factor.)
  Without being bound by theory, the reduction of MCP1 expression by REDD14 may also underlie the observed cooperative effect of simultaneous inhibition of VEGF and RTP801
  (Note: MCP1 is a known pro-inflammatory chemokine involved in pathogenesis of AMD.)
  Similar results are obtained using inhibitors to 801L.
  Additional AMD models which may be used to test the methods of the present invention:
  Ccl-2 or Ccr-2 deficient animals—deficiency in either of these proteins causes the development of some of the main features of AMD. Animals deficient in these proteins can be used to test the methods of the present invention.
  For further information on AMD animal models, see: Chader, *Vision research* 42 (2002) 393-399; Ambati et al., *Nature Medicine* 9(11) (2003) 1390-1397; Tolentino et al., *Retina* 24 (2004) 132-138.

Example 3

Models and Results Relating to COPD and Emphysema

The compounds of the present invention are tested in the following an animal models and are shown to prevent emphysema:
  Cigarette smoke-induced emphysema model: chronic exposure to cigarette smoke causes emphysema in several animals such as, inter alia, mouse, guinea pig.
  Lung protease activity as a trigger of emphysema.
  VEGFR inhibition model of emphysema.
  Bronchial instillation with human neutrophil/pancreatic elastase in rodents.
  MMP (matrix metalloprotease)-induced enphysema.
  Inflammation-induced emphysema.
  Additionally, emphysema models may be generated through genetic means (e.g., mice carrying the TSK mutation), and emphysematous animals may be generated by known modifiers of susceptibility to emphysema such as, inter alia, lung injury, alveolar hypoplasia, hyperoxia, glucocorticoid treatment and nutrition.
Evaluation of the Influence of Lack of RTP801L on Disease Progression in Mouse Models of Emphysema by Inhibiting Endogenous RTP801L Employing Intralung Delivery RTP801L—Inactivating siRNA
  CS-induced inflammation is induced by 7 day smoking in 2 groups of C57BL6 mice, 10 mice per group. Group 1: CS+delivery of control siRNA; Group 2: CS+RTP801L siRNA. Control groups of mice are instilled with either type of siRNA but kept in room air conditions. The lungs are subsequently agarose-inflated, fixed and imbedded in paraffin, and development oxidative stress in the KO mice is assessed by:
    a) immunohistochemical localization and quantitation of 8-oxo-dG in the lung sections;

b) immunohistochemical localization and quantitation of active caspase 3 in the lung sections using specific antibodies, or quantitative evaluation of the number of TUNEL-positive cells;

c) measurement of ceramide concentration in the lung extracts;

d) measurement of caspase activity in the lung extracts.

Methods

Exposure to Cigarette Smoking (CS)

Exposure is carried out (7 h/day, 7 days/week) by burning 2R4F reference cigarettes (2.45 mg nicotine per cigarette; purchased from the Tobacco Research Institute, University of Kentucky, Lexington, Ky., USA) using a smoking machine (Model TE-10, Teague Enterprises, Davis, Calif., USA). Each smoldering cigarette is puffed for 2 s, once every minute for a total of eight puffs, at a flow rate of 1.05 L/min, to provide a standard puff of 35 cm3. The smoke machine is adjusted to produce a mixture of sidestream smoke (89%) and mainstream smoke (11%) by burning five cigarettes at one time. Chamber atmosphere is monitored for total suspended particulates and carbon monoxide, with concentrations of 90 mg/m3 and 350 ppm, respectively.

Morphologic and Morphometric Analyses

After exposing the mice to CS or instillation of RTP801L expressing plasmid, the mice are anesthetized with halothane and the lungs are inflated with 0.5% low-melting agarose at a constant pressure of 25 cm as previously described. The inflated lungs are fixed in 10% buffered formalin and embedded in paraffin. Sections (5 μm) are stained with hematoxylin and eosin. Mean alveolar diameter, alveolar length, and mean linear intercepts are determined by computer-assisted morphometry with the Image Pro Plus software (Media Cybernetics, Silver Spring, Md., USA). The lung sections in each group are coded and representative images (15 per lung section) are acquired by an investigator masked to the identity of the slides, with a Nikon E800 microscope, 20× lens. The results show that siRNA to 801L prevents emphysema caused by smoking as measured by the four parameters described above.

Bronchoalveolar Lavage (BAL) and Phenotyping

Following exposure to CS or instillation of RTP801L expressing plasmid, the mice are anesthetized with sodium pentobarbital. The BAL fluid collected from the lungs of the mice is centrifuged (500' g at 4° C.), and the cell pellet is resuspended in phosphate-buffered saline. The total number of cells in the lavage fluid is determined, and 2×104 cells are cytocentrifuged (Shandon Southern Products, Pittsburgh, Pa., USA) onto glass slides and stained with Wright-Giemsa stain. Differential cell counts are performed on 300 cells, according to standard cytologic techniques.

Identification of Alveolar Apoptotic Cell Populations in the Lungs.

To identify the different alveolar cell types undergoing apoptosis in the lungs, an immunohistochemical staining of active caspase 3 is performed in the lung sections from the room air (RA) as well as CS exposed mice. To identify the apoptotic type II epithelial cells in the lungs, after active caspase 3 labeling, the lung sections are incubated first with anti-mouse surfactant protein C (SpC) antibody and then with an anti-rabbit Texas red antibody. Apoptotic endothelial cells are identified by incubating the sections first with the anti-mouse CD 31 antibody and then with the biotinylated rabbit anti-mouse secondary antibody. The lung sections are rinsed in PBS and then incubated with the streptavidin-Texas red conjugated complex. The apoptotic macrophages in the lungs are identified by incubating the sections first with the rat anti-mouse Mac-3 antibody and then with the anti-rat Texas red antibody. Finally, DAPI is applied to all lung sections, incubated for 5 minutes, washed and mounted with Vectashield HardSet mounting medium. DAPI and fluorescein are visualized at 330-380 nm and 465-495 nm, respectively. Images of the lung sections are acquired with the Nikon E800 microscope, 40× lens.

Immunohistochemical Localization of Active Caspase-3

Immunohistochemical staining of active caspase-3 assay is performed using anti-active caspase-3 antibody and the active caspase-3-positive cells are counted with a macro, using Image Pro Plus program. The counts are normalized by the sum of the alveolar profiles herein named as alveolar length and expressed in μm. Alveolar length correlates inversely with mean linear intercept, i.e., as the alveolar septa are destroyed, mean linear intercepts increases as total alveolar length, i.e., total alveolar septal length decreases.

Caspase 3 Activity Assay

The caspase-3/7 activity is measured in lung tissue extracts using a fluorometric assay according to the manufacturer's instructions. Snap-frozen lung tissue (n=3 per group) was homogenized with the assay buffer, followed by sonication and centrifugation at 800×g. After removal of nuclei and cellular debris, the supernatant (300 μg protein) is then incubated with the pro-fluorescent substrate at room temperature for 1 h and the fluorescence intensity was measured utilizing a Typhoon phosphoimager (Amersham Biosciences, Inc., Piscataway, N.J., USA). The results are expressed as the rate of specific caspase-3 substrate cleavage, expressed in units of caspase 3 enzymatic activity, normalized by total protein concentration. Active recombinant caspase 3 was utilized as the assay standard (0-4 U). Tissue lysates without substrate, assay buffer alone, and lysates with caspase 3 inhibitor were utilized as negative controls.

Immunohistochemical Localization of 8-Oxo-dG

For the immunohistochemical localization and quantification of 8-oxo-dG, lung sections from the mice exposed to CS or instilled with RTP801L expressing plasmid are incubated with anti-8-oxo-dG antibody and stained using InnoGenex™ Iso-IHC DAB kit using mouse antibodies. The 8-oxo-dG-positive cells are counted with a macro (using Image Pro Plus), and the counts were normalized by alveolar length as described.

Instillation of Plasmid DNA into Mouse Lungs

Plasmid DNA of RTP801L expressing and control vectors are prepared under endotoxin-free DNA isolation kit. For intra-tracheal instillation, 50 ug of plasmid DNA is delivered in 80 ul sterile perfluorocarbon. The oxygen carrying properties of perfluorocarbon make it well-tolerated at these volumes, while its physical-chemical properties allow for extremely efficient distal lung delivery when instilled intratracheally. Mice are anesthetized by brief inhalational halothane exposure, the tongue is gently pulled forward by forceps and the trachea instilled with perfluorocarbon solution applied at the base of the tongue via a blunt angiocatheter.

Instillation of siRNA into Mouse Lungs.

Mice are anesthetized with an intra-peritoneal injection of Ketamine/Xylazine (115/22 mg/kg). 50 μg of siRNA is instilled intranasally in 50 μl volume of 0.9% NaCl by delivering five consecutive 10 μl portions. At the end of the intranasal instillation, the mouse's head is held straight up for 1 minute to ensure that all the instilled solution drains inside.

For further information, see: Rangasamy T, Cho C Y, Thimmulappa, R K, Zhen L, Srisuma S S, Kensler T W, Yamamoto M, Petrache I, Tuder R M, Biswal S. *Genetic ablation of Nrf2 enhances susceptibility to cigarette smoke-iduced emphysema in mice. Submitted to Journal of Clininical Investigation*; Yasunori Kasahara, Rubin M. Tuder, Carlyne D. Cool, David A. Lynch, Sonia C. Flores, and Norbert F. Voelkel. *Endothelial Cell Death and Decreased Expression of Vascular Endothelial Growth Factor and Vascular Endothelial Growth Factor Receptor 2 in Emphysema*. Am J Respir Crit. Care Med Vol 163. pp 737-744, 2001; Yasunori Kasahara, Rubin M. Tuder, Laimute Taraseviciene-Stewart, Timothy D. Le Cras, Steven Abman, Peter K. Hirth, Johannes Waltenberger, and Norbert F. Voelkel. *Inhibition of VEGF receptors causes lung cell apoptosis and emphysema*. J. Clin. Invest. 106:1311-1319 (2000); and a review on the topic: Robin M. Tuder, Sharon McGrath and Enid Neptune, *The pathological mechanisms of emphysema models: what do they have in common?*, Pulmonary Pharmacology & Therpaeutics 2002.

Example 4

Models and Results Relating to Microvascular Disorders

The compounds of the present invention are tested in animal models of a range of microvascular disorders as described below.

1. Diabetic Retinopathy

RTP801L promotes neuronal cell apoptosis and generation of reactive oxygen species in vitro. The inventor of the current invention also found that in RTP801 knockout (KO) mice subjected to the model of retinopathy of prematurity (ROP), pathologic neovascularization NV was reduced under hypoxic conditions, despite elevations in VEGF, whereas the lack of this gene did not influence physiologic neonatal retinal NV. Moreover, in this model, lack of RTP801 was also protective against hypoxic neuronal apoptosis and hyperoxic vaso-obliteration.

Experiment 1

Diabetes is induced in 8 wk old RTP801L KO and C57/129sv wildtype (WT) littermate mice by intraperitoneal injection of STZ. After 4 weeks, ERG (single white flash, $1.4\times10^4$ ftc, 5 ms) is obtained from the left eye after 1 hour of dark adaptation. RVP is assessed from both eyes using the Evans-blue albumin permeation technique.

Experiment 2

Diabetes is induced in RTP801L knockout and in control wild type mice with the matched genetic background. In addition, it is induced in C57B16 mice, which are subsequently used for intravitreal injection of anti-RTP801L and control siRNAs. For diabetes induction, the mice are injected with streptozotocin (STZ 90 mg/kg/d for 2 days after overnight fast). Animal physiology is monitored throughout the study for changes in blood glucose, body weight, and hematocrit. Vehicle-injected mice serve as controls. The appropriate animals are treated by intravitreal injections of 1 ug of REDD14 anti-RTP801L siRNA or 1 ug of anti-GFP control siRNA. siRNA is injected twice in the course of the study— on day 0, when the first STZ injection is performed, and on day 14 after the STZ injection.

Retinal vascular leakage is measured using the Evans-blue (EB) dye technique on the animals after 4 weeks duration of diabetes. Mice have a catheter implanted into the right jugular vein 24 hours prior to Evans Blue (EB) measurements. Retinal permeability measurements in both eyes of each animal follows a standard Evans-blue protocol.

2. Retinopathy of Prematurity

Retinopathy of prematurity is induced by exposing the test animals to hypoxic and hyperoxic conditions, and subsequently testing the effects on the retina.

3. Myocardial Infarction

Myocardial infarction is induced by Left Anterior Descending artery ligation in mice, both short term and long term.

4. Microvascular Ischemic Conditions

Animal models for assessing ischemic conditions include:
1. Closed Head Injury (CHI)—Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.
2. Transient middle cerebral artery occlusion (MCAO)—a 90 to 120 minutes transient focal ischemia is performed in adult, male Sprague Dawley rats, 300-370 gr. The method employed is the intraluminal suture MCAO (Longa et al., Stroke, 30, 84, 1989, and Dogan et al., J. Neurochem. 72, 765, 1999). Briefly, under halothane anesthesia, a 3-O-nylon suture material coated with Poly-L-Lysine is inserted into the right internal carotid artery (ICA) through a hole in the external carotid artery. The nylon thread is pushed into the ICA to the right MCA origin (20-23 mm). 90-120 minutes later the thread is pulled off, the animal is closed and allowed to recover.
3. Permanent middle cerebral artery occlusion (MCAO)— occlusion is permanent, unilateral-induced by electrocoagulation of MCA. Both methods lead to focal brain ischemia of the ipsilateral side of the brain cortex leaving the contralateral side intact (control). The left MCA is exposed via a temporal craniectomy, as described for rats by Tamura A. et al., *J Cereb Blood Flow Metab.* 1981; 1:53-60. The MCA and its lenticulostriatal branch are occluded proximally to the medial border of the olfactory tract with microbipolar coagulation. The wound is sutured, and animals returned to their home cage in a room warmed at 26° C. to 28° C. The temperature of the animals is maintained all the time with an automatic thermostat.

5. Acute Renal Failure (ARF)

Testing active siRNA for treating ARF may be done using sepsis-induced ARF or ischemia-reperfusion-induced ARF.
1. Sepsis Induced ARF Two predictive animal models of sepsis-induced ARF are described by Miyaji T, Hu X, Yuen P S, Muramatsu Y, Iyer S, Hewitt S M, Star R A, 2003, *Ethyl pyruvate decreases sepsis-induced acute renal failure and multiple organ damage in aged mice*, Kidney Int. November; 64(5):1620-31. These two models are lipopolysaccharide administration and cecal ligation puncture in mice, preferably in aged mice.
2. Ischemia-Reperfusion-Induced ARF This predictive animal model is described by Kelly K J, Plotkin Z, Vulgamott S L, Dagher P C, 2003 January, *P53 mediates the apoptotic response to GTP depletion after renal ischemia-reperfusion: protective role of a p53 inhibitor*, J Am Soc Nephrol.; 14(1):128-38.

Ischemia-reperfusion injury is induced in rats following 45 minutes bilateral kidney arterial clamp and subsequent release of the clamp to allow 24 hours of reperfusion. anti RTP801L siRNA or GFP siRNA (negative control) are injected into the jugular vein 2 hrs prior to and 30 minutes following the clamp. Additional siRNA is given via the tail vein at 4 and 8 hrs after the clamp. ARF progression is monitored by measurement of serum creatinine levels before and 24 hrs post surgery. At the end of the experiment, the rats are perfused via an indwelling femoral line with warm PBS followed by 4% paraformaldehyde. The left kidneys are removed and stored in 4% paraformaldehyde for subsequent histological analysis. Acute renal failure is frequently defined as an acute increase of the serum creatinine level from baseline. An increase of at least 0.5 mg per dL or 44.2 μmmol per L of serum creatinine is considered as an indication for acute renal failure. Serum creatinine is measured at time zero before the surgery and at 24 hours post ARF surgery. siRNA to 801L prevents production of ARF in this model To study the distribution of siRNA in the rat kidney, Cy3-labeled 19-mer blunt-ended siRNA molecules (2 mg/kg) having alternating O-methyl modification in the sugar residues were administered iv for 3-5 min, after which in vivo imaging was conducted using two-photon confocal microscopy. The confocal microscopy analysis revealed that the majority of siRNA in the kidneys is concentrated in the endosomal compartment of proximal tubular cells. Both endosomal and cytoplasmic siRNA fluorescence were relatively stable during the first 2 hrs post delivery and disappeared at 24 hrs.

The expression of RTP801L during ischemia-reperfurion induced ARF was examined in rat kidneys. In both kidney regions, cortex and medulla, RTP801L transcript level is decreased in the ARF-10 hr group relative to the control group transcript level. RTP801L transcript level is also elevated (up-regulated) in the kidney medulla, 3 and 6 hrs following the ARF operation (bilateral renal artery clamp).

Example 5

Preparation of siRNAs

Using proprietary algorithms and the known sequence of gene RTP801L (SEQ ID NO:1), the sequences of many potential siRNAs were generated. siRNA molecules according to the above specifications were prepared essentially as described herein.

The siRNAs of the present invention can be synthesized by any of the methods which are well-known in the art for synthesis of ribonucleic (or deoxyribonucleic) oligonucleotides. For example, a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The siRNA molecules of the invention may be synthesized by procedures known in the art e.g. the procedures as described in Usman et al., 1987, J. Am. Chem. Soc., 109, 7845; Scaringe et al., 1990, Nucleic Acids Res., 18, 5433; Wincott et al., 1995, Nucleic Acids Res. 23, 2677-2684; and Wincott et al., 1997, Methods Mol. Bio., 74, 59, and may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired. Alternatively, the nucleic acid molecules of the present invention can be synthesized separately and joined together post-synthetically, for example, by ligation (Moore et al., 1992, Science 256, 9923; Draper et al., International PCT publication No. WO93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204), or by hybridization following synthesis and/or deprotection. The siRNA molecules of the invention can also be synthesized via a tandem synthesis methodology, as described in US patent application publication No. US2004/0019001 (McSwiggen) wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

For further information, see PCT publication No. WO 2004/015107 (ATUGEN).

As described above, the siRNAs consisting of the sequences set forth in Table A (below) were constructed such that alternate sugars have 2'-O-methyl modification i.e. alternate nucleotides were thus modified. In these preferred embodiments, in one strand of the siRNA the modified nucleotides were numbers 1, 3, 5, 7, 9, 11, 13, 15, 17 and 19 and in the opposite strand the modified nucleotides were numbers 2, 4, 6, 8, 10, 12, 14, 16 and 18. Thus these siRNAs are blunt-ended 19-mer RNA molecules with alternate 2-0'-methyl modifications as described above.

TABLE A

| No | Sp-Source | Sense siRNA | AntiSense siRNA | human 34222182 cds = 204-785 |
|---|---|---|---|---|
| 1 | human | GCCAGUGUUCUAACAAACU | AGUUUGUUAGAACACUGGC | [2242-2260](19/19) |
| 2 | human | UAGCCAGUGUUCUAACAAA | UUUGUUAGAACACUGGCUA | [2240-2258](19/19) |
| 3 | human | GUGACUUCCUCACUCUAAU | AUUAGAGUGAGGAAGUCAC | [1385-1403](19/19) |
| 4 | human | AGCCAGUGUUCUAACAAAC | GUUUGUUAGAACACUGGCU | [2241-2259](19/19) |
| 5 | human | GAGUGAAUGAUGAAUACCU | AGGUAUUCAUCAUUCACUC | [1577-1595](19/19) |
| 6 | human | GACUUCCUCACUCUAAUGU | ACAUUAGAGUGAGGAAGUC | [1387-1405](19/19) |
| 7 | human | GUUCUAACAAACUAAACUC | GAGUUUAGUUUGUUAGAAC | [2248-2266](19/19) |
| 8 | human | GAAUGAUGAAUACCUGUGA | UCACAGGUAUUCAUCAUUC | [1581-1599](19/19) |
| 9 | human | UCCUCACUCUAAUGUUUUA | UAAAACAUUAGAGUGAGGA | [1391-1409](19/19) |
| 10 | human, mouse, rat, chimpanzee | GCCAGAAUUUGGUUAAAAU | AUUUUAACCAAAUUCUGGC | [364-382](19/19) |
| 11 | human | ACGGGUCAAUUUACGAAGU | ACUUCGUAAAUUGACCCGU | [1809-1827](19/19) |
| 12 | human | UCCAUUGAGUGAAUGAUGA | UCAUCAUUCACUCAAUGGA | [1571-1589](19/19) |
| 13 | human | UUCCUCACUCUAAUGUUUU | AAAACAUUAGAGUGAGGAA | [1390-1408](19/19) |
| 14 | human | GCACCCAGAUUUUUUCCAC | GUGGAAAAAAUCUGGGUGC | [1901-1919](19/19) |
| 15 | human | GUGGUGCCAUUUCAGUAAC | GUUACUGAAAUGGCACCAC | [1428-1446](19/19) |
| 16 | human | CCUCACUCUAAUGUUUUAA | UUAAAACAUUAGAGUGAGG | [1392-1410](19/19) |
| 17 | human | CUUCCUCACUCUAAUGUUU | AAACAUUAGAGUGAGGAAG | [1389-1407](19/19) |
| 18 | human | GGCUUUUUUUCUCUAAGU | ACUUAGAGAAAAAAAGCC | [1153-1171](19/19) |

TABLE A-continued

| | | | | |
|---|---|---|---|---|
| 19 | human | UCCCAUUUUUGUACAGAAU | AUUCUGUACAAAAAUGGGA | [1005-1023](19/19) |
| 20 | human | GAGAAGUGAUUCAAAAUAG | CUAUUUUGAAUCACUUCUC | [967-985](19/19) |
| 21 | human | GGAGAAGUGAUUCAAAAUA | UAUUUUGAAUCACUUCUCC | [966-984](19/19) |
| 22 | human | GUCAGCUAAAGUCAUUUGU | ACAAAUGACUUUAGCUGAC | [841-859](19/19) |
| 23 | human, chimpanzee | CCGGCCAGCAUUUCAGAAU | AUUCUGAAAUGCUGGCCGG | [237-255](19/19) |
| 24 | human, chimpanzee, dog | AUGCUGGAGAACUGUCUGU | ACAGACAGUUCUCCAGCAU | [381-399](19/19) |
| 25 | human, chimpanzee, dog | AAAUGCUGGAGAACUGUCU | AGACAGUUCUCCAGCAUUU | [379-397](19/19) |
| 26 | human, chimpanzee | UGGUUAAAAUGCUGGAGAA | UUCUCCAGCAUUUUAACCA | [373-391](19/19) |
| 27 | human, chimpanzee | UUGGUUAAAAUGCUGGAGA | UCUCCAGCAUUUUAACCAA | [372-390](19/19) |
| 28 | human | UAGCUCCACUUCACAUGCU | AGCAUGUGAAGUGGAGCUA | [2118-2136](19/19) |
| 29 | human | AGCUCCACUCAACAAUGU | ACAUUGUUGAGUGGAGGCU | [2023-2041](19/19) |
| 30 | human | ACCCAGAUUUUUUCCACCU | AGGUGGAAAAAAUCUGGGU | [1903-1921](19/19) |
| 31 | human | UGCACCCAGAUUUUUUCCA | UGGAAAAAAUCUGGGUGCA | [1900-1918](19/19) |
| 32 | human | AAACGGGUCAAUUUACGAA | UUCGUAAAUUGACCCGUUU | [1807-1825](19/19) |
| 33 | human | AUGAUGAAUACCUGUGAGG | CCUCACAGGUAUUCAUCAU | [1583-1601](19/19) |
| 34 | human | UUGAGUGAAUGAUGAAUAC | GUAUUCAUCAUUCACUCAA | [1575-1593](19/19) |
| 35 | human | CGGCAAUAAUGGAACUGCU | AGCAGUUCCAUUAUUGCCG | [1353-1371](19/19) |
| 36 | human | GCCUAUCAAAACUUCCAAA | UUUGGAAGUUUUGAUAGGC | [1218-1236](19/19) |
| 37 | human | UGGCUUUUUUUUCUCUAAG | CUUAGAGAAAAAAAAGCCA | [1152-1170](19/19) |
| 38 | human | GCCCAUUUGAGUUUUACAU | AUGUAAAACUCAAAUGGGC | [1057-1075](19/19) |
| 39 | human, chimpanzee | GGCCAGCAUUUCAGAAUUG | CAAUUCUGAAAUGCUGGCC | [239-257](19/19) |
| 40 | human, chimpanzee | CGGCCAGCAUUUCAGAAUU | AAUUCUGAAAUGCUGGCCG | [238-256](19/19) |
| 41 | human | GCGUCGUACCUACUUUUGA | UCAAAAGUAGGUACGACGC | [589-607](19/19) |
| 42 | human | UAGCGUCGUACCUACUUUU | AAAAGUAGGUACGACGCUA | [587-605](19/19) |
| 43 | human, rat, dog | AUGCACGUGAACUUGGAAA | UUUCCAAGUUCACGUGCAU | [525-543](19/19) |
| 44 | human | UUGUCCUUUUUCCACUAAC | GUUAGUGGAAAAAGGACAA | [2441-2459](19/19) |
| 45 | human | GUUGUCCUUUUUCCACUAA | UUAGUGGAAAAAGGACAAC | [2440-2458](19/19) |
| 46 | human | CUGUUGUCCUUUUUCCACU | AGUGGAAAAAGGACAACAG | [2438-2456](19/19) |
| 47 | human, chimpanzee, dog | CUGGAGAACUGUCUGUCCA | UGGACAGACAGUUCUCCAG | [384-402](19/19) |
| 48 | human | GCCAAUCUUUAUAGAAUUG | CAAUUCUAUAAAGAUUGGC | [2294-2312](19/19) |
| 49 | human | GUUCAAAUUAGCCAGUGUU | AACACUGGCUAAUUUGAAC | [2232-2250](19/19) |
| 50 | human, mouse, rat, chimpanzee | UGCCAGAAUUUGGUUAAAA | UUUUAACCAAAUUCUGGCA | [363-381](19/19) |
| 51 | human | CCCAGAUUUUUUCCACCUU | AAGGUGGAAAAAAUCUGGG | [1904-1922](19/19) |
| 52 | human | CACCCAGAUUUUUUCCACC | GGUGGAAAAAAUCUGGGUG | [1902-1920](19/19) |
| 53 | human | CAAUUUACGAAGUCUGCAU | AUGCAGACUUCGUAAAUUG | [1815-1833](19/19) |
| 54 | human | GGGUCAAUUUACGAAGUCU | AGACUUCGUAAAUUGACCC | [1811-1829](19/19) |
| 55 | human | AACGGGUCAAUUUACGAAG | CUUCGUAAAUUGACCCGUU | [1808-1826](19/19) |
| 56 | human | UGAAACGGGUCAAUUUACG | CGUAAAUUGACCCGUUUCA | [1805-1823](19/19) |
| 57 | human | UGGUGCCAUUUCAGUAACC | GGUUACUGAAAUGGCACCA | [1429-1447](19/19) |
| 58 | human | UGGAACUGCUUCACUGUUU | AAACAGUGAAGCAGUUCCA | [1362-1380](19/19) |
| 59 | human | AAGGUAGGAUUAAGUAGGU | ACCUACUUAAUCCUACCUU | [1286-1304](19/19) |
| 60 | human | CAGGAGGUAGGAUUAAGU | ACUUAAUCCUACCUUCCUG | [1282-1300](19/19) |
| 61 | human | AGCCUAUCAAAACUUCCAA | UUGGAAGUUUUGAUAGGCU | [1217-1235](19/19) |
| 62 | human | AACCAGAUUUGCCUAUUUU | AAAAUAGGCAAAUCUGGUU | [1123-1141](19/19) |
| 63 | human | GUACAGAAUUGAAUGGGAU | AUCCCAUUCAAUUCUGUAC | [1015-1033](19/19) |
| 64 | human | AUCCCAUUUUUGUACAGAA | UUCUGUACAAAAAUGGGAU | [1004-1022](19/19) |
| 65 | human | CAGCUAAAGUCAUUUGUAG | CUACAAAUGACUUUAGCUG | [843-861](19/19) |
| 66 | human | AUGAUUGGGUAGUAAAACU | AGUUUUACUACCCAAUCAU | [813-831](19/19) |
| 67 | human | AGGGUCCUAAAAAGGGAAA | UUUCCCUUUUUAGGACCCU | [776-794](19/19) |
| 68 | human, rat, dog | ACGUGAACUUGGAAAUUGA | UCAAUUUCCAAGUUCACGU | [529-547](19/19) |
| 69 | human, mouse, chimpanzee | GAAUUGCUCAAGAUGUCCU | AGGACAUCUUGAGCAAUUC | [463-481](19/19) |
| 70 | human, mouse, chimpanzee | GAGAAUUGCUCAAGAUGUC | GACAUCUUGAGCAAUUCUC | [461-479](19/19) |
| 71 | human, mouse, chimpanzee | AGAGAAUUGCUCAAGAUGU | ACAUCUUGAGCAAUUCUCU | [460-478](19/19) |
| 72 | human, mouse, chimpanzee | CCAGAGAAUUGCUCAAGAU | AUCUUGAGCAAUUCUCUGG | [458-476](19/19) |
| 73 | human, mouse, chimpanzee | CCCAGAGAAUUGCUCAAGA | UCUUGAGCAAUUCUCUGGG | [457-475](19/19) |
| 74 | human, chimpanzee, dog | AACUGUCUGUCCAAAUCAA | UUGAUUUGGACAGACAGUU | [390-408](19/19) |
| 75 | human | UGUCCUUUUUCCACUAACA | UGUUAGUGGAAAAAGGACA | [2442-2460](19/19) |
| 76 | human | GAACUGUUGUCCUUUUUCC | GGAAAAAGGACAACAGUUC | [2435-2453](19/19) |
| 77 | human, chimpanzee, dog | GGAGAACUGUCUGUCCAAA | UUUGGACAGACAGUUCUCC | [386-404](19/19) |
| 78 | human | CAGUGUUCUAACAAACUAA | UUAGUUUGUUAGAACACUG | [2244-2262](19/19) |
| 79 | human | AAAUUAGCCAGUGUUCUAA | UUAGAACACUGGCUAAUUU | [2236-2254](19/19) |
| 80 | human | GACCUAAAAUGUCACUGUU | AACAGUGACAUUUUAGGUC | [2216-2234](19/19) |
| 81 | human, chimpanzee | UUGCCAGAAUUUGGUUAAA | UUUAACCAAAUUCUGGCAA | [362-380](19/19) |
| 82 | human | UGGAUAAGGAGCUUAUUCA | UGAAUAAGCUCCUUAUCCA | [2080-2098](19/19) |
| 83 | human | AGCAAGGCUUUCAUAUCCU | AGGAUAUGAAAGCCUUGCU | [2049-2067](19/19) |
| 84 | human | CUCCACUCAACAAUGUUCA | UGAACAUUGUUGAGUGGAG | [2026-2044](19/19) |
| 85 | human | UUAGCCUCCACUCAACAAU | AUUGUUGAGUGGAGGCUAA | [2021-2039](19/19) |
| 86 | human | AGAGAAUUUAGCCUCCACU | AGUGGAGGCUAAAUUCUCU | [2014-2032](19/19) |
| 87 | human | AGAUCAUUAUCUCUUUCCU | AGGAAAGAGAUAAUGAUCU | [1981-1999](19/19) |

TABLE A-continued

| | | | |
|---|---|---|---|
| 88 | human | GGCCUUAUUUUUGUCUUA UAAGACAAAAAAUAAGGCC | [1950-1968](19/19) |
| 89 | human | CAGAUUUUUCCACCUUGG CCAAGGUGGAAAAAAUCUG | [1906-1924](19/19) |
| 90 | human | CCAGAUUUUUUCCACCUUG CAAGGUGGAAAAAAUCUGG | [1905-1923](19/19) |
| 91 | human | GCCUAGAGAAUGAAACUCA UGAGUUUCAUUCUCUAGGC | [1862-1880](19/19) |
| 92 | human | UACGAAGUCUGCAUUGGCU AGCCAAUGCAGACUUCGUA | [1820-1838](19/19) |
| 93 | human | CGGGUCAAUUUACGAAGUC GACUUCGUAAAUUGACCCG | [1810-1828](19/19) |
| 94 | human | GAAACGGGUCAAUUUACGA UCGUAAAUUGACCCGUUUC | [1806-1824](19/19) |
| 95 | human | GUCCCUCUCUGAUUCACUU AAGUGAAUCAGAGAGGGAC | [1626-1644](19/19) |
| 96 | human | GAGAGGGGACUCCUAAGAA UUCUUAGGAGUCCCCUCUC | [78-96](19/19) |
| 97 | human | GAAGGUAGGAUUAAGUAGG CCUACUUAAUCCUACCUUC | [1285-1303](19/19) |
| 98 | human | UAGCCUAUCAAAACUUCCA UGGAAGUUUUGAUAGGCUA | [1216-1234](19/19) |
| 99 | human | CCAUUUUUGUACAGAAUUG CAAUUCUGUACAAAAAUGG | [1007-1025](19/19) |
| 100 | human | UAGAUCCCAUUUUUGUACA UGUACAAAAAUGGGAUCUA | [1001-1019](19/19) |
| 101 | human | GCAGCUAACAGGCUGAUUU AAAUCAGCCUGUUAGCUGC | [937-955](19/19) |
| 102 | human | GUGUUUCACAUUCAUAGCA UGCUAUGAAUGUGAAACAC | [915-933](19/19) |
| 103 | human | GUCCUAAAAAGGGAAAAUA UAUUUUCCCUUUUUAGGAC | [779-797](19/19) |
| 104 | human | GGGUCCUAAAAAGGGAAAA UUUUCCCUUUUUAGGACCC | [777-795](19/19) |
| 105 | human | AAGGGUCCUAAAAAGGGAA UUCCCUUUUUAGGACCCUU | [775-793](19/19) |
| 106 | human | CAGGGACUUUUUCUUUAGU ACUAAAGAAAAAGUCCCUG | [653-671](19/19) |
| 107 | human, rat, dog | UGCACGUGAACUUGGAAAU AUUUCCAAGUUCACGUGCA | [526-544](19/19) |
| 108 | human, mouse, rat, dog | GUGUUAUGCACGUGAACUU AAGUUCACGUGCAUAACAC | [520-538](19/19) |
| 109 | human, mouse | GUUGUGUUAUGCACGUGAA UUCACGUGCAUAACACAAC | [517-535](19/19) |
| 110 | human | GAGGUUGUGUUAUGCACGU ACGUGCAUAACACAACCUC | [514-532](19/19) |
| 111 | human, mouse, chimpanzee | GACCCAGAGAAUUGCUCAA UUGAGCAAUUCUCUGGGUC | [455-473](19/19) |
| 112 | human, chimpanzee | AAGCAAACUAAACUUGGUU AACCAAGUUUAGUUUGCUU | [408-426](19/19) |
| 113 | human, chimpanzee | CCAAAUCAAAGCAAACUAA UUAGUUUGCUUUGAUUUGG | [400-418](19/19) |
| 114 | human | GGAAGGCUGUUAAAUUAAU AUUAAUUUAACAGCCUUCC | [2512-2530](19/19) |
| 115 | human | UGCCUGUUAUGCUUACAAA UUUGUAAGCAUAACAGGCA | [2478-2496](19/19) |
| 116 | human | UUGCCUGUUAUGCUUACAA UUGUAAGCAUAACAGGCAA | [2477-2495](19/19) |
| 117 | human | UGACUCUCUUGCCUGUUAU AUAACAGGCAAGAGAGUCA | [2469-2487](19/19) |
| 118 | human | GUCCUUUUUCCACUAACAG CUGUUAGUGGAAAAAGGAC | [2443-2461](19/19) |
| 119 | human | UAGAACUGUUGUCCUUUUU AAAAAGGACAACAGUUCUA | [2433-2451](19/19) |
| 120 | human | GUAGAACUGUUGUCCUUUU AAAAGGACAACAGUUCUAC | [2432-2450](19/19) |
| 121 | human, chimpanzee, dog | GAGAACUGUCUGUCCAAAU AUUUGGACAGACAGUUCUC | [387-405](19/19) |
| 122 | human | GCCAAGAUAAAUCAAUGUU AACAUUGAUUUAUCUUGGC | [2314-2332](19/19) |
| 123 | human | ACAAAGCCAAUCUUUAUAG CUAUAAAGAUUGGCUUUGU | [2289-2307](19/19) |
| 124 | human | AUGUCACUGUUCAAAUUAG CUAAUUUGAACAGUGACAU | [2224-2242](19/19) |
| 125 | human | GUGAUCCUGUUACUGAUAC GUAUCAGUAACAGGAUCAC | [2190-2208](19/19) |
| 126 | human, chimpanzee | GAAUUUGGUUAAAAUGCUG CAGCAUUUUAACCAAAUUC | [368-386](19/19) |
| 127 | human | AGGCUUUCAUAUCCUUGCU AGCAAGGAUAUGAAAGCCU | [2053-2071](19/19) |
| 128 | human | CAGCAAGGCUUUCAUAUCC GGAUAUGAAAGCCUUGCUG | [2048-2066](19/19) |
| 129 | human | GCCUCCACUCAACAAUGUU AACAUUGUUGAGUGGAGGC | [2024-2042](19/19) |
| 130 | human | GAAUUUAGCCUCCACUCAA UUGAGUGGAGGCUAAAUUC | [2017-2035](19/19) |
| 131 | human | GAGAGAAUUUAGCCUCCAC GUGGAGGCUAAAUUCUCUC | [2013-2031](19/19) |
| 132 | human | UAGAUCAUUAUCUCUUUCC GGAAAGAGAUAAUGAUCUA | [1980-1998](19/19) |
| 133 | human | AGGCCUUAUUUUUGUCUU AAGACAAAAAAUAAGGCCU | [1949-1967](19/19) |
| 134 | human | AAGGCCUUAUUUUUGUCU AGACAAAAAAUAAGGCCUU | [1948-1966](19/19) |
| 135 | human | GCAUGCACCCAGAUUUUUU AAAAAAUCUGGGUGCAUGC | [1897-1915](19/19) |
| 136 | human | GGUCAAUUUACGAAGUCUG CAGACUUCGUAAAUUGACC | [1812-1830](19/19) |
| 137 | human | GGGCUUUUCUGGGAAUUGA UCAAUUCCCAGAAAAGCCC | [1725-1743](19/19) |
| 138 | human | AUACCUGUGAGGAUAGGAA UUCCUAUCCUCACAGGUAU | [1590-1608](19/19) |
| 139 | human | ACUCUUCCAUUGAGUGAAU AUUCACUCAAUGGAAGAGU | [1566-1584](19/19) |
| 140 | human, chimpanzee | GGGAUUAUGUUGUUCCUGA UCAGGAACAACAUAAUCCC | [307-325](19/19) |
| 141 | human | UGCCAUUUCAGUAACCACG CGUGGUUACUGAAAUGGCA | [1432-1450](19/19) |
| 142 | human | UGUGGUGCCAUUUCAGUAA UUACUGAAAUGGCACCACA | [1427-1445](19/19) |
| 143 | human | AGCUUGUGGUGCCAUUUCA UGAAAUGGCACCACAAGCU | [1423-1441](19/19) |
| 144 | human | CUCUAAUGUUUUAAAGAGG CCUCUUUAAAACAUUAGAG | [1397-1415](19/19) |
| 145 | human | GAACUGCUUCACUGUUUCU AGAAACAGUGAAGCAGUUC | [1364-1382](19/19) |
| 146 | human | GGAACUGCUUCACUGUUUC GAAACAGUGAAGCAGUUCC | [1363-1381](19/19) |
| 147 | human | ACGGCAAUAAUGGAACUGC GCAGUUCCAUUAUUGCCGU | [1352-1370](19/19) |
| 148 | human | ACCCUAGGUAAGAGUAAAU AUUUACUCUUACCUAGGGU | [1323-1341](19/19) |
| 149 | human | CUCUAAGUUUUCAGAGGAU AUCCUCUGAAAACUUAGAG | [1164-1182](19/19) |
| 150 | human | GCUUGGUAAUAGACUAUAU AUAUAGUCUAUUACCAAGC | [1103-1121](19/19) |
| 151 | human | AGGCUUGGUAAUAGACUAU AUAGUCUAUUACCAAGCCU | [1101-1119](19/19) |
| 152 | human | GAGUUUACAUUUGAUUCC GGAAUCAAAUGUAAACUC | [1065-1083](19/19) |
| 153 | Human | GAAGCCCAUUUGAGUUUUA UAAAACUCAAAUGGGCUUC | [1054-1072](19/19) |
| 154 | human, chimpanzee | GAGCCUGCUAAGUGAUUUU AAAAUCACUUAGCAGGCUC | [281-299](19/19) |
| 155 | human | UGUACAGAAUUGAAUGGGA UCCCAUUCAAUUCUGUACA | [1014-1032](19/19) |
| 156 | human | UUGUACAGAAUUGAAUGGG CCCAUUCAAUUCUGUACAA | [1013-1031](19/19) |
| 157 | human | GUGAUUCAAAAUAGUGUAG CUACACUAUUUUGAAUCAC | [972-990](19/19) |
| 158 | human | UUGGAGAAGUGAUUCAAAA UUUUGAAUCACUUCUCCAA | [964-982](19/19) |
| 159 | human | CAGGCGAUUUUUCUGGCCU GGCCAGAAAAAUCGCCUG | [945-963](19/19) |
| 160 | human | GCUAACAGGCUGAUUUUCU AGAAAAUCAGCCUGUUAGC | [940-958](19/19) |
| 161 | human | GCUAAAGUCAUUUGUAGUU AACUACAAAUGACUUUAGC | [845-863](19/19) |
| 162 | human | UAGUCAGCUAAAGUCAUUU AAAUGACUUUAGCUGACUA | [839-857](19/19) |
| 163 | human | CUAGUCAGCUAAAGUCAUU AAUGACUUUAGCUGACUAG | [838-856](19/19) |
| 164 | human | UGAUUGGGUAGUAAAACUA UAGUUUUACUACCCAAUCA | [814-832](19/19) |

TABLE A-continued

| # | Species | Sequence 1 | Sequence 2 | Position |
|---|---|---|---|---|
| 165 | human, chimpanzee | GCAUUUCAGAAUUGCUGGA | UCCAGCAAUUCUGAAAUGC | [244-262](19/19) |
| 166 | human | GAAGGGUCCUAAAAAGGGA | UCCCUUUUUAGGACCCUUC | [774-792](19/19) |
| 167 | human | GGUUUCAGGAGAACUCUGA | UCAGAGUUCUCCUGAAACC | [690-708](19/19) |
| 168 | human | UCCUCUGGUUUCAGGAGAA | UUCUCCUGAAACCAGAGGA | [684-702](19/19) |
| 169 | human | AGGGACUUUUUCUUUAGUA | UACUAAAGAAAAAGUCCCU | [654-672](19/19) |
| 170 | human, chimpanzee | CUACUUUUGAGCUUACACU | AGUGUAAGCUCAAAAGUAG | [598-616](19/19) |
| 171 | human | CUAGCGUCGUACCUACUUU | AAAGUAGGUACGACGCUAG | [586-604](19/19) |
| 172 | human, mouse, rat, chimpanzee | GUAAAAAGCUGGAUAGGAU | AUCCUAUCCAGCUUUUUAC | [556-574](19/19) |
| 173 | human, mouse, rat, dog | UUAUGCACGUGAACUUGGA | UCCAAGUUCACGUGCAUAA | [523-541](19/19) |
| 174 | human, mouse | GGUUGUGUUAUGCACGUGA | UCACGUGCAUAACACAACC | [516-534](19/19) |
| 175 | human | GCGAGGUUGUGUUAUGCAC | GUGCAUAACACAACCUCGC | [512-530](19/19) |
| 176 | human, chimpanzee | AAAGCAAACUAAACUUGGU | ACCAAGUUUAGUUUGCUUU | [407-425](19/19) |
| 177 | human | CUGUUAUGCUUACAAAAUG | CAUUUUGUAAGCAUAACAG | [2481-2499](19/19) |
| 178 | human | UCCUUUUUCCACUAACAGU | ACUGUUAGUGGAAAAAGGA | [2444-2462](19/19) |
| 179 | human | CAAUCUUUAUAGAAUUGGG | CCCAAUUCUAUAAAGAUUG | [2296-2314](19/19) |
| 180 | human | CCAAUCUUUAUAGAAUUGG | CCAAUUCUAUAAAGAUUGG | [2295-2313](19/19) |
| 181 | human | AUACUACAAAGCCAAUCUU | AAGAUUGGCUUUGUAGUAU | [2284-2302](19/19) |
| 182 | human | CCAGUGUUCUACAAACUA | UAGUUUGUUAGAACACUGG | [2243-2261](19/19) |
| 183 | human | ACUGUUCAAAUUAGCCAGU | ACUGGCUAAUUUGAACAGU | [2229-2247](19/19) |
| 184 | human | CCUAAAAUGUCACUGUUCA | UGAACAGUGACAUUUUAGG | [2218-2236](19/19) |
| 185 | human | UGACCUAAAAUGUCACUGU | ACAGUGACAUUUUAGGUCA | [2215-2233](19/19) |
| 186 | human | UAAGUGACCUAAAAUGUCA | UGACAUUUUAGGUCACUUA | [2211-2229](19/19) |
| 187 | human | CUAUAAGUGACCUAAAAUG | CAUUUUAGGUCACUUAUAG | [2208-2226](19/19) |
| 188 | human | GUGUGAUCCUGUUACUGAU | AUCAGUAACAGGAUCACAC | [2188-2206](19/19) |
| 189 | human | CCACUUCACAUGCUGGAGA | UCUCCAGCAUGUGAAGUGG | [2123-2141](19/19) |
| 190 | human | GGCUUUCAUAUCCUUGCUG | CAGCAAGGAUAUGAAAGCC | [2054-2072](19/19) |
| 191 | human | GCAAGGCUUUCAUAUCCUU | AAGGAUAUGAAAGCCUUGC | [2050-2068](19/19) |
| 192 | human | CACUCAACAAUGUUCAAUU | AAUUGAACAUUGUUGAGUG | [2029-2047](19/19) |
| 193 | human | UAGCCUCCACUCAACAAUG | CAUUGUUGAGUGGAGGCUA | [2022-2040](19/19) |
| 194 | human | GUAGAUCAUUAUCUCUUUC | GAAAGAGAUAAUGAUCUAC | [1979-1997](19/19) |
| 195 | human | CCACCUUGGAUACCUGUCA | UGACAGGUAUCCAAGGUGG | [1916-1934](19/19) |
| 196 | human | AUGCAUGCACCCAGAUUUU | AAAAUCUGGGUGCAUGCAU | [1895-1913](19/19) |
| 197 | human | UUGAAACGGGUCAAUUUAC | GUAAAUUGACCCGUUUCAA | [1804-1822](19/19) |
| 198 | human, chimpanzee | UCAACGAGGUAAUAUUUGA | UCAAAUAUUACCUCGUUGA | [334-352](19/19) |
| 199 | human, chimpanzee | ACCUCAACGAGGUAAUAUU | AAUAUUACCUCGUUGAGGU | [331-349](19/19) |
| 200 | human, chimpanzee | CCAACCUCAACGAGGUAAU | AUUACCUCGUUGAGGUUGG | [328-346](19/19) |
| 201 | human | GUGCUUAAUCUCAGAUGAA | UUCAUCUGAGAUUAAGCAC | [1674-1692](19/19) |
| 202 | human | CUAGUCCCUCUCUGAUUCA | UGAAUCAGAGAGGGACUAG | [1623-1641](19/19) |
| 203 | human | AUGAAUACCUGUGAGGAUA | UAUCCUCACAGGUAUUCAU | [1586-1604](19/19) |
| 204 | human | AGAGGGGACUCCUAAGAAG | CUUCUUAGGAGUCCCCUCU | [79-97](19/19) |
| 205 | human | GAUUACUCUUCCAUUGAGU | ACUCAAUGGAAGAGUAAUC | [1562-1580](19/19) |
| 206 | human | UGAUUACUCUUCCAUUGAG | CUCAAUGGAAGAGUAAUCA | [1561-1579](19/19) |
| 207 | human | UAGUUGAUUACUCUUCCAU | AUGGAAGAGUAAUCAACUA | [1557-1575](19/19) |
| 208 | human | GUAGUUGAUUACUCUUCCA | UGGAAGAGUAAUCAACUAC | [1556-1574](19/19) |
| 209 | human | GUGUUGAAUACUGUCUUUA | UAAAGACAGUAUUCAACAC | [1497-1515](19/19) |
| 210 | human | AAGCUCAGUUUCCCCUGUU | AACAGGGGAAACUGAGCUU | [1473-1491](19/19) |
| 211 | human | ACCACGUGUUGUUUUAGA | UCUAAAACAACACCGUGGU | [1445-1463](19/19) |
| 212 | human | GUGCCAUUUCAGUAACCAC | GUGGUUACUGAAAUGGCAC | [1431-1449](19/19) |
| 213 | human | GGUGCCAUUUCAGUAACCA | UGGUUACUGAAAUGGCACC | [1430-1448](19/19) |
| 214 | human | CUGCUUCACUGUUUCUUGG | CCAAGAAACAGUGAAGCAG | [1367-1385](19/19) |
| 215 | human | AACUGCUUCACUGUUUCUU | AAGAAACAGUGAAGCAGUU | [1365-1383](19/19) |
| 216 | human | CAAUAAUGGAACUGCUUCA | UGAAGCAGUUCCAUUAUUG | [1356-1374](19/19) |
| 217 | human | AGGUAAGAGUAAAUGAGAA | UUCUCAUUUACUCUUACCU | [1328-1346](19/19) |
| 218 | human | GGAUUAAGUAGGUGAGUUU | AAACUCACCUACUUAAUCC | [1292-1310](19/19) |
| 219 | human | GACUCAAAUUUGAAGGGUU | AACCCUUCAAAUUUGAGUC | [1257-1275](19/19) |
| 220 | human | CAGAUUUGCCUAUUUUGAU | AUCAAAAUAGGCAAAUCUG | [1126-1144](19/19) |
| 221 | human | CCAGAUUUGCCUAUUUUGA | UCAAAAUAGGCAAAUCUGG | [1125-1143](19/19) |
| 222 | human | AUAUAAACCAGAUUUGCCU | AGGCAAAUCUGGUUUAUAU | [1118-1136](19/19) |
| 223 | human | GGCUUGGUAAUAGACUAUA | UAUAGUCUAUUACCAAGCC | [1102-1120](19/19) |
| 224 | human | UUCCACAAUUUGGUUUCAG | CUGAAACCAAAUUGUGGAA | [1080-1098](19/19) |
| 225 | human | UUUGAUUCCACAAUUUGGU | ACCAAAUUGUGGAAUCAAA | [1075-1093](19/19) |
| 226 | human | GGAAUAGGUAAGCAAAAGU | ACUUUUGCUUACCUAUUCC | [1034-1052](19/19) |
| 227 | human | CAGAAUUGAAUGGGAUGGA | UCCAUCCCAUUCAAUUCUG | [1018-1036](19/19) |
| 228 | human | GAUCCCAUUUUUGUACAGA | UCUGUACAAAAAUGGGAUC | [1003-1021](19/19) |
| 229 | human | AGAUCCCAUUUUUGUACAG | CUGUACAAAAAUGGGAUCU | [1002-1020](19/19) |
| 230 | human | GUGUAGAUUUUCUGCAUAG | CUAUGCAGAAAAUCUACAC | [985-1003](19/19) |
| 231 | human | AGGCUGAUUUUCUGGCCUU | AAGGCCAGAAAAUCAGCCU | [946-964](19/19) |
| 232 | human | CACAUUCAUAGCAACUGCA | UGCAGUUGCUAUGAAUGUG | [921-939](19/19) |
| 233 | human | CCCCACCUGCCCUAAAAUAA | UUAUUUUAGGGCAGGUGGGG | [866-884](19/19) |
| 234 | human | AGCUAAAGUCAUUUGUAGU | ACUACAAAUGACUUUAGCU | [844-862](19/19) |
| 235 | human | UCAGCUAAAGUCAUUUGUA | UACAAAUGACUUUAGCUGA | [842-860](19/19) |
| 236 | human | CAGCUAGUCAGCUAAAGUC | GACUUUAGCUGACUAGCUG | [835-853](19/19) |
| 237 | human | UGGGUAGUAAAACUAUUCA | UGAAUAGUUUUACUACCCA | [818-836](19/19) |
| 238 | human | GAUUAUUUCAUGAUUGGGU | ACCCAAUCAUGAAAUAAUC | [804-822](19/19) |
| 239 | human | GGUCCUAAAAAGGGAAAAU | AUUUUCCCUUUUUAGGACC | [778-796](19/19) |
| 240 | human, chimpanzee | CAGCAUUUCAGAAUUGCUG | CAGCAAUUCUGAAAUGCUG | [242-260](19/19) |
| 241 | human, chimpanzee | GCCAGCAUUUCAGAAUUGC | GCAAUUCUGAAAUGCUGGC | [240-258](19/19) |
| 242 | human | AGAACUCUGAUCCUCAGCU | AGCUGAGGAUCAGAGUUCU | [699-717](19/19) |

TABLE A-continued

| | | | |
|---|---|---|---|
| 243 | human | UAAGAAGCCACCUGCCUGU ACAGGCAGGUGGCUUCUUA | [91-109](19/19) |
| 244 | human | CUCCUCUGGUUUCAGGAGA UCUCCUGAAACCAGAGGAG | [683-701](19/19) |
| 245 | human | GGGACUUUUCUUUAGUAG CUACUAAAGAAAAAGUCCC | [655-673](19/19) |
| 246 | human, chimpanzee | AGCUUACACUUGUGUUUAA UUAAACACAAGUGUAAGCU | [607-625](19/19) |
| 247 | human | GUCGUACCUACUUUUGAGC GCUCAAAAGUAGGUACGAC | [591-609](19/19) |
| 248 | human | AGCGUCGUACCUACUUUUG CAAAAGUAGGUACGACGCU | [588-606](19/19) |
| 249 | human, rat, chimpanzee | AAGCUGGAUAGGAUUGUGU ACACAAUCCUAUCCAGCUU | [561-579](19/19) |
| 250 | human, chimpanzee | UUGCGAGGUUGUGUUAUGC GCAUAACACAACCUCGCAA | [510-528](19/19) |
| 251 | human, mouse, chimpanzee, dog | UUGCUCAAGAUGUCCUGCG CGCAGGACAUCUUGAGCAA | [466-484](19/19) |
| 252 | human, mouse, chimpanzee | ACCCAGAGAAUUGCUCAAG CUUGAGCAAUUCUCUGGGU | [456-474](19/19) |
| 253 | human, chimpanzee | UCAAAGCAAACUAAACUUG CAAGUUUAGUUUGCUUUGA | [405-423](19/19) |
| 254 | human, chimpanzee | UCCAAAUCAAAGCAAACUA UAGUUUGCUUUGAUUUGGA | [399-417](19/19) |
| 255 | human | AUGGAAGGCUGUUAAAUUA UAAUUUAACAGCCUUCCAU | [2510-2528](19/19) |
| 256 | human, chimpanzee, dog | CUGUCCAAAUCAAAGCAAA UUUGCUUUGAUUUGGACAG | [396-414](19/19) |
| 257 | human, chimpanzee, dog | GUCUGUCCAAAUCAAAGCA UGCUUUGAUUUGGACAGAC | [394-412](19/19) |
| 258 | human | GUUAUGCUUACAAAAUGGU ACCAUUUUGUAAGCAUAAC | [2483-2501](19/19) |
| 259 | human | UUGACUCUCUUGCCUGUUA UAACAGGCAAGAGAGUCAA | [2468-2486](19/19) |
| 260 | human | CCUUUUUCCACUAACAGUU AACUGUUAGUGGAAAAAGG | [2445-2463](19/19) |
| 261 | human, chimpanzee, dog | GAACUGUCUGUCCAAAUCA UGAUUUGGACAGACAGUUC | [389-407](19/19) |
| 262 | human | UGGGCAUCGAUGUAGAACU AGUUCUACAUCGAUGCCCA | [2421-2439](19/19) |
| 263 | human | AAAGGUUCACUGUGUUUCU AGAAACACAGUGAACCUUU | [2359-2377](19/19) |
| 264 | human | UCCAAAGGUUCACUGUGUU AACACAGUGAACCUUUGGA | [2356-2374](19/19) |
| 265 | human | GCAUGUCUAUUGUUAAGCU ACUUAACAAUAGACAUGC | [2338-2356](19/19) |
| 266 | human | UCAAUGUUGUUUUGCAUGU ACAUGCAAAACAACAUUGA | [2325-2343](19/19) |
| 267 | human | UUGGGCCAAGAUAAAUCAA UUGAUUUAUCUUGGCCCAA | [2310-2328](19/19) |
| 268 | human | AUUGGGCCAAGAUAAAUCA UGAUUUAUCUUGGCCCAAU | [2309-2327](19/19) |
| 269 | human | CAAAGCCAAUCUUUAUAGA UCUAUAAAGAUUGGCUUUG | [2290-2308](19/19) |
| 270 | human | CUACAAAGCCAAUCUUUAU AUAAAGAUUGGCUUUGUAG | [2287-2305](19/19) |
| 271 | human | ACUAAACUCUUCAAAUGCU AGCAUUUGAAGAGUUUAGU | [2258-2276](19/19) |
| 272 | human | GUGUUCUAACAAACUAAAC GUUUAGUUUGUUAGAACAC | [2246-2264](19/19) |
| 273 | human | UCACUGUUCAAAUUAGCCA UGGCUAAUUUGAACAGUGA | [2227-2245](19/19) |
| 274 | human | CUGUUACUGAUACUAUAAG CUUAUAGUAUCAGUAACAG | [2196-2214](19/19) |
| 275 | human | UCCUGUUACUGAUACUAUA UAUAGUAUCAGUAACAGGA | [2194-2212](19/19) |
| 276 | human | AUCCUGUUACUGAUACUAU AUAGUAUCAGUAACAGGAU | [2193-2211](19/19) |
| 277 | human | CAGGUGUGAUCCUGUUACU AGUAACAGGAUCACACCUG | [2185-2203](19/19) |
| 278 | human | UAGGGACAGAUGUAUUCAU AAUGAAUACAUCUGUCCCUA | [2148-2166](19/19) |
| 279 | human | GCUAUUAGCUCCACUUCAC GUGAAGUGGAGCUAAUAGC | [2113-2131](19/19) |
| 280 | human | GCCCUAGCUAUUAGCUCCA UGGAGCUAAUAGCUAGGGC | [2107-2125](19/19) |
| 281 | human | UCGUGGAUAAGGAGCUUAU AUAAGCUCCUUAUCCACGA | [2077-2095](19/19) |
| 282 | human | AAGGCUUUCAUAUCCUUGC GCAAGGAUAUGAAAGCCUU | [2052-2070](19/19) |
| 283 | human | CCACUCAACAAUGUUCAAU AUUGAACAUUGUUGAGUGG | [2028-2046](19/19) |
| 284 | human | CCUCCACUCAACAAUGUUC GAACAUUGUUGAGUGGAGG | [2025-2043](19/19) |
| 285 | human | GGAUACCUGUCACUAGGGA UCCCUAGUGACAGGUAUCC | [1923-1941](19/19) |
| 286 | human | ACCUUGGAUACCUGUCACU AGUGACAGGUAUCCAAGGU | [1918-1936](19/19) |
| 287 | human | UCACCGUCCAGAUAACCAU AUGGUUAUCUGGACGGUGA | [1878-1896](19/19) |
| 288 | human | AACUCACCGUCCAGAUAAC GUUAUCUGGACGGUGAGUU | [1875-1893](19/19) |
| 289 | human | GAGAUAUGGUUUAUAGUAC GUACUAUAAACCAUAUCUC | [1842-1860](19/19) |
| 290 | human | GCAUUGGCUAUGGAGAUAU AUAUCUCCAUAGCCAAUGC | [1830-1848](19/19) |
| 291 | human, chimpanzee | AACGAGGUAAUAUUUGAGG CCUCAAAUAUUACCUCGUU | [336-354](19/19) |
| 292 | human, chimpanzee | CAACGAGGUAAUAUUUGAG CUCAAAUAUUACCUCGUUG | [335-353](19/19) |
| 293 | human | CUGUAUACUACCACUUUGA UCAAAGUGGUAGUAUACAG | [1781-1799](19/19) |
| 294 | human | UAGCUGUAUACUACCACUU AAGUGGUAGUAUACAGCUA | [1778-1796](19/19) |
| 295 | human | GUAGCUGUAUACUACCACU AGUGGUAGUAUACAGCUAC | [1777-1795](19/19) |
| 296 | human | UGGCAGUGUUAUCUCAUCU AGAUGAGAUAACACUGCCA | [1704-1722](19/19) |
| 297 | human | UCUCAGAUGAACCAUUUCA UGAAAUGGUUCAUCUGAGA | [1682-1700](19/19) |
| 298 | human | UAAUCUCAGAUGAACCAUU AAUGGUUCAUCUGAGAUUA | [1679-1697](19/19) |
| 299 | human | CCCUCUCUGAUUCACUUAG CUAAGUGAAUCAGAGAGGG | [1628-1646](19/19) |
| 300 | human | AGUCCCUCUCUGAUUCACU AGUGAAUCAGAGAGGGACU | [1625-1643](19/19) |
| 301 | human | UAGUCCCUCUCUGAUUCAC GUGAAUCAGAGAGGGACUA | [1624-1642](19/19) |
| 302 | human | UUGAUUACUCUUCCAUUGA UCAAUGGAAGAGUAAUCAA | [1560-1578](19/19) |
| 303 | human | GUGUAGUUGAUUACUCUUC GAAGAGUAAUCAACUACAC | [1554-1572](19/19) |
| 304 | human | CCCCUGUUCUUAAGUGUUG CAACACUUAAGAACAGGGG | [1484-1502](19/19) |
| 305 | human | UUCCCCUGUUCUUAAGUGU ACACUUAAGAACAGGGGAA | [1482-1500](19/19) |
| 306 | human | CAGUUUCCCUGUUCUUAA UUAAGAACAGGGGAAACUG | [1478-1496](19/19) |
| 307 | human | GCCUUUAUAAGCUCAGUUU ACUGAGCUUAUAAAGGC | [1465-1483](19/19) |
| 308 | human | GUGUUGUUUUAGAUGCCUU AAGGCAUCUAAAACAACAC | [1451-1469](19/19) |
| 309 | human | ACGGUGUUGUUUUAGAUGC GCAUCUAAAACAACACCGU | [1448-1466](19/19) |
| 310 | human | CCACGGUGUUGUUUUAGAU AUCUAAAACAACACCGUGG | [1446-1464](19/19) |
| 311 | human | UCAGUAACCACGGUGUUGU ACAACACCGUGGUUACUGA | [1439-1457](19/19) |
| 312 | human | CCAUUUCAGUAACCACGGU ACCGUGGUUACUGAAAUGG | [1434-1452](19/19) |
| 313 | human | GUAGGAUUAAGUAGGUGAG CUCACCUACUUAAUCCUAC | [1289-1307](19/19) |
| 314 | human | GGUAGGAUUAAGUAGGUGA UCACCUACUUAAUCCUACC | [1288-1306](19/19) |
| 315 | human | AAGGGUUUUUAGACAGGAA UUCCUGUCUAAAAACCCUU | [1269-1287](19/19) |
| 316 | human | UUGAAGGGUUUUUAGACAG CUGUCUAAAAACCCUUCAA | [1266-1284](19/19) |

TABLE A-continued

| | | | |
|---|---|---|---|
| 317 human | | CAGUUCCUGACUCAAAUUU AAAUUUGAGUCAGGAACUG | [1249-1267](19/19) |
| 318 human | | ACCAGUUCCUGACUCAAAU AUUUGAGUCAGGAACUGGU | [1247-1265](19/19) |
| 319 human | | CCUAUCAAAACUUCCAAAA UUUUGGAAGUUUUGAUAGG | [1219-1237](19/19) |
| 320 human, chimpanzee | | UGCUAAGUGAUUUUGCUA UGUCAAAAUCACUUAGCA | [286-304](19/19) |
| 321 human | | UCCACAAUUUGGUUUCAGG CCUGAAACCAAAUUGUGGA | [1081-1099](19/19) |
| 322 human | | UGAUUCCACAAUUUGGUUU AAACCAAAUUGUGGAAUCA | [1077-1095](19/19) |
| 323 human | | AUAGAUCCCAUUUUUGUAC GUACAAAAAUGGGAUCUAU | [1000-1018](19/19) |
| 324 human, chimpanzee | | CAGAGAGCCUGCUAAGUGA UCACUUAGCAGGCUCUCUG | [277-295](19/19) |
| 325 human | | GUAGAUUUCUGCAUAGAU AUCUAUGCAGAAAAUCUAC | [987-1005](19/19) |
| 326 human | | UAGUGUAGAUUUUCUGCAU AUGCAGAAAAUCUACACUA | [983-1001](19/19) |
| 327 human | | AUAGUGUAGAUUUUCUGCA UGCAGAAAAUCUACACUAU | [982-1000](19/19) |
| 328 human | | UGUUUCACAUUCAUAGCAA UUGCUAUGAAUGUGAAACA | [916-934](19/19) |
| 329 human | | CACCUGCCCUAAAUAAGAA UUCUUAUUUAGGGCAGGUG | [869-887](19/19) |
| 330 human | | AAAGUCAUUUGUAGUUUGC GCAAACUACAAAUGACUUU | [848-866](19/19) |
| 331 human | | GCUAGUCAGCUAAAGUCAU AUGACUUUAGCUGACUAGC | [837-855](19/19) |
| 332 human | | UCAGCUAGUCAGCUAAAGU ACUUUAGCUGACUAGCUGA | [834-852](19/19) |
| 333 human | | GGGUAGUAAAACUAUUCAG UGAAAUAGUUUUACUACCC | [819-837](19/19) |
| 334 human, chimpanzee | | CCAGCAUUUCAGAAUUGCU AGCAAUUCUGAAAUGCUGG | [241-259](19/19) |
| 335 human, mouse | | CAGCUCAGGAUUUCGACUU AAGUCGAAAUCCUGAGCUG | [713-731](19/19) |
| 336 human, rat | | GAACUCUGAUCCUCAGCUC GAGCUGAGGAUCAGAGUUC | [700-718](19/19) |
| 337 human | | CGCUUCUCCUCUGGUUUCA UGAAACCAGAGGAGAAGCG | [678-696](19/19) |
| 338 human | | GACUUUUUCUUUAGUAGAG CUCUACUAAAGAAAAAGUC | [657-675](19/19) |
| 339 human | | UCAGGGACUUUUUCUUUAG CUAAAGAAAAAGUCCCUGA | [652-670](19/19) |
| 340 human, chimpanzee | | UUCAGGGACUUUUUCUUUA UAAAGAAAAAGUCCCUGAA | [651-669](19/19) |
| 341 human, chimpanzee | | CUUUUGAGCUUACACUUGU ACAAGUGUAAGCUCAAAAG | [601-619](19/19) |
| 342 human | | UACCUACUUUUGAGCUUAC GUAAGCUCAAAAGUAGGUA | [595-613](19/19) |
| 343 human | | GUACCUACUUUUGAGCUUA UAAGCUCAAAAGUAGGUAC | [594-612](19/19) |
| 344 human, rat, chimpanzee, dog | | GUGAACUUGGAAAUUGAAA UUUCAAUUUCCAAGUUCAC | [531-549](19/19) |
| 345 human, rat, dog | | GCACGUGAACUUGGAAAUU AAUUUCCAAGUUCACGUGC | [527-545](19/19) |
| 346 human, mouse, chimpanzee, dog | | UCCCUGAGAAACUGACCCA UGGGUCAGUUUCUCAGGGA | [442-460](19/19) |
| 347 human, chimpanzee | | AGGUCCUUGUCCCUGAGAA UUCUCAGGGACAAGGACCU | [433-451](19/19) |
| 348 human, chimpanzee | | GCAAACUAAACUUGGUUGC GCAACCAAGUUUAGUUUGC | [410-428](19/19) |
| 349 human, chimpanzee | | GUCCAAAUCAAAGCAAACU AGUUUGCUUUGAUUUGGAC | [398-416](19/19) |
| 350 human, chimpanzee, dog | | UCUGUCCAAAUCAAAGCAA UUGCUUUGAUUUGGACAGA | [395-413](19/19) |
| 351 human | | CCUGUUAUGCUUACAAAAU AUUUUGUAAGCAUAACAGG | [2480-2498](19/19) |
| 352 human | | GCCUGUUAUGCUUACAAAA UUUUGUAAGCAUAACAGGC | [2479-2497](19/19) |
| 353 human | | CAGUUAUCUUUGACUCUCU AGAGAGUCAAAGAUAACUG | [2459-2477](19/19) |
| 354 human | | CACUAACAGUUAUCUUUGA UCAAAGAUAACUGUUAGUG | [2453-2471](19/19) |
| 355 human | | UCCACUAACAGUUAUCUUU AAAGAUAACUGUUAGUGGA | [2451-2469](19/19) |
| 356 human, chimpanzee, dog | | AGAACUGUCUGUCCAAAUC GAUUUGGACAGACAGUUCU | [388-406](19/19) |
| 357 human | | UGACUGGGCAAGGCUUCUU AAGAAGCCUUGCCCAGUCA | [2403-2421](19/19) |
| 358 human | | UCACUGUGUUUCUGCCGCU AGCGGCAGAAACACAGUGA | [2365-2383](19/19) |
| 359 human | | AAGGUUCACUGUGUUUCUG CAGAAACACAGUGAACCUU | [2360-2378](19/19) |
| 360 human | | CCAAGAUAAAUCAAUGUUG CAACAUUGAUUUAUCUUGG | [2315-2333](19/19) |
| 361 human | | GAUACUACAAAGCCAAUCU AGAUUGGCUUUGUAGUAUC | [2283-2301](19/19) |
| 362 human | | AAAGAUACUACAAAGCCAA UUGGCUUUGUAGUAUCUUU | [2280-2298](19/19) |
| 363 human | | GAAAGAUACUACAAAGCCA UGGCUUUGUAGUAUCUUUC | [2279-2297](19/19) |
| 364 human | | UGGAAAGAUACUACAAAGC GCUUUGUAGUAUCUUUCCA | [2277-2295](19/19) |
| 365 human | | UUGGAAAGAUACUACAAAG CUUUGUAGUAUCUUUCCAA | [2276-2294](19/19) |
| 366 human | | UGCUUGGAAAGAUACUACA UGUAGUAUCUUUCCAAGCA | [2273-2291](19/19) |
| 367 human | | AUGCUUGGAAAGAUACUAC GUAGUAUCUUUCCAAGCAU | [2272-2290](19/19) |
| 368 human | | CUAAACUCUUCAAAUGCUU AAGCAUUUGAAGAGUUUAG | [2259-2277](19/19) |
| 369 human | | AAGUGACCUAAAAUGUCAC GUGACAUUUUAGGUCACUU | [2212-2230](19/19) |
| 370 human | | UGAUCCUGUUACUGAUACU AGUAUCAGUAACAGGAUCA | [2191-2209](19/19) |
| 371 human | | ACAGGUGUGAUCCUGUUAC GUAACAGGAUCACACCUGU | [2184-2202](19/19) |
| 372 human | | AUCCUGGUGUUACUGAAAA UUUUCAGUAACACCAGGAU | [2165-2183](19/19) |
| 373 human | | GGACAGAUGUAUUCAUCCU AGGAUGAAUACAUCUGUCC | [2151-2169](19/19) |
| 374 human | | AGCUCCACUUCACAUGCUG CAGCAUGUGAAGUGGAGCU | [2119-2137](19/19) |
| 375 human | | AGCUAUUAGCUCCACUUCA CAGAAGUGGAGCUAAUAGCU | [2112-2130](19/19) |
| 376 human, chimpanzee | | CUUGCCAGAAUUUGGUUAA UUAACCAAAUUCUGGCAAG | [361-379](19/19) |
| 377 human | | AAGGAGCUUAUUCAGGUUU AAACCUGAAUAAGCUCCUU | [2085-2103](19/19) |
| 378 human | | GCUUUCAUAUCCUUGCUGU ACAGCAAGGAUAUGAAAGC | [2055-2073](19/19) |
| 379 human | | UGAGAGAAUUUAGCCUCCA UGGAGGCUAAAUUCUCUCA | [2012-2030](19/19) |
| 380 human | | AUGAGAGAAUUUAGCCUCC GGAGGCUAAAUUCUCUCAU | [2011-2029](19/19) |
| 381 human, chimpanzee | | GGAAUCAACUUGCCAGAAU AUUCUGGCAAGUUGAUUCC | [353-371](19/19) |
| 382 human | | UAGGGAAUAAUAAAGGCCU AGGCCUUUAUUAUUCCCUA | [1936-1954](19/19) |
| 383 human | | UCACUAGGGAAUAAUAAAG CUUUAUUAUUCCCUAGUGA | [1932-1950](19/19) |
| 384 human | | ACCUGUCACUAGGGAAUAA UUAUUCCCUAGUGACAGGU | [1927-1945](19/19) |
| 385 human | | AUACCUGUCACUAGGGAAU AUUCCCUAGUGACAGGUAU | [1925-1943](19/19) |
| 386 human | | UUGGAUACCUGUCACUAGG CCUAGUGACAGGUAUCCAA | [1921-1939](19/19) |
| 387 human | | CACCUUGGAUACCUGUCAC GUGACAGGUAUCCAAGGUG | [1917-1935](19/19) |
| 388 human | | ACCGUCCAGAUAACCAUGC GCAUGGUUAUCUGGACGGU | [1880-1898](19/19) |
| 389 human | | GAAGUCUGCAUUGGCUAUG CAUAGCCAAUGCAGACUUC | [1823-1841](19/19) |
| 390 human | | GAAUUAUUGAAACGGGUCA UGACCCGUUUCAAUAAUUC | [1798-1816](19/19) |
| 391 human | | UAGUAGCUGUAUACUACCA UGGUAGUAUACAGCUACUA | [1775-1793](19/19) |
| 392 human | | GGGUAGUAGCUGUAUACUA UAGUAUACAGCUACUACCC | [1772-1790](19/19) |

TABLE A-continued

| | | | | |
|---|---|---|---|---|
| 393 | human | GUCAAGGGUAGUAGCUGUA | UACAGCUACUACCCUUGAC | [1767-1785](19/19) |
| 394 | human | UGAAGUAUCUCUCCUUAAC | GUUAAGGAGAGAUACUUCA | [1741-1759](19/19) |
| 395 | human | UUGAAGUAUCUCUCCUUAA | UUAAGGAGAGAUACUUCAA | [1740-1758](19/19) |
| 396 | human | GGGAAUUGAAGUAUCUCUC | GAGAGAUACUUCAAUUCCC | [1735-1753](19/19) |
| 397 | human | UGGGAAUUGAAGUAUCUCU | AGAGAUACUUCAAUUCCCA | [1734-1752](19/19) |
| 398 | human | GGCUUUUCUGGGAAUUGAA | UUCAAUUCCCAGAAAAGCC | [1726-1744](19/19) |
| 399 | human, chimpanzee | CCCAACCUCAACGAGGUAA | UUACCUCGUUGAGGUUGGG | [327-345](19/19) |
| 400 | human | GCAGUGUUAUCUCAUCUCU | AGAGAUGAGAUAACACUGC | [1706-1724](19/19) |
| 401 | human | CUCAGAUGAACCAUUUCAC | GUGAAAUGGUUCAUCUGAG | [1683-1701](19/19) |
| 402 | human, chimpanzee | CUGAACCCAACCUCAACGA | UCGUUGAGGUUGGGUUCAG | [322-340](19/19) |
| 403 | human | CUGAUUCACUUAGUAAUCU | AGAUUACUAAGUGAAUCAG | [1634-1652](19/19) |
| 404 | human | CUCUGAUUCACUUAGUAAU | AUUACUAAGUGAAUCAGAG | [1632-1650](19/19) |
| 405 | human | CCUCUCUGAUUCACUUAGU | ACUAAGUGAAUCAGAGAGG | [1629-1647](19/19) |
| 406 | human, chimpanzee | AGGAAACAGAGCCGUUGAC | GUCAACGGCUCUGUUUCCU | [184-202](19/19) |
| 407 | human | UACUCUUCCAUUGAGUGAA | UUCACUCAAUGGAAGAGUA | [1565-1583](19/19) |
| 408 | human | GUGUGUAGUUGAUUACUCU | AGAGUAAUCAACUACACAC | [1552-1570](19/19) |
| 409 | human | GAACUGAUAUUUUUGUGUG | CACACAAAAAUAUCAGUUC | [1538-1556](19/19) |
| 410 | human | AAGUGUUGAAUACUGUCUU | AAGACAGUAUUCAACACUU | [1495-1513](19/19) |
| 411 | human | UCCCCUGUUCUUAAGUGUU | AACACUUAAGAACAGGGGA | [1483-1501](19/19) |
| 412 | human | GCUCAGUUUCCCCUGUUCU | AGAACAGGGGAAACUGAGC | [1475-1493](19/19) |
| 413 | human | AGCUCAGUUUCCCCUGUUC | GAACAGGGGAAACUGAGCU | [1474-1492](19/19) |
| 414 | human, chimpanzee | GGAUUAUGUUGUUCCUGAA | UUCAGGAACAACAUAAUCC | [308-326](19/19) |
| 415 | human | UAAGCUCAGUUUCCCCUGU | ACAGGGGAAACUGAGCUUA | [1472-1490](19/19) |
| 416 | human | UGCCUUUAUAAGCUCAGUU | AACUGAGCUUAUAAAGGCA | [1464-1482](19/19) |
| 417 | human | AGAUGCCUUUAUAAGCUCA | UGAGCUUAUAAAGGCAUCU | [1461-1479](19/19) |
| 418 | human | UUAGAUGCCUUUAUAAGCU | AGCUUAUAAAGGCAUCUAA | [1459-1477](19/19) |
| 419 | human | CGGUGUUGUUUUAGAUGCC | GGCAUCUAAAACAACACCG | [1449-1467](19/19) |
| 420 | human | UAACCACGGUGUUGUUUUA | UAAAACAACACCGUGGUUA | [1443-1461](19/19) |
| 421 | human, chimpanzee | CUACUGGGAUUAUGUUGUU | AACAACAUAAUCCCAGUAG | [302-320](19/19) |
| 422 | human, mouse, chimpanzee | ACUACUGGGAUUAUGUUGU | ACAACAUAAUCCCAGUAGU | [301-319](19/19) |
| 423 | human | AUGGAACUGCUUCACUGUU | AACAGUGAAGCAGUUCCAU | [1361-1379](19/19) |
| 424 | human | UUACGGCAAUAAUGGAACU | AGUUCCAUUAUUGCCGUAA | [1350-1368](19/19) |
| 425 | human | AGGUGAGUUUAAUUAAAGC | GCUUUAAUUAAACUCACCU | [1301-1319](19/19) |
| 426 | human | AGGAUUAAGUAGGUGAGUU | AACUCACCUACUUAAUCCU | [1291-1309](19/19) |
| 427 | human | ACAGGAAGGUAGGAUUAAG | CUUAAUCCUACCUUCCUGU | [1281-1299](19/19) |
| 428 | human | AGGGUUUUUAGACAGGAAG | CUUCCUGUCUAAAAACCCU | [1270-1288](19/19) |
| 429 | human | GAAGGGUUUUUAGACAGGA | UCCUGUCUAAAAACCCUUC | [1268-1286](19/19) |
| 430 | human | UGAAGGGUUUUUAGACAGG | CCUGUCUAAAAACCCUUCA | [1267-1285](19/19) |
| 431 | human | UUUGAAGGGUUUUUAGACA | UGUCUAAAAACCCUUCAAA | [1265-1283](19/19) |
| 432 | human, chimpanzee | GUGAUUUUGACUACUGGGA | UCCCAGUAGUCAAAAUCAC | [292-310](19/19) |
| 433 | human | UCCUGACUCAAAUUUGAAG | CUUCAAAUUUGAGUCAGGA | [1253-1271](19/19) |
| 434 | human | UCUCUAAGUUUUCAGAGGA | UCCUCUGAAAACUUAGAGA | [1163-1181](19/19) |
| 435 | human | AGGUAGGCUUGGUAAUAGA | UCUAUUACCAAGCCUACCU | [1097-1115](19/19) |
| 436 | human | ACAAUUUGGUUUCAGGUAG | CUACCUGAAACCAAAUUGU | [1084-1102](19/19) |
| 437 | human | GUUUUACAUUUGAUUCCAC | GUGGAAUCAAAUGUAAAAC | [1067-1085](19/19) |
| 438 | human | AAGCCCAUUUGAGUUUUAC | GUAAAACUCAAAUGGGCUU | [1055-1073](19/19) |
| 439 | human | UAGAAGCCCAUUUGAGUUU | AAACUCAAAUGGGCUUCUA | [1052-1070](19/19) |
| 440 | human | AAGCAAAAGUAGAAGCCCA | UGGGCUUCUACUUUUGCUU | [1043-1061](19/19) |
| 441 | human | UAGGUAAGCAAAAGUAGAA | UUCUACUUUUGCUUACCUA | [1038-1056](19/19) |
| 442 | human | GAAUAGGUAAGCAAAAGUA | UACUUUUGCUUACCUAUUC | [1035-1053](19/19) |
| 443 | human | GGAUGGAAUAGGUAAGCAA | UUGCUUACCUAUUCCAUCC | [1030-1048](19/19) |
| 444 | human | GGGAUGGAAUAGGUAAGCA | UGCUUACCUAUUCCAUCCC | [1029-1047](19/19) |
| 445 | human | AGAAUUGAAUGGGAUGGAA | UUCCAUCCCAUUCAAUUCU | [1019-1037](19/19) |
| 446 | human | CUGCAUAGAUCCCAUUUUU | AAAAAUGGGAUCUAUGCAG | [996-1014](19/19) |
| 447 | human | UAGAUUUUCUGCAUAGAUC | GAUCUAUGCAGAAAAUCUA | [988-1006](19/19) |
| 448 | human | GGCCUUUGGAGAAGUGAUU | AAUCACUUCUCCAAAGGCC | [959-977](19/19) |
| 449 | human, chimpanzee | ACUGUGGCUAUCACCCAGA | UCUGGGUGAUAGCCACAGU | [262-280](19/19) |
| 450 | human | GGCUGAUUUUCUGGCCUUU | AAAGGCCAGAAAAUCAGCC | [947-965](19/19) |
| 451 | human | ACAGGCUGAUUUUCUGGCC | GGCCAGAAAAUCAGCCUGU | [944-962](19/19) |
| 452 | human | AACAGGCUGAUUUUCUGGC | GCCAGAAAAUCAGCCUGUU | [943-961](19/19) |
| 453 | human | CUGCAGCUAACAGGCUGAU | AUCAGCCUGUUAGCUGCAG | [935-953](19/19) |
| 454 | human | AGCAACUGCAGCUAACAGG | CCUGUUAGCUGCAGUUGCU | [930-948](19/19) |
| 455 | human | UAGCAACUGCAGCUAACAG | CUGUUAGCUGCAGUUGCUA | [929-947](19/19) |
| 456 | human | UCAUAGCAACUGCAGCUAA | UUAGCUGCAGUUGCUAUGA | [926-944](19/19) |
| 457 | human | UCACAUUCAUAGCAACUGC | GCAGUUGCUAUGAAUGUGA | [920-938](19/19) |
| 458 | human, chimpanzee | CAGAAAUUGCUGGACUGUGG | CCACAGUCCAGCAAUUCUG | [250-268](19/19) |
| 459 | human | GCCCUAAAUAAGAAACCCC | GGGGUUUCUUAUUUAGGGC | [874-892](19/19) |
| 460 | human | CCACCUGCCCUAAAUAAGA | UCUUAUUUAGGGCAGGUGG | [868-886](19/19) |
| 461 | human | GUCAUUUGUAGUUUGCCCC | GGGGCAAACUACAAAUGAC | [851-869](19/19) |
| 462 | human | GUAAAACUAUUCAGCUAGU | ACUAGCUGAAUAGUUUUAC | [824-842](19/19) |
| 463 | human | UUGGGUAGUAAAACUAUUC | GAAUAGUUUUACUACCCAA | [817-835](19/19) |
| 464 | human | CCUCAGCUCAGGAUUUCGA | UCGAAAUCCUGAGCUGAGG | [710-728](19/19) |
| 465 | human | GGAGAACUCUGAUCCUCAG | CUGAGGAUCAGAGUUCUCC | [697-715](19/19) |
| 466 | human | UCGCUUCUCCUCUGGUUUU | GAAACCAGAGGAGAAGCGA | [677-695](19/19) |
| 467 | human | GUCGCUUCUCCUCUGGUUU | AAACCAGAGGAGAAGCGAC | [676-694](19/19) |
| 468 | human | GGACUUUUCUUUAGUAGA | UCUACUAAAGAAAAGUCC | [656-674](19/19) |
| 469 | human, chimpanzee | UGGACUAGCUUCAGGGACU | AGUCCCUGAAGCUAGUCCA | [642-660](19/19) |
| 470 | human, chimpanzee, dog | UGCUCAUGGACUAGCUUCA | UGAAGCUAGUCCAUGAGCA | [636-654](19/19) |

TABLE A-continued

| | | | | |
|---|---|---|---|---|
| 471 | human | ACCUACUUUUGAGCUUACA | UGUAAGCUCAAAAGUAGGU | [596-614](19/19) |
| 472 | human | UCGUACCUACUUUUGAGCU | AGCUCAAAAGUAGGUACGA | [592-610](19/19) |
| 473 | human | CGUCGUACCUACUUUUGAG | CUCAAAAGUAGGUACGACG | [590-608](19/19) |
| 474 | human, rat, dog | CACGUGAACUUGGAAAUUG | CAAUUUCCAAGUUCACGUG | [528-546](19/19) |
| 475 | human, chimpanzee | UGCGAGGUUGUGUUAUGCA | UGCAUAACACAACCUCGCA | [511-529](19/19) |
| 476 | human, chimpanzee, dog | UUGUCCCUGAGAAACUGAC | GUCAGUUUCUCAGGGACAA | [439-457](19/19) |
| 477 | human, chimpanzee, dog | UCCUUGUCCCUGAGAAACU | AGUUUCUCAGGGACAAGGA | [436-454](19/19) |
| 478 | human, chimpanzee | UGACCAUGGUUGCAACUGG | CCAGUUGCAACCAUGGUCA | [199-217](19/19) |
| 479 | human, chimpanzee | AACUAAACUUGGUUGCUCA | UGAGCAACCAAGUUUAGUU | [413-431](19/19) |
| 480 | human, chimpanzee | AGCAAACUAAACUUGGUUG | CAACCAAGUUUAGUUUGCU | [409-427](19/19) |
| 481 | human | UGUUAUGCUUACAAAAUGG | CCAUUUUGUAAGCAUAACA | [2482-2500](19/19) |
| 482 | human, chimpanzee, dog | ACUGUCUGUCCAAAUCAAA | UUUGAUUUGGACAGACAGU | [391-409](19/19) |
| 483 | human | CUAACAGUUAUCUUUGACU | AGUCAAAGAUAACUGUUAG | [2455-2473](19/19) |
| 484 | human | GGGCAUCGAUGUAGAACUG | CAGUUCUACAUCGAUGCCC | [2422-2440](19/19) |
| 485 | human | UCCUGGAGUUGUCACCACU | AGUGGUGACAACUCCAGGA | [2385-2403](19/19) |
| 486 | human | UUGUUAAGCUCCAAAGGUU | AACCUUUGGAGCUUAACAA | [2347-2365](19/19) |
| 487 | human | UUGCAUGUCUAUUGUUAAG | CUUAACAAUAGACAUGCAA | [2336-2354](19/19) |
| 488 | human | AUGUUGUUUUGCAUGUCUA | UAGACAUGCAAAACAACAU | [2328-2346](19/19) |
| 489 | human | AAGAUACUACAAAGCCAAU | AUUGGCUUUGUAGUAUCUU | [2281-2299](19/19) |
| 490 | human | CUUGGAAAGAUACUACAAA | UUUGUAGUAUCUUUCCAAG | [2275-2293](19/19) |
| 491 | human | UGUCACUGUUCAAAUUAGC | GCUAAUUUGAACAGUGACA | [2225-2243](19/19) |
| 492 | human | UGAUACUAUAAGUGACCUA | UAGGUCACUUAUAGUAUCA | [2203-2221](19/19) |
| 493 | human, mouse, rat, chimpanzee | CCGUUGACCAUGGUUGCAA | UUGCAACCAUGGUCAACGG | [195-213](19/19) |
| 494 | human | GUGUUACUGAAAAACAGGU | ACCGUUUUUCAGUAACAC | [2171-2189](19/19) |
| 495 | human | AGGGACAGAUGUAUUCAUC | GAUGAAUACAUCUGUCCCU | [2149-2167](19/19) |
| 496 | human | GGCGUAGGGACAGAUGUAU | AUACAUCUGUCCCUACGCC | [2144-2162](19/19) |
| 497 | human | CUCCACUUCACAUGCUGGA | UCCAGCAUGUGAAGUGGAG | [2121-2139](19/19) |
| 498 | human | UUCCUGCCCUAGCUAUUAG | CUAAUAGCUAGGGCAGGAA | [2102-2120](19/19) |
| 499 | human | AGGGAGCUUAUUCAGGUUUC | GAAACCUGAAUAAGCUCCU | [2086-2104](19/19) |
| 500 | human | AUAAGGAGCUUAUUCAGGU | ACCUGAAUAAGCUCCUUAU | [2083-2101](19/19) |
| 501 | human, chimpanzee | CAACUUGCCAGAAUUUGGU | ACCAAAUUCUGGCAAGUUG | [358-376](19/19) |
| 502 | human | AAUUCAGCAAGGCUUUCAU | AUGAAAGCCUUGCUGAAUU | [2044-2062](19/19) |
| 503 | human | UCAACAAUGUUCAAUUCAG | CUGAAUUGAACAUUGUUGA | [2032-2050](19/19) |
| 504 | human | UCCACUCAACAAUGUUCAA | UUGAACAUUGUUGAGUGGA | [2027-2045](19/19) |
| 505 | human | UUCCAACUAAGUAGAUCAU | AUGAUCUACUUAGUUGGAA | [1969-1987](19/19) |
| 506 | human | AGGGAAUAAUAAAGGCCUU | AAGGCCUUUAUUAUUCCCU | [1937-1955](19/19) |
| 507 | human | CACUAGGGAAUAAUAAAGG | CCUUUAUUAUUCCCUAGUG | [1933-1951](19/19) |
| 508 | human, chimpanzee | GAGGAAUCAACUUGCCAGA | UCUGGCAAGUUGAUUCCUC | [351-369](19/19) |
| 509 | human | CCUGUCACUAGGGAAUAAU | AUUAUUCCCUAGUGACAGG | [1928-1946](19/19) |
| 510 | human | CAUGCAUGCACCCAGAUUU | AAAUCUGGGUGCAUGCAUG | [1894-1912](19/19) |
| 511 | human | GUCCAGAUAACCAUGCAUG | CAUGCAUGGUUAUCUGGAC | [1883-1901](19/19) |
| 512 | human | CCGUCCAGAUAACCAUGCA | UGCAUGGUUAUCUGGACGG | [1881-1899](19/19) |
| 513 | human | GAAUGAAACUCACCGUCCA | UGGACGGUGAGUUUCAUUC | [1869-1887](19/19) |
| 514 | human | GAGAAUGAAACUCACCGUC | GACGGUGAGUUUCAUUCUC | [1867-1885](19/19) |
| 515 | human | ACAGCCUAGAGAAUGAAAC | GUUUCAUUCUCUAGGCUGU | [1859-1877](19/19) |
| 516 | human | CUGCAUUGGCUAUGGAGAU | AUCUCCAUAGCCAAUGCAG | [1828-1846](19/19) |
| 517 | human | AGUCUGCAUUGGCUAUGGA | UCCAUAGCCAAUGCAGACU | [1825-1843](19/19) |
| 518 | human | AAGUCUGCAUUGGCUAUGG | CCAUAGCCAAUGCAGACUU | [1824-1842](19/19) |
| 519 | human | UUGAAUUAUUGAAACGGGU | ACCCGUUUCAAUAAUUCAA | [1796-1814](19/19) |
| 520 | human | GCUGUAUACUACCACUUUG | CAAAGUGGUAGUAUACAGC | [1780-1798](19/19) |
| 521 | human | AAGGGUAGUAGCUGUAUAC | GUAUACAGCUACUACCCUU | [1770-1788](19/19) |
| 522 | human | GAAGUAUCUCUCCUUAACC | GGUUAAGGAGAGAUACUUC | [1742-1760](19/19) |
| 523 | human | UUCUGGGAAUUGAAGUAUC | GAUACUUCAAUUCCCAGAA | [1731-1749](19/19) |
| 524 | human, chimpanzee | AACCCAACCUCAACGAGGU | ACCUCGUUGAGGUUGGGUU | [325-343](19/19) |
| 525 | human | AUGAACCAUUUCACCAUGG | CCAUGGUGAAAUGGUUCAU | [1688-1706](19/19) |
| 526 | human | AGAUGAACCAUUUCACCAU | AUGGUGAAAUGGUUCAUCU | [1686-1704](19/19) |
| 527 | human | AAUCUCAGAUGAACCAUUU | AAAUGGUUCAUCUGAGAUU | [1680-1698](19/19) |
| 528 | human | UGUGCUUAAUCUCAGAUGA | UCAUCUGAGAUUAAGCACA | [1673-1691](19/19) |
| 529 | human | AUGUGCUUAAUCUCAGAUG | CAUCUGAGAUUAAGCACAU | [1672-1690](19/19) |
| 530 | human | ACAUGUGCUUAAUCUCAGA | UCUGAGAUUAAGCACAUGU | [1670-1688](19/19) |
| 531 | human | UACAUGUGCUUAAUCUCAG | CUGAGAUUAAGCACAUGUA | [1669-1687](19/19) |
| 532 | human | CCUCUUUUCAGUAUUACAU | AUGUAAUACUGAAAAGAGG | [1655-1673](19/19) |
| 533 | human | CUCUCGAUUCACUUAGUA | UACUAAGUGAAUCGAGAG | [1630-1648](19/19) |
| 534 | human, chimpanzee | AUGUUGUUCCUGAACCCAA | UUGGGUUCAGGAACAACAU | [313-331](19/19) |
| 535 | human | CCCUGUUCUUAAGUGUUGA | UCAACACUUAAGAACAGGG | [1485-1503](19/19) |
| 536 | human | AUGCCUUUAUAAGCUCAGU | ACUGAGCUUAUAAAGGCAU | [1463-1481](19/19) |
| 537 | human, chimpanzee | CUGGGAUUAUGUGUUCCUG | AGGAACACAUAAUCCCAG | [305-323](19/19) |
| 538 | human | CUAAUGUUUAAAGAGGCA | UGCCUCUUUAAAACAUUAG | [1399-1417](19/19) |
| 539 | human, chimpanzee | UUGACUACGGGAUUAUGU | ACAUAAUCCCAGUAGUCAA | [298-316](19/19) |
| 540 | human | UGAGAAAUAUUACGGCAAU | AUUGCCGUAAUAUUUCUCA | [1341-1359](19/19) |
| 541 | human | AUGAGAAAUAUUACGGCAA | UUGCCGUAAUAUUUCUCAU | [1340-1358](19/19) |
| 542 | human | GGUAAGAGUAAAUGAGAAA | UUUCUCAUUUACUCUUACC | [1329-1347](19/19) |
| 543 | human | CUAGGUAAGAGUAAAUGAG | CUCAUUUACUCUUACCUAG | [1326-1344](19/19) |
| 544 | human | AACCCUAGGUAAGAGUAAA | UUUACUCUUACCUAGGGUU | [1322-1340](19/19) |
| 545 | human | GGUGAGUUUAAUUAAAGCU | AGCUUUAAUUAAACUCACC | [1302-1320](19/19) |
| 546 | human | UAGACAGGAAGGUAGGAUU | AAUCCUACCUUCCUGUCUA | [1278-1296](19/19) |

TABLE A-continued

| | | | |
|---|---|---|---|
| 547 | human | UGACUCAAAUUUGAAGGGU ACCCUUCAAAUUUGAGUCA | [1256-1274](19/19) |
| 548 | human | CUGACUCAAAUUUGAAGGG CCCUUCAAAUUUGAGUCAG | [1255-1273](19/19) |
| 549 | human | CACCAGUUCCUGACUCAAA UUUGAGUCAGGAACUGGUG | [1246-1264](19/19) |
| 550 | human | ACCACCAGUUCCUGACUCA UGAGUCAGGAACUGGUGGU | [1244-1262](19/19) |
| 551 | human | AAAGCCCACACCACCAGUU AACUGGUGGUGUGGGCUUU | [1235-1253](19/19) |
| 552 | human | UAGGCUUGGUAAUAGACUA UAGUCUAUUACCAAGCCUA | [1100-1118](19/19) |
| 553 | human | CAAUUUGGUUUCAGGUAGG CCUACCUGAAACCAAAUUG | [1085-1103](19/19) |
| 554 | human | AGCCCAUUUGAGUUUUACA UGUAAAACUCAAAUGGGCU | [1056-1074](19/19) |
| 555 | human, chimpanzee | GCCUGCUAAGUGAUUUUGA UCAAAAUCACUUAGCAGGC | [283-301](19/19) |
| 556 | human | AGCAAAAGUAGAAGCCCAU AUGGGCUUCUACUUUUGCU | [1044-1062](19/19) |
| 557 | human | GUAAGCAAAAGUAGAAGCC GGCUUCUACUUUUGCUUAC | [1041-1059](19/19) |
| 558 | human, chimpanzee | GAGAGCCUGCUAAGUGAUU AAUCACUUAGCAGGCUCUC | [279-297](19/19) |
| 559 | human | GCAUAGAUCCCAUUUUUGU ACAAAAAUGGGAUCUAUGC | [998-1016](19/19) |
| 560 | human | AGUGUAGAUUUUCUGCAUA UAUGCAGAAAAUCUACACU | [984-1002](19/19) |
| 561 | human | UGGAGAAGUGAUUCAAAAU AUUUUGAAUCACUUCUCCA | [965-983](19/19) |
| 562 | human | ACUGCAGCUAACAGGCUGA UCAGCCUGUUAGCUGCAGU | [934-952](19/19) |
| 563 | human | CUGUGUUUCACAUUCUAUG CUAUGAAUGUGAAACACAG | [913-931](19/19) |
| 564 | human | UUCUGUGUUUCACAUUCAU AUGAAUGUGAAACACAGAA | [911-929](19/19) |
| 565 | human | CCCAAAUGUAGUCUCUUUU AAAAGAGACUACAUUUGGG | [890-908](19/19) |
| 566 | human | CCCCAAAUGUAGUCUCUUU AAAGAGACUACAUUUGGGG | [889-907](19/19) |
| 567 | human | AACCCCAAAUGUAGUCUCU AGAGACUACAUUUGGGGUU | [887-905](19/19) |
| 568 | human | CUGCCCUAAAUAAGAAACC GGUUUCUUAUUUAGGGCAG | [872-890](19/19) |
| 569 | human | ACCUGCCCUAAAUAAGAAA UUUCUUAUUUAGGGCAGGU | [870-888](19/19) |
| 570 | human | CCCACCUGCCCUAAAUAAG CUUAUUUAGGGCAGGUGGG | [867-885](19/19) |
| 571 | human | CUCACUGAUUGGAACAACA UGUUGUUCCAAUCAGUGAG | [749-767](19/19) |
| 572 | human | CUCAGGAUUUCGACUUGUU AACAAGUCGAAAUCCUAGAG | [716-734](19/19) |
| 573 | human, mouse | GCUCAGGAUUUCGACUUGU ACAAGUCGAAAUCCUGAGC | [715-733](19/19) |
| 574 | human, mouse | AGCUCAGGAUUUCGACUUG CAAGUCGAAAUCCUGAGCU | [714-732](19/19) |
| 575 | human | AGGAGAACUCUGAUCCUCA UGAGGAUCAGAGUUCUCCU | [696-714](19/19) |
| 576 | human, chimpanzee | GGCAGUUUGAGCAGCAAGA UCUUGCUGCUCAAACUGCC | [216-234](19/19) |
| 577 | human, chimpanzee | UGAGCUUACACUUGUGUUU AAACACAAGUGUAAGCUCA | [605-623](19/19) |
| 578 | human, chimpanzee | UUUGAGCUUACACUUGUGU ACACAAGUGUAAGCUCAAA | [603-621](19/19) |
| 579 | human | GUGUGUGAUUCUAGCGUCG CGACGCUAGAAUCACACAC | [576-594](19/19) |
| 580 | human | UUGUGUGUGAUUCUAGCGU ACGCUAGAAUCACACACAA | [574-592](19/19) |
| 581 | human, rat, chimpanzee | UGGAUAGGAUUGUGUGUGA UCACACACAAUCCUAUCCA | [565-583](19/19) |
| 582 | human, rat, chimpanzee | AAAAGCUGGAUAGGAUUGU ACAAUCCUAUCCAGCUUUU | [559-577](19/19) |
| 583 | human, mouse, chimpanzee, dog | GUAUGUAAAAGCUGGAUA UAUCCAGCUUUUUACAUAC | [552-570](19/19) |
| 584 | human, mouse, chimpanzee | AUGUAUGUAAAAGCUGGA UCCAGCUUUUUACAUACAU | [550-568](19/19) |
| 585 | human, mouse, chimpanzee | CUGACCCAGAGAAUUGCUC GAGCAAUUCUCUGGGUCAG | [453-471](19/19) |
| 586 | human, chimpanzee | AUGGUUGCAACUGGCAGUU AACUGCCAGUUGCAACCAU | [204-222](19/19) |
| 587 | human | UGGAAGGCUGUUAAAUUAA UUAAUUUAACAGCCUUCCA | [2511-2529](19/19) |
| 588 | human | GCUUAUGGAAGGCUGUUAA UUAACAGCCUUCCAUAAGC | [2506-2524](19/19) |
| 589 | human, chimpanzee, dog | CUGUCUGUCCAAAUCAAAG CUUUGAUUUGGACAGACAG | [392-410](19/19) |
| 590 | human | AUGUAGAACUGUUGUCCUU AAGGACAACAGUUCUACAU | [2430-2448](19/19) |
| 591 | human | GCAUCGAUGUAGAACUGUU AACAGUUCUACAUCGAUGC | [2424-2442](19/19) |
| 592 | human | AAUGUUGUUUUGCAUGUCU AGACAUGCAAAACAACAUU | [2327-2345](19/19) |
| 593 | human | UGGGCCAAGAUAAAUCAAU AUUGAUUUAUCUUGGCCCA | [2311-2329](19/19) |
| 594 | human | GAAUUGGGCCAAGAUAAAU AUUUAUCUUGGCCCAAUUC | [2307-2325](19/19) |
| 595 | human | AGAAUUGGGCCAAGAUAAA UUUAUCUUGGCCCAAUUCU | [2306-2324](19/19) |
| 596 | human | CUCUUCAAAUGCUUGGAAA UUUCCAAGCAUUUGAAGAG | [2264-2282](19/19) |
| 597 | human | ACUCUUCAAAUGCUUGGAA UUCCAAGCAUUUGAAGAGU | [2263-2281](19/19) |
| 598 | human | GUCACUGUUCAAAUUAGCC GGCUAAUUUGAACAGUGAC | [2226-2244](19/19) |
| 599 | human | GUGACCUAAAAUGUCACUG CAGUGACAUUUUAGGUCAC | [2214-2232](19/19) |
| 600 | human | CUGAUACUAUAAGUGACCU AGGUCACUUAUAGUAUCAG | [2202-2220](19/19) |
| 601 | human | ACUGAUACUAUAAGUGACC GGUCACUUAUAGUAUCAGU | [2201-2219](19/19) |
| 602 | human | UACUGAUACUAUAAGUGAC GUCACUUAUAGUAUCAGUA | [2200-2218](19/19) |
| 603 | human | GAUCCUGUUACUGAUACUA UAGUAUCAGUAACAGGAUC | [2192-2210](19/19) |
| 604 | human | GGUGUGAUCCUGUUACUGA UCAGUAACAGGAUCACACC | [2187-2205](19/19) |
| 605 | human | CUGAAAAACAGGUGUGAUC GAUCACACCUGUUUUUCAG | [2177-2195](19/19) |
| 606 | human | UGGUGUUACUGAAAAACAG CUGUUUUUCAGUAACACCA | [2169-2187](19/19) |
| 607 | human | CUGGUGUUACUGAAAAACA UGUUUUUCAGUAACACCAG | [2168-2186](19/19) |
| 608 | human | UCCUGGUGUUACUGAAAAA UUUUUCAGUAACACCAGGA | [2166-2184](19/19) |
| 609 | human | ACAGAUGUAUUCAUCCUGG CCAGGAUGAAUACAUCUGU | [2153-2171](19/19) |
| 610 | human | GACAGAUGUAUUCAUCCUG CAGGAUGAAUACAUCUGUC | [2152-2170](19/19) |
| 611 | human | GCGUAGGGACGAUGUAUU AAUACAUCGUCCCUACGC | [2145-2163](19/19) |
| 612 | human | UCCUGCCCUAGCUAUUAGC GCUAAUAGCUAGGGCAGGA | [2103-2121](19/19) |
| 613 | human | GUGGAUAAGGAGCUUAUUC GAAUAAGCUCCUUAUCCAC | [2079-2097](19/19) |
| 614 | human | UGCUGUGGGUCGUGGAUAA UUAUCCACGACCCACAGCA | [2068-2086](19/19) |
| 615 | human, chimpanzee | GAAUCAACUUGCCAGAAUU AAUUCUGGCAAGUUGAUUC | [354-372](19/19) |
| 616 | human | CCAACUAAGUAGAUCAUUA UAAUGAUCUACUUAGUUGG | [1971-1989](19/19) |
| 617 | human | AAAGGCCUUAUUUUUGUC GACAAAAAUAAGGCCUUU | [1947-1965](19/19) |
| 618 | human | GGAAUAAUAAAGGCCUUAU AUAAGGCCUUUAUUAUUCC | [1939-1957](19/19) |
| 619 | human | GGGAAUAAUAAAGGCCUUA UAAGGCCUUUAUUAUUCCC | [1938-1956](19/19) |
| 620 | human | AACCAUGCAUGCACCCAGA UCUGGGUGCAUGCAUGGUU | [1891-1909](19/19) |

| | | | |
|---|---|---|---|
| 621 | human | CAGAUAACCAUGCAUGCAC GUGCAUGCAUGGUUAUCUG | [1886-1904](19/19) |
| 622 | human | CUCACCGUCCAGAUAACCA UGGUUAUCUGGACGGUGAG | [1877-1895](19/19) |
| 623 | human | AUGAAACUCACCGUCCAGA UCUGGACGGUGAGUUUCAU | [1871-1889](19/19) |
| 624 | human | AGAGAAUGAAACUCACCGU ACGGUGAGUUUCAUUCUCU | [1866-1884](19/19) |
| 625 | human | GUACAGCCUAGAGAAUGAA UUCAUUCUCUAGGCUGUAC | [1857-1875](19/19) |
| 626 | human | AUGGUUUAUAGUACAGCCU AGGCUGUACUAUAAACCAU | [1847-1865](19/19) |
| 627 | human | AUGGAGAUAUGGUUUAUAG CUAUAAACCAUAUCUCCAU | [1839-1857](19/19) |
| 628 | human | UGGCUAUGGAGAUAUGGUU AACCAUAUCUCCAUAGCCA | [1834-1852](19/19) |
| 629 | human | UGCAUUGGCUAUGGAGAUA UAUCUCCAUAGCCAAUGCA | [1829-1847](19/19) |
| 630 | human | GUAUACUACCACUUUGAAU AUUCAAAGUGGUAGUAUAC | [1783-1801](19/19) |
| 631 | human | AGCUGUAUACUACCACUUU AAAGUGGUAGUAUACAGCU | [1779-1797](19/19) |
| 632 | human | GGUAGUAGCUGUAUACUAC GUAGUAUACAGCUACUACC | [1773-1791](19/19) |
| 633 | human | CAAGGGUAGUAGCUGUAUA UAUACAGCUACUACCCUUG | [1769-1787](19/19) |
| 634 | human | UCCUUAACCCCAAUUGUCA UGACAAUUGGGGUUAAGGA | [1752-1770](19/19) |
| 635 | human | AAGUAUCUCUCCUUAACCC GGGUUAAGGAGAGAUACUU | [1743-1761](19/19) |
| 636 | human | UCUGGGAAUUGAAGUAUCU AGAUACUUCAAUUCCCAGA | [1732-1750](19/19) |
| 637 | human | UUUCUGGGAAUUGAAGUAU AUACUUCAAUUCCCAGAAA | [1730-1748](19/19) |
| 638 | human | GGCAGUGUUAUCUCAUCUC GAGAUGAGAUAACACUGCC | [1705-1723](19/19) |
| 639 | human | AUGGCAGUGUUAUCUCAUC GAUGAGAUAACACUGCCAU | [1703-1721](19/19) |
| 640 | human | CACCAUGGCAGUGUUAUCU AGAUAACACUGCCAUGGUG | [1699-1717](19/19) |
| 641 | human | UGCUUAAUCUCAGAUGAAC GUUCAUCUGAGAUUAAGCA | [1675-1693](19/19) |
| 642 | human | CAUGUGCUUAAUCUCAGAU AUCUGAGAUUAAGCACAUG | [1671-1689](19/19) |
| 643 | human | UUACAUGUGCUUAAUCUCA UGAGAUUAAGCACAUGUAA | [1668-1686](19/19) |
| 644 | human | CAGUAUUACAUGUGCUUAA UUAAGCACAUGUAAUACUG | [1663-1681](19/19) |
| 645 | human | UCACUUUAGUAAUCUAUCCU AGGAUAGAUUACUAAGUGA | [1639-1657](19/19) |
| 646 | human | CUGUGAGGAUAGGAAAUUA UAAUUUCCUAUCCUCACAG | [1594-1612](19/19) |
| 647 | human | AGUGUUGAAUACUGUCUUU AAAGACAGUAUUCAACACU | [1496-1514](19/19) |
| 648 | human | UAAGUGUUGAAUACUGUCU AGACAGUAUUCAACACUUA | [1494-1512](19/19) |
| 649 | human | CUGUUCUUAAGUGUUGAAU AUUCAACACUUAAGAACAG | [1487-1505](19/19) |
| 650 | human | CCUGUUCUUAAGUGUUGAA UUCAACACUUAAGAACAGG | [1486-1504](19/19) |
| 651 | human | GAUGCCUUUAUAAGCUCAG CUGAGCUUAUAAAGGCAUC | [1462-1480](19/19) |
| 652 | human | UAGAUGCCUUUAUAAGCUC GAGCUUAUAAAGGCAUCUA | [1460-1478](19/19) |
| 653 | human | GGUGUUGUUUUAGAUGCCU AGGCAUCUAAAAACAACACC | [1450-1468](19/19) |
| 654 | human | UAAAGAGGCAACAAAAGCU AGCUUUUGUUGCCUCUUUA | [1408-1426](19/19) |
| 655 | human | GUUUUAAAGAGGCAACAAA UUUGUUGCCUCUUUAAAAC | [1404-1422](19/19) |
| 656 | human | AUGUUUUAAAGAGGCAACA UGUUGCCUCUUUAAAACAU | [1402-1420](19/19) |
| 657 | human | GCUUCACUGUUUCUUGGUG CACCAAGAAACAGUGAAGC | [1369-1387](19/19) |
| 658 | human | GAGAAUAUUACGGCAAUA UAUUGCCGUAAUAUUCUC | [1342-1360](19/19) |
| 659 | human | ACUCAAAUUUGAAGGGUUU AAACCCUUCAAAUUUGAGU | [1258-1276](19/19) |
| 660 | human, chimpanzee | AAGUGAUUUUGACUACUGG CCAGUAGUCAAAAUCACUU | [290-308](19/19) |
| 661 | human, chimpanzee | UAAGUGAUUUUGACUACUG CAGUAGUCAAAAUCACUUA | [289-307](19/19) |
| 662 | human | CACAGAAUCAUACUAAAUG CAUUUAGUAUGAUUCUGUG | [1192-1210](19/19) |
| 663 | human, chimpanzee | GCUAAGUGAUUUUGACUAC GUAGUCAAAAUCACUUAGC | [287-305](19/19) |
| 664 | human | CAGGUAGGCUUGGUAAUAG CUAUUACCAAGCCUACCUG | [1096-1114](19/19) |
| 665 | human | UGGGAUGGAAUAGGUAAGC GCUUACCUAUUCCAUCCCA | [1028-1046](19/19) |
| 666 | human | AUGGGAUGGAAUAGGUAAG CUUACCUAUUCCAUCCCAU | [1027-1045](19/19) |
| 667 | human | UAGUCUCUUUUCUUUCUGU ACAGAAAGAAAAGAGACUA | [898-916](19/19) |
| 668 | human | AAGAAUCCCCAAAUGUAGU ACUACAUUUGGGGUUUCUU | [883-901](19/19) |
| 669 | human | CCCUAAAUAAGAAACCCCA UGGGGUUUCUUAUUUAGGG | [875-893](19/19) |
| 670 | human | GAACAACAGUGAUUGAGG CCUUCAAUCACUGUUGUUC | [760-778](19/19) |
| 671 | human | CUGAUUGGAACAACAGUGA UCACUGUUGUUCCAAUCAG | [753-771](19/19) |
| 672 | human | GAUCCUCAGCUCAGGAUUU AAAUCCUGAGCUGAGGAUC | [707-725](19/19) |
| 673 | human | UUCAGGAGAACUCUGAUCC GGAUCAGAGUUCUCCUGAA | [693-711](19/19) |
| 674 | human | UAGUAGAGGUCGCUUCUCC GGAGAAGCGACCUCUACUA | [668-686](19/19) |
| 675 | human, chimpanzee | GCUUCAGGGACUUUUUCUU AAGAAAAAGUCCCUGAAGC | [649-667](19/19) |
| 676 | human, chimpanzee, dog | AAGCAGGAGAACUGCUCAU AUGAGCAGUUCUCCUGCUU | [624-642](19/19) |
| 677 | human, chimpanzee | GAGCUUACACUUGUGUUUA UAAACACAAGUGUAAGCUC | [606-624](19/19) |
| 678 | human | GUGUGAUUCUAGCGUCGUA UACGACGCUAGAAUCACAC | [578-596](19/19) |
| 679 | human, chimpanzee | AGGAUUGUGUGUGAUUCUA UAGAAUCACACACAAUCCU | [570-588](19/19) |
| 680 | human, chimpanzee | GGUCCUUGUCCCUGAGAAA UUUCUCAGGGACAAGGACC | [434-452](19/19) |
| 681 | human | ACAAAAUGGUGAUGGCUUA UAAGCCAUCACCAUUUUGU | [2492-2510](19/19) |
| 682 | human | CUCUCUUGCCUGUUAUGCU AGCAUAACAGGCAAGAGAG | [2472-2490](19/19) |
| 683 | human | AUCUUUGACUCUCUUGCCU AGGCAAGAGAGUCAAAGAU | [2464-2482](19/19) |
| 684 | human | UUCCACUAACAGUUAUCUU AAGAUAACUGUUAGUGGAA | [2450-2468](19/19) |
| 685 | human | UCGAUGUAGAACUGUUGUC GACAACAGUUCUACAUCGA | [2427-2445](19/19) |
| 686 | human | UCUUGGGCAUCGAUGUAGA UCUACAUCGAUGCCCAAGA | [2418-2436](19/19) |
| 687 | human | AAGGCUUCUUGGGCAUCGA UCGAUGCCCAAGAAGCCUU | [2412-2430](19/19) |
| 688 | human | GUCUAUUGUUAAGCUCCAA UUGGAGCUUAACAAUAGAC | [2342-2360](19/19) |
| 689 | human | UGUCUAUUGUUAAGCUCCA UGGAGCUUAACAAUAGACA | [2341-2359](19/19) |
| 690 | human | UGCAUGUCUAUUGUUAAGC GCUUAACAAUAGACAUGCA | [2337-2355](19/19) |
| 691 | human | UGUUUGCAUGUCUAUUGU ACAAUAGACAUGCAAAACA | [2332-2350](19/19) |
| 692 | human | UUGUUUGCAUGUCUAUUG CAAUAGACAUGCAAACAA | [2331-2349](19/19) |
| 693 | human | AGUGACCUAAAAUGUCACU AGUGACAUUUUAGGUCACU | [2213-2231](19/19) |
| 694 | human | GUUACUGAUACUAUAAGUG CACUUAUAGUAUCAGUAAC | [2198-2216](19/19) |
| 695 | human | AAACAGGUGUGAUCCUGUU AACAGGAUCACACCUGUUU | [2182-2200](19/19) |
| 696 | human | UCAUCCUGGUGUUACUGAA UUCAGUAACACCAGGAUGA | [2163-2181](19/19) |
| 697 | human | GAUGUAUUCAUCCUGGUGU ACACCAGGAUGAAUACAUC | [2156-2174](19/19) |
| 698 | human | CUAGCUAUUAGCUCCACUU AAGUGGAGCUAAUAGCUAG | [2110-2128](19/19) |
| 699 | human | UAAGGAGCUUAUUCAGGUU AACCUGAAUAAGCUCCUUA | [2084-2102](19/19) |

TABLE A-continued

| | | | | |
|---|---|---|---|---|
| 700 | human | GUCGUGGAUAAGGAGCUUA | UAAGCUCCUUAUCCACGAC | [2076-2094](19/19) |
| 701 | human | UGUGGGUCGUGGAUAAGGA | UCCUUAUCCACGACCCACA | [2071-2089](19/19) |
| 702 | human | UUCAUAUCCUUGCUGUGGG | CCCACAGCAAGGAUAUGAA | [2058-2076](19/19) |
| 703 | human | UAAUGAGAGAAUUUAGCCU | AGGCUAAAUUCUCUCAUUA | [2009-2027](19/19) |
| 704 | human | GUUAAUGAGAGAAUUUAGC | GCUAAAUUCUCUCAUUAAC | [2007-2025](19/19) |
| 705 | human | CUUAUUCCAACUAAGUAGA | UCUACUUAGUUGGAAUAAG | [1965-1983](19/19) |
| 706 | human | UUGUCUUAUUCCAACUAAG | CUUAGUUGGAAUAAGACAA | [1961-1979](19/19) |
| 707 | human | GUCACUAGGGAAUAAUAAA | UUUAUUAUUCCCUAGUGAC | [1931-1949](19/19) |
| 708 | human | CUGUCACUAGGGAAUAAUA | UAUUAUUCCCUAGUGACAG | [1929-1947](19/19) |
| 709 | human | CGUCCAGAUAACCAUGCAU | AUGCAUGGUUAUCUGGACG | [1882-1900](19/19) |
| 710 | human | UAGAGAAUGAAACUCACCG | CGGUGAGUUUCAUUCUCUA | [1865-1883](19/19) |
| 711 | human | CUACCACUUUGAAUUAUUG | CAAUAAUUCAAAGUGGUAG | [1788-1806](19/19) |
| 712 | human | UGUCAAGGGUAGUAGCUGU | ACAGCUACUACCCUUGACA | [1766-1784](19/19) |
| 713 | human | CUCUCCUUAACCCCAAUUG | CAAUUGGGGUUAAGGAGAG | [1749-1767](19/19) |
| 714 | human | GAUGAACCAUUUCACCAUG | CAUGGUGAAAUGGUUCAUC | [1687-1705](19/19) |
| 715 | human | UUUCAGUAUUACAUGUGCU | AGCACAUGUAAUACUGAAA | [1660-1678](19/19) |
| 716 | human, chimpanzee | UUCCUGAACCCAACCUCAA | UUGAGGUUGGGUUCAGGAA | [319-337](19/19) |
| 717 | human | GUAAUCUAUCCUCUUUUCA | UGAAAAGAGGAUAGAUUAC | [1646-1664](19/19) |
| 718 | human, chimpanzee | UUGUUCCUGAACCCAACCU | AGGUUGGGUUCAGGAACAA | [316-334](19/19) |
| 719 | human | GGAAAUUAGUUCUGAGAUC | GAUCUCAGAACUAAUUCC | [1605-1623](19/19) |
| 720 | human | AGGAUAGGAAAUUAGUUCU | AGAACUAAUUUCCUAUCCU | [1599-1617](19/19) |
| 721 | human | UGUGAGGAUAGGAAAUUAG | CUAAUUCCUAUCCUCACA | [1595-1613](19/19) |
| 722 | human | CCUGUGAGGAUAGGAAAUU | AAUUCCUAUCCUCACAGG | [1593-1611](19/19) |
| 723 | human | CUGAUAUUUUGUGUGUAG | CUACACACAAAAAUAUCAG | [1541-1559](19/19) |
| 724 | human | GUUCUUAAGUGUUGAAUAC | GUAUUCAACACUUAAGAAC | [1489-1507](19/19) |
| 725 | human, chimpanzee | ACUGGGAUUAUGUUGUUCC | GGAACAACAUAAUCCCAGU | [304-322](19/19) |
| 726 | human | GGUGACUUCCUCACUCUAA | UUAGAGUGAGGAAGUCACC | [1384-1402](19/19) |
| 727 | human | UUGGUGACUUCCUCACUCU | AGAGUGAGGAAGUCACCAA | [1382-1400](19/19) |
| 728 | human | CACUGUUUCUUGGUGACUU | AAGUCACCAAGAAACAGUG | [1373-1391](19/19) |
| 729 | human | CUUCACUGUUUCUUGGUGA | UCACCAAGAAACAGUGAAG | [1370-1388](19/19) |
| 730 | human | UAUUACGGCAAUAAUGGAA | UUCCAUUAUUGCCGUAAUA | [1348-1366](19/19) |
| 731 | human | UAGGUAAGAGUAAAUGAGA | UCUCAUUUACUCUUACCUA | [1327-1345](19/19) |
| 732 | human | CCCUAGGUAAGAGUAAAUG | CAUUUACUCUUACCUAGGG | [1324-1342](19/19) |
| 733 | human | UUAGACAGGAAGGUAGGAU | AUCCUACCUUCCUGUCUAA | [1277-1295](19/19) |
| 734 | human, chimpanzee | CUAAGUGAUUUUGACUACU | AGUAGUCAAAAUCACUUAG | [288-306](19/19) |
| 735 | human | AGAAGCCCAUUUGAGUUUU | AAAACUCAAAUGGGCUUCU | [1053-1071](19/19) |
| 736 | human | GUAGAAGCCCAUUUGAGUU | AACUCAAAUGGGCUUCUAC | [1051-1069](19/19) |
| 737 | human | AGUAGAAGCCCAUUUGAG | CUCAAAUGGGCUUCUACU | [1049-1067](19/19) |
| 738 | human | CAAAAGUAGAAGCCCAUUU | AAAUGGGCUUCUACUUUUG | [1046-1064](19/19) |
| 739 | human, chimpanzee | AGCCUGCUAAGUGAUUUUG | CAAAAUCACUUAGCAGGCU | [282-300](19/19) |
| 740 | human | GGUAAGCAAAAGUAGAAGC | GCUUCUACUUUUGCUUACC | [1040-1058](19/19) |
| 741 | human | AGGUAAGCAAAAGUAGAAG | CUUCUACUUUUGCUUACCU | [1039-1057](19/19) |
| 742 | human | UGGAAUAGGUAAGCAAAAG | CUUUUGCUUACCUAUUCCA | [1033-1051](19/19) |
| 743 | human | AUGGAAUAGGUAAGCAAAA | UUUUGCUUACCUAUUCCAU | [1032-1050](19/19) |
| 744 | human | UUGAAUGGGAUGGAAUAGG | CCUAUUCCAUCCCAUUCAA | [1023-1041](19/19) |
| 745 | human, chimpanzee | AGAGCCUGCUAAGUGAUUU | AAAUCACUUAGCAGGCUCU | [280-298](19/19) |
| 746 | human | UCUGCAUAGAUCCCAUUUU | AAAAUGGGAUCUAUGCAGA | [995-1013](19/19) |
| 747 | human | UUCUGGCCUUUGGAGAAGU | ACUUCUCCAAAGGCCAGAA | [955-973](19/19) |
| 748 | human | UUUCUGUGUUUCACAUUCA | UGAAUGUGAAACACAGAAA | [910-928](19/19) |
| 749 | human | GUAGUCUCUUUUCUUUCUG | CAGAAAGAAAAGAGACUAC | [897-915](19/19) |
| 750 | human | GAAACCCCAAAUGUAGUCU | AGACUACAUUUGGGGUUUC | [885-903](19/19) |
| 751 | human | GUAGUAAAACUAUUCAGCU | AGCUGAAUAGUUUUACUAC | [821-839](19/19) |
| 752 | human | GGUAGUAAAACUAUUCAGC | GCUGAAUAGUUUUACUACC | [820-838](19/19) |
| 753 | human | GAUUGGAACAACAGUGAUU | AAUCUGUUGUUCCAAUC | [755-773](19/19) |
| 754 | human | UACUCACUGAUUGGAACAA | UUGUUCCAAUCAGUGAGUA | [747-765](19/19) |
| 755 | human, rat | GAUUUCGACUUGUUAAGAA | UUCUUAACAAGUCGAAAUC | [721-739](19/19) |
| 756 | human | AGGAUUUCGACUUGUUAAG | CUUAACAAGUCGAAAUCCU | [719-737](19/19) |
| 757 | human | UCAGGAGAACUCUGAUCCU | AGGAUCAGAGUUCUCCUGA | [694-712](19/19) |
| 758 | human, chimpanzee | GGACUAGCUUCAGGGACUU | AAGUCCCUGAAGCUAGUCC | [643-661](19/19) |
| 759 | human, chimpanzee, dog | CUCAUGGACUAGCUUCAGG | CCUGAAGCUAGUCCAUGAG | [638-656](19/19) |
| 760 | human, chimpanzee, dog | GAGAACUGCUCAUGGACUA | UAGUCCAUGAGCAGUUCUC | [630-648](19/19) |
| 761 | human, chimpanzee, dog | GGAGAACUGCUCAUGGACU | AGUCCAUGAGCAGUUCUCC | [629-647](19/19) |
| 762 | human, chimpanzee, dog | CAGGAGAACUGCUCAUGGA | UCCAUGAGCAGUUCUCCUG | [627-645](19/19) |
| 763 | human, chimpanzee | GCUUACACUUGUGUUUAAG | CUUAAACACAAGUGUAAGC | [608-626](19/19) |
| 764 | human, chimpanzee | GGAUUGUGUGUGAUUCUAG | CUAGAAUCACACACAAUCC | [571-589](19/19) |
| 765 | human, rat, chimpanzee | GGAUAGGAUUGUGUGUGAU | AUCACACACAAUCCUAUCC | [566-584](19/19) |
| 766 | human, chimpanzee | GGUUGCAACUGGCAGUUUG | CAAACUGCCAGUUGCAACC | [206-224](19/19) |
| 767 | human, chimpanzee | UAAACUGGUUGCUCAAAG | CUUUGAGCAACCAAGUUUA | [416-434](19/19) |
| 768 | human | GGCUUAUGGAAGGCUGUUA | UAACAGCCUUCCAUAAGCC | [2505-2523](19/19) |
| 769 | human | AAAUGGUGAUGGCUUAUGG | CCAUAAGCCAUCACCAUUU | [2495-2513](19/19) |
| 770 | human | UCUCUUGCCUGUUAUGCUU | AAGCAUAACAGGCAAGAGA | [2473-2491](19/19) |
| 771 | human | UUCUUGGGCAUCGAUGUAG | CUACAUCGAUGCCCAAGAA | [2417-2435](19/19) |
| 772 | human | AAGCUCCAAAGGUUCACUG | CAGUGAACCUUUGGAGCUU | [2352-2370](19/19) |
| 773 | human | UCUAUUGUUAAGCUCCAAA | UUUGGAGCUUAACAAUAGA | [2343-2361](19/19) |
| 774 | human | GGGCCAAGAUAAAUCAAUG | CAUUGAUUUAUCUUGGCCC | [2312-2330](19/19) |

TABLE A-continued

| | | | |
|---|---|---|---|
| 775 | human | UAGAAUUGGGCCAAGAUAA UUAUCUUGGCCCAAUUCUA | [2305-2323](19/19) |
| 776 | human | GGAAAGAUACUACAAAGCC GGCUUUGUAGUAUCUUUCC | [2278-2296](19/19) |
| 777 | human | UCAAAUGCUUGGAAAGAUA UAUCUUUCCAAGCAUUUGA | [2268-2286](19/19) |
| 778 | human | GUUACUGAAAAACAGGUGU ACACCUGUUUUUCAGUAAC | [2173-2191](19/19) |
| 779 | human | AUGUAUUCAUCCUGGUGUU AACACCAGGAUGAAUACAU | [2157-2175](19/19) |
| 780 | human | CAGAUGUAUUCAUCCUGGU ACCAGGAUGAAUACAUCUG | [2154-2172](19/19) |
| 781 | human | UGCCCUAGCUAUUAGCUCC GGAGCUAAUAGCUAGGGCA | [2106-2124](19/19) |
| 782 | human | GAGCUUAUUCAGGUUUCCU AGGAAACCUGAAUAAGCU | [2088-2106](19/19) |
| 783 | human | GGAGCUUAUUCAGGUUUCC GGAAACCUGAAUAAGCUCC | [2087-2105](19/19) |
| 784 | human | UCAUAUCCUUGCUGUGGGU ACCCACAGCAAGGAUAUGA | [2059-2077](19/19) |
| 785 | human | GUUCAAUUCAGCAAGGCUU AAGCCUUGCUGAAUUGAAC | [2040-2058](19/19) |
| 786 | human | CAACAAUGUUCAAUUCAGC GCUGAAUUGAACAUUGUUG | [2033-2051](19/19) |
| 787 | human | GUCUUAUUCCAACUAAGUA UACUUAGUUGGAAUAAGAC | [1963-1981](19/19) |
| 788 | human | CUAGGGAAUAAUAAAGGCC GGCCUUUAUUAUUCCCUAG | [1935-1953](19/19) |
| 789 | human | UAACCAUGCAUGCACCCAG CUGGGUGCAUGCAUGGUUA | [1890-1908](19/19) |
| 790 | human | AGAUAACCAUGCAUGCACC GGUGCAUGCAUGGUUAUCU | [1887-1905](19/19) |
| 791 | human | AGCCUAGAGAAUGAAACUC GAGUUUCAUUCUCUAGGCU | [1861-1879](19/19) |
| 792 | human | UUAUAGUACAGCCUAGAGA UCUCUAGGCUGUACUAUAA | [1852-1870](19/19) |
| 793 | human | GCUAUGGAGAUAUGGUUUA UAAACCAUAUCUCCAUAGC | [1836-1854](19/19) |
| 794 | human | UCUCUCCUUAACCCCAAUU AAUUGGGGUUAAGGAGAGA | [1748-1766](19/19) |
| 795 | human | AUCUCUCCUUAACCCCAAU AUUGGGGUUAAGGAGAGAU | [1747-1765](19/19) |
| 796 | human | CUGGGCUUUUCUGGGAAUU AAUUCCCAGAAAAGCCCAG | [1723-1741](19/19) |
| 797 | human | AACCAUUUCACCAUGGCAG CUGCCAUGGUGAAAUGGUU | [1691-1709](19/19) |
| 798 | human | UUCAGUAUUACAUGUGCUU AAGCACAUGUAAUACUGAA | [1661-1679](19/19) |
| 799 | human | UCCUCUUUUCAGUAUUACA UGUAAUACUGAAAAGAGGA | [1654-1672](19/19) |
| 800 | human | AUCCUCUUUUCAGUAUUAC GUAAUACUGAAAAGAGGAU | [1653-1671](19/19) |
| 801 | human | CUAUCCUCUUUUCAGUAUU AAUACUGAAAAGAGGAUAG | [1651-1669](19/19) |
| 802 | human | AAUCUAUCCUCUUUUCAGU ACUGAAAAGAGGAUAGAUU | [1648-1666](19/19) |
| 803 | human | UUCACUUAGUAAUCUAUCC GGAUAGAUUACUAAGUGAA | [1638-1656](19/19) |
| 804 | human | UAGGAAAUUAGUUCUGAGA UCUCAGAACUAAUUUCCUA | [1603-1621](19/19) |
| 805 | human | GGAUAGGAAAUUAGUUCUG CAGAACUAAUUUCCUAUCC | [1600-1618](19/19) |
| 806 | human | GAGGAUAGGAAAUUAGUUC GAACUAAUUUCCUAUCCUC | [1598-1616](19/19) |
| 807 | human | GUGAGGAUAGGAAAUUAGU ACUAAUUUCCUAUCCUCAC | [1596-1614](19/19) |
| 808 | human | GUAGGCUUGGUAAUAGACU AGUCUAUUACCAAGCCUAC | [1099-1117](19/19) |
| 809 | human, chimpanzee | CCUGCUAAGUGAUUUUGAC GUCAAAAUCACUUAGCAGG | [284-302](19/19) |
| 810 | human | UGCAUAGAUCCCAUUUUUG CAAAAAUGGGAUCUAUGCA | [997-1015](19/19) |
| 811 | human | UUCUUUCUGUGUUUUCACAU AUGUGAAACACAGAAAGAA | [907-925](19/19) |
| 812 | human | CAAAUGUAGUCUCUUUUCU AGAAAAGAGACUACAUUUG | [892-910](19/19) |
| 813 | human | AAACCCCAAAUGUAGUCUC GAGACUACAUUUGGGGUUU | [886-904](19/19) |
| 814 | human | UGCCCUAAAUAAGAAACCC GGGUUUCUUAUUUAGGGCA | [873-891](19/19) |
| 815 | human | AAACUAUUCAGCUAGUCAG CUGACUAGCUGAAUAGUUU | [827-845](19/19) |
| 816 | human | GUGAUUGAAGGGUCCUAAA UUUAGGACCCUUCAAUCAC | [768-786](19/19) |
| 817 | human | UCAGGAUUUCGACUUGUUA UAACAAGUCGAAAUCCUGA | [717-735](19/19) |
| 818 | human | UAGAGGUCGCUUCUCCUCU AGAGGAGAAGCGACCUCUA | [671-689](19/19) |
| 819 | human, chimpanzee, dog | AACUGCUCAUGGACUAGCU AGCUAGUCCAUGAGCAGUU | [633-651](19/19) |
| 820 | human | GGUGAUGGCUUAUGGAAGG CCUUCCAUAAGCCAUCACC | [2499-2517](19/19) |
| 821 | human | AGGCUUCUUGGGCAUCGAU AUCGAUGCCCAAGAAGCCU | [2413-2431](19/19) |
| 822 | human | UAAGCUCCAAAGGUUCACU AGUGAACCUUUGGAGCUUA | [2351-2369](19/19) |
| 823 | human | GGCCAAGAUAAAUCAAUGU ACAUUGAUUUAUCUUGGCC | [2313-2331](19/19) |
| 824 | human | UUCAAAUGCUUGGAAAGAU AUCUUUCCAAGCAUUUGAA | [2267-2285](19/19) |
| 825 | human | GGGACAGAUGUAUUCAUCC GGAUGAAUACAUCUGUCCC | [2150-2168](19/19) |
| 826 | human | AGCUUAUUCAGGUUUCCUG CAGGAAACCUGAAUAAGCU | [2089-2107](19/19) |
| 827 | human | AUUCCAACUAAGUAUACUA AGAUCUACUUAGUUGGAAU | [1968-1986](19/19) |
| 828 | human | AGUACAGCCUAGAGAAUGA UCAUUCUCUAGGCUGUACU | [1856-1874](19/19) |
| 829 | human | AUAGUACAGCCUAGAGAAU AUUCUCUAGGCUGUACUAU | [1854-1872](19/19) |
| 830 | human | GGUUUAUAGUACAGCCUAG CUAGGCUGUACUAUAAACC | [1849-1867](19/19) |
| 831 | human | GAUAUGGUUUAUAGUACAG CUGUACUAUAAACCAUAUC | [1844-1862](19/19) |
| 832 | human | GGAGAUAUGGUUUAUAGUA UACUAUAAACCAUAUCUCC | [1841-1859](19/19) |
| 833 | human | AACCCCAAUUGUCAAGGGU ACCCUUGACAAUUGGGGUU | [1757-1775](19/19) |
| 834 | human | UAUCUCUCCUUAACCCCAA UUGGGGUUAAGGAGAGAUA | [1746-1764](19/19) |
| 835 | human | GUAUCUCUCCUUAACCCCA UGGGGUUAAGGAGAGAUAC | [1745-1763](19/19) |
| 836 | human | UCUGGGCUUUUCUGGGAAU AUUCCCAGAAAAGCCCAGA | [1722-1740](19/19) |
| 837 | human | GAACCAUUUCACCAUGGCA UGCCAUGGUGAAAUGGUUC | [1690-1708](19/19) |
| 838 | human | UCUAUCCUCUUUUCAGUAU AUACUGAAAAGAGGAUAGA | [1650-1668](19/19) |
| 839 | human | UGUGUGUAGUUGAUUACUC GAGUAAUCAACUACACACA | [1551-1569](19/19) |
| 840 | human | CUUAAGUGUUGAAUACUGU ACAGUAUUCAACACUUAAG | [1492-1510](19/19) |
| 841 | human | UCUUAAGUGUUGAAUACUG CAGUAUUCAACACUUAAGA | [1491-1509](19/19) |
| 842 | human | AAACCAGAUUUGCCUAUUU AAAUAGGCAAAUCUGGUUU | [1122-1140](19/19) |
| 843 | human | CCUUUGGAGAAGUGAUUCA UGAAUCACUUCUCCAAAGG | [961-979](19/19) |
| 844 | human | UGGCCUUUGGAGAAGUGAU AUCACUUCUCCAAAGGCCA | [958-976](19/19) |
| 845 | human | UGUAGCUCUUUUCUUUCU AGAAAGAAAAGAGACUACA | [896-914](19/19) |
| 846 | human | CUAAAUAAGAAACCCCAAA UUUGGGGUUUCUUAUUUAG | [877-895](19/19) |
| 847 | human | CCUGCCCUAAAUAAGAAAC GUUUCUUAUUUAGGGCAGG | [871-889](19/19) |
| 848 | human | AAACUUUACUCACUGAUG CAUCACGUGAGUAAAGUUU | [741-759](19/19) |
| 849 | human | GAAAAACUUUACUCACUG CAGUGAGUAAAGUUUUUC | [737-755](19/19) |
| 850 | human, rat | GGAUUUCGACUUGUUAAGA UCUUAACAAGUCGAAAUCC | [720-738](19/19) |
| 851 | human | CAGGAUUUCGACUUGUUAA UUAACAAGUCGAAAUCCUG | [718-736](19/19) |
| 852 | human, chimpanzee | CUGGCAGUUUGAGCAGCAA UUGCUGCUCAAACUGCCAG | [214-232](19/19) |
| 853 | human, chimpanzee | ACUGGCAGUUUGAGCAGCA UGCUGCUCAAACUGCCAGU | [213-231](19/19) |

TABLE A-continued

| | | | |
|---|---|---|---|
| 854 | human, chimpanzee | UAGGAUUGUGUGUGAUUCU AGAAUCACACACAAUCCUA | [569-587](19/19) |
| 855 | human, rat, chimpanzee | CUGGAUAGGAUUGUGUGUG CACACACAAUCCUAUCCAG | [564-582](19/19) |
| 856 | human, chimpanzee | CAAAGGUCCUUGUCCCUGA UCAGGGACAAGGACCUUUG | [430-448](19/19) |
| 857 | human, chimpanzee | GUUGCUCAAAGGUCCUUGU ACAAGGACCUUUGAGCAAC | [424-442](19/19) |
| 858 | human, chimpanzee | AAACUUGGUUGCUCAAAGG CCUUUGAGCAACCAAGUUU | [417-435](19/19) |
| 859 | human | UGGUGAUGGCUUAUGGAAG CUUCCAUAAGCCAUCACCA | [2498-2516](19/19) |
| 860 | human | GGAGUUGUCACCACUGACU AGUCAGUGGUGACAACUCC | [2389-2407](19/19) |
| 861 | human | ACAAUGUUCAAUUCAGCAA UUGCUGAAUUGAACAUUGU | [2035-2053](19/19) |
| 862 | human, chimpanzee | UGAGGAAUCAACUUGCCAG CUGGCAAGUUGAUUCCUCA | [350-368](19/19) |
| 863 | human | UGGAGAUAUGGUUUAUAGU ACUAUAAACCAUAUCUCCA | [1840-1858](19/19) |
| 864 | human | CUAUGGAGAUAUGGUUUAU AUAAACCAUAUCUCCAUAG | [1837-1855](19/19) |
| 865 | human | CCCCAAUUGUCAAGGGUAG CUACCCUUGACAAUUGGGG | [1759-1777](19/19) |
| 866 | human | UAACCCCAAUUGUCAAGGG CCCUUGACAAUUGGGGUUA | [1756-1774](19/19) |
| 867 | human | ACUUAGUAAUCUAUCCUCU AGAGGAUAGAUUACUAAGU | [1641-1659](19/19) |
| 868 | human | CACUUAGUAAUCUAUCCUC GAGGAUAGAUUACUAAGUG | [1640-1658](19/19) |
| 869 | human | AGGAAAUUAGUUCUGAGAU AUCAGAACUAAUUUCCU | [1604-1622](19/19) |
| 870 | human | UGGUGACUUCCUCACUCUA UAGAGUGAGGAAGUCACCA | [1383-1401](19/19) |
| 871 | human | GUUUCAGGUAGGCUUGGUA UACCAAGCCUACCUGAAAC | [1092-1110](19/19) |
| 872 | human | AUAGGUAAGCAAAAGUAGA UCUACUUUUGCUUACCUAU | [1037-1055](19/19) |
| 873 | human | ACAACAGUGAUUGAAGGGU ACCCUUCAAUCACUGUUGU | [762-780](19/19) |
| 874 | human, chimpanzee, dog | GAACUGCUCAUGGACUAGC GCUAGUCCAUGAGCAGUUC | [632-650](19/19) |
| 875 | human, chimpanzee, dog | GUGUUUAAGCAGGAGAACU AGUUCUCCUGCUUAAACAC | [618-636](19/19) |
| 876 | human, mouse, rat, chimpanzee | GAGAAACUGACCCAGAGAA UUCUCUGGGUCAGUUUCUC | [447-465](19/19) |
| 877 | human | CAAUGUUCAAUUCAGCAAG CUUGCUGAAUUGAACAUUG | [2036-2054](19/19) |
| 878 | human | GGCUAUGGAGAUAUGGUUU AAACCAUAUCUCCAUAGCC | [1835-1853](19/19) |
| 879 | human | AUAGGAAAUUAGUUCUGAG CUCAGAACUAAUUUCCUAU | [1602-1620](19/19) |
| 880 | human | GAUAGGAAAUUAGUUCUGA UCAGAACUAAUUUCCUAUC | [1601-1619](19/19) |
| 881 | human | AUAAACCAGAUUUGCCUAU AUAGGCAAAUCUGGUUUAU | [1120-1138](19/19) |
| 882 | human | CAACAGUGAUUGAAGGGUC GACCCUUCAAUCACUGUUG | [763-781](19/19) |
| 883 | human, chimpanzee | UGGUUGCUCAAAGGUCCUU AAGGACCUUUGAGCAACCA | [422-440](19/19) |
| 884 | human, chimpanzee | UUGGUUGCUCAAAGGUCCU AGGACCUUUGAGCAACCAA | [421-439](19/19) |
| 885 | human | AUGCUUACAAAAUGGUGAU AUCACCAUUUUGUAAGCAU | [2486-2504](19/19) |
| 886 | human | CUGGAGUUGUCACCACUGA UCAGUGGUGACAACUCCAG | [2387-2405](19/19) |
| 887 | human | CUCCAAAGGUUCUGUGU ACACAGUGAACCUUUGGAG | [2355-2373](19/19) |
| 888 | human, chimpanzee | GAGGUAAUAUUUGAGGAAU AUUCCUCAAAUAUUACCUC | [339-357](19/19) |
| 889 | human, chimpanzee | ACGAGGUAAUAUUUGAGGA UCCUCAAAUAUUACCUCGU | [337-355](19/19) |
| 890 | human | GUUCCUGACUCAAAUUUGA UCAAAUUUGAGUCAGGAAC | [1251-1269](19/19) |
| 891 | human | CUGAUCCUCAGCUCAGGAU AUCCUGAGCUGAGGAUCAG | [705-723](19/19) |
| 892 | human, chimpanzee | AGGUAAUAUUUGAGGAAUC GAUUCCUCAAAUAUUACCU | [340-358](19/19) |
| 893 | human, chimpanzee | CGAGGUAAUAUUUGAGGAA UUCCUCAAAUAUUACCUCG | [338-356](19/19) |
| 894 | human | AUCAAAACUUCCAAAAGCC GGCUUUUGGAAGUUUUGAU | [1222-1240](19/19) |
| 895 | human | UAUCAAAACUUCCAAAAGC GCUUUUGGAAGUUUUGAUA | [1221-1239](19/19) |
| 896 | human | CUGAUUUUCUGGCCUUUGG CCAAAGGCCAGAAAAUCAG | [949-967](19/19) |
| 897 | human, chimpanzee, dog | CACUUGUGUUUAAGCAGGA UCCUGCUUAAACACAAGUG | [613-631](19/19) |
| 898 | human | UAUGCUUACAAAAUGGUGA UCACCAUUUUGUAAGCAUA | [2485-2503](19/19) |
| 899 | human | GAAUUGAAGUAUCUCUCCU AGGAGAGAUACUUCAAUUC | [1737-1755](19/19) |
| 900 | human | UUCCUGACUCAAAUUUGAA UUCAAAUUUGAGUCAGGAA | [1252-1270](19/19) |
| 901 | human | UUCUCUAAGUUUUCAGAGG CCUCUGAAAACUUAGAGAA | [1162-1180](19/19) |
| 902 | human | UGAAUGGGAUGGAAUAGGU ACCUAUUCCAUCCCAUUCA | [1024-1042](19/19) |
| 903 | human | GAAGUGAUUCAAAAUAGUG CACUAUUUUGAAUCACUUC | [969-987](19/19) |
| 904 | human | UUGAAGGGUCCUAAAAAGG CCUUUUUAGGACCCUUCAA | [772-790](19/19) |
| 905 | human, rat | CGACUUGUUAAGAAAAAAC GUUUUUUCUUAACAAGUCG | [726-744](19/19) |
| 906 | human, chimpanzee, dog | UUGUGUUUAAGCAGGAGAA UUCUCCUGCUUAAACACAA | [616-634](19/19) |
| 907 | human, chimpanzee, dog | ACACUUGUGUUUAAGCAGG CCUGCUUAAACACAAGUGU | [612-630](19/19) |
| 908 | human, chimpanzee | UUACACUUGUGUUUAAGCA UGCUUAAACACAAGUGUAA | [610-628](19/19) |
| 909 | human, mouse, rat, chimpanzee | AGAAACUGACCCAGAGAAU UUCUCUGGGUCAGUUUCU | [448-466](19/19) |
| 910 | human | CCAUGGCAGUGUUAUCUCA UGAGAUAACACUGCCAUGG | [1701-1719](19/19) |
| 911 | human | AUUGAAGGGUCCUAAAAAG CUUUUUAGGACCCUUCAAU | [771-789](19/19) |
| 912 | human | UGGAACAACAGUGAUUGAA UUCAAUCACUGUUGUUCCA | [758-776](19/19) |
| 913 | human, chimpanzee, dog | GCAACUGGCAGUUUAGCA UGCUCAAACUGCCAGUUGC | [210-228](19/19) |
| 914 | human, chimpanzee | GGUAAUAUUUGAGGAAUCA UGAUUCCUCAAAUAUUACC | [341-359](19/19) |
| 915 | human, mouse, rat, chimpanzee, dog | CUGAGAAACUGACCCAGAG CUCUGGGUCAGUUUCUCAG | [445-463](19/19) |
| 916 | human | CUCUGGGCUUUUCUGGGAA UUCCCAGAAAAGCCCAGAG | [1721-1739](19/19) |
| 917 | human | UUGGAACAACAGUGAUUGA UCAAUCACUGUUGUUCCAA | [757-775](19/19) |
| 918 | human | UGAUGGCUUAUGGAAGGCU AGCCUUCCAUAAGCCAUCA | [2501-2519](19/19) |
| 919 | human | GUGAUGGCUUAUGGAAGGC GCCUUCCAUAAGCCAUCAC | [2500-2518](19/19) |
| 920 | human | UUGGCUAUGGAGAUAUGGU ACCAUAUCUCCAUAGCCAA | [1833-1851](19/19) |
| 921 | human | CUCUUUUCUUCUGUGUUUU AAACACAGAAGAAAAGAG | [902-920](19/19) |
| 922 | human | GGAACAACAGUGAUUGAAG CUUCAAUCACUGUUGUUCC | [759-777](19/19) |

TABLE A-continued

| | | | | |
|---|---|---|---|---|
| 923 | human | UCUCUGGGCUUUUCUGGGA | UCCCAGAAAAGCCCAGAGA | [1720-1738](19/19) |
| 924 | human | UCUCUUUUCUUUCUGUGUU | AACACAGAAAGAAAAGAGA | [901-919](19/19) |
| 925 | human | GUCUCUUUUCUUUCUGUGU | ACACAGAAAGAAAAGAGAC | [900-918](19/19) |

| No | mouse 31541838 | rat 62644440 | chimpanzee 55622975 | dog 74002279 |
|---|---|---|---|---|
| 1 | — | — | — | — |
| 2 | — | — | — | — |
| 3 | — | — | — | — |
| 4 | — | — | — | — |
| 5 | — | — | — | — |
| 6 | — | — | — | — |
| 7 | — | — | [531-541](11/11) | — |
| 8 | — | — | — | — |
| 9 | — | — | — | — |
| 10 | [362-380](19/19) | [243-261](19/19) | [484-502](19/19) | — |
| 11 | — | — | — | — |
| 12 | — | — | — | — |
| 13 | — | — | — | — |
| 14 | — | — | — | — |
| 15 | — | — | — | — |
| 16 | — | — | — | — |
| 17 | — | — | — | — |
| 18 | — | — | — | — |
| 19 | — | — | — | — |
| 20 | — | — | — | — |
| 21 | — | — | — | — |
| 22 | — | — | — | — |
| 23 | [235-251](17/17) | [117-132](16/16) | [357-375](19/19) | — |
| 24 | [383-397](15/15) | [264-278](15/15) | [501-519](19/19) | [363-381](19/19) |
| 25 | [377-395](18/19) | [258-276](18/19) | [499-517](19/19) | [361-379](19/19) |
| 26 | [371-389](18/19) | [252-270](18/19) | [493-511](19/19) | [359-373](15/15) |
| 27 | [370-388](18/19) | [251-269](18/19) | [492-510](19/19) | [354-372](18/19) |
| 28 | — | — | — | — |
| 29 | — | — | — | — |
| 30 | — | — | — | — |
| 31 | — | — | — | — |
| 32 | — | — | — | — |
| 33 | — | — | — | — |
| 34 | — | — | — | — |
| 35 | — | — | — | — |
| 36 | — | — | — | [1182-1194](13/13) |
| 37 | — | — | — | — |
| 38 | — | — | — | — |
| 39 | [237-251](15/15) | [118-132](15/15) | [359-377](19/19) | — |
| 40 | [236-251](16/16) | [117-132](16/16) | [358-376](19/19) | — |
| 41 | — | — | [711-727](16/17) | — |
| 42 | — | — | — | — |
| 43 | [523-539](17/17) | [404-422](19/19) | [645-663](18/19) | [507-525](19/19) |
| 44 | — | — | — | — |
| 45 | — | — | — | — |
| 46 | — | — | — | — |
| 47 | [383-400](18/18) | [264-281](18/18) | [504-522](19/19) | [366-384](19/19) |
| 48 | — | — | — | — |
| 49 | — | — | — | — |
| 50 | [361-379](19/19) | [242-260](19/19) | [483-501](19/19) | — |
| 51 | — | — | — | — |
| 52 | — | — | — | — |
| 53 | — | — | — | — |
| 54 | — | — | — | — |
| 55 | — | — | — | — |
| 56 | — | — | — | — |
| 57 | — | — | — | — |
| 58 | — | — | — | [1333-1343](11/11) |
| 59 | — | — | — | — |
| 60 | — | — | — | — |
| 61 | — | — | — | [1182-1194](13/13) |
| 62 | — | — | — | — |
| 63 | — | — | — | — |
| 64 | — | — | — | — |
| 65 | [845-856](12/12) | — | — | [834-844](11/11) |
| 66 | — | — | — | — |
| 67 | — | — | — | — |
| 68 | [527-545](18/19) | [408-426](19/19) | [651-667](17/17) | [511-529](19/19) |
| 69 | [461-479](19/19) | [342-360](18/19) | [583-601](19/19) | [447-463](17/17) |
| 70 | [459-477](19/19) | — | [581-599](19/19) | [447-461](15/15) |
| 71 | [458-476](19/19) | — | [580-598](19/19) | [442-460](18/19) |
| 72 | [456-474](19/19) | [337-355](18/19) | [578-596](19/19) | [440-458](18/19) |
| 73 | [455-473](19/19) | [336-354](18/19) | [577-595](19/19) | [439-457](18/19) |

TABLE A-continued

| | | | | |
|---|---|---|---|---|
| 74 | [388-406](18/19) | [269-287](18/19) | [510-528](19/19) | [372-390](19/19) |
| 75 | — | — | — | — |
| 76 | — | — | — | — |
| 77 | [384-400](17/17) | [265-282](18/18) | [506-524](19/19) | [368-386](19/19) |
| 78 | — | — | — | — |
| 79 | — | — | — | — |
| 80 | — | — | — | — |
| 81 | [361-378](18/18) | [242-259](18/18) | [482-500](19/19) | — |
| 82 | — | — | — | — |
| 83 | — | — | — | — |
| 84 | — | — | — | — |
| 85 | — | — | — | — |
| 86 | — | — | — | — |
| 87 | — | — | — | — |
| 88 | — | — | — | — |
| 89 | — | — | — | — |
| 90 | — | — | — | — |
| 91 | — | — | — | — |
| 92 | — | — | — | — |
| 93 | — | — | — | — |
| 94 | — | — | — | — |
| 95 | [1278-1288](11/11) | — | — | — |
| 96 | — | — | — | — |
| 97 | — | — | — | — |
| 98 | — | — | — | [1182-1194](13/13) |
| 99 | — | — | — | — |
| 100 | — | — | — | — |
| 101 | — | — | — | — |
| 102 | — | — | — | — |
| 103 | — | — | — | — |
| 104 | — | — | — | — |
| 105 | — | — | — | — |
| 106 | — | — | [773-789](17/17) | — |
| 107 | [524-539](16/16) | [405-423](19/19) | [646-664](18/19) | [508-526](19/19) |
| 108 | [518-536](19/19) | [399-417](19/19) | — | [502-520](19/19) |
| 109 | [515-533](19/19) | [398-414](17/17) | [637-655](18/19) | [501-517](17/17) |
| 110 | [514-530](17/17) | [398-411](14/14) | [634-649](16/16) | [496-514](18/19) |
| 111 | [453-471](19/19) | [334-348](15/15) | [575-593](19/19) | — |
| 112 | — | — | [528-546](19/19) | — |
| 113 | [402-413](12/12) | [279-294](15/16) | [520-538](19/19) | [382-397](16/16) |
| 114 | — | — | — | — |
| 115 | — | — | — | — |
| 116 | — | — | — | — |
| 117 | — | — | — | — |
| 118 | — | — | — | — |
| 119 | — | — | — | — |
| 120 | — | — | — | — |
| 121 | [385-400](16/16) | [266-282](17/17) | [507-525](19/19) | [369-387](19/19) |
| 122 | — | — | — | — |
| 123 | — | — | — | — |
| 124 | — | — | — | — |
| 125 | — | — | — | — |
| 126 | [366-381](16/16) | [247-262](16/16) | [488-506](19/19) | — |
| 127 | — | — | — | — |
| 128 | — | — | — | — |
| 129 | — | — | — | — |
| 130 | — | — | — | — |
| 131 | — | — | — | — |
| 132 | — | — | — | — |
| 133 | — | — | — | — |
| 134 | — | — | — | — |
| 135 | — | — | — | — |
| 136 | — | — | — | — |
| 137 | — | — | — | — |
| 138 | — | — | — | — |
| 139 | — | — | — | — |
| 140 | [305-323](18/19) | — | [427-445](19/19) | — |
| 141 | — | — | — | — |
| 142 | — | — | — | — |
| 143 | — | — | — | — |
| 144 | — | — | — | — |
| 145 | — | — | — | [1333-1345](13/13) |
| 146 | — | — | — | [1333-1344](12/12) |
| 147 | — | — | — | — |
| 148 | — | — | — | — |
| 149 | — | — | — | — |
| 150 | — | — | — | — |
| 151 | — | — | — | — |
| 152 | — | — | — | — |
| 153 | — | — | — | — |

TABLE A-continued

| | | | | |
|---|---|---|---|---|
| 154 | [283-296](14/14) | [164-177](14/14) | [401-419](19/19) | [263-281](18/19) |
| 155 | — | — | — | — |
| 156 | — | — | — | — |
| 157 | — | — | — | — |
| 158 | — | — | — | — |
| 159 | [939-949](11/11) | — | — | — |
| 160 | [939-949](11/11) | — | — | — |
| 161 | [845-858](14/14) | — | — | [834-845](12/12) |
| 162 | — | — | — | — |
| 163 | — | — | — | — |
| 164 | — | — | — | — |
| 165 | — | — | [364-382](19/19) | — |
| 166 | — | — | — | — |
| 167 | — | — | — | — |
| 168 | — | — | — | — |
| 169 | — | — | [774-789](16/16) | — |
| 170 | — | — | [718-736](19/19) | — |
| 171 | — | — | — | — |
| 172 | [554-572](19/19) | [435-453](19/19) | [676-694](19/19) | [538-552](15/15) |
| 173 | [521-539](19/19) | [402-420](19/19) | [643-661](18/19) | [505-523](19/19) |
| 174 | [514-532](19/19) | [398-413](16/16) | [636-654](18/19) | [501-516](16/16) |
| 175 | [514-528](15/15) | [398-409](12/12) | [632-649](18/18) | [494-512](18/19) |
| 176 | — | [527-545](19/19) | — | — |
| 177 | — | — | — | — |
| 178 | — | — | — | — |
| 179 | — | — | — | — |
| 180 | — | — | — | — |
| 181 | [1571-1581](11/11) | — | — | — |
| 182 | — | — | — | — |
| 183 | — | — | — | — |
| 184 | — | — | — | — |
| 185 | — | — | — | — |
| 186 | — | — | — | — |
| 187 | — | — | — | — |
| 188 | — | — | — | — |
| 189 | — | — | — | — |
| 190 | — | — | — | — |
| 191 | — | — | — | — |
| 192 | — | — | — | — |
| 193 | — | — | — | — |
| 194 | — | — | — | — |
| 195 | — | — | — | — |
| 196 | — | — | — | — |
| 197 | — | — | — | — |
| 198 | — | — | [454-472](19/19) | — |
| 199 | [329-341](13/13) | [210-222](13/13) | [451-469](19/19) | — |
| 200 | [326-341](16/16) | [207-222](16/16) | [448-466](19/19) | — |
| 201 | — | — | — | — |
| 202 | [1278-1288](11/11) | — | — | — |
| 203 | — | — | — | — |
| 204 | — | — | — | — |
| 205 | — | — | — | — |
| 206 | — | — | — | — |
| 207 | — | — | — | — |
| 208 | — | — | — | — |
| 209 | — | — | — | — |
| 210 | — | — | — | — |
| 211 | — | — | — | — |
| 212 | — | — | — | — |
| 213 | — | — | — | — |
| 214 | — | — | — | [1333-1346](14/14) |
| 215 | — | — | — | [1333-1346](14/14) |
| 216 | — | — | — | — |
| 217 | — | — | — | — |
| 218 | — | — | — | — |
| 219 | — | — | — | — |
| 220 | — | — | — | — |
| 221 | — | — | — | — |
| 222 | — | — | — | — |
| 223 | — | — | — | — |
| 224 | — | — | — | — |
| 225 | — | — | — | — |
| 226 | — | — | — | — |
| 227 | — | — | — | — |
| 228 | — | — | — | — |
| 229 | — | — | — | — |
| 230 | — | — | — | — |
| 231 | [939-949](11/11) | — | — | — |
| 232 | — | — | — | — |
| 233 | — | — | — | — |

TABLE A-continued

| | | | | |
|---|---|---|---|---|
| 234 | [845-857](13/13) | — | — | [834-845](12/12) |
| 235 | [845-855](11/11) | — | — | — |
| 236 | — | — | — | — |
| 237 | — | — | — | — |
| 238 | — | — | — | — |
| 239 | — | — | — | — |
| 240 | [240-251](12/12) | [121-139](18/19) | [362-380](19/19) | — |
| 241 | [238-251](14/14) | [119-137](18/19) | [360-378](19/19) | — |
| 242 | — | [579-596](18/18) | — | — |
| 243 | — | — | — | — |
| 244 | — | — | — | — |
| 245 | — | — | [775-789](15/15) | — |
| 246 | [613-623](11/11) | — | [727-745](19/19) | [589-607](18/19) |
| 247 | — | — | [711-729](18/19) | — |
| 248 | — | — | — | — |
| 249 | [559-577](18/19) | [440-458](19/19) | [681-699](19/19) | — |
| 250 | [514-526](13/13) | — | [630-648](19/19) | — |
| 251 | [464-482](19/19) | [345-363](18/19) | [586-604](19/19) | [448-466](19/19) |
| 252 | [454-472](19/19) | [335-353](18/19) | [576-594](19/19) | — |
| 253 | [403-421](18/19) | [284-300](16/17) | [525-543](19/19) | [387-397](11/11) |
| 254 | [397-413](16/17) | [278-294](16/17) | [519-537](19/19) | [381-397](17/17) |
| 255 | — | — | — | — |
| 256 | [394-412](18/19) | — | [516-534](19/19) | [378-396](19/19) |
| 257 | — | — | [514-532](19/19) | [376-394](19/19) |
| 258 | — | — | — | — |
| 259 | — | — | — | — |
| 260 | — | — | — | — |
| 261 | [387-405](18/19) | [268-282](15/15) | [509-527](19/19) | [371-389](19/19) |
| 262 | — | — | — | — |
| 263 | — | — | — | — |
| 264 | — | — | — | — |
| 265 | — | — | — | — |
| 266 | — | — | — | — |
| 267 | — | — | — | — |
| 268 | — | — | — | — |
| 269 | — | — | — | — |
| 270 | — | — | — | — |
| 271 | — | — | — | — |
| 272 | — | — | — | — |
| 273 | — | — | — | — |
| 274 | — | — | — | — |
| 275 | — | — | — | — |
| 276 | — | — | — | — |
| 277 | — | — | — | — |
| 278 | — | — | — | — |
| 279 | — | — | — | — |
| 280 | — | — | — | — |
| 281 | — | — | — | — |
| 282 | — | — | — | — |
| 283 | — | — | — | — |
| 284 | — | — | — | — |
| 285 | — | — | — | — |
| 286 | — | — | — | — |
| 287 | — | — | — | — |
| 288 | — | — | — | — |
| 289 | — | — | — | — |
| 290 | — | — | — | — |
| 291 | — | — | [456-474](19/19) | — |
| 292 | — | — | [455-473](19/19) | — |
| 293 | — | — | — | — |
| 294 | — | — | — | — |
| 295 | — | — | — | — |
| 296 | — | — | — | — |
| 297 | — | — | — | — |
| 298 | — | — | — | — |
| 299 | — | — | — | — |
| 300 | [1278-1288](11/11) | — | — | — |
| 301 | [1278-1288](11/11) | — | — | — |
| 302 | — | — | — | — |
| 303 | — | — | — | — |
| 304 | — | — | — | — |
| 305 | — | — | — | — |
| 306 | — | — | — | — |
| 307 | — | — | — | — |
| 308 | — | — | — | — |
| 309 | — | — | — | — |
| 310 | — | — | — | — |
| 311 | — | — | — | — |
| 312 | — | — | — | — |
| 313 | — | — | — | — |

TABLE A-continued

| | | | | |
|---|---|---|---|---|
| 314 | — | — | — | — |
| 315 | — | — | — | — |
| 316 | — | — | — | — |
| 317 | — | — | — | — |
| 318 | — | — | — | — |
| 319 | — | — | — | [1182-1194](13/13) |
| 320 | [284-302](18/19) | [165-183](18/19) | [406-424](19/19) | [268-286](18/19) |
| 321 | — | — | — | — |
| 322 | — | — | — | — |
| 323 | — | — | — | — |
| 324 | [283-293](11/11) | [164-174](11/11) | [397-415](19/19) | [263-273](11/11) |
| 325 | — | — | — | — |
| 326 | — | — | — | — |
| 327 | — | — | — | — |
| 328 | — | — | — | — |
| 329 | — | — | — | — |
| 330 | [845-861](17/17) | — | — | [834-845](12/12) |
| 331 | — | — | — | — |
| 332 | — | — | — | — |
| 333 | — | — | — | — |
| 334 | [239-251](13/13) | [120-138](18/19) | [361-379](19/19) | — |
| 335 | [711-729](19/19) | [592-610](18/19) | — | — |
| 336 | — | [579-597](19/19) | — | — |
| 337 | [676-686](11/11) | — | — | — |
| 338 | [777-789](13/13) | — | — | — |
| 339 | — | — | [772-789](18/18) | — |
| 340 | — | — | [771-789](19/19) | — |
| 341 | — | — | [721-739](19/19) | — |
| 342 | — | — | [717-733](17/17) | — |
| 343 | — | — | [717-732](16/16) | — |
| 344 | [529-547](18/19) | [410-428](19/19) | [651-669](19/19) | [513-531](19/19) |
| 345 | [525-539](15/15) | [406-424](19/19) | [651-665](15/15) | [509-527](19/19) |
| 346 | [440-458](19/19) | [323-339](17/17) | [562-580](19/19) | [424-442](19/19) |
| 347 | [439-449](11/11) | — | [553-571](19/19) | [417-433](17/17) |
| 348 | [408-426](18/19) | — | [530-548](19/19) | — |
| 349 | [396-413](17/18) | [277-294](17/18) | [518-536](19/19) | [380-397](18/18) |
| 350 | — | — | [515-533](19/19) | [377-395](19/19) |
| 351 | — | — | — | — |
| 352 | — | — | — | — |
| 353 | — | — | — | — |
| 354 | — | — | — | — |
| 355 | — | — | — | — |
| 356 | [386-400](15/15) | [267-282](16/16) | [508-526](19/19) | [370-388](19/19) |
| 357 | — | — | — | — |
| 358 | [2460-2470](11/11) | — | — | — |
| 359 | [2460-2470](11/11) | — | — | — |
| 360 | — | — | — | — |
| 361 | [1571-1581](11/11) | — | — | — |
| 362 | [1571-1581](11/11) | — | — | — |
| 363 | [1571-1581](11/11) | — | — | — |
| 364 | [1571-1581](11/11) | — | — | — |
| 365 | [1571-1581](11/11) | — | — | — |
| 366 | — | — | — | — |
| 367 | — | — | — | — |
| 368 | — | — | — | — |
| 369 | — | — | — | — |
| 370 | — | — | — | — |
| 371 | — | — | — | — |
| 372 | — | — | — | — |
| 373 | — | — | — | — |
| 374 | — | — | — | — |
| 375 | — | — | — | — |
| 376 | [361-377](17/17) | [242-258](17/17) | [481-499](19/19) | — |
| 377 | — | — | — | — |
| 378 | — | — | — | — |
| 379 | — | — | — | — |
| 380 | — | — | — | — |
| 381 | — | — | [473-491](19/19) | [340-351](12/12) |
| 382 | — | — | — | — |
| 383 | — | — | — | — |
| 384 | — | — | — | — |
| 385 | — | — | — | — |
| 386 | — | — | — | — |
| 387 | — | — | — | — |
| 388 | — | — | — | — |
| 389 | — | — | — | — |
| 390 | — | — | — | — |
| 391 | — | — | — | — |
| 392 | — | — | — | — |
| 393 | — | — | — | — |

TABLE A-continued

| | | | | |
|---|---|---|---|---|
| 394 | — | — | — | — |
| 395 | — | — | — | — |
| 396 | — | — | — | — |
| 397 | — | — | — | — |
| 398 | — | — | — | — |
| 399 | [325-341](17/17) | [206-222](17/17) | [447-465](19/19) | [309-325](16/17) |
| 400 | — | — | — | — |
| 401 | — | — | — | — |
| 402 | [320-338](18/19) | [206-219](14/14) | [442-460](19/19) | [306-319](14/14) |
| 403 | — | — | — | — |
| 404 | — | — | — | — |
| 405 | — | — | — | — |
| 406 | [183-200](18/18) | [64-81](18/18) | [304-322](19/19) | [167-184](18/18) |
| 407 | — | — | — | — |
| 408 | — | — | — | — |
| 409 | — | — | — | — |
| 410 | — | — | — | — |
| 411 | — | — | — | — |
| 412 | — | — | — | — |
| 413 | — | — | — | — |
| 414 | [306-323](17/18) | — | [428-446](19/19) | — |
| 415 | — | — | — | — |
| 416 | — | — | — | — |
| 417 | — | — | — | — |
| 418 | — | — | — | — |
| 419 | — | — | — | — |
| 420 | — | — | — | — |
| 421 | [300-317](18/18) | [181-195](15/15) | [422-440](19/19) | [284-302](18/19) |
| 422 | [299-317](19/19) | [180-195](16/16) | [421-439](19/19) | [283-301](18/19) |
| 423 | — | | | |
| 424 | — | — | — | — |
| 425 | — | — | — | — |
| 426 | — | — | — | — |
| 427 | — | — | — | — |
| 428 | — | — | — | — |
| 429 | — | — | — | — |
| 430 | — | — | — | — |
| 431 | — | — | — | — |
| 432 | [290-308](18/19) | [171-189](18/19) | [412-430](19/19) | [275-292](18/18) |
| 433 | — | — | — | — |
| 434 | — | — | — | — |
| 435 | — | — | — | — |
| 436 | — | — | — | — |
| 437 | — | — | — | — |
| 438 | — | — | — | — |
| 439 | — | — | — | — |
| 440 | — | — | — | — |
| 441 | — | — | — | — |
| 442 | — | — | — | — |
| 443 | — | — | — | — |
| 444 | — | — | — | — |
| 445 | — | — | — | — |
| 446 | — | — | — | — |
| 447 | — | — | — | — |
| 448 | — | — | — | — |
| 449 | [263-275](13/13) | — | [382-400](19/19) | — |
| 450 | — | — | — | — |
| 451 | [939-949](11/11) | — | — | — |
| 452 | [939-949](11/11) | — | — | — |
| 453 | — | — | — | — |
| 454 | — | — | — | — |
| 455 | — | — | — | — |
| 456 | — | — | — | — |
| 457 | — | — | — | — |
| 458 | — | — | [370-388](19/19) | — |
| 459 | — | — | — | — |
| 460 | — | — | — | — |
| 461 | [846-862](17/17) | — | — | [834-845](12/12) |
| 462 | — | — | — | — |
| 463 | — | — | — | — |
| 464 | [709-726](18/18) | — | — | — |
| 465 | — | [579-594](16/16) | — | — |
| 466 | [675-686](12/12) | — | — | — |
| 467 | [674-686](13/13) | — | — | — |
| 468 | — | — | [776-789](14/14) | — |
| 469 | — | — | [762-780](19/19) | [624-640](17/17) |
| 470 | — | — | [756-774](19/19) | [618-636](19/19) |
| 471 | — | — | [717-734](18/18) | — |
| 472 | — | — | [712-730](18/19) | — |
| 473 | — | — | [711-728](17/18) | — |

TABLE A-continued

| | | | | |
|---|---|---|---|---|
| 474 | [526-544](18/19) | [407-425](19/19) | [651-666](16/16) | [510-528](19/19) |
| 475 | [514-527](14/14) | [398-408](11/11) | [631-649](19/19) | [493-511](18/19) |
| 476 | [439-455](17/17) | [323-336](14/14) | [559-577](19/19) | [421-439](19/19) |
| 477 | [439-452](14/14) | [323-333](11/11) | [556-574](19/19) | [418-436](19/19) |
| 478 | [197-212](16/16) | [78-93](16/16) | [319-337](19/19) | — |
| 479 | [415-428](14/14) | — | [533-551](19/19) | [402-413](12/12) |
| 480 | [407-425](18/19) | — | [529-547](19/19) | — |
| 481 | — | — | — | — |
| 482 | [389-407](18/19) | [270-288](18/19) | [511-529](19/19) | [373-391](19/19) |
| 483 | — | — | — | — |
| 484 | — | — | — | — |
| 485 | — | — | — | — |
| 486 | — | — | — | — |
| 487 | — | — | — | — |
| 488 | — | — | — | — |
| 489 | [1571-1581](11/11) | — | — | — |
| 490 | — | — | — | — |
| 491 | — | — | — | — |
| 492 | — | — | — | — |
| 493 | [193-211](19/19) | [74-92](19/19) | [315-333](19/19) | [177-195](18/19) |
| 494 | — | — | — | — |
| 495 | — | — | — | — |
| 496 | — | — | — | — |
| 497 | — | — | — | — |
| 498 | — | — | — | — |
| 499 | — | — | — | — |
| 500 | — | — | — | — |
| 501 | [356-374](18/19) | [237-255](18/19) | [478-496](19/19) | [340-357](17/18) |
| 502 | [2157-2167](11/11) | — | — | — |
| 503 | — | — | — | — |
| 504 | — | — | — | — |
| 505 | — | — | — | — |
| 506 | — | — | — | — |
| 507 | — | — | — | — |
| 508 | — | — | [471-489](19/19) | [340-351](12/12) |
| 509 | — | — | — | — |
| 510 | — | — | — | — |
| 511 | — | — | — | — |
| 512 | — | — | — | — |
| 513 | — | — | — | — |
| 514 | — | — | — | — |
| 515 | — | — | — | — |
| 516 | — | — | — | — |
| 517 | — | — | — | — |
| 518 | — | — | — | — |
| 519 | — | — | — | — |
| 520 | — | — | — | — |
| 521 | — | — | — | — |
| 522 | — | — | — | — |
| 523 | — | — | — | — |
| 524 | [325-341](17/17) | [206-222](17/17) | [445-463](19/19) | [307-325](18/19) |
| 525 | — | — | — | — |
| 526 | — | — | — | — |
| 527 | — | — | — | — |
| 528 | — | — | — | — |
| 529 | — | — | — | — |
| 530 | — | — | — | — |
| 531 | — | — | — | — |
| 532 | — | — | — | — |
| 533 | — | — | — | — |
| 534 | — | — | [433-451](19/19) | — |
| 535 | — | — | — | — |
| 536 | — | — | — | — |
| 537 | [303-317](15/15) | [184-195](12/12) | [425-443](19/19) | — |
| 538 | — | — | — | — |
| 539 | [298-314](17/17) | [179-195](17/17) | [418-436](19/19) | [280-295](16/16) |
| 540 | — | — | — | — |
| 541 | — | — | — | — |
| 542 | — | — | — | — |
| 543 | — | — | — | — |
| 544 | — | — | — | — |
| 545 | — | — | — | — |
| 546 | — | — | — | — |
| 547 | — | — | — | — |
| 548 | — | — | — | — |
| 549 | — | — | — | — |
| 550 | — | — | — | — |
| 551 | — | — | — | — |
| 552 | — | — | — | — |
| 553 | — | — | — | — |

TABLE A-continued

| | | | | |
|---|---|---|---|---|
| 554 | — | — | — | — |
| 555 | [283-296](14/14) | [164-177](14/14) | [403-421](19/19) | — |
| 556 | — | — | — | — |
| 557 | — | — | — | — |
| 558 | [283-295](13/13) | [164-176](13/13) | [399-417](19/19) | [263-279](16/17) |
| 559 | — | — | — | — |
| 560 | — | — | — | — |
| 561 | — | — | — | — |
| 562 | — | — | — | — |
| 563 | — | — | — | — |
| 564 | — | — | — | — |
| 565 | — | — | — | — |
| 566 | — | — | — | — |
| 567 | — | — | — | — |
| 568 | — | — | — | — |
| 569 | — | — | — | — |
| 570 | — | — | — | — |
| 571 | [751-761](11/11) | [632-642](11/11) | — | [736-749](14/14) |
| 572 | [714-731](18/18) | [599-613](15/15) | — | — |
| 573 | [713-731](19/19) | [594-612](18/19) | — | — |
| 574 | [712-730](19/19) | [593-611](18/19) | — | — |
| 575 | [579-593](15/15) | — | — | — |
| 576 | [214-232](18/19) | [95-113](18/19) | [336-354](19/19) | [198-216](18/19) |
| 577 | — | — | [725-743](19/19) | [588-605](17/18) |
| 578 | — | — | [723-741](19/19) | — |
| 579 | — | — | [696-714](18/19) | [558-571](14/14) |
| 580 | — | [453-468](15/16) | [694-709](16/16) | [556-571](16/16) |
| 581 | — | [444-462](19/19) | [685-703](19/19) | [547-565](18/19) |
| 582 | [557-572](16/16) | [438-456](19/19) | [679-697](19/19) | [541-559](19/19) |
| 583 | [550-568](19/19) | [434-449](16/16) | [672-690](19/19) | [534-552](19/19) |
| 584 | [548-566](19/19) | [429-447](18/19) | [670-688](19/19) | [534-550](17/17) |
| 585 | [451-469](19/19) | [332-348](17/17) | [573-591](19/19) | [435-453](18/19) |
| 586 | [202-220](18/19) | [83-101](18/19) | [324-342](19/19) | [186-204](18/19) |
| 587 | — | — | — | — |
| 588 | — | — | — | — |
| 589 | [390-408](18/19) | [271-289](18/19) | [512-530](19/19) | [374-392](19/19) |
| 590 | — | — | — | — |
| 591 | — | — | — | — |
| 592 | — | — | — | — |
| 593 | — | — | — | — |
| 594 | — | — | — | — |
| 595 | — | — | — | — |
| 596 | — | — | — | — |
| 597 | — | — | — | — |
| 598 | — | — | — | — |
| 599 | — | — | — | — |
| 600 | — | — | — | — |
| 601 | — | — | — | — |
| 602 | — | — | — | — |
| 603 | — | — | — | — |
| 604 | — | — | — | — |
| 605 | — | — | — | — |
| 606 | — | — | — | — |
| 607 | — | — | — | — |
| 608 | — | — | — | — |
| 609 | — | — | — | — |
| 610 | — | — | — | — |
| 611 | — | — | — | — |
| 612 | — | — | — | — |
| 613 | — | — | — | — |
| 614 | — | — | — | — |
| 615 | — | — | [474-492](19/19) | [340-351](12/12) |
| 616 | — | — | — | — |
| 617 | — | — | — | — |
| 618 | — | — | — | — |
| 619 | — | — | — | — |
| 620 | — | — | — | — |
| 621 | — | — | — | — |
| 622 | — | — | — | — |
| 623 | — | — | — | — |
| 624 | — | — | — | — |
| 625 | — | — | — | — |
| 626 | — | — | — | — |
| 627 | — | — | — | — |
| 628 | — | — | — | — |
| 629 | — | — | — | — |
| 630 | — | — | — | — |
| 631 | — | — | — | — |
| 632 | — | — | — | — |
| 633 | — | — | — | — |

TABLE A-continued

| | | | | |
|---|---|---|---|---|
| 634 | — | — | — | — |
| 635 | — | — | — | — |
| 636 | — | — | — | — |
| 637 | — | — | — | — |
| 638 | — | — | — | — |
| 639 | — | — | — | — |
| 640 | — | — | — | — |
| 641 | — | — | — | — |
| 642 | — | — | — | — |
| 643 | — | — | — | — |
| 644 | — | — | — | — |
| 645 | — | — | — | — |
| 646 | — | — | — | — |
| 647 | — | — | — | — |
| 648 | — | — | — | — |
| 649 | — | — | — | — |
| 650 | — | — | — | — |
| 651 | — | — | — | — |
| 652 | — | — | — | — |
| 653 | — | — | — | — |
| 654 | — | — | — | — |
| 655 | — | — | — | — |
| 656 | — | — | — | — |
| 657 | — | — | — | [1333-1346](14/14) |
| 658 | — | — | — | — |
| 659 | — | — | — | — |
| 660 | — | — | [410-428](19/19) | [275-290](16/16) |
| 661 | — | — | [409-427](19/19) | [275-289](15/15) |
| 662 | — | — | — | — |
| 663 | [285-303](18/19) | [166-184](18/19) | [407-425](19/19) | [269-287](18/19) |
| 664 | — | — | — | — |
| 665 | — | — | — | — |
| 666 | — | — | — | — |
| 667 | — | — | — | — |
| 668 | — | — | — | [866-878](13/13) |
| 669 | — | — | — | — |
| 670 | — | — | — | — |
| 671 | [751-767](16/17) | [632-648](16/17) | — | [736-751](16/16) |
| 672 | [709-723](15/15) | [586-604](18/19) | — | — |
| 673 | [579-590](12/12) | — | — | — |
| 674 | [670-684](15/15) | [552-564](13/13) | — | [657-667](11/11) |
| 675 | — | — | [769-787](19/19) | [606-624](19/19) |
| 676 | — | — | [744-762](19/19) | [606-624](19/19) |
| 677 | — | — | [726-744](19/19) | [588-606](18/19) |
| 678 | — | — | [698-715](17/18) | [560-571](12/12) |
| 679 | — | [449-463](15/15) | [690-708](19/19) | [554-570](17/17) |
| 680 | [439-450](12/12) | — | [554-572](19/19) | [417-434](18/18) |
| 681 | — | — | — | — |
| 682 | — | — | — | — |
| 683 | — | — | — | — |
| 684 | — | — | — | — |
| 685 | — | — | — | — |
| 686 | — | — | — | — |
| 687 | — | — | — | — |
| 688 | — | — | — | — |
| 689 | — | — | — | — |
| 690 | — | — | — | — |
| 691 | — | — | — | — |
| 692 | — | — | — | — |
| 693 | — | — | — | — |
| 694 | — | — | — | — |
| 695 | — | — | — | — |
| 696 | — | — | — | — |
| 697 | — | — | — | — |
| 698 | — | — | — | — |
| 699 | — | — | — | — |
| 700 | — | — | — | — |
| 701 | — | — | — | — |
| 702 | — | — | — | — |
| 703 | — | — | — | — |
| 704 | — | — | — | — |
| 705 | — | — | — | — |
| 706 | — | — | — | — |
| 707 | — | — | — | — |
| 708 | — | — | — | — |
| 709 | — | — | — | — |
| 710 | — | — | — | — |
| 711 | — | — | — | — |
| 712 | — | — | — | — |
| 713 | — | — | — | — |

TABLE A-continued

| | | | | |
|---|---|---|---|---|
| 714 | — | — | — | — |
| 715 | — | — | — | — |
| 716 | [319-335](16/17) | [206-216](11/11) | [439-457](19/19) | [301-319](18/19) |
| 717 | — | — | — | — |
| 718 | — | — | [436-454](19/19) | [298-316](18/19) |
| 719 | — | — | — | — |
| 720 | — | — | — | — |
| 721 | — | — | — | — |
| 722 | — | — | — | — |
| 723 | — | — | — | — |
| 724 | — | — | — | — |
| 725 | [302-317](16/16) | [183-195](13/13) | [424-442](19/19) | — |
| 726 | — | — | — | — |
| 727 | — | — | — | — |
| 728 | — | — | — | [1336-1346](11/11) |
| 729 | — | — | — | [1333-1346](14/14) |
| 730 | — | — | — | — |
| 731 | — | — | — | — |
| 732 | — | — | — | — |
| 733 | — | — | — | — |
| 734 | [286-304](18/19) | [167-185](18/19) | [408-426](19/19) | [270-288](18/19) |
| 735 | — | — | — | — |
| 736 | — | — | — | — |
| 737 | — | — | — | — |
| 738 | — | — | — | — |
| 739 | [283-296](14/14) | [164-177](14/14) | [402-420](19/19) | — |
| 740 | — | — | — | — |
| 741 | — | — | — | — |
| 742 | — | — | — | — |
| 743 | — | — | — | — |
| 744 | — | — | — | — |
| 745 | [283-296](14/14) | [164-177](14/14) | [400-418](19/19) | [263-280](17/18) |
| 746 | — | — | — | — |
| 747 | — | — | — | — |
| 748 | — | — | — | — |
| 749 | — | — | — | — |
| 750 | — | — | — | [867-878](12/12) |
| 751 | — | — | — | — |
| 752 | — | — | — | — |
| 753 | — | — | — | [737-751](15/15) |
| 754 | [745-761](16/17) | [626-642](16/17) | — | [736-747](12/12) |
| 755 | [719-737](18/19) | [600-618](19/19) | — | — |
| 756 | [717-731](15/15) | [599-616](18/18) | — | — |
| 757 | — | [579-591](13/13) | — | — |
| 758 | — | — | [763-781](19/19) | [625-640](16/16) |
| 759 | — | — | [758-776](19/19) | [620-638](19/19) |
| 760 | — | — | [750-768](19/19) | [612-630](19/19) |
| 761 | — | — | [749-767](19/19) | [611-629](19/19) |
| 762 | — | — | [747-765](19/19) | [609-627](19/19) |
| 763 | [613-624](12/12) | — | [728-746](19/19) | [594-608](15/15) |
| 764 | — | [450-468](18/19) | [691-709](19/19) | [554-571](18/18) |
| 765 | — | [445-463](19/19) | [686-704](19/19) | [548-566](18/19) |
| 766 | — | — | [326-344](19/19) | [192-206](15/15) |
| 767 | [415-428](14/14) | — | [536-554](19/19) | [402-415](14/14) |
| 768 | — | — | — | — |
| 769 | — | — | — | — |
| 770 | — | — | — | — |
| 771 | — | — | — | — |
| 772 | — | — | — | — |
| 773 | — | — | — | — |
| 774 | — | — | — | — |
| 775 | — | — | — | — |
| 776 | [1571-1581](11/11) | — | — | — |
| 777 | — | — | — | — |
| 778 | — | — | — | — |
| 779 | — | — | — | — |
| 780 | — | — | — | — |
| 781 | — | — | — | — |
| 782 | — | — | — | — |
| 783 | — | — | — | — |
| 784 | — | — | — | — |
| 785 | [2152-2167](15/16) | — | — | — |
| 786 | — | — | — | — |
| 787 | — | — | — | — |
| 788 | — | — | — | — |
| 789 | — | — | — | — |
| 790 | — | — | — | — |
| 791 | — | — | — | — |
| 792 | — | — | — | — |
| 793 | — | — | — | — |

TABLE A-continued

| | | | | |
|---|---|---|---|---|
| 794 | — | — | — | — |
| 795 | — | — | — | — |
| 796 | — | — | — | — |
| 797 | — | — | — | — |
| 798 | — | — | — | — |
| 799 | — | — | — | — |
| 800 | — | — | — | — |
| 801 | — | — | — | — |
| 802 | — | — | — | — |
| 803 | — | — | — | — |
| 804 | — | — | — | — |
| 805 | — | — | — | — |
| 806 | — | — | — | — |
| 807 | — | — | — | — |
| 808 | — | — | — | — |
| 809 | [283-296](14/14) | [164-177](14/14) | [404-422](19/19) | — |
| 810 | — | — | — | — |
| 811 | — | — | — | — |
| 812 | — | — | — | — |
| 813 | — | — | — | [868-878](11/11) |
| 814 | — | — | — | — |
| 815 | — | — | — | — |
| 816 | — | — | — | — |
| 817 | [715-731](17/17) | [599-614](16/16) | — | — |
| 818 | [670-686](17/17) | [552-564](13/13) | — | [657-667](11/11) |
| 819 | — | — | [753-771](19/19) | [615-633](19/19) |
| 820 | — | — | — | — |
| 821 | — | — | — | — |
| 822 | — | — | — | — |
| 823 | — | — | — | — |
| 824 | — | — | — | — |
| 825 | — | — | — | — |
| 826 | — | — | — | — |
| 827 | — | — | — | — |
| 828 | — | — | — | — |
| 829 | — | — | — | — |
| 830 | — | — | — | — |
| 831 | — | — | — | — |
| 832 | — | — | — | — |
| 833 | — | — | — | — |
| 834 | — | — | — | — |
| 835 | — | — | — | — |
| 836 | — | — | — | — |
| 837 | — | — | — | — |
| 838 | — | — | — | — |
| 839 | — | — | — | — |
| 840 | — | — | — | — |
| 841 | — | — | — | — |
| 842 | — | — | — | — |
| 843 | — | — | — | — |
| 844 | — | — | — | — |
| 845 | — | — | — | — |
| 846 | — | — | — | [866-877](12/12) |
| 847 | — | — | — | — |
| 848 | — | — | — | — |
| 849 | — | — | — | — |
| 850 | [718-736](18/19) | [599-617](19/19) | — | — |
| 851 | [716-731](16/16) | [599-615](17/17) | — | — |
| 852 | [214-227](14/14) | [95-108](14/14) | [334-352](19/19) | [196-211](16/16) |
| 853 | [214-227](14/14) | [95-108](14/14) | [333-351](19/19) | [195-211](17/17) |
| 854 | — | [448-463](16/16) | [689-707](19/19) | [554-569](16/16) |
| 855 | [562-580](18/19) | [443-461](19/19) | [684-702](19/19) | [546-564](18/19) |
| 856 | — | — | [550-568](19/19) | [412-430](18/19) |
| 857 | [597-607](11/11) | [478-488](11/11) | [544-562](19/19) | — |
| 858 | [415-433](18/19) | — | [537-555](19/19) | [402-415](14/14) |
| 859 | — | — | — | — |
| 860 | — | — | — | — |
| 861 | — | — | — | — |
| 862 | — | — | [470-488](19/19) | [340-350](11/11) |
| 863 | — | — | — | — |
| 864 | — | — | — | — |
| 865 | — | — | — | — |
| 866 | — | — | — | — |
| 867 | — | — | — | — |
| 868 | — | — | — | — |
| 869 | — | — | — | — |
| 870 | — | — | — | — |
| 871 | — | — | — | — |
| 872 | — | — | — | — |
| 873 | — | — | — | — |

TABLE A-continued

| | | | | |
|---|---|---|---|---|
| 874 | — | — | [752-770](19/19) | [614-632](19/19) |
| 875 | [616-631](16/16) | — | [738-756](19/19) | [600-618](19/19) |
| 876 | [445-463](19/19) | [326-344](19/19) | [567-585](19/19) | [429-445](17/17) |
| 877 | — | — | — | — |
| 878 | — | — | — | — |
| 879 | — | — | — | — |
| 880 | — | — | — | — |
| 881 | — | — | — | — |
| 882 | — | — | — | — |
| 883 | [597-607](11/11) | [478-488](11/11) | [542-560](19/19) | [404-422](18/19) |
| 884 | [597-607](11/11) | [478-488](11/11) | [541-559](19/19) | [403-421](18/19) |
| 885 | — | — | — | — |
| 886 | — | — | — | — |
| 887 | — | — | — | — |
| 888 | — | — | [459-477](19/19) | [321-337](16/17) |
| 889 | — | — | [457-475](19/19) | [321-337](16/17) |
| 890 | — | — | — | — |
| 891 | [703-721](18/19) | [584-602](18/19) | — | — |
| 892 | — | — | [460-478](19/19) | [322-337](15/16) |
| 893 | — | — | [458-476](19/19) | [321-337](16/17) |
| 894 | — | — | — | [1182-1200](18/19) |
| 895 | — | — | — | [1182-1199](17/18) |
| 896 | — | — | — | — |
| 897 | [613-629](17/17) | — | [733-751](19/19) | [595-613](19/19) |
| 898 | — | — | — | — |
| 899 | — | — | — | — |
| 900 | — | — | — | — |
| 901 | — | — | — | — |
| 902 | — | — | — | — |
| 903 | — | — | — | — |
| 904 | — | — | — | — |
| 905 | — | [605-623](19/19) | — | [708-724](16/17) |
| 906 | [614-631](18/18) | — | [736-754](19/19) | [598-616](19/19) |
| 907 | [613-628](16/16) | — | [732-750](19/19) | [594-612](19/19) |
| 908 | [613-626](14/14) | — | [730-748](19/19) | [594-610](17/17) |
| 909 | [446-464](19/19) | [327-345](19/19) | [568-586](19/19) | [430-445](16/16) |
| 910 | — | — | — | — |
| 911 | — | — | — | — |
| 912 | — | — | — | [740-758](18/19) |
| 913 | [208-226](18/19) | [89-107](18/19) | [330-348](19/19) | [192-210](19/19) |
| 914 | — | — | [461-479](19/19) | [327-337](11/11) |
| 915 | [443-461](19/19) | [324-342](19/19) | [565-583](19/19) | [427-445](19/19) |
| 916 | — | — | — | — |
| 917 | — | — | — | [739-757](18/19) |
| 918 | — | — | — | — |
| 919 | — | — | — | — |
| 920 | — | — | — | — |
| 921 | — | — | — | — |
| 922 | — | — | — | [741-759](18/19) |
| 923 | — | — | — | — |
| 924 | — | — | — | — |
| 925 | — | — | — | - |

Note that in the above Table A, the sense strands of siRNAs 1-925 have SEQ ID NOS: 3-927 respectively, and the antisense strands of siRNAs 1-925 have SEQ ID NOS: 928-1852 respectively.

Further note that the coding region of gene RTP801L, as presented in FIG. 1, is between nucleotides 204-785. Therefore, any siRNA within this region targets the coding region of RTP801L, and any siRNA outside this region targets the non-coding region of RTP801L i.e. the 5'UTR or the 3' UTR. The exact region targeted by each siRNA is given in Table A (column 5).

Additionally, all sequences presented in Table A are depicted in the direction 5' to 3'.

Example 6

Pharmacology and Drug Delivery

The nucleotide sequences of the present invention are delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell.

The compounds or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The treatment generally has a length proportional to the length of the disease process and drug effectiveness and the patient species being treated. It is noted that humans are treated generally longer than the mice or other experimental animals exemplified herein.

The compounds of the present invention are administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention.

When administering the compound of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compound in tablets, suspensions, solutions, emulsions, capsules, powders, syrups and the like are usable. Known techniques which deliver it orally or intravenously and retain the biological activity are preferred. In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-2 weeks or longer, preferably for 24- to 48 hrs or by continuous infusion during a period of 1-2 weeks or longer.

Administration of Compounds of the Present Invention to the Eye

The compounds of the present invention can be administered to the eye topically or in the form of an injection, such as an intravitreal injection, a sub-retinal injection or a bilateral injection. Further information on administration of the compounds of the present invention can be found in Tolentino et al., Retina 24 (2004) 132-138; Reich et al., Molecular vision 9 (2003) 210-216.

Pulmonary Administration of Compounds of the Present Invention

The therapeutic compositions of the present invention are preferably administered into the lung by inhalation of an aerosol containing these compositions/compounds, or by intranasal or intratracheal instillation of said compositions. Formulating the compositions in liposomes may benefit absorption. Additionally, the compositions may include a PFC liquid such as perflubron, and the compositions may be formulated as a complex of the compounds of the invention with polyethylemeimine (PEI).

For further information on pulmonary delivery of pharmaceutical compositions see Weiss et al., *Human gene therapy* 10:2287-2293 (1999); Densmore et al., *Molecular therapy* 1:180-188 (1999); Gautam et al., *Molecular therapy* 3:551-556 (2001); and Shahiwala & Misra, *AAPS PharmSciTech* 5 (2004). Additionally, respiratory formulations for siRNA are described in U.S. patent application No. 2004/0063654 of Davis et el.

Further, the compounds of the present invention may be administered topically where appropriate (such as in the case of diabetic foot ulcers for example), optionally in a lipid/liposome formulation.

A preferred administration mode is topical delivery of the RTP801L inhibitors onto the round window membrane of the cochlea as disclosed for example in Tanaka et al. (Hear Res. 2003 March; 177(1-2):21-31).

In the treatment of pressure sores or other wounds, the administration of the pharmaceutical composition is preferably by topical application to the damages area, but the compositions may also be administered systemically.

Additional formulations for improved delivery of the compounds of the present invention can include non-formulated compounds, compounds covalently bound to cholesterol, and compounds bound to targeting antibodies (Song et al., Antibody mediated in vivo delivery of small interfering RNAs via cell-surface receptors, Nat. Biotechnol. 2005 June; 23(6): 709-17).

Example 7

Model Systems for Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active inhibitors of the invention (such as siRNA) for treating pressure sore, ulcers and similar wounds is done in the mouse model described in Reid R R, Sull A C, Mogford J E, Roy N, Mustoe T A. Cyclical Magnetic Pressure Necrosis: *A Novel Murine Model of Cutaneous Ischemia-Reperfusion Injury*. J Surgical Research. 116: 172-180, 2004.

Additionally, a rabbit model is described by Mustoe et al, JCI, 1991; Ahn & Mustoe, Ann Pl Surg, 1991 and is used for testing the siRNAs of the invention.

Example 8

Model Systems for Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

Testing the active inhibitors of the invention (such as siRNA) for treating spinal cord injury is done in the rat spinal cord contusion model as described by Young, W. in *Prog Brain Res.* 2002; 137:231-55. Other predictive animal models of spinal cord injury are described in the following references:

Gruner, J. A. (1992). "A monitored contusion model of spinal cord injury in the rat." J Neurotrauma 9(2): 123; Hasegawa, K. and M. Grumet (2003). "Trauma-induced tumorigenesis of cells implanted into the rat spinal cord." J Neurosurg 98(5): 1065-71; and Huang, P. P. and W. Young (1994). "The effects of arterial blood gas values on lesion volumes in a graded rat spinal cord contusion model." J Neurotrauma 11(5): 547.

Example 9

Model Systems for Glaucoma

Testing the active inhibitors of the invention (such as siRNA) for treating or preventing Glaucoma is done in the animal model for example as described by Pease et al., J. Glaucoma, 2006, 15(6):512-9 (Manometric calibration and comparison of TonoLab and TonoPen tonometers in rats with experimental glaucoma and in normal mice).

Example 10

Model Systems for Ischemia and Reperfusion Injury Following Lung Transplantation in Rats Testing the active inhibitors of the invention (such as siRNA) for treating or preventing Ischemia and reperfusion injury following lung transplantation is done in the animal model for example as described by Mizobuchi et al., J. Heart Lung Transplant 2004:23:889-93.

Example 11

Model Systems for Acute Lung Injury (ALI)

Intratracheal (i.t) administration of LPS (Lipopolysaccharide), a bacterial cell wall component, is an accepted experimental model of acute lung injury (ALI), as LPS stimulates profound lung recruitment of inflammatory cells and the subsequent development of systemic inflammation. (See, for example, Fang W F, Cho J H, He Q, Lin M C, Wu C C, Voelkel N F, Douglas I S. "Lipid A Fraction of LPS Induces a Discrete MAPK Activation in Acute Lung Injury" Am J Physiol Lung Cell Mol. Physiol. 2007 May 11; Hagiwara S, Iwasaka H, Noguchi T. "Nafamostat mesilate inhibits the expression of HMGB1 in lipopolysaccharide-induced acute lung injury" J. Anesth. 2007; 21(2):164-70. Epub 2007 May 30.).

Time-dependent changes of RTP801L gene expression in mice lungs during the first 24 hours (time points 0.5; 1; 2; 4; 8 & 24 hours), after Intratracheal (i.t) administration of LPS was assessed. The assessment of gene expression was done using qPCR.

The results indicate that the level of the RTP801L transcript is gradually decreased following LPS instillation.

Example 12

Model Systems for Acute Respiratory Distress Syndrome

Testing the active inhibitors of the invention (such as siRNA) for treating Acute respiratory distress syndrome is done in the animal model as described by Chen et al. in *J Biomed Sci.* 2003; 10(6 Pt 1):588-92.

Example 13

Model Systems for Hearing Loss Conditions (i) Distribution of Cy3-PTEN siRNA in the Cochlea Following Local Application to the Round Window of the Ear:

A solution of 1 µg/100 µl of Cy3-PTEN siRNA (total of 0.3-0.4 µg) PBS was applied to the round window of chinchillas. The Cy3-labelled cells within the treated cochlea were analyzed 24-48 hours post siRNA round window application after sacrifice of the chinchillas. The pattern of labeling within the cochlea was similar following 24 h and 48 h and includes labeling in the basal turn of cochlea, in the middle turn of cochlea and in the apical turn of cochlea. Application of Cy3-PTEN siRNA onto scala tympani revealed labelling mainly in the basal turn of the cochlea and the middle turn of the cochlea. The Cy3 signal was persistance to up to 15 days after the application of the Cy3-PTEN siRNA. These results indicate for the first time that local application of siRNA molecules within the round window leads to significant penetration of the siRNA molecules to the basal, middle and apical turns of the cochlea. The active inhibitors of the invention (such as siRNA) are tested in this model.

(ii) Animal Model of Carboplatin-Induced or Cisplatin-Induced Hair Cell Death in the Cochlea of Chinchilla:

Chinchillas are pre-treated by direct administration of specific siRNAs to 801L (siRNA Nos: 72 or 73 in Table A) in saline to the left ear of each animal. Saline is given to the right ear of each animal as placebo. Two days following the administration of the specific siRNA, the animals are treated with carboplatin (75 mg/kg ip) or cisplatin (intraperitoneal infusion of 13 mg/kg over 30 minutes). After sacrifice of the chinchillas (two weeks post carboplatin treatment) the percentage of dead cells of inner hair cells (IHC) and outer hair cells (OHC) is calculated in the left ear (siRNA treated) and in the right ear (saline treated). The percentage of dead cells is lower in the siRNA treated ear than in the control (Iii) Animal Model of Acoustic-Induced Hair Cell Death in the Cochlea of Chinchilla:

The activity of specific siRNA to 801L (siRNA Nos: 72 or 73 in Table A) in an acoustic trauma model is studied in chinchilla. The animals are exposed to an octave band of noise centered at 4 kHz for 2.5 h at 105 dB. The left ear of the noise-exposed chinchillas is pre-treated (48 h before the acoustic trauma) with 30 µg of either siRNA in ~10 µL of saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the siRNA-treated ear are lower (better) than the untreated (saline) ear. In addition, the amount of inner and outer hair cell loss is determined in the siRNA-treated and the control ear. It is found that the thresholds in the siRNA-treated ear are lower than the untreated (saline) ear Also, the amount of hair cell loss is lower in the siRNA-treated ear than in the control ear.

Example 14

REDD2 siRNA Activity

The following synthetic stabilized siRNA molecules against 801L gene, generated as a stock solution 100 uM in double distilled water, were tested.

| | SiRNA oligos |
|---|---|
| 1 | DDIT4L__216 (table A ID 915) |
| 2 | DDIT4L__218 (table A ID 876) |
| 3 | DDIT4L__15 (table A ID 493) |
| 4 | DDIT4L__229 (table A ID 72) |
| 5 | DDIT4L__228 (table A ID 73) |

Thus, the siRNAs tested were blunt-ended 19mers wherein alternate sugars have a 2'-O-methyl modification, having the sequences presented in Table A, Nos. 915, 876, 493, 72 and 73. The 2-O-methyl modification is present on nucleotides 1, 3, 5, 7, 9, 11, 13, 15, 17 and 19 of the antisense strand and nucleotides 2, 4, 6, 8, 10, 12, 14, 16 and 18 of the sense strand. The siRNAs tested were unphosphorylated but the parallel phosphorylated molecules are used to achieve essentially identical results. The inventors of the present application have shown elsewhere (PCT Patent Publication Nos. WO 2006/0354 and 2006/023544) that unphosphorylated and the parallel phosphorylated siRNA modified compounds have similar activity The following negative controls were used:

a) Cy3-labeled synthetic stabilized siRNA against human, mouse and rat PTEN gene (PTEN-Cy3). Stock solution 20 mg/ml in double distilled.

b) Synthetic stabilized siRNA against GFP (GFP siRNA). Stock solution 20 mg/ml in double distilled.

The cells used in the experiment were 801 wt and Ko mouse embryonic fibroblasts (MEF) cells and 293T embryonic kidney cells.

The transfection reagent used was Lipofectamine 2000 (Invitrogene, Cat#11668-019).

Methods $3 \times 10^5$ and $1 \times 10^5$ 801 wt MEF and 293T cells were seeded per well of the 6 wells plate, respectively. 24 h subsequently, cells were transfected with:

a. DDIT4L siRNA molecules at final concentrations per well of 0.5-40 nM
b. GFP siRNA molecules at final concentrations per well of 0.5-40 nM
c. PTEN-Cy3 siRNA at final concentrations per well of 20-40 nM Transfection mixture per each well contained 3 µl lipofectamine 2000 reagent (in 250 µl serum free medium).

RNA was extracted from cells 72 h following transfection. In the last 8 h of incubation, 500 uM H2O2 was added to wt MEF cells.

RNA was prepared from the cells and processed, and qPCR was performed for the evaluation of REDD2 mRNA levels, using mouse or human REDD2-specific oligonucleotides and Cyclophylin as a reference gene.

RESULTS AND CONCLUSIONS

Figure 4:
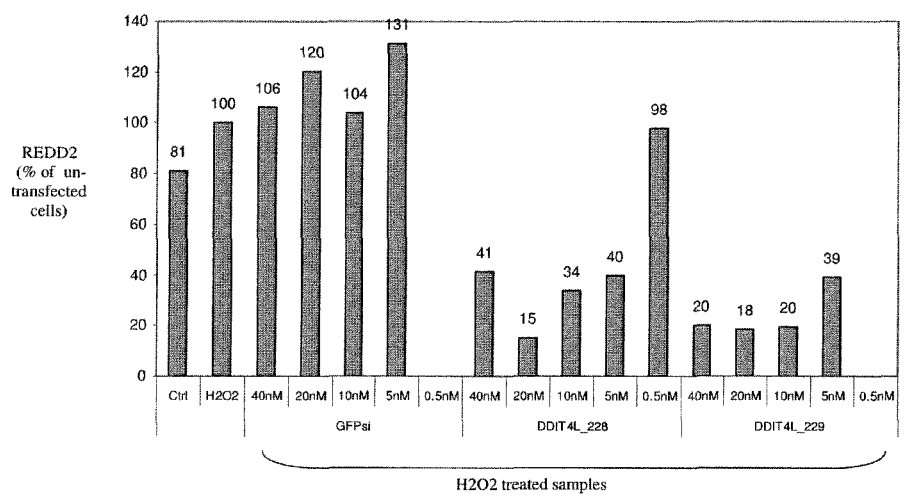
FIG. 4 demonstrates dose dependent activity of REDD2 siRNAs as measured in 801 wt MEF cells.
Figure 5:
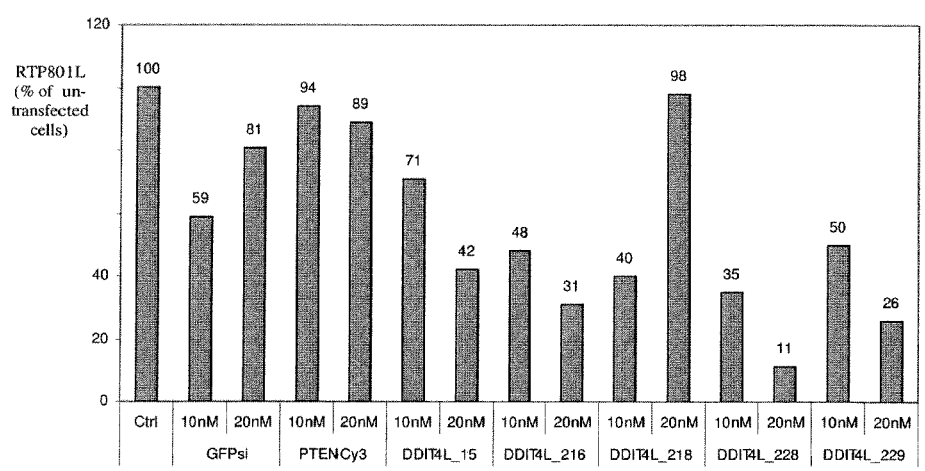
FIG. 5 shows activity results of REDD2 siRNAs on the endogenous REDD2 gene in wt 293T cells.
Figure 6:
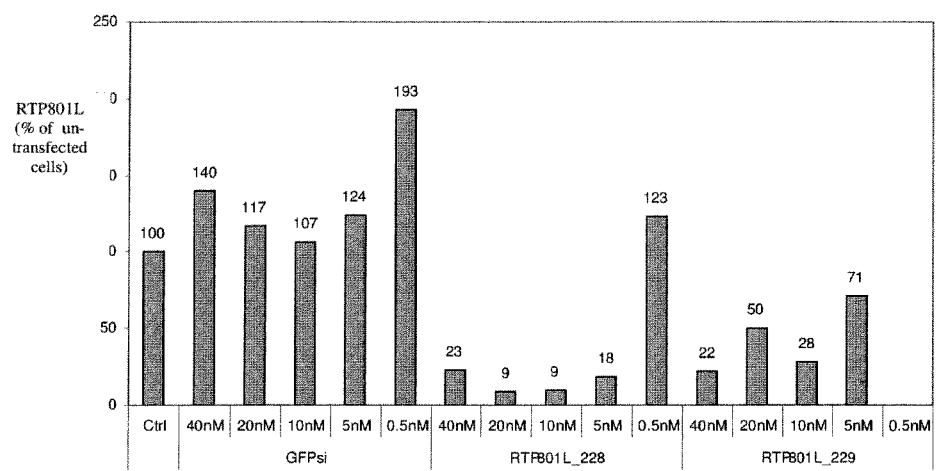
FIG. 6 demonstrates dose dependent activity of RTP801L siRNA as measured in 293T cells.

As shown in FIGS. 3-6, the best active siRNA oligos in both mouse and human genes were DDIT4L__228 (Table A ID 72) and DDIT4L__229 (Table A ID 73). DDIT4L__228 was slightly more active on the human RTP801L gene than DDIT4L__229. Both siRNAs 72 and 73 were more active than siRNAs 915, 876 and 493, as can be seen from FIGS. 3-6.

What is claimed:

1. A method of treating a subject suffering from an optic neuropathy selected from glaucoma and ischemic optic neuropathy (ION), comprising administering to the subject an RTP801L inhibitor in an amount effective to down-regulate expression of an RTP801L gene,
   wherein the RTP801L inhibitor is administered to an eye of the subject via an intravitreal injection; and
   wherein the RTP801L inhibitor comprises an siRNA which specifically down regulates the expression of the RTP801L gene, so as to thereby treat the subject.

2. The method of claim 1, wherein the glaucoma is acute glaucoma, chronic glaucoma or neovascular glaucoma.

3. The method of claim 1, wherein the glaucoma comprises damage to the optic nerve.

4. The method of claim 1, wherein the RTP801L inhibitor is a double-stranded oligonucleotide having the structure:

```
5' UCUUGAGCAAUUCUCUGGG 3'  antisense strand (SEQ ID NO: 1000)
   |||||||||||||||||||
3' AGAACUCGUUAAGAGACCC 5'  sense strand (SEQ ID NO: 75)
``` wherein alternating ribonucleotides in the antisense strand and the sense strand are 2'-O-methyl sugar modified ribonucleotides; wherein the ribonucleotides at the 5' terminus and the 3' terminus of the antisense strand are 2'-O-methyl sugar modified; and wherein the ribonucleotides at the 5' terminus and the 3' terminus of the sense strand are unmodified; and wherein each of the antisense strand and the sense strand is 19 nucleotides in length.

5. The method of claim 1, wherein the RTP801L inhibitor is a double stranded oligonucleotide having the structure

```
5' AUCUUGAGCAAUUCUCUGG 3'  antisense strand (SEQ ID NO: 999)
   |||||||||||||||||||
3' UAGAACUCGUUAAGAGACC 5'  sense strand (SEQ ID NO: 74)
``` wherein alternating ribonucleotides in the antisense strand and the sense strand are 2'-O-methyl sugar modified ribonucleotides; wherein the ribonucleotides at the 5' terminus and the 3' terminus of the antisense strand are 2'-O-methyl sugar modified; wherein the ribonucleotides at the 5' terminus and the 3' terminus of the sense strand are unmodified; and wherein each of the antisense strand and the sense strand is 19 nucleotides in length.

6. A method of treating a subject suffering from an optic neuropathy selected from glaucoma and ischemic optic neuropathy (ION) comprising administering to the subject an RTP801L inhibitor in an amount effective to down-regulate expression of an RTP801L gene,
   wherein the RTP801L inhibitor is administered to an eye of subject via an intravitreal injection;
   wherein the RTP801L inhibitor is a double-stranded oligonucleotide having the structure;

5' UCUUGAGCAAUUCUCUGGG 3'  antisense strand (SEQ ID NO: 1000)
   |||||||||||||||||||
3' AGAACUCGUUAAGAGACCC 5'  sense strand (SEQ ID NO: 75); or the structure:

5' AUCUUGAGCAAUUCUCUGG 3'  antisense strand (SEQ ID NO: 999)
   |||||||||||||||||||
3' UAGAACUCGUUAAGAGACC 5'  sense strand (SEQ ID NO: 74);

and wherein each of the antisense strand and the sense strand is 19 nucleotides in length.

7. The method of claim 6, wherein alternating ribonucleotides in the antisense strand and the sense strand are 2'-O-methyl sugar modified ribonucleotides; wherein the ribonucleotides at the 5 terminus and the 3' terminus of the antisense strand are 2'-O-methyl sugar modified; and wherein the ribonucleotides at the 5' terminus and the 3 terminus of the sense strand are unmodified.

* * * * *